US009822105B2

(12) United States Patent
Major et al.

(10) Patent No.: US 9,822,105 B2
(45) Date of Patent: Nov. 21, 2017

(54) DIAMINOTRIAZINE COMPOUNDS AS HERBICIDES

(71) Applicant: BASF SE, Ludwigshafen (DE)

(72) Inventors: Julia Major, Freinsheim (DE); Florian Vogt, Mannheim (DE); Frederick Calo, Duesseldorf (DE); Thomas Seitz, Viernheim (DE); Doreen Schachtschabel, Mannheim (DE); Trevor William Newton, Neustadt (DE); Kristin Hanzlik, Bobenheim am Berg (DE); Johannes Hutzler, Waldsee (DE); Klaus Kreuz, Denzlingen (DE); Stefan Tresch, Kirchheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/305,823

(22) PCT Filed: Apr. 22, 2015

(86) PCT No.: PCT/EP2015/058696
§ 371 (c)(1),
(2) Date: Oct. 21, 2016

(87) PCT Pub. No.: WO2015/162169
PCT Pub. Date: Oct. 29, 2015

(65) Prior Publication Data
US 2017/0050954 A1 Feb. 23, 2017

(30) Foreign Application Priority Data

Apr. 23, 2014 (EP) ..................... 14165624

(51) Int. Cl.
C07D 413/12 (2006.01)
C07D 405/12 (2006.01)
(Continued)

(52) U.S. Cl.
CPC ........... *C07D 413/12* (2013.01); *A01N 43/68* (2013.01); *A01N 43/76* (2013.01); *C07D 251/18* (2013.01); *C07D 405/12* (2013.01); *C07D 405/14* (2013.01)

(58) Field of Classification Search
CPC ...... A01N 43/68; A01N 43/76; C07D 251/18; C07D 405/12; C07D 405/14; C07D 413/12
(Continued)

(56) References Cited

U.S. PATENT DOCUMENTS 3,816,419 A 6/1974 Cross et al.
3,932,167 A 1/1976 Cross et al.
(Continued)

FOREIGN PATENT DOCUMENTS

CA 997762 9/1976
CA 2081413 5/1993
(Continued)

OTHER PUBLICATIONS

Baindur et al., "2-Hydroxy-4,5-diamino-[1,3,5]triazines: A Novel Class of VEGF-R2 (KDR) Tyrosine Kinase Inhibitors," J. Med. Chem., vol. 48, (2005), pp. 1717-1720.
(Continued)

Primary Examiner — Johann R Richter
Assistant Examiner — Courtney Brown
(74) Attorney, Agent, or Firm — Brinks Gilson & Lione

(57) ABSTRACT

The present invention relates to diaminotriazine compounds and to their use as herbicides. The present invention also relates to agrochemical compositions for crop protection and to a method for controlling unwanted vegetation.

wherein

A is a fused saturated or unsaturated, 5-, 6-membered carbocycle or a fused saturated or unsaturated, 5-, 6-membered heterocycle;

P is 1 or 2 q is 0, 1, 2 or 3;

$R^b$ is inter alia halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, etc.;

$R^1$ is inter alia H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, etc.;

$R^2$ is inter alia H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, etc;

X is a radical selected from the group consisting of
$CR^3R^4R^5$
phenyl, which is unsubstituted or carries 1, 2, 3, 4 or 5 radicals $R^{Ar}$;
$NR^{3a}R^{3b}$,
$OR^{3c}$,
$S(O)_kR^{3d}$, k being 1, 2 or 3,
and
including their agriculturally acceptable salts.

20 Claims, No Drawings

(51) Int. Cl.
*A01N 43/68* (2006.01)
*C07D 405/14* (2006.01)
*C07D 251/18* (2006.01)
*A01N 43/76* (2006.01)

(58) Field of Classification Search
USPC ........................................................ 504/230
See application file for complete search history.

(56) References Cited

U.S. PATENT DOCUMENTS

| | | | |
|---|---|---|---|
| 3,983,117 | A | 9/1976 | Scheuermann et al. |
| 5,015,285 | A | 5/1991 | Rheinheimer et al. |
| 5,332,717 | A | 7/1994 | Lüthy et al. |
| 6,069,114 | A * | 5/2000 | Lorenz .................. A01N 43/68 504/219 |
| 7,002,011 | B1 | 2/2006 | Zindel et al. |
| 8,153,788 | B2 | 4/2012 | Ahrens et al. |
| 8,586,503 | B2 | 11/2013 | Hacker et al. |
| RE46,095 | E | 8/2016 | Hacker et al. |

FOREIGN PATENT DOCUMENTS

| | | |
|---|---|---|
| DE | 2226474 | 2/1973 |
| DE | 19607450 | 9/1997 |
| DE | 19744711 | 4/1999 |
| DE | 19830902 | 1/2000 |
| DE | 102006059941 | 6/2008 |
| EP | 0360163 | 3/1990 |
| EP | 0545149 | 6/1993 |
| EP | 0864567 | 9/1998 |
| EP | 1479397 | 11/2004 |
| EP | 2092825 | 8/2009 |
| FR | 2235126 | 1/1975 |
| WO | WO 9105781 | 5/1991 |
| WO | WO 9407868 | 4/1994 |
| WO | WO 2004031184 | 4/2004 |
| WO | WO 2011140527 | 11/2011 |
| WO | WO 2014064094 | 5/2014 |
| WO | WO 2015007711 | 1/2015 |
| WO | WO 2015144881 | 10/2015 |
| WO | WO 2015150541 | 10/2015 |
| WO | WO 2015155129 | 10/2015 |
| WO | WO 2015155272 | 10/2015 |
| WO | WO 2015155273 | 10/2015 |
| WO | WO 2015162166 | 10/2015 |

OTHER PUBLICATIONS

Cuthbertson and Moffatt, "Contributions to the Chemistry of Synthetic Antimaterials. Part VI. Some Derivatives of 1:3:5-Triazine," J. Chem. Soc., (1948), pp. 561-564.
International Preliminary Report on Patentability, issued in PCT/EP2015/058696, dated Oct. 25, 2016.
International Search Report, issued in PCT/EP2015/058696, dated Jun. 8, 2015.
Patwa and Parikh, "Preparation of 2,4-Diarylamino-s-Triazin-6-yl-Phenylsulphones. Part 1," Chemical Era, (1975), pp. 17-18.
Rosowsky et al., "Quinazolines. I. Formation of a Guanidinoquinazoline During the Three-Component Synthesis of a 4,6-Diamino-1-aryl-1,2-dihydro-s-Triazine," The Journal of Organic Chemistry, vol. 29, No. 10, (1064), pp. 2881-2887.
Search Report, issued in EP Application No. 14165624.9, dated Jul. 15, 2014.

* cited by examiner

DIAMINOTRIAZINE COMPOUNDS AS HERBICIDES

This application is a National Stage application of International Application No. PCT/EP2015/058696, filed Apr. 22, 2015. This application also claims priority under 35 U.S.C. §119 to European Patent Application No. 14165624.9, filed Apr. 23, 2014.

The present invention relates to diaminotriazine compounds and to their use as herbicides. The present invention also relates to agrochemical compositions for crop protection and to a method for controlling unwanted vegetation.

U.S. Pat. No. 3,816,419 describes 4-haloalkyl or 4-haloalkenyl-2,4-diaminotriazines and their use as herbicides. Similar compounds are known from U.S. Pat. No. 3,932,167.

DE 197 44 711 describes herbicidally active 2,4-diamino-1,3,5-triazine compounds, which carry a group A-Z in the 6-position, where A is alkylene and Z is a carbocylic or heterocyclic radical.

DE 198 30 902 describes amino-chloro-triazine compounds and their use as herbicides.

WO 91/05781, EP 0360163 and WO 94/07868 describe triazine compounds as herbicide. The compounds of these documents differ in the presence of a linker to the bicyclus, wherein the linker is limited to O or S, instead of nitrogen of the present invention.

EP 2092825, DE 102006059941, DE19607450 and EP 0864 567 describe triazine compounds as herbicide. The compounds of these documents differ in the account of the bicyclus.

EP 0545 149 describes 6-triflouromethyl-1,3,5-triazine compounds and their use as intermediates for crop protecting agents.

However, the herbicidal properties of the known triazine type compounds are not always entirely satisfactory.

Earlier filed EP 12189762.3 describes 2-(o-fluorophenyl) amino-6-aminotriazine compounds having herbicide activity.

Earlier filed EP 13176634.7 describes 2-(hetaryl)amino-6-aminotriazine compounds having herbicide activity.

Earlier filed EP 14162309.01 (unpublished) describes further (o-fluoro-2-phenyl)diaminotriazine compounds having herbicide activity.

It is therefore an object of the present invention to provide compounds having improved herbicidal action, in particular good herbicide activity at low application rates. Moreover, the herbicids should be sufficiently compatible with crop plants for commercial utilization.

These and further objects are achieved by diaminotriazine compounds of formula (I), defined below, and by their agriculturally suitable salts.

Accordingly, the present invention relates to
A diaminotriazine compound of formula (I)

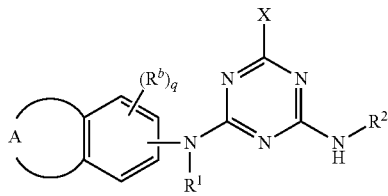

wherein
A is a fused saturated or unsaturated, 5-or 6-membered carbocycle or a fused saturated or unsaturated, 5-or 6-membered heterocycle having 1, 2 or 3 heteroatoms or heteroatom moieties, selected from O, S, $S(O)_p$, N or $NR^c$ as ring members,
where the carbocycle and the heterocycle are unsubstituted or carry 1, 2, 3 or 4 radicals $R^A$;
p is 0, 1 or 2
a is 0, 1, 2 or 3;
$R^A$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, it being possible that $R^A$ are identical or different, it being possible that two radicals $R^A$ which are bound at the same carbon atom may together be =O or =$NR^d$;
$R^b$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, for q=2 or 3 it being possible that $R^b$ are identical or different;
$R^c$ is selected from the group consisting of H, OH, $S(O)_2NH_2$, CN, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkoxy, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 16 aforementioned radicals are unsubstituted, partly or completely halogenated,
$R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;
$R^1$ is selected from the group consisting of H, OH, $S(O)_2NH_2$, CN, $C_3$-$C_6$-cycloalkyl, $C_3$-$C_6$-cycloalkoxy, $C_1$-$C_6$-alkyl, $C_2$-$C_6$-alkenyl, $C_2$-$C_6$-alkynyl, ($C_3$-$C_6$- cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 17 aforementioned radicals are unsubstituted, partly or completely halogenated, phenyl, phenyl-$C_1$-$C_6$-alkyl, phenylsulfonyl, phenylaminosulfonyl, phenylaminocarbonyl, phenyl($C_1$-$C_6$-alkyl)aminocarbonyl, phenylcarbonyl and phenoxycarbonyl, wherein phenyl in the last 8 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is selected from the group consisting of H, OH, $S(O)_2NH_2$, CN, $C_3$-$C_6$-cycloalkyl, $C_3$-$C_6$-cycloalkoxy, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 17 aforementioned radicals are unsubstituted, partly or completely halogenated, phenyl, phenylsulfonyl, phenylaminosulfonyl, phenyl-$C_1$-$C_6$ alkyl, phenoxy, phenylaminocarbonyl, phenyl($C_1$-$C_6$-alkyl)aminocarbonyl, phenylcarbonyl and phenoxycarbonyl, wherein phenyl in the last 8 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

X is a radical selected from the group consisting of
$CR^3R^4R^5$
phenyl, which is unsubstituted or carries 1, 2, 3, 4 or 5 radicals $R^{Ar}$ which are identical or different;
$NR^{3a}R^{3b}$,
$OR^{3c}$ and
$S(O)_kR^{3d}$ with k being 0, 1 or 2;
wherein
$R^3$ is selected from the group consisting of H, halogen, OH, CN, $C_1$-$C_6$-alkyl, ($C_1$-$C_6$-alkoxy)-$C_1$-$C_6$-alkyl, $C_3$-$C_6$-cycloalkyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, ($C_3$-$C_6$-cycloalkyl)-$C_1$-$C_4$-alkoxy, where the aliphatic and cycloaliphatic parts of the 9 aforementioned radicals are unsubstituted, partly or completely halogenated;
$R^4$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;
$R^5$ is selected from the group consisting of halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated;
$R^4$ and $R^5$ together with the carbon atom to which they are attached form a moiety selected from the group consisting of carbonyl, thiocarbonyl, $C_3$-$C_6$-cycloalkyl, $C_3$-$C_6$-cycloalkenyl, three- to six-membered saturated or partially unsaturated heterocyclyl, and the moiety $>C=CR^xR^y$, where $R^x$ and $R^y$ are hydrogen, $C_1$-$C_4$-alkyl or $C_1$-$C_4$-haloalkyl;

$R^{Ar}$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)carbonyloxy, $C_3$-$C_6$-cycloalkyl, $C_3$-$C_6$-cycloalkoxy, ($C_3$-$C_6$-cycloalkyl)-$C_1$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, $R^{3a}$, $R^{3b}$, $R^{3c}$ or $R^{3d}$ are independently of one another are selected from the group consisting of H, CN, $S(O)_2NH_2$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, ($C_3$-$C_6$-cycloalkyl)-$C_1$-$C_6$-alkyl, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 16 aforementioned radicals are unsubstituted, partly or completely halogenated, phenyl, phenylsulfonyl, phenyl-$C_1$-$C_6$ alkyl, phenylaminosulfonyl, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, or $R^{3a}$, $R^{3b}$ together with the nitrogen atom, to which they are bound, form an N-bound, mono—or bicyclic heterocyclic radical, which may have 1, 2, 3 or 4 further heteroatoms which are selected from N, O and S, which is unsubstituted or substituted by one or more identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, one of $R^{3a}$, $R^{3b}$ may also be OH, $C_1$-$C_6$-alkoxy, $C_3$-$C_6$-cycloalkoxy, ($C_3$-$C_6$-cycloalkyl)-$C_1$-$C_4$-alkoxy, $C_2$-$C_6$-alkenyloxy, $C_2$-$C_6$-alkynyloxy, ($C_1$-$C_6$-alkoxy)-$C_1$-$C_6$-alkoxy, where the aliphatic and cycloaliphatic parts of the 6 aforementioned radicals are unsubstituted, partly or completely halogenated, or phenoxy, which is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

including their agriculturally acceptable salts.

The following compounds:
4-(1,3-benzothiazol-4-ylamino)-6-[benzyl(methyl)amino]-1,3,5-triazin-2-ol, N-[4-(1,3-benzothiazol-4-ylamino)-6-[(1-methyl-1-phenyl-ethyl)amino]-1,3,5-triazin-2-yl]hydroxylamine, N4-(1,3-benzothiazol-4-yl)-6- methoxy-N2-(1-methyl-1-phenyl-ethyl)-1,3,5-triazine-2,4-diamine, 4-(1,3-benzothiazol-4-ylamino)-6-[(1-methyl-1-phenyl-ethyl)amino]-1,3,5-triazin-2-ol, 4-(1,3-benzothiazol-4-ylamino)-6-(benzylamino)-1,3,5-triazin-2-ol, 4-(1,3-benzothiazol-4-ylamino)-6-[benzyl(ethyl)amino]-1,3,5-triazin-2-ol, 4-(1,3-benzothiazol-4-ylamino)-6-[benzyl(isopropyl)amino]-1,3,5-triazin-2-ol, 4-[1,3-benzothiazol-4-yl(methyl)amino]-6-[(1-methyl-1-phenyl-ethyl)amino]-1,3,5-triazin-2-ol, 4-(1H-benzimidazol-4-ylamino)-6-[(1-methyl-1-phenyl-ethyl)amino]-1,3,5-triazin-2-ol, are known from N. Baindur, J. of Med. Chem. 48 (6), 2005, S.1717, which are used as VEGF R2 tyrosine kinase inhibitor, 6-methyl-N4-(1-naphthyl)-1,3,5-triazine-2,4-diamine, known from A. Rosowsky J. of Org. Chem. 29 (10), 1964, S. 2881 shows inhibitory activity against certain tumors, 4-(Benzothiazol-6-ylamino)-6-(N-ethylbenzylamino)-[1,3,5]triazin-2-ol, 4-(Benzothiazol-6-ylamino)-6-(benzylamino)-[1,3,5]triazin-2-ol, (S)-4-(Benzothiazol-6-ylamino)-6-(1-phenylethylamino)-[1,3,5]triazin-2-ol, (R)-4-(Benzothiazol-6-ylamino)-6-(1-phenylethylamino)-[1,3,5]triazin-2-ol, 4-(Benzothiazol-6-ylamino)-6-(1-methyl-1-phenylethylamino)-[1,3,5]triazin-2-ol, 4-(Benzothiazol-6-ylamino)-6-[methyl-(2-pyridyl-2-ylethyl)amino]-[1,3,5]triazin-2-ol, 4-(1-methyl-1-phenylethylamino)-6-(quinolin-6-ylamino)-[1,3,5]triazin-2-ol, N-[4-(Benzothiazol-6-ylamino)-6-(1-methyl-1-phenylethylamino)-[1,3,5]triazin-2-yl]-hydroxylamine, N-(Benzothiazol-6-yl)-N'-(1-methyl-1-phenyethyl)-[1,3,5]triazin-2,4,6-triamine, N-(Benzothiazol-6-yl)-6-methoxy-N'-(1-methyl-1-phenyethyl)-[1,3,5]triazin-2,4-diamine, N-(Benzothiazol-6-yl)-6-benzyloxy-N'-(1-methyl-1-phenyethyl)-[1,3,5]triazin-2,4-diamine, known from WO 2004/031184, which are used as kinase inhibitor, 6-(chloromethyl)-N4-(1-naphthyl)-1,3,5-triazine-2,4-diamine, known from WO 2011/140527, which is used as inhibitor for transitional endoplasmatic reticulum ATPase, 4-[6-[[4-(ethylamino)-6-methoxy-1,3,5-triazin-2-yl]amino]-3-methyl-benzofuran-2-yl]benzonitrile, 4-[6-[[4-(butylamino)-6-methoxy-1,3,5-triazin-2-yl]amino]-3-methyl-benzofuran-2-yl]benzonitrile, 4-[6-[[4,6-bis(butylamino)-1,3,5-triazin-2-yl]amino]-3-methyl-benzofuran-2-yl]benzonitrile and the following compounds of formula (A)

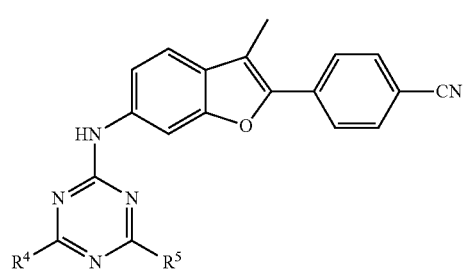

(A)

wherein $R^4$ and $R^5$ have the following meanings:

| $R^4$ | $R^5$ |
|---|---|
| $NH_2$ | $OCH_3$ |
| $NHC_2H_5$ | $OCH_3$ |
| $NHC_8H_{17}$ | $OCH_3$ |
| $N(C_4H_9)_2$ | $OCH_3$ |
| $NHC_2H_4OH$ | $OCH_3$ |
| $NHC_2H_4OC_2H_5$ | $OCH_3$ |
| $NHC_2H_4NH_4$ | $OCH_3$ |
| $NHCH_2$-phenyl | $OCH_3$ |
| NH-phenyl | $OCH_3$ |
| $OC_2H_5$ | $NH2$ |
| $OC_2H_5$ | $NHC_2H_5$ |
| $OC_2H_5$ | $NHC_8H_{17}$ |
| $OC_2H_5$ | $N(C_4H_9)_2$ |
| $OC_2H_5$ | $NHC_2H_4OH$ |
| $OC_2H_5$ | $NHC_2H_4OC_2H_5$ |
| $OC_2H_5$ | $NHC_2H_4NH_2$ |
| $OC_2H_5$ | $NHCH_2$-phenyl |
| $OC_2H_5$ | NH-phenyl | known from FR 2 235 126, compounds A, B, C, D, E, F, G, H, I, J, K, L, M, N, O P and Q

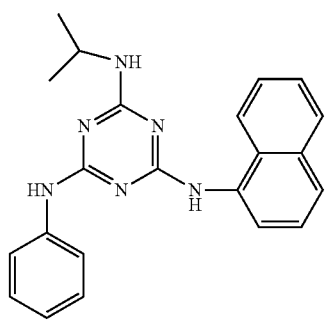

A

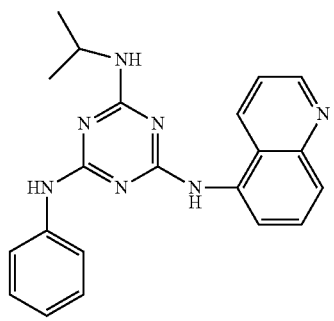

B

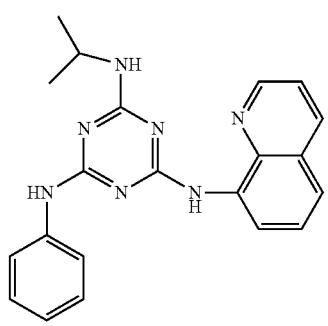

C

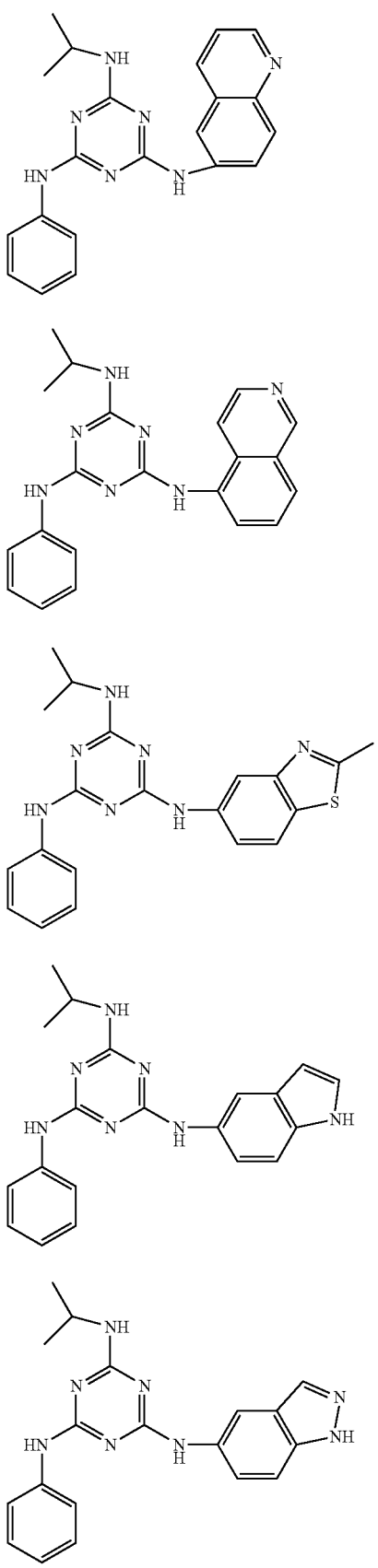
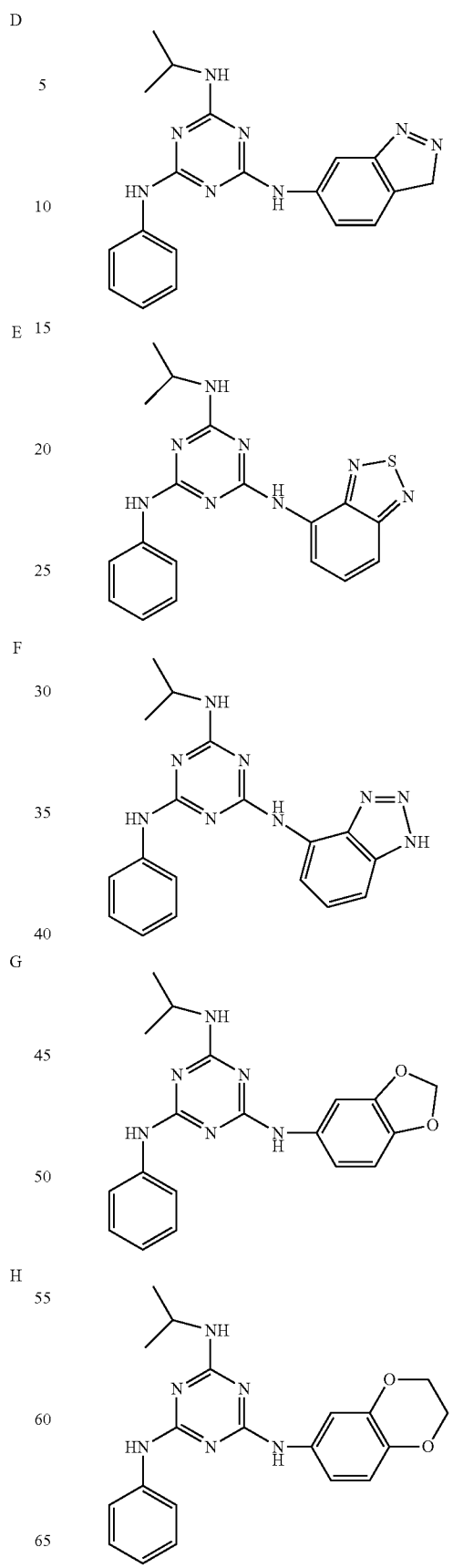

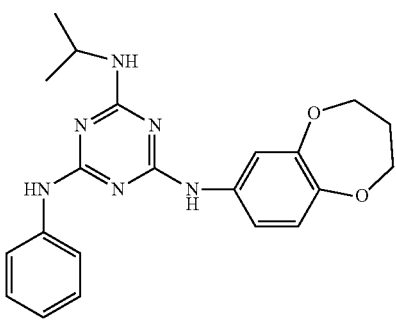

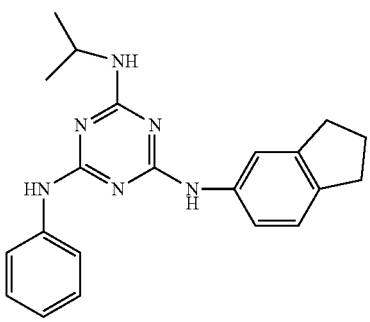

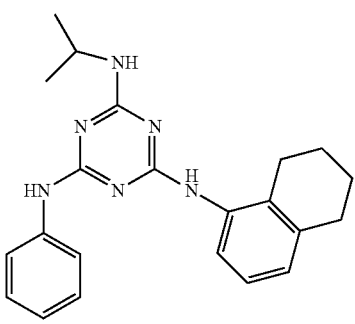

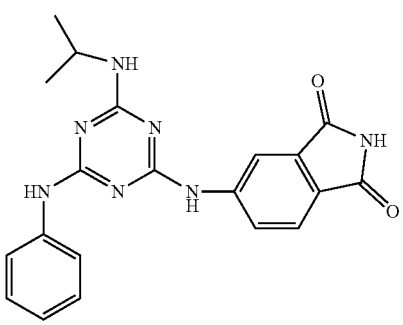

known from EP 1 479 397, which are used as anti-dementia agent, and the acceptable salts thereof are not part of the present invention.

The present invention also relates to diaminotriazine compounds of formula (I)

![Formula I structure]

wherein
A is a fused saturated or unsaturated, 5- or 6-membered carbocycle or a fused saturated or unsaturated, 5- or 6-membered heterocycle having 1, 2 or 3 heteroatoms or heteroatom moieties, selected from O, S, $S(O)_p$, N or $NR^c$ as ring members,
where the carbocycle and the heterocycle are unsubstituted or carry 1, 2, 3 or 4 radicals RA;

P is 1 or 2 a is 0, 1, 2 or 3;

$R^A$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, it being possible that $R^A$ are identical or different, it being possible that two radicals $R^A$ which are bound at the same carbon atom may together be =O or =$NR^d$;

$R^b$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, for q=2 or 3 it being possible that $R^b$ are identical or different;

$R^c$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated,
  phenyl, phenyl-$C_1$-$C_6$-alkyl, phenylsulfonyl, phenylaminosulfonyl, phenylaminocarbonyl, phenyl($C_1$-$C_6$-alkyl)aminocarbonyl, phenylcarbonyl and phenoxycarbonyl,
  wherein phenyl in the last 8 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated,
  phenyl, phenylsulfonyl, phenylaminosulfonyl, phenyl-$C_1$-$C_6$ alkyl, phenoxy, phenylaminocarbonyl, phenyl($C_1$-$C_6$-alkyl)aminocarbonyl, phenylcarbonyl and phenoxycarbonyl,
  wherein phenyl in the last 8 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

X is a radical selected from the group consisting of
  $CR^3R^4R^5$
  phenyl, which is unsubstituted or carries 1, 2, 3, 4 or 5 radicals $R^{Ar}$ which are identical or different;
  $NR^{3a}R^{3b}$,
  $OR^{3c}$ and
  $S(O)_kR^{3d}$ with k being 1, 2 or 3,
wherein
$R^3$ is selected from the group consisting of H, halogen, OH, CN, $C_1$-$C_6$-alkyl, ($C_1$-$C_6$-alkoxy)-$C_1$-$C_6$-alkyl, $C_3$-$C_6$-cycloalkyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, ($C_3$-$C_6$-cycloalkyl)-$C_1$-$C_4$-alkoxy, where the aliphatic and cycloaliphatic parts of the 9 aforementioned radicals are unsubstituted, partly or completely halogenated;

$R^4$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^5$ is selected from the group consisting of halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated;

$R^4$ and $R^5$ together with the carbon atom to which they are attached form a moiety selected from the group consisting of carbonyl, thiocarbonyl, $C_3$-$C_6$-cycloalkyl, $C_3$-$C_6$-cycloalkenyl, three- to six-membered saturated or partially unsaturated heterocyclyl, and the moiety $>C=CR^xR^y$, where $R^x$ and $R^y$ are hydrogen, $C_1$-$C_4$-alkyl or $C_1$-$C_4$-haloalkyl;

$R^{Ar}$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, $R^{3a}$, $R^{3b}$, $R^{3c}$ or $R^{3d}$ are independently of one another are selected from the group consisting of H, CN, $S(O)_2NH_2$, $C_1$-$C_6$-alkyl, $C_2$-$C_6$-alkenyl, $C_2$-$C_6$-alkynyl, $C_3$-$C_6$-cycloalkyl, ($C_3$-$C_6$-cycloalkyl)-$C_1$-$C_6$-alkyl, ($C_1$-$C_6$-alkoxy)-$C_1$-$C_6$-alkyl, ($C_1$-$C_6$-alkyl)-carbonyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated,
  phenyl, phenylsulfonyl, phenyl-$C_1$-$C_6$ alkyl, phenylaminosulfonyl, phenylcarbonyl and phenoxycarbonyl,
  wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, or $R^{3a}$, $R^{3b}$ together with the nitrogen atom, to which they are bound, form an N-bound, mono—or bicyclic heterocyclic radical, which may have 1, 2, 3 or 4 further heteroatoms which are selected from N, O and S, which is unsubstituted or substituted by one or more identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, one of $R^{3a}$, $R^{3b}$ may also be OH, $C_1$-$C_6$-alkoxy, $C_3$-$C_6$-cycloalkoxy, ($C_3$-$C_6$-cycloalkyl)-$C_1$-$C_4$-alkoxy, $C_2$-$C_6$-alkenyloxy, $C_2$-$C_6$-alkynyloxy, ($C_1$-$C_6$-alkoxy)-$C_1$-$C_6$-alkoxy, where the aliphatic and cycloaliphatic parts of the 6 aforementioned radicals are unsubstituted, partly or completely halogenated, or phenoxy, which is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

including their agriculturally acceptable salts.

The present invention also relates to agrochemical compositions comprising at least one diaminotriazine compound of formula (I) and at least one auxiliary customary for formulating crop protection agents.

The present invention also relates to the use of diaminotriazine compound of formula (I) as herbicides, i.e. for controlling unwanted and/or harmful vegetation or plants.

The present invention furthermore provides a method for controlling unwanted plants. The method includes allowing a herbicidally effective amount of at least one diaminotriazine compound of the formula (I) to act on the unwanted plants or vegetation, their seeds and/or their habitat. Application can be done before, during and/or after, preferably during and/or after, the emergence of the unwanted plants.

Moreover, the invention relates to processes for preparing diaminotriazine compound of formula (I) and to intermediates.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation", "unwanted vegetation", unwanted plants" and "harmful plants" are synonyms.

In the context of substituents, the term "one or more substitutents" means that the number of substituents is e.g. from 1 to 10, in particular 1, 2, 3, 4, 5, 6, 7 or 8.

If the diaminotriazine compounds of formula (I) as described herein is capable of forming geometrical isomers, for example E/Z isomers, the invention relates to both the pure isomers and mixtures thereof. Likewise, the invention relates to the use of the pure pure isomers and to the use of their mixtures and to compositions containing the pure isomers or mixtures thereof.

If the diaminotriazine compounds of formula (I) as described herein have one or more centres of chirality and, as a consequence, are present as enantiomers or diastereomers, the invention relates to both the pure enantiomers or diastereomers, and mixtures thereof. Likeweise, the invention relates to the use of the pure enantiomers or diastereomers and to the use of the mixtures thereof and to compositions containing the pure enantiomers or diastereomers or mixtures thereof.

If the diaminotriazine compounds of formula (I) as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, ($C_1$-$C_4$-alkoxy)-$C_1$-$C_4$-alkyl, hydroxy-($C_1$-$C_4$-alkoxy)-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethyl-ammonium (olamine salt), 2-(2-hydroxyeth-1-oxy)eth-1-ylammonium (diglycolamine salt), di(2-hydroxyeth-1-yl)-ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogen-phosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the variables, e.g. A, $R^A$, $R^b$, $R^c$, $R^d$, $R^1$, $R^2$, X, $R^3$, $R^4$, $R^5$, $R^{4r}$, $R^{3a}$, $R^{3b}$, $R^{3c}$, $R^{3d}$, $Y^1$, $Y^2$, Q are—like the term halogen—collective terms for individual enumerations of the individual group members. The term halogen denotes in each case fluorine, chlorine, bromine or iodine. All hydrocarbon chains, i.e. all alkyl, haloalkyl, alkenyl, alkynyl, alkoxy, alkenyloxy, alkynyloxy, alkylthio, alkylsulfinyl, alkylsulfonyl, (alkyl)amino, di(alkyl)amino, alkoxyalkyl, alkoxyalkoxy, (alky)carbonyl, (alkoxy)carbonyl chains can be straight-chain or branched, the prefix $C_n$-$C_m$ denoting in each case the possible number of carbon atoms in the group. The same applies to composed radicals, such as cycloalkylalkyl and phenylalkyl.

Examples of such meanings are:

$C_1$-$C_4$-alkyl and also the $C_1$-$C_4$-alkyl moieties of $C_1$-$C_4$-alkoxy, $C_1$-$C_4$-alkylthio, $C_1$-$C_4$-alkylsulfonyl, ($C_1$-$C_4$-alkyl)carbonyl, ($C_1$-$C_4$-alkyl)carbonyl, ($C_1$-$C_4$-alkoxy) carbonyl, ($C_1$-$C_4$-alkyl)carbonyloxy, $C_1$-$C_4$-alkyoxy-$C_1$-$C_4$-alkyl, $C_3$-$C_6$-cycloalkyl-$C_1$-$C_4$-alkyl, ($C_1$-$C_4$-alkylamino)carbonyl, di($C_1$-$C_4$-alkyl)aminocarbonyl, ($C_1$-$C_4$-alkylamino)sulfonyl, di($C_1$-$C_4$-alkyl)aminosulfonyl or phenyl-$C_1$-$C_4$-alkyl: for example $CH_3$, $C_2H_5$, n-propyl, $CH(CH_3)_2$, n-butyl, $CH(CH3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkoxy, $C_1$-$C_6$-alkylthio, $C_1$-$C_6$-alkylsulfonyl, ($C_1$-$C_6$-alkyl)carbonyl, ($C_1$-$C_6$-alkyl)carbonyl, ($C_1$-$C_6$-alkoxy) carbonyl, ($C_1$-$C_6$-alkyl)carbonyloxy, $C_1$-$C_6$-alkyoxy-$C_1$-$C_6$-alkyl, $C_3$-$C_6$-cycloalkyl-$C_1$-$C_6$-alkyl, phenyl ($C_1$-$C_6$-alkyl)aminocarbonyl, ($C_1$-$C_6$-alkylamino) carbonyl, di($C_1$-$C_6$-alkyl)aminocarbonyl, ($C_1$-$C_6$-alkylamino)sulfonyl, di($C_1$-$C_6$-alkyl)aminosulfonyl or phenyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_2$-$C_6$-alkenyl and also the $C_2$-$C_6$-alkenyl moieties of ($C_1$-$C_6$-alkoxy)-$C_2$-$C_6$-alkenyl: a linear or branched ethylenically unsaturated hydrocarbon group having 2 to 6 carbon atoms and a C=C-double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkynyl and also the $C_2$-$C_6$-alkynyl moieties of ($C_1$-$C_6$-alkoxy)-$C_2$-$C_6$-alkynyl: linear or branched unsaturated hydrocarbon group having 2 to 6 carbon atoms and containing at least one C≡C-triple bond, such as ethynyl, 1-propynyl, 2-propynyl (propargyl), 1-butynyl, 2-butynyl, 3-butynyl, 1-methyl-2-propynyl and the like;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl: monocyclic saturated hydrocarbons having 3 to 6 ring members, such as cyclopropyl, cyclobutyl, cyclopentyl and cyclohexyl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of ($C_1$-$C_6$-alkoxy)carbonyl, ($C_1$-$C_6$-alkoxy)sulfonyl, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy2-fluoroethoxy, 2-chloroethoxy, 2-bromoethxoy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloro-propoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 4-fluorobutoxy, nonafluorobutoxy, 1,1,2,2,-tetrafluoroethoxy and 1-trifluoromethyl-1,2,2,2-tetrafluoroethoxy;

$C_1$-$C_6$-haloalkoxy: $C_1$-$C_4$-alkoxy as mentioned above: $C_1$-$C_4$-haloalkoxy as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_2$-$C_6$-alkenyloxy: $C_2$-$C_6$-alkenyl as defined above, which is bound via an oxygen atom, such as ethenyloxy (vinyloxy), 1-propenyloxy, 2-propenyloxy (allyloxy), 1-butenyloxy, 2-butenyloxy, 3-butenyloxy 1-methyl-2-propenyloxy and the like;

$C_2$-$C_6$-alkynyloxy: $C_2$-$C_6$-alkynyl as defined above, which is bound via an oxygen atom, such as ethynyloxy, 1-propynyl, 2-propynyloxy (propargyloxy), 1-butynyloxy, 2-butynyloxy, 3-butynyloxy 1-methyl-2-propynyloxy and the like;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—): z.B. methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentyl-sulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-di-methylpropylsulfonyl, 1,2-di-methylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethyl-propylsulfonyl, 1,2,2-trimethylpropylsulfonyl, 1-ethyl-1-methylpropylsulfonyl and 1-ethyl-2-methylpropylsulfonyl;

($C_1$-$C_4$-alkyl)amino and also the ($C_1$-$C_4$-alkylamino) moieties of ($C_1$-$C_4$-alkylamino)carbonyl or ($C_1$-$C_4$-alkylamino)sulfonyl: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino and also the ($C_1$-$C_6$-alkylamino) moieties of ($C_1$-$C_6$-alkylamino)carbonyl, phenyl($C_1$-$C_6$-alkyl)aminocarbonyl or ($C_1$-$C_6$-alkylamino)sulfonyl: ($C_1$-$C_4$-alkyl)amino as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino and also the di($C_1$-$C_4$-alkylamino) moieties of di($C_1$-$C_4$-alkylamino)carbonyl or di($C_1$-$C_4$-alkylamino)sulfonyl: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethypamino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethyl-ethyl)-N-(2-methylpropyl)amino;

di($C_1$-$C_6$-alkyl)amino and also the di($C_1$-$C_6$-alkylamino) moieties of di($C_1$-$C_6$-alkylamino)carbonyl or di($C_1$-$C_6$-alkylamino)sulfonyl: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methyl-butyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl) amino, N-methyl-N-(1-methylpentyl)amino, N-methyl-N-(2-methylpentyl)amino, N-methyl-N-(3-methylpentyl)amino, N-methyl-N-(4-methylpentyl) amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl) amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl) amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl) amino, N-ethyl-N-(2,3-dimethylbutyl)amino, N-ethyl-N-(3,3-dimethylbutyl)amino, N-ethyl-N-(1- ethylbutyl)-amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-di-pentylamino, N-propyl-N-hexylamino, N-butyl-N-hexylamino, N-pentyl-N-hexylamino or N,N-dihexylamino;

$C_3$-$C_6$-cycloalkyl and also the $C_3$-$C_6$-cycloalkyl moieties of ($C_3$-$C_6$-cycloalkyl)-carbonyl, ($C_3$-$C_6$-cycloalkyl)-$C_1$-$C_6$-alkyl, ($C_3$-$C_6$-cycloalkyl)carbonyl and ($C_3$-$C_6$-cycloalkyl)-$C_1$-$C_6$-alkoxy: a cycloaliphatic radical having 3 to 6 carbon atoms, such as cyclopropyl, cyclobutyl, cyclopentyl and cyclohexyl;

$C_3$-$C_6$-cycloalkoxy: a cycloaliphatic radical having 3 to 6 carbon atoms and bound via an oxygen atom, such as cyclopropyloxy, cyclobutyloxy, cyclopentyloxy and cyclohexyloxy;

($C_3$-$C_6$-cycloalkyl)-$C_1$-$C_6$-alkyl: $C_1$-$C_6$-alkyl, in particular $C_1$-$C_4$-alkyl as defined above, such as methyl or ethyl, wherein 1 hydrogen atom is replaced by $C_3$-$C_6$-cycloalkyl as defined above, examples including cyclopropylmethyl ($CH_2$-cyclopropyl), cyclobutyl methyl, cyclopentylmethyl, cycloexylmethyl, 1-cyclopropylethyl (CH($CH_3$)-cyclopropyl), 1-cyclobutylethyl, 1-cyclopentylethyl, 1-cycloexylethyl, 2-cyclopropylethyl ($CH_2CH_2$-cyclopropyl), 2-cyclobutylethyl, 2-cyclopentylethyl or 2-cycloexylethyl;

($C_3$-$C_6$-cycloalkyl)-$C_1$-$C_6$-alkoxy: $C_1$-$C_6$-alkoxy, in particular $C_1$-$C_4$-alkoxy as defined above, such as methoxy or ethoxy, wherein 1 hydrogen atom is replaced by $C_3$-$C_6$-cycloalkyl as defined above, examples including cyclopropylmethoxy (O$CH_2$-cyclopropyl), cyclobutyl methoxy, cyclopentylmethoxy, cycloexylmethoxy, 1-cyclopropylethoxy (O—CH($CH_3$)-cyclopropyl), 1-cyclobutylethoxy, 1-cyclopentylethoxy, 1-cycloexylethoxy, 2-cyclopropylethoxy (O$CH_2CH_2$)-cyclopropyl), 2-cyclobutylethoxy, 2-cyclopentylethoxy and 2-cycloexylethoxy;

($C_1$-$C_6$-alkoxy)-$C_1$-$C_6$-alkyl: $C_1$-$C_6$-alkyl, in particular $C_1$-$C_4$-alkyl as defined above, such as methyl, ethyl or isopropyl, wherein 1 hydrogen atom is replaced by $C_1$-$C_6$-alkoxy as defined above, examples including methoxymethyl, ethoxymethyl, n-propoxymethyl, butoxymethyl, 1-methoxyethyl, 1-ethoxyethyl, 1-(n-propoxy)ethyl, 1-butoxyethyl, 2-methoxyethyl, 2-ethoxyethyl, 2-(n-propoxy)ethyl, 2-butoxyethyl, 2-methoxypropyl, 2-ethoxypropyl, 2-(n-propoxy)propyl, 2-butoxypropyl;

($C_1$-$C_6$-alkoxy)-$C_1$-$C_6$-alkoxy: $C_1$-$C_6$-alkoxy, in particular $C_1$-$C_4$-alkoxy as defined above, such as methoxy or ethoxy, wherein 1 hydrogen atom is replaced by $C_1$-$C_6$-alkoxy as defined above, examples including methoxymethoxy, ethoxymethoxy, n-propoxymethoxy, butoxymethoxy, 2-methoxyethoxy, 2-ethoxyethoxy, 2-(n-propoxy)ethoxy and 2-butoxyethoxy;

($C_1$-$C_6$-alkoxy)-$C_2$-$C_6$-alkenyl: $C_2$-$C_6$-alkenyl, in particular $C_2$-$C_4$-alkenyl as defined above, such as ethenyl, propenyl, 1-butenyl or 2-butenyl, wherein 1 hydrogen atom is replaced by $C_1$-$C_6$-alkoxy as defined above;

($C_1$-$C_6$-alkoxy)-$C_2$-$C_6$-alkynyl: $C_2$-$C_6$-alkynyl, in particular $C_2$-$C_4$-alkynyl as defined above, such as ethynyl, propynyl or 2-butynyl, wherein 1 hydrogen atom is replaced by $C_1$-$C_6$-alkoxy as defined above;

($C_1$-$C_6$-alkyl)carbonyl: $C_1$-$C_6$-alkyl as mentioned above, which is bound to the remainder of the molecule by a carbonyl group;

($C_1$-$C_6$-alkoxy)carbonyl: $C_1$-$C_6$-alkyloxy as mentioned above, which is bound to the remainder of the molecule by a carbonyl group;

($C_1$-$C_6$-alkylamino)carbonyl: ($C_1$-$C_6$-alkyl)amino as mentioned above, which is bound to the remainder of the molecule by a carbonyl group;

($C_1$-$C_6$-alkylamino)sulfonyl: ($C_1$-$C_6$-alkyl)amino as mentioned above, which is bound to the remainder of the molecule by a sulfonyl group;

di($C_1$-$C_6$-alkylamino)carbonyl: di($C_1$-$C_6$-alkyl)amino as mentioned above, which is bound to the remainder of the molecule by a carbonyl group;

di($C_1$-$C_6$-alkylamino)sulfonyl: di($C_1$-$C_6$-alkyl)amino as mentioned above, which is bound to the remainder of the molecule by a sulfonyl group;

phenyl-$C_1$-$C_6$-alkyl: $C_1$-$C_6$-alkyl, in particular $C_1$-$C_4$-alkyl as defined above, such as methyl or ethyl, wherein 1 hydrogen atom is replaced by phenyl, examples including benzyl, 1-phenylethyl, 2-phenylethyl, 1-phenylpropyl, 2-phenylpropyl, 1-phenyl-1-methylethyl etc.;

three- to six-membered heterocyclyl: monocyclic saturated or partially unsaturated hydrocarbon having three to six ring members as mentioned above which, in addition to carbon atoms, contains one or two heteroatoms selected from O, S and N;

for example saturated heterocycles such as 2-oxiranyl, 2-oxetanyl, 3-oxetanyl, 2-aziridinyl, 3-thietanyl, 1-azetidinyl, 2-azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydro-thiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, tetrahydro-1,3-oxazin-2-yl, tetrahydro-1,3-oxazin-6-yl, 2-morpholinyl, 3-morpholinyl or 4-morpholinyl, for example 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl;

partially unsaturated heterocycles such as 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-di-hydroimidazol-3-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 5,6-dihydro-4H-1,3-oxazin-2-yl;

5- and 6-membered hetaryl which conatins 1, 2 or 3 heteroatoms selected from O, S and N:

5-membered or 6-membered heteroaromatic radical, which besides carbon atoms contains 1, 2 or 3 heteroatoms as ring members, which are selected from O, S and N e.g. 1, 2 or 3 nitrogen atoms or 1 oxygen or sulfur atom and optionally 1 or 2 nitogen atoms:

in particular:

five-membered monocyclic heteroaryl which contains one to three heteroatoms selected from O, S and N:

for example 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl etc.;

six-membered monocyclic heteroaryl contains one to three nitrogen atoms as ring members:

for example 2-pyridinyl (2-pyridyl), 3-pyridinyl (3-pyridyl), 4-pyridinyl (4-pyridyl), 1-oxopyridin-2-yl, 1-oxopyridin-3-yl, 1-oxopyridin-4-yl,3-pyridazinyl, 4-pyridazinyl, 2-pyrimidinyl, 4-pyrimidinyl, 5-pyrimidinyl, 2-pyrazinyl and 1,2,3-triazinyl, 1,2,4-triazinyl and 1,3,5-triazinyl.

The preferred embodiments of the invention mentioned herein below have to be understood as being preferred either independently from each other or in combination with one another. Particular groups of embodiments of the invention relate to those diaminotriazines of formula (I), wherein the variables $R^1$, $R^2$, A, X, $R^b$ and q, either independently of one another or in combination with one another, have the following meanings:

Particular groups of embodiments relate to the diaminotriazine compounds of formula (I), wherein A is a fused saturated or unsaturated 5- or 6-membered heterocycle having 1, 2 or 3 heteroatoms or heteroatom moieties, selected from O, S, $S(O)_p$, N or $NR^c$ as ring members,where the heterocycle are unsubstituted or carry 1, 2, 3 or 4 radicals $R^A$ as defined above, and and where $R^c$ has the meaning as defined above.

In this context $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$NR^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that that two radicals $R^A$ which are bound at the same carbon atom may together be =O or S, likewise even more particularly selected from the group consisting of F, Cl, methyl, methoxy and that that two radicals $R^A$ which are bound at the same carbon atom may together be =O or S.

More particular

A is a fused saturated 5- or 6-membered heterocycle having 1, 2 or 3 heteroatoms or heteroatom moieties, selected from O, S, $S(O)_p$, N or $NR^c$ in particular O or S as ring members, where the heterocycle are unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =N $R^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated; more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that two radicals $R^A$ which are bound at the same carbon atom may together be =O or S, likewise even more particularly selected from the group consisting of F, Cl, methyl, methoxy and that that two radicals $R^A$ which are bound at the same carbon atom may together be =O or S.

Likewise more particular

A is a fused saturated 5- or 6-membered heterocycle having 1, 2 or 3 heteroatoms or heteroatom moieties, selected from O, S, $S(O)_p$, N or $NR^c$ in particular O, N or $NR^c$ as ring members, where the heterocycle are unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =N $R^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, Br, methyl and that two radicals $R^A$ which are bound at the same carbon atom may together be =O or S.

Likewise more particular

A is a fused unsaturated 5- or 6-membered heterocycle having 1, 2 or 3 heteroatoms or heteroatom moieties, selected from O, S, $S(O)_p$, N or $NR^c$ in particular O or S as ring members, where the heterocycle are unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =N $R^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated; more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, Br, methyl and that two radicals $R^A$ which are bound at the same carbon atom may together be =O or S.

Likewise more particular

A is a fused unsaturated 5- or 6-membered heterocycle having 1, 2 or 3 heteroatoms or heteroatom moieties, selected from O, S, $S(O)_p$, N or $NR^c$ in particular O, N or $NR^c$ as ring members, where the heterocycle are unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =N $R^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, Br, methyl and that two radicals $R^A$ which are bound at the same carbon atom may together be =O or S.

Irrespective of its occurrence $R^c$ is particulary selected from the group consisting of H, $S(O)_2NH_2$, CN, $C_1$-$C_4$-alkyl, $C_1$-$C_4$-haloalkyl, $C_2$-$C_4$-alkenyl, $C_2$-$C_4$-alkynyl. More particular $R^c$ is selected from the group consisting of H, $S(O)_2NH_2$, CN, methyl, ethyl.

A further particular group of embodiements relates to the diaminotriazine compounds of formula (I), wherein A is a fused saturated or unsaturated, 5-, 6-membered carbocycle, which is unsubstituted or carry 1, 2, 3 or 4 radicals $R^A$ as defined above.

In this context $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$NR^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated; more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, Br, methyl and that two radicals $R^A$ which are bound at the same carbon atom may together be =O or S.

More particular

A is a fused saturated 5- or 6-membered carbocycle, which is unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =N $R^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated; more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, Br, methyl and that two radicals $R^A$ which are bound at the same carbon atom may together be =O or S.

Further particular groups of embodiment relate to the diaminotriazine compound of formula (I), wherein $R^b$ is defined above.

In particular $R^b$ is selected from the group consisting of halogen, CN, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, where the aliphatic parts of the 6 aforementioned radicals are unsubstituted, partly or completely halogenated and for q=2 or 3 it being possible that $R^b$ are identical or different.

More particular $R^b$ is selected halogen, CN, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy, $C_1$-$C_4$-haloalkoxy, $C_2$-$C_4$-alkenyloxy, $C_2$-$C_4$-alkynyloxy.

Even more particular $R^b$ is selected F, Cl, Br, methyl.

A preferred embodiment relate to the diaminotriazine compound of formula (I), wherein

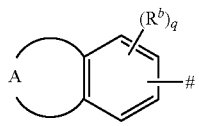

is represented by the moiety

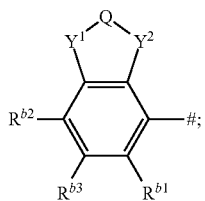

wherein $R^{b1}$, $R^{b2}$ and $R^{b3}$ are identical or different and are hydrogen or have one of the meanings of $R^b$ as defined above;

$Y^1$, $Y^2$ independently of each other are O, S or $NR^c$, wherein $R^c$ is as defined above and preferrably selected from the group consisting of of H, $S(O)_2NH_2$, CN, $C_1$-$C_4$-alkyl, $C_1$-$C_4$-haloalkyl, $C_2$-$C_4$-alkenyl, $C_2$-$C_4$-alkynyl. More particular $R^c$ is selected from the group consisting of H, $S(O)_2NH_2$, CN, methyl, ethyl;

Q is $CR^{A1}R^{A2}$ or $CR^{A3}R^{A4}$—$CR^{A5}R^{A6}$ wherein $R^{A1}$, $R^{A2}$, $R^{A3}$, $R^{A4}$, $R^{A5}$, $R^{A6}$ are identical or different and are hydrogen or have one of the meanings given for $R^A$ defined above;

A is a fused saturated or unsaturated 5- or 6-membered heterocycle having 1, 2 or 3 heteroatoms or heteroatom moieties, selected from O, S, $S(O)_p$, N or $NR^c$ as ring members,where the heterocycle are unsubstituted or carry 1, 2, 3 or 4 radicals $R^A$ as defined above, preferrably selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$NR^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that two radicals $R^A$ which are bound at the same carbon atom may together be =O or S.

More particular

A is a fused saturated 5- or 6-membered heterocycle having 1, 2 or 3 heteroatoms or heteroatom moieties, selected from O, S, $S(O)_p$, N or $NR^c$ in particular O or S as ring members, where the heterocycle are unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$NR^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated; more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that two radicals $R^A$ which are bound at the same carbon atom may together be =O or S and where $R^c$ has the meaning as defined above.

Likewise more particular

A is a fused unsaturated 5- or 6-membered heterocycle having 1, 2 or 3 heteroatoms or heteroatom moieties, selected from O, S, S(O)$_p$, N or NR$^c$ in particular O or S as ring members, where the heterocycle are unsubstituted or carry 1, 2, 3 or 4 radicals R$^A$ as defined above, and where R$^A$ is in particular selected from the group consisting of halogen, CN, C$_1$-C$_6$-alkyl, C$_1$-C$_6$-alkoxy, C$_1$-C$_6$-haloalkyl, C$_1$-C$_6$-haloalkoxy, C$_3$-C$_6$-cycloalkyl, (C$_3$-C$_6$-cycloalkyl)-C$_1$-C$_4$-alkoxy, C$_2$-C$_6$-alkenyl, C$_2$-C$_6$-alkynyl, C$_2$-C$_6$-alkenyloxy and C$_2$-C$_6$-alkynyloxy, and where the cycloaliphatic parts of the last 2 mentioned radicals may carry 1, 2, 3, 4, 5 or 6 methyl groups, and it being possible that R$^A$ are identical or different, it being possible that two radicals R$^A$ which are bound at the same carbon atom may together be =O, S, or =NR$^d$; wherein R$^d$ is selected from the group consisting of H, CN, C$_1$-C$_6$-alkyl, C$_2$-C$_6$-alkenyl, C$_2$-C$_6$-alkynyl, (C$_3$-C$_6$-cycloalkyl)-C$_1$-C$_4$-alkyl, C$_1$-C$_6$-alkoxy, C$_2$-C$_6$-alkenyloxy, C$_2$-C$_6$-alkynyloxy, (C$_1$-C$_6$-alkoxy)-C$_1$-C$_6$-alkyl, where the aliphatic and cycloaliphatic parts of the 8 aforementioned radicals are unsubstituted, partly or completely halogenated; more particular selected from the group consisting of halogen, CN, C$_1$-C$_4$-alkyl, C$_1$-C$_4$-alkoxy, C$_1$-C$_4$-haloalkyl, C$_1$-C$_4$-haloalkoxy and it being possible that R$^A$ are identical or different and that two radicals R$^A$ which are bound at the same carbon atom may together be =O, S, even more particularly selected from the group consisting of F, Cl, methyl and that two radicals R$^A$ which are bound at the same carbon atom may together be =O or S and where R$^c$ has the meaning as defined above.

Likewise more particular

A is a fused saturated 5- or 6-membered heterocycle having 1, 2 or 3 heteroatoms or heteroatom moieties, selected from O, S, S(O)$_p$, N or NR$^c$ in particular O, N or NR$^c$ as ring members, where the heterocycle are unsubstituted or carry 1, 2, 3 or 4 radicals R$^A$ as defined above, and where R$^A$ is in particular selected from the group consisting of halogen, CN, C$_1$-C$_6$-alkyl, C$_1$-C$_6$-haloalkyl, C$_1$-C$_6$-haloalkoxy, C$_3$-C$_6$-cycloalkyl, (C$_3$-C$_6$-cycloalkyl)-C$_1$-C$_4$-alkoxy, C$_2$-C$_6$-alkenyl, C$_2$-C$_6$-alkynyl, C$_2$-C$_6$-alkenyloxy and C$_2$-C$_6$-alkynyloxy, and where the cycloaliphatic parts of the last 2 mentioned radicals may carry 1, 2, 3, 4, 5 or 6 methyl groups, and it being possible that R$^A$ are identical or different, it being possible that two radicals R$^A$ which are bound at the same carbon atom may together be =O, S, or =NR$^d$; wherein R$^d$ is selected from the group consisting of H, CN, C$_1$-C$_6$-alkyl, C$_2$-C$_6$-alkenyl, C$_2$-C$_6$-alkynyl, (C$_3$-C$_6$-cycloalkyl)-C$_1$-C$_4$-alkyl, C$_1$-C$_6$-alkoxy, C$_2$-C$_6$-alkenyloxy, C$_2$-C$_6$-alkynyloxy, (C$_1$-C$_6$-alkoxy)-C$_1$-C$_6$-alkyl, where the aliphatic and cycloaliphatic parts of the 8 aforementioned radicals are unsubstituted, partly or completely halogenated; more particular selected from the group consisting of halogen, CN, C$_1$-C$_4$-alkyl, C$_1$-C$_4$-alkoxy, C$_1$-C$_4$-haloalkyl, C$_1$-C$_4$-haloalkoxy and it being possible that R$^A$ are identical or different and that two radicals R$^A$ which are bound at the same carbon atom may together be =O, S, even more particularly selected from the group consisting of F, Cl, methyl and that two radicals R$^A$ which are bound at the same carbon atom may together be =O or S and where R$^c$ has the meaning as defined above.

Likewise more particular

A is a fused unsaturated 5- or 6-membered heterocycle having 1, 2 or 3 heteroatoms or heteroatom moieties, selected from O, S, S(O)$_p$, N or NR$^c$ in particular O, N or NR$^c$ as ring members, where the heterocycle are unsubstituted or carry 1, 2, 3 or 4 radicals R$^A$ as defined above, and where R$^A$ is in particular selected from the group consisting of halogen, CN, C$_1$-C$_6$-alkyl, C$_1$-C$_6$-alkoxy, C$_1$-C$_6$-haloalkyl, C$_1$-C$_6$-haloalkoxy, C$_3$-C$_6$-cycloalkyl, (C$_3$-C$_6$-cycloalkyl)-C$_1$-C$_4$-alkoxy, C$_2$-C$_6$-alkenyl, C$_2$-C$_6$-alkynyl, C$_2$-C$_6$-alkenyloxy and C$_2$-C$_6$-alkynyloxy, and where the cycloaliphatic parts of the last 2 mentioned radicals may carry 1, 2, 3, 4, 5 or 6 methyl groups, and it being possible that R$^A$ are identical or different, it being possible that two radicals R$^A$ which are bound at the same carbon atom may together be =O, S, or =NR$^d$; wherein R$^d$ is selected from the group consisting of H, CN, C$_1$-C$_6$-alkyl, C$_2$-C$_6$-alkenyl, C$_2$-C$_6$-alkynyl, (C$_3$-C$_6$-cycloalkyl)-C$_1$-C$_4$-alkyl, C$_1$-C$_6$-alkoxy, C$_2$-C$_6$-alkenyloxy, C$_2$-C$_6$-alkynyloxy, (C$_1$-C$_6$-alkoxy)-C$_1$-C$_6$-alkyl, where the aliphatic and cycloaliphatic parts of the 8 aforementioned radicals are unsubstituted, partly or completely halogenated; more particular selected from the group consisting of halogen, CN, C$_1$-C$_4$-alkyl, C$_1$-C$_4$-alkoxy, C$_1$-C$_4$-haloalkyl, C$_1$-C$_4$-haloalkoxy and it being possible that R$^A$ are identical or different and that two radicals R$^A$ which are bound at the same carbon atom may together be =O, S, even more particularly selected from the group consisting of F, Cl, methyl and that two radicals R$^A$ which are bound at the same carbon atom may together be =O or S and where R$^c$ has the meaning as defined above.

In particular

Y$^1$ is O, S, NR$^c$, wherein R$^c$ has the meaning as defined above,

Y$^2$ is O, S, NR$^c$, wherein R$^c$ has the meaning as defined above,

Q is CR$^{41}$R$^{42}$, wherein R$^{41}$, R$^{42}$ are identical or different and are hydrogen or have one of the meanings of R$^A$ defined above, R$^{b1}$ is hydrogen or has one of the meanings of R$^b$ as defined above, R$^{b2}$ are hydrogen and one of the meanings of R$^b$ as defined above, R$^{b3}$ is hydrogen or has one of the meanings of R$^b$ as defined above.

More particular

Y$^1$ is O, S,

Y$^2$ is O, S,

Q is CR$^{41}$R$^{42}$, wherein R$^{41}$, R$^{42}$ are identical or different and are hydrogen, halogen, C$_1$-C$_4$-alkyl, C$_1$-C$_4$-haloalkyl, C$_1$-C$_4$-alkoxy, C$_1$-C$_4$-haloalkoxy, R$^{b1}$ are hydrogen, CN, halogen or C$_1$-C$_4$-alkyl, in particular hydrogen, CN, methyl, fluorine, chlorine or bromine, R$^{b2}$ are hydrogen or halogen, in particular hydrogen, fluorine, chlorine or bromine, R$^{b3}$ are hydrogen, CN halogen or C$_1$-C$_4$-alkyl in particular hydrogen, CN, methyl, fluorine, chlorine or bromine.

Even more particular

Y$^1$ and Y$^2$ are each O, S,

Q CR$^{41}$R$^{42}$, wherein R$^{41}$ and R$^{42}$ are identical or different and are hydrogen, F, Cl, methyl, or R$^{41}$ and R$^{42}$ together may be =O, R$^{b1}$ are hydrogen, halogen, such as F, Cl, Br, methyl, CN, R$^{b2}$ are hydrogen, F, Cl, Br, R$^{b3}$ are hydrogen, F, Cl, Br.

Likewise in particular

Y$^1$ is O, S, NR$^c$, wherein R$^c$ has the meaning as defined above, $Y^2$ is O, S, $NR^c$, wherein $R^c$ has the meaning as defined above, Q is $CR^{43}R^{44}$—$CR^{45}R^{46}$, wherein $R^{43}$, $R^{44}$, $R^{45}$, $R^{46}$ are identical or different and are hydrogen or have one of the meanings of $R^A$ defined above, $R^{b1}$ are hydrogen and one of the meanings of $R^b$ as defined above, $R^{b2}$ are hydrogen and one of the meanings of $R^b$ as defined above, $R^{b3}$ are hydrogen and one of the meanings of $R^b$ as defined above.

More particular $Y^1$ is O, S, $Y^2$ is O, S,

Q is $CR^{43}R^{44}$—$CR^{45}R^{46}$, wherein $R^{43}$, $R^{44}$, $R^{45}$, $R^{46}$ are identical or different and are hydrogen, halogen, $C_1$-$C_4$-alkyl, $C_1$-$C_4$-haloalkyl, $C_1$-$C_4$-alkoxy, $C_1$-$C_4$-haloalkoxy, $R^{b1}$ are hydrogen, CN, halogen or $C_1$-$C_4$-alkyl, in particular hydrogen, CN, methyl, fluorine, chlorine or bromine, $R^{b2}$ are hydrogen or halogen, in particular hydrogen, flourine or bromine, $R^{b3}$ are hydrogen, CN halogen or $C_1$-$C_4$-alkyl in particular hydrogen, CN, methyl, fluorine, chlorine or bromine.

Even more particular $Y^1$ and $Y^2$ are each O, S,

Q $CR^{43}R^{44}$—$CR^{45}R^{46}$, wherein $R^{43}$, $R^{44}$, $R^{45}$, $R^{46}$ are identical or different and are hydrogen, F, Cl, methyl, $R^{b1}$ are hydrogen, halogen, such as F, Cl, Br, methyl, CN, $R^{b2}$ are hydrogen, F, Cl, Br, $R^{b3}$ are hydrogen, F, Cl, Br.

Likewise in particular $Y^1$ is O, N or $NR^C$, wherein $R^c$ has the meaning as defined above, $Y^2$ is O, N or $NR^C$, wherein $R^c$ has the meaning as defined above, Q is $CR^{41}$, $R^{42}$, wherein $R^{41}$, $R^{42}$ are identical or different and are hydrogen, halogen, $C_1$-$C_4$-alkyl, $C_1$-$C_4$-haloalkyl, $C_1$-$C_4$-alkoxy, $C_1$-$C_4$-haloalkoxy, $R^{b1}$ are hydrogen, CN, halogen or $C_1$-$C_4$-alkyl, in particular hydrogen, CN, methyl, flourine or bromine, $R^{b2}$ are hydrogen or halogen, in particular hydrogen, flourine or bromine, $R^{b3}$ are hydrogen, CN halogen or $C_1$-$C_4$-alkyl in particular hydrogen, CN, methyl, flourine or bromine.

Likewise a further preferred embodiment relate to the diaminotriazine compound of formula (I), wherein

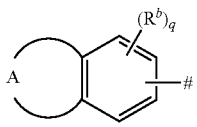

is represented by the moiety

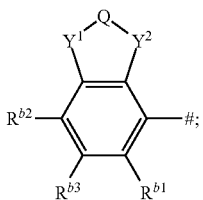

wherein $R^{b1}$, $R^{b2}$ and $R^{b3}$ are identical or different and are hydrogen or have one of the meanings of $R^b$ as defined above;

$Y^1$, $Y^2$ independently of each other are $CR^{A'}$, $R^{A''}$, wherein $R^{A'}$, $R^{A''}$ are identical or different and are hydrogen or have one of the meanings given for $R^A$ defined above;

Q is $CR^{41}R^{42}$ or $CR^{43}R^{44}$—$CR^{45}R^{46}$ wherein $R^{41}$, $R^{42}$, $R^{43}$, $R^{44}$, $R^{45}$, $R^{46}$ are identical or different and are hydrogen or have one of the meanings given for $R^A$ defined above;

A is a fused saturated or unsaturated 5- or 6-membered carbocycle which is unsubstituted or carry 1, 2, 3 or 4 radicals $R^A$ as defined above, preferably selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$NR^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that two radicals $R^A$ which are bound at the same carbon atom may together be =O or S.

More particular

A is a fused saturated 5- or 6-membered carbocycle which is unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$NR^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated; more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that two radicals $R^A$ which are bound at the same carbon atom may together be =O or S.

In particular
- $Y^1$ is $CR^{A'}R^{A''}$, wherein $R^{A'}$ and $R^{A''}$ are identical or different having the meaning as defined above,
- $Y^2$ is $CR^{A'}R^{A''}$, wherein $R^{A'}$ and $R^{A''}$ are identical or different having the meaning as defined above,
- Q is $CR^{A1}R^{A2}$, wherein $R^{A1}$, $R^{A1}$ are identical or different and are hydrogen or have one of the meanings of $R^A$ defined above,
- $R^{b1}$ are hydrogen and one of the meanings of $R^b$ as defined above,
- $R^{b2}$ are hydrogen and one of the meanings of $R^b$ as defined above,
- $R^{b3}$ are hydrogen and one of the meanings of $R^b$ as defined above.

More particular
- $Y^1$ is $CR^{A'}R^{A''}$, wherein $R^{A'}$, $R^{A''}$ are identical or different and are hydrogen or have one of the meanings given for $R^A$
- $Y^2$ is $CR^{A'}R^{A''}$, wherein $R^{A'}$, $R^{A''}$ are identical or different and are hydrogen or have one of the meanings given for $R^A$
- Q is $CR^{A1}R^{A2}$, wherein $R^{A1}$, $R^{A2}$ are identical or different and are hydrogen, halogen, $C_1$-$C_4$-alkyl, $C_1$-$C_4$-haloalkyl, $C_1$-$C_4$-alkoxy, $C_1$-$C_4$-haloalkoxy,
- $R^{b1}$ are hydrogen, CN, halogen or $C_1$-$C_4$-alkyl, in particular hydrogen, CN, methyl, flourine or bromine,
- $R^{b2}$ are hydrogen or halogen, in particular hydrogen, flourine or bromine,
- $R^{b3}$ are hydrogen, CN halogen or $C_1$-$C_4$-alkyl in particular hydrogen, CN, methyl, fluorine, chlorine or bromine.

Even more particular
- $Y^1$ and $Y^2$ are $CR^{A'}R^{A''}$, wherein $R^{A'}$, $R^{A''}$ are identical or different and are hydrogen or have one of the meanings given for $R^A$,
- Q $CR^{A1}R^{A2}$, wherein $R^{A1}$ and $R^{A2}$ are identical or different and are hydrogen, F, Cl, methyl, or $R^{A1}$ and $R^{A2}$ together may be =O,
- $R^{b1}$ are hydrogen, halogen, such as F, Cl, Br, methyl, CN,
- $R^{b2}$ are hydrogen, F, Cl, Br,
- $R^{b3}$ are hydrogen, F, Cl, Br.

Further particular groups of embodiment relate to the diaminotriazine compound of formula (I), wherein:
$R^1$ is H, OH, $S(O)_2NH_2$, CN, $C_1$-$C_6$-alkyl, $C_2$-$C_6$-alkenyl, $C_2$-$C_6$-alkynyl, $(C_3$-$C_6$-cycloalkyl)-$C_1$-$C_4$-alkyl, $C_1$-$C_6$-alkoxy, $(C_1$-$C_6$-alkoxy)-$C_1$-$C_6$-alkyl, $(C_1$-$C_6$-alkyl)-carbonyl, $(C_3$-$C_6$-cycloalkyl)-carbonyl, $(C_1$-$C_6$-alkoxy)carbonyl, $(C_1$-$C_6$-alkyl)sulfonyl, $(C_1$-$C_6$-alkylamino)carbonyl, $di(C_1$-$C_6$-alkyl)aminocarbonyl, $(C_1$-$C_6$-alkylamino)sulfonyl, $di(C_1$-$C_6$-alkyl)aminosulfonyl and $(C_1$-$C_6$-alkoxy)sulfonyl, where the aliphatic and cycloaliphatic parts of the 15 aforementioned radicals are unsubstituted, partly or completely halogenated, phenyl, phenylsulfonyl, phenylaminosulfonyl, phenylcarbonyl and phenoxycarbonyl,
  - wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;
  - preferably, H, CN, $C_1$-$C_6$-alkyl, $(C_1$-$C_6$-alkoxy)-$C_1$-$C_6$-alkyl, $(C_1$-$C_6$-alkyl)carbonyl $(C_3$-$C_6$-cycloalkyl)-carbonyl or $(C_1$-$C_6$-alkyl)sulfonyl, where the aliphatic parts of the 5 aforementioned radicals unsubstituted partly or completely halogenated, phenyl and phenyl-$C_1$-$C_6$ alkyl,
  - wherein phenyl in the last 2 mentioned radical is unsubstituted or substituted by 1, 2, 3, 4, or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy; in particular H, CN, $C_1$-$C_6$-alkyl, $C_1$-$C_6$-haloalkyl, $(C_1$-$C_6$-alkoxy)-$C_1$-$C_6$-alkyl, $C_1$-$C_6$-alkoxy, $(C_1$-$C_6$-alkyl)carbonyl, $(C_3$-$C_6$-cycloalkyl)-carbonyl, $(C_1$-$C_6$-haloalkyl)carbonyl, $(C_1$-$C_6$-alkyl)sulfonyl or $(C_1$-$C_6$-haloalkyl)sulfonyl; more particularly H, CN, $C_1$-$C_4$-alkyl, $(C_1$-$C_4$-alkoxy)-$C_1$-$C_4$-alkyl, $C_1$-$C_4$-alkoxy, $(C_1$-$C_4$-alkyl)carbonyl, $(C_3$-$C_6$-cycloalkyl)-carbonyl, or $(C_1$-$C_4$-alkyl)sulfonyl;even more particularly H, CN, $CH_3$, $CH_2OCH_3$, $OCH_3$, $C(O)CH_3$, $C(O)$cyclopropyl or $SO_2CH_3$; especially hydrogen.

Further particular groups of embodiments relate to the diaminotriazine compounds of formula (I), wherein;
$R^2$ is H, OH, $S(O)_2NH_2$, CN, $C_1$-$C_6$-alkyl, $C_2$-$C_6$-alkenyl, $C_2$-$C_6$-alkynyl, $(C_3$-$C_6$-cycloalkyl)-$C_1$-$C_4$-alkyl, $C_1$-$C_6$-alkoxy, $(C_1$-$C_6$-alkoxy)-$C_1$-$C_6$-alkyl, $(C_1$-$C_6$-alkyl)carbonyl, $(C_1$-$C_6$-alkoxy)carbonyl, $(C_3$-$C_6$-cycloalkyl)-carbonyl, $(C_1$-$C_6$-alkyl)sulfonyl, $(C_1$-$C_6$-alkylamino)carbonyl, $di(C_1$-$C_6$-alkyl)aminocarbonyl, $(C_1$-$C_6$-alkylamino)sulfonyl, $di(C_1$-$C_6$-alkyl)aminosulfonyl and $(C_1$-$C_6$-alkoxy)sulfonyl,
  where the aliphatic and cycloaliphatic parts of the 15 aforementioned radicals are unsubstituted, partly or completely halogenated, phenyl, phenylsulfonyl, phenylaminosulfonyl, phenyl-$C_1$-$C_6$ alkyl, phenoxy, phenylcarbonyl and phenoxycarbonyl,
  wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;
  preferably, H, CN, $C_1$-$C_6$-alkyl, $(C_1$-$C_6$-alkoxy)-$C_1$-$C_6$-alkyl, $(C_1$-$C_6$-alkyl)carbonyl, $(C_3$-$C_6$-cycloalkyl)-carbonyl or $(C_7$-$C_6$-alkyl)sulfonyl, where the aliphatic parts of the 4 aforementioned radicals unsubstituted partly or completely halogenated; phenyl and phenyl-$C_1$-$C_6$ alkyl,
  wherein phenyl in the last 2 mentioned radical is unsubstituted or substituted by 1, 2, 3, 4, or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;
  in particular H, CN, $C_1$-$C_6$-alkyl, $(C_1$-$C_6$-alkoxy)-$C_1$-$C_6$-alkyl, $(C_1$-$C_6$-alkyl)carbonyl, $(C_3$-$C_6$-cycloalkyl)-carbonyl, or $(C_1$-$C_6$-alkyl)sulfonyl; more particularly H, CN, $C_1$-$C_4$-alkyl, $(C_1$-$C_4$-alkoxy)-$C_1$-$C_4$-alkyl, $(C_1$-$C_4$-alkyl)carbonyl, $(C_3$-$C_6$-cycloalkyl)-carbonyl, or $(C_1$-$C_4$-alkyl)sulfonyl; even more particularly H, CN, $CH_3$, $CH_2OCH_3$, $C(O)CH_3$, $C(O)$cyclopropyl or $SO_2CH_3$; especially hydrogen.

Among the compounds of formula (I) further particular groups (1) of embodiments relate to the diaminotriazine compounds of formula (I), wherein X is $CR^3R^4R^5$, wherein $R^3$, $R^4$, $R^5$ have the meaning defined above,
Also preferred are diaminotriazine compounds of formula (I), wherein
$R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy, in particular from the group consisting of hydrogen, fluorine, chlorine, $C_1$-$C_4$-alkyl, such as methyl, ethyl, n-propyl, 2-propyl, n-butyl, 2-butyl, isobutyl or tert.-butyl, $C_1$-$C_4$-haloalkyl, such as difluoromethyl, trifluoromethyl, 2,2,2-trifluoroethyl, 1,1-difluoroethyl, 1,1,2,2-tetrafluoroethyl or pentafluoroethyl, $C_1$-$C_4$-alkoxy, such as methoxy or ethoxy and $C_1$-$C_4$-haloalkoxy, such as difluoromethoxy or trifluoromethoxy.

Further particular groups (1) of embodiments relate to the diaminotriazine compounds of formula (I), wherein
$R^4$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy, in particular from the group consisting of hydrogen, fluorine, chlorine and $C_1$-$C_4$-alkyl, more particularly from hydrogen, fluorine and methyl, especially from hydrogen and fluorine. In groups (1) of embodiments, $R^5$ is as defined above.

Further particular groups (1) of embodiments relate to the diaminotriazine compounds of formula (I), wherein
$R^5$ is selected from the group consisting of $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, $C_1$-$C_6$-alkoxy and $C_1$-$C_6$-alkoxy-$C_1$-$C_6$-alkyl or from $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, $C_1$-$C_6$-alkoxy and $C_1$-$C_6$-alkoxy-$C_1$-$C_6$-alkyl. In groups (1) of embodiments, $R^5$ is in particular selected from the group consisting of methyl, $C_2$-$C_4$-alkyl, such as ethyl, n-propyl, 2-propyl, n-butyl, 2-butyl, isobutyl or tert.-butyl, $C_1$-$C_4$-haloalkyl, such as difluoromethyl, trifluoromethyl, 2,2,2-trifluoroethyl, 1,1-difluoroethyl, 1,1,2,2-tetrafluoroethyl or pentafluoroethyl, $C_2$-$C_4$-alkenyl, such as vinyl or allyl, $C_3$-$C_4$-alkynyl, such as propargyl, $C_3$-$C_6$-cycloalkyl, such as cyclopropyl, cyclobutyl, cylopentyl or cyclohexyl, and $C_1$-$C_4$-alkoxy-$C_1$-$C_4$-alkyl, such as methoxymethyl, ethoxymethyl, 2-methoxyethyl or 2-ethoxyethyl.

Further particular groups (2) of embodiments relate to the diaminotriazine compounds of formula (I), wherein $R^4$ and $R^5$ together with the carbon atom to which they are attached form a moiety selected from the group consisting of carbonyl, $C_3$-$C_6$-cycloalkan-1,1-diyl, ipso-$C_3$-$C_6$-cycloalkendiyl, three- to six-membered saturated or partially unsaturated ipso-heterocyclodiyl, where the carbocycle and the heterocycle are unsubstituted, partly or completely halogenated or carry from 1 to 6 $C_1$-$C_6$-alkyl groups, and the moiety >C=$CR^xR^y$, where $R^x$ and $R^y$ are hydrogen, $C_1$-$C_4$-alkyl or $C_1$-$C_4$-haloalkyl.

In groups (2) of embodiments, $R^4$ and $R^5$ together with the carbon atom to which they are attached form in particular a moiety selected from the group consisting of $C_3$-$C_6$-cycloalkan-1,1-diyl, ipso-$C_3$-$C_6$-cycloalkendiyl, three- to six-membered saturated or partially unsaturated ipso-heterocyclodiyl, where the carbocycle and the heterocycle are unsubstituted, partly or completely halogenated or carry from 1 to 6 $C_1$-$C_6$-alkyl groups and where the heterocycle preferably has 1 or 2 oxygen atoms as ring members.

In groups (2) of embodiments, $R^4$ and $R^5$ together with the carbon atom to which they are attached more particularly form a moiety selected from the group consisting of $C_3$-$C_6$-cycloalkan-1,1-diylor three- to six-membered saturated ipso-heterocyclodiyl, where the carbocycle and the heterocycle are unsubstituted, partly or completely halogenated or carry from 1 to 6 $C_1$-$C_6$-alkyl groups, and where heterocyclyl preferably has 1 or 2 oxygen atoms as ring members.

Further particular groups (2a) of embodiments relate to the diaminotriazine compounds of formula (I), wherein $R^4$ and $R^5$ together with the carbon atom to which they are attached form $C_3$-$C_6$-cycloalkan-1,1-diyl, in particular cyclopropan-1,1-diyl, cyclobutan-1,1-diyl, cyclopentan-1,1-diyl or cyclohexan-1,1-diyl, said $C_3$-$C_6$-cycloalkan-1,1-diyl being unsubstituted, partly or completely halogenated or carrying from 1 to 6 $C_1$-$C_6$-alkyl groups, in particular methyl groups. In groups (2a) of embodiments $R^4$ and $R^5$ together with the carbon atom to which they are attached form in particular $C_3$-$C_6$-cycloalkan-1,1-diyl which is unsubstituted.

Further particular groups (2b) of embodiments relate to the diaminotriazine compounds of formula (I), wherein $R^4$ and $R^5$ together with the carbon atom to which they are attached form three- to six-membered saturated ipso-heterocyclodiyl,
in particular said heterocycle preferably has 1 or 2 oxygen atoms as ring members
in particular oxiran-1,1-diyl, oxiran-2,2-diyl, oxetan-1,1-diyl, oxetan-2,2-diyl, oxetan-3,3-diyl oxan-1,1-diyl, oxan-2,2-diyl, oxan-3,3-diyl or oxan-4,4-diyl, said heterocycle being unsubstituted, partly or completely halogenated or carrying from 1 to 6 $C_1$-$C_6$-alkyl groups
even more particular 2-tetrahydrofuranyl, 3-tetrahydrofuranyl. In groups (2b) of embodiments $R^4$ and $R^5$ together with the carbon atom to which they are attached form three- to six-membered saturated ipso-heterocyclodiyl, in particular oxiran-1,1-diyl, oxiran-2,2-diyl, oxetan-1,1-diyl, oxetan-2,2-diyl, oxetan-3,3-diyl oxan-1,1-diyl, oxan-2,2-diyl, oxan-3,3-diyl or oxan-4,4-diyl said heterocycle being unsubstituted.

Especially preferred examples of $CR^3R^4R^5$ are those radicals, where $R^3$, $R^4$ and $R^5$ are given in rows 1 to 64 of table 1a.

TABLE 1a

| no. | $R^3$ | $R^4$ | $R^5$ |
|---|---|---|---|
| 1. | H | $CH_3$ | $CH_3$ |
| 2. | F | F | $CH_3$ |
| 3. | F | H | $CH_3$ |
| 4. | F | $CH_3$ | $CH_3$ |
| 5. | $CH_3$ | $CH_3$ | $CH_3$ |
| 6. | F | H | $C_2H_5$ |
| 7. | H | $CH_3$ | $C_2H_5$ |
| 8. | F | $CH_3$ | $C_2H_5$ |
| 9. | H | $OCH_3$ | $CH_3$ |
| 10. | H | $OCH_3$ | $C_2H_5$ |
| 11. | F | $C_2H_5$ | $C_2H_5$ |
| 12. | H | $OCH_3$ | $C_2H_5$ |
| 13. | H | H | $CH(CH_3)_2$ |
| 14. | H | F | $CH(CH_3)_2$ |
| 15. | F | F | $CH(CH_3)_2$ |
| 16. | H | $CH_3$ | $CH(CH_3)_2$ |
| 17. | H | $OCH_3$ | $CH(CH_3)_2$ |
| 18. | F | $CH_3$ | $CH(CH_3)_2$ |
| 19. | H | H | $CH_2CH_2CH_3$ |
| 20. | H | F | $CH_2CH_2CH_3$ |
| 21. | F | F | $CH_2CH_2CH_3$ |
| 22. | H | $CH_3$ | $CH_2CH_2CH_3$ |
| 23. | H | $OCH_3$ | $CH_2CH_2CH_3$ |
| 24. | F | $CH_3$ | $CH_2CH_2CH_3$ |
| 25. | H | H | $C(CH_3)_3$ |
| 26. | H | F | $C(CH_3)_3$ |
| 27. | F | F | $C(CH_3)_3$ |
| 28. | H | $CH_3$ | $C(CH_3)_3$ |
| 29. | H | $OCH_3$ | $C(CH_3)_3$ |
| 30. | F | $CH_3$ | $C(CH_3)_3$ |
| 31. | H | H | Cyclopropyl |
| 32. | H | F | Cyclopropyl |
| 33. | F | F | Cyclopropyl |
| 34. | H | $CH_3$ | Cyclopropyl |
| 35. | H | $OCH_3$ | Cyclopropyl |
| 36. | F | $CH_3$ | Cyclopropyl |
| 37. | H | $CH_3$ | $CF_3$ |
| 38. | F | $CH_3$ | $CF_3$ |
| 39. | H | | $CH_2$—$CH_2$ |
| 40. | $CH_3$ | | $CH_2$—$CH_2$ |
| 41. | $OCH_3$ | | $CH_2$—$CH_2$ |
| 42. | F | | $CH_2$—$CH_2$ |
| 43. | Cl | | $CH_2$—$CH_2$ |
| 44. | H | | $CH_2$—$CH_2$—$CH_2$ |
| 45. | $CH_3$ | | $CH_2$—$CH_2$—$CH_2$ |
| 46. | $OCH_3$ | | $CH_2$—$CH_2$—$CH_2$ |
| 47. | F | | $CH_2$—$CH_2$—$CH_2$ |
| 48. | Cl | | $CH_2$—$CH_2$—$CH_2$ |

TABLE 1a-continued

| no. | R³ | R⁴ | R⁵ |
|---|---|---|---|
| 49. | H | | CH₂—CH₂—CH₂—CH₂ |
| 50. | CH₃ | | CH₂—CH₂—CH₂—CH₂ |
| 51. | OCH₃ | | CH₂—CH₂—CH₂—CH₂ |
| 52. | F | | CH₂—CH₂—CH₂—CH₂ |
| 53. | Cl | | CH₂—CH₂—CH₂—CH₂ |
| 54. | H | | CH₂—CH₂—CH₂—CH₂—CH₂ |
| 55. | CH₃ | | CH₂—CH₂—CH₂—CH₂—CH₂ |
| 56. | OCH₃ | | CH₂—CH₂—CH₂—CH₂—CH₂ |
| 57. | F | | CH₂—CH₂—CH₂—CH₂—CH₂ |
| 58. | Cl | | CH₂—CH₂—CH₂—CH₂—CH₂ |
| 59. | H | | O—CH₂—CH₂—CH₂ |
| 60. | CH₃ | | O—CH₂—CH₂—CH₂ |
| 61. | OCH₃ | | O—CH₂—CH₂—CH₂ |
| 62. | H | | O—CH₂—CH₂—CH₂—CH₂ |
| 63. | CH₃ | | O—CH₂—CH₂—CH₂—CH₂ |
| 64. | OCH₃ | | O—CH₂—CH₂—CH₂—CH₂ |

Further particular groups (3) of embodiments relate to the diaminotriazine compounds of formula (I), wherein X is phenyl which is unsubstituted or may carry, 1, 2, 3, 4 or 5 radicals $R^{Ar}$ as defined above, which are in particular selected from the group consisting of halogen, CN, $C_1$-$C_6$-alkyl, $C_1$-$C_6$-alkoxy, $C_1$-$C_6$-haloalkyl, $C_3$-$C_6$-cycloalkyl, $C_3$-$C_6$-cycloalkoxy, ($C_3$-$C_6$-cycloalkyl)methoxy, $C_2$-$C_6$-alkynyl, $C_2$-$C_6$-alkenyl, $C_2$-$C_6$-alkynyloxy, $C_2$-$C_6$-alkenyloxy, $C_1$-$C_6$-haloalkoxy;

wherein $R^{Ar}$ is more particular selected from the group consisting of halogen, $C_1$-$C_4$-alkyl, $C_2$-$C_4$-alkynyl, $C_2$-$C_4$-alkynyloxy, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-cycloalkoxy, ($C_3$-$C_6$-cycloalkyl)methoxy, CN;

wherein $R^{Ar}$ is especially selected from the group consisting of F, Cl, methoxy, ethoxy, CN;

Especially preferred examples for X is substituted or ansubstituted phenyl are given in rows 1 to 563 of table 2a.

TABLE 2a

| no. | X |
|---|---|
| 1. | C₆H₅ |
| 2. | 2-F—C₆H₄ |
| 3. | 3-F—C₆H₄ |
| 4. | 4-F—C₆H₄ |
| 5. | 2-Cl—C₆H₄ |
| 6. | 3-Cl—C₆H₄ |
| 7. | 4-Cl—C₆H₄ |
| 8. | 2-Br—C₆H₄ |
| 9. | 3-Br—C₆H₄ |
| 10. | 4-Br—C₆H₄ |
| 11. | 2-I—C₆H₄ |
| 12. | 3-I—C₆H₄ |
| 13. | 4-I—C₆H₄ |
| 14. | 2-CN—C₆H₄ |
| 15. | 3-CN—C₆H₄ |
| 16. | 4-CN—C₆H₄ |
| 17. | 2-OCH₃—C₆H₄ |
| 18. | 3-OCH₃—C₆H₄ |
| 19. | 4-OCH₃—C₆H₄ |
| 20. | 2-OCH₂F—C₆H₄ |
| 21. | 3-OCH₂F—C₆H₄ |
| 22. | 4-OCH₂F—C₆H₄ |
| 23. | 2-OCHF₂—C₆H₄ |
| 24. | 3-OCHF₂—C₆H₄ |
| 25. | 4-OCHF₂—C₆H₄ |
| 26. | 2-OCHF₂—C₆H₄ |
| 27. | 3-OCHF₂—C₆H₄ |
| 28. | 4-OCHF₂—C₆H₄ |
| 29. | 2-OCF₃—C₆H₄ |
| 30. | 3-OCF₃—C₆H₄ |
| 31. | 4-OCF₃—C₆H₄ |
| 32. | 3-OCH₂Cl—C₆H₄ |
| 33. | 4-OCH₂Cl—C₆H₄ |
| 34. | 2-OCH₂Cl—C₆H₄ |
| 35. | 3-OCH₂Cl—C₆H₄ |
| 36. | 4-OCH₂Cl—C₆H₄ |
| 37. | 2-OCHCl₂—C₆H₄ |
| 38. | 3-OCHCl₂—C₆H₄ |
| 39. | 4-OCHCl₂—C₆H₄ |
| 40. | 2-OCCl₃—C₆H₄ |
| 41. | 3-OCCl₃—C₆H₄ |
| 42. | 4-OCCl₃—C₆H₄ |
| 43. | 2-CH₂CH₃—C₆H₄ |
| 44. | 3-CH₂CH₃—C₆H₄ |
| 45. | 4-CH₂CH₃—C₆H₄ |
| 46. | 2-CF₂CHF₂—C₆H₄ |
| 47. | 3-CF₂CHF₂—C₆H₄ |
| 48. | 4-CF₂CHF₂—C₆H₄ |
| 49. | 2,3-F₂—C₆H₃ |
| 50. | 2,4-F₂—C₆H₃ |
| 51. | 2,5-F₂—C₆H₃ |
| 52. | 2,6-F₂—C₆H₃ |
| 53. | 3,4-F₂—C₆H₃ |
| 54. | 3,5-F₂—C₆H₃ |
| 55. | 2,3-Cl₂—C₆H₃ |
| 56. | 2,4-Cl₂—C₆H₃ |
| 57. | 2,5-Cl₂—C₆H₃ |
| 58. | 2,6-Cl₂—C₆H₃ |
| 59. | 3,4-Cl₂—C₆H₃ |
| 60. | 3,5-Cl₂—C₆H₃ |
| 61. | 2,3-Br₂—C₆H₃ |
| 62. | 2,4-Br₂—C₆H₃ |
| 63. | 2,5-Br₂—C₆H₃ |
| 64. | 2,6-Br₂—C₆H₃ |
| 65. | 3,4-Br₂—C₆H₃ |
| 66. | 3,5-Br₂—C₆H₃ |
| 67. | 2,3-I₂—C₆H₃ |
| 68. | 2,4-I₂—C₆H₃ |
| 69. | 2,5-I₂—C₆H₃ |
| 70. | 2,6-I₂—C₆H₃ |
| 71. | 3,4-I₂—C₆H₃ |
| 72. | 3,5-I₂—C₆H₃ |
| 73. | 2,3-(OCH₃)₂—C₆H₃ |
| 74. | 2,4-(OCH₃)₂—C₆H₃ |
| 75. | 2,5-(OCH₃)₂—C₆H₃ |
| 76. | 2,6-(OCF₃)₂—C₆H₃ |
| 77. | 3,4-(OCF₃)₂—C₆H₃ |
| 78. | 3,5-(OCH₃)₂—C₆H₃ |
| 79. | 2-F-3-Cl—C₆H₃ |
| 80. | 2-F-4-Cl—C₆H₃ |
| 81. | 2-F-5-Cl—C₆H₃ |
| 82. | 2-F-6-Cl—C₆H₃ |
| 83. | 3-F-2-Cl—C₆H₃ |
| 84. | 3-F-4-Cl—C₆H₃ |
| 85. | 3-F-5-Cl—C₆H₃ |
| 86. | 3-F-6-Cl—C₆H₃ |
| 87. | 4-F-2-Cl—C₆H₃ |
| 88. | 4-F-3-Cl—C₆H₃ |
| 89. | 4-F-5-Cl—C₆H₃ |
| 90. | 4-F-6-Cl—C₆H₃ |
| 91. | 2-F-3-Br—C₆H₃ |
| 92. | 2-F-4-Br—C₆H₃ |
| 93. | 2-F-5-Br—C₆H₃ |
| 94. | 2-F-6-Br—C₆H₃ |
| 95. | 3-F-2-Br—C₆H₃ |
| 96. | 3-F-4-Br—C₆H₃ |
| 97. | 3-F-5-Br—C₆H₃ |
| 98. | 3-F-6-Br—C₆H₃ |
| 99. | 4-F-2-Br—C₆H₃ |
| 100. | 4-F-3-Br—C₆H₃ |
| 101. | 4-F-5-Br—C₆H₃ |
| 102. | 4-F-6-Br—C₆H₃ |
| 103. | 2-F-3-I—C₆H₃ |
| 104. | 2-F-4-I—C₆H₃ |
| 105. | 2-F-5-I—C₆H₃ |
| 106. | 2-F-6-I—C₆H₃ |
| 107. | 3-F-2-I—C₆H₃ |
| 108. | 3-F-4-I—C₆H₃ |
| 109. | 3-F-5-I—C₆H₃ |
| 110. | 3-F-6-I—C₆H₃ |

TABLE 2a-continued

| no. | X |
|---|---|
| 111. | 4-F-2-I—C$_6$H$_3$ |
| 112. | 4-F-3-I—C$_6$H$_3$ |
| 113. | 4-F-5-I—C$_6$H$_3$ |
| 114. | 4-F-6-I—C$_6$H$_3$ |
| 115. | 2-F-3-OCH$_3$—C$_6$H$_3$ |
| 116. | 2-F-4-OCH$_3$—C$_6$H$_3$ |
| 117. | 2-F-5-OCH$_3$—C$_6$H$_3$ |
| 118. | 2-F-6-OCH$_3$—C$_6$H$_3$ |
| 119. | 3-F-2-OCH$_3$—C$_6$H$_3$ |
| 120. | 3-F-4-OCH$_3$—C$_6$H$_3$ |
| 121. | 3-F-5-OCH$_3$—C$_6$H$_3$ |
| 122. | 3-F-6-OCH$_3$—C$_6$H$_3$ |
| 123. | 4-F-2-OCH$_3$—C$_6$H$_3$ |
| 124. | 4-F-3-OCH$_3$—C$_6$H$_3$ |
| 125. | 4-F-5-OCH$_3$—C$_6$H$_3$ |
| 126. | 4-F-6-OCH$_3$—C$_6$H$_3$ |
| 127. | 2-F-3-OCF$_3$—C$_6$H$_3$ |
| 128. | 2-F-4-OCF$_3$—C$_6$H$_3$ |
| 129. | 2-F-5-OCF$_3$—C$_6$H$_3$ |
| 130. | 2-F-6-OCF$_3$—C$_6$H$_3$ |
| 131. | 3-F-2-OCF$_3$—C$_6$H$_3$ |
| 132. | 3-F-4-OCF$_3$—C$_6$H$_3$ |
| 133. | 3-F-5-OCF$_3$—C$_6$H$_3$ |
| 134. | 3-F-6-OCF$_3$—C$_6$H$_3$ |
| 135. | 4-F-2-OCF$_3$—C$_6$H$_3$ |
| 136. | 4-F-3-OCF$_3$—C$_6$H$_3$ |
| 137. | 4-F-5-OCF$_3$—C$_6$H$_3$ |
| 138. | 4-F-6-OCF$_3$—C$_6$H$_3$ |
| 139. | 2-F-3-CF$_3$—C$_6$H$_3$ |
| 140. | 2-F-4-CF$_3$—C$_6$H$_3$ |
| 141. | 2-F-5-CF$_3$—C$_6$H$_3$ |
| 142. | 2-F-6-CF$_3$—C$_6$H$_3$ |
| 143. | 3-F-2-CF$_3$—C$_6$H$_3$ |
| 144. | 3-F-4-CF$_3$—C$_6$H$_3$ |
| 145. | 3-F-5-CF$_3$—C$_6$H$_3$ |
| 146. | 3-F-6-CF$_3$—C$_6$H$_3$ |
| 147. | 4-F-2-CF$_3$—C$_6$H$_3$ |
| 148. | 4-F-3-CF$_3$—C$_6$H$_3$ |
| 149. | 4-F-5-CF$_3$—C$_6$H$_3$ |
| 150. | 4-F-6-CF$_3$—C$_6$H$_3$ |
| 151. | 2-Cl-3-F—C$_6$H$_3$ |
| 152. | 2-Cl-4-F—C$_6$H$_3$ |
| 153. | 2-Cl-5-F—C$_6$H$_3$ |
| 154. | 2-Cl-6-F—C$_6$H$_3$ |
| 155. | 3-Cl-2-F—C$_6$H$_3$ |
| 156. | 3-Cl-4-F—C$_6$H$_3$ |
| 157. | 3-Cl-5-F—C$_6$H$_3$ |
| 158. | 3-Cl-6-F—C$_6$H$_3$ |
| 159. | 4-Cl-2-F—C$_6$H$_3$ |
| 160. | 4-Cl-3-F—C$_6$H$_3$ |
| 161. | 4-Cl-5-F—C$_6$H$_3$ |
| 162. | 4-Cl-6-F—C$_6$H$_3$ |
| 163. | 2-Cl-3-Br—C$_6$H$_3$ |
| 164. | 2-Cl-4-Br—C$_6$H$_3$ |
| 165. | 2-Cl-5-Br—C$_6$H$_3$ |
| 166. | 2-Cl-6-Br—C$_6$H$_3$ |
| 167. | 3-Cl-2-Br—C$_6$H$_3$ |
| 168. | 3-Cl-4-Br—C$_6$H$_3$ |
| 169. | 3-Cl-5-Br—C$_6$H$_3$ |
| 170. | 3-Cl-6-Br—C$_6$H$_3$ |
| 171. | 4-Cl-2-Br—C$_6$H$_3$ |
| 172. | 4-Cl-3-Br—C$_6$H$_3$ |
| 173. | 4-Cl-5-Br—C$_6$H$_3$ |
| 174. | 4-Cl-6-Br—C$_6$H$_3$ |
| 175. | 2-Cl-3-I—C$_6$H$_3$ |
| 176. | 2-Cl-4-I—C$_6$H$_3$ |
| 177. | 2-Cl-5-I—C$_6$H$_3$ |
| 178. | 2-Cl-6-I—C$_6$H$_3$ |
| 179. | 3-Cl-2-I—C$_6$H$_3$ |
| 180. | 3-Cl-4-I—C$_6$H$_3$ |
| 181. | 3-Cl-5-I—C$_6$H$_3$ |
| 182. | 3-Cl-6-I—C$_6$H$_3$ |
| 183. | 4-Cl-2-I—C$_6$H$_3$ |
| 184. | 4-Cl-3-I—C$_6$H$_3$ |
| 185. | 4-Cl-5-I—C$_6$H$_3$ |
| 186. | 4-Cl-6-I—C$_6$H$_3$ |
| 187. | 2-Cl-3-OCH$_3$—C$_6$H$_3$ |
| 188. | 2-Cl-4-OCH$_3$—C$_6$H$_3$ |
| 189. | 2-Cl-5-OCH$_3$—C$_6$H$_3$ |
| 190. | 2-Cl-6-OCH$_3$—C$_6$H$_3$ |
| 191. | 3-Cl-2-OCH$_3$—C$_6$H$_3$ |
| 192. | 3-Cl-4-OCH$_3$—C$_6$H$_3$ |
| 193. | 3-Cl-5-OCH$_3$—C$_6$H$_3$ |
| 194. | 3-Cl-6-OCH$_3$—C$_6$H$_3$ |
| 195. | 4-Cl-2-OCH$_3$—C$_6$H$_3$ |
| 196. | 4-Cl-3-OCH$_3$—C$_6$H$_3$ |
| 197. | 4-Cl-5-OCH$_3$—C$_6$H$_3$ |
| 198. | 4-Cl-6-OCH$_3$—C$_6$H$_3$ |
| 199. | 2-Cl-3-OCF$_3$—C$_6$H$_3$ |
| 200. | 2-Cl-4-OCF$_3$—C$_6$H$_3$ |
| 201. | 2-Cl-5-OCF$_3$—C$_6$H$_3$ |
| 202. | 2-Cl-6-OCF$_3$—C$_6$H$_3$ |
| 203. | 3-Cl-2-OCF$_3$—C$_6$H$_3$ |
| 204. | 3-Cl-4-OCF$_3$—C$_6$H$_3$ |
| 205. | 3-Cl-5-OCF$_3$—C$_6$H$_3$ |
| 206. | 3-Cl-6-OCF$_3$—C$_6$H$_3$ |
| 207. | 4-Cl-2-OCF$_3$—C$_6$H$_3$ |
| 208. | 4-Cl-3-OCF$_3$—C$_6$H$_3$ |
| 209. | 4-Cl-5-OCF$_3$—C$_6$H$_3$ |
| 210. | 4-Cl-6-OCF$_3$—C$_6$H$_3$ |
| 211. | 2-Br-3-F—C$_6$H$_3$ |
| 212. | 2-Br-4-F—C$_6$H$_3$ |
| 213. | 2-Br-5-F—C$_6$H$_3$ |
| 214. | 2-Br-6-F—C$_6$H$_3$ |
| 215. | 3-Br-2-F—C$_6$H$_3$ |
| 216. | 3-Br-4-F—C$_6$H$_3$ |
| 217. | 3-Br-5-F—C$_6$H$_3$ |
| 218. | 3-Br-6-F—C$_6$H$_3$ |
| 219. | 4-Br-2-F—C$_6$H$_3$ |
| 220. | 4-Br-3-F—C$_6$H$_3$ |
| 221. | 4-Br-5-F—C$_6$H$_3$ |
| 222. | 4-Br-6-F—C$_6$H$_3$ |
| 223. | 2-Br-3-Cl—C$_6$H$_3$ |
| 224. | 2-Br-4-Cl—C$_6$H$_3$ |
| 225. | 2-Br-5-Cl—C$_6$H$_3$ |
| 226. | 2-Br-6-Cl—C$_6$H$_3$ |
| 227. | 3-Br-2-Cl—C$_6$H$_3$ |
| 228. | 3-Br-4-Cl—C$_6$H$_3$ |
| 229. | 3-Br-5-Cl—C$_6$H$_3$ |
| 230. | 3-Br-6-Cl—C$_6$H$_3$ |
| 231. | 4-Br-2-Cl—C$_6$H$_3$ |
| 232. | 4-Br-3-Cl—C$_6$H$_3$ |
| 233. | 4-Br-5-Cl—C$_6$H$_3$ |
| 234. | 4-Br-6-Cl—C$_6$H$_3$ |
| 235. | 2-Br-3-I—C$_6$H$_3$ |
| 236. | 2-Br-4-I—C$_6$H$_3$ |
| 237. | 2-Br-5-I—C$_6$H$_3$ |
| 238. | 2-Br-6-I—C$_6$H$_3$ |
| 239. | 3-Br-2-I—C$_6$H$_3$ |
| 240. | 3-Br-4-I—C$_6$H$_3$ |
| 241. | 3-Br-5-I—C$_6$H$_3$ |
| 242. | 3-Br-6-I—C$_6$H$_3$ |
| 243. | 4-Br-2-I—C$_6$H$_3$ |
| 244. | 4-Br-3-I—C$_6$H$_3$ |
| 245. | 4-Br-5-I—C$_6$H$_3$ |
| 246. | 4-Br-6-I—C$_6$H$_3$ |
| 247. | 2-Br-3-OCH$_3$—C$_6$H$_3$ |
| 248. | 2-Br-4-OCH$_3$—C$_6$H$_3$ |
| 249. | 2-Br-5-OCH$_3$—C$_6$H$_3$ |
| 250. | 2-Br-6-OCH$_3$—C$_6$H$_3$ |
| 251. | 3-Br-2-OCH$_3$—C$_6$H$_3$ |
| 252. | 3-Br-4-OCH$_3$—C$_6$H$_3$ |
| 253. | 3-Br-5-OCH$_3$—C$_6$H$_3$ |
| 254. | 3-Br-6-OCH$_3$—C$_6$H$_3$ |
| 255. | 4-Br-2-OCH$_3$—C$_6$H$_3$ |
| 256. | 4-Br-3-OCH$_3$—C$_6$H$_3$ |
| 257. | 4-Br-5-OCH$_3$—C$_6$H$_3$ |
| 258. | 4-Br-6-OCH$_3$—C$_6$H$_3$ |
| 259. | 2-Br-3-OCF$_3$—C$_6$H$_3$ |
| 260. | 2-Br-4-OCF$_3$—C$_6$H$_3$ |
| 261. | 2-Br-5-OCF$_3$—C$_6$H$_3$ |
| 262. | 2-Br-6-OCF$_3$—C$_6$H$_3$ |
| 263. | 3-Br-2-OCF$_3$—C$_6$H$_3$ |
| 264. | 3-Br-4-OCF$_3$—C$_6$H$_3$ |
| 265. | 3-Br-5-OCF$_3$—C$_6$H$_3$ |
| 266. | 3-Br-6-OCF$_3$—C$_6$H$_3$ |

TABLE 2a-continued

| no. | X |
|---|---|
| 267. | 4-Br-2-OCF$_3$—C$_6$H$_3$ |
| 268. | 4-Br-3-OCF$_3$—C$_6$H$_3$ |
| 269. | 4-Br-5-OCF$_3$—C$_6$H$_3$ |
| 270. | 4-Br-6-OCF$_3$—C$_6$H$_3$ |
| 271. | 2,3,4-F$_3$—C$_6$H$_2$ |
| 272. | 2,3,5-F$_3$—C$_6$H$_2$ |
| 273. | 2,3,6-F$_3$—C$_6$H$_2$ |
| 274. | 2,4,5-F$_3$—C$_6$H$_2$ |
| 275. | 2,4,6-F$_3$—C$_6$H$_2$ |
| 276. | 3,4,5-F$_3$—C$_6$H$_2$ |
| 277. | 2,3,4-Cl$_3$—C$_6$H$_2$ |
| 278. | 2,3,5-Cl$_3$—C$_6$H$_2$ |
| 279. | 2,3,6-Cl$_3$—C$_6$H$_2$ |
| 280. | 2,4,5-Cl$_3$—C$_6$H$_2$ |
| 281. | 2,4,6-Cl$_3$—C$_6$H$_2$ |
| 282. | 3,4,5-Cl$_3$—C$_6$H$_2$ |
| 283. | 2,3,4-Br$_3$—C$_6$H$_2$ |
| 284. | 2,3,5-Br$_3$—C$_6$H$_2$ |
| 285. | 2,3,6-Br$_3$—C$_6$H$_2$ |
| 286. | 2,4,5-Br$_3$—C$_6$H$_2$ |
| 287. | 2,4,6-Br$_3$—C$_6$H$_2$ |
| 288. | 3,4,5-Br$_3$—C$_6$H$_2$ |
| 289. | 2,3,4-(OCH$_3$)$_3$—C$_6$H$_2$ |
| 290. | 2,3,5-(OCH$_3$)$_3$—C$_6$H$_2$ |
| 291. | 2,3,6-(OCH$_3$)$_3$—C$_6$H$_2$ |
| 292. | 2,4,5-(OCH$_3$)$_3$—C$_6$H$_2$ |
| 293. | 2,4,6-(OCH$_3$)$_3$—C$_6$H$_2$ |
| 294. | 3,4,5-(OCH$_3$)$_3$—C$_6$H$_2$ |
| 295. | 2,3-F$_2$-4-Cl—C$_6$H$_2$ |
| 296. | 2,3-F$_2$-5-Cl—C$_6$H$_2$ |
| 297. | 2,3-F$_2$-6-Cl—C$_6$H$_2$ |
| 298. | 2,4-F$_2$-3-Cl—C$_6$H$_2$ |
| 299. | 2,4-F$_2$-5-Cl—C$_6$H$_2$ |
| 300. | 2,4-F$_2$-6-Cl—C$_6$H$_2$ |
| 301. | 2,5-F$_2$-3-Cl—C$_6$H$_2$ |
| 302. | 2,5-F$_2$-4-Cl—C$_6$H$_2$ |
| 303. | 2,5-F$_2$-6-Cl—C$_6$H$_2$ |
| 304. | 2,6-F$_2$-3-Cl—C$_6$H$_2$ |
| 305. | 2,6-F$_2$-4-Cl—C$_6$H$_2$ |
| 306. | 2,3-F$_2$-4-Br—C$_6$H$_2$ |
| 307. | 2,3-F$_2$-5-Br—C$_6$H$_2$ |
| 308. | 2,3-F$_2$-6-Br—C$_6$H$_2$ |
| 309. | 2,4-F$_2$-3-Br—C$_6$H$_2$ |
| 310. | 2,4-F$_2$-5-Br—C$_6$H$_2$ |
| 311. | 2,4-F$_2$-6-Br—C$_6$H$_2$ |
| 312. | 2,5-F$_2$-3-Br—C$_6$H$_2$ |
| 313. | 2,5-F$_2$-4-Br—C$_6$H$_2$ |
| 314. | 2,5-F$_2$-6-Br—C$_6$H$_2$ |
| 315. | 2,6-F$_2$-3-Br—C$_6$H$_2$ |
| 316. | 2,6-F$_2$-4-Br—C$_6$H$_2$ |
| 317. | 2,3-F$_2$-4-OCH$_3$—C$_6$H$_2$ |
| 318. | 2,3-F$_2$-5-OCH$_3$—C$_6$H$_2$ |
| 319. | 2,3-F$_2$-6-OCH$_3$—C$_6$H$_2$ |
| 320. | 2,4-F$_2$-3-OCH$_3$—C$_6$H$_2$ |
| 321. | 2,4-F$_2$-5-OCH$_3$—C$_6$H$_2$ |
| 322. | 2,4-F$_2$-6-OCH$_3$—C$_6$H$_2$ |
| 323. | 2,5-F$_2$-3-OCH$_3$—C$_6$H$_2$ |
| 324. | 2,5-F$_2$-4-OCH$_3$—C$_6$H$_2$ |
| 325. | 2,5-F$_2$-6-OCH$_3$—C$_6$H$_2$ |
| 326. | 2,6-F$_2$-3-OCH$_3$—C$_6$H$_2$ |
| 327. | 2,6-F$_2$-4-OCH$_3$—C$_6$H$_2$ |
| 328. | 2,3-Cl$_2$-4-F—C$_6$H$_2$ |
| 329. | 2,3-Cl$_2$-5-F—C$_6$H$_2$ |
| 330. | 2,3-Cl$_2$-6-F—C$_6$H$_2$ |
| 331. | 2,4-Cl$_2$-3-F—C$_6$H$_2$ |
| 332. | 2,4-Cl$_2$-5-F—C$_6$H$_2$ |
| 333. | 2,4-Cl$_2$-6-F—C$_6$H$_2$ |
| 334. | 2,5-Cl$_2$-3-F—C$_6$H$_2$ |
| 335. | 2,5-Cl$_2$-4-F—C$_6$H$_2$ |
| 336. | 2,5-Cl$_2$-6-F—C$_6$H$_2$ |
| 337. | 2,6-Cl$_2$-3-F—C$_6$H$_2$ |
| 338. | 2,6-Cl$_2$-4-F—C$_6$H$_2$ |
| 339. | 2,3-Cl$_2$-4-Br—C$_6$H$_2$ |
| 340. | 2,3-Cl$_2$-5-Br—C$_6$H$_2$ |
| 341. | 2,3-Cl$_2$-6-Br—C$_6$H$_2$ |
| 342. | 2,4-Cl$_2$-3-Br—C$_6$H$_2$ |
| 343. | 2,4-Cl$_2$-5-Br—C$_6$H$_2$ |
| 344. | 2,4-Cl$_2$-6-Br—C$_6$H$_2$ |
| 345. | 2,5-Cl$_2$-3-Br—C$_6$H$_2$ |
| 346. | 2,5-Cl$_2$-4-Br—C$_6$H$_2$ |
| 347. | 2,5-Cl$_2$-6-Br—C$_6$H$_2$ |
| 348. | 2,6-Cl$_2$-3-Br—C$_6$H$_2$ |
| 349. | 2,6-Cl$_2$-4-Br—C$_6$H$_2$ |
| 350. | 2,3-Cl$_2$-4-OCH$_3$—C$_6$H$_2$ |
| 351. | 2,3-Cl$_2$-5-OCH$_3$—C$_6$H$_2$ |
| 352. | 2,3-Cl$_2$-6-OCH$_3$—C$_6$H$_2$ |
| 353. | 2,4-Cl$_2$-3-OCH$_3$—C$_6$H$_2$ |
| 354. | 2,4-Cl$_2$-5-OCH$_3$—C$_6$H$_2$ |
| 355. | 2,4-Cl$_2$-6-OCH$_3$—C$_6$H$_2$ |
| 356. | 2,5-Cl$_2$-3-OCH$_3$—C$_6$H$_2$ |
| 357. | 2,5-Cl$_2$-4-OCH$_3$—C$_6$H$_2$ |
| 358. | 2,5-Cl$_2$-6-OCH$_3$—C$_6$H$_2$ |
| 359. | 2,6-Cl$_2$-3-OCH$_3$—C$_6$H$_2$ |
| 360. | 2,6-Cl$_2$-4-OCH$_3$—C$_6$H$_2$ |
| 361. | 2,3-Br$_2$-4-F—C$_6$H$_2$ |
| 362. | 2,3-Br$_2$-5-F—C$_6$H$_2$ |
| 363. | 2,3-Br$_2$-6-F—C$_6$H$_2$ |
| 364. | 2,4-Br$_2$-3-F—C$_6$H$_2$ |
| 365. | 2,4-Br$_2$-5-F—C$_6$H$_2$ |
| 366. | 2,4-Br$_2$-6-F—C$_6$H$_2$ |
| 367. | 2,5-Br$_2$-3-F—C$_6$H$_2$ |
| 368. | 2,5-Br$_2$-4-F—C$_6$H$_2$ |
| 369. | 2,5-Br$_2$-6-F—C$_6$H$_2$ |
| 370. | 2,6-Br$_2$-3-F—C$_6$H$_2$ |
| 371. | 2,6-Br$_2$-4-F—C$_6$H$_2$ |
| 372. | 2,3-Br$_2$-4-Cl—C$_6$H$_2$ |
| 373. | 2,3-Br$_2$-5-Cl—C$_6$H$_2$ |
| 374. | 2,3-Br$_2$-6-Cl—C$_6$H$_2$ |
| 375. | 2,4-Br$_2$-3-Cl—C$_6$H$_2$ |
| 376. | 2,4-Br$_2$-5-Cl—C$_6$H$_2$ |
| 377. | 2,4-Br$_2$-6-Cl—C$_6$H$_2$ |
| 378. | 2,5-Br$_2$-3-Br—C$_6$H$_2$ |
| 379. | 2,5-Br$_2$-4-Cl—C$_6$H$_2$ |
| 380. | 2,5-Br$_2$-6-Cl—C$_6$H$_2$ |
| 381. | 2,6-Br$_2$—Cl—C$_6$H$_2$ |
| 382. | 2,6-Br$_2$-4-Cl—C$_6$H$_2$ |
| 383. | 2,3-Br$_2$-4-OCH$_3$—C$_6$H$_2$ |
| 384. | 2,3-Br$_2$-5-OCH$_3$—C$_6$H$_2$ |
| 385. | 2,3-Br$_2$-6-OCH$_3$—C$_6$H$_2$ |
| 386. | 2,4-Br$_2$-3-OCH$_3$—C$_6$H$_2$ |
| 387. | 2,4-Br$_2$-5-OCH$_3$—C$_6$H$_2$ |
| 388. | 2,4-Br$_2$-6-OCH$_3$—C$_6$H$_2$ |
| 389. | 2,5-Br$_2$-3-OCH$_3$—C$_6$H$_2$ |
| 390. | 2,5-Br$_2$-4-OCH$_3$—C$_6$H$_2$ |
| 391. | 2,5-Br$_2$-6-OCH$_3$—C$_6$H$_2$ |
| 392. | 2,6-Br$_2$-3-OCH$_3$—C$_6$H$_2$ |
| 393. | 2,6-Br$_2$-4-OCH$_3$—C$_6$H$_2$ |
| 394. | 2-F-3-Cl-4-OCH$_3$—C$_6$H$_2$ |
| 395. | 2-F-3-Cl-5-OCH$_3$—C$_6$H$_2$ |
| 396. | 2-F-3-Cl-6-OCH$_3$—C$_6$H$_2$ |
| 397. | 2-F-5-Cl-4-OCH$_3$—C$_6$H$_2$ |
| 398. | 2-F-6-Cl-4-OCH$_3$—C$_6$H$_2$ |
| 399. | 2-F-3-OCH$_3$-4-Cl—C$_6$H$_2$ |
| 400. | 2-F-3-OCH$_3$-5-Cl—C$_6$H$_2$ |
| 401. | 2-F-3-OCH$_3$-6-Cl—C$_6$H$_2$ |
| 402. | 2-F-5-OCH$_3$-4-Cl—C$_6$H$_2$ |
| 403. | 2-F-6-OCH$_3$-4-Cl—C$_6$H$_2$ |
| 404. | 3-F-4-Cl-5-OCH$_3$—C$_6$H$_2$ |
| 405. | 3-F-2-Cl-5-OCH$_3$—C$_6$H$_2$ |
| 406. | 3-F-6-Cl-5-OCH$_3$—C$_6$H$_2$ |
| 407. | 3-F-4-Cl-2-OCH$_3$—C$_6$H$_2$ |
| 408. | 3-F-4-Cl-6-OCH$_3$—C$_6$H$_2$ |
| 409. | 3-F-4-OCH$_3$-5-Cl—C$_6$H$_2$ |
| 410. | 3-F-2-OCH$_3$-5-Cl—C$_6$H$_2$ |
| 411. | 3-F-6-OCH$_3$-5-Cl—C$_6$H$_2$ |
| 412. | 3-F-4-OCH$_3$-2-Cl—C$_6$H$_2$ |
| 413. | 3-F-4-OCH$_3$-6-Cl—C$_6$H$_2$ |
| 414. | 4-F-3-Cl-5-OCH$_3$—C$_6$H$_2$ |
| 415. | 4-F-3-Cl-2-OCH$_3$—C$_6$H$_2$ |
| 416. | 4-F-3-Cl-6-OCH$_3$—C$_6$H$_2$ |
| 417. | 4-F-2-Cl-5-OCH$_3$—C$_6$H$_2$ |
| 418. | 4-F-2-Cl-6-OCH$_3$—C$_6$H$_2$ |
| 419. | 4-F-3-OCH$_3$-5-Cl—C$_6$H$_2$ |
| 420. | 4-F-3-OCH$_3$-2-Cl—C$_6$H$_2$ |
| 421. | 4-F-3-OCH$_3$-6-Cl—C$_6$H$_2$ |
| 422. | 4-F-2-OCH$_3$-5-Cl—C$_6$H$_2$ |

TABLE 2a-continued

| no. | X |
|---|---|
| 423. | 4-F-2-OCH$_3$-6-Cl—C$_6$H$_2$ |
| 424. | 5-F-3-Cl-4-OCH$_3$—C$_6$H$_2$ |
| 425. | 5-F-3-Cl-2-OCH$_3$—C$_6$H$_2$ |
| 426. | 5-F-3-Cl-6-OCH$_3$—C$_6$H$_2$ |
| 427. | 5-F-2-Cl-4-OCH$_3$—C$_6$H$_2$ |
| 428. | 5-F-6-Cl-4-OCH$_3$—C$_6$H$_2$ |
| 429. | 5-F-3-OCH$_3$-4-Cl—C$_6$H$_2$ |
| 430. | 5-F-3-OCH$_3$-2-Cl—C$_6$H$_2$ |
| 431. | 5-F-3-OCH$_3$-6-Cl—C$_6$H$_2$ |
| 432. | 5-F-2-OCH$_3$-4-Cl—C$_6$H$_2$ |
| 433. | 5-F-6-OCH$_3$-4-Cl—C$_6$H$_2$ |
| 434. | 6-F-5-Cl-4-OCH$_3$—C$_6$H$_2$ |
| 435. | 6-F-5-Cl-3-OCH$_3$—C$_6$H$_2$ |
| 436. | 6-F-5-Cl-2-OCH$_3$—C$_6$H$_2$ |
| 437. | 6-F-3-Cl-4-OCH$_3$—C$_6$H$_2$ |
| 438. | 6-F-2-Cl-4-OCH$_3$—C$_6$H$_2$ |
| 439. | 6-F-5-OCH$_3$-4-Cl—C$_6$H$_2$ |
| 440. | 6-F-5-OCH$_3$-3-Cl—C$_6$H$_2$ |
| 441. | 6-F-5-OCH$_3$-2-Cl—C$_6$H$_2$ |
| 442. | 6-F-3-OCH$_3$-4-Cl—C$_6$H$_2$ |
| 443. | 6-F-2-OCH$_3$-4-Cl—C$_6$H$_2$ |
| 444. | 2-Cl-3-F-4-OCH$_3$—C$_6$H$_2$ |
| 445. | 2-Cl-3-F-5-OCH$_3$—C$_6$H$_2$ |
| 446. | 2-Cl-3-F-6-OCH$_3$—C$_6$H$_2$ |
| 447. | 2-Cl-5-F-4-OCH$_3$—C$_6$H$_2$ |
| 448. | 2-Cl-6-F-4-OCH$_3$—C$_6$H$_2$ |
| 449. | 2-Cl-3-OCH$_3$-4-F—C$_6$H$_2$ |
| 450. | 2-Cl-3-OCH$_3$-5-F—C$_6$H$_2$ |
| 451. | 2-Cl-3-OCH$_3$-6-F—C$_6$H$_2$ |
| 452. | 2-Cl-5-OCH$_3$-4-F—C$_6$H$_2$ |
| 453. | 2-Cl-6-OCH$_3$-4-F—C$_6$H$_2$ |
| 454. | 3-Cl-4-F-5-OCH$_3$—C$_6$H$_2$ |
| 455. | 3-Cl-2-F-5-OCH$_3$—C$_6$H$_2$ |
| 456. | 3-Cl-6-F-5-OCH$_3$—C$_6$H$_2$ |
| 457. | 3-Cl-4-F-2-OCH$_3$—C$_6$H$_2$ |
| 458. | 3-Cl-4-F-6-OCH$_3$—C$_6$H$_2$ |
| 459. | 3-Cl-4-OCH$_3$-5-F—C$_6$H$_2$ |
| 460. | 3-Cl-2-OCH$_3$-5-F—C$_6$H$_2$ |
| 461. | 3-Cl-6-OCH$_3$-5-F—C$_6$H$_2$ |
| 462. | 3-Cl-4-OCH$_3$-2-F—C$_6$H$_2$ |
| 463. | 3-Cl-4-OCH$_3$-6-F—C$_6$H$_2$ |
| 464. | 4-Cl-3-F-5-OCH$_3$—C$_6$H$_2$ |
| 465. | 4-Cl-3-F-2-OCH$_3$—C$_6$H$_2$ |
| 466. | 4-Cl-3-F-6-OCH$_3$—C$_6$H$_2$ |
| 467. | 4-Cl-2-F-5-OCH$_3$—C$_6$H$_2$ |
| 468. | 4-Cl-2-F-6-OCH$_3$—C$_6$H$_2$ |
| 469. | 4-Cl-3-OCH$_3$-5-F—C$_6$H$_2$ |
| 470. | 4-Cl-3-OCH$_3$-2-F—C$_6$H$_2$ |
| 471. | 4-Cl-3-OCH$_3$-6-F—C$_6$H$_2$ |
| 472. | 4-Cl-2-OCH$_3$-5-F—C$_6$H$_2$ |
| 473. | 4-Cl-2-OCH$_3$-6-F—C$_6$H$_2$ |
| 474. | 5-Cl-3-F-4-OCH$_3$—C$_6$H$_2$ |
| 475. | 5-Cl-3-F-2-OCH$_3$—C$_6$H$_2$ |
| 476. | 5-Cl-3-F-6-OCH$_3$—C$_6$H$_2$ |
| 477. | 5-Cl-2-F-4-OCH$_3$—C$_6$H$_2$ |
| 478. | 5-Cl-6-F-4-OCH$_3$—C$_6$H$_2$ |
| 479. | 5-Cl-3-OCH$_3$-4-F—C$_6$H$_2$ |
| 480. | 5-Cl-3-OCH$_3$-2-F—C$_6$H$_2$ |
| 481. | 5-Cl-3-OCH$_3$-6-F—C$_6$H$_2$ |
| 482. | 5-Cl-2-OCH$_3$-4-F—C$_6$H$_2$ |
| 483. | 5-Cl-6-OCH$_3$-4-F—C$_6$H$_2$ |
| 484. | 6-Cl-5-F-4-OCH$_3$—C$_6$H$_2$ |
| 485. | 6-Cl-5-F-3-OCH$_3$—C$_6$H$_2$ |
| 486. | 6-Cl-5-F-2-OCH$_3$—C$_6$H$_2$ |
| 487. | 6-Cl-3-F-4-OCH$_3$—C$_6$H$_2$ |
| 488. | 6-Cl-2-F-4-OCH$_3$—C$_6$H$_2$ |
| 489. | 6-Cl-5-OCH$_3$-4-F—C$_6$H$_2$ |
| 490. | 6-Cl-5-OCH$_3$-3-F—C$_6$H$_2$ |
| 491. | 6-Cl-5-OCH$_3$-2-F—C$_6$H$_2$ |
| 492. | 6-Cl-3-OCH$_3$-4-F—C$_6$H$_2$ |
| 493. | 6-Cl-2-OCH$_3$-4-F—C$_6$H$_2$ |
| 494. | 2-OCH$_3$-3-Cl-4-F—C$_6$H$_2$ |
| 495. | 2-OCH$_3$-3-Cl-5-F—C$_6$H$_2$ |
| 496. | 2-OCH$_3$-3-Cl-6-F—C$_6$H$_2$ |
| 497. | 2-OCH$_3$-5-Cl-4-F—C$_6$H$_2$ |
| 498. | 2-OCH$_3$-6-Cl-4-F—C$_6$H$_2$ |
| 499. | 2-OCH$_3$-3-F-4-Cl—C$_6$H$_2$ |
| 500. | 2-OCH$_3$-3-F-5-Cl—C$_6$H$_2$ |
| 501. | 2-OCH$_3$-3-F-6-Cl—C$_6$H$_2$ |
| 502. | 2-OCH$_3$-5-F-4-Cl—C$_6$H$_2$ |
| 503. | 2-OCH$_3$-6-F-4-Cl—C$_6$H$_2$ |
| 504. | 3-OCH$_3$-4-Cl-5-F—C$_6$H$_2$ |
| 505. | 3-OCH$_3$-2-Cl-5-F—C$_6$H$_2$ |
| 506. | 3-OCH$_3$-6-Cl-5-F—C$_6$H$_2$ |
| 507. | 3-OCH$_3$-4-Cl-2-F—C$_6$H$_2$ |
| 508. | 3-OCH$_3$-4-Cl-6-F—C$_6$H$_2$ |
| 509. | 3-OCH$_3$-4-F-5-Cl—C$_6$H$_2$ |
| 510. | 3-OCH$_3$-2-F-5-Cl—C$_6$H$_2$ |
| 511. | 3-OCH$_3$-6-F-5-Cl—C$_6$H$_2$ |
| 512. | 3-OCH$_3$-4-F-2-Cl—C$_6$H$_2$ |
| 513. | 3-OCH$_3$-4-F-6-Cl—C$_6$H$_2$ |
| 514. | 4-OCH$_3$-3-Cl-5-F—C$_6$H$_2$ |
| 515. | 4-OCH$_3$-3-Cl-2-F—C$_6$H$_2$ |
| 516. | 4-OCH$_3$-3-Cl-6-F—C$_6$H$_2$ |
| 517. | 4-OCH$_3$-2-Cl-5-F—C$_6$H$_2$ |
| 518. | 4-OCH$_3$-2-Cl-6-F—C$_6$H$_2$ |
| 519. | 4-OCH$_3$-3-F-5-Cl—C$_6$H$_2$ |
| 520. | 4-OCH$_3$-3-F-2-Cl—C$_6$H$_2$ |
| 521. | 4-OCH$_3$-3-F-6-Cl—C$_6$H$_2$ |
| 522. | 4-OCH$_3$-2-F-5-Cl—C$_6$H$_2$ |
| 523. | 4-OCH$_3$-2-F-6-Cl—C$_6$H$_2$ |
| 524. | 5-OCH$_3$-3-Cl-4-F—C$_6$H$_2$ |
| 525. | 5-OCH$_3$-3-Cl-2-F—C$_6$H$_2$ |
| 526. | 5-OCH$_3$-3-Cl-6-F—C$_6$H$_2$ |
| 527. | 5-OCH$_3$-2-Cl-4-F—C$_6$H$_2$ |
| 528. | 5-OCH$_3$-6-Cl-4-F—C$_6$H$_2$ |
| 529. | 5-OCH$_3$-3-F-4-Cl—C$_6$H$_2$ |
| 530. | 5-OCH$_3$-3-F-2-Cl—C$_6$H$_2$ |
| 531. | 5-OCH$_3$-3-F-6-Cl—C$_6$H$_2$ |
| 532. | 5-OCH$_3$-2-F-4-Cl—C$_6$H$_2$ |
| 533. | 5-OCH$_3$-6-F-4-Cl—C$_6$H$_2$ |
| 534. | 6-OCH$_3$-5-Cl-4-F—C$_6$H$_2$ |
| 535. | 6-OCH$_3$-5-Cl-3-F—C$_6$H$_2$ |
| 536. | 6-OCH$_3$-5-Cl-2-F—C$_6$H$_2$ |
| 537. | 6-OCH$_3$-3-Cl-4-F—C$_6$H$_2$ |
| 538. | 6-OCH$_3$-2-Cl-4-F—C$_6$H$_2$ |
| 539. | 6-OCH$_3$-5-F-4-Cl—C$_6$H$_2$ |
| 540. | 6-OCH$_3$-5-F-3-Cl—C$_6$H$_2$ |
| 541. | 6-OCH$_3$-5-F-2-Cl—C$_6$H$_2$ |
| 542. | 6-OCH$_3$-3-F-4-Cl—C$_6$H$_2$ |
| 543. | 6-OCH$_3$-2-F-4-Cl—C$_6$H$_2$ |
| 544. | 2,3,4,5-F$_4$—C$_6$H |
| 545. | 2,3,4,5-Cl$_4$—C$_6$H |
| 546. | 2,3,4,5-Br$_4$—C$_6$H |
| 547. | 2,3,4,5-(OCH$_3$)$_4$—C$_6$H |
| 548. | 2,3,5,6-F$_4$-4-Cl—C$_6$ |
| 549. | 2,4,5,6-F$_4$-3-Cl—C$_6$ |
| 550. | 2,3,4,6-F$_4$-5-Cl—C$_6$ |
| 551. | 2,3,4,5-F$_4$-6-Cl—C$_6$ |
| 552. | 3,4,5,6-F$_4$-2-Cl—C$_6$ |
| 553. | 2,3,5,6-F$_4$-4-Br—C$_6$ |
| 554. | 2,4,5,6-F$_4$-3-Br—C$_6$ |
| 555. | 2,3,4,6-F$_4$-5-Br—C$_6$ |
| 556. | 2,3,4,5-F$_4$-6-Br—C$_6$ |
| 557. | 3,4,5,6-F$_4$-2-Br—C$_6$ |
| 558. | 2,3,5,6-F$_4$-4-OCH$_3$—C$_6$ |
| 559. | 2,4,5,6-F$_4$-3-OCH$_3$—C$_6$ |
| 560. | 2,3,4,6-F$_4$-5-OCH$_3$—C$_6$ |
| 561. | 2,3,4,5-F$_4$-6-OCH$_3$—C$_6$ |
| 562. | 3,4,5,6-F$_4$-2-OCH$_3$—C$_6$ |
| 563. | 2,3,4,5,6-F$_5$—C$_6$ |

Further particular groups (4) of embodiments relate to the diaminotriazine compounds of formula (I), wherein
X is OR$^{3c}$, where
R$^{3c}$ is in particular selected from the group consisting of
C$_1$-C$_6$-alkyl, (C$_1$-C$_6$-alkoxy)-C$_1$-C$_6$-alkyl, C$_3$-C$_6$-cycloalkyl, (C$_1$-C$_6$-alkyl)-carbonyl, (C$_1$-C$_6$-alkoxy)carbonyl, (C$_1$-C$_6$-alkyl)sulfonyl, where the aliphatic parts of the 6 aforementioned radicals unsubstituted, partly or completely halogenated; phenyl, phenylsulfonyl or phenyl-C$_1$-C$_6$ alkyl,
wherein phenyl in the last 3 mentioned radicals is unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy more particularly from the group consisting of C$_1$-C$_4$-alkyl, (C$_1$-C$_4$-alkoxy)-C$_1$-C$_4$-alkyl, C$_3$-C$_4$-cycloalkyl, (C$_1$-C$_4$-alkyl)-carbonyl, (C$_1$-C$_4$-alkoxy)carbonyl, (C$_1$-C$_4$-alkyl)sulfonyl, where the aliphatic parts of the 6 aforementioned radicals unsubstituted, partly or completely halogenated;

especially C$_1$-C$_4$-alkyl, such as CH$_3$, CH$_3$CH$_2$, CH(CH$_3$)$_2$, CH$_2$CH(CH$_3$)$_2$, C(CH$_3$)$_3$, or C$_1$-C$_4$-haloalkyl, such as CH$_2$CF$_3$, CF(CH$_3$)$_2$, CH(CF$_3$)$_2$ or CH(CH$_3$)CF$_3$.

Further particular groups (5) of embodiments relate to the diaminotriazine compounds of formula (I), wherein X is S(O)$_k$R$^{3d}$, wherein k and R$^{3d}$ are as defined above where R$^{3d}$ is in particular selected from the group consisting of H, C$_1$-C$_6$-alkyl, (C$_1$-C$_6$-alkoxy)-C$_1$-C$_6$-alkyl, C$_3$-C$_6$-cycloalkyl, (C$_1$-C$_6$-alkyl)-carbonyl, (C$_1$-C$_6$-alkoxy)carbonyl, (C$_1$-C$_6$-alkyl)sulfonyl, where the aliphatic parts of the 6 aforementioned radicals unsubstituted, partly or completely halogenated; phenyl, phenylsulfonyl or phenyl-C$_1$-C$_6$ alkyl, wherein phenyl in the last 3 mentioned radicals is unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy more particularly from the group consisting of C$_1$-C$_4$-alkyl, (C$_1$-C$_4$-alkoxy)-C$_1$-C$_4$-alkyl, C$_3$-C$_4$-cycloalkyl, (C$_1$-C$_4$-alkyl)-carbonyl, (C$_1$-C$_4$-alkoxy)carbonyl, (C$_1$-C$_4$-alkyl)sulfonyl, where the aliphatic parts of the 6 aforementioned radicals unsubstituted, partly or completely halogenated especially C$_1$-C$_4$-alkyl, such as CH$_3$, CH$_3$CH$_2$, CH(CH$_3$)$_2$, CH$_2$CH(CH$_3$)$_2$, C(CH$_3$)$_3$, or C$_1$-C$_4$-haloalkyl, such as CH$_2$CF$_3$, CF(CH$_3$)$_2$, CH(CF$_3$)$_2$ or CH(CH$_3$)CF$_3$.

In this particular group (2) of embodiments, where X is S(O)$_k$R$^{3d}$ the variable k is preferably 0 or 2 and especially 0.

Further particular groups (6) of embodiments relate to the diaminotriazine compounds of formula (I), wherein X is NR$^{3a}$R$^{3b}$, wherein R$^{3a}$ and R$^{3b}$ are as defined above and wherein at least one of R$^{3a}$ and R$^{3b}$ is preferably different from H, and where R$^{3a}$ R$^{3b}$ are independently of one another H, CN, S(O)$_2$N H$_2$, C$_1$-C$_6$-alkyl, C$_1$-C$_6$-alkoxy, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, (C$_1$-C$_6$-alkoxy)-C$_1$-C$_6$-alkyl, (C$_1$-C$_6$-alkyl)-carbonyl, (C$_3$-C$_6$-cycloalkyl)-carbonyl, (C$_1$-C$_6$-alkoxy)carbonyl, (C$_1$-C$_6$-alkyl)sulfonyl, C$_1$-C$_6$-alkylamino)carbonyl, di(C$_1$-C$_6$-alkyl)aminocarbonyl, (C$_1$-C$_6$-alkylamino)sulfonyl, di(C$_1$-C$_6$-alkyl)aminosulfonyl and (C$_1$-C$_6$-alkoxy)sulfonyl where the aliphatic parts of the 16 aforementioned radicals are unsubstituted, partly or completely halogenated, phenyl, phenylsulfonyl or phenyl-C$_1$-C$_6$ alkyl, wherein phenyl in the last 3 mentioned radicals is unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy, one of R$^{3a}$, R$^{3b}$ may also be OH, C$_1$-C$_6$-alkoxy, C$_3$-C$_6$-cycloalkoxy, (C$_1$-C$_6$-alkoxy)-C$_1$-C$_6$-alkoxy, where the aliphatic and cycloaliphatic parts of the 3 aforementioned radicals are unsubstituted, partly or completely halogenated;

R$^{3a}$ R$^{3b}$ are independently of one another more particularly selected from the group consisting of H, C$_1$-C$_4$-alkyl, such as CH$_3$, CH$_3$CH$_2$, CH(CH$_3$)$_2$, CH$_2$CH(CH$_3$)$_2$, or C(CH$_3$)$_3$, C$_1$-C$_4$-haloalkyl, such as CH$_2$CF$_3$, CF(CH$_3$)$_2$, CH(CF$_3$)$_2$ or CH(CH$_3$)CF$_3$, C$_1$-C$_4$-alkoxy, such as methoxy, ethoxy, propoxy, 1-methylethoxy butoxy, 1-methylpropoxy, 2-methylpropoxy and 1,1-dimethylethoxy, phenyl and phenyl-C$_1$-C$_4$ alkyl, such as benzyl, 1-phenylethyl or 2-phenylethyl, wherein phenyl in phenyl and phenyl-C$_1$-C$_4$ alkyl is unsubstituted or substituted by 1, 2, 3, 4 or 5 identical or different substituents selected from the group consisting of halogen, CN, C$_1$-C$_4$-alkyl, C$_3$-C$_4$-cycloalkyl, C$_1$-C$_4$-haloalkyl, C$_1$-C$_4$-alkoxy and C$_1$-C$_4$-haloalkoxy Likewise more particularly R$^{3a}$R$^{3b}$ are independently of one another more particularly selected from the group consisting of H, C$_1$-C$_4$-alkyl, such as CH$_3$, CH$_3$CH$_2$, CH(CH$_3$)$_2$, CH$_2$CH(CH$_3$)$_2$, or C(CH$_3$)$_3$, C$_1$-C$_4$-haloalkyl, such as CH$_2$CF$_3$, CF(CH$_3$)$_2$, CH(CF$_3$)$_2$ or CH(CH$_3$)CF$_3$, phenyl and phenyl-C$_1$-C$_4$ alkyl, such as benzyl, 1-phenylethyl or 2-phenylethyl, wherein phenyl in phenyl and phenyl-C$_1$-C$_4$ alkyl is unsubstituted or substituted by 1, 2, 3, 4 or 5 identical or different substituents selected from the group consisting of halogen, CN, C$_1$-C$_4$-alkyl, C$_3$-C$_4$-cycloalkyl, C$_1$-C$_4$-haloalkyl, C$_1$-C$_4$-alkoxy and C$_1$-C$_4$-haloalkoxy;

especially from the group consisting of hydrogen, C$_1$-C$_4$-alkyl, such as CH$_3$, CH$_3$CH$_2$, CH(CH$_3$)$_2$, CH$_2$CH(CH$_3$)$_2$, C(CH$_3$)$_3$, phenyl and benzyl.

Further particular groups of (6.a) embodiments relate to the diaminotriazine compounds of formula (I), wherein X is NR$^{3a}$R$^{3b}$, wherein R$^{3a}$, R$^{3b}$ together with the nitrogen atom, to which they are bound, form an N bound saturated or unsaturated mono— or bicyclic heterocyclic radical, which may have 1, 2, 3 or 4, in particular 1 or 2, further heteroatoms which are selected from N, O and S, which heterocyclic radical is substituted or unsubstituted by one or more, e. g. 1, 2, 3, 4, 5 ,6, 7 or 8 identical or different substituents selected from the group consisting of halogen, CN, NO$_2$, C$_1$-C$_6$-alkyl, C$_1$-C$_6$-haloalkyl, C$_1$-C$_6$-alkoxy, (C$_1$-C$_6$-alkoxy)-C$_1$-C$_6$-alkyl and C$_1$-C$_6$-haloalkoxy, in particular selected from the group consisting halogen, CN, NO$_2$, C$_1$-C$_2$-alkyl, C$_1$-C$_2$-haloalkyl, (C$_1$-C$_2$-alkoxy)-C$_1$-C$_2$-alkyl, C$_1$-C$_2$-alkoxy and C$_1$-C$_2$-haloalkoxy;

R$^{3a}$, R$^{3b}$ together with the nitrogen atom, to which they are bound, in particular form an N bound saturated monoheterocyclic radical, which may have 1 or 2 further heteroatoms which are selected from N and O, which heterocyclic radical is substituted or unsubstituted by one or more, e. g. 1, 2, 3, 4, 5, 6, 7 or 8 identical or different substituents selected from the group consisting of halogen, CN, NO$_2$, C$_1$-C$_6$-alkyl, C$_1$-C$_6$-haloalkyl, C$_1$-C$_6$-alkoxy, (C$_1$-C$_6$-alkoxy)-C$_1$-C$_6$-alkyl and C$_1$-C$_6$-haloalkoxy, in particular selected from the group consisting halogen, CN, NO$_2$, C$_1$-C$_2$-alkyl, C$_1$-C$_2$-haloalkyl, (C$_1$-C$_2$-alkoxy)-C$_1$-C$_2$-alkyl, C$_1$-C$_2$-alkoxy and C$_1$-C$_2$-haloalkoxy;

R$^{3a}$, R$^{3b}$ together with the nitrogen atom, to which they are bound, more particularly form an N bound saturated mono- or bicyclic heterocyclic radical, which is selected from the group consisting of 1-aziridinyl, 1-azetidinyl, 1-piperidinyl, 1-pyrrolidinyl, azepan-1-yl, azocan-1-yl, morpholin-4-yl, isoxazolidine-2-yl, oxazolidine-3-yl, piperazine-1-yl, octahydroisoindol-2-yl, octahydroindol-1-yl, octahydro-2H-quinolin-1-yl, azabicyclo[2.2.1]heptan-3-yl and azabicyclo[2.2.1]heptan-7-yl, where the aforementioned radicals are unsubstituted or substituted by one or more identical or different substituents selected from the group consisting of halogen, CN, NO$_2$, C$_1$-C$_2$- alkyl, $C_1$-$C_2$-haloalkyl, ($C_1$-$C_2$-alkoxy)-$C_1$-$C_2$-alkyl, $C_1$-$C_2$-alkoxy and $C_1$-$C_2$-haloalkoxy;

$R^{3a}$, $R^{3b}$ together with the nitrogen atom, to which they are bound, especially form an N-bound saturated monocyclic heterocyclic radical, which is selected from the group consisting of 1-azetidinyl, 1-piperidinyl, 1-pyrrolidinyl, azepan-1-yl, azocan-1-yl, morpholin-4-yl, where the aforementioned radicals are unsubstituted or substituted by one or more identical or different substituents selected from the group consisting of halogen, CN, $NO_2$, $C_1$-$C_2$-alkyl, $C_1$-$C_2$-haloalkyl, ($C_1$-$C_2$-alkoxy)-$C_1$-$C_2$-alkyl, $C_1$-$C_2$-alkoxy and $C_1$-$C_2$-haloalkoxy.

Especially preferred examples of X, wherein X is $NR^{3a}R^{3b}$, $OR^{3c}$ or $S(O)_kR^{3d}$ are given in rows 1 to 75 of table 3a.

TABLE 3a

| no. | X |
|---|---|
| 1 | NH—$CH_3$ |
| 2 | N($CH_3$)$_2$ |
| 3 | NH—$C_2H_5$ |
| 4 | N($CH_3$)—$C_2H_5$ |
| 5 | N($C_2H_5$)$_2$ |
| 6 | NH—CH($CH_3$)$_2$ |
| 7 | NH—C($CH_3$)$_3$ |
| 8 | NH—$OCH_3$ |
| 9 | N($CH_3$)—$OCH_3$ |
| 10 | NH—$OC_2H_5$ |
| 11 | NH—$C_6H_5$ |
| 12 | NH—$CH_2C_6H_5$ |
| 13 | N($CH_3$)$C_6H_5$ |
| 14 | N1 |
| 15 | N2 |
| 16 | N3 |
| 17 | N4 |
| 18 | N5 |
| 19 | N6 |
| 20 | N7 |
| 21 | (R/S)-N8 |
| 22 | (R)-N8 |
| 23 | (S)-N8 |
| 24 | E-N9 |
| 25 | Z-N9 |
| 26 | E-N10 |
| 27 | Z-N10 |
| 28 | N11 |
| 29 | N12 |
| 30 | N13 |
| 31 | (R/S)-N14 |
| 32 | (R)-N14 |
| 33 | (S)-N14 |
| 34 | O—$CH_3$ |
| 35 | O—$C_2H_5$ |
| 36 | O—$CH_2CF_3$ |
| 37 | O—CH($CH_3$)$_2$ |
| 38 | O—C($CH_3$)$_3$ |
| 39 | O—CH($C_2H_5$)$_2$ |
| 40 | O—$CH_2$CH($CH_3$)$_2$ |
| 41 | O—CH($CH_3$)($CF_3$) |
| 42 | O—CF($CH_3$)$_2$ |
| 43 | O—C($CF_3$)($CH_3$)$_2$ |
| 44 | O—$CH_2OCH_3$ |
| 45 | O—$CH_2CH_2OCH_3$ |
| 46 | O—$C_6H_5$ |
| 47 | O—c-$C_3H_5$ |
| 48 | O—c-$C_5H_9$ |
| 49 | O—c-$C_6H_{11}$ |
| 50 | O—O1 |
| 51 | O—O2 |
| 52 | O—O3 |
| 53 | O—$CH_2$—c-$C_3H_5$ |
| 54 | O—$CH_2$—c-$C_5H_9$ |
| 55 | S—$CH_3$ |
| 56 | S—$C_2H_5$ |
| 57 | S—$CH_2CF_3$ |
| 58 | S—CH($CH_3$)$_2$ |

TABLE 3a-continued

| no. | X |
|---|---|
| 59 | S—C($CH_3$)$_3$ |
| 60 | S—CH($C_2H_5$)$_2$ |
| 61 | S—$CH_2$CH($CH_3$)$_2$ |
| 62 | S—CH($CH_3$)($CF_3$) |
| 63 | S—CF($CH_3$)$_2$ |
| 64 | S—C($CF_3$)($CH_3$)$_2$ |
| 65 | S—$CH_2OCH_3$ |
| 66 | S—$CH_2CH_2OCH_3$ |
| 67 | S—$C_6H_5$ |
| 68 | S—c-$C_3H_5$ |
| 69 | S—c-$C_5H_9$ |
| 70 | S—c-$C_6H_{11}$ |
| 71 | S—O1 |
| 72 | S—O2 |
| 73 | S—O3 |
| 74 | S—$CH_2$—c-$C_3H_5$ |
| 75 | S—$CH_2$—c-$C_5H_9$ |

In table 3a the abbreviations given in the following table A1 are used:

TABLE A1

| c-$C_3H_5$ | cyclopropyl |
|---|---|
| c-$C_5H_9$ | cyclopentyl |
| c-$C_6H_{11}$ | cyclohexyl |
| $C_6H_5$ | Phenyl |
| N1 | azetidin-1-yl |
| N2 | aziridin-1-yl |
| N3 | pyrrolidin-1-yl |
| N4 | piperidin-1-yl |
| N5 | azepan-1-yl |
| N6 | azocan-1-yl |
| N7 | azonan-1-yl |
| (R/S)-N8 | (R/S)-2-methylpyrrolidin-1-yl |
| (R)-N8 | (R)-2-methylpyrrolidin-1-yl |
| (S)-N8 | (S)-2-methylpyrrolidin-1-yl |
| E-N9 | E-2,5-dimethylpyrrolidin-1-yl |
| Z-N9 | Z-2,5-dimethylpyrrolidin-1-yl |
| E-N10 | E-3,5-dimethylpiperidin-1-yl |
| Z-N10 | S-3,5-dimethylpiperidin-1-yl |
| N11 | morpholin-4-yl |
| N12 | 4-methylpiperazin-1-yl |
| N13 | Isoxazolidin-2-yl |
| (R/S)-N14 | (2R)-2-(methoxymethyl)pyrrolidin-1-yl |
| (R)-N14 | (2S)-2-(methoxymethyl)pyrrolidin-1-yl |
| (S)-N14 | (2R/S)-2-(methoxymethyl)pyrrolidin-1-yl |
| O1 | oxetan-2-yl |
| O2 | oxetan-3-yl |
| O3 | oxan-4-yl |

Particularly preferred are the diaminotriazine compounds of formula (I), and likewise the diaminotriazine compounds of formula (I) according to embodiment groups (1), (2), (2a), (2b), (3), (4), (5), (6) and (6a), wherein A is defined above, $R^1$ is hydrogen; and $R^2$ is hydrogen.

Particularly preferred are the diaminotriazine compounds of formula (I), and likewise the diaminotriazine compounds of formula (I) according to embodiment groups (1), (2), (2a), (2b) wherein $R^1$ is hydrogen;

$R^2$ is hydrogen;

X is as defined for groups (1), (2), (2a) and (2b) of embodiments.

Particularly preferred are the diaminotriazine compounds of formula (I), and likewise the diaminotriazine compounds of formula (I) according to embodiment groups (3), (4), (5), (6) and (6a) wherein
$R^1$ is hydrogen;
$R^2$ is hydrogen;
X is as defined for groups (3), (4), (5), (6) and (6a) of embodiments.

Particularly preferred are the diaminotriazine compounds of formula (I), and likewise the diaminotriazine compounds of formula (I) according to embodiment groups (1), (2), (2a), (2b), (3), (6) and (6a) wherein
$R^1$ is hydrogen;
$R^2$ is hydrogen;
X is as defined for groups (1), (2), (2a), (2b), (3), (6) and (6a) of embodiments and wherein

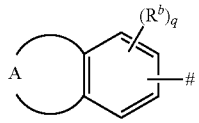

is represented by the moiety

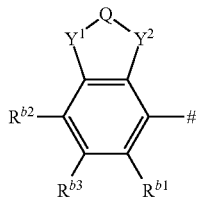

$R^{b1}$, $R^{b2}$ and $R^{b3}$ are identical or different and are hydrogen or have one of the meanings of $R^b$ as defined above;
$Y^1$, $Y^2$ independently of each other are O, S or $NR^c$, wherein $R^c$ is as defined above and preferably selected from the group consisting of of H, $S(O)_2NH_2$, CN, $C_1$-$C_4$-alkyl, $C_1$-$C_4$-haloalkyl, $C_2$-$C_4$-alkenyl, $C_2$-$C_4$-alkynyl. More particular $R^c$ is selected from the group consisting of H, $S(O)_2NH_2$, CN, methyl, ethyl;
Q is $CR^{A1}R^{A2}$ or $CR^{A3}R^{A4}$—$CR^{A5}R^{A6}$ wherein $R^{A1}$, $R^{A2}$, $R^{A3}$, $R^4$, $R^{A5}$, $R^{A6}$ are identical or different and are hydrogen or have one of the meanings given for $R^A$ defined above;
A is a fused saturated or unsaturated 5- or 6-membered heteroocycle having 1, 2 or 3 heteroatoms or heteroatom moieties, selected from O, S, $S(O)_p$, N or $NR^c$ as ring members, where the heterocycle are unsubstituted or carry 1, 2, 3 or 4 radicals $R^A$ as defined above, preferably selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$NR^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;
more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S,
even more particularly selected from the group consisting of F, Cl, methyl and that that two radicals $R^A$ which are bound at the same carbon atom may together be =O or S.

More particular
A is a fused saturated 5- or 6-membered heterocycle having 1, 2 or 3 heteroatoms or heteroatom moieties, selected from O, S, $S(O)_p$, N or $NR^c$ in particular O or S as ring members, where the heterocycle are unsubstituted or carry 1, 2, 3 or 4 radicals $R^A$ as defined above, and where $R^A$ is
in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$N R^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;
more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S,
even more particularly selected from the group consisting of F, Cl, methyl and that two radicals $R^A$ which are bound at the same carbon atom may together be =O or S
and where $R^c$ has the meaning as defined above. Likewise more particular
A is a fused unsaturated 5- or 6-membered heterocycle having 1, 2 or 3 heteroatoms or heteroatom moieties, selected from O, S, $S(O)_p$, N or $NR^c$ in particular O or S as ring members, where the heterocycle are unsubstituted or carry 1, 2, 3 or 4 radicals $R^A$ as defined above, and where $R^A$ is
in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =$NR^d$; wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

more particular selected from the group consisting of halogen, CN, $C_1$-$C_4$-alkyl, $C_1$-C4-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that two radicals $R^A$ which are bound at the same carbon atom may together be =O or S and where $R^c$ has the meaning as defined above.

Likewise more particular

A is a fused saturated 5- or 6-membered heterocycle having 1, 2 or 3 heteroatoms or heteroatom moieties, selected from O, S, S(O)$_p$, N or NR$^c$ in particular O, N or NR$^c$ as ring members, where the heterocycle are unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =NR$^d$;

wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that two radicals $R^A$ which are bound at the same carbon atom may together be =O or S and where $R^c$ has the meaning as defined above.

Likewise more particular

A is a fused unsaturated 5- or 6-membered heterocycle having 1, 2 or 3 heteroatoms or heteroatom moieties, selected from O, S, S(O)$_p$, N or NR$^c$ in particular O, N or NR$^C$ as ring members, where the heterocycle are unsubstituted or carry 1, 2, 3 or 4 radicals $R^A$ as defined above, and where $R^A$ is in particular selected from the group consisting of halogen, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, ($C_3$-$C_6$-cycloalkyl)-$C_1$-$C_4$-alkoxy, $C_2$-$C_6$-alkenyl, $C_2$-$C_6$-alkynyl, $C_2$-$C_6$-alkenyloxy and $C_2$-$C_6$-alkynyloxy, and where the cycloaliphatic parts of the last 2 mentioned radicals may carry 1, 2, 3, 4, 5 or 6 methyl groups, and it being possible that $R^A$ are identical or different, it being possible that two radicals $R^A$ which are bound at the same carbon atom may together be =O, S, or =NR$^d$;

wherein $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

more particular selected from the group consisting of halogen, CN, $C_1$-$C_4$-alkyl, $C_1$-$C_4$-alkoxy, $C_1$-$C_4$-haloalkyl, $C_1$-$C_4$-haloalkoxy and it being possible that $R^A$ are identical or different and that two radicals $R^A$ which are bound at the same carbon atom may together be =O, S, even more particularly selected from the group consisting of F, Cl, methyl and that two radicals $R^A$ which are bound at the same carbon atom may together be =O or S and where $R^c$ has the meaning as defined above.

In particular $Y^1$ is O, S, NR$^c$, wherein $R^c$ has the meaning as defined above, $Y^2$ is O, S, NR$^c$, wherein $R^c$ has the meaning as defined above, Q is CR$^{A1}$R$^{A2}$, wherein R$^{A1}$R$^{A2}$ are identical or different and are hydrogen or have one of the meanings of $R^A$ defied above, $R^{b1}$ are hydrogen and one of the meanings of $R^b$ as defined above, $R^{b2}$ are hydrogen and one of the meanings of $R^b$ as defined above, $R^{b3}$ are hydrogen and one of the meanings of $R^b$ as defined above, More particular $Y^1$ is O, S, $Y^2$ is O, S, Q is CR$^{A1}$R$^{A2}$, wherein R$^{A1}$R$^{A2}$ are identical or different and are hydrogen, halogen, $C_1$-$C_4$-alkyl, $C_1$-$C_4$-haloalkyl, $C_1$-$C_4$-alkoxy, $C_1$-$C_4$-haloalkoxy, $R^{b1}$ are hydrogen, CN, halogen or $C_1$-$C_4$-alkyl, in particular hydrogen, CN, methyl, flourine or bromine, $R^{b2}$ are hydrogen or halogen, in particular hydrogen, flourine or bromine, $R^{b3}$ are hydrogen, CN halogen or $C_1$-$C_4$-alkyl in particular hydrogen, CN, methyl, flourine or bromine.

Even more particular $Y^1$ and $Y^2$ are each O, S,

Q CR$^{A1}$R$^{A2}$, wherein R$^{A1}$ and R$^{A2}$ are identical or different and are hydrogen, F, Cl, methyl, or R$^{A1}$ and R$^{A2}$ together may be =O, $R^{b1}$ are hydrogen, halogen, such as F, Cl, Br, methyl, CN, $R^{b2}$ are hydrogen, F, Cl, Br, $R^{b3}$ are hydrogen, F, Cl, Br.

Likewise in particular $Y^1$ is O, S, NR$^c$, wherein $R^c$ has the meaning as defined above, $Y^2$ is O, S, NR$^c$, wherein $R^c$ has the meaning as defined above, Q is CR$^{A3}$R$^{A4}$—CR$^{A5}$R$^{A6}$, wherein R$^{A3}$, R$^{A4}$, R$^{A5}$, R$^{A6}$ are identical or different and are hydrogen or have one of the meanings of $R^A$ defined above, $R^{b1}$ are hydrogen and one of the meanings of $R^b$ as defined above, $R^{b2}$ are hydrogen and one of the meanings of $R^b$ as defined above, $R^{b3}$ are hydrogen and one of the meanings of $R^b$ as defined above.

More particular $Y^1$ is O, S, $Y^2$ is O, S,

Q is $CR^{A3}R^{A4}$—$R^{A5}R^{A6}$, wherein $R^{A3}$, $R^{A4}$, $R^{A5}$, $R^{A6}$ are identical or different and are hydrogen, halogen, $C_1$-$C_4$-alkyl, $C_1$-$C_4$-haloalkyl, $C_1$-$C_4$-alkoxy, $C_1$-$C_4$-haloalkoxy, $R^{b1}$ are hydrogen, CN, halogen or $C_1$-$C_4$-alkyl, in particular hydrogen, CN, methyl, flourine or bromine, $R^{b2}$ are hydrogen or halogen, in particular hydrogen, flourine or bromine, $R^{b3}$ are hydrogen, CN halogen or $C_1$-$C_4$-alkyl in particular hydrogen, CN, methyl, flourine or bromine.

Even more particular $Y^1$ and $Y^2$ are each O, S,

Q $CR^{A3}R^{A4}$—$CR^{A5}R^{A6}$, wherein $R^{A3}$, $R^{A4}$, $R^{A5}$, $R^{A6}$ are identical or different and are hydrogen, F, Cl, methyl, $R^{b1}$ are hydrogen, halogen, such as F, Cl, Br, methyl, CN, $R^{b2}$ are hydrogen, F, Cl, Br, $R^{b3}$ are hydrogen, F, Cl, Br.

Likewise in particular $Y^1$ is O, N or $NR^c$, wherein $R^c$ has the meaning as defined above, $Y^2$ is O, N or $NR^c$, wherein $R^c$ has the meaning as defined above, Q is $CR^{A1}R^{A2}$, wherein $R^{A1}$, $R^{A2}$ are identical or different and are hydrogen, halogen, $C_1$-$C_4$-alkyl, $C_1$-$C_4$-haloalkyl, $C_1$-$C_4$-alkoxy, $C_1$-$C_4$-haloalkoxy, $R^{b1}$ are hydrogen, CN, halogen or $C_1$-$C_4$-alkyl, in particular hydrogen, CN, methyl, flourine or bromine, $R^{b2}$ are hydrogen or halogen, in particular hydrogen, flourine or bromine, $R^{b3}$ are hydrogen, CN halogen or $C_1$-$C_4$-alkyl in particular hydrogen, CN, methyl, flourine or bromine.

Particularly preferred is given to diaminotriazine compounds of formula (I.a), which correspondes to formula (I), wherein $R^1$ is hydrogen, $R^2$ is hydrogen and $R^{b1}$, $R^{b2}$, $R^{b3}$, $R^{A1}$, $R^{A2}$, $Y^1$ and $Y^2$ are given in table A, and wherein X is as defined above and in particular X is selected from the group consisting of $CF(CH_3)_2$, $CFCH_3CH_2CH_3$, $CHFCH_3$, $CHFCH_2CH_3$, $CF(CH_2CH_3)_2$, $CF_2CH_3$, t-butyl, i-butyl, s-butyl, 1-chloro-cyclobutyl, 2,2-dimethylpropyl, i-propyl, 1-fluoropropyl, cyclobutyl, cyclopentyl, cyclohexyl, 1-cyclopropylethyl, 1-methylcyclobutyl, 1-methylcyclopentyl, $C(CH_3)_2OCH_3$, 1-methylcyclohexyl, 1-methoxyethyl, 1-methoxy-cyclopentyl, 1-methoxy-cyclobutyl, 1-methoxyl-cyclohexyl, 1-fluorcyclopentyl, 1-fluor-cyclohexyl, 1-chlor-cyclopentyl, 1-chlor-cyclohexyl, 1-chlor-cyclobutyl, 2-methylpyrrolidin-1-yl, 2,2,2-trifluoroethoxy, azetidine, pyrrolidin-1-yl, piperidyl, methoxy(methyl)amino, 2-tetrahydrofuranyl, 2,4,6-tri-fluoro-phenyl, 2,6-difluoro-phenyl, 2-fluoro-phenyl or methoxy.

Examples of these compounds are those given in table A-1 to A-41.

Particular preference is given to diaminotriazine compounds of formula (I.a), which corresponds to diaminotriazines of formula (I) wherein $R^1$ and $R^2$ is hydrogen $R^{b1}$, $R^{b2}$, $R^{b3}$, $R^{A1}$, $R^{A2}$, $Y^1$ and $Y^2$ are defined in table A.

Table A-1: Compunds Compounds of formula (I.a), where X is $CFCH_3CH_2CH_3$ and $R^{b1}$, $R^{b2}$, $R^{b3}$, $R^{A1}$, $R^{A2}$, $Y^1$ and $Y^2$ are defined the rows of table A.

Table A-2: Compounds of formula (I.a), where X is $CF(CH_3)_2$ and $R^{b1}$, $R^{b2}$, $R^{b3}$, $R^{A1}$, $R^{A2}$, $Y^1$ and $Y^2$ are defined the rows of table A.

Table A-3: Compounds of formula (I.a), where X is $CHFCH_3$ and $R^{b1}$, $R^{b2}$, $R^{b3}$, $R^{A1}$, $R^{A2}$, $Y^1$ and $Y^2$ are defined the rows of table A.

Table A-4: Compounds of formula (I.a), where X is $CHFCH_2CH_3$ and $R^{b1}$, $R^{b2}$, $R^{b3}$, $R^{A1}$, $R^{A2}$, $Y^1$ and $Y^2$ are defined the rows of table A.

Table A-5: Compounds of formula (I.a), where X is $CF(CH_2CH_3)_2$ and $R^{b1}$, $R^{b2}$, $R^{b3}$, $R^{A1}$, $R^{A2}$, $Y^1$ and $Y^2$ are defined the rows of table A.

Table A-6: Compounds of formula (I.a), where X is $CF_2CH_3$ and $R^{b1}$, $R^{b2}$, $R^{b3}$, $R^{A1}$, $R^{A2}$, $Y^1$ and $Y^2$ are defined the rows of table A.

Table A-7: Compounds of formula (I.a), where X is t-butyl and $R^{b1}$, $R^{b2}$, $R^{b3}$, $R^{A1}$, $R^{A2}$, $Y^1$ and $Y^2$ are defined the rows of table A.

Table A-8: Compounds of formula (I.a), where X is i-butyl and $R^{b1}$, $R^{b2}$, $R^{b3}$, $R^{A1}$, $R^{A2}$, $Y^1$ and $Y^2$ are defined the rows of table A.

Table A-9: Compounds of formula (I.a), where X is 2,2-dimethylpropyl and $R^{b1}$, $R^{b2}$, $R^{b3}$, $R^{A1}$, $R^{A2}$, $Y^1$ and $Y^2$ are defined the rows of table A.

Table A-10: Compounds of formula (I.a), where X is i-propyl and $R^{b1}$, $R^{b2}$, $R^{b3}$, $R^{A1}$, $R^{A2}$, $Y^1$ and $Y^2$ are defined the rows of table A.

Table A-11: Compounds of formula (I.a), where X is cyclobutyl and $R^{b1}$, $R^{b2}$, $R^{b3}$, $R^{A1}$, $R^{A2}$, $Y^1$ and $Y^2$ are defined the rows of table A.

Table A-12: Compounds of formula (I.a), where X is cyclopentyl and $R^{b1}$, $R^{b2}$, $R^{b3}$, $R^{A1}$, $R^{A2}$, $Y^1$ and $Y^2$ are defined the rows of table A.

Table A-13: Compounds of formula (I.a), where X is cyclohexyl and $R^{b1}$, $R^{b2}$, $R^{b3}$, $R^{A1}$, $R^{A2}$, $Y^1$ and $Y^2$ are defined the rows of table A.

Table A-14: Compounds of formula (I.a), where X is 1-cyclopropylethyl and $R^{b1}$, $R^{b2}$, $R^{b3}$, $R^{A1}$, $R^{A2}$, $Y^1$ and $Y^2$ are defined the rows of table A.

Table A-15: Compounds of formula (I.a), where X is 1-methylcyclobutyl and $R^{b1}$, $R^{b2}$, $R^{b3}$, $R^{A1}$, $R^{A2}$, $Y^1$ and $Y^2$ are defined the rows of table A.

Table A-16: Compounds of formula (I.a), where X is 1-methylcyclopentyl and $R^{b1}$, $R^{b2}$, $R^{b3}$, $R^{A1}$, $R^{A2}$, $Y^1$ and $Y^2$ are defined the rows of table A.

Table A-17: Compounds of formula (I.a), where X is $C(CH_3)_2OCH_3$ and $R^{b1}$, $R^{b2}$, $R^{b3}$, $R^{A1}$, $R^{A2}$, $Y^1$ and $Y^2$ are defined the rows of table A.

Table A-18: Compounds of formula (I.a), where X is 1-methylcyclohexyl and $R^{b1}$, $R^{b2}$, $R^{b3}$, $R^{A1}$, $R^{A2}$, $Y^1$ and $Y^2$ are defined the rows of table A.

Table A-19: Compounds of formula (I.a), where X is 1-methoxyethyl and $R^{b1}$, $R^{b2}$, $R^{b3}$, $R^{A1}$, $R^{A2}$, $Y^1$ and $Y^2$ are defined the rows of table A.

Table A-20: Compounds of formula (I.a), where X is 1-methoxy-cyclopentyl and $R^{b1}$, $R^{b2}$, $R^{b3}$, $R^{A1}$, $R^{A2}$, $Y^1$ and $Y^2$ are defined the rows of table A.

Table A-21: Compounds of formula (I.a), where X is 1-methoxy-cyclobutyl and $R^{b1}$, $R^{b2}$, $R^{b3}$, $R^{A1}$, $R^{A2}$, $Y^1$ and $Y^2$ are defined the rows of table A.

Table A-22: Compounds of formula (I.a), where X is 1-methoxyl-cyclohexyl and $R^{b1}$, $R^{b2}$, $R^{b3}$, $R^{A1}$, $R^{A2}$, $Y^1$ and $Y^2$ are defined the rows of table A.

Table A-23: Compounds of formula (I.a), where X is 1-fluorcyclopentyl and $R^{b1}$, $R^{b2}$, $R^{b3}$, $R^{A1}$, $R^{A2}$, $Y^1$ and $Y^2$ are defined the rows of table A.

Table A-24: Compounds of formula (I.a), where X is 1-fluorcyclohexyl and $R^{b1}$, $R^{b2}$, $R^{b3}$, $R^{A1}$, $R^{A2}$, $Y^1$ and $Y^2$ are defined the rows of table A.

Table A-25: Compounds of formula (I.a), where X is 1-chlor-cyclopentyl and $R^{b1}$, $R^{b2}$, $R^{b3}$, $R^{A1}$, $R^{A2}$, $Y^1$ and $Y^2$ are defined the rows of table A.

Table A-26: Compounds of formula (I.a), where X is 1-chlor-cyclohexyl and $R^{b1}$, $R^{b2}$, $R^{b3}$, $R^{A1}$, $R^{A2}$, $Y^1$ and $Y^2$ are defined the rows of table A.

Table A-27: Compounds of formula (I.a), where X is 1-chlor-cyclobutyl and $R^{b1}, R^{b2}, R^{b3}, R^{A1}, R^{A2}, Y^1$ and $Y^2$ are defined the rows of table A.

Table A-28: Compounds of formula (I.a), where X is 2-methylpyrrolidin-1-yl and $R^{b1}, R^{b2}, R^{b3}, R^{A1}, R^{A2}, Y^1$ and $Y^2$ are defined the rows of table A.

Table A-29: Compounds of formula (I.a), where X is 2,2,2-trifluoroethoxy and $R^{b1}, R^{b2}, R^{b3}, R^{A1}, R^{A2}, Y^1$ and $Y^2$ are defined the rows of table A.

Table A-30: Compounds of formula (I.a), where X is azitidine and $R^{b1}, R^{b2}, R^{b3}, R^{A1}, R^{A2}, Y^1$ and $Y^2$ are defined the rows of table A.

Table A-31: Compounds of formula (I.a), where X is pyrrolidin-1-yl and $R^{b1}, R^{b2}, R^{b3}, R^{A1}, R^{A2}, Y^1$ and $Y^2$ are defined the rows of table A.

Table A-32: Compounds of formula (I.a), where X is 2-tetrahydrofuranyl and $R^{b1}, R^{b2}, R^{b3}, R^{A1}, R^{A2}, Y^1$ and $Y^2$ are defined the rows of table A.

Table A-33: Compounds of formula (I.a), where X is 2,4,6-tri-fluoro-phenyl and $R^{b1}, R^{b2}, R^{b3}, R^{A1}, R^{A2}, Y^1$ and $Y^2$ are defined the rows of table A.

Table A-34: Compounds of formula (I.a), where X is 2,6-difluoro-phenyl and $R^{b1}, R^{b2}, R^{b3}, R^{A1}, R^{A2}, Y^1$ and $Y^2$ are defined the rows of table A.

Table A-35: Compounds of formula (I.a), where X is 2-fluoro-phenyl and $R^{b1}, R^{b2}, R^{b3}, R^{A1}, R^{A2}, Y^1$ and $Y^2$ are defined the rows of table A.

Table A-36: Compounds of formula (I.a), where X is 1-chlor-cyclobutyl and $R^{b1}, R^{b2}, R^{b3}, R^{A1}, R^{A2}, Y^1$ and $Y^2$ are defined the rows of table A.

Table A-37: Compounds of formula (I.a), where X is s-butyl and $R^{b1}, R^{b2}, R^{b3}, R^{A1}, R^{A2}, Y^1$ and $Y^2$ are defined the rows of table A.

Table A-38: Compounds of formula (I.a), where X is piperidyl and $R^{b1}, R^{b2}, R^{b3}, R^{A1}, R^{A2}, Y^1$ and $Y^2$ are defined the rows of table A.

Table A-39: Compounds of formula (I.a), where X is methoxy(methyl)amino and $R^{b1}, R^{b2}, R^{b3}, R^{A1}, R^{A2}, Y^1$ and $Y^2$ are defined the rows of table A.

Table A-40: Compounds of formula (I.a), where X is 1-fluoro-propyl and $R^{b1}, R^{b2}, R^{b3}, R^{A1}, R^{A2}, Y^1$ and $Y^2$ are defined the rows of table A.

Table A-41: Compounds of formula (I.a), where X is methoxy and $R^{b1}, R^{b2}, R^{b3}, R^{A1}, R^{A2}, Y^1$ and $Y^2$ are defined the rows of table A.

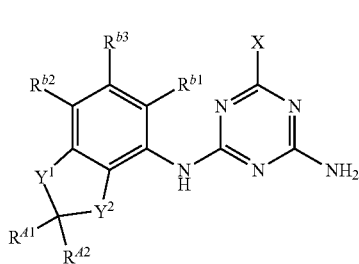

(I.a)

TABLE A

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 1. | H | H | H | H | H | O | O |
| 2. | F | H | H | H | H | O | O |
| 3. | Cl | H | H | H | H | O | O |
| 4. | Br | H | H | H | H | O | O |
| 5. | I | H | H | H | H | O | O |
| 6. | CH$_3$ | H | H | H | H | O | O |
| 7. | CN | H | H | H | H | O | O |
| 8. | H | F | H | H | H | O | O |
| 9. | F | F | H | H | H | O | O |
| 10. | Cl | F | H | H | H | O | O |
| 11. | Br | F | H | H | H | O | O |
| 12. | I | F | H | H | H | O | O |
| 13. | CH$_3$ | F | H | H | H | O | O |
| 14. | CN | F | H | H | H | O | O |
| 15. | H | H | F | H | H | O | O |
| 16. | F | H | F | H | H | O | O |
| 17. | Cl | H | F | H | H | O | O |
| 18. | Br | H | F | H | H | O | O |
| 19. | I | H | F | H | H | O | O |
| 20. | CH$_3$ | H | F | H | H | O | O |
| 21. | CN | H | F | H | H | O | O |
| 22. | H | F | F | H | H | O | O |
| 23. | F | F | F | H | H | O | O |
| 24. | Cl | F | F | H | H | O | O |
| 25. | Br | F | F | H | H | O | O |
| 26. | I | F | F | H | H | O | O |
| 27. | CH$_3$ | F | F | H | H | O | O |
| 28. | CN | F | F | H | H | O | O |
| 29. | H | Cl | H | H | H | O | O |
| 30. | Cl | Cl | H | H | H | O | O |
| 31. | Cl | Cl | H | H | H | O | O |
| 32. | Br | Cl | H | H | H | O | O |
| 33. | I | Cl | H | H | H | O | O |
| 34. | CH$_3$ | Cl | H | H | H | O | O |
| 35. | CN | Cl | H | H | H | O | O |
| 36. | H | H | Cl | H | H | O | O |
| 37. | Cl | H | Cl | H | H | O | O |
| 38. | Cl | H | Cl | H | H | O | O |
| 39. | Br | H | Cl | H | H | O | O |
| 40. | I | H | Cl | H | H | O | O |
| 41. | CH$_3$ | H | Cl | H | H | O | O |
| 42. | CN | H | Cl | H | H | O | O |
| 43. | H | Cl | Cl | H | H | O | O |
| 44. | Cl | Cl | Cl | H | H | O | O |
| 45. | Cl | Cl | Cl | H | H | O | O |
| 46. | Br | Cl | Cl | H | H | O | O |
| 47. | I | Cl | Cl | H | H | O | O |
| 48. | CH$_3$ | Cl | Cl | H | H | O | O |
| 49. | CN | Cl | Cl | H | H | O | O |
| 50. | H | Br | H | H | H | O | O |
| 51. | F | Br | H | H | H | O | O |
| 52. | Cl | Br | H | H | H | O | O |
| 53. | Br | Br | H | H | H | O | O |
| 54. | I | Br | H | H | H | O | O |
| 55. | CH$_3$ | Br | H | H | H | O | O |
| 56. | CN | Br | H | H | H | O | O |
| 57. | H | H | Br | H | H | O | O |
| 58. | F | H | Br | H | H | O | O |
| 59. | Cl | H | Br | H | H | O | O |
| 60. | Br | H | Br | H | H | O | O |
| 61. | I | H | Br | H | H | O | O |
| 62. | CH$_3$ | H | Br | H | H | O | O |
| 63. | CN | H | Br | H | H | O | O |
| 64. | H | Br | Br | H | H | O | O |
| 65. | F | Br | Br | H | H | O | O |
| 66. | Cl | Br | Br | H | H | O | O |
| 67. | Br | Br | Br | H | H | O | O |
| 68. | I | Br | Br | H | H | O | O |
| 69. | CH$_3$ | Br | Br | H | H | O | O |
| 70. | CN | H | Br | H | H | O | O |
| 71. | H | I | H | H | H | O | O |
| 72. | F | I | H | H | H | O | O |
| 73. | Cl | I | H | H | H | O | O |
| 74. | Br | I | H | H | H | O | O |
| 75. | I | I | H | H | H | O | O |
| 76. | CH$_3$ | I | H | H | H | O | O |
| 77. | CN | I | H | H | H | O | O |
| 78. | H | H | I | H | H | O | O |
| 79. | F | H | I | H | H | O | O |
| 80. | Cl | H | I | H | H | O | O |
| 81. | Br | H | I | H | H | O | O |
| 82. | I | H | I | H | H | O | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 83. | CH$_3$ | H | I | H | H | O | O |
| 84. | CN | H | I | H | H | O | O |
| 85. | H | I | I | H | H | O | O |
| 86. | F | I | I | H | H | O | O |
| 87. | Cl | I | I | H | H | O | O |
| 88. | Br | I | I | H | H | O | O |
| 89. | I | I | I | H | H | O | O |
| 90. | CH$_3$ | I | I | H | H | O | O |
| 91. | CN | I | I | H | H | O | O |
| 92. | H | F | Cl | H | H | O | O |
| 93. | D | F | Cl | H | H | O | O |
| 94. | F | F | Cl | H | H | O | O |
| 95. | Cl | F | Cl | H | H | O | O |
| 96. | Br | F | Cl | H | H | O | O |
| 97. | I | F | Cl | H | H | O | O |
| 98. | CH$_3$ | F | Cl | H | H | O | O |
| 99. | CN | F | Cl | H | H | O | O |
| 100. | H | F | Br | H | H | O | O |
| 101. | F | F | Br | H | H | O | O |
| 102. | Cl | F | Br | H | H | O | O |
| 103. | Br | F | Br | H | H | O | O |
| 104. | I | F | Br | H | H | O | O |
| 105. | CH$_3$ | F | Br | H | H | O | O |
| 106. | CN | F | Br | H | H | O | O |
| 107. | H | F | I | H | H | O | O |
| 108. | F | F | I | H | H | O | O |
| 109. | Cl | F | I | H | H | O | O |
| 110. | Br | F | I | H | H | O | O |
| 111. | I | F | I | H | H | O | O |
| 112. | CH$_3$ | F | I | H | H | O | O |
| 113. | CN | F | I | H | H | O | O |
| 114. | H | Cl | F | H | H | O | O |
| 115. | F | Cl | F | H | H | O | O |
| 116. | Cl | Cl | F | H | H | O | O |
| 117. | Br | Cl | F | H | H | O | O |
| 118. | I | Cl | F | H | H | O | O |
| 119. | CH$_3$ | Cl | F | H | H | O | O |
| 120. | CN | Cl | F | H | H | O | O |
| 121. | H | Cl | Br | H | H | O | O |
| 122. | F | Cl | Br | H | H | O | O |
| 123. | Cl | Cl | Br | H | H | O | O |
| 124. | Br | Cl | Br | H | H | O | O |
| 125. | I | Cl | Br | H | H | O | O |
| 126. | CH$_3$ | Cl | Br | H | H | O | O |
| 127. | CN | Cl | Br | H | H | O | O |
| 128. | H | Cl | I | H | H | O | O |
| 129. | F | Cl | I | H | H | O | O |
| 130. | Cl | Cl | I | H | H | O | O |
| 131. | Br | Cl | I | H | H | O | O |
| 132. | I | Cl | I | H | H | O | O |
| 133. | CH$_3$ | Cl | I | H | H | O | O |
| 134. | CN | Cl | I | H | H | O | O |
| 135. | H | Br | F | H | H | O | O |
| 136. | F | Br | F | H | H | O | O |
| 137. | Cl | Br | F | H | H | O | O |
| 138. | Br | Br | F | H | H | O | O |
| 139. | I | Br | F | H | H | O | O |
| 140. | CH$_3$ | Br | F | H | H | O | O |
| 141. | CN | Br | F | H | H | O | O |
| 142. | H | Br | Cl | H | H | O | O |
| 143. | F | Br | Cl | H | H | O | O |
| 144. | Cl | Br | Cl | H | H | O | O |
| 145. | Br | Br | Cl | H | H | O | O |
| 146. | I | Br | Cl | H | H | O | O |
| 147. | CH$_3$ | Br | Cl | H | H | O | O |
| 148. | CN | Br | Cl | H | H | O | O |
| 149. | H | Br | I | H | H | O | O |
| 150. | F | Br | I | H | H | O | O |
| 151. | Cl | Br | I | H | H | O | O |
| 152. | Br | Br | I | H | H | O | O |
| 153. | I | Br | I | H | H | O | O |
| 154. | CH$_3$ | Br | I | H | H | O | O |
| 155. | CN | Br | I | H | H | O | O |
| 156. | H | I | F | H | H | O | O |
| 157. | F | I | F | H | H | O | O |
| 158. | Cl | I | F | H | H | O | O |
| 159. | Br | I | F | H | H | O | O |
| 160. | I | I | F | H | H | O | O |
| 161. | CH$_3$ | I | F | H | H | O | O |
| 162. | CN | I | F | H | H | O | O |
| 163. | H | I | Cl | H | H | O | O |
| 164. | F | I | Cl | H | H | O | O |
| 165. | Cl | I | Cl | H | H | O | O |
| 166. | Br | I | Cl | H | H | O | O |
| 167. | I | I | Cl | H | H | O | O |
| 168. | CH$_3$ | I | Cl | H | H | O | O |
| 169. | CN | I | Cl | H | H | O | O |
| 170. | H | I | Br | H | H | O | O |
| 171. | F | I | Br | H | H | O | O |
| 172. | Cl | I | Br | H | H | O | O |
| 173. | Br | I | Br | H | H | O | O |
| 174. | I | I | Br | H | H | O | O |
| 175. | CH$_3$ | I | Br | H | H | O | O |
| 176. | CN | I | Br | H | H | O | O |
| 177. | H | H | H | CH$_3$ | H | O | O |
| 178. | F | H | H | CH$_3$ | H | O | O |
| 179. | Cl | H | H | CH$_3$ | H | O | O |
| 180. | Br | H | H | CH$_3$ | H | O | O |
| 181. | I | H | H | CH$_3$ | H | O | O |
| 182. | CH$_3$ | H | H | CH$_3$ | H | O | O |
| 183. | CN | H | H | CH$_3$ | H | O | O |
| 184. | H | F | H | CH$_3$ | H | O | O |
| 185. | F | F | H | CH$_3$ | H | O | O |
| 186. | Cl | F | H | CH$_3$ | H | O | O |
| 187. | Br | F | H | CH$_3$ | H | O | O |
| 188. | I | F | H | CH$_3$ | H | O | O |
| 189. | CH$_3$ | F | H | CH$_3$ | H | O | O |
| 190. | CN | F | H | CH$_3$ | H | O | O |
| 191. | H | H | F | CH$_3$ | H | O | O |
| 192. | F | H | F | CH$_3$ | H | O | O |
| 193. | Cl | H | F | CH$_3$ | H | O | O |
| 194. | Br | H | F | CH$_3$ | H | O | O |
| 195. | I | H | F | CH$_3$ | H | O | O |
| 196. | CH$_3$ | H | F | CH$_3$ | H | O | O |
| 197. | CN | H | F | CH$_3$ | H | O | O |
| 198. | H | F | F | CH$_3$ | H | O | O |
| 199. | F | F | F | CH$_3$ | H | O | O |
| 200. | Cl | F | F | CH$_3$ | H | O | O |
| 201. | Br | F | F | CH$_3$ | H | O | O |
| 202. | I | F | F | CH$_3$ | H | O | O |
| 203. | CH$_3$ | F | F | CH$_3$ | H | O | O |
| 204. | CN | F | F | CH$_3$ | H | O | O |
| 205. | H | Cl | H | CH$_3$ | H | O | O |
| 206. | Cl | Cl | H | CH$_3$ | H | O | O |
| 207. | Cl | Cl | H | CH$_3$ | H | O | O |
| 208. | Br | Cl | H | CH$_3$ | H | O | O |
| 209. | I | Cl | H | CH$_3$ | H | O | O |
| 210. | CH$_3$ | Cl | H | CH$_3$ | H | O | O |
| 211. | CN | Cl | H | CH$_3$ | H | O | O |
| 212. | H | H | Cl | CH$_3$ | H | O | O |
| 213. | Cl | H | Cl | CH$_3$ | H | O | O |
| 214. | Cl | H | Cl | CH$_3$ | H | O | O |
| 215. | Br | H | Cl | CH$_3$ | H | O | O |
| 216. | I | H | Cl | CH$_3$ | H | O | O |
| 217. | CH$_3$ | H | Cl | CH$_3$ | H | O | O |
| 218. | CN | H | Cl | CH$_3$ | H | O | O |
| 219. | H | Cl | Cl | CH$_3$ | H | O | O |
| 220. | Cl | Cl | Cl | CH$_3$ | H | O | O |
| 221. | Cl | Cl | Cl | CH$_3$ | H | O | O |
| 222. | Br | Cl | Cl | CH$_3$ | H | O | O |
| 223. | I | Cl | Cl | CH$_3$ | H | O | O |
| 224. | CH$_3$ | Cl | Cl | CH$_3$ | H | O | O |
| 225. | CN | Cl | Cl | CH$_3$ | H | O | O |
| 226. | H | Br | H | CH$_3$ | H | O | O |
| 227. | F | Br | H | CH$_3$ | H | O | O |
| 228. | Cl | Br | H | CH$_3$ | H | O | O |
| 229. | Br | Br | H | CH$_3$ | H | O | O |
| 230. | I | Br | H | CH$_3$ | H | O | O |
| 231. | CH$_3$ | Br | H | CH$_3$ | H | O | O |
| 232. | CN | Br | H | CH$_3$ | H | O | O |
| 233. | H | H | Br | CH$_3$ | H | O | O |
| 234. | F | H | Br | CH$_3$ | H | O | O |
| 235. | Cl | H | Br | CH$_3$ | H | O | O |
| 236. | Br | H | Br | CH$_3$ | H | O | O |
| 237. | I | H | Br | CH$_3$ | H | O | O |
| 238. | CH$_3$ | H | Br | CH$_3$ | H | O | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 239. | CN | H | Br | $CH_3$ | H | O | O |
| 240. | H | Br | Br | $CH_3$ | H | O | O |
| 241. | F | Br | Br | $CH_3$ | H | O | O |
| 242. | Cl | Br | Br | $CH_3$ | H | O | O |
| 243. | Br | Br | Br | $CH_3$ | H | O | O |
| 244. | I | Br | Br | $CH_3$ | H | O | O |
| 245. | $CH_3$ | Br | Br | $CH_3$ | H | O | O |
| 246. | CN | H | Br | $CH_3$ | H | O | O |
| 247. | H | I | H | $CH_3$ | H | O | O |
| 248. | F | I | H | $CH_3$ | H | O | O |
| 249. | Cl | I | H | $CH_3$ | H | O | O |
| 250. | Br | I | H | $CH_3$ | H | O | O |
| 251. | I | I | H | $CH_3$ | H | O | O |
| 252. | $CH_3$ | I | H | $CH_3$ | H | O | O |
| 253. | CN | I | H | $CH_3$ | H | O | O |
| 254. | H | H | I | $CH_3$ | H | O | O |
| 255. | F | H | I | $CH_3$ | H | O | O |
| 256. | Cl | H | I | $CH_3$ | H | O | O |
| 257. | Br | H | I | $CH_3$ | H | O | O |
| 258. | I | H | I | $CH_3$ | H | O | O |
| 259. | $CH_3$ | H | I | $CH_3$ | H | O | O |
| 260. | CN | H | I | $CH_3$ | H | O | O |
| 261. | H | I | I | $CH_3$ | H | O | O |
| 262. | F | I | I | $CH_3$ | H | O | O |
| 263. | Cl | I | I | $CH_3$ | H | O | O |
| 264. | Br | I | I | $CH_3$ | H | O | O |
| 265. | I | I | I | $CH_3$ | H | O | O |
| 266. | $CH_3$ | I | I | $CH_3$ | H | O | O |
| 267. | CN | I | I | $CH_3$ | H | O | O |
| 268. | H | F | Cl | $CH_3$ | H | O | O |
| 269. | D | F | Cl | $CH_3$ | H | O | O |
| 270. | F | F | Cl | $CH_3$ | H | O | O |
| 271. | Cl | F | Cl | $CH_3$ | H | O | O |
| 272. | Br | F | Cl | $CH_3$ | H | O | O |
| 273. | I | F | Cl | $CH_3$ | H | O | O |
| 274. | $CH_3$ | F | Cl | $CH_3$ | H | O | O |
| 275. | CN | F | Cl | $CH_3$ | H | O | O |
| 276. | H | F | Br | $CH_3$ | H | O | O |
| 277. | F | F | Br | $CH_3$ | H | O | O |
| 278. | Cl | F | Br | $CH_3$ | H | O | O |
| 279. | Br | F | Br | $CH_3$ | H | O | O |
| 280. | I | F | Br | $CH_3$ | H | O | O |
| 281. | $CH_3$ | F | Br | $CH_3$ | H | O | O |
| 282. | CN | F | Br | $CH_3$ | H | O | O |
| 283. | H | F | I | $CH_3$ | H | O | O |
| 284. | F | F | I | $CH_3$ | H | O | O |
| 285. | Cl | F | I | $CH_3$ | H | O | O |
| 286. | Br | F | I | $CH_3$ | H | O | O |
| 287. | I | F | I | $CH_3$ | H | O | O |
| 288. | $CH_3$ | F | I | $CH_3$ | H | O | O |
| 289. | CN | F | I | $CH_3$ | H | O | O |
| 290. | H | Cl | F | $CH_3$ | H | O | O |
| 291. | F | Cl | F | $CH_3$ | H | O | O |
| 292. | Cl | Cl | F | $CH_3$ | H | O | O |
| 293. | Br | Cl | F | $CH_3$ | H | O | O |
| 294. | I | Cl | F | $CH_3$ | H | O | O |
| 295. | $CH_3$ | Cl | F | $CH_3$ | H | O | O |
| 296. | CN | Cl | F | $CH_3$ | H | O | O |
| 297. | H | Cl | Br | $CH_3$ | H | O | O |
| 298. | F | Cl | Br | $CH_3$ | H | O | O |
| 299. | Cl | Cl | Br | $CH_3$ | H | O | O |
| 300. | Br | Cl | Br | $CH_3$ | H | O | O |
| 301. | I | Cl | Br | $CH_3$ | H | O | O |
| 302. | $CH_3$ | Cl | Br | $CH_3$ | H | O | O |
| 303. | CN | Cl | Br | $CH_3$ | H | O | O |
| 304. | H | Cl | I | $CH_3$ | H | O | O |
| 305. | F | Cl | I | $CH_3$ | H | O | O |
| 306. | Cl | Cl | I | $CH_3$ | H | O | O |
| 307. | Br | Cl | I | $CH_3$ | H | O | O |
| 308. | I | Cl | I | $CH_3$ | H | O | O |
| 309. | $CH_3$ | Cl | I | $CH_3$ | H | O | O |
| 310. | CN | Cl | I | $CH_3$ | H | O | O |
| 311. | H | Br | F | $CH_3$ | H | O | O |
| 312. | F | Br | F | $CH_3$ | H | O | O |
| 313. | Cl | Br | F | $CH_3$ | H | O | O |
| 314. | Br | Br | F | $CH_3$ | H | O | O |
| 315. | I | Br | F | $CH_3$ | H | O | O |
| 316. | $CH_3$ | Br | F | $CH_3$ | H | O | O |
| 317. | CN | Br | F | $CH_3$ | H | O | O |
| 318. | H | Br | Cl | $CH_3$ | H | O | O |
| 319. | F | Br | Cl | $CH_3$ | H | O | O |
| 320. | Cl | Br | Cl | $CH_3$ | H | O | O |
| 321. | Br | Br | Cl | $CH_3$ | H | O | O |
| 322. | I | Br | Cl | $CH_3$ | H | O | O |
| 323. | $CH_3$ | Br | Cl | $CH_3$ | H | O | O |
| 324. | CN | Br | Cl | $CH_3$ | H | O | O |
| 325. | H | Br | I | $CH_3$ | H | O | O |
| 326. | F | Br | I | $CH_3$ | H | O | O |
| 327. | Cl | Br | I | $CH_3$ | H | O | O |
| 328. | Br | Br | I | $CH_3$ | H | O | O |
| 329. | I | Br | I | $CH_3$ | H | O | O |
| 330. | $CH_3$ | Br | I | $CH_3$ | H | O | O |
| 331. | CN | Br | I | $CH_3$ | H | O | O |
| 332. | H | I | F | $CH_3$ | H | O | O |
| 333. | F | I | F | $CH_3$ | H | O | O |
| 334. | Cl | I | F | $CH_3$ | H | O | O |
| 335. | Br | I | F | $CH_3$ | H | O | O |
| 336. | I | I | F | $CH_3$ | H | O | O |
| 337. | $CH_3$ | I | F | $CH_3$ | H | O | O |
| 338. | CN | I | F | $CH_3$ | H | O | O |
| 339. | H | I | Cl | $CH_3$ | H | O | O |
| 340. | F | I | Cl | $CH_3$ | H | O | O |
| 341. | Cl | I | Cl | $CH_3$ | H | O | O |
| 342. | Br | I | Cl | $CH_3$ | H | O | O |
| 343. | I | I | Cl | $CH_3$ | H | O | O |
| 344. | $CH_3$ | I | Cl | $CH_3$ | H | O | O |
| 345. | CN | I | Cl | $CH_3$ | H | O | O |
| 346. | H | I | Br | $CH_3$ | H | O | O |
| 347. | F | I | Br | $CH_3$ | H | O | O |
| 348. | Cl | I | Br | $CH_3$ | H | O | O |
| 349. | Br | I | Br | $CH_3$ | H | O | O |
| 350. | I | I | Br | $CH_3$ | H | O | O |
| 351. | $CH_3$ | I | Br | $CH_3$ | H | O | O |
| 352. | CN | I | Br | $CH_3$ | H | O | O |
| 353. | H | H | H | $CH_3$ | $CH_3$ | O | O |
| 354. | F | H | H | $CH_3$ | $CH_3$ | O | O |
| 355. | Cl | H | H | $CH_3$ | $CH_3$ | O | O |
| 356. | Br | H | H | $CH_3$ | $CH_3$ | O | O |
| 357. | I | H | H | $CH_3$ | $CH_3$ | O | O |
| 358. | $CH_3$ | H | H | $CH_3$ | $CH_3$ | O | O |
| 359. | CN | H | H | $CH_3$ | $CH_3$ | O | O |
| 360. | H | F | H | $CH_3$ | $CH_3$ | O | O |
| 361. | F | F | H | $CH_3$ | $CH_3$ | O | O |
| 362. | Cl | F | H | $CH_3$ | $CH_3$ | O | O |
| 363. | Br | F | H | $CH_3$ | $CH_3$ | O | O |
| 364. | I | F | H | $CH_3$ | $CH_3$ | O | O |
| 365. | $CH_3$ | F | H | $CH_3$ | $CH_3$ | O | O |
| 366. | CN | F | H | $CH_3$ | $CH_3$ | O | O |
| 367. | H | H | F | $CH_3$ | $CH_3$ | O | O |
| 368. | F | H | F | $CH_3$ | $CH_3$ | O | O |
| 369. | Cl | H | F | $CH_3$ | $CH_3$ | O | O |
| 370. | Br | H | F | $CH_3$ | $CH_3$ | O | O |
| 371. | I | H | F | $CH_3$ | $CH_3$ | O | O |
| 372. | $CH_3$ | H | F | $CH_3$ | $CH_3$ | O | O |
| 373. | CN | H | F | $CH_3$ | $CH_3$ | O | O |
| 374. | H | F | F | $CH_3$ | $CH_3$ | O | O |
| 375. | F | F | F | $CH_3$ | $CH_3$ | O | O |
| 376. | Cl | F | F | $CH_3$ | $CH_3$ | O | O |
| 377. | Br | F | F | $CH_3$ | $CH_3$ | O | O |
| 378. | I | F | F | $CH_3$ | $CH_3$ | O | O |
| 379. | $CH_3$ | F | F | $CH_3$ | $CH_3$ | O | O |
| 380. | CN | F | F | $CH_3$ | $CH_3$ | O | O |
| 381. | H | Cl | H | $CH_3$ | $CH_3$ | O | O |
| 382. | Cl | Cl | H | $CH_3$ | $CH_3$ | O | O |
| 383. | Cl | Cl | H | $CH_3$ | $CH_3$ | O | O |
| 384. | Br | Cl | H | $CH_3$ | $CH_3$ | O | O |
| 385. | I | Cl | H | $CH_3$ | $CH_3$ | O | O |
| 386. | $CH_3$ | Cl | H | $CH_3$ | $CH_3$ | O | O |
| 387. | CN | Cl | H | $CH_3$ | $CH_3$ | O | O |
| 388. | H | H | Cl | $CH_3$ | $CH_3$ | O | O |
| 389. | Cl | H | Cl | $CH_3$ | $CH_3$ | O | O |
| 390. | Cl | H | Cl | $CH_3$ | $CH_3$ | O | O |
| 391. | Br | H | Cl | $CH_3$ | $CH_3$ | O | O |
| 392. | I | H | Cl | $CH_3$ | $CH_3$ | O | O |
| 393. | $CH_3$ | H | Cl | $CH_3$ | $CH_3$ | O | O |
| 394. | CN | H | Cl | $CH_3$ | $CH_3$ | O | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 395. | H | Cl | Cl | CH$_3$ | CH$_3$ | O | O |
| 396. | F | Cl | Cl | CH$_3$ | CH$_3$ | O | O |
| 397. | Cl | Cl | Cl | CH$_3$ | CH$_3$ | O | O |
| 398. | Br | Cl | Cl | CH$_3$ | CH$_3$ | O | O |
| 399. | I | Cl | Cl | CH$_3$ | CH$_3$ | O | O |
| 400. | CH$_3$ | Cl | Cl | CH$_3$ | CH$_3$ | O | O |
| 401. | CN | Cl | Cl | CH$_3$ | CH$_3$ | O | O |
| 402. | H | Br | H | CH$_3$ | CH$_3$ | O | O |
| 403. | F | Br | H | CH$_3$ | CH$_3$ | O | O |
| 404. | Cl | Br | H | CH$_3$ | CH$_3$ | O | O |
| 405. | Br | Br | H | CH$_3$ | CH$_3$ | O | O |
| 406. | I | Br | H | CH$_3$ | CH$_3$ | O | O |
| 407. | CH$_3$ | Br | H | CH$_3$ | CH$_3$ | O | O |
| 408. | CN | Br | H | CH$_3$ | CH$_3$ | O | O |
| 409. | H | H | Br | CH$_3$ | CH$_3$ | O | O |
| 410. | F | H | Br | CH$_3$ | CH$_3$ | O | O |
| 411. | Cl | H | Br | CH$_3$ | CH$_3$ | O | O |
| 412. | Br | H | Br | CH$_3$ | CH$_3$ | O | O |
| 413. | I | H | Br | CH$_3$ | CH$_3$ | O | O |
| 414. | CH$_3$ | H | Br | CH$_3$ | CH$_3$ | O | O |
| 415. | CN | H | Br | CH$_3$ | CH$_3$ | O | O |
| 416. | H | Br | Br | CH$_3$ | CH$_3$ | O | O |
| 417. | F | Br | Br | CH$_3$ | CH$_3$ | O | O |
| 418. | Cl | Br | Br | CH$_3$ | CH$_3$ | O | O |
| 419. | Br | Br | Br | CH$_3$ | CH$_3$ | O | O |
| 420. | I | Br | Br | CH$_3$ | CH$_3$ | O | O |
| 421. | CH$_3$ | Br | Br | CH$_3$ | CH$_3$ | O | O |
| 422. | CN | H | Br | CH$_3$ | CH$_3$ | O | O |
| 423. | H | I | H | CH$_3$ | CH$_3$ | O | O |
| 424. | F | I | H | CH$_3$ | CH$_3$ | O | O |
| 425. | Cl | I | H | CH$_3$ | CH$_3$ | O | O |
| 426. | Br | I | H | CH$_3$ | CH$_3$ | O | O |
| 427. | I | I | H | CH$_3$ | CH$_3$ | O | O |
| 428. | CH$_3$ | I | H | CH$_3$ | CH$_3$ | O | O |
| 429. | CN | I | H | CH$_3$ | CH$_3$ | O | O |
| 430. | H | H | I | CH$_3$ | CH$_3$ | O | O |
| 431. | F | H | I | CH$_3$ | CH$_3$ | O | O |
| 432. | Cl | H | I | CH$_3$ | CH$_3$ | O | O |
| 433. | Br | H | I | CH$_3$ | CH$_3$ | O | O |
| 434. | I | H | I | CH$_3$ | CH$_3$ | O | O |
| 435. | CH$_3$ | H | I | CH$_3$ | CH$_3$ | O | O |
| 436. | CN | H | I | CH$_3$ | CH$_3$ | O | O |
| 437. | H | I | I | CH$_3$ | CH$_3$ | O | O |
| 438. | F | I | I | CH$_3$ | CH$_3$ | O | O |
| 439. | Cl | I | I | CH$_3$ | CH$_3$ | O | O |
| 440. | Br | I | I | CH$_3$ | CH$_3$ | O | O |
| 441. | I | I | I | CH$_3$ | CH$_3$ | O | O |
| 442. | CH$_3$ | I | I | CH$_3$ | CH$_3$ | O | O |
| 443. | CN | I | I | CH$_3$ | CH$_3$ | O | O |
| 444. | H | F | Cl | CH$_3$ | CH$_3$ | O | O |
| 445. | D | F | Cl | CH$_3$ | CH$_3$ | O | O |
| 446. | F | F | Cl | CH$_3$ | CH$_3$ | O | O |
| 447. | Cl | F | Cl | CH$_3$ | CH$_3$ | O | O |
| 448. | Br | F | Cl | CH$_3$ | CH$_3$ | O | O |
| 449. | I | F | Cl | CH$_3$ | CH$_3$ | O | O |
| 450. | CH$_3$ | F | Cl | CH$_3$ | CH$_3$ | O | O |
| 451. | CN | F | Cl | CH$_3$ | CH$_3$ | O | O |
| 452. | H | F | Br | CH$_3$ | CH$_3$ | O | O |
| 453. | F | F | Br | CH$_3$ | CH$_3$ | O | O |
| 454. | Cl | F | Br | CH$_3$ | CH$_3$ | O | O |
| 455. | Br | F | Br | CH$_3$ | CH$_3$ | O | O |
| 456. | I | F | Br | CH$_3$ | CH$_3$ | O | O |
| 457. | CH$_3$ | F | Br | CH$_3$ | CH$_3$ | O | O |
| 458. | CN | F | Br | CH$_3$ | CH$_3$ | O | O |
| 459. | H | F | I | CH$_3$ | CH$_3$ | O | O |
| 460. | F | F | I | CH$_3$ | CH$_3$ | O | O |
| 461. | Cl | F | I | CH$_3$ | CH$_3$ | O | O |
| 462. | Br | F | I | CH$_3$ | CH$_3$ | O | O |
| 463. | I | F | I | CH$_3$ | CH$_3$ | O | O |
| 464. | CH$_3$ | F | I | CH$_3$ | CH$_3$ | O | O |
| 465. | CN | F | I | CH$_3$ | CH$_3$ | O | O |
| 466. | H | Cl | F | CH$_3$ | CH$_3$ | O | O |
| 467. | F | Cl | F | CH$_3$ | CH$_3$ | O | O |
| 468. | Cl | Cl | F | CH$_3$ | CH$_3$ | O | O |
| 469. | Br | Cl | F | CH$_3$ | CH$_3$ | O | O |
| 470. | I | Cl | F | CH$_3$ | CH$_3$ | O | O |
| 471. | CH$_3$ | Cl | F | CH$_3$ | CH$_3$ | O | O |
| 472. | CN | Cl | F | CH$_3$ | CH$_3$ | O | O |
| 473. | H | Cl | Br | CH$_3$ | CH$_3$ | O | O |
| 474. | F | Cl | Br | CH$_3$ | CH$_3$ | O | O |
| 475. | Cl | Cl | Br | CH$_3$ | CH$_3$ | O | O |
| 476. | Br | Cl | Br | CH$_3$ | CH$_3$ | O | O |
| 477. | I | Cl | Br | CH$_3$ | CH$_3$ | O | O |
| 478. | CH$_3$ | Cl | Br | CH$_3$ | CH$_3$ | O | O |
| 479. | CN | Cl | Br | CH$_3$ | CH$_3$ | O | O |
| 480. | H | Cl | I | CH$_3$ | CH$_3$ | O | O |
| 481. | F | Cl | I | CH$_3$ | CH$_3$ | O | O |
| 482. | Cl | Cl | I | CH$_3$ | CH$_3$ | O | O |
| 483. | Br | Cl | I | CH$_3$ | CH$_3$ | O | O |
| 484. | I | Cl | I | CH$_3$ | CH$_3$ | O | O |
| 485. | CH$_3$ | Cl | I | CH$_3$ | CH$_3$ | O | O |
| 486. | CN | Cl | I | CH$_3$ | CH$_3$ | O | O |
| 487. | H | Br | F | CH$_3$ | CH$_3$ | O | O |
| 488. | F | Br | F | CH$_3$ | CH$_3$ | O | O |
| 489. | Cl | Br | F | CH$_3$ | CH$_3$ | O | O |
| 490. | Br | Br | F | CH$_3$ | CH$_3$ | O | O |
| 491. | I | Br | F | CH$_3$ | CH$_3$ | O | O |
| 492. | CH$_3$ | Br | F | CH$_3$ | CH$_3$ | O | O |
| 493. | CN | Br | F | CH$_3$ | CH$_3$ | O | O |
| 494. | H | Br | Cl | CH$_3$ | CH$_3$ | O | O |
| 495. | F | Br | Cl | CH$_3$ | CH$_3$ | O | O |
| 496. | Cl | Br | Cl | CH$_3$ | CH$_3$ | O | O |
| 497. | Br | Br | Cl | CH$_3$ | CH$_3$ | O | O |
| 498. | I | Br | Cl | CH$_3$ | CH$_3$ | O | O |
| 499. | CH$_3$ | Br | Cl | CH$_3$ | CH$_3$ | O | O |
| 500. | CN | Br | Cl | CH$_3$ | CH$_3$ | O | O |
| 501. | H | Br | I | CH$_3$ | CH$_3$ | O | O |
| 502. | F | Br | I | CH$_3$ | CH$_3$ | O | O |
| 503. | Cl | Br | I | CH$_3$ | CH$_3$ | O | O |
| 504. | Br | Br | I | CH$_3$ | CH$_3$ | O | O |
| 505. | I | Br | I | CH$_3$ | CH$_3$ | O | O |
| 506. | CH$_3$ | Br | I | CH$_3$ | CH$_3$ | O | O |
| 507. | CN | Br | I | CH$_3$ | CH$_3$ | O | O |
| 508. | H | I | F | CH$_3$ | CH$_3$ | O | O |
| 509. | F | I | F | CH$_3$ | CH$_3$ | O | O |
| 510. | Cl | I | F | CH$_3$ | CH$_3$ | O | O |
| 511. | Br | I | F | CH$_3$ | CH$_3$ | O | O |
| 512. | I | I | F | CH$_3$ | CH$_3$ | O | O |
| 513. | CH$_3$ | I | F | CH$_3$ | CH$_3$ | O | O |
| 514. | CN | I | F | CH$_3$ | CH$_3$ | O | O |
| 515. | H | I | Cl | CH$_3$ | CH$_3$ | O | O |
| 516. | F | I | Cl | CH$_3$ | CH$_3$ | O | O |
| 517. | Cl | I | Cl | CH$_3$ | CH$_3$ | O | O |
| 518. | Br | I | Cl | CH$_3$ | CH$_3$ | O | O |
| 519. | I | I | Cl | CH$_3$ | CH$_3$ | O | O |
| 520. | CH$_3$ | I | Cl | CH$_3$ | CH$_3$ | O | O |
| 521. | CN | I | Cl | CH$_3$ | CH$_3$ | O | O |
| 522. | H | I | Br | CH$_3$ | CH$_3$ | O | O |
| 523. | F | I | Br | CH$_3$ | CH$_3$ | O | O |
| 524. | Cl | I | Br | CH$_3$ | CH$_3$ | O | O |
| 525. | Br | I | Br | CH$_3$ | CH$_3$ | O | O |
| 526. | I | I | Br | CH$_3$ | CH$_3$ | O | O |
| 527. | CH$_3$ | I | Br | CH$_3$ | CH$_3$ | O | O |
| 528. | CN | I | Br | CH$_3$ | CH$_3$ | O | O |
| 529. | H | H | H | F | F | O | O |
| 530. | F | H | H | F | F | O | O |
| 531. | Cl | H | H | F | F | O | O |
| 532. | Br | H | H | F | F | O | O |
| 533. | I | H | H | F | F | O | O |
| 534. | CH$_3$ | H | H | F | F | O | O |
| 535. | CN | H | H | F | F | O | O |
| 536. | H | F | H | F | F | O | O |
| 537. | F | F | H | F | F | O | O |
| 538. | Cl | F | H | F | F | O | O |
| 539. | Br | F | H | F | F | O | O |
| 540. | I | F | H | F | F | O | O |
| 541. | CH$_3$ | F | H | F | F | O | O |
| 542. | CN | F | H | F | F | O | O |
| 543. | H | H | F | F | F | O | O |
| 544. | F | H | F | F | F | O | O |
| 545. | Cl | H | F | F | F | O | O |
| 546. | Br | H | F | F | F | O | O |
| 547. | I | H | F | F | F | O | O |
| 548. | CH$_3$ | H | F | F | F | O | O |
| 549. | CN | H | F | F | F | O | O |
| 550. | H | F | F | F | F | O | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 551. | F | F | F | F | F | O | O |
| 552. | Cl | F | F | F | F | O | O |
| 553. | Br | F | F | F | F | O | O |
| 554. | I | F | F | F | F | O | O |
| 555. | CH$_3$ | F | F | F | F | O | O |
| 556. | CN | F | F | F | F | O | O |
| 557. | H | Cl | H | F | F | O | O |
| 558. | Cl | Cl | H | F | F | O | O |
| 559. | Cl | Cl | H | F | F | O | O |
| 560. | Br | Cl | H | F | F | O | O |
| 561. | I | Cl | H | F | F | O | O |
| 562. | CH$_3$ | Cl | H | F | F | O | O |
| 563. | CN | Cl | H | F | F | O | O |
| 564. | H | H | Cl | F | F | O | O |
| 565. | Cl | H | Cl | F | F | O | O |
| 566. | Cl | H | Cl | F | F | O | O |
| 567. | Br | H | Cl | F | F | O | O |
| 568. | I | H | Cl | F | F | O | O |
| 569. | CH$_3$ | H | Cl | F | F | O | O |
| 570. | CN | H | Cl | F | F | O | O |
| 571. | H | Cl | Cl | F | F | O | O |
| 572. | Cl | Cl | Cl | F | F | O | O |
| 573. | Cl | Cl | Cl | F | F | O | O |
| 574. | Br | Cl | Cl | F | F | O | O |
| 575. | I | Cl | Cl | F | F | O | O |
| 576. | CH$_3$ | Cl | Cl | F | F | O | O |
| 577. | CN | Cl | Cl | F | F | O | O |
| 578. | H | Br | H | F | F | O | O |
| 579. | F | Br | H | F | F | O | O |
| 580. | Cl | Br | H | F | F | O | O |
| 581. | Br | Br | H | F | F | O | O |
| 582. | I | Br | H | F | F | O | O |
| 583. | CH$_3$ | Br | H | F | F | O | O |
| 584. | CN | Br | H | F | F | O | O |
| 585. | H | H | Br | F | F | O | O |
| 586. | F | H | Br | F | F | O | O |
| 587. | Cl | H | Br | F | F | O | O |
| 588. | Br | H | Br | F | F | O | O |
| 589. | I | H | Br | F | F | O | O |
| 590. | CH$_3$ | H | Br | F | F | O | O |
| 591. | CN | H | Br | F | F | O | O |
| 592. | H | Br | Br | F | F | O | O |
| 593. | F | Br | Br | F | F | O | O |
| 594. | Cl | Br | Br | F | F | O | O |
| 595. | Br | Br | Br | F | F | O | O |
| 596. | I | Br | Br | F | F | O | O |
| 597. | CH$_3$ | Br | Br | F | F | O | O |
| 598. | CN | H | Br | F | F | O | O |
| 599. | H | I | H | F | F | O | O |
| 600. | F | I | H | F | F | O | O |
| 601. | Cl | I | H | F | F | O | O |
| 602. | Br | I | H | F | F | O | O |
| 603. | I | I | H | F | F | O | O |
| 604. | CH$_3$ | I | H | F | F | O | O |
| 605. | CN | I | H | F | F | O | O |
| 606. | H | H | I | F | F | O | O |
| 607. | F | H | I | F | F | O | O |
| 608. | Cl | H | I | F | F | O | O |
| 609. | Br | H | I | F | F | O | O |
| 610. | I | H | I | F | F | O | O |
| 611. | CH$_3$ | H | I | F | F | O | O |
| 612. | CN | H | I | F | F | O | O |
| 613. | H | I | I | F | F | O | O |
| 614. | F | I | I | F | F | O | O |
| 615. | Cl | I | I | F | F | O | O |
| 616. | Br | I | I | F | F | O | O |
| 617. | I | I | I | F | F | O | O |
| 618. | CH$_3$ | I | I | F | F | O | O |
| 619. | CN | I | I | F | F | O | O |
| 620. | H | F | Cl | F | F | O | O |
| 621. | D | F | Cl | F | F | O | O |
| 622. | F | F | Cl | F | F | O | O |
| 623. | Cl | F | Cl | F | F | O | O |
| 624. | Br | F | Cl | F | F | O | O |
| 625. | I | F | Cl | F | F | O | O |
| 626. | CH$_3$ | F | Cl | F | F | O | O |
| 627. | CN | F | Cl | F | F | O | O |
| 628. | H | F | Br | F | F | O | O |
| 629. | F | F | Br | F | F | O | O |
| 630. | Cl | F | Br | F | F | O | O |
| 631. | Br | F | Br | F | F | O | O |
| 632. | I | F | Br | F | F | O | O |
| 633. | CH$_3$ | F | Br | F | F | O | O |
| 634. | CN | F | Br | F | F | O | O |
| 635. | H | F | I | F | F | O | O |
| 636. | F | F | I | F | F | O | O |
| 637. | Cl | F | I | F | F | O | O |
| 638. | Br | F | I | F | F | O | O |
| 639. | I | F | I | F | F | O | O |
| 640. | CH$_3$ | F | I | F | F | O | O |
| 641. | CN | F | I | F | F | O | O |
| 642. | H | Cl | F | F | F | O | O |
| 643. | F | Cl | F | F | F | O | O |
| 644. | Cl | Cl | F | F | F | O | O |
| 645. | Br | Cl | F | F | F | O | O |
| 646. | I | Cl | F | F | F | O | O |
| 647. | CH$_3$ | Cl | F | F | F | O | O |
| 648. | CN | Cl | F | F | F | O | O |
| 649. | H | Cl | Br | F | F | O | O |
| 650. | F | Cl | Br | F | F | O | O |
| 651. | Cl | Cl | Br | F | F | O | O |
| 652. | Br | Cl | Br | F | F | O | O |
| 653. | I | Cl | Br | F | F | O | O |
| 654. | CH$_3$ | Cl | Br | F | F | O | O |
| 655. | CN | Cl | Br | F | F | O | O |
| 656. | H | Cl | I | F | F | O | O |
| 657. | F | Cl | I | F | F | O | O |
| 658. | Cl | Cl | I | F | F | O | O |
| 659. | Br | Cl | I | F | F | O | O |
| 660. | I | Cl | I | F | F | O | O |
| 661. | CH$_3$ | Cl | I | F | F | O | O |
| 662. | CN | Cl | I | F | F | O | O |
| 663. | H | Br | F | F | F | O | O |
| 664. | F | Br | F | F | F | O | O |
| 665. | Cl | Br | F | F | F | O | O |
| 666. | Br | Br | F | F | F | O | O |
| 667. | I | Br | F | F | F | O | O |
| 668. | CH$_3$ | Br | F | F | F | O | O |
| 669. | CN | Br | F | F | F | O | O |
| 670. | H | Br | Cl | F | F | O | O |
| 671. | F | Br | Cl | F | F | O | O |
| 672. | Cl | Br | Cl | F | F | O | O |
| 673. | Br | Br | Cl | F | F | O | O |
| 674. | I | Br | Cl | F | F | O | O |
| 675. | CH$_3$ | Br | Cl | F | F | O | O |
| 676. | CN | Br | Cl | F | F | O | O |
| 677. | H | Br | I | F | F | O | O |
| 678. | F | Br | I | F | F | O | O |
| 679. | Cl | Br | I | F | F | O | O |
| 680. | Br | Br | I | F | F | O | O |
| 681. | I | Br | I | F | F | O | O |
| 682. | CH$_3$ | Br | I | F | F | O | O |
| 683. | CN | Br | I | F | F | O | O |
| 684. | H | I | F | F | F | O | O |
| 685. | F | I | F | F | F | O | O |
| 686. | Cl | I | F | F | F | O | O |
| 687. | Br | I | F | F | F | O | O |
| 688. | I | I | F | F | F | O | O |
| 689. | CH$_3$ | I | F | F | F | O | O |
| 690. | CN | I | F | F | F | O | O |
| 691. | H | I | Cl | F | F | O | O |
| 692. | F | I | Cl | F | F | O | O |
| 693. | Cl | I | Cl | F | F | O | O |
| 694. | Br | I | Cl | F | F | O | O |
| 695. | I | I | Cl | F | F | O | O |
| 696. | CH$_3$ | I | Cl | F | F | O | O |
| 697. | CN | I | Cl | F | F | O | O |
| 698. | H | I | Br | F | F | O | O |
| 699. | F | I | Br | F | F | O | O |
| 700. | Cl | I | Br | F | F | O | O |
| 701. | Br | I | Br | F | F | O | O |
| 702. | I | I | Br | F | F | O | O |
| 703. | CH$_3$ | I | Br | F | F | O | O |
| 704. | CN | I | Br | F | F | O | O |
| 705. | H | H | H | =O | | O | O |
| 706. | F | H | H | =O | | O | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 707. | Cl | H | H | | =O | O | O |
| 708. | Br | H | H | | =O | O | O |
| 709. | I | H | H | | =O | O | O |
| 710. | CH$_3$ | H | H | | =O | O | O |
| 711. | CN | H | H | | =O | O | O |
| 712. | H | F | H | | =O | O | O |
| 713. | F | F | H | | =O | O | O |
| 714. | Cl | F | H | | =O | O | O |
| 715. | Br | F | H | | =O | O | O |
| 716. | I | F | H | | =O | O | O |
| 717. | CH$_3$ | F | H | | =O | O | O |
| 718. | CN | F | H | | =O | O | O |
| 719. | H | H | F | | =O | O | O |
| 720. | F | H | F | | =O | O | O |
| 721. | Cl | H | F | | =O | O | O |
| 722. | Br | H | F | | =O | O | O |
| 723. | I | H | F | | =O | O | O |
| 724. | CH$_3$ | H | F | | =O | O | O |
| 725. | CN | H | F | | =O | O | O |
| 726. | H | F | F | | =O | O | O |
| 727. | F | F | F | | =O | O | O |
| 728. | Cl | F | F | | =O | O | O |
| 729. | Br | F | F | | =O | O | O |
| 730. | I | F | F | | =O | O | O |
| 731. | CH$_3$ | F | F | | =O | O | O |
| 732. | CN | F | F | | =O | O | O |
| 733. | H | Cl | H | | =O | O | O |
| 734. | Cl | Cl | H | | =O | O | O |
| 735. | Cl | Cl | H | | =O | O | O |
| 736. | Br | Cl | H | | =O | O | O |
| 737. | I | Cl | H | | =O | O | O |
| 738. | CH$_3$ | Cl | H | | =O | O | O |
| 739. | CN | Cl | H | | =O | O | O |
| 740. | H | H | Cl | | =O | O | O |
| 741. | Cl | H | Cl | | =O | O | O |
| 742. | Cl | H | Cl | | =O | O | O |
| 743. | Br | H | Cl | | =O | O | O |
| 744. | I | H | Cl | | =O | O | O |
| 745. | CH$_3$ | H | Cl | | =O | O | O |
| 746. | CN | H | Cl | | =O | O | O |
| 747. | H | Cl | Cl | | =O | O | O |
| 748. | Cl | Cl | Cl | | =O | O | O |
| 749. | Cl | Cl | Cl | | =O | O | O |
| 750. | Br | Cl | Cl | | =O | O | O |
| 751. | I | Cl | Cl | | =O | O | O |
| 752. | CH$_3$ | Cl | Cl | | =O | O | O |
| 753. | CN | Cl | Cl | | =O | O | O |
| 754. | H | Br | H | | =O | O | O |
| 755. | F | Br | H | | =O | O | O |
| 756. | Cl | Br | H | | =O | O | O |
| 757. | Br | Br | H | | =O | O | O |
| 758. | I | Br | H | | =O | O | O |
| 759. | CH$_3$ | Br | H | | =O | O | O |
| 760. | CN | Br | H | | =O | O | O |
| 761. | H | H | Br | | =O | O | O |
| 762. | F | H | Br | | =O | O | O |
| 763. | Cl | H | Br | | =O | O | O |
| 764. | Br | H | Br | | =O | O | O |
| 765. | I | H | Br | | =O | O | O |
| 766. | CH$_3$ | H | Br | | =O | O | O |
| 767. | CN | H | Br | | =O | O | O |
| 768. | H | Br | Br | | =O | O | O |
| 769. | F | Br | Br | | =O | O | O |
| 770. | Cl | Br | Br | | =O | O | O |
| 771. | Br | Br | Br | | =O | O | O |
| 772. | I | Br | Br | | =O | O | O |
| 773. | CH$_3$ | Br | Br | | =O | O | O |
| 774. | CN | Br | Br | | =O | O | O |
| 775. | H | I | H | | =O | O | O |
| 776. | F | I | H | | =O | O | O |
| 777. | Cl | I | H | | =O | O | O |
| 778. | Br | I | H | | =O | O | O |
| 779. | I | I | H | | =O | O | O |
| 780. | CH$_3$ | I | H | | =O | O | O |
| 781. | CN | I | H | | =O | O | O |
| 782. | H | H | I | | =O | O | O |
| 783. | F | H | I | | =O | O | O |
| 784. | Cl | H | I | | =O | O | O |
| 785. | Br | H | I | | =O | O | O |
| 786. | I | H | I | | =O | O | O |
| 787. | CH$_3$ | H | I | | =O | O | O |
| 788. | CN | H | I | | =O | O | O |
| 789. | H | I | I | | =O | O | O |
| 790. | F | I | I | | =O | O | O |
| 791. | Cl | I | I | | =O | O | O |
| 792. | Br | I | I | | =O | O | O |
| 793. | I | I | I | | =O | O | O |
| 794. | CH$_3$ | I | I | | =O | O | O |
| 795. | CN | I | I | | =O | O | O |
| 796. | H | F | Cl | | =O | O | O |
| 797. | D | F | Cl | | =O | O | O |
| 798. | F | F | Cl | | =O | O | O |
| 799. | Cl | F | Cl | | =O | O | O |
| 800. | Br | F | Cl | | =O | O | O |
| 801. | I | F | Cl | | =O | O | O |
| 802. | CH$_3$ | F | Cl | | =O | O | O |
| 803. | CN | F | Cl | | =O | O | O |
| 804. | H | F | Br | | =O | O | O |
| 805. | F | F | Br | | =O | O | O |
| 806. | Cl | F | Br | | =O | O | O |
| 807. | Br | F | Br | | =O | O | O |
| 808. | I | F | Br | | =O | O | O |
| 809. | CH$_3$ | F | Br | | =O | O | O |
| 810. | CN | F | Br | | =O | O | O |
| 811. | H | F | I | | =O | O | O |
| 812. | F | F | I | | =O | O | O |
| 813. | Cl | F | I | | =O | O | O |
| 814. | Br | F | I | | =O | O | O |
| 815. | I | F | I | | =O | O | O |
| 816. | CH$_3$ | F | I | | =O | O | O |
| 817. | CN | F | I | | =O | O | O |
| 818. | H | Cl | F | | =O | O | O |
| 819. | F | Cl | F | | =O | O | O |
| 820. | Cl | Cl | F | | =O | O | O |
| 821. | Br | Cl | F | | =O | O | O |
| 822. | I | Cl | F | | =O | O | O |
| 823. | CH$_3$ | Cl | F | | =O | O | O |
| 824. | CN | Cl | F | | =O | O | O |
| 825. | H | Cl | Br | | =O | O | O |
| 826. | F | Cl | Br | | =O | O | O |
| 827. | Cl | Cl | Br | | =O | O | O |
| 828. | Br | Cl | Br | | =O | O | O |
| 829. | I | Cl | Br | | =O | O | O |
| 830. | CH$_3$ | Cl | Br | | =O | O | O |
| 831. | CN | Cl | Br | | =O | O | O |
| 832. | H | Cl | I | | =O | O | O |
| 833. | F | Cl | I | | =O | O | O |
| 834. | Cl | Cl | I | | =O | O | O |
| 835. | Br | Cl | I | | =O | O | O |
| 836. | I | Cl | I | | =O | O | O |
| 837. | CH$_3$ | Cl | I | | =O | O | O |
| 838. | CN | Cl | I | | =O | O | O |
| 839. | H | Br | F | | =O | O | O |
| 840. | F | Br | F | | =O | O | O |
| 841. | Cl | Br | F | | =O | O | O |
| 842. | Br | Br | F | | =O | O | O |
| 843. | I | Br | F | | =O | O | O |
| 844. | CH$_3$ | Br | F | | =O | O | O |
| 845. | CN | Br | F | | =O | O | O |
| 846. | H | Br | Cl | | =O | O | O |
| 847. | F | Br | Cl | | =O | O | O |
| 848. | Cl | Br | Cl | | =O | O | O |
| 849. | Br | Br | Cl | | =O | O | O |
| 850. | I | Br | Cl | | =O | O | O |
| 851. | CH$_3$ | Br | Cl | | =O | O | O |
| 852. | CN | Br | Cl | | =O | O | O |
| 853. | H | Br | I | | =O | O | O |
| 854. | F | Br | I | | =O | O | O |
| 855. | Cl | Br | I | | =O | O | O |
| 856. | Br | Br | I | | =O | O | O |
| 857. | I | Br | I | | =O | O | O |
| 858. | CH$_3$ | Br | I | | =O | O | O |
| 859. | CN | Br | I | | =O | O | O |
| 860. | H | I | F | | =O | O | O |
| 861. | F | I | F | | =O | O | O |
| 862. | Cl | I | F | | =O | O | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 863. | Br | I | F | | =O | O | O |
| 864. | I | I | F | | =O | O | O |
| 865. | CH₃ | I | F | | =O | O | O |
| 866. | CN | I | F | | =O | O | O |
| 867. | H | I | Cl | | =O | O | O |
| 868. | F | I | Cl | | =O | O | O |
| 869. | Cl | I | Cl | | =O | O | O |
| 870. | Br | I | Cl | | =O | O | O |
| 871. | I | I | Cl | | =O | O | O |
| 872. | CH₃ | I | Cl | | =O | O | O |
| 873. | CN | I | Cl | | =O | O | O |
| 874. | H | I | Br | | =O | O | O |
| 875. | F | I | Br | | =O | O | O |
| 876. | Cl | I | Br | | =O | O | O |
| 877. | Br | I | Br | | =O | O | O |
| 878. | I | I | Br | | =O | O | O |
| 879. | CH₃ | I | Br | | =O | O | O |
| 880. | CN | I | Br | | =O | O | O |
| 881. | H | H | H | | =S | O | O |
| 882. | F | H | H | | =S | O | O |
| 883. | Cl | H | H | | =S | O | O |
| 884. | Br | H | H | | =S | O | O |
| 885. | I | H | H | | =S | O | O |
| 886. | CH₃ | H | H | | =S | O | O |
| 887. | CN | H | H | | =S | O | O |
| 888. | H | F | H | | =S | O | O |
| 889. | F | F | H | | =S | O | O |
| 890. | Cl | F | H | | =S | O | O |
| 891. | Br | F | H | | =S | O | O |
| 892. | I | F | H | | =S | O | O |
| 893. | CH₃ | F | H | | =S | O | O |
| 894. | CN | F | H | | =S | O | O |
| 895. | H | H | F | | =S | O | O |
| 896. | F | H | F | | =S | O | O |
| 897. | Cl | H | F | | =S | O | O |
| 898. | Br | H | F | | =S | O | O |
| 899. | I | H | F | | =S | O | O |
| 900. | CH₃ | H | F | | =S | O | O |
| 901. | CN | H | F | | =S | O | O |
| 902. | H | F | F | | =S | O | O |
| 903. | F | F | F | | =S | O | O |
| 904. | Cl | F | F | | =S | O | O |
| 905. | Br | F | F | | =S | O | O |
| 906. | I | F | F | | =S | O | O |
| 907. | CH₃ | F | F | | =S | O | O |
| 908. | CN | F | F | | =S | O | O |
| 909. | H | Cl | H | | =S | O | O |
| 910. | Cl | Cl | H | | =S | O | O |
| 911. | Cl | Cl | H | | =S | O | O |
| 912. | Br | Cl | H | | =S | O | O |
| 913. | I | Cl | H | | =S | O | O |
| 914. | CH₃ | Cl | H | | =S | O | O |
| 915. | CN | Cl | H | | =S | O | O |
| 916. | H | H | Cl | | =S | O | O |
| 917. | Cl | H | Cl | | =S | O | O |
| 918. | Cl | H | Cl | | =S | O | O |
| 919. | Br | H | Cl | | =S | O | O |
| 920. | I | H | Cl | | =S | O | O |
| 921. | CH₃ | H | Cl | | =S | O | O |
| 922. | CN | H | Cl | | =S | O | O |
| 923. | H | Cl | Cl | | =S | O | O |
| 924. | Cl | Cl | Cl | | =S | O | O |
| 925. | Cl | Cl | Cl | | =S | O | O |
| 926. | Br | Cl | Cl | | =S | O | O |
| 927. | I | Cl | Cl | | =S | O | O |
| 928. | CH₃ | Cl | Cl | | =S | O | O |
| 929. | CN | Cl | Cl | | =S | O | O |
| 930. | H | Br | H | | =S | O | O |
| 931. | F | Br | H | | =S | O | O |
| 932. | Cl | Br | H | | =S | O | O |
| 933. | Br | Br | H | | =S | O | O |
| 934. | I | Br | H | | =S | O | O |
| 935. | CH₃ | Br | H | | =S | O | O |
| 936. | CN | Br | H | | =S | O | O |
| 937. | H | H | Br | | =S | O | O |
| 938. | F | H | Br | | =S | O | O |
| 939. | Cl | H | Br | | =S | O | O |
| 940. | Br | H | Br | | =S | O | O |
| 941. | I | H | Br | | =S | O | O |
| 942. | CH₃ | H | Br | | =S | O | O |
| 943. | CN | H | Br | | =S | O | O |
| 944. | H | Br | Br | | =S | O | O |
| 945. | F | Br | Br | | =S | O | O |
| 946. | Cl | Br | Br | | =S | O | O |
| 947. | Br | Br | Br | | =S | O | O |
| 948. | I | Br | Br | | =S | O | O |
| 949. | CH₃ | Br | Br | | =S | O | O |
| 950. | CN | Br | Br | | =S | O | O |
| 951. | H | I | H | | =S | O | O |
| 952. | F | I | H | | =S | O | O |
| 953. | Cl | I | H | | =S | O | O |
| 954. | Br | I | H | | =S | O | O |
| 955. | I | I | H | | =S | O | O |
| 956. | CH₃ | I | H | | =S | O | O |
| 957. | CN | I | H | | =S | O | O |
| 958. | H | H | I | | =S | O | O |
| 959. | F | H | I | | =S | O | O |
| 960. | Cl | H | I | | =S | O | O |
| 961. | Br | H | I | | =S | O | O |
| 962. | I | H | I | | =S | O | O |
| 963. | CH₃ | H | I | | =S | O | O |
| 964. | CN | H | I | | =S | O | O |
| 965. | H | I | I | | =S | O | O |
| 966. | F | I | I | | =S | O | O |
| 967. | Cl | I | I | | =S | O | O |
| 968. | Br | I | I | | =S | O | O |
| 969. | I | I | I | | =S | O | O |
| 970. | CH₃ | I | I | | =S | O | O |
| 971. | CN | I | I | | =S | O | O |
| 972. | H | F | Cl | | =S | O | O |
| 973. | D | F | Cl | | =S | O | O |
| 974. | F | F | Cl | | =S | O | O |
| 975. | Cl | F | Cl | | =S | O | O |
| 976. | Br | F | Cl | | =S | O | O |
| 977. | I | F | Cl | | =S | O | O |
| 978. | CH₃ | F | Cl | | =S | O | O |
| 979. | CN | F | Cl | | =S | O | O |
| 980. | H | F | Br | | =S | O | O |
| 981. | F | F | Br | | =S | O | O |
| 982. | Cl | F | Br | | =S | O | O |
| 983. | Br | F | Br | | =S | O | O |
| 984. | I | F | Br | | =S | O | O |
| 985. | CH₃ | F | Br | | =S | O | O |
| 986. | CN | F | Br | | =S | O | O |
| 987. | H | F | I | | =S | O | O |
| 988. | F | F | I | | =S | O | O |
| 989. | Cl | F | I | | =S | O | O |
| 990. | Br | F | I | | =S | O | O |
| 991. | I | F | I | | =S | O | O |
| 992. | CH₃ | F | I | | =S | O | O |
| 993. | CN | F | I | | =S | O | O |
| 994. | H | Cl | F | | =S | O | O |
| 995. | F | Cl | F | | =S | O | O |
| 996. | Cl | Cl | F | | =S | O | O |
| 997. | Br | Cl | F | | =S | O | O |
| 998. | I | Cl | F | | =S | O | O |
| 999. | CH₃ | Cl | F | | =S | O | O |
| 1000. | CN | Cl | F | | =S | O | O |
| 1001. | H | Cl | Br | | =S | O | O |
| 1002. | F | Cl | Br | | =S | O | O |
| 1003. | Cl | Cl | Br | | =S | O | O |
| 1004. | Br | Cl | Br | | =S | O | O |
| 1005. | I | Cl | Br | | =S | O | O |
| 1006. | CH₃ | Cl | Br | | =S | O | O |
| 1007. | CN | Cl | Br | | =S | O | O |
| 1008. | H | Cl | I | | =S | O | O |
| 1009. | F | Cl | I | | =S | O | O |
| 1010. | Cl | Cl | I | | =S | O | O |
| 1011. | Br | Cl | I | | =S | O | O |
| 1012. | I | Cl | I | | =S | O | O |
| 1013. | CH₃ | Cl | I | | =S | O | O |
| 1014. | CN | Cl | I | | =S | O | O |
| 1015. | H | Br | F | | =S | O | O |
| 1016. | F | Br | F | | =S | O | O |
| 1017. | Cl | Br | F | | =S | O | O |
| 1018. | Br | Br | F | | =S | O | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 1019. | I | Br | F | | =S | O | O |
| 1020. | CH$_3$ | Br | F | | =S | O | O |
| 1021. | CN | Br | F | | =S | O | O |
| 1022. | H | Br | Cl | | =S | O | O |
| 1023. | F | Br | Cl | | =S | O | O |
| 1024. | Cl | Br | Cl | | =S | O | O |
| 1025. | Br | Br | Cl | | =S | O | O |
| 1026. | I | Br | Cl | | =S | O | O |
| 1027. | CH$_3$ | Br | Cl | | =S | O | O |
| 1028. | CN | Br | Cl | | =S | O | O |
| 1029. | H | Br | I | | =S | O | O |
| 1030. | F | Br | I | | =S | O | O |
| 1031. | Cl | Br | I | | =S | O | O |
| 1032. | Br | Br | I | | =S | O | O |
| 1033. | I | Br | I | | =S | O | O |
| 1034. | CH$_3$ | Br | I | | =S | O | O |
| 1035. | CN | Br | I | | =S | O | O |
| 1036. | H | I | F | | =S | O | O |
| 1037. | F | I | F | | =S | O | O |
| 1038. | Cl | I | F | | =S | O | O |
| 1039. | Br | I | F | | =S | O | O |
| 1040. | I | I | F | | =S | O | O |
| 1041. | CH$_3$ | I | F | | =S | O | O |
| 1042. | CN | I | F | | =S | O | O |
| 1043. | H | I | Cl | | =S | O | O |
| 1044. | F | I | Cl | | =S | O | O |
| 1045. | Cl | I | Cl | | =S | O | O |
| 1046. | Br | I | Cl | | =S | O | O |
| 1047. | I | I | Cl | | =S | O | O |
| 1048. | CH$_3$ | I | Cl | | =S | O | O |
| 1049. | CN | I | Cl | | =S | O | O |
| 1050. | H | I | Br | | =S | O | O |
| 1051. | F | I | Br | | =S | O | O |
| 1052. | Cl | I | Br | | =S | O | O |
| 1053. | Br | I | Br | | =S | O | O |
| 1054. | I | I | Br | | =S | O | O |
| 1055. | CH$_3$ | I | Br | | =S | O | O |
| 1056. | CN | I | Br | | =S | O | O |
| 1057. | H | H | H | H | H | O | CH$_2$ |
| 1058. | F | H | H | H | H | O | CH$_2$ |
| 1059. | Cl | H | H | H | H | O | CH$_2$ |
| 1060. | Br | H | H | H | H | O | CH$_2$ |
| 1061. | I | H | H | H | H | O | CH$_2$ |
| 1062. | CH$_3$ | H | H | H | H | O | CH$_2$ |
| 1063. | CN | H | H | H | H | O | CH$_2$ |
| 1064. | H | F | H | H | H | O | CH$_2$ |
| 1065. | F | F | H | H | H | O | CH$_2$ |
| 1066. | Cl | F | H | H | H | O | CH$_2$ |
| 1067. | Br | F | H | H | H | O | CH$_2$ |
| 1068. | I | F | H | H | H | O | CH$_2$ |
| 1069. | CH$_3$ | F | H | H | H | O | CH$_2$ |
| 1070. | CN | F | H | H | H | O | CH$_2$ |
| 1071. | H | H | F | H | H | O | CH$_2$ |
| 1072. | F | H | F | H | H | O | CH$_2$ |
| 1073. | Cl | H | F | H | H | O | CH$_2$ |
| 1074. | Br | H | F | H | H | O | CH$_2$ |
| 1075. | I | H | F | H | H | O | CH$_2$ |
| 1076. | CH$_3$ | H | F | H | H | O | CH$_2$ |
| 1077. | CN | H | F | H | H | O | CH$_2$ |
| 1078. | H | F | F | H | H | O | CH$_2$ |
| 1079. | F | F | F | H | H | O | CH$_2$ |
| 1080. | Cl | F | F | H | H | O | CH$_2$ |
| 1081. | Br | F | F | H | H | O | CH$_2$ |
| 1082. | I | F | F | H | H | O | CH$_2$ |
| 1083. | CH$_3$ | F | F | H | H | O | CH$_2$ |
| 1084. | CN | F | F | H | H | O | CH$_2$ |
| 1085. | H | Cl | H | H | H | O | CH$_2$ |
| 1086. | Cl | Cl | H | H | H | O | CH$_2$ |
| 1087. | Cl | Cl | H | H | H | O | CH$_2$ |
| 1088. | Br | Cl | H | H | H | O | CH$_2$ |
| 1089. | I | Cl | H | H | H | O | CH$_2$ |
| 1090. | CH$_3$ | Cl | H | H | H | O | CH$_2$ |
| 1091. | CN | Cl | H | H | H | O | CH$_2$ |
| 1092. | H | H | Cl | H | H | O | CH$_2$ |
| 1093. | Cl | H | Cl | H | H | O | CH$_2$ |
| 1094. | Cl | H | Cl | H | H | O | CH$_2$ |
| 1095. | Br | H | Cl | H | H | O | CH$_2$ |
| 1096. | I | H | Cl | H | H | O | CH$_2$ |
| 1097. | CH$_3$ | H | Cl | H | H | O | CH$_2$ |
| 1098. | CN | H | Cl | H | H | O | CH$_2$ |
| 1099. | H | Cl | Cl | H | H | O | CH$_2$ |
| 1100. | Cl | Cl | Cl | H | H | O | CH$_2$ |
| 1101. | Cl | Cl | Cl | H | H | O | CH$_2$ |
| 1102. | Br | Cl | Cl | H | H | O | CH$_2$ |
| 1103. | I | Cl | Cl | H | H | O | CH$_2$ |
| 1104. | CH$_3$ | Cl | Cl | H | H | O | CH$_2$ |
| 1105. | CN | Cl | Cl | H | H | O | CH$_2$ |
| 1106. | H | Br | H | H | H | O | CH$_2$ |
| 1107. | F | Br | H | H | H | O | CH$_2$ |
| 1108. | Cl | Br | H | H | H | O | CH$_2$ |
| 1109. | Br | Br | H | H | H | O | CH$_2$ |
| 1110. | I | Br | H | H | H | O | CH$_2$ |
| 1111. | CH$_3$ | Br | H | H | H | O | CH$_2$ |
| 1112. | CN | Br | H | H | H | O | CH$_2$ |
| 1113. | H | H | Br | H | H | O | CH$_2$ |
| 1114. | F | H | Br | H | H | O | CH$_2$ |
| 1115. | Cl | H | Br | H | H | O | CH$_2$ |
| 1116. | Br | H | Br | H | H | O | CH$_2$ |
| 1117. | I | H | Br | H | H | O | CH$_2$ |
| 1118. | CH$_3$ | H | Br | H | H | O | CH$_2$ |
| 1119. | CN | H | Br | H | H | O | CH$_2$ |
| 1120. | H | Br | Br | H | H | O | CH$_2$ |
| 1121. | F | Br | Br | H | H | O | CH$_2$ |
| 1122. | Cl | Br | Br | H | H | O | CH$_2$ |
| 1123. | Br | Br | Br | H | H | O | CH$_2$ |
| 1124. | I | Br | Br | H | H | O | CH$_2$ |
| 1125. | CH$_3$ | Br | Br | H | H | O | CH$_2$ |
| 1126. | CN | H | Br | H | H | O | CH$_2$ |
| 1127. | H | I | H | H | H | O | CH$_2$ |
| 1128. | F | I | H | H | H | O | CH$_2$ |
| 1129. | Cl | I | H | H | H | O | CH$_2$ |
| 1130. | Br | I | H | H | H | O | CH$_2$ |
| 1131. | I | I | H | H | H | O | CH$_2$ |
| 1132. | CH$_3$ | I | H | H | H | O | CH$_2$ |
| 1133. | CN | I | H | H | H | O | CH$_2$ |
| 1134. | H | H | I | H | H | O | CH$_2$ |
| 1135. | F | H | I | H | H | O | CH$_2$ |
| 1136. | Cl | H | I | H | H | O | CH$_2$ |
| 1137. | Br | H | I | H | H | O | CH$_2$ |
| 1138. | I | H | I | H | H | O | CH$_2$ |
| 1139. | CH$_3$ | H | I | H | H | O | CH$_2$ |
| 1140. | CN | H | I | H | H | O | CH$_2$ |
| 1141. | H | I | I | H | H | O | CH$_2$ |
| 1142. | F | I | I | H | H | O | CH$_2$ |
| 1143. | Cl | I | I | H | H | O | CH$_2$ |
| 1144. | Br | I | I | H | H | O | CH$_2$ |
| 1145. | I | I | I | H | H | O | CH$_2$ |
| 1146. | CH$_3$ | I | I | H | H | O | CH$_2$ |
| 1147. | CN | I | I | H | H | O | CH$_2$ |
| 1148. | H | F | Cl | H | H | O | CH$_2$ |
| 1149. | D | F | Cl | H | H | O | CH$_2$ |
| 1150. | F | F | Cl | H | H | O | CH$_2$ |
| 1151. | Cl | F | Cl | H | H | O | CH$_2$ |
| 1152. | Br | F | Cl | H | H | O | CH$_2$ |
| 1153. | I | F | Cl | H | H | O | CH$_2$ |
| 1154. | CH$_3$ | F | Cl | H | H | O | CH$_2$ |
| 1155. | CN | F | Cl | H | H | O | CH$_2$ |
| 1156. | H | F | Br | H | H | O | CH$_2$ |
| 1157. | F | F | Br | H | H | O | CH$_2$ |
| 1158. | Cl | F | Br | H | H | O | CH$_2$ |
| 1159. | Br | F | Br | H | H | O | CH$_2$ |
| 1160. | I | F | Br | H | H | O | CH$_2$ |
| 1161. | CH$_3$ | F | Br | H | H | O | CH$_2$ |
| 1162. | CN | F | Br | H | H | O | CH$_2$ |
| 1163. | H | F | I | H | H | O | CH$_2$ |
| 1164. | F | F | I | H | H | O | CH$_2$ |
| 1165. | Cl | F | I | H | H | O | CH$_2$ |
| 1166. | Br | F | I | H | H | O | CH$_2$ |
| 1167. | I | F | I | H | H | O | CH$_2$ |
| 1168. | CH$_3$ | F | I | H | H | O | CH$_2$ |
| 1169. | CN | F | I | H | H | O | CH$_2$ |
| 1170. | H | Cl | F | H | H | O | CH$_2$ |
| 1171. | F | Cl | F | H | H | O | CH$_2$ |
| 1172. | Cl | Cl | F | H | H | O | CH$_2$ |
| 1173. | Br | Cl | F | H | H | O | CH$_2$ |
| 1174. | I | Cl | F | H | H | O | CH$_2$ |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 1175. | CH$_3$ | Cl | F | H | H | O | CH$_2$ |
| 1176. | CN | Cl | F | H | H | O | CH$_2$ |
| 1177. | H | Cl | Br | H | H | O | CH$_2$ |
| 1178. | F | Cl | Br | H | H | O | CH$_2$ |
| 1179. | Cl | Cl | Br | H | H | O | CH$_2$ |
| 1180. | Br | Cl | Br | H | H | O | CH$_2$ |
| 1181. | I | Cl | Br | H | H | O | CH$_2$ |
| 1182. | CH$_3$ | Cl | Br | H | H | O | CH$_2$ |
| 1183. | CN | Cl | Br | H | H | O | CH$_2$ |
| 1184. | H | Cl | I | H | H | O | CH$_2$ |
| 1185. | F | Cl | I | H | H | O | CH$_2$ |
| 1186. | Cl | Cl | I | H | H | O | CH$_2$ |
| 1187. | Br | Cl | I | H | H | O | CH$_2$ |
| 1188. | I | Cl | I | H | H | O | CH$_2$ |
| 1189. | CH$_3$ | Cl | I | H | H | O | CH$_2$ |
| 1190. | CN | Cl | I | H | H | O | CH$_2$ |
| 1191. | H | Br | F | H | H | O | CH$_2$ |
| 1192. | F | Br | F | H | H | O | CH$_2$ |
| 1193. | Cl | Br | F | H | H | O | CH$_2$ |
| 1194. | Br | Br | F | H | H | O | CH$_2$ |
| 1195. | I | Br | F | H | H | O | CH$_2$ |
| 1196. | CH$_3$ | Br | F | H | H | O | CH$_2$ |
| 1197. | CN | Br | F | H | H | O | CH$_2$ |
| 1198. | H | Br | Cl | H | H | O | CH$_2$ |
| 1199. | F | Br | Cl | H | H | O | CH$_2$ |
| 1200. | Cl | Br | Cl | H | H | O | CH$_2$ |
| 1201. | Br | Br | Cl | H | H | O | CH$_2$ |
| 1202. | I | Br | Cl | H | H | O | CH$_2$ |
| 1203. | CH$_3$ | Br | Cl | H | H | O | CH$_2$ |
| 1204. | CN | Br | Cl | H | H | O | CH$_2$ |
| 1205. | H | Br | I | H | H | O | CH$_2$ |
| 1206. | F | Br | I | H | H | O | CH$_2$ |
| 1207. | Cl | Br | I | H | H | O | CH$_2$ |
| 1208. | Br | Br | I | H | H | O | CH$_2$ |
| 1209. | I | Br | I | H | H | O | CH$_2$ |
| 1210. | CH$_3$ | Br | I | H | H | O | CH$_2$ |
| 1211. | CN | Br | I | H | H | O | CH$_2$ |
| 1212. | H | I | F | H | H | O | CH$_2$ |
| 1213. | F | I | F | H | H | O | CH$_2$ |
| 1214. | Cl | I | F | H | H | O | CH$_2$ |
| 1215. | Br | I | F | H | H | O | CH$_2$ |
| 1216. | I | I | F | H | H | O | CH$_2$ |
| 1217. | CH$_3$ | I | F | H | H | O | CH$_2$ |
| 1218. | CN | I | F | H | H | O | CH$_2$ |
| 1219. | H | I | Cl | H | H | O | CH$_2$ |
| 1220. | F | I | Cl | H | H | O | CH$_2$ |
| 1221. | Cl | I | Cl | H | H | O | CH$_2$ |
| 1222. | Br | I | Cl | H | H | O | CH$_2$ |
| 1223. | I | I | Cl | H | H | O | CH$_2$ |
| 1224. | CH$_3$ | I | Cl | H | H | O | CH$_2$ |
| 1225. | CN | I | Cl | H | H | O | CH$_2$ |
| 1226. | H | I | Br | H | H | O | CH$_2$ |
| 1227. | F | I | Br | H | H | O | CH$_2$ |
| 1228. | Cl | I | Br | H | H | O | CH$_2$ |
| 1229. | Br | I | Br | H | H | O | CH$_2$ |
| 1230. | I | I | Br | H | H | O | CH$_2$ |
| 1231. | CH$_3$ | I | Br | H | H | O | CH$_2$ |
| 1232. | CN | I | Br | H | H | O | CH$_2$ |
| 1233. | H | H | H | CH$_3$ | H | O | CH$_2$ |
| 1234. | F | H | H | CH$_3$ | H | O | CH$_2$ |
| 1235. | Cl | H | H | CH$_3$ | H | O | CH$_2$ |
| 1236. | Br | H | H | CH$_3$ | H | O | CH$_2$ |
| 1237. | I | H | H | CH$_3$ | H | O | CH$_2$ |
| 1238. | CH$_3$ | H | H | CH$_3$ | H | O | CH$_2$ |
| 1239. | CN | H | H | CH$_3$ | H | O | CH$_2$ |
| 1240. | H | F | H | CH$_3$ | H | O | CH$_2$ |
| 1241. | F | F | H | CH$_3$ | H | O | CH$_2$ |
| 1242. | Cl | F | H | CH$_3$ | H | O | CH$_2$ |
| 1243. | Br | F | H | CH$_3$ | H | O | CH$_2$ |
| 1244. | I | F | H | CH$_3$ | H | O | CH$_2$ |
| 1245. | CH$_3$ | F | H | CH$_3$ | H | O | CH$_2$ |
| 1246. | CN | F | H | CH$_3$ | H | O | CH$_2$ |
| 1247. | H | H | F | CH$_3$ | H | O | CH$_2$ |
| 1248. | F | H | F | CH$_3$ | H | O | CH$_2$ |
| 1249. | Cl | H | F | CH$_3$ | H | O | CH$_2$ |
| 1250. | Br | H | F | CH$_3$ | H | O | CH$_2$ |
| 1251. | I | H | F | CH$_3$ | H | O | CH$_2$ |
| 1252. | CH$_3$ | H | F | CH$_3$ | H | O | CH$_2$ |
| 1253. | CN | H | F | CH$_3$ | H | O | CH$_2$ |
| 1254. | H | F | F | CH$_3$ | H | O | CH$_2$ |
| 1255. | F | F | F | CH$_3$ | H | O | CH$_2$ |
| 1256. | Cl | F | F | CH$_3$ | H | O | CH$_2$ |
| 1257. | Br | F | F | CH$_3$ | H | O | CH$_2$ |
| 1258. | I | F | F | CH$_3$ | H | O | CH$_2$ |
| 1259. | CH$_3$ | F | F | CH$_3$ | H | O | CH$_2$ |
| 1260. | CN | F | F | CH$_3$ | H | O | CH$_2$ |
| 1261. | H | Cl | H | CH$_3$ | H | O | CH$_2$ |
| 1262. | Cl | Cl | H | CH$_3$ | H | O | CH$_2$ |
| 1263. | Cl | Cl | H | CH$_3$ | H | O | CH$_2$ |
| 1264. | Br | Cl | H | CH$_3$ | H | O | CH$_2$ |
| 1265. | I | Cl | H | CH$_3$ | H | O | CH$_2$ |
| 1266. | CH$_3$ | Cl | H | CH$_3$ | H | O | CH$_2$ |
| 1267. | CN | Cl | H | CH$_3$ | H | O | CH$_2$ |
| 1268. | H | H | Cl | CH$_3$ | H | O | CH$_2$ |
| 1269. | Cl | H | Cl | CH$_3$ | H | O | CH$_2$ |
| 1270. | Cl | H | Cl | CH$_3$ | H | O | CH$_2$ |
| 1271. | Br | H | Cl | CH$_3$ | H | O | CH$_2$ |
| 1272. | I | H | Cl | CH$_3$ | H | O | CH$_2$ |
| 1273. | CH$_3$ | H | Cl | CH$_3$ | H | O | CH$_2$ |
| 1274. | CN | H | Cl | CH$_3$ | H | O | CH$_2$ |
| 1275. | H | Cl | Cl | CH$_3$ | H | O | CH$_2$ |
| 1276. | Cl | Cl | Cl | CH$_3$ | H | O | CH$_2$ |
| 1277. | Cl | Cl | Cl | CH$_3$ | H | O | CH$_2$ |
| 1278. | Br | Cl | Cl | CH$_3$ | H | O | CH$_2$ |
| 1279. | I | Cl | Cl | CH$_3$ | H | O | CH$_2$ |
| 1280. | CH$_3$ | Cl | Cl | CH$_3$ | H | O | CH$_2$ |
| 1281. | CN | Cl | Cl | CH$_3$ | H | O | CH$_2$ |
| 1282. | H | Br | H | CH$_3$ | H | O | CH$_2$ |
| 1283. | F | Br | H | CH$_3$ | H | O | CH$_2$ |
| 1284. | Cl | Br | H | CH$_3$ | H | O | CH$_2$ |
| 1285. | Br | Br | H | CH$_3$ | H | O | CH$_2$ |
| 1286. | I | Br | H | CH$_3$ | H | O | CH$_2$ |
| 1287. | CH$_3$ | Br | H | CH$_3$ | H | O | CH$_2$ |
| 1288. | CN | Br | H | CH$_3$ | H | O | CH$_2$ |
| 1289. | H | H | Br | CH$_3$ | H | O | CH$_2$ |
| 1290. | F | H | Br | CH$_3$ | H | O | CH$_2$ |
| 1291. | Cl | H | Br | CH$_3$ | H | O | CH$_2$ |
| 1292. | Br | H | Br | CH$_3$ | H | O | CH$_2$ |
| 1293. | I | H | Br | CH$_3$ | H | O | CH$_2$ |
| 1294. | CH$_3$ | H | Br | CH$_3$ | H | O | CH$_2$ |
| 1295. | CN | H | Br | CH$_3$ | H | O | CH$_2$ |
| 1296. | H | Br | Br | CH$_3$ | H | O | CH$_2$ |
| 1297. | F | Br | Br | CH$_3$ | H | O | CH$_2$ |
| 1298. | Cl | Br | Br | CH$_3$ | H | O | CH$_2$ |
| 1299. | Br | Br | Br | CH$_3$ | H | O | CH$_2$ |
| 1300. | I | Br | Br | CH$_3$ | H | O | CH$_2$ |
| 1301. | CH$_3$ | Br | Br | CH$_3$ | H | O | CH$_2$ |
| 1302. | CN | H | Br | CH$_3$ | H | O | CH$_2$ |
| 1303. | H | I | H | CH$_3$ | H | O | CH$_2$ |
| 1304. | F | I | H | CH$_3$ | H | O | CH$_2$ |
| 1305. | Cl | I | H | CH$_3$ | H | O | CH$_2$ |
| 1306. | Br | I | H | CH$_3$ | H | O | CH$_2$ |
| 1307. | I | I | H | CH$_3$ | H | O | CH$_2$ |
| 1308. | CH$_3$ | I | H | CH$_3$ | H | O | CH$_2$ |
| 1309. | CN | I | H | CH$_3$ | H | O | CH$_2$ |
| 1310. | H | H | I | CH$_3$ | H | O | CH$_2$ |
| 1311. | F | H | I | CH$_3$ | H | O | CH$_2$ |
| 1312. | Cl | H | I | CH$_3$ | H | O | CH$_2$ |
| 1313. | Br | H | I | CH$_3$ | H | O | CH$_2$ |
| 1314. | I | H | I | CH$_3$ | H | O | CH$_2$ |
| 1315. | CH$_3$ | H | I | CH$_3$ | H | O | CH$_2$ |
| 1316. | CN | H | I | CH$_3$ | H | O | CH$_2$ |
| 1317. | H | I | I | CH$_3$ | H | O | CH$_2$ |
| 1318. | F | I | I | CH$_3$ | H | O | CH$_2$ |
| 1319. | Cl | I | I | CH$_3$ | H | O | CH$_2$ |
| 1320. | Br | I | I | CH$_3$ | H | O | CH$_2$ |
| 1321. | I | I | I | CH$_3$ | H | O | CH$_2$ |
| 1322. | CH$_3$ | I | I | CH$_3$ | H | O | CH$_2$ |
| 1323. | CN | I | I | CH$_3$ | H | O | CH$_2$ |
| 1324. | H | F | Cl | CH$_3$ | H | O | CH$_2$ |
| 1325. | D | F | Cl | CH$_3$ | H | O | CH$_2$ |
| 1326. | F | F | Cl | CH$_3$ | H | O | CH$_2$ |
| 1327. | Cl | F | Cl | CH$_3$ | H | O | CH$_2$ |
| 1328. | Br | F | Cl | CH$_3$ | H | O | CH$_2$ |
| 1329. | I | F | Cl | CH$_3$ | H | O | CH$_2$ |
| 1330. | CH$_3$ | F | Cl | CH$_3$ | H | O | CH$_2$ |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 1331. | CN | F | Cl | $CH_3$ | H | O | $CH_2$ |
| 1332. | H | F | Br | $CH_3$ | H | O | $CH_2$ |
| 1333. | F | F | Br | $CH_3$ | H | O | $CH_2$ |
| 1334. | Cl | F | Br | $CH_3$ | H | O | $CH_2$ |
| 1335. | Br | F | Br | $CH_3$ | H | O | $CH_2$ |
| 1336. | I | F | Br | $CH_3$ | H | O | $CH_2$ |
| 1337. | $CH_3$ | F | Br | $CH_3$ | H | O | $CH_2$ |
| 1338. | CN | F | Br | $CH_3$ | H | O | $CH_2$ |
| 1339. | H | F | I | $CH_3$ | H | O | $CH_2$ |
| 1340. | F | F | I | $CH_3$ | H | O | $CH_2$ |
| 1341. | Cl | F | I | $CH_3$ | H | O | $CH_2$ |
| 1342. | Br | F | I | $CH_3$ | H | O | $CH_2$ |
| 1343. | I | F | I | $CH_3$ | H | O | $CH_2$ |
| 1344. | $CH_3$ | F | I | $CH_3$ | H | O | $CH_2$ |
| 1345. | CN | F | I | $CH_3$ | H | O | $CH_2$ |
| 1346. | H | Cl | F | $CH_3$ | H | O | $CH_2$ |
| 1347. | F | Cl | F | $CH_3$ | H | O | $CH_2$ |
| 1348. | Cl | Cl | F | $CH_3$ | H | O | $CH_2$ |
| 1349. | Br | Cl | F | $CH_3$ | H | O | $CH_2$ |
| 1350. | I | Cl | F | $CH_3$ | H | O | $CH_2$ |
| 1351. | $CH_3$ | Cl | F | $CH_3$ | H | O | $CH_2$ |
| 1352. | CN | Cl | F | $CH_3$ | H | O | $CH_2$ |
| 1353. | H | Cl | Br | $CH_3$ | H | O | $CH_2$ |
| 1354. | F | Cl | Br | $CH_3$ | H | O | $CH_2$ |
| 1355. | Cl | Cl | Br | $CH_3$ | H | O | $CH_2$ |
| 1356. | Br | Cl | Br | $CH_3$ | H | O | $CH_2$ |
| 1357. | I | Cl | Br | $CH_3$ | H | O | $CH_2$ |
| 1358. | $CH_3$ | Cl | Br | $CH_3$ | H | O | $CH_2$ |
| 1359. | CN | Cl | Br | $CH_3$ | H | O | $CH_2$ |
| 1360. | H | Cl | I | $CH_3$ | H | O | $CH_2$ |
| 1361. | F | Cl | I | $CH_3$ | H | O | $CH_2$ |
| 1362. | Cl | Cl | I | $CH_3$ | H | O | $CH_2$ |
| 1363. | Br | Cl | I | $CH_3$ | H | O | $CH_2$ |
| 1364. | I | Cl | I | $CH_3$ | H | O | $CH_2$ |
| 1365. | $CH_3$ | Cl | I | $CH_3$ | H | O | $CH_2$ |
| 1366. | CN | Cl | I | $CH_3$ | H | O | $CH_2$ |
| 1367. | H | Br | F | $CH_3$ | H | O | $CH_2$ |
| 1368. | F | Br | F | $CH_3$ | H | O | $CH_2$ |
| 1369. | Cl | Br | F | $CH_3$ | H | O | $CH_2$ |
| 1370. | Br | Br | F | $CH_3$ | H | O | $CH_2$ |
| 1371. | I | Br | F | $CH_3$ | H | O | $CH_2$ |
| 1372. | $CH_3$ | Br | F | $CH_3$ | H | O | $CH_2$ |
| 1373. | CN | Br | F | $CH_3$ | H | O | $CH_2$ |
| 1374. | H | Br | Cl | $CH_3$ | H | O | $CH_2$ |
| 1375. | F | Br | Cl | $CH_3$ | H | O | $CH_2$ |
| 1376. | Cl | Br | Cl | $CH_3$ | H | O | $CH_2$ |
| 1377. | Br | Br | Cl | $CH_3$ | H | O | $CH_2$ |
| 1378. | I | Br | Cl | $CH_3$ | H | O | $CH_2$ |
| 1379. | $CH_3$ | Br | Cl | $CH_3$ | H | O | $CH_2$ |
| 1380. | CN | Br | Cl | $CH_3$ | H | O | $CH_2$ |
| 1381. | H | Br | I | $CH_3$ | H | O | $CH_2$ |
| 1382. | F | Br | I | $CH_3$ | H | O | $CH_2$ |
| 1383. | Cl | Br | I | $CH_3$ | H | O | $CH_2$ |
| 1384. | Br | Br | I | $CH_3$ | H | O | $CH_2$ |
| 1385. | I | Br | I | $CH_3$ | H | O | $CH_2$ |
| 1386. | $CH_3$ | Br | I | $CH_3$ | H | O | $CH_2$ |
| 1387. | CN | Br | I | $CH_3$ | H | O | $CH_2$ |
| 1388. | H | I | F | $CH_3$ | H | O | $CH_2$ |
| 1389. | F | I | F | $CH_3$ | H | O | $CH_2$ |
| 1390. | Cl | I | F | $CH_3$ | H | O | $CH_2$ |
| 1391. | Br | I | F | $CH_3$ | H | O | $CH_2$ |
| 1392. | I | I | F | $CH_3$ | H | O | $CH_2$ |
| 1393. | $CH_3$ | I | F | $CH_3$ | H | O | $CH_2$ |
| 1394. | CN | I | F | $CH_3$ | H | O | $CH_2$ |
| 1395. | H | I | Cl | $CH_3$ | H | O | $CH_2$ |
| 1396. | F | I | Cl | $CH_3$ | H | O | $CH_2$ |
| 1397. | Cl | I | Cl | $CH_3$ | H | O | $CH_2$ |
| 1398. | Br | I | Cl | $CH_3$ | H | O | $CH_2$ |
| 1399. | I | I | Cl | $CH_3$ | H | O | $CH_2$ |
| 1400. | $CH_3$ | I | Cl | $CH_3$ | H | O | $CH_2$ |
| 1401. | CN | I | Cl | $CH_3$ | H | O | $CH_2$ |
| 1402. | H | I | Br | $CH_3$ | H | O | $CH_2$ |
| 1403. | F | I | Br | $CH_3$ | H | O | $CH_2$ |
| 1404. | Cl | I | Br | $CH_3$ | H | O | $CH_2$ |
| 1405. | Br | I | Br | $CH_3$ | H | O | $CH_2$ |
| 1406. | I | I | Br | $CH_3$ | H | O | $CH_2$ |
| 1407. | $CH_3$ | I | Br | $CH_3$ | H | O | $CH_2$ |
| 1408. | CN | I | Br | $CH_3$ | H | O | $CH_2$ |
| 1409. | H | H | H | $CH_3$ | $CH_3$ | O | $CH_2$ |
| 1410. | F | H | H | $CH_3$ | $CH_3$ | O | $CH_2$ |
| 1411. | Cl | H | H | $CH_3$ | $CH_3$ | O | $CH_2$ |
| 1412. | Br | H | H | $CH_3$ | $CH_3$ | O | $CH_2$ |
| 1413. | I | H | H | $CH_3$ | $CH_3$ | O | $CH_2$ |
| 1414. | $CH_3$ | H | H | $CH_3$ | $CH_3$ | O | $CH_2$ |
| 1415. | CN | H | H | $CH_3$ | $CH_3$ | O | $CH_2$ |
| 1416. | H | F | H | $CH_3$ | $CH_3$ | O | $CH_2$ |
| 1417. | F | F | H | $CH_3$ | $CH_3$ | O | $CH_2$ |
| 1418. | Cl | F | H | $CH_3$ | $CH_3$ | O | $CH_2$ |
| 1419. | Br | F | H | $CH_3$ | $CH_3$ | O | $CH_2$ |
| 1420. | I | F | H | $CH_3$ | $CH_3$ | O | $CH_2$ |
| 1421. | $CH_3$ | F | H | $CH_3$ | $CH_3$ | O | $CH_2$ |
| 1422. | CN | F | H | $CH_3$ | $CH_3$ | O | $CH_2$ |
| 1423. | H | H | F | $CH_3$ | $CH_3$ | O | $CH_2$ |
| 1424. | F | H | F | $CH_3$ | $CH_3$ | O | $CH_2$ |
| 1425. | Cl | H | F | $CH_3$ | $CH_3$ | O | $CH_2$ |
| 1426. | Br | H | F | $CH_3$ | $CH_3$ | O | $CH_2$ |
| 1427. | I | H | F | $CH_3$ | $CH_3$ | O | $CH_2$ |
| 1428. | $CH_3$ | H | F | $CH_3$ | $CH_3$ | O | $CH_2$ |
| 1429. | CN | H | F | $CH_3$ | $CH_3$ | O | $CH_2$ |
| 1430. | H | F | F | $CH_3$ | $CH_3$ | O | $CH_2$ |
| 1431. | F | F | F | $CH_3$ | $CH_3$ | O | $CH_2$ |
| 1432. | Cl | F | F | $CH_3$ | $CH_3$ | O | $CH_2$ |
| 1433. | Br | F | F | $CH_3$ | $CH_3$ | O | $CH_2$ |
| 1434. | I | F | F | $CH_3$ | $CH_3$ | O | $CH_2$ |
| 1435. | $CH_3$ | F | F | $CH_3$ | $CH_3$ | O | $CH_2$ |
| 1436. | CN | F | F | $CH_3$ | $CH_3$ | O | $CH_2$ |
| 1437. | H | Cl | H | $CH_3$ | $CH_3$ | O | $CH_2$ |
| 1438. | Cl | Cl | H | $CH_3$ | $CH_3$ | O | $CH_2$ |
| 1439. | Cl | Cl | H | $CH_3$ | $CH_3$ | O | $CH_2$ |
| 1440. | Br | Cl | H | $CH_3$ | $CH_3$ | O | $CH_2$ |
| 1441. | I | Cl | H | $CH_3$ | $CH_3$ | O | $CH_2$ |
| 1442. | $CH_3$ | Cl | H | $CH_3$ | $CH_3$ | O | $CH_2$ |
| 1443. | CN | Cl | H | $CH_3$ | $CH_3$ | O | $CH_2$ |
| 1444. | H | H | Cl | $CH_3$ | $CH_3$ | O | $CH_2$ |
| 1445. | Cl | H | Cl | $CH_3$ | $CH_3$ | O | $CH_2$ |
| 1446. | Cl | H | Cl | $CH_3$ | $CH_3$ | O | $CH_2$ |
| 1447. | Br | H | Cl | $CH_3$ | $CH_3$ | O | $CH_2$ |
| 1448. | I | H | Cl | $CH_3$ | $CH_3$ | O | $CH_2$ |
| 1449. | $CH_3$ | H | Cl | $CH_3$ | $CH_3$ | O | $CH_2$ |
| 1450. | CN | H | Cl | $CH_3$ | $CH_3$ | O | $CH_2$ |
| 1451. | H | Cl | Cl | $CH_3$ | $CH_3$ | O | $CH_2$ |
| 1452. | Cl | Cl | Cl | $CH_3$ | $CH_3$ | O | $CH_2$ |
| 1453. | Cl | Cl | Cl | $CH_3$ | $CH_3$ | O | $CH_2$ |
| 1454. | Br | Cl | Cl | $CH_3$ | $CH_3$ | O | $CH_2$ |
| 1455. | I | Cl | Cl | $CH_3$ | $CH_3$ | O | $CH_2$ |
| 1456. | $CH_3$ | Cl | Cl | $CH_3$ | $CH_3$ | O | $CH_2$ |
| 1457. | CN | Cl | Cl | $CH_3$ | $CH_3$ | O | $CH_2$ |
| 1458. | H | Br | H | $CH_3$ | $CH_3$ | O | $CH_2$ |
| 1459. | F | Br | H | $CH_3$ | $CH_3$ | O | $CH_2$ |
| 1460. | Cl | Br | H | $CH_3$ | $CH_3$ | O | $CH_2$ |
| 1461. | Br | Br | H | $CH_3$ | $CH_3$ | O | $CH_2$ |
| 1462. | I | Br | H | $CH_3$ | $CH_3$ | O | $CH_2$ |
| 1463. | $CH_3$ | Br | H | $CH_3$ | $CH_3$ | O | $CH_2$ |
| 1464. | CN | Br | H | $CH_3$ | $CH_3$ | O | $CH_2$ |
| 1465. | H | H | Br | $CH_3$ | $CH_3$ | O | $CH_2$ |
| 1466. | F | H | Br | $CH_3$ | $CH_3$ | O | $CH_2$ |
| 1467. | Cl | H | Br | $CH_3$ | $CH_3$ | O | $CH_2$ |
| 1468. | Br | H | Br | $CH_3$ | $CH_3$ | O | $CH_2$ |
| 1469. | I | H | Br | $CH_3$ | $CH_3$ | O | $CH_2$ |
| 1470. | $CH_3$ | H | Br | $CH_3$ | $CH_3$ | O | $CH_2$ |
| 1471. | CN | H | Br | $CH_3$ | $CH_3$ | O | $CH_2$ |
| 1472. | H | Br | Br | $CH_3$ | $CH_3$ | O | $CH_2$ |
| 1473. | F | Br | Br | $CH_3$ | $CH_3$ | O | $CH_2$ |
| 1474. | Cl | Br | Br | $CH_3$ | $CH_3$ | O | $CH_2$ |
| 1475. | Br | Br | Br | $CH_3$ | $CH_3$ | O | $CH_2$ |
| 1476. | I | Br | Br | $CH_3$ | $CH_3$ | O | $CH_2$ |
| 1477. | $CH_3$ | Br | Br | $CH_3$ | $CH_3$ | O | $CH_2$ |
| 1478. | CN | H | Br | $CH_3$ | $CH_3$ | O | $CH_2$ |
| 1479. | H | I | H | $CH_3$ | $CH_3$ | O | $CH_2$ |
| 1480. | F | I | H | $CH_3$ | $CH_3$ | O | $CH_2$ |
| 1481. | Cl | I | H | $CH_3$ | $CH_3$ | O | $CH_2$ |
| 1482. | Br | I | H | $CH_3$ | $CH_3$ | O | $CH_2$ |
| 1483. | I | I | H | $CH_3$ | $CH_3$ | O | $CH_2$ |
| 1484. | $CH_3$ | I | H | $CH_3$ | $CH_3$ | O | $CH_2$ |
| 1485. | CN | I | H | $CH_3$ | $CH_3$ | O | $CH_2$ |
| 1486. | H | H | I | $CH_3$ | $CH_3$ | O | $CH_2$ |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 1487. | F | H | I | $CH_3$ | $CH_3$ | O | $CH_2$ |
| 1488. | Cl | H | I | $CH_3$ | $CH_3$ | O | $CH_2$ |
| 1489. | Br | H | I | $CH_3$ | $CH_3$ | O | $CH_2$ |
| 1490. | I | H | I | $CH_3$ | $CH_3$ | O | $CH_2$ |
| 1491. | $CH_3$ | H | I | $CH_3$ | $CH_3$ | O | $CH_2$ |
| 1492. | CN | H | I | $CH_3$ | $CH_3$ | O | $CH_2$ |
| 1493. | H | I | I | $CH_3$ | $CH_3$ | O | $CH_2$ |
| 1494. | F | I | I | $CH_3$ | $CH_3$ | O | $CH_2$ |
| 1495. | Cl | I | I | $CH_3$ | $CH_3$ | O | $CH_2$ |
| 1496. | Br | I | I | $CH_3$ | $CH_3$ | O | $CH_2$ |
| 1497. | I | I | I | $CH_3$ | $CH_3$ | O | $CH_2$ |
| 1498. | $CH_3$ | I | I | $CH_3$ | $CH_3$ | O | $CH_2$ |
| 1499. | CN | I | I | $CH_3$ | $CH_3$ | O | $CH_2$ |
| 1500. | H | F | Cl | $CH_3$ | $CH_3$ | O | $CH_2$ |
| 1501. | D | F | Cl | $CH_3$ | $CH_3$ | O | $CH_2$ |
| 1502. | F | F | Cl | $CH_3$ | $CH_3$ | O | $CH_2$ |
| 1503. | Cl | F | Cl | $CH_3$ | $CH_3$ | O | $CH_2$ |
| 1504. | Br | F | Cl | $CH_3$ | $CH_3$ | O | $CH_2$ |
| 1505. | I | F | Cl | $CH_3$ | $CH_3$ | O | $CH_2$ |
| 1506. | $CH_3$ | F | Cl | $CH_3$ | $CH_3$ | O | $CH_2$ |
| 1507. | CN | F | Cl | $CH_3$ | $CH_3$ | O | $CH_2$ |
| 1508. | H | F | Br | $CH_3$ | $CH_3$ | O | $CH_2$ |
| 1509. | F | F | Br | $CH_3$ | $CH_3$ | O | $CH_2$ |
| 1510. | Cl | F | Br | $CH_3$ | $CH_3$ | O | $CH_2$ |
| 1511. | Br | F | Br | $CH_3$ | $CH_3$ | O | $CH_2$ |
| 1512. | I | F | Br | $CH_3$ | $CH_3$ | O | $CH_2$ |
| 1513. | $CH_3$ | F | Br | $CH_3$ | $CH_3$ | O | $CH_2$ |
| 1514. | CN | F | Br | $CH_3$ | $CH_3$ | O | $CH_2$ |
| 1515. | H | F | I | $CH_3$ | $CH_3$ | O | $CH_2$ |
| 1516. | F | F | I | $CH_3$ | $CH_3$ | O | $CH_2$ |
| 1517. | Cl | F | I | $CH_3$ | $CH_3$ | O | $CH_2$ |
| 1518. | Br | F | I | $CH_3$ | $CH_3$ | O | $CH_2$ |
| 1519. | I | F | I | $CH_3$ | $CH_3$ | O | $CH_2$ |
| 1520. | $CH_3$ | F | I | $CH_3$ | $CH_3$ | O | $CH_2$ |
| 1521. | CN | F | I | $CH_3$ | $CH_3$ | O | $CH_2$ |
| 1522. | H | Cl | F | $CH_3$ | $CH_3$ | O | $CH_2$ |
| 1523. | F | Cl | F | $CH_3$ | $CH_3$ | O | $CH_2$ |
| 1524. | Cl | Cl | F | $CH_3$ | $CH_3$ | O | $CH_2$ |
| 1525. | Br | Cl | F | $CH_3$ | $CH_3$ | O | $CH_2$ |
| 1526. | I | Cl | F | $CH_3$ | $CH_3$ | O | $CH_2$ |
| 1527. | $CH_3$ | Cl | F | $CH_3$ | $CH_3$ | O | $CH_2$ |
| 1528. | CN | Cl | F | $CH_3$ | $CH_3$ | O | $CH_2$ |
| 1529. | H | Cl | Br | $CH_3$ | $CH_3$ | O | $CH_2$ |
| 1530. | F | Cl | Br | $CH_3$ | $CH_3$ | O | $CH_2$ |
| 1531. | Cl | Cl | Br | $CH_3$ | $CH_3$ | O | $CH_2$ |
| 1532. | Br | Cl | Br | $CH_3$ | $CH_3$ | O | $CH_2$ |
| 1533. | I | Cl | Br | $CH_3$ | $CH_3$ | O | $CH_2$ |
| 1534. | $CH_3$ | Cl | Br | $CH_3$ | $CH_3$ | O | $CH_2$ |
| 1535. | CN | Cl | Br | $CH_3$ | $CH_3$ | O | $CH_2$ |
| 1536. | H | Cl | I | $CH_3$ | $CH_3$ | O | $CH_2$ |
| 1537. | F | Cl | I | $CH_3$ | $CH_3$ | O | $CH_2$ |
| 1538. | Cl | Cl | I | $CH_3$ | $CH_3$ | O | $CH_2$ |
| 1539. | Br | Cl | I | $CH_3$ | $CH_3$ | O | $CH_2$ |
| 1540. | I | Cl | I | $CH_3$ | $CH_3$ | O | $CH_2$ |
| 1541. | $CH_3$ | Cl | I | $CH_3$ | $CH_3$ | O | $CH_2$ |
| 1542. | CN | Cl | I | $CH_3$ | $CH_3$ | O | $CH_2$ |
| 1543. | H | Br | F | $CH_3$ | $CH_3$ | O | $CH_2$ |
| 1544. | F | Br | F | $CH_3$ | $CH_3$ | O | $CH_2$ |
| 1545. | Cl | Br | F | $CH_3$ | $CH_3$ | O | $CH_2$ |
| 1546. | Br | Br | F | $CH_3$ | $CH_3$ | O | $CH_2$ |
| 1547. | I | Br | F | $CH_3$ | $CH_3$ | O | $CH_2$ |
| 1548. | $CH_3$ | Br | F | $CH_3$ | $CH_3$ | O | $CH_2$ |
| 1549. | CN | Br | F | $CH_3$ | $CH_3$ | O | $CH_2$ |
| 1550. | H | Br | Cl | $CH_3$ | $CH_3$ | O | $CH_2$ |
| 1551. | F | Br | Cl | $CH_3$ | $CH_3$ | O | $CH_2$ |
| 1552. | Cl | Br | Cl | $CH_3$ | $CH_3$ | O | $CH_2$ |
| 1553. | Br | Br | Cl | $CH_3$ | $CH_3$ | O | $CH_2$ |
| 1554. | I | Br | Cl | $CH_3$ | $CH_3$ | O | $CH_2$ |
| 1555. | $CH_3$ | Br | Cl | $CH_3$ | $CH_3$ | O | $CH_2$ |
| 1556. | CN | Br | Cl | $CH_3$ | $CH_3$ | O | $CH_2$ |
| 1557. | H | Br | I | $CH_3$ | $CH_3$ | O | $CH_2$ |
| 1558. | F | Br | I | $CH_3$ | $CH_3$ | O | $CH_2$ |
| 1559. | Cl | Br | I | $CH_3$ | $CH_3$ | O | $CH_2$ |
| 1560. | Br | Br | I | $CH_3$ | $CH_3$ | O | $CH_2$ |
| 1561. | I | Br | I | $CH_3$ | $CH_3$ | O | $CH_2$ |
| 1562. | $CH_3$ | Br | I | $CH_3$ | $CH_3$ | O | $CH_2$ |
| 1563. | CN | Br | I | $CH_3$ | $CH_3$ | O | $CH_2$ |
| 1564. | H | I | F | $CH_3$ | $CH_3$ | O | $CH_2$ |
| 1565. | F | I | F | $CH_3$ | $CH_3$ | O | $CH_2$ |
| 1566. | Cl | I | F | $CH_3$ | $CH_3$ | O | $CH_2$ |
| 1567. | Br | I | F | $CH_3$ | $CH_3$ | O | $CH_2$ |
| 1568. | I | I | F | $CH_3$ | $CH_3$ | O | $CH_2$ |
| 1569. | $CH_3$ | I | F | $CH_3$ | $CH_3$ | O | $CH_2$ |
| 1570. | CN | I | F | $CH_3$ | $CH_3$ | O | $CH_2$ |
| 1571. | H | I | Cl | $CH_3$ | $CH_3$ | O | $CH_2$ |
| 1572. | F | I | Cl | $CH_3$ | $CH_3$ | O | $CH_2$ |
| 1573. | Cl | I | Cl | $CH_3$ | $CH_3$ | O | $CH_2$ |
| 1574. | Br | I | Cl | $CH_3$ | $CH_3$ | O | $CH_2$ |
| 1575. | I | I | Cl | $CH_3$ | $CH_3$ | O | $CH_2$ |
| 1576. | $CH_3$ | I | Cl | $CH_3$ | $CH_3$ | O | $CH_2$ |
| 1577. | CN | I | Cl | $CH_3$ | $CH_3$ | O | $CH_2$ |
| 1578. | H | I | Br | $CH_3$ | $CH_3$ | O | $CH_2$ |
| 1579. | F | I | Br | $CH_3$ | $CH_3$ | O | $CH_2$ |
| 1580. | Cl | I | Br | $CH_3$ | $CH_3$ | O | $CH_2$ |
| 1581. | Br | I | Br | $CH_3$ | $CH_3$ | O | $CH_2$ |
| 1582. | I | I | Br | $CH_3$ | $CH_3$ | O | $CH_2$ |
| 1583. | $CH_3$ | I | Br | $CH_3$ | $CH_3$ | O | $CH_2$ |
| 1584. | CN | I | Br | $CH_3$ | $CH_3$ | O | $CH_2$ |
| 1585. | H | H | H | F | F | O | $CH_2$ |
| 1586. | F | H | H | F | F | O | $CH_2$ |
| 1587. | Cl | H | H | F | F | O | $CH_2$ |
| 1588. | Br | H | H | F | F | O | $CH_2$ |
| 1589. | I | H | H | F | F | O | $CH_2$ |
| 1590. | $CH_3$ | H | H | F | F | O | $CH_2$ |
| 1591. | CN | H | H | F | F | O | $CH_2$ |
| 1592. | H | F | H | F | F | O | $CH_2$ |
| 1593. | F | F | H | F | F | O | $CH_2$ |
| 1594. | Cl | F | H | F | F | O | $CH_2$ |
| 1595. | Br | F | H | F | F | O | $CH_2$ |
| 1596. | I | F | H | F | F | O | $CH_2$ |
| 1597. | $CH_3$ | F | H | F | F | O | $CH_2$ |
| 1598. | CN | F | H | F | F | O | $CH_2$ |
| 1599. | H | H | F | F | F | O | $CH_2$ |
| 1600. | F | H | F | F | F | O | $CH_2$ |
| 1601. | Cl | H | F | F | F | O | $CH_2$ |
| 1602. | Br | H | F | F | F | O | $CH_2$ |
| 1603. | I | H | F | F | F | O | $CH_2$ |
| 1604. | $CH_3$ | H | F | F | F | O | $CH_2$ |
| 1605. | CN | H | F | F | F | O | $CH_2$ |
| 1606. | H | F | F | F | F | O | $CH_2$ |
| 1607. | F | F | F | F | F | O | $CH_2$ |
| 1608. | Cl | F | F | F | F | O | $CH_2$ |
| 1609. | Br | F | F | F | F | O | $CH_2$ |
| 1610. | I | F | F | F | F | O | $CH_2$ |
| 1611. | $CH_3$ | F | F | F | F | O | $CH_2$ |
| 1612. | CN | F | F | F | F | O | $CH_2$ |
| 1613. | H | Cl | H | F | F | O | $CH_2$ |
| 1614. | Cl | Cl | H | F | F | O | $CH_2$ |
| 1615. | Cl | Cl | H | F | F | O | $CH_2$ |
| 1616. | Br | Cl | H | F | F | O | $CH_2$ |
| 1617. | I | Cl | H | F | F | O | $CH_2$ |
| 1618. | $CH_3$ | Cl | H | F | F | O | $CH_2$ |
| 1619. | CN | Cl | H | F | F | O | $CH_2$ |
| 1620. | H | H | Cl | F | F | O | $CH_2$ |
| 1621. | Cl | H | Cl | F | F | O | $CH_2$ |
| 1622. | Cl | H | Cl | F | F | O | $CH_2$ |
| 1623. | Br | H | Cl | F | F | O | $CH_2$ |
| 1624. | I | H | Cl | F | F | O | $CH_2$ |
| 1625. | $CH_3$ | H | Cl | F | F | O | $CH_2$ |
| 1626. | CN | H | Cl | F | F | O | $CH_2$ |
| 1627. | H | Cl | Cl | F | F | O | $CH_2$ |
| 1628. | Cl | Cl | Cl | F | F | O | $CH_2$ |
| 1629. | Cl | Cl | Cl | F | F | O | $CH_2$ |
| 1630. | Br | Cl | Cl | F | F | O | $CH_2$ |
| 1631. | I | Cl | Cl | F | F | O | $CH_2$ |
| 1632. | $CH_3$ | Cl | Cl | F | F | O | $CH_2$ |
| 1633. | CN | Cl | Cl | F | F | O | $CH_2$ |
| 1634. | H | Br | H | F | F | O | $CH_2$ |
| 1635. | F | Br | H | F | F | O | $CH_2$ |
| 1636. | Cl | Br | H | F | F | O | $CH_2$ |
| 1637. | Br | Br | H | F | F | O | $CH_2$ |
| 1638. | I | Br | H | F | F | O | $CH_2$ |
| 1639. | $CH_3$ | Br | H | F | F | O | $CH_2$ |
| 1640. | CN | Br | H | F | F | O | $CH_2$ |
| 1641. | H | H | Br | F | F | O | $CH_2$ |
| 1642. | F | H | Br | F | F | O | $CH_2$ |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 1643. | Cl | H | Br | F | F | O | CH$_2$ |
| 1644. | Br | H | Br | F | F | O | CH$_2$ |
| 1645. | I | H | Br | F | F | O | CH$_2$ |
| 1646. | CH$_3$ | H | Br | F | F | O | CH$_2$ |
| 1647. | CN | H | Br | F | F | O | CH$_2$ |
| 1648. | H | Br | Br | F | F | O | CH$_2$ |
| 1649. | F | Br | Br | F | F | O | CH$_2$ |
| 1650. | Cl | Br | Br | F | F | O | CH$_2$ |
| 1651. | Br | Br | Br | F | F | O | CH$_2$ |
| 1652. | I | Br | Br | F | F | O | CH$_2$ |
| 1653. | CH$_3$ | Br | Br | F | F | O | CH$_2$ |
| 1654. | CN | H | Br | F | F | O | CH$_2$ |
| 1655. | H | I | H | F | F | O | CH$_2$ |
| 1656. | F | I | H | F | F | O | CH$_2$ |
| 1657. | Cl | I | H | F | F | O | CH$_2$ |
| 1658. | Br | I | H | F | F | O | CH$_2$ |
| 1659. | I | I | H | F | F | O | CH$_2$ |
| 1660. | CH$_3$ | I | H | F | F | O | CH$_2$ |
| 1661. | CN | I | H | F | F | O | CH$_2$ |
| 1662. | H | H | I | F | F | O | CH$_2$ |
| 1663. | F | H | I | F | F | O | CH$_2$ |
| 1664. | Cl | H | I | F | F | O | CH$_2$ |
| 1665. | Br | H | I | F | F | O | CH$_2$ |
| 1666. | I | H | I | F | F | O | CH$_2$ |
| 1667. | CH$_3$ | H | I | F | F | O | CH$_2$ |
| 1668. | CN | H | I | F | F | O | CH$_2$ |
| 1669. | H | I | I | F | F | O | CH$_2$ |
| 1670. | F | I | I | F | F | O | CH$_2$ |
| 1671. | Cl | I | I | F | F | O | CH$_2$ |
| 1672. | Br | I | I | F | F | O | CH$_2$ |
| 1673. | I | I | I | F | F | O | CH$_2$ |
| 1674. | CH$_3$ | I | I | F | F | O | CH$_2$ |
| 1675. | CN | I | I | F | F | O | CH$_2$ |
| 1676. | H | F | Cl | F | F | O | CH$_2$ |
| 1677. | D | F | Cl | F | F | O | CH$_2$ |
| 1678. | F | F | Cl | F | F | O | CH$_2$ |
| 1679. | Cl | F | Cl | F | F | O | CH$_2$ |
| 1680. | Br | F | Cl | F | F | O | CH$_2$ |
| 1681. | I | F | Cl | F | F | O | CH$_2$ |
| 1682. | CH$_3$ | F | Cl | F | F | O | CH$_2$ |
| 1683. | CN | F | Cl | F | F | O | CH$_2$ |
| 1684. | H | F | Br | F | F | O | CH$_2$ |
| 1685. | F | F | Br | F | F | O | CH$_2$ |
| 1686. | Cl | F | Br | F | F | O | CH$_2$ |
| 1687. | Br | F | Br | F | F | O | CH$_2$ |
| 1688. | I | F | Br | F | F | O | CH$_2$ |
| 1689. | CH$_3$ | F | Br | F | F | O | CH$_2$ |
| 1690. | CN | F | Br | F | F | O | CH$_2$ |
| 1691. | H | F | I | F | F | O | CH$_2$ |
| 1692. | F | F | I | F | F | O | CH$_2$ |
| 1693. | Cl | F | I | F | F | O | CH$_2$ |
| 1694. | Br | F | I | F | F | O | CH$_2$ |
| 1695. | I | F | I | F | F | O | CH$_2$ |
| 1696. | CH$_3$ | F | I | F | F | O | CH$_2$ |
| 1697. | CN | F | I | F | F | O | CH$_2$ |
| 1698. | H | Cl | F | F | F | O | CH$_2$ |
| 1699. | F | Cl | F | F | F | O | CH$_2$ |
| 1700. | Cl | Cl | F | F | F | O | CH$_2$ |
| 1701. | Br | Cl | F | F | F | O | CH$_2$ |
| 1702. | I | Cl | F | F | F | O | CH$_2$ |
| 1703. | CH$_3$ | Cl | F | F | F | O | CH$_2$ |
| 1704. | CN | Cl | F | F | F | O | CH$_2$ |
| 1705. | H | Cl | Br | F | F | O | CH$_2$ |
| 1706. | F | Cl | Br | F | F | O | CH$_2$ |
| 1707. | Cl | Cl | Br | F | F | O | CH$_2$ |
| 1708. | Br | Cl | Br | F | F | O | CH$_2$ |
| 1709. | I | Cl | Br | F | F | O | CH$_2$ |
| 1710. | CH$_3$ | Cl | Br | F | F | O | CH$_2$ |
| 1711. | CN | Cl | Br | F | F | O | CH$_2$ |
| 1712. | H | Cl | I | F | F | O | CH$_2$ |
| 1713. | F | Cl | I | F | F | O | CH$_2$ |
| 1714. | Cl | Cl | I | F | F | O | CH$_2$ |
| 1715. | Br | Cl | I | F | F | O | CH$_2$ |
| 1716. | I | Cl | I | F | F | O | CH$_2$ |
| 1717. | CH$_3$ | Cl | I | F | F | O | CH$_2$ |
| 1718. | CN | Cl | I | F | F | O | CH$_2$ |
| 1719. | H | Br | F | F | F | O | CH$_2$ |
| 1720. | F | Br | F | F | F | O | CH$_2$ |
| 1721. | Cl | Br | F | F | F | O | CH$_2$ |
| 1722. | Br | Br | F | F | F | O | CH$_2$ |
| 1723. | I | Br | F | F | F | O | CH$_2$ |
| 1724. | CH$_3$ | Br | F | F | F | O | CH$_2$ |
| 1725. | CN | Br | F | F | F | O | CH$_2$ |
| 1726. | H | Br | Cl | F | F | O | CH$_2$ |
| 1727. | F | Br | Cl | F | F | O | CH$_2$ |
| 1728. | Cl | Br | Cl | F | F | O | CH$_2$ |
| 1729. | Br | Br | Cl | F | F | O | CH$_2$ |
| 1730. | I | Br | Cl | F | F | O | CH$_2$ |
| 1731. | CH$_3$ | Br | Cl | F | F | O | CH$_2$ |
| 1732. | CN | Br | Cl | F | F | O | CH$_2$ |
| 1733. | H | Br | I | F | F | O | CH$_2$ |
| 1734. | F | Br | I | F | F | O | CH$_2$ |
| 1735. | Cl | Br | I | F | F | O | CH$_2$ |
| 1736. | Br | Br | I | F | F | O | CH$_2$ |
| 1737. | I | Br | I | F | F | O | CH$_2$ |
| 1738. | CH$_3$ | Br | I | F | F | O | CH$_2$ |
| 1739. | CN | Br | I | F | F | O | CH$_2$ |
| 1740. | H | I | F | F | F | O | CH$_2$ |
| 1741. | F | I | F | F | F | O | CH$_2$ |
| 1742. | Cl | I | F | F | F | O | CH$_2$ |
| 1743. | Br | I | F | F | F | O | CH$_2$ |
| 1744. | I | I | F | F | F | O | CH$_2$ |
| 1745. | CH$_3$ | I | F | F | F | O | CH$_2$ |
| 1746. | CN | I | F | F | F | O | CH$_2$ |
| 1747. | H | I | Cl | F | F | O | CH$_2$ |
| 1748. | F | I | Cl | F | F | O | CH$_2$ |
| 1749. | Cl | I | Cl | F | F | O | CH$_2$ |
| 1750. | Br | I | Cl | F | F | O | CH$_2$ |
| 1751. | I | I | Cl | F | F | O | CH$_2$ |
| 1752. | CH$_3$ | I | Cl | F | F | O | CH$_2$ |
| 1753. | CN | I | Cl | F | F | O | CH$_2$ |
| 1754. | H | I | Br | F | F | O | CH$_2$ |
| 1755. | F | I | Br | F | F | O | CH$_2$ |
| 1756. | Cl | I | Br | F | F | O | CH$_2$ |
| 1757. | Br | I | Br | F | F | O | CH$_2$ |
| 1758. | I | I | Br | F | F | O | CH$_2$ |
| 1759. | CH$_3$ | I | Br | F | F | O | CH$_2$ |
| 1760. | CN | I | Br | F | F | O | CH$_2$ |
| 1761. | H | H | H |  | =O | O | CH$_2$ |
| 1762. | F | H | H |  | =O | O | CH$_2$ |
| 1763. | Cl | H | H |  | =O | O | CH$_2$ |
| 1764. | Br | H | H |  | =O | O | CH$_2$ |
| 1765. | I | H | H |  | =O | O | CH$_2$ |
| 1766. | CH$_3$ | H | H |  | =O | O | CH$_2$ |
| 1767. | CN | H | H |  | =O | O | CH$_2$ |
| 1768. | H | F | H |  | =O | O | CH$_2$ |
| 1769. | F | F | H |  | =O | O | CH$_2$ |
| 1770. | Cl | F | H |  | =O | O | CH$_2$ |
| 1771. | Br | F | H |  | =O | O | CH$_2$ |
| 1772. | I | F | H |  | =O | O | CH$_2$ |
| 1773. | CH$_3$ | F | H |  | =O | O | CH$_2$ |
| 1774. | CN | F | H |  | =O | O | CH$_2$ |
| 1775. | H | H | F |  | =O | O | CH$_2$ |
| 1776. | F | H | F |  | =O | O | CH$_2$ |
| 1777. | Cl | H | F |  | =O | O | CH$_2$ |
| 1778. | Br | H | F |  | =O | O | CH$_2$ |
| 1779. | I | H | F |  | =O | O | CH$_2$ |
| 1780. | CH$_3$ | H | F |  | =O | O | CH$_2$ |
| 1781. | CN | H | F |  | =O | O | CH$_2$ |
| 1782. | H | F | F |  | =O | O | CH$_2$ |
| 1783. | F | F | F |  | =O | O | CH$_2$ |
| 1784. | Cl | F | F |  | =O | O | CH$_2$ |
| 1785. | Br | F | F |  | =O | O | CH$_2$ |
| 1786. | I | F | F |  | =O | O | CH$_2$ |
| 1787. | CH$_3$ | F | F |  | =O | O | CH$_2$ |
| 1788. | CN | F | F |  | =O | O | CH$_2$ |
| 1789. | H | Cl | H |  | =O | O | CH$_2$ |
| 1790. | Cl | Cl | H |  | =O | O | CH$_2$ |
| 1791. | Cl | Cl | H |  | =O | O | CH$_2$ |
| 1792. | Br | Cl | H |  | =O | O | CH$_2$ |
| 1793. | I | Cl | H |  | =O | O | CH$_2$ |
| 1794. | CH$_3$ | Cl | H |  | =O | O | CH$_2$ |
| 1795. | CN | Cl | H |  | =O | O | CH$_2$ |
| 1796. | H | H | Cl |  | =O | O | CH$_2$ |
| 1797. | Cl | H | Cl |  | =O | O | CH$_2$ |
| 1798. | Cl | H | Cl |  | =O | O | CH$_2$ |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 1799. | Br | H | Cl | =O | O | $CH_2$ |
| 1800. | I | H | Cl | =O | O | $CH_2$ |
| 1801. | $CH_3$ | H | Cl | =O | O | $CH_2$ |
| 1802. | CN | H | Cl | =O | O | $CH_2$ |
| 1803. | H | Cl | Cl | =O | O | $CH_2$ |
| 1804. | Cl | Cl | Cl | =O | O | $CH_2$ |
| 1805. | Cl | Cl | Cl | =O | O | $CH_2$ |
| 1806. | Br | Cl | Cl | =O | O | $CH_2$ |
| 1807. | I | Cl | Cl | =O | O | $CH_2$ |
| 1808. | $CH_3$ | Cl | Cl | =O | O | $CH_2$ |
| 1809. | CN | Cl | Cl | =O | O | $CH_2$ |
| 1810. | H | Br | H | =O | O | $CH_2$ |
| 1811. | F | Br | H | =O | O | $CH_2$ |
| 1812. | Cl | Br | H | =O | O | $CH_2$ |
| 1813. | Br | Br | H | =O | O | $CH_2$ |
| 1814. | I | Br | H | =O | O | $CH_2$ |
| 1815. | $CH_3$ | Br | H | =O | O | $CH_2$ |
| 1816. | CN | Br | H | =O | O | $CH_2$ |
| 1817. | H | H | Br | =O | O | $CH_2$ |
| 1818. | F | H | Br | =O | O | $CH_2$ |
| 1819. | Cl | H | Br | =O | O | $CH_2$ |
| 1820. | Br | H | Br | =O | O | $CH_2$ |
| 1821. | I | H | Br | =O | O | $CH_2$ |
| 1822. | $CH_3$ | H | Br | =O | O | $CH_2$ |
| 1823. | CN | H | Br | =O | O | $CH_2$ |
| 1824. | H | Br | Br | =O | O | $CH_2$ |
| 1825. | F | Br | Br | =O | O | $CH_2$ |
| 1826. | Cl | Br | Br | =O | O | $CH_2$ |
| 1827. | Br | Br | Br | =O | O | $CH_2$ |
| 1828. | I | Br | Br | =O | O | $CH_2$ |
| 1829. | $CH_3$ | Br | Br | =O | O | $CH_2$ |
| 1830. | CN | Br | Br | =O | O | $CH_2$ |
| 1831. | H | I | H | =O | O | $CH_2$ |
| 1832. | F | I | H | =O | O | $CH_2$ |
| 1833. | Cl | I | H | =O | O | $CH_2$ |
| 1834. | Br | I | H | =O | O | $CH_2$ |
| 1835. | I | I | H | =O | O | $CH_2$ |
| 1836. | $CH_3$ | I | H | =O | O | $CH_2$ |
| 1837. | CN | I | H | =O | O | $CH_2$ |
| 1838. | H | H | I | =O | O | $CH_2$ |
| 1839. | F | H | I | =O | O | $CH_2$ |
| 1840. | Cl | H | I | =O | O | $CH_2$ |
| 1841. | Br | H | I | =O | O | $CH_2$ |
| 1842. | I | H | I | =O | O | $CH_2$ |
| 1843. | $CH_3$ | H | I | =O | O | $CH_2$ |
| 1844. | CN | H | I | =O | O | $CH_2$ |
| 1845. | H | I | I | =O | O | $CH_2$ |
| 1846. | F | I | I | =O | O | $CH_2$ |
| 1847. | Cl | I | I | =O | O | $CH_2$ |
| 1848. | Br | I | I | =O | O | $CH_2$ |
| 1849. | I | I | I | =O | O | $CH_2$ |
| 1850. | $CH_3$ | I | I | =O | O | $CH_2$ |
| 1851. | CN | I | I | =O | O | $CH_2$ |
| 1852. | H | F | Cl | =O | O | $CH_2$ |
| 1853. | D | F | Cl | =O | O | $CH_2$ |
| 1854. | F | F | Cl | =O | O | $CH_2$ |
| 1855. | Cl | F | Cl | =O | O | $CH_2$ |
| 1856. | Br | F | Cl | =O | O | $CH_2$ |
| 1857. | I | F | Cl | =O | O | $CH_2$ |
| 1858. | $CH_3$ | F | Cl | =O | O | $CH_2$ |
| 1859. | CN | F | Cl | =O | O | $CH_2$ |
| 1860. | H | F | Br | =O | O | $CH_2$ |
| 1861. | F | F | Br | =O | O | $CH_2$ |
| 1862. | Cl | F | Br | =O | O | $CH_2$ |
| 1863. | Br | F | Br | =O | O | $CH_2$ |
| 1864. | I | F | Br | =O | O | $CH_2$ |
| 1865. | $CH_3$ | F | Br | =O | O | $CH_2$ |
| 1866. | CN | F | Br | =O | O | $CH_2$ |
| 1867. | H | F | I | =O | O | $CH_2$ |
| 1868. | F | F | I | =O | O | $CH_2$ |
| 1869. | Cl | F | I | =O | O | $CH_2$ |
| 1870. | Br | F | I | =O | O | $CH_2$ |
| 1871. | I | F | I | =O | O | $CH_2$ |
| 1872. | $CH_3$ | F | I | =O | O | $CH_2$ |
| 1873. | CN | F | I | =O | O | $CH_2$ |
| 1874. | H | Cl | F | =O | O | $CH_2$ |
| 1875. | F | Cl | F | =O | O | $CH_2$ |
| 1876. | Cl | Cl | F | =O | O | $CH_2$ |
| 1877. | Br | Cl | F | =O | O | $CH_2$ |
| 1878. | I | Cl | F | =O | O | $CH_2$ |
| 1879. | $CH_3$ | Cl | F | =O | O | $CH_2$ |
| 1880. | CN | Cl | F | =O | O | $CH_2$ |
| 1881. | H | Cl | Br | =O | O | $CH_2$ |
| 1882. | F | Cl | Br | =O | O | $CH_2$ |
| 1883. | Cl | Cl | Br | =O | O | $CH_2$ |
| 1884. | Br | Cl | Br | =O | O | $CH_2$ |
| 1885. | I | Cl | Br | =O | O | $CH_2$ |
| 1886. | $CH_3$ | Cl | Br | =O | O | $CH_2$ |
| 1887. | CN | Cl | Br | =O | O | $CH_2$ |
| 1888. | H | Cl | I | =O | O | $CH_2$ |
| 1889. | F | Cl | I | =O | O | $CH_2$ |
| 1890. | Cl | Cl | I | =O | O | $CH_2$ |
| 1891. | Br | Cl | I | =O | O | $CH_2$ |
| 1892. | I | Cl | I | =O | O | $CH_2$ |
| 1893. | $CH_3$ | Cl | I | =O | O | $CH_2$ |
| 1894. | CN | Cl | I | =O | O | $CH_2$ |
| 1895. | H | Br | F | =O | O | $CH_2$ |
| 1896. | F | Br | F | =O | O | $CH_2$ |
| 1897. | Cl | Br | F | =O | O | $CH_2$ |
| 1898. | Br | Br | F | =O | O | $CH_2$ |
| 1899. | I | Br | F | =O | O | $CH_2$ |
| 1900. | $CH_3$ | Br | F | =O | O | $CH_2$ |
| 1901. | CN | Br | F | =O | O | $CH_2$ |
| 1902. | H | Br | Cl | =O | O | $CH_2$ |
| 1903. | F | Br | Cl | =O | O | $CH_2$ |
| 1904. | Cl | Br | Cl | =O | O | $CH_2$ |
| 1905. | Br | Br | Cl | =O | O | $CH_2$ |
| 1906. | I | Br | Cl | =O | O | $CH_2$ |
| 1907. | $CH_3$ | Br | Cl | =O | O | $CH_2$ |
| 1908. | CN | Br | Cl | =O | O | $CH_2$ |
| 1909. | H | Br | I | =O | O | $CH_2$ |
| 1910. | F | Br | I | =O | O | $CH_2$ |
| 1911. | Cl | Br | I | =O | O | $CH_2$ |
| 1912. | Br | Br | I | =O | O | $CH_2$ |
| 1913. | I | Br | I | =O | O | $CH_2$ |
| 1914. | $CH_3$ | Br | I | =O | O | $CH_2$ |
| 1915. | CN | Br | I | =O | O | $CH_2$ |
| 1916. | H | I | F | =O | O | $CH_2$ |
| 1917. | F | I | F | =O | O | $CH_2$ |
| 1918. | Cl | I | F | =O | O | $CH_2$ |
| 1919. | Br | I | F | =O | O | $CH_2$ |
| 1920. | I | I | F | =O | O | $CH_2$ |
| 1921. | $CH_3$ | I | F | =O | O | $CH_2$ |
| 1922. | CN | I | F | =O | O | $CH_2$ |
| 1923. | H | I | Cl | =O | O | $CH_2$ |
| 1924. | F | I | Cl | =O | O | $CH_2$ |
| 1925. | Cl | I | Cl | =O | O | $CH_2$ |
| 1926. | Br | I | Cl | =O | O | $CH_2$ |
| 1927. | I | I | Cl | =O | O | $CH_2$ |
| 1928. | $CH_3$ | I | Cl | =O | O | $CH_2$ |
| 1929. | CN | I | Cl | =O | O | $CH_2$ |
| 1930. | H | I | Br | =O | O | $CH_2$ |
| 1931. | F | I | Br | =O | O | $CH_2$ |
| 1932. | Cl | I | Br | =O | O | $CH_2$ |
| 1933. | Br | I | Br | =O | O | $CH_2$ |
| 1934. | I | I | Br | =O | O | $CH_2$ |
| 1935. | $CH_3$ | I | Br | =O | O | $CH_2$ |
| 1936. | CN | I | Br | =O | O | $CH_2$ |
| 1937. | H | H | H | =S | O | $CH_2$ |
| 1938. | F | H | H | =S | O | $CH_2$ |
| 1939. | Cl | H | H | =S | O | $CH_2$ |
| 1940. | Br | H | H | =S | O | $CH_2$ |
| 1941. | I | H | H | =S | O | $CH_2$ |
| 1942. | $CH_3$ | H | H | =S | O | $CH_2$ |
| 1943. | CN | H | H | =S | O | $CH_2$ |
| 1944. | H | F | H | =S | O | $CH_2$ |
| 1945. | F | F | H | =S | O | $CH_2$ |
| 1946. | Cl | F | H | =S | O | $CH_2$ |
| 1947. | Br | F | H | =S | O | $CH_2$ |
| 1948. | I | F | H | =S | O | $CH_2$ |
| 1949. | $CH_3$ | F | H | =S | O | $CH_2$ |
| 1950. | CN | F | H | =S | O | $CH_2$ |
| 1951. | H | H | F | =S | O | $CH_2$ |
| 1952. | F | H | F | =S | O | $CH_2$ |
| 1953. | Cl | H | F | =S | O | $CH_2$ |
| 1954. | Br | H | F | =S | O | $CH_2$ |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 1955. | I | H | F | | =S | O | CH$_2$ |
| 1956. | CH$_3$ | H | F | | =S | O | CH$_2$ |
| 1957. | CN | H | F | | =S | O | CH$_2$ |
| 1958. | H | F | F | | =S | O | CH$_2$ |
| 1959. | F | F | F | | =S | O | CH$_2$ |
| 1960. | Cl | F | F | | =S | O | CH$_2$ |
| 1961. | Br | F | F | | =S | O | CH$_2$ |
| 1962. | I | F | F | | =S | O | CH$_2$ |
| 1963. | CH$_3$ | F | F | | =S | O | CH$_2$ |
| 1964. | CN | F | F | | =S | O | CH$_2$ |
| 1965. | H | Cl | H | | =S | O | CH$_2$ |
| 1966. | Cl | Cl | H | | =S | O | CH$_2$ |
| 1967. | Cl | Cl | H | | =S | O | CH$_2$ |
| 1968. | Br | Cl | H | | =S | O | CH$_2$ |
| 1969. | I | Cl | H | | =S | O | CH$_2$ |
| 1970. | CH$_3$ | Cl | H | | =S | O | CH$_2$ |
| 1971. | CN | Cl | H | | =S | O | CH$_2$ |
| 1972. | H | H | Cl | | =S | O | CH$_2$ |
| 1973. | Cl | H | Cl | | =S | O | CH$_2$ |
| 1974. | Cl | H | Cl | | =S | O | CH$_2$ |
| 1975. | Br | H | Cl | | =S | O | CH$_2$ |
| 1976. | I | H | Cl | | =S | O | CH$_2$ |
| 1977. | CH$_3$ | H | Cl | | =S | O | CH$_2$ |
| 1978. | CN | H | Cl | | =S | O | CH$_2$ |
| 1979. | H | Cl | Cl | | =S | O | CH$_2$ |
| 1980. | Cl | Cl | Cl | | =S | O | CH$_2$ |
| 1981. | Cl | Cl | Cl | | =S | O | CH$_2$ |
| 1982. | Br | Cl | Cl | | =S | O | CH$_2$ |
| 1983. | I | Cl | Cl | | =S | O | CH$_2$ |
| 1984. | CH$_3$ | Cl | Cl | | =S | O | CH$_2$ |
| 1985. | CN | Cl | Cl | | =S | O | CH$_2$ |
| 1986. | H | Br | H | | =S | O | CH$_2$ |
| 1987. | F | Br | H | | =S | O | CH$_2$ |
| 1988. | Cl | Br | H | | =S | O | CH$_2$ |
| 1989. | Br | Br | H | | =S | O | CH$_2$ |
| 1990. | I | Br | H | | =S | O | CH$_2$ |
| 1991. | CH$_3$ | Br | H | | =S | O | CH$_2$ |
| 1992. | CN | Br | H | | =S | O | CH$_2$ |
| 1993. | H | H | Br | | =S | O | CH$_2$ |
| 1994. | F | H | Br | | =S | O | CH$_2$ |
| 1995. | Cl | H | Br | | =S | O | CH$_2$ |
| 1996. | Br | H | Br | | =S | O | CH$_2$ |
| 1997. | I | H | Br | | =S | O | CH$_2$ |
| 1998. | CH$_3$ | H | Br | | =S | O | CH$_2$ |
| 1999. | CN | H | Br | | =S | O | CH$_2$ |
| 2000. | H | Br | Br | | =S | O | CH$_2$ |
| 2001. | F | Br | Br | | =S | O | CH$_2$ |
| 2002. | Cl | Br | Br | | =S | O | CH$_2$ |
| 2003. | Br | Br | Br | | =S | O | CH$_2$ |
| 2004. | I | Br | Br | | =S | O | CH$_2$ |
| 2005. | CH$_3$ | Br | Br | | =S | O | CH$_2$ |
| 2006. | CN | Br | Br | | =S | O | CH$_2$ |
| 2007. | H | I | H | | =S | O | CH$_2$ |
| 2008. | F | I | H | | =S | O | CH$_2$ |
| 2009. | Cl | I | H | | =S | O | CH$_2$ |
| 2010. | Br | I | H | | =S | O | CH$_2$ |
| 2011. | I | I | H | | =S | O | CH$_2$ |
| 2012. | CH$_3$ | I | H | | =S | O | CH$_2$ |
| 2013. | CN | I | H | | =S | O | CH$_2$ |
| 2014. | H | H | I | | =S | O | CH$_2$ |
| 2015. | F | H | I | | =S | O | CH$_2$ |
| 2016. | Cl | H | I | | =S | O | CH$_2$ |
| 2017. | Br | H | I | | =S | O | CH$_2$ |
| 2018. | I | H | I | | =S | O | CH$_2$ |
| 2019. | CH$_3$ | H | I | | =S | O | CH$_2$ |
| 2020. | CN | H | I | | =S | O | CH$_2$ |
| 2021. | H | I | I | | =S | O | CH$_2$ |
| 2022. | F | I | I | | =S | O | CH$_2$ |
| 2023. | Cl | I | I | | =S | O | CH$_2$ |
| 2024. | Br | I | I | | =S | O | CH$_2$ |
| 2025. | I | I | I | | =S | O | CH$_2$ |
| 2026. | CH$_3$ | I | I | | =S | O | CH$_2$ |
| 2027. | CN | I | I | | =S | O | CH$_2$ |
| 2028. | H | F | Cl | | =S | O | CH$_2$ |
| 2029. | D | F | Cl | | =S | O | CH$_2$ |
| 2030. | F | F | Cl | | =S | O | CH$_2$ |
| 2031. | Cl | F | Cl | | =S | O | CH$_2$ |
| 2032. | Br | F | Cl | | =S | O | CH$_2$ |
| 2033. | I | F | Cl | | =S | O | CH$_2$ |
| 2034. | CH$_3$ | F | Cl | | =S | O | CH$_2$ |
| 2035. | CN | F | Cl | | =S | O | CH$_2$ |
| 2036. | H | F | Br | | =S | O | CH$_2$ |
| 2037. | F | F | Br | | =S | O | CH$_2$ |
| 2038. | Cl | F | Br | | =S | O | CH$_2$ |
| 2039. | Br | F | Br | | =S | O | CH$_2$ |
| 2040. | I | F | Br | | =S | O | CH$_2$ |
| 2041. | CH$_3$ | F | Br | | =S | O | CH$_2$ |
| 2042. | CN | F | Br | | =S | O | CH$_2$ |
| 2043. | H | F | I | | =S | O | CH$_2$ |
| 2044. | F | F | I | | =S | O | CH$_2$ |
| 2045. | Cl | F | I | | =S | O | CH$_2$ |
| 2046. | Br | F | I | | =S | O | CH$_2$ |
| 2047. | I | F | I | | =S | O | CH$_2$ |
| 2048. | CH$_3$ | F | I | | =S | O | CH$_2$ |
| 2049. | CN | F | I | | =S | O | CH$_2$ |
| 2050. | H | Cl | F | | =S | O | CH$_2$ |
| 2051. | F | Cl | F | | =S | O | CH$_2$ |
| 2052. | Cl | Cl | F | | =S | O | CH$_2$ |
| 2053. | Br | Cl | F | | =S | O | CH$_2$ |
| 2054. | I | Cl | F | | =S | O | CH$_2$ |
| 2055. | CH$_3$ | Cl | F | | =S | O | CH$_2$ |
| 2056. | CN | Cl | F | | =S | O | CH$_2$ |
| 2057. | H | Cl | Br | | =S | O | CH$_2$ |
| 2058. | F | Cl | Br | | =S | O | CH$_2$ |
| 2059. | Cl | Cl | Br | | =S | O | CH$_2$ |
| 2060. | Br | Cl | Br | | =S | O | CH$_2$ |
| 2061. | I | Cl | Br | | =S | O | CH$_2$ |
| 2062. | CH$_3$ | Cl | Br | | =S | O | CH$_2$ |
| 2063. | CN | Cl | Br | | =S | O | CH$_2$ |
| 2064. | H | Cl | I | | =S | O | CH$_2$ |
| 2065. | F | Cl | I | | =S | O | CH$_2$ |
| 2066. | Cl | Cl | I | | =S | O | CH$_2$ |
| 2067. | Br | Cl | I | | =S | O | CH$_2$ |
| 2068. | I | Cl | I | | =S | O | CH$_2$ |
| 2069. | CH$_3$ | Cl | I | | =S | O | CH$_2$ |
| 2070. | CN | Cl | I | | =S | O | CH$_2$ |
| 2071. | H | Br | F | | =S | O | CH$_2$ |
| 2072. | F | Br | F | | =S | O | CH$_2$ |
| 2073. | Cl | Br | F | | =S | O | CH$_2$ |
| 2074. | Br | Br | F | | =S | O | CH$_2$ |
| 2075. | I | Br | F | | =S | O | CH$_2$ |
| 2076. | CH$_3$ | Br | F | | =S | O | CH$_2$ |
| 2077. | CN | Br | F | | =S | O | CH$_2$ |
| 2078. | H | Br | Cl | | =S | O | CH$_2$ |
| 2079. | F | Br | Cl | | =S | O | CH$_2$ |
| 2080. | Cl | Br | Cl | | =S | O | CH$_2$ |
| 2081. | Br | Br | Cl | | =S | O | CH$_2$ |
| 2082. | I | Br | Cl | | =S | O | CH$_2$ |
| 2083. | CH$_3$ | Br | Cl | | =S | O | CH$_2$ |
| 2084. | CN | Br | Cl | | =S | O | CH$_2$ |
| 2085. | H | Br | I | | =S | O | CH$_2$ |
| 2086. | F | Br | I | | =S | O | CH$_2$ |
| 2087. | Cl | Br | I | | =S | O | CH$_2$ |
| 2088. | Br | Br | I | | =S | O | CH$_2$ |
| 2089. | I | Br | I | | =S | O | CH$_2$ |
| 2090. | CH$_3$ | Br | I | | =S | O | CH$_2$ |
| 2091. | CN | Br | I | | =S | O | CH$_2$ |
| 2092. | H | I | F | | =S | O | CH$_2$ |
| 2093. | F | I | F | | =S | O | CH$_2$ |
| 2094. | Cl | I | F | | =S | O | CH$_2$ |
| 2095. | Br | I | F | | =S | O | CH$_2$ |
| 2096. | I | I | F | | =S | O | CH$_2$ |
| 2097. | CH$_3$ | I | F | | =S | O | CH$_2$ |
| 2098. | CN | I | F | | =S | O | CH$_2$ |
| 2099. | H | I | Cl | | =S | O | CH$_2$ |
| 2100. | F | I | Cl | | =S | O | CH$_2$ |
| 2101. | Cl | I | Cl | | =S | O | CH$_2$ |
| 2102. | Br | I | Cl | | =S | O | CH$_2$ |
| 2103. | I | I | Cl | | =S | O | CH$_2$ |
| 2104. | CH$_3$ | I | Cl | | =S | O | CH$_2$ |
| 2105. | CN | I | Cl | | =S | O | CH$_2$ |
| 2106. | H | I | Br | | =S | O | CH$_2$ |
| 2107. | F | I | Br | | =S | O | CH$_2$ |
| 2108. | Cl | I | Br | | =S | O | CH$_2$ |
| 2109. | Br | I | Br | | =S | O | CH$_2$ |
| 2110. | I | I | Br | | =S | O | CH$_2$ |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 2111. | CH$_3$ | I | Br | | =S | O | CH$_2$ |
| 2112. | CN | I | Br | | =S | O | CH$_2$ |
| 2113. | H | H | H | H | H | CH$_2$ | O |
| 2114. | F | H | H | H | H | CH$_2$ | O |
| 2115. | Cl | H | H | H | H | CH$_2$ | O |
| 2116. | Br | H | H | H | H | CH$_2$ | O |
| 2117. | I | H | H | H | H | CH$_2$ | O |
| 2118. | CH$_3$ | H | H | H | H | CH$_2$ | O |
| 2119. | CN | H | H | H | H | CH$_2$ | O |
| 2120. | H | F | H | H | H | CH$_2$ | O |
| 2121. | F | F | H | H | H | CH$_2$ | O |
| 2122. | Cl | F | H | H | H | CH$_2$ | O |
| 2123. | Br | F | H | H | H | CH$_2$ | O |
| 2124. | I | F | H | H | H | CH$_2$ | O |
| 2125. | CH$_3$ | F | H | H | H | CH$_2$ | O |
| 2126. | CN | F | H | H | H | CH$_2$ | O |
| 2127. | H | H | F | H | H | CH$_2$ | O |
| 2128. | F | H | F | H | H | CH$_2$ | O |
| 2129. | Cl | H | F | H | H | CH$_2$ | O |
| 2130. | Br | H | F | H | H | CH$_2$ | O |
| 2131. | I | H | F | H | H | CH$_2$ | O |
| 2132. | CH$_3$ | H | F | H | H | CH$_2$ | O |
| 2133. | CN | H | F | H | H | CH$_2$ | O |
| 2134. | H | F | F | H | H | CH$_2$ | O |
| 2135. | F | F | F | H | H | CH$_2$ | O |
| 2136. | Cl | F | F | H | H | CH$_2$ | O |
| 2137. | Br | F | F | H | H | CH$_2$ | O |
| 2138. | I | F | F | H | H | CH$_2$ | O |
| 2139. | CH$_3$ | F | F | H | H | CH$_2$ | O |
| 2140. | CN | F | F | H | H | CH$_2$ | O |
| 2141. | H | Cl | H | H | H | CH$_2$ | O |
| 2142. | Cl | Cl | H | H | H | CH$_2$ | O |
| 2143. | Cl | Cl | H | H | H | CH$_2$ | O |
| 2144. | Br | Cl | H | H | H | CH$_2$ | O |
| 2145. | I | Cl | H | H | H | CH$_2$ | O |
| 2146. | CH$_3$ | Cl | H | H | H | CH$_2$ | O |
| 2147. | CN | Cl | H | H | H | CH$_2$ | O |
| 2148. | H | H | Cl | H | H | CH$_2$ | O |
| 2149. | Cl | H | Cl | H | H | CH$_2$ | O |
| 2150. | Cl | H | Cl | H | H | CH$_2$ | O |
| 2151. | Br | H | Cl | H | H | CH$_2$ | O |
| 2152. | I | H | Cl | H | H | CH$_2$ | O |
| 2153. | CH$_3$ | H | Cl | H | H | CH$_2$ | O |
| 2154. | CN | H | Cl | H | H | CH$_2$ | O |
| 2155. | H | Cl | Cl | H | H | CH$_2$ | O |
| 2156. | Cl | Cl | Cl | H | H | CH$_2$ | O |
| 2157. | Cl | Cl | Cl | H | H | CH$_2$ | O |
| 2158. | Br | Cl | Cl | H | H | CH$_2$ | O |
| 2159. | I | Cl | Cl | H | H | CH$_2$ | O |
| 2160. | CH$_3$ | Cl | Cl | H | H | CH$_2$ | O |
| 2161. | CN | Cl | Cl | H | H | CH$_2$ | O |
| 2162. | H | Br | H | H | H | CH$_2$ | O |
| 2163. | F | Br | H | H | H | CH$_2$ | O |
| 2164. | Cl | Br | H | H | H | CH$_2$ | O |
| 2165. | Br | Br | H | H | H | CH$_2$ | O |
| 2166. | I | Br | H | H | H | CH$_2$ | O |
| 2167. | CH$_3$ | Br | H | H | H | CH$_2$ | O |
| 2168. | CN | Br | H | H | H | CH$_2$ | O |
| 2169. | H | H | Br | H | H | CH$_2$ | O |
| 2170. | F | H | Br | H | H | CH$_2$ | O |
| 2171. | Cl | H | Br | H | H | CH$_2$ | O |
| 2172. | Br | H | Br | H | H | CH$_2$ | O |
| 2173. | I | H | Br | H | H | CH$_2$ | O |
| 2174. | CH$_3$ | H | Br | H | H | CH$_2$ | O |
| 2175. | CN | H | Br | H | H | CH$_2$ | O |
| 2176. | H | Br | Br | H | H | CH$_2$ | O |
| 2177. | F | Br | Br | H | H | CH$_2$ | O |
| 2178. | Cl | Br | Br | H | H | CH$_2$ | O |
| 2179. | Br | Br | Br | H | H | CH$_2$ | O |
| 2180. | I | Br | Br | H | H | CH$_2$ | O |
| 2181. | CH$_3$ | Br | Br | H | H | CH$_2$ | O |
| 2182. | CN | H | Br | H | H | CH$_2$ | O |
| 2183. | H | I | H | H | H | CH$_2$ | O |
| 2184. | F | I | H | H | H | CH$_2$ | O |
| 2185. | Cl | I | H | H | H | CH$_2$ | O |
| 2186. | Br | I | H | H | H | CH$_2$ | O |
| 2187. | I | I | H | H | H | CH$_2$ | O |
| 2188. | CH$_3$ | I | H | H | H | CH$_2$ | O |
| 2189. | CN | I | H | H | H | CH$_2$ | O |
| 2190. | H | H | I | H | H | CH$_2$ | O |
| 2191. | F | H | I | H | H | CH$_2$ | O |
| 2192. | Cl | H | I | H | H | CH$_2$ | O |
| 2193. | Br | H | I | H | H | CH$_2$ | O |
| 2194. | I | H | I | H | H | CH$_2$ | O |
| 2195. | CH$_3$ | H | I | H | H | CH$_2$ | O |
| 2196. | CN | H | I | H | H | CH$_2$ | O |
| 2197. | H | I | I | H | H | CH$_2$ | O |
| 2198. | F | I | I | H | H | CH$_2$ | O |
| 2199. | Cl | I | I | H | H | CH$_2$ | O |
| 2200. | Br | I | I | H | H | CH$_2$ | O |
| 2201. | I | I | I | H | H | CH$_2$ | O |
| 2202. | CH$_3$ | I | I | H | H | CH$_2$ | O |
| 2203. | CN | I | I | H | H | CH$_2$ | O |
| 2204. | H | F | Cl | H | H | CH$_2$ | O |
| 2205. | D | F | Cl | H | H | CH$_2$ | O |
| 2206. | F | F | Cl | H | H | CH$_2$ | O |
| 2207. | Cl | F | Cl | H | H | CH$_2$ | O |
| 2208. | Br | F | Cl | H | H | CH$_2$ | O |
| 2209. | I | F | Cl | H | H | CH$_2$ | O |
| 2210. | CH$_3$ | F | Cl | H | H | CH$_2$ | O |
| 2211. | CN | F | Cl | H | H | CH$_2$ | O |
| 2212. | H | F | Br | H | H | CH$_2$ | O |
| 2213. | F | F | Br | H | H | CH$_2$ | O |
| 2214. | Cl | F | Br | H | H | CH$_2$ | O |
| 2215. | Br | F | Br | H | H | CH$_2$ | O |
| 2216. | I | F | Br | H | H | CH$_2$ | O |
| 2217. | CH$_3$ | F | Br | H | H | CH$_2$ | O |
| 2218. | CN | F | Br | H | H | CH$_2$ | O |
| 2219. | H | F | I | H | H | CH$_2$ | O |
| 2220. | F | F | I | H | H | CH$_2$ | O |
| 2221. | Cl | F | I | H | H | CH$_2$ | O |
| 2222. | Br | F | I | H | H | CH$_2$ | O |
| 2223. | I | F | I | H | H | CH$_2$ | O |
| 2224. | CH$_3$ | F | I | H | H | CH$_2$ | O |
| 2225. | CN | F | I | H | H | CH$_2$ | O |
| 2226. | H | Cl | F | H | H | CH$_2$ | O |
| 2227. | F | Cl | F | H | H | CH$_2$ | O |
| 2228. | Cl | Cl | F | H | H | CH$_2$ | O |
| 2229. | Br | Cl | F | H | H | CH$_2$ | O |
| 2230. | I | Cl | F | H | H | CH$_2$ | O |
| 2231. | CH$_3$ | Cl | F | H | H | CH$_2$ | O |
| 2232. | CN | Cl | F | H | H | CH$_2$ | O |
| 2233. | H | Cl | Br | H | H | CH$_2$ | O |
| 2234. | F | Cl | Br | H | H | CH$_2$ | O |
| 2235. | Cl | Cl | Br | H | H | CH$_2$ | O |
| 2236. | Br | Cl | Br | H | H | CH$_2$ | O |
| 2237. | I | Cl | Br | H | H | CH$_2$ | O |
| 2238. | CH$_3$ | Cl | Br | H | H | CH$_2$ | O |
| 2239. | CN | Cl | Br | H | H | CH$_2$ | O |
| 2240. | H | Cl | I | H | H | CH$_2$ | O |
| 2241. | F | Cl | I | H | H | CH$_2$ | O |
| 2242. | Cl | Cl | I | H | H | CH$_2$ | O |
| 2243. | Br | Cl | I | H | H | CH$_2$ | O |
| 2244. | I | Cl | I | H | H | CH$_2$ | O |
| 2245. | CH$_3$ | Cl | I | H | H | CH$_2$ | O |
| 2246. | CN | Cl | I | H | H | CH$_2$ | O |
| 2247. | H | Br | F | H | H | CH$_2$ | O |
| 2248. | F | Br | F | H | H | CH$_2$ | O |
| 2249. | Cl | Br | F | H | H | CH$_2$ | O |
| 2250. | Br | Br | F | H | H | CH$_2$ | O |
| 2251. | I | Br | F | H | H | CH$_2$ | O |
| 2252. | CH$_3$ | Br | F | H | H | CH$_2$ | O |
| 2253. | CN | Br | F | H | H | CH$_2$ | O |
| 2254. | H | Br | Cl | H | H | CH$_2$ | O |
| 2255. | F | Br | Cl | H | H | CH$_2$ | O |
| 2256. | Cl | Br | Cl | H | H | CH$_2$ | O |
| 2257. | Br | Br | Cl | H | H | CH$_2$ | O |
| 2258. | I | Br | Cl | H | H | CH$_2$ | O |
| 2259. | CH$_3$ | Br | Cl | H | H | CH$_2$ | O |
| 2260. | CN | Br | Cl | H | H | CH$_2$ | O |
| 2261. | H | Br | I | H | H | CH$_2$ | O |
| 2262. | F | Br | I | H | H | CH$_2$ | O |
| 2263. | Cl | Br | I | H | H | CH$_2$ | O |
| 2264. | Br | Br | I | H | H | CH$_2$ | O |
| 2265. | I | Br | I | H | H | CH$_2$ | O |
| 2266. | CH$_3$ | Br | I | H | H | CH$_2$ | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 2267. | CN | Br | I | H | H | $CH_2$ | O |
| 2268. | H | I | F | H | H | $CH_2$ | O |
| 2269. | F | I | F | H | H | $CH_2$ | O |
| 2270. | Cl | I | F | H | H | $CH_2$ | O |
| 2271. | Br | I | F | H | H | $CH_2$ | O |
| 2272. | I | I | F | H | H | $CH_2$ | O |
| 2273. | $CH_3$ | I | F | H | H | $CH_2$ | O |
| 2274. | CN | I | F | H | H | $CH_2$ | O |
| 2275. | H | I | Cl | H | H | $CH_2$ | O |
| 2276. | F | I | Cl | H | H | $CH_2$ | O |
| 2277. | Cl | I | Cl | H | H | $CH_2$ | O |
| 2278. | Br | I | Cl | H | H | $CH_2$ | O |
| 2279. | I | I | Cl | H | H | $CH_2$ | O |
| 2280. | $CH_3$ | I | Cl | H | H | $CH_2$ | O |
| 2281. | CN | I | Cl | H | H | $CH_2$ | O |
| 2282. | H | I | Br | H | H | $CH_2$ | O |
| 2283. | F | I | Br | H | H | $CH_2$ | O |
| 2284. | Cl | I | Br | H | H | $CH_2$ | O |
| 2285. | Br | I | Br | H | H | $CH_2$ | O |
| 2286. | I | I | Br | H | H | $CH_2$ | O |
| 2287. | $CH_3$ | I | Br | H | H | $CH_2$ | O |
| 2288. | CN | I | Br | H | H | $CH_2$ | O |
| 2289. | H | H | H | $CH_3$ | H | $CH_2$ | O |
| 2290. | F | H | H | $CH_3$ | H | $CH_2$ | O |
| 2291. | Cl | H | H | $CH_3$ | H | $CH_2$ | O |
| 2292. | Br | H | H | $CH_3$ | H | $CH_2$ | O |
| 2293. | I | H | H | $CH_3$ | H | $CH_2$ | O |
| 2294. | $CH_3$ | H | H | $CH_3$ | H | $CH_2$ | O |
| 2295. | CN | H | H | $CH_3$ | H | $CH_2$ | O |
| 2296. | H | F | H | $CH_3$ | H | $CH_2$ | O |
| 2297. | F | F | H | $CH_3$ | H | $CH_2$ | O |
| 2298. | Cl | F | H | $CH_3$ | H | $CH_2$ | O |
| 2299. | Br | F | H | $CH_3$ | H | $CH_2$ | O |
| 2300. | I | F | H | $CH_3$ | H | $CH_2$ | O |
| 2301. | $CH_3$ | F | H | $CH_3$ | H | $CH_2$ | O |
| 2302. | CN | F | H | $CH_3$ | H | $CH_2$ | O |
| 2303. | H | H | F | $CH_3$ | H | $CH_2$ | O |
| 2304. | F | H | F | $CH_3$ | H | $CH_2$ | O |
| 2305. | Cl | H | F | $CH_3$ | H | $CH_2$ | O |
| 2306. | Br | H | F | $CH_3$ | H | $CH_2$ | O |
| 2307. | I | H | F | $CH_3$ | H | $CH_2$ | O |
| 2308. | $CH_3$ | H | F | $CH_3$ | H | $CH_2$ | O |
| 2309. | CN | H | F | $CH_3$ | H | $CH_2$ | O |
| 2310. | H | F | F | $CH_3$ | H | $CH_2$ | O |
| 2311. | F | F | F | $CH_3$ | H | $CH_2$ | O |
| 2312. | Cl | F | F | $CH_3$ | H | $CH_2$ | O |
| 2313. | Br | F | F | $CH_3$ | H | $CH_2$ | O |
| 2314. | I | F | F | $CH_3$ | H | $CH_2$ | O |
| 2315. | $CH_3$ | F | F | $CH_3$ | H | $CH_2$ | O |
| 2316. | CN | F | F | $CH_3$ | H | $CH_2$ | O |
| 2317. | H | Cl | H | $CH_3$ | H | $CH_2$ | O |
| 2318. | F | Cl | H | $CH_3$ | H | $CH_2$ | O |
| 2319. | Cl | Cl | H | $CH_3$ | H | $CH_2$ | O |
| 2320. | Br | Cl | H | $CH_3$ | H | $CH_2$ | O |
| 2321. | I | Cl | H | $CH_3$ | H | $CH_2$ | O |
| 2322. | $CH_3$ | Cl | H | $CH_3$ | H | $CH_2$ | O |
| 2323. | CN | Cl | H | $CH_3$ | H | $CH_2$ | O |
| 2324. | H | H | Cl | $CH_3$ | H | $CH_2$ | O |
| 2325. | Cl | H | Cl | $CH_3$ | H | $CH_2$ | O |
| 2326. | Cl | H | Cl | $CH_3$ | H | $CH_2$ | O |
| 2327. | Br | H | Cl | $CH_3$ | H | $CH_2$ | O |
| 2328. | I | H | Cl | $CH_3$ | H | $CH_2$ | O |
| 2329. | $CH_3$ | H | Cl | $CH_3$ | H | $CH_2$ | O |
| 2330. | CN | H | Cl | $CH_3$ | H | $CH_2$ | O |
| 2331. | H | Cl | Cl | $CH_3$ | H | $CH_2$ | O |
| 2332. | Cl | Cl | Cl | $CH_3$ | H | $CH_2$ | O |
| 2333. | Cl | Cl | Cl | $CH_3$ | H | $CH_2$ | O |
| 2334. | Br | Cl | Cl | $CH_3$ | H | $CH_2$ | O |
| 2335. | I | Cl | Cl | $CH_3$ | H | $CH_2$ | O |
| 2336. | $CH_3$ | Cl | Cl | $CH_3$ | H | $CH_2$ | O |
| 2337. | CN | Cl | Cl | $CH_3$ | H | $CH_2$ | O |
| 2338. | H | Br | H | $CH_3$ | H | $CH_2$ | O |
| 2339. | F | Br | H | $CH_3$ | H | $CH_2$ | O |
| 2340. | Cl | Br | H | $CH_3$ | H | $CH_2$ | O |
| 2341. | Br | Br | H | $CH_3$ | H | $CH_2$ | O |
| 2342. | I | Br | H | $CH_3$ | H | $CH_2$ | O |
| 2343. | $CH_3$ | Br | H | $CH_3$ | H | $CH_2$ | O |
| 2344. | CN | Br | H | $CH_3$ | H | $CH_2$ | O |
| 2345. | H | H | Br | $CH_3$ | H | $CH_2$ | O |
| 2346. | F | H | Br | $CH_3$ | H | $CH_2$ | O |
| 2347. | Cl | H | Br | $CH_3$ | H | $CH_2$ | O |
| 2348. | Br | H | Br | $CH_3$ | H | $CH_2$ | O |
| 2349. | I | H | Br | $CH_3$ | H | $CH_2$ | O |
| 2350. | $CH_3$ | H | Br | $CH_3$ | H | $CH_2$ | O |
| 2351. | CN | H | Br | $CH_3$ | H | $CH_2$ | O |
| 2352. | H | Br | Br | $CH_3$ | H | $CH_2$ | O |
| 2353. | F | Br | Br | $CH_3$ | H | $CH_2$ | O |
| 2354. | Cl | Br | Br | $CH_3$ | H | $CH_2$ | O |
| 2355. | Br | Br | Br | $CH_3$ | H | $CH_2$ | O |
| 2356. | I | Br | Br | $CH_3$ | H | $CH_2$ | O |
| 2357. | $CH_3$ | Br | Br | $CH_3$ | H | $CH_2$ | O |
| 2358. | CN | H | Br | $CH_3$ | H | $CH_2$ | O |
| 2359. | H | I | H | $CH_3$ | H | $CH_2$ | O |
| 2360. | F | I | H | $CH_3$ | H | $CH_2$ | O |
| 2361. | Cl | I | H | $CH_3$ | H | $CH_2$ | O |
| 2362. | Br | I | H | $CH_3$ | H | $CH_2$ | O |
| 2363. | I | I | H | $CH_3$ | H | $CH_2$ | O |
| 2364. | $CH_3$ | I | H | $CH_3$ | H | $CH_2$ | O |
| 2365. | CN | I | H | $CH_3$ | H | $CH_2$ | O |
| 2366. | H | H | I | $CH_3$ | H | $CH_2$ | O |
| 2367. | F | H | I | $CH_3$ | H | $CH_2$ | O |
| 2368. | Cl | H | I | $CH_3$ | H | $CH_2$ | O |
| 2369. | Br | H | I | $CH_3$ | H | $CH_2$ | O |
| 2370. | I | H | I | $CH_3$ | H | $CH_2$ | O |
| 2371. | $CH_3$ | H | I | $CH_3$ | H | $CH_2$ | O |
| 2372. | CN | H | I | $CH_3$ | H | $CH_2$ | O |
| 2373. | H | I | I | $CH_3$ | H | $CH_2$ | O |
| 2374. | F | I | I | $CH_3$ | H | $CH_2$ | O |
| 2375. | Cl | I | I | $CH_3$ | H | $CH_2$ | O |
| 2376. | Br | I | I | $CH_3$ | H | $CH_2$ | O |
| 2377. | I | I | I | $CH_3$ | H | $CH_2$ | O |
| 2378. | $CH_3$ | I | I | $CH_3$ | H | $CH_2$ | O |
| 2379. | CN | I | I | $CH_3$ | H | $CH_2$ | O |
| 2380. | H | F | Cl | $CH_3$ | H | $CH_2$ | O |
| 2381. | D | F | Cl | $CH_3$ | H | $CH_2$ | O |
| 2382. | F | F | Cl | $CH_3$ | H | $CH_2$ | O |
| 2383. | Cl | F | Cl | $CH_3$ | H | $CH_2$ | O |
| 2384. | Br | F | Cl | $CH_3$ | H | $CH_2$ | O |
| 2385. | I | F | Cl | $CH_3$ | H | $CH_2$ | O |
| 2386. | $CH_3$ | F | Cl | $CH_3$ | H | $CH_2$ | O |
| 2387. | CN | F | Cl | $CH_3$ | H | $CH_2$ | O |
| 2388. | H | F | Br | $CH_3$ | H | $CH_2$ | O |
| 2389. | F | F | Br | $CH_3$ | H | $CH_2$ | O |
| 2390. | Cl | F | Br | $CH_3$ | H | $CH_2$ | O |
| 2391. | Br | F | Br | $CH_3$ | H | $CH_2$ | O |
| 2392. | I | F | Br | $CH_3$ | H | $CH_2$ | O |
| 2393. | $CH_3$ | F | Br | $CH_3$ | H | $CH_2$ | O |
| 2394. | CN | F | Br | $CH_3$ | H | $CH_2$ | O |
| 2395. | H | F | I | $CH_3$ | H | $CH_2$ | O |
| 2396. | F | F | I | $CH_3$ | H | $CH_2$ | O |
| 2397. | Cl | F | I | $CH_3$ | H | $CH_2$ | O |
| 2398. | Br | F | I | $CH_3$ | H | $CH_2$ | O |
| 2399. | I | F | I | $CH_3$ | H | $CH_2$ | O |
| 2400. | $CH_3$ | F | I | $CH_3$ | H | $CH_2$ | O |
| 2401. | CN | F | I | $CH_3$ | H | $CH_2$ | O |
| 2402. | H | Cl | F | $CH_3$ | H | $CH_2$ | O |
| 2403. | F | Cl | F | $CH_3$ | H | $CH_2$ | O |
| 2404. | Cl | Cl | F | $CH_3$ | H | $CH_2$ | O |
| 2405. | Br | Cl | F | $CH_3$ | H | $CH_2$ | O |
| 2406. | I | Cl | F | $CH_3$ | H | $CH_2$ | O |
| 2407. | $CH_3$ | Cl | F | $CH_3$ | H | $CH_2$ | O |
| 2408. | CN | Cl | F | $CH_3$ | H | $CH_2$ | O |
| 2409. | H | Cl | Br | $CH_3$ | H | $CH_2$ | O |
| 2410. | F | Cl | Br | $CH_3$ | H | $CH_2$ | O |
| 2411. | Cl | Cl | Br | $CH_3$ | H | $CH_2$ | O |
| 2412. | Br | Cl | Br | $CH_3$ | H | $CH_2$ | O |
| 2413. | I | Cl | Br | $CH_3$ | H | $CH_2$ | O |
| 2414. | $CH_3$ | Cl | Br | $CH_3$ | H | $CH_2$ | O |
| 2415. | CN | Cl | Br | $CH_3$ | H | $CH_2$ | O |
| 2416. | H | Cl | I | $CH_3$ | H | $CH_2$ | O |
| 2417. | F | Cl | I | $CH_3$ | H | $CH_2$ | O |
| 2418. | Cl | Cl | I | $CH_3$ | H | $CH_2$ | O |
| 2419. | Br | Cl | I | $CH_3$ | H | $CH_2$ | O |
| 2420. | I | Cl | I | $CH_3$ | H | $CH_2$ | O |
| 2421. | $CH_3$ | Cl | I | $CH_3$ | H | $CH_2$ | O |
| 2422. | CN | Cl | I | $CH_3$ | H | $CH_2$ | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 2423. | H | Br | F | $CH_3$ | H | $CH_2$ | O |
| 2424. | F | Br | F | $CH_3$ | H | $CH_2$ | O |
| 2425. | Cl | Br | F | $CH_3$ | H | $CH_2$ | O |
| 2426. | Br | Br | F | $CH_3$ | H | $CH_2$ | O |
| 2427. | I | Br | F | $CH_3$ | H | $CH_2$ | O |
| 2428. | $CH_3$ | Br | F | $CH_3$ | H | $CH_2$ | O |
| 2429. | CN | Br | F | $CH_3$ | H | $CH_2$ | O |
| 2430. | H | Br | Cl | $CH_3$ | H | $CH_2$ | O |
| 2431. | F | Br | Cl | $CH_3$ | H | $CH_2$ | O |
| 2432. | Cl | Br | Cl | $CH_3$ | H | $CH_2$ | O |
| 2433. | Br | Br | Cl | $CH_3$ | H | $CH_2$ | O |
| 2434. | I | Br | Cl | $CH_3$ | H | $CH_2$ | O |
| 2435. | $CH_3$ | Br | Cl | $CH_3$ | H | $CH_2$ | O |
| 2436. | CN | Br | Cl | $CH_3$ | H | $CH_2$ | O |
| 2437. | H | Br | I | $CH_3$ | H | $CH_2$ | O |
| 2438. | F | Br | I | $CH_3$ | H | $CH_2$ | O |
| 2439. | Cl | Br | I | $CH_3$ | H | $CH_2$ | O |
| 2440. | Br | Br | I | $CH_3$ | H | $CH_2$ | O |
| 2441. | I | Br | I | $CH_3$ | H | $CH_2$ | O |
| 2442. | $CH_3$ | Br | I | $CH_3$ | H | $CH_2$ | O |
| 2443. | CN | Br | I | $CH_3$ | H | $CH_2$ | O |
| 2444. | H | I | F | $CH_3$ | H | $CH_2$ | O |
| 2445. | F | I | F | $CH_3$ | H | $CH_2$ | O |
| 2446. | Cl | I | F | $CH_3$ | H | $CH_2$ | O |
| 2447. | Br | I | F | $CH_3$ | H | $CH_2$ | O |
| 2448. | I | I | F | $CH_3$ | H | $CH_2$ | O |
| 2449. | $CH_3$ | I | F | $CH_3$ | H | $CH_2$ | O |
| 2450. | CN | I | F | $CH_3$ | H | $CH_2$ | O |
| 2451. | H | I | Cl | $CH_3$ | H | $CH_2$ | O |
| 2452. | F | I | Cl | $CH_3$ | H | $CH_2$ | O |
| 2453. | Cl | I | Cl | $CH_3$ | H | $CH_2$ | O |
| 2454. | Br | I | Cl | $CH_3$ | H | $CH_2$ | O |
| 2455. | I | I | Cl | $CH_3$ | H | $CH_2$ | O |
| 2456. | $CH_3$ | I | Cl | $CH_3$ | H | $CH_2$ | O |
| 2457. | CN | I | Cl | $CH_3$ | H | $CH_2$ | O |
| 2458. | H | I | Br | $CH_3$ | H | $CH_2$ | O |
| 2459. | F | I | Br | $CH_3$ | H | $CH_2$ | O |
| 2460. | Cl | I | Br | $CH_3$ | H | $CH_2$ | O |
| 2461. | Br | I | Br | $CH_3$ | H | $CH_2$ | O |
| 2462. | I | I | Br | $CH_3$ | H | $CH_2$ | O |
| 2463. | $CH_3$ | I | Br | $CH_3$ | H | $CH_2$ | O |
| 2464. | CN | I | Br | $CH_3$ | H | $CH_2$ | O |
| 2465. | H | H | H | $CH_3$ | $CH_3$ | $CH_2$ | O |
| 2466. | F | H | H | $CH_3$ | $CH_3$ | $CH_2$ | O |
| 2467. | Cl | H | H | $CH_3$ | $CH_3$ | $CH_2$ | O |
| 2468. | Br | H | H | $CH_3$ | $CH_3$ | $CH_2$ | O |
| 2469. | I | H | H | $CH_3$ | $CH_3$ | $CH_2$ | O |
| 2470. | $CH_3$ | H | H | $CH_3$ | $CH_3$ | $CH_2$ | O |
| 2471. | CN | H | H | $CH_3$ | $CH_3$ | $CH_2$ | O |
| 2472. | H | F | H | $CH_3$ | $CH_3$ | $CH_2$ | O |
| 2473. | F | F | H | $CH_3$ | $CH_3$ | $CH_2$ | O |
| 2474. | Cl | F | H | $CH_3$ | $CH_3$ | $CH_2$ | O |
| 2475. | Br | F | H | $CH_3$ | $CH_3$ | $CH_2$ | O |
| 2476. | I | F | H | $CH_3$ | $CH_3$ | $CH_2$ | O |
| 2477. | $CH_3$ | F | H | $CH_3$ | $CH_3$ | $CH_2$ | O |
| 2478. | CN | F | H | $CH_3$ | $CH_3$ | $CH_2$ | O |
| 2479. | H | H | F | $CH_3$ | $CH_3$ | $CH_2$ | O |
| 2480. | F | H | F | $CH_3$ | $CH_3$ | $CH_2$ | O |
| 2481. | Cl | H | F | $CH_3$ | $CH_3$ | $CH_2$ | O |
| 2482. | Br | H | F | $CH_3$ | $CH_3$ | $CH_2$ | O |
| 2483. | I | H | F | $CH_3$ | $CH_3$ | $CH_2$ | O |
| 2484. | $CH_3$ | H | F | $CH_3$ | $CH_3$ | $CH_2$ | O |
| 2485. | CN | H | F | $CH_3$ | $CH_3$ | $CH_2$ | O |
| 2486. | H | F | F | $CH_3$ | $CH_3$ | $CH_2$ | O |
| 2487. | F | F | F | $CH_3$ | $CH_3$ | $CH_2$ | O |
| 2488. | Cl | F | F | $CH_3$ | $CH_3$ | $CH_2$ | O |
| 2489. | Br | F | F | $CH_3$ | $CH_3$ | $CH_2$ | O |
| 2490. | I | F | F | $CH_3$ | $CH_3$ | $CH_2$ | O |
| 2491. | $CH_3$ | F | F | $CH_3$ | $CH_3$ | $CH_2$ | O |
| 2492. | CN | F | F | $CH_3$ | $CH_3$ | $CH_2$ | O |
| 2493. | H | Cl | H | $CH_3$ | $CH_3$ | $CH_2$ | O |
| 2494. | Cl | Cl | H | $CH_3$ | $CH_3$ | $CH_2$ | O |
| 2495. | Cl | Cl | H | $CH_3$ | $CH_3$ | $CH_2$ | O |
| 2496. | Br | Cl | H | $CH_3$ | $CH_3$ | $CH_2$ | O |
| 2497. | I | Cl | H | $CH_3$ | $CH_3$ | $CH_2$ | O |
| 2498. | $CH_3$ | Cl | H | $CH_3$ | $CH_3$ | $CH_2$ | O |
| 2499. | CN | Cl | H | $CH_3$ | $CH_3$ | $CH_2$ | O |
| 2500. | H | H | Cl | $CH_3$ | $CH_3$ | $CH_2$ | O |
| 2501. | Cl | H | Cl | $CH_3$ | $CH_3$ | $CH_2$ | O |
| 2502. | Cl | H | Cl | $CH_3$ | $CH_3$ | $CH_2$ | O |
| 2503. | Br | H | Cl | $CH_3$ | $CH_3$ | $CH_2$ | O |
| 2504. | I | H | Cl | $CH_3$ | $CH_3$ | $CH_2$ | O |
| 2505. | $CH_3$ | H | Cl | $CH_3$ | $CH_3$ | $CH_2$ | O |
| 2506. | CN | H | Cl | $CH_3$ | $CH_3$ | $CH_2$ | O |
| 2507. | H | Cl | Cl | $CH_3$ | $CH_3$ | $CH_2$ | O |
| 2508. | Cl | Cl | Cl | $CH_3$ | $CH_3$ | $CH_2$ | O |
| 2509. | Cl | Cl | Cl | $CH_3$ | $CH_3$ | $CH_2$ | O |
| 2510. | Br | Cl | Cl | $CH_3$ | $CH_3$ | $CH_2$ | O |
| 2511. | I | Cl | Cl | $CH_3$ | $CH_3$ | $CH_2$ | O |
| 2512. | $CH_3$ | Cl | Cl | $CH_3$ | $CH_3$ | $CH_2$ | O |
| 2513. | CN | Cl | Cl | $CH_3$ | $CH_3$ | $CH_2$ | O |
| 2514. | H | Br | H | $CH_3$ | $CH_3$ | $CH_2$ | O |
| 2515. | F | Br | H | $CH_3$ | $CH_3$ | $CH_2$ | O |
| 2516. | Cl | Br | H | $CH_3$ | $CH_3$ | $CH_2$ | O |
| 2517. | Br | Br | H | $CH_3$ | $CH_3$ | $CH_2$ | O |
| 2518. | I | Br | H | $CH_3$ | $CH_3$ | $CH_2$ | O |
| 2519. | $CH_3$ | Br | H | $CH_3$ | $CH_3$ | $CH_2$ | O |
| 2520. | CN | Br | H | $CH_3$ | $CH_3$ | $CH_2$ | O |
| 2521. | H | H | Br | $CH_3$ | $CH_3$ | $CH_2$ | O |
| 2522. | F | H | Br | $CH_3$ | $CH_3$ | $CH_2$ | O |
| 2523. | Cl | H | Br | $CH_3$ | $CH_3$ | $CH_2$ | O |
| 2524. | Br | H | Br | $CH_3$ | $CH_3$ | $CH_2$ | O |
| 2525. | I | H | Br | $CH_3$ | $CH_3$ | $CH_2$ | O |
| 2526. | $CH_3$ | H | Br | $CH_3$ | $CH_3$ | $CH_2$ | O |
| 2527. | CN | H | Br | $CH_3$ | $CH_3$ | $CH_2$ | O |
| 2528. | H | Br | Br | $CH_3$ | $CH_3$ | $CH_2$ | O |
| 2529. | F | Br | Br | $CH_3$ | $CH_3$ | $CH_2$ | O |
| 2530. | Cl | Br | Br | $CH_3$ | $CH_3$ | $CH_2$ | O |
| 2531. | Br | Br | Br | $CH_3$ | $CH_3$ | $CH_2$ | O |
| 2532. | I | Br | Br | $CH_3$ | $CH_3$ | $CH_2$ | O |
| 2533. | $CH_3$ | Br | Br | $CH_3$ | $CH_3$ | $CH_2$ | O |
| 2534. | CN | H | Br | $CH_3$ | $CH_3$ | $CH_2$ | O |
| 2535. | H | I | H | $CH_3$ | $CH_3$ | $CH_2$ | O |
| 2536. | F | I | H | $CH_3$ | $CH_3$ | $CH_2$ | O |
| 2537. | Cl | I | H | $CH_3$ | $CH_3$ | $CH_2$ | O |
| 2538. | Br | I | H | $CH_3$ | $CH_3$ | $CH_2$ | O |
| 2539. | I | I | H | $CH_3$ | $CH_3$ | $CH_2$ | O |
| 2540. | $CH_3$ | I | H | $CH_3$ | $CH_3$ | $CH_2$ | O |
| 2541. | CN | I | H | $CH_3$ | $CH_3$ | $CH_2$ | O |
| 2542. | H | H | I | $CH_3$ | $CH_3$ | $CH_2$ | O |
| 2543. | F | H | I | $CH_3$ | $CH_3$ | $CH_2$ | O |
| 2544. | Cl | H | I | $CH_3$ | $CH_3$ | $CH_2$ | O |
| 2545. | Br | H | I | $CH_3$ | $CH_3$ | $CH_2$ | O |
| 2546. | I | H | I | $CH_3$ | $CH_3$ | $CH_2$ | O |
| 2547. | $CH_3$ | H | I | $CH_3$ | $CH_3$ | $CH_2$ | O |
| 2548. | CN | H | I | $CH_3$ | $CH_3$ | $CH_2$ | O |
| 2549. | H | I | I | $CH_3$ | $CH_3$ | $CH_2$ | O |
| 2550. | F | I | I | $CH_3$ | $CH_3$ | $CH_2$ | O |
| 2551. | Cl | I | I | $CH_3$ | $CH_3$ | $CH_2$ | O |
| 2552. | Br | I | I | $CH_3$ | $CH_3$ | $CH_2$ | O |
| 2553. | I | I | I | $CH_3$ | $CH_3$ | $CH_2$ | O |
| 2554. | $CH_3$ | I | I | $CH_3$ | $CH_3$ | $CH_2$ | O |
| 2555. | CN | I | I | $CH_3$ | $CH_3$ | $CH_2$ | O |
| 2556. | H | F | Cl | $CH_3$ | $CH_3$ | $CH_2$ | O |
| 2557. | D | F | Cl | $CH_3$ | $CH_3$ | $CH_2$ | O |
| 2558. | F | F | Cl | $CH_3$ | $CH_3$ | $CH_2$ | O |
| 2559. | Cl | F | Cl | $CH_3$ | $CH_3$ | $CH_2$ | O |
| 2560. | Br | F | Cl | $CH_3$ | $CH_3$ | $CH_2$ | O |
| 2561. | I | F | Cl | $CH_3$ | $CH_3$ | $CH_2$ | O |
| 2562. | $CH_3$ | F | Cl | $CH_3$ | $CH_3$ | $CH_2$ | O |
| 2563. | CN | F | Cl | $CH_3$ | $CH_3$ | $CH_2$ | O |
| 2564. | H | F | Br | $CH_3$ | $CH_3$ | $CH_2$ | O |
| 2565. | F | F | Br | $CH_3$ | $CH_3$ | $CH_2$ | O |
| 2566. | Cl | F | Br | $CH_3$ | $CH_3$ | $CH_2$ | O |
| 2567. | Br | F | Br | $CH_3$ | $CH_3$ | $CH_2$ | O |
| 2568. | I | F | Br | $CH_3$ | $CH_3$ | $CH_2$ | O |
| 2569. | $CH_3$ | F | Br | $CH_3$ | $CH_3$ | $CH_2$ | O |
| 2570. | CN | F | Br | $CH_3$ | $CH_3$ | $CH_2$ | O |
| 2571. | H | F | I | $CH_3$ | $CH_3$ | $CH_2$ | O |
| 2572. | F | F | I | $CH_3$ | $CH_3$ | $CH_2$ | O |
| 2573. | Cl | F | I | $CH_3$ | $CH_3$ | $CH_2$ | O |
| 2574. | Br | F | I | $CH_3$ | $CH_3$ | $CH_2$ | O |
| 2575. | I | F | I | $CH_3$ | $CH_3$ | $CH_2$ | O |
| 2576. | $CH_3$ | F | I | $CH_3$ | $CH_3$ | $CH_2$ | O |
| 2577. | CN | F | I | $CH_3$ | $CH_3$ | $CH_2$ | O |
| 2578. | H | Cl | F | $CH_3$ | $CH_3$ | $CH_2$ | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 2579. | F | Cl | F | CH₃ | CH₃ | CH₂ | O |
| 2580. | Cl | Cl | F | CH₃ | CH₃ | CH₂ | O |
| 2581. | Br | Cl | F | CH₃ | CH₃ | CH₂ | O |
| 2582. | I | Cl | F | CH₃ | CH₃ | CH₂ | O |
| 2583. | CH₃ | Cl | F | CH₃ | CH₃ | CH₂ | O |
| 2584. | CN | Cl | F | CH₃ | CH₃ | CH₂ | O |
| 2585. | H | Cl | Br | CH₃ | CH₃ | CH₂ | O |
| 2586. | F | Cl | Br | CH₃ | CH₃ | CH₂ | O |
| 2587. | Cl | Cl | Br | CH₃ | CH₃ | CH₂ | O |
| 2588. | Br | Cl | Br | CH₃ | CH₃ | CH₂ | O |
| 2589. | I | Cl | Br | CH₃ | CH₃ | CH₂ | O |
| 2590. | CH₃ | Cl | Br | CH₃ | CH₃ | CH₂ | O |
| 2591. | CN | Cl | Br | CH₃ | CH₃ | CH₂ | O |
| 2592. | H | Cl | I | CH₃ | CH₃ | CH₂ | O |
| 2593. | F | Cl | I | CH₃ | CH₃ | CH₂ | O |
| 2594. | Cl | Cl | I | CH₃ | CH₃ | CH₂ | O |
| 2595. | Br | Cl | I | CH₃ | CH₃ | CH₂ | O |
| 2596. | I | Cl | I | CH₃ | CH₃ | CH₂ | O |
| 2597. | CH₃ | Cl | I | CH₃ | CH₃ | CH₂ | O |
| 2598. | CN | Cl | I | CH₃ | CH₃ | CH₂ | O |
| 2599. | H | Br | F | CH₃ | CH₃ | CH₂ | O |
| 2600. | F | Br | F | CH₃ | CH₃ | CH₂ | O |
| 2601. | Cl | Br | F | CH₃ | CH₃ | CH₂ | O |
| 2602. | Br | Br | F | CH₃ | CH₃ | CH₂ | O |
| 2603. | I | Br | F | CH₃ | CH₃ | CH₂ | O |
| 2604. | CH₃ | Br | F | CH₃ | CH₃ | CH₂ | O |
| 2605. | CN | Br | F | CH₃ | CH₃ | CH₂ | O |
| 2606. | H | Br | Cl | CH₃ | CH₃ | CH₂ | O |
| 2607. | F | Br | Cl | CH₃ | CH₃ | CH₂ | O |
| 2608. | Cl | Br | Cl | CH₃ | CH₃ | CH₂ | O |
| 2609. | Br | Br | Cl | CH₃ | CH₃ | CH₂ | O |
| 2610. | I | Br | Cl | CH₃ | CH₃ | CH₂ | O |
| 2611. | CH₃ | Br | Cl | CH₃ | CH₃ | CH₂ | O |
| 2612. | CN | Br | Cl | CH₃ | CH₃ | CH₂ | O |
| 2613. | H | Br | I | CH₃ | CH₃ | CH₂ | O |
| 2614. | F | Br | I | CH₃ | CH₃ | CH₂ | O |
| 2615. | Cl | Br | I | CH₃ | CH₃ | CH₂ | O |
| 2616. | Br | Br | I | CH₃ | CH₃ | CH₂ | O |
| 2617. | I | Br | I | CH₃ | CH₃ | CH₂ | O |
| 2618. | CH₃ | Br | I | CH₃ | CH₃ | CH₂ | O |
| 2619. | CN | Br | I | CH₃ | CH₃ | CH₂ | O |
| 2620. | H | I | F | CH₃ | CH₃ | CH₂ | O |
| 2621. | F | I | F | CH₃ | CH₃ | CH₂ | O |
| 2622. | Cl | I | F | CH₃ | CH₃ | CH₂ | O |
| 2623. | Br | I | F | CH₃ | CH₃ | CH₂ | O |
| 2624. | I | I | F | CH₃ | CH₃ | CH₂ | O |
| 2625. | CH₃ | I | F | CH₃ | CH₃ | CH₂ | O |
| 2626. | CN | I | F | CH₃ | CH₃ | CH₂ | O |
| 2627. | H | I | Cl | CH₃ | CH₃ | CH₂ | O |
| 2628. | F | I | Cl | CH₃ | CH₃ | CH₂ | O |
| 2629. | Cl | I | Cl | CH₃ | CH₃ | CH₂ | O |
| 2630. | Br | I | Cl | CH₃ | CH₃ | CH₂ | O |
| 2631. | I | I | Cl | CH₃ | CH₃ | CH₂ | O |
| 2632. | CH₃ | I | Cl | CH₃ | CH₃ | CH₂ | O |
| 2633. | CN | I | Cl | CH₃ | CH₃ | CH₂ | O |
| 2634. | H | I | Br | CH₃ | CH₃ | CH₂ | O |
| 2635. | F | I | Br | CH₃ | CH₃ | CH₂ | O |
| 2636. | Cl | I | Br | CH₃ | CH₃ | CH₂ | O |
| 2637. | Br | I | Br | CH₃ | CH₃ | CH₂ | O |
| 2638. | I | I | Br | CH₃ | CH₃ | CH₂ | O |
| 2639. | CH₃ | I | Br | CH₃ | CH₃ | CH₂ | O |
| 2640. | CN | I | Br | CH₃ | CH₃ | CH₂ | O |
| 2641. | H | H | H | F | F | CH₂ | O |
| 2642. | F | H | H | F | F | CH₂ | O |
| 2643. | Cl | H | H | F | F | CH₂ | O |
| 2644. | Br | H | H | F | F | CH₂ | O |
| 2645. | I | H | H | F | F | CH₂ | O |
| 2646. | CH₃ | H | H | F | F | CH₂ | O |
| 2647. | CN | H | H | F | F | CH₂ | O |
| 2648. | H | F | H | F | F | CH₂ | O |
| 2649. | F | F | H | F | F | CH₂ | O |
| 2650. | Cl | F | H | F | F | CH₂ | O |
| 2651. | Br | F | H | F | F | CH₂ | O |
| 2652. | I | F | H | F | F | CH₂ | O |
| 2653. | CH₃ | F | H | F | F | CH₂ | O |
| 2654. | CN | F | H | F | F | CH₂ | O |
| 2655. | H | H | F | F | F | CH₂ | O |
| 2656. | F | H | F | F | F | CH₂ | O |
| 2657. | Cl | H | F | F | F | CH₂ | O |
| 2658. | Br | H | F | F | F | CH₂ | O |
| 2659. | I | H | F | F | F | CH₂ | O |
| 2660. | CH₃ | H | F | F | F | CH₂ | O |
| 2661. | CN | H | F | F | F | CH₂ | O |
| 2662. | H | F | F | F | F | CH₂ | O |
| 2663. | F | F | F | F | F | CH₂ | O |
| 2664. | Cl | F | F | F | F | CH₂ | O |
| 2665. | Br | F | F | F | F | CH₂ | O |
| 2666. | I | F | F | F | F | CH₂ | O |
| 2667. | CH₃ | F | F | F | F | CH₂ | O |
| 2668. | CN | F | F | F | F | CH₂ | O |
| 2669. | H | Cl | H | F | F | CH₂ | O |
| 2670. | Cl | Cl | H | F | F | CH₂ | O |
| 2671. | Cl | Cl | H | F | F | CH₂ | O |
| 2672. | Br | Cl | H | F | F | CH₂ | O |
| 2673. | I | Cl | H | F | F | CH₂ | O |
| 2674. | CH₃ | Cl | H | F | F | CH₂ | O |
| 2675. | CN | Cl | H | F | F | CH₂ | O |
| 2676. | H | H | Cl | F | F | CH₂ | O |
| 2677. | Cl | H | Cl | F | F | CH₂ | O |
| 2678. | Cl | H | Cl | F | F | CH₂ | O |
| 2679. | Br | H | Cl | F | F | CH₂ | O |
| 2680. | I | H | Cl | F | F | CH₂ | O |
| 2681. | CH₃ | H | Cl | F | F | CH₂ | O |
| 2682. | CN | H | Cl | F | F | CH₂ | O |
| 2683. | H | Cl | Cl | F | F | CH₂ | O |
| 2684. | Cl | Cl | Cl | F | F | CH₂ | O |
| 2685. | Cl | Cl | Cl | F | F | CH₂ | O |
| 2686. | Br | Cl | Cl | F | F | CH₂ | O |
| 2687. | I | Cl | Cl | F | F | CH₂ | O |
| 2688. | CH₃ | Cl | Cl | F | F | CH₂ | O |
| 2689. | CN | Cl | Cl | F | F | CH₂ | O |
| 2690. | H | Br | H | F | F | CH₂ | O |
| 2691. | F | Br | H | F | F | CH₂ | O |
| 2692. | Cl | Br | H | F | F | CH₂ | O |
| 2693. | Br | Br | H | F | F | CH₂ | O |
| 2694. | I | Br | H | F | F | CH₂ | O |
| 2695. | CH₃ | Br | H | F | F | CH₂ | O |
| 2696. | CN | Br | H | F | F | CH₂ | O |
| 2697. | H | H | Br | F | F | CH₂ | O |
| 2698. | F | H | Br | F | F | CH₂ | O |
| 2699. | Cl | H | Br | F | F | CH₂ | O |
| 2700. | Br | H | Br | F | F | CH₂ | O |
| 2701. | I | H | Br | F | F | CH₂ | O |
| 2702. | CH₃ | H | Br | F | F | CH₂ | O |
| 2703. | CN | H | Br | F | F | CH₂ | O |
| 2704. | H | Br | Br | F | F | CH₂ | O |
| 2705. | F | Br | Br | F | F | CH₂ | O |
| 2706. | Cl | Br | Br | F | F | CH₂ | O |
| 2707. | Br | Br | Br | F | F | CH₂ | O |
| 2708. | I | Br | Br | F | F | CH₂ | O |
| 2709. | CH₃ | Br | Br | F | F | CH₂ | O |
| 2710. | CN | H | Br | F | F | CH₂ | O |
| 2711. | H | I | H | F | F | CH₂ | O |
| 2712. | F | I | H | F | F | CH₂ | O |
| 2713. | Cl | I | H | F | F | CH₂ | O |
| 2714. | Br | I | H | F | F | CH₂ | O |
| 2715. | I | I | H | F | F | CH₂ | O |
| 2716. | CH₃ | I | H | F | F | CH₂ | O |
| 2717. | CN | I | H | F | F | CH₂ | O |
| 2718. | H | H | I | F | F | CH₂ | O |
| 2719. | F | H | I | F | F | CH₂ | O |
| 2720. | Cl | H | I | F | F | CH₂ | O |
| 2721. | Br | H | I | F | F | CH₂ | O |
| 2722. | I | H | I | F | F | CH₂ | O |
| 2723. | CH₃ | H | I | F | F | CH₂ | O |
| 2724. | CN | H | I | F | F | CH₂ | O |
| 2725. | H | I | I | F | F | CH₂ | O |
| 2726. | F | I | I | F | F | CH₂ | O |
| 2727. | Cl | I | I | F | F | CH₂ | O |
| 2728. | Br | I | I | F | F | CH₂ | O |
| 2729. | I | I | I | F | F | CH₂ | O |
| 2730. | CH₃ | I | I | F | F | CH₂ | O |
| 2731. | CN | I | I | F | F | CH₂ | O |
| 2732. | H | F | Cl | F | F | CH₂ | O |
| 2733. | D | F | Cl | F | F | CH₂ | O |
| 2734. | F | F | Cl | F | F | CH₂ | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 2735. | Cl | F | Cl | F | F | CH$_2$ | O |
| 2736. | Br | F | Cl | F | F | CH$_2$ | O |
| 2737. | I | F | Cl | F | F | CH$_2$ | O |
| 2738. | CH$_3$ | F | Cl | F | F | CH$_2$ | O |
| 2739. | CN | F | Cl | F | F | CH$_2$ | O |
| 2740. | H | F | Br | F | F | CH$_2$ | O |
| 2741. | F | F | Br | F | F | CH$_2$ | O |
| 2742. | Cl | F | Br | F | F | CH$_2$ | O |
| 2743. | Br | F | Br | F | F | CH$_2$ | O |
| 2744. | I | F | Br | F | F | CH$_2$ | O |
| 2745. | CH$_3$ | F | Br | F | F | CH$_2$ | O |
| 2746. | CN | F | Br | F | F | CH$_2$ | O |
| 2747. | H | F | I | F | F | CH$_2$ | O |
| 2748. | F | F | I | F | F | CH$_2$ | O |
| 2749. | Cl | F | I | F | F | CH$_2$ | O |
| 2750. | Br | F | I | F | F | CH$_2$ | O |
| 2751. | I | F | I | F | F | CH$_2$ | O |
| 2752. | CH$_3$ | F | I | F | F | CH$_2$ | O |
| 2753. | CN | F | I | F | F | CH$_2$ | O |
| 2754. | H | Cl | F | F | F | CH$_2$ | O |
| 2755. | F | Cl | F | F | F | CH$_2$ | O |
| 2756. | Cl | Cl | F | F | F | CH$_2$ | O |
| 2757. | Br | Cl | F | F | F | CH$_2$ | O |
| 2758. | I | Cl | F | F | F | CH$_2$ | O |
| 2759. | CH$_3$ | Cl | F | F | F | CH$_2$ | O |
| 2760. | CN | Cl | F | F | F | CH$_2$ | O |
| 2761. | H | Cl | Br | F | F | CH$_2$ | O |
| 2762. | F | Cl | Br | F | F | CH$_2$ | O |
| 2763. | Cl | Cl | Br | F | F | CH$_2$ | O |
| 2764. | Br | Cl | Br | F | F | CH$_2$ | O |
| 2765. | I | Cl | Br | F | F | CH$_2$ | O |
| 2766. | CH$_3$ | Cl | Br | F | F | CH$_2$ | O |
| 2767. | CN | Cl | Br | F | F | CH$_2$ | O |
| 2768. | H | Cl | I | F | F | CH$_2$ | O |
| 2769. | F | Cl | I | F | F | CH$_2$ | O |
| 2770. | Cl | Cl | I | F | F | CH$_2$ | O |
| 2771. | Br | Cl | I | F | F | CH$_2$ | O |
| 2772. | I | Cl | I | F | F | CH$_2$ | O |
| 2773. | CH$_3$ | Cl | I | F | F | CH$_2$ | O |
| 2774. | CN | Cl | I | F | F | CH$_2$ | O |
| 2775. | H | Br | F | F | F | CH$_2$ | O |
| 2776. | F | Br | F | F | F | CH$_2$ | O |
| 2777. | Cl | Br | F | F | F | CH$_2$ | O |
| 2778. | Br | Br | F | F | F | CH$_2$ | O |
| 2779. | I | Br | F | F | F | CH$_2$ | O |
| 2780. | CH$_3$ | Br | F | F | F | CH$_2$ | O |
| 2781. | CN | Br | F | F | F | CH$_2$ | O |
| 2782. | H | Br | Cl | F | F | CH$_2$ | O |
| 2783. | F | Br | Cl | F | F | CH$_2$ | O |
| 2784. | Cl | Br | Cl | F | F | CH$_2$ | O |
| 2785. | Br | Br | Cl | F | F | CH$_2$ | O |
| 2786. | I | Br | Cl | F | F | CH$_2$ | O |
| 2787. | CH$_3$ | Br | Cl | F | F | CH$_2$ | O |
| 2788. | CN | Br | Cl | F | F | CH$_2$ | O |
| 2789. | H | Br | I | F | F | CH$_2$ | O |
| 2790. | F | Br | I | F | F | CH$_2$ | O |
| 2791. | Cl | Br | I | F | F | CH$_2$ | O |
| 2792. | Br | Br | I | F | F | CH$_2$ | O |
| 2793. | I | Br | I | F | F | CH$_2$ | O |
| 2794. | CH$_3$ | Br | I | F | F | CH$_2$ | O |
| 2795. | CN | Br | I | F | F | CH$_2$ | O |
| 2796. | H | I | F | F | F | CH$_2$ | O |
| 2797. | F | I | F | F | F | CH$_2$ | O |
| 2798. | Cl | I | F | F | F | CH$_2$ | O |
| 2799. | Br | I | F | F | F | CH$_2$ | O |
| 2800. | I | I | F | F | F | CH$_2$ | O |
| 2801. | CH$_3$ | I | F | F | F | CH$_2$ | O |
| 2802. | CN | I | F | F | F | CH$_2$ | O |
| 2803. | H | I | Cl | F | F | CH$_2$ | O |
| 2804. | F | I | Cl | F | F | CH$_2$ | O |
| 2805. | Cl | I | Cl | F | F | CH$_2$ | O |
| 2806. | Br | I | Cl | F | F | CH$_2$ | O |
| 2807. | I | I | Cl | F | F | CH$_2$ | O |
| 2808. | CH$_3$ | I | Cl | F | F | CH$_2$ | O |
| 2809. | CN | I | Cl | F | F | CH$_2$ | O |
| 2810. | H | I | Br | F | F | CH$_2$ | O |
| 2811. | F | I | Br | F | F | CH$_2$ | O |
| 2812. | Cl | I | Br | F | F | CH$_2$ | O |
| 2813. | Br | I | Br | F | F | CH$_2$ | O |
| 2814. | I | I | Br | F | F | CH$_2$ | O |
| 2815. | CH$_3$ | I | Br | F | F | CH$_2$ | O |
| 2816. | CN | I | Br | F | F | CH$_2$ | O |
| 2817. | H | H | H | | =O | CH$_2$ | O |
| 2818. | F | H | H | | =O | CH$_2$ | O |
| 2819. | Cl | H | H | | =O | CH$_2$ | O |
| 2820. | Br | H | H | | =O | CH$_2$ | O |
| 2821. | I | H | H | | =O | CH$_2$ | O |
| 2822. | CH$_3$ | H | H | | =O | CH$_2$ | O |
| 2823. | CN | H | H | | =O | CH$_2$ | O |
| 2824. | H | F | H | | =O | CH$_2$ | O |
| 2825. | F | F | H | | =O | CH$_2$ | O |
| 2826. | Cl | F | H | | =O | CH$_2$ | O |
| 2827. | Br | F | H | | =O | CH$_2$ | O |
| 2828. | I | F | H | | =O | CH$_2$ | O |
| 2829. | CH$_3$ | F | H | | =O | CH$_2$ | O |
| 2830. | CN | F | H | | =O | CH$_2$ | O |
| 2831. | H | H | F | | =O | CH$_2$ | O |
| 2832. | F | H | F | | =O | CH$_2$ | O |
| 2833. | Cl | H | F | | =O | CH$_2$ | O |
| 2834. | Br | H | F | | =O | CH$_2$ | O |
| 2835. | I | H | F | | =O | CH$_2$ | O |
| 2836. | CH$_3$ | H | F | | =O | CH$_2$ | O |
| 2837. | CN | H | F | | =O | CH$_2$ | O |
| 2838. | H | F | F | | =O | CH$_2$ | O |
| 2839. | F | F | F | | =O | CH$_2$ | O |
| 2840. | Cl | F | F | | =O | CH$_2$ | O |
| 2841. | Br | F | F | | =O | CH$_2$ | O |
| 2842. | I | F | F | | =O | CH$_2$ | O |
| 2843. | CH$_3$ | F | F | | =O | CH$_2$ | O |
| 2844. | CN | F | F | | =O | CH$_2$ | O |
| 2845. | H | Cl | H | | =O | CH$_2$ | O |
| 2846. | Cl | Cl | H | | =O | CH$_2$ | O |
| 2847. | Cl | Cl | H | | =O | CH$_2$ | O |
| 2848. | Br | Cl | H | | =O | CH$_2$ | O |
| 2849. | I | Cl | H | | =O | CH$_2$ | O |
| 2850. | CH$_3$ | Cl | H | | =O | CH$_2$ | O |
| 2851. | CN | Cl | H | | =O | CH$_2$ | O |
| 2852. | H | H | Cl | | =O | CH$_2$ | O |
| 2853. | Cl | H | Cl | | =O | CH$_2$ | O |
| 2854. | Cl | H | Cl | | =O | CH$_2$ | O |
| 2855. | Br | H | Cl | | =O | CH$_2$ | O |
| 2856. | I | H | Cl | | =O | CH$_2$ | O |
| 2857. | CH$_3$ | H | Cl | | =O | CH$_2$ | O |
| 2858. | CN | H | Cl | | =O | CH$_2$ | O |
| 2859. | H | Cl | Cl | | =O | CH$_2$ | O |
| 2860. | Cl | Cl | Cl | | =O | CH$_2$ | O |
| 2861. | Cl | Cl | Cl | | =O | CH$_2$ | O |
| 2862. | Br | Cl | Cl | | =O | CH$_2$ | O |
| 2863. | I | Cl | Cl | | =O | CH$_2$ | O |
| 2864. | CH$_3$ | Cl | Cl | | =O | CH$_2$ | O |
| 2865. | CN | Cl | Cl | | =O | CH$_2$ | O |
| 2866. | H | Br | H | | =O | CH$_2$ | O |
| 2867. | F | Br | H | | =O | CH$_2$ | O |
| 2868. | Cl | Br | H | | =O | CH$_2$ | O |
| 2869. | Br | Br | H | | =O | CH$_2$ | O |
| 2870. | I | Br | H | | =O | CH$_2$ | O |
| 2871. | CH$_3$ | Br | H | | =O | CH$_2$ | O |
| 2872. | CN | Br | H | | =O | CH$_2$ | O |
| 2873. | H | H | Br | | =O | CH$_2$ | O |
| 2874. | F | H | Br | | =O | CH$_2$ | O |
| 2875. | Cl | H | Br | | =O | CH$_2$ | O |
| 2876. | Br | H | Br | | =O | CH$_2$ | O |
| 2877. | I | H | Br | | =O | CH$_2$ | O |
| 2878. | CH$_3$ | H | Br | | =O | CH$_2$ | O |
| 2879. | CN | H | Br | | =O | CH$_2$ | O |
| 2880. | H | Br | Br | | =O | CH$_2$ | O |
| 2881. | F | Br | Br | | =O | CH$_2$ | O |
| 2882. | Cl | Br | Br | | =O | CH$_2$ | O |
| 2883. | Br | Br | Br | | =O | CH$_2$ | O |
| 2884. | I | Br | Br | | =O | CH$_2$ | O |
| 2885. | CH$_3$ | Br | Br | | =O | CH$_2$ | O |
| 2886. | CN | Br | Br | | =O | CH$_2$ | O |
| 2887. | H | I | H | | =O | CH$_2$ | O |
| 2888. | F | I | H | | =O | CH$_2$ | O |
| 2889. | Cl | I | H | | =O | CH$_2$ | O |
| 2890. | Br | I | H | | =O | CH$_2$ | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 2891. | I | I | H | | =O | $CH_2$ | O |
| 2892. | $CH_3$ | I | H | | =O | $CH_2$ | O |
| 2893. | CN | I | H | | =O | $CH_2$ | O |
| 2894. | H | H | I | | =O | $CH_2$ | O |
| 2895. | F | H | I | | =O | $CH_2$ | O |
| 2896. | Cl | H | I | | =O | $CH_2$ | O |
| 2897. | Br | H | I | | =O | $CH_2$ | O |
| 2898. | I | H | I | | =O | $CH_2$ | O |
| 2899. | $CH_3$ | H | I | | =O | $CH_2$ | O |
| 2900. | CN | H | I | | =O | $CH_2$ | O |
| 2901. | H | I | I | | =O | $CH_2$ | O |
| 2902. | F | I | I | | =O | $CH_2$ | O |
| 2903. | Cl | I | I | | =O | $CH_2$ | O |
| 2904. | Br | I | I | | =O | $CH_2$ | O |
| 2905. | I | I | I | | =O | $CH_2$ | O |
| 2906. | $CH_3$ | I | I | | =O | $CH_2$ | O |
| 2907. | CN | I | I | | =O | $CH_2$ | O |
| 2908. | H | F | Cl | | =O | $CH_2$ | O |
| 2909. | D | F | Cl | | =O | $CH_2$ | O |
| 2910. | F | F | Cl | | =O | $CH_2$ | O |
| 2911. | Cl | F | Cl | | =O | $CH_2$ | O |
| 2912. | Br | F | Cl | | =O | $CH_2$ | O |
| 2913. | I | F | Cl | | =O | $CH_2$ | O |
| 2914. | $CH_3$ | F | Cl | | =O | $CH_2$ | O |
| 2915. | CN | F | Cl | | =O | $CH_2$ | O |
| 2916. | H | F | Br | | =O | $CH_2$ | O |
| 2917. | F | F | Br | | =O | $CH_2$ | O |
| 2918. | Cl | F | Br | | =O | $CH_2$ | O |
| 2919. | Br | F | Br | | =O | $CH_2$ | O |
| 2920. | I | F | Br | | =O | $CH_2$ | O |
| 2921. | $CH_3$ | F | Br | | =O | $CH_2$ | O |
| 2922. | CN | F | Br | | =O | $CH_2$ | O |
| 2923. | H | F | I | | =O | $CH_2$ | O |
| 2924. | F | F | I | | =O | $CH_2$ | O |
| 2925. | Cl | F | I | | =O | $CH_2$ | O |
| 2926. | Br | F | I | | =O | $CH_2$ | O |
| 2927. | I | F | I | | =O | $CH_2$ | O |
| 2928. | $CH_3$ | F | I | | =O | $CH_2$ | O |
| 2929. | CN | F | I | | =O | $CH_2$ | O |
| 2930. | H | Cl | F | | =O | $CH_2$ | O |
| 2931. | F | Cl | F | | =O | $CH_2$ | O |
| 2932. | Cl | Cl | F | | =O | $CH_2$ | O |
| 2933. | Br | Cl | F | | =O | $CH_2$ | O |
| 2934. | I | Cl | F | | =O | $CH_2$ | O |
| 2935. | $CH_3$ | Cl | F | | =O | $CH_2$ | O |
| 2936. | CN | Cl | F | | =O | $CH_2$ | O |
| 2937. | H | Cl | Br | | =O | $CH_2$ | O |
| 2938. | F | Cl | Br | | =O | $CH_2$ | O |
| 2939. | Cl | Cl | Br | | =O | $CH_2$ | O |
| 2940. | Br | Cl | Br | | =O | $CH_2$ | O |
| 2941. | I | Cl | Br | | =O | $CH_2$ | O |
| 2942. | $CH_3$ | Cl | Br | | =O | $CH_2$ | O |
| 2943. | CN | Cl | Br | | =O | $CH_2$ | O |
| 2944. | H | Cl | I | | =O | $CH_2$ | O |
| 2945. | F | Cl | I | | =O | $CH_2$ | O |
| 2946. | Cl | Cl | I | | =O | $CH_2$ | O |
| 2947. | Br | Cl | I | | =O | $CH_2$ | O |
| 2948. | I | Cl | I | | =O | $CH_2$ | O |
| 2949. | $CH_3$ | Cl | I | | =O | $CH_2$ | O |
| 2950. | CN | Cl | I | | =O | $CH_2$ | O |
| 2951. | H | Br | F | | =O | $CH_2$ | O |
| 2952. | F | Br | F | | =O | $CH_2$ | O |
| 2953. | Cl | Br | F | | =O | $CH_2$ | O |
| 2954. | Br | Br | F | | =O | $CH_2$ | O |
| 2955. | I | Br | F | | =O | $CH_2$ | O |
| 2956. | $CH_3$ | Br | F | | =O | $CH_2$ | O |
| 2957. | CN | Br | F | | =O | $CH_2$ | O |
| 2958. | H | Br | Cl | | =O | $CH_2$ | O |
| 2959. | F | Br | Cl | | =O | $CH_2$ | O |
| 2960. | Cl | Br | Cl | | =O | $CH_2$ | O |
| 2961. | Br | Br | Cl | | =O | $CH_2$ | O |
| 2962. | I | Br | Cl | | =O | $CH_2$ | O |
| 2963. | $CH_3$ | Br | Cl | | =O | $CH_2$ | O |
| 2964. | CN | Br | Cl | | =O | $CH_2$ | O |
| 2965. | H | Br | I | | =O | $CH_2$ | O |
| 2966. | F | Br | I | | =O | $CH_2$ | O |
| 2967. | Cl | Br | I | | =O | $CH_2$ | O |
| 2968. | Br | Br | I | | =O | $CH_2$ | O |
| 2969. | I | Br | I | | =O | $CH_2$ | O |
| 2970. | $CH_3$ | Br | I | | =O | $CH_2$ | O |
| 2971. | CN | Br | I | | =O | $CH_2$ | O |
| 2972. | H | I | F | | =O | $CH_2$ | O |
| 2973. | F | I | F | | =O | $CH_2$ | O |
| 2974. | Cl | I | F | | =O | $CH_2$ | O |
| 2975. | Br | I | F | | =O | $CH_2$ | O |
| 2976. | I | I | F | | =O | $CH_2$ | O |
| 2977. | $CH_3$ | I | F | | =O | $CH_2$ | O |
| 2978. | CN | I | F | | =O | $CH_2$ | O |
| 2979. | H | I | Cl | | =O | $CH_2$ | O |
| 2980. | F | I | Cl | | =O | $CH_2$ | O |
| 2981. | Cl | I | Cl | | =O | $CH_2$ | O |
| 2982. | Br | I | Cl | | =O | $CH_2$ | O |
| 2983. | I | I | Cl | | =O | $CH_2$ | O |
| 2984. | $CH_3$ | I | Cl | | =O | $CH_2$ | O |
| 2985. | CN | I | Cl | | =O | $CH_2$ | O |
| 2986. | H | I | Br | | =O | $CH_2$ | O |
| 2987. | F | I | Br | | =O | $CH_2$ | O |
| 2988. | Cl | I | Br | | =O | $CH_2$ | O |
| 2989. | Br | I | Br | | =O | $CH_2$ | O |
| 2990. | I | I | Br | | =O | $CH_2$ | O |
| 2991. | $CH_3$ | I | Br | | =O | $CH_2$ | O |
| 2992. | CN | I | Br | | =O | $CH_2$ | O |
| 2993. | H | H | H | | =S | $CH_2$ | O |
| 2994. | F | H | H | | =S | $CH_2$ | O |
| 2995. | Cl | H | H | | =S | $CH_2$ | O |
| 2996. | Br | H | H | | =S | $CH_2$ | O |
| 2997. | I | H | H | | =S | $CH_2$ | O |
| 2998. | $CH_3$ | H | H | | =S | $CH_2$ | O |
| 2999. | CN | H | H | | =S | $CH_2$ | O |
| 3000. | H | F | H | | =S | $CH_2$ | O |
| 3001. | F | F | H | | =S | $CH_2$ | O |
| 3002. | Cl | F | H | | =S | $CH_2$ | O |
| 3003. | Br | F | H | | =S | $CH_2$ | O |
| 3004. | I | F | H | | =S | $CH_2$ | O |
| 3005. | $CH_3$ | F | H | | =S | $CH_2$ | O |
| 3006. | CN | F | H | | =S | $CH_2$ | O |
| 3007. | H | H | F | | =S | $CH_2$ | O |
| 3008. | F | H | F | | =S | $CH_2$ | O |
| 3009. | Cl | H | F | | =S | $CH_2$ | O |
| 3010. | Br | H | F | | =S | $CH_2$ | O |
| 3011. | I | H | F | | =S | $CH_2$ | O |
| 3012. | $CH_3$ | H | F | | =S | $CH_2$ | O |
| 3013. | CN | H | F | | =S | $CH_2$ | O |
| 3014. | H | F | F | | =S | $CH_2$ | O |
| 3015. | F | F | F | | =S | $CH_2$ | O |
| 3016. | Cl | F | F | | =S | $CH_2$ | O |
| 3017. | Br | F | F | | =S | $CH_2$ | O |
| 3018. | I | F | F | | =S | $CH_2$ | O |
| 3019. | $CH_3$ | F | F | | =S | $CH_2$ | O |
| 3020. | CN | F | F | | =S | $CH_2$ | O |
| 3021. | H | Cl | H | | =S | $CH_2$ | O |
| 3022. | Cl | Cl | H | | =S | $CH_2$ | O |
| 3023. | Cl | Cl | H | | =S | $CH_2$ | O |
| 3024. | Br | Cl | H | | =S | $CH_2$ | O |
| 3025. | I | Cl | H | | =S | $CH_2$ | O |
| 3026. | $CH_3$ | Cl | H | | =S | $CH_2$ | O |
| 3027. | CN | Cl | H | | =S | $CH_2$ | O |
| 3028. | H | H | Cl | | =S | $CH_2$ | O |
| 3029. | Cl | H | Cl | | =S | $CH_2$ | O |
| 3030. | Cl | H | Cl | | =S | $CH_2$ | O |
| 3031. | Br | H | Cl | | =S | $CH_2$ | O |
| 3032. | I | H | Cl | | =S | $CH_2$ | O |
| 3033. | $CH_3$ | H | Cl | | =S | $CH_2$ | O |
| 3034. | CN | H | Cl | | =S | $CH_2$ | O |
| 3035. | H | Cl | Cl | | =S | $CH_2$ | O |
| 3036. | Cl | Cl | Cl | | =S | $CH_2$ | O |
| 3037. | Cl | Cl | Cl | | =S | $CH_2$ | O |
| 3038. | Br | Cl | Cl | | =S | $CH_2$ | O |
| 3039. | I | Cl | Cl | | =S | $CH_2$ | O |
| 3040. | $CH_3$ | Cl | Cl | | =S | $CH_2$ | O |
| 3041. | CN | Cl | Cl | | =S | $CH_2$ | O |
| 3042. | H | Br | H | | =S | $CH_2$ | O |
| 3043. | F | Br | H | | =S | $CH_2$ | O |
| 3044. | Cl | Br | H | | =S | $CH_2$ | O |
| 3045. | Br | Br | H | | =S | $CH_2$ | O |
| 3046. | I | Br | H | | =S | $CH_2$ | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 3047. | CH₃ | Br | H | | =S | CH₂ | O |
| 3048. | CN | Br | H | | =S | CH₂ | O |
| 3049. | H | H | Br | | =S | CH₂ | O |
| 3050. | F | H | Br | | =S | CH₂ | O |
| 3051. | Cl | H | Br | | =S | CH₂ | O |
| 3052. | Br | H | Br | | =S | CH₂ | O |
| 3053. | I | H | Br | | =S | CH₂ | O |
| 3054. | CH₃ | H | Br | | =S | CH₂ | O |
| 3055. | CN | H | Br | | =S | CH₂ | O |
| 3056. | H | Br | Br | | =S | CH₂ | O |
| 3057. | F | Br | Br | | =S | CH₂ | O |
| 3058. | Cl | Br | Br | | =S | CH₂ | O |
| 3059. | Br | Br | Br | | =S | CH₂ | O |
| 3060. | I | Br | Br | | =S | CH₂ | O |
| 3061. | CH₃ | Br | Br | | =S | CH₂ | O |
| 3062. | CN | Br | Br | | =S | CH₂ | O |
| 3063. | H | I | H | | =S | CH₂ | O |
| 3064. | F | I | H | | =S | CH₂ | O |
| 3065. | Cl | I | H | | =S | CH₂ | O |
| 3066. | Br | I | H | | =S | CH₂ | O |
| 3067. | I | I | H | | =S | CH₂ | O |
| 3068. | CH₃ | I | H | | =S | CH₂ | O |
| 3069. | CN | I | H | | =S | CH₂ | O |
| 3070. | H | H | I | | =S | CH₂ | O |
| 3071. | F | H | I | | =S | CH₂ | O |
| 3072. | Cl | H | I | | =S | CH₂ | O |
| 3073. | Br | H | I | | =S | CH₂ | O |
| 3074. | I | H | I | | =S | CH₂ | O |
| 3075. | CH₃ | H | I | | =S | CH₂ | O |
| 3076. | CN | H | I | | =S | CH₂ | O |
| 3077. | H | I | I | | =S | CH₂ | O |
| 3078. | F | I | I | | =S | CH₂ | O |
| 3079. | Cl | I | I | | =S | CH₂ | O |
| 3080. | Br | I | I | | =S | CH₂ | O |
| 3081. | I | I | I | | =S | CH₂ | O |
| 3082. | CH₃ | I | I | | =S | CH₂ | O |
| 3083. | CN | I | I | | =S | CH₂ | O |
| 3084. | H | F | Cl | | =S | CH₂ | O |
| 3085. | D | F | Cl | | =S | CH₂ | O |
| 3086. | F | F | Cl | | =S | CH₂ | O |
| 3087. | Cl | F | Cl | | =S | CH₂ | O |
| 3088. | Br | F | Cl | | =S | CH₂ | O |
| 3089. | I | F | Cl | | =S | CH₂ | O |
| 3090. | CH₃ | F | Cl | | =S | CH₂ | O |
| 3091. | CN | F | Cl | | =S | CH₂ | O |
| 3092. | H | F | Br | | =S | CH₂ | O |
| 3093. | F | F | Br | | =S | CH₂ | O |
| 3094. | Cl | F | Br | | =S | CH₂ | O |
| 3095. | Br | F | Br | | =S | CH₂ | O |
| 3096. | I | F | Br | | =S | CH₂ | O |
| 3097. | CH₃ | F | Br | | =S | CH₂ | O |
| 3098. | CN | F | Br | | =S | CH₂ | O |
| 3099. | H | F | I | | =S | CH₂ | O |
| 3100. | F | F | I | | =S | CH₂ | O |
| 3101. | Cl | F | I | | =S | CH₂ | O |
| 3102. | Br | F | I | | =S | CH₂ | O |
| 3103. | I | F | I | | =S | CH₂ | O |
| 3104. | CH₃ | F | I | | =S | CH₂ | O |
| 3105. | CN | F | I | | =S | CH₂ | O |
| 3106. | H | Cl | F | | =S | CH₂ | O |
| 3107. | F | Cl | F | | =S | CH₂ | O |
| 3108. | Cl | Cl | F | | =S | CH₂ | O |
| 3109. | Br | Cl | F | | =S | CH₂ | O |
| 3110. | I | Cl | F | | =S | CH₂ | O |
| 3111. | CH₃ | Cl | F | | =S | CH₂ | O |
| 3112. | CN | Cl | F | | =S | CH₂ | O |
| 3113. | H | Cl | Br | | =S | CH₂ | O |
| 3114. | F | Cl | Br | | =S | CH₂ | O |
| 3115. | Cl | Cl | Br | | =S | CH₂ | O |
| 3116. | Br | Cl | Br | | =S | CH₂ | O |
| 3117. | I | Cl | Br | | =S | CH₂ | O |
| 3118. | CH₃ | Cl | Br | | =S | CH₂ | O |
| 3119. | CN | Cl | Br | | =S | CH₂ | O |
| 3120. | H | Cl | I | | =S | CH₂ | O |
| 3121. | F | Cl | I | | =S | CH₂ | O |
| 3122. | Cl | Cl | I | | =S | CH₂ | O |
| 3123. | Br | Cl | I | | =S | CH₂ | O |
| 3124. | I | Cl | I | | =S | CH₂ | O |
| 3125. | CH₃ | Cl | I | | =S | CH₂ | O |
| 3126. | CN | Cl | I | | =S | CH₂ | O |
| 3127. | H | Br | F | | =S | CH₂ | O |
| 3128. | F | Br | F | | =S | CH₂ | O |
| 3129. | Cl | Br | F | | =S | CH₂ | O |
| 3130. | Br | Br | F | | =S | CH₂ | O |
| 3131. | I | Br | F | | =S | CH₂ | O |
| 3132. | CH₃ | Br | F | | =S | CH₂ | O |
| 3133. | CN | Br | F | | =S | CH₂ | O |
| 3134. | H | Br | Cl | | =S | CH₂ | O |
| 3135. | F | Br | Cl | | =S | CH₂ | O |
| 3136. | Cl | Br | Cl | | =S | CH₂ | O |
| 3137. | Br | Br | Cl | | =S | CH₂ | O |
| 3138. | I | Br | Cl | | =S | CH₂ | O |
| 3139. | CH₃ | Br | Cl | | =S | CH₂ | O |
| 3140. | CN | Br | Cl | | =S | CH₂ | O |
| 3141. | H | Br | I | | =S | CH₂ | O |
| 3142. | F | Br | I | | =S | CH₂ | O |
| 3143. | Cl | Br | I | | =S | CH₂ | O |
| 3144. | Br | Br | I | | =S | CH₂ | O |
| 3145. | I | Br | I | | =S | CH₂ | O |
| 3146. | CH₃ | Br | I | | =S | CH₂ | O |
| 3147. | CN | Br | I | | =S | CH₂ | O |
| 3148. | H | I | F | | =S | CH₂ | O |
| 3149. | F | I | F | | =S | CH₂ | O |
| 3150. | Cl | I | F | | =S | CH₂ | O |
| 3151. | Br | I | F | | =S | CH₂ | O |
| 3152. | I | I | F | | =S | CH₂ | O |
| 3153. | CH₃ | I | F | | =S | CH₂ | O |
| 3154. | CN | I | F | | =S | CH₂ | O |
| 3155. | H | I | Cl | | =S | CH₂ | O |
| 3156. | F | I | Cl | | =S | CH₂ | O |
| 3157. | Cl | I | Cl | | =S | CH₂ | O |
| 3158. | Br | I | Cl | | =S | CH₂ | O |
| 3159. | I | I | Cl | | =S | CH₂ | O |
| 3160. | CH₃ | I | Cl | | =S | CH₂ | O |
| 3161. | CN | I | Cl | | =S | CH₂ | O |
| 3162. | H | I | Br | | =S | CH₂ | O |
| 3163. | F | I | Br | | =S | CH₂ | O |
| 3164. | Cl | I | Br | | =S | CH₂ | O |
| 3165. | Br | I | Br | | =S | CH₂ | O |
| 3166. | I | I | Br | | =S | CH₂ | O |
| 3167. | CH₃ | I | Br | | =S | CH₂ | O |
| 3168. | CN | I | Br | | =S | CH₂ | O |
| 3169. | H | H | H | CH₃ | OCH₂CH₃ | O | O |
| 3170. | F | H | H | CH₃ | OCH₂CH₃ | O | O |
| 3171. | Cl | H | H | CH₃ | OCH₂CH₃ | O | O |
| 3172. | Br | H | H | CH₃ | OCH₂CH₃ | O | O |
| 3173. | I | H | H | CH₃ | OCH₂CH₃ | O | O |
| 3174. | CH₃ | H | H | CH₃ | OCH₂CH₃ | O | O |
| 3175. | CN | H | H | CH₃ | OCH₂CH₃ | O | O |
| 3176. | H | F | H | CH₃ | OCH₂CH₃ | O | O |
| 3177. | F | F | H | CH₃ | OCH₂CH₃ | O | O |
| 3178. | Cl | F | H | CH₃ | OCH₂CH₃ | O | O |
| 3179. | Br | F | H | CH₃ | OCH₂CH₃ | O | O |
| 3180. | I | F | H | CH₃ | OCH₂CH₃ | O | O |
| 3181. | CH₃ | F | H | CH₃ | OCH₂CH₃ | O | O |
| 3182. | CN | F | H | CH₃ | OCH₂CH₃ | O | O |
| 3183. | H | H | F | CH₃ | OCH₂CH₃ | O | O |
| 3184. | F | H | F | CH₃ | OCH₂CH₃ | O | O |
| 3185. | Cl | H | F | CH₃ | OCH₂CH₃ | O | O |
| 3186. | Br | H | F | CH₃ | OCH₂CH₃ | O | O |
| 3187. | I | H | F | CH₃ | OCH₂CH₃ | O | O |
| 3188. | CH₃ | H | F | CH₃ | OCH₂CH₃ | O | O |
| 3189. | CN | H | F | CH₃ | OCH₂CH₃ | O | O |
| 3190. | H | F | F | CH₃ | OCH₂CH₃ | O | O |
| 3191. | F | F | F | CH₃ | OCH₂CH₃ | O | O |
| 3192. | Cl | F | F | CH₃ | OCH₂CH₃ | O | O |
| 3193. | Br | F | F | CH₃ | OCH₂CH₃ | O | O |
| 3194. | I | F | F | CH₃ | OCH₂CH₃ | O | O |
| 3195. | CH₃ | F | F | CH₃ | OCH₂CH₃ | O | O |
| 3196. | CN | F | F | CH₃ | OCH₂CH₃ | O | O |
| 3197. | H | Cl | H | CH₃ | OCH₂CH₃ | O | O |
| 3198. | Cl | Cl | H | CH₃ | OCH₂CH₃ | O | O |
| 3199. | Cl | Cl | H | CH₃ | OCH₂CH₃ | O | O |
| 3200. | Br | Cl | H | CH₃ | OCH₂CH₃ | O | O |
| 3201. | I | Cl | H | CH₃ | OCH₂CH₃ | O | O |
| 3202. | CH₃ | Cl | H | CH₃ | OCH₂CH₃ | O | O |

TABLE A-continued

| no. | $R^{b1}$ | $R^{b3}$ | $R^{b2}$ | $R^{A1}$ | $R^{A2}$ | $Y^1$ | $Y^2$ |
|---|---|---|---|---|---|---|---|
| 3203. | CN | Cl | H | CH$_3$ | OCH$_2$CH$_3$ | O | O |
| 3204. | H | H | Cl | CH$_3$ | OCH$_2$CH$_3$ | O | O |
| 3205. | Cl | H | Cl | CH$_3$ | OCH$_2$CH$_3$ | O | O |
| 3206. | Cl | H | Cl | CH$_3$ | OCH$_2$CH$_3$ | O | O |
| 3207. | Br | H | Cl | CH$_3$ | OCH$_2$CH$_3$ | O | O |
| 3208. | I | H | Cl | CH$_3$ | OCH$_2$CH$_3$ | O | O |
| 3209. | CH$_3$ | H | Cl | CH$_3$ | OCH$_2$CH$_3$ | O | O |
| 3210. | CN | H | Cl | CH$_3$ | OCH$_2$CH$_3$ | O | O |
| 3211. | H | Cl | Cl | CH$_3$ | OCH$_2$CH$_3$ | O | O |
| 3212. | Cl | Cl | Cl | CH$_3$ | OCH$_2$CH$_3$ | O | O |
| 3213. | Cl | Cl | Cl | CH$_3$ | OCH$_2$CH$_3$ | O | O |
| 3214. | Br | Cl | Cl | CH$_3$ | OCH$_2$CH$_3$ | O | O |
| 3215. | I | Cl | Cl | CH$_3$ | OCH$_2$CH$_3$ | O | O |
| 3216. | CH$_3$ | Cl | Cl | CH$_3$ | OCH$_2$CH$_3$ | O | O |
| 3217. | CN | Cl | Cl | CH$_3$ | OCH$_2$CH$_3$ | O | O |
| 3218. | H | Br | H | CH$_3$ | OCH$_2$CH$_3$ | O | O |
| 3219. | F | Br | H | CH$_3$ | OCH$_2$CH$_3$ | O | O |
| 3220. | Cl | Br | H | CH$_3$ | OCH$_2$CH$_3$ | O | O |
| 3221. | Br | Br | H | CH$_3$ | OCH$_2$CH$_3$ | O | O |
| 3222. | I | Br | H | CH$_3$ | OCH$_2$CH$_3$ | O | O |
| 3223. | CH$_3$ | Br | H | CH$_3$ | OCH$_2$CH$_3$ | O | O |
| 3224. | CN | Br | H | CH$_3$ | OCH$_2$CH$_3$ | O | O |
| 3225. | H | H | Br | CH$_3$ | OCH$_2$CH$_3$ | O | O |
| 3226. | F | H | Br | CH$_3$ | OCH$_2$CH$_3$ | O | O |
| 3227. | Cl | H | Br | CH$_3$ | OCH$_2$CH$_3$ | O | O |
| 3228. | Br | H | Br | CH$_3$ | OCH$_2$CH$_3$ | O | O |
| 3229. | I | H | Br | CH$_3$ | OCH$_2$CH$_3$ | O | O |
| 3230. | CH$_3$ | H | Br | CH$_3$ | OCH$_2$CH$_3$ | O | O |
| 3231. | CN | H | Br | CH$_3$ | OCH$_2$CH$_3$ | O | O |
| 3232. | H | Br | Br | CH$_3$ | OCH$_2$CH$_3$ | O | O |
| 3233. | F | Br | Br | CH$_3$ | OCH$_2$CH$_3$ | O | O |
| 3234. | Cl | Br | Br | CH$_3$ | OCH$_2$CH$_3$ | O | O |
| 3235. | Br | Br | Br | CH$_3$ | OCH$_2$CH$_3$ | O | O |
| 3236. | I | Br | Br | CH$_3$ | OCH$_2$CH$_3$ | O | O |
| 3237. | CH$_3$ | Br | Br | CH$_3$ | OCH$_2$CH$_3$ | O | O |
| 3238. | CN | H | Br | CH$_3$ | OCH$_2$CH$_3$ | O | O |
| 3239. | H | I | H | CH$_3$ | OCH$_2$CH$_3$ | O | O |
| 3240. | F | I | H | CH$_3$ | OCH$_2$CH$_3$ | O | O |
| 3241. | Cl | I | H | CH$_3$ | OCH$_2$CH$_3$ | O | O |
| 3242. | Br | I | H | CH$_3$ | OCH$_2$CH$_3$ | O | O |
| 3243. | I | I | H | CH$_3$ | OCH$_2$CH$_3$ | O | O |
| 3244. | CH$_3$ | I | H | CH$_3$ | OCH$_2$CH$_3$ | O | O |
| 3245. | CN | I | H | CH$_3$ | OCH$_2$CH$_3$ | O | O |
| 3246. | H | H | I | CH$_3$ | OCH$_2$CH$_3$ | O | O |
| 3247. | F | H | I | CH$_3$ | OCH$_2$CH$_3$ | O | O |
| 3248. | Cl | H | I | CH$_3$ | OCH$_2$CH$_3$ | O | O |
| 3249. | Br | H | I | CH$_3$ | OCH$_2$CH$_3$ | O | O |
| 3250. | I | H | I | CH$_3$ | OCH$_2$CH$_3$ | O | O |
| 3251. | CH$_3$ | H | I | CH$_3$ | OCH$_2$CH$_3$ | O | O |
| 3252. | CN | H | I | CH$_3$ | OCH$_2$CH$_3$ | O | O |
| 3253. | H | I | I | CH$_3$ | OCH$_2$CH$_3$ | O | O |
| 3254. | F | I | I | CH$_3$ | OCH$_2$CH$_3$ | O | O |
| 3255. | Cl | I | I | CH$_3$ | OCH$_2$CH$_3$ | O | O |
| 3256. | Br | I | I | CH$_3$ | OCH$_2$CH$_3$ | O | O |
| 3257. | I | I | I | CH$_3$ | OCH$_2$CH$_3$ | O | O |
| 3258. | CH$_3$ | I | I | CH$_3$ | OCH$_2$CH$_3$ | O | O |
| 3259. | CN | I | I | CH$_3$ | OCH$_2$CH$_3$ | O | O |
| 3260. | H | F | Cl | CH$_3$ | OCH$_2$CH$_3$ | O | O |
| 3261. | D | F | Cl | CH$_3$ | OCH$_2$CH$_3$ | O | O |
| 3262. | F | F | Cl | CH$_3$ | OCH$_2$CH$_3$ | O | O |
| 3263. | Cl | F | Cl | CH$_3$ | OCH$_2$CH$_3$ | O | O |
| 3264. | Br | F | Cl | CH$_3$ | OCH$_2$CH$_3$ | O | O |
| 3265. | I | F | Cl | CH$_3$ | OCH$_2$CH$_3$ | O | O |
| 3266. | CH$_3$ | F | Cl | CH$_3$ | OCH$_2$CH$_3$ | O | O |
| 3267. | CN | F | Cl | CH$_3$ | OCH$_2$CH$_3$ | O | O |
| 3268. | H | F | Br | CH$_3$ | OCH$_2$CH$_3$ | O | O |
| 3269. | F | F | Br | CH$_3$ | OCH$_2$CH$_3$ | O | O |
| 3270. | Cl | F | Br | CH$_3$ | OCH$_2$CH$_3$ | O | O |
| 3271. | Br | F | Br | CH$_3$ | OCH$_2$CH$_3$ | O | O |
| 3272. | I | F | Br | CH$_3$ | OCH$_2$CH$_3$ | O | O |
| 3273. | CH$_3$ | F | Br | CH$_3$ | OCH$_2$CH$_3$ | O | O |
| 3274. | CN | F | Br | CH$_3$ | OCH$_2$CH$_3$ | O | O |
| 3275. | H | F | I | CH$_3$ | OCH$_2$CH$_3$ | O | O |
| 3276. | F | F | I | CH$_3$ | OCH$_2$CH$_3$ | O | O |
| 3277. | Cl | F | I | CH$_3$ | OCH$_2$CH$_3$ | O | O |
| 3278. | Br | F | I | CH$_3$ | OCH$_2$CH$_3$ | O | O |
| 3279. | I | F | I | CH$_3$ | OCH$_2$CH$_3$ | O | O |
| 3280. | CH$_3$ | F | I | CH$_3$ | OCH$_2$CH$_3$ | O | O |
| 3281. | CN | F | I | CH$_3$ | OCH$_2$CH$_3$ | O | O |
| 3282. | H | Cl | F | CH$_3$ | OCH$_2$CH$_3$ | O | O |
| 3283. | F | Cl | F | CH$_3$ | OCH$_2$CH$_3$ | O | O |
| 3284. | Cl | Cl | F | CH$_3$ | OCH$_2$CH$_3$ | O | O |
| 3285. | Br | Cl | F | CH$_3$ | OCH$_2$CH$_3$ | O | O |
| 3286. | I | Cl | F | CH$_3$ | OCH$_2$CH$_3$ | O | O |
| 3287. | CH$_3$ | Cl | F | CH$_3$ | OCH$_2$CH$_3$ | O | O |
| 3288. | CN | Cl | F | CH$_3$ | OCH$_2$CH$_3$ | O | O |
| 3289. | H | Cl | Br | CH$_3$ | OCH$_2$CH$_3$ | O | O |
| 3290. | F | Cl | Br | CH$_3$ | OCH$_2$CH$_3$ | O | O |
| 3291. | Cl | Cl | Br | CH$_3$ | OCH$_2$CH$_3$ | O | O |
| 3292. | Br | Cl | Br | CH$_3$ | OCH$_2$CH$_3$ | O | O |
| 3293. | I | Cl | Br | CH$_3$ | OCH$_2$CH$_3$ | O | O |
| 3294. | CH$_3$ | Cl | Br | CH$_3$ | OCH$_2$CH$_3$ | O | O |
| 3295. | CN | Cl | Br | CH$_3$ | OCH$_2$CH$_3$ | O | O |
| 3296. | H | Cl | I | CH$_3$ | OCH$_2$CH$_3$ | O | O |
| 3297. | F | Cl | I | CH$_3$ | OCH$_2$CH$_3$ | O | O |
| 3298. | Cl | Cl | I | CH$_3$ | OCH$_2$CH$_3$ | O | O |
| 3299. | Br | Cl | I | CH$_3$ | OCH$_2$CH$_3$ | O | O |
| 3300. | I | Cl | I | CH$_3$ | OCH$_2$CH$_3$ | O | O |
| 3301. | CH$_3$ | Cl | I | CH$_3$ | OCH$_2$CH$_3$ | O | O |
| 3302. | CN | Cl | I | CH$_3$ | OCH$_2$CH$_3$ | O | O |
| 3303. | H | Br | F | CH$_3$ | OCH$_2$CH$_3$ | O | O |
| 3304. | F | Br | F | CH$_3$ | OCH$_2$CH$_3$ | O | O |
| 3305. | Cl | Br | F | CH$_3$ | OCH$_2$CH$_3$ | O | O |
| 3306. | Br | Br | F | CH$_3$ | OCH$_2$CH$_3$ | O | O |
| 3307. | I | Br | F | CH$_3$ | OCH$_2$CH$_3$ | O | O |
| 3308. | CH$_3$ | Br | F | CH$_3$ | OCH$_2$CH$_3$ | O | O |
| 3309. | CN | Br | F | CH$_3$ | OCH$_2$CH$_3$ | O | O |
| 3310. | H | Br | Cl | CH$_3$ | OCH$_2$CH$_3$ | O | O |
| 3311. | F | Br | Cl | CH$_3$ | OCH$_2$CH$_3$ | O | O |
| 3312. | Cl | Br | Cl | CH$_3$ | OCH$_2$CH$_3$ | O | O |
| 3313. | Br | Br | Cl | CH$_3$ | OCH$_2$CH$_3$ | O | O |
| 3314. | I | Br | Cl | CH$_3$ | OCH$_2$CH$_3$ | O | O |
| 3315. | CH$_3$ | Br | Cl | CH$_3$ | OCH$_2$CH$_3$ | O | O |
| 3316. | CN | Br | Cl | CH$_3$ | OCH$_2$CH$_3$ | O | O |
| 3317. | H | Br | I | CH$_3$ | OCH$_2$CH$_3$ | O | O |
| 3318. | F | Br | I | CH$_3$ | OCH$_2$CH$_3$ | O | O |
| 3319. | Cl | Br | I | CH$_3$ | OCH$_2$CH$_3$ | O | O |
| 3320. | Br | Br | I | CH$_3$ | OCH$_2$CH$_3$ | O | O |
| 3321. | I | Br | I | CH$_3$ | OCH$_2$CH$_3$ | O | O |
| 3322. | CH$_3$ | Br | I | CH$_3$ | OCH$_2$CH$_3$ | O | O |
| 3323. | CN | Br | I | CH$_3$ | OCH$_2$CH$_3$ | O | O |
| 3324. | H | I | F | CH$_3$ | OCH$_2$CH$_3$ | O | O |
| 3325. | F | I | F | CH$_3$ | OCH$_2$CH$_3$ | O | O |
| 3326. | Cl | I | F | CH$_3$ | OCH$_2$CH$_3$ | O | O |
| 3327. | Br | I | F | CH$_3$ | OCH$_2$CH$_3$ | O | O |
| 3328. | I | I | F | CH$_3$ | OCH$_2$CH$_3$ | O | O |
| 3329. | CH$_3$ | I | F | CH$_3$ | OCH$_2$CH$_3$ | O | O |
| 3330. | CN | I | F | CH$_3$ | OCH$_2$CH$_3$ | O | O |
| 3331. | H | I | Cl | CH$_3$ | OCH$_2$CH$_3$ | O | O |
| 3332. | F | I | Cl | CH$_3$ | OCH$_2$CH$_3$ | O | O |
| 3333. | Cl | I | Cl | CH$_3$ | OCH$_2$CH$_3$ | O | O |
| 3334. | Br | I | Cl | CH$_3$ | OCH$_2$CH$_3$ | O | O |
| 3335. | I | I | Cl | CH$_3$ | OCH$_2$CH$_3$ | O | O |
| 3336. | CH$_3$ | I | Cl | CH$_3$ | OCH$_2$CH$_3$ | O | O |
| 3337. | CN | I | Cl | CH$_3$ | OCH$_2$CH$_3$ | O | O |
| 3338. | H | I | Br | CH$_3$ | OCH$_2$CH$_3$ | O | O |
| 3339. | F | I | Br | CH$_3$ | OCH$_2$CH$_3$ | O | O |
| 3340. | Cl | I | Br | CH$_3$ | OCH$_2$CH$_3$ | O | O |
| 3341. | Br | I | Br | CH$_3$ | OCH$_2$CH$_3$ | O | O |
| 3342. | I | I | Br | CH$_3$ | OCH$_2$CH$_3$ | O | O |
| 3343. | CH$_3$ | I | Br | CH$_3$ | OCH$_2$CH$_3$ | O | O |
| 3344. | CN | I | Br | CH$_3$ | OCH$_2$CH$_3$ | O | O |

Particularly preferred is given to diaminotriazine compounds of formula (I.b), which corresponds to formula (I), wherein R$^1$ is hydrogen, R$^2$ is hydrogen and R$^{b1}$, R$^{b2}$, R$^{b3}$, R$^{A1}$, R$^{A2}$, R$^c$ are given in table B, and wherein X is as defined above and in particular X is selected from the group consisting of CF(CH$_3$)$_2$, CFCH$_3$CH$_2$CH$_3$, CHFCH$_3$, CHFCH$_2$CH$_3$, CF(CH$_2$CH$_3$)$_2$, CF$_2$CH$_3$, t-butyl, i-butyl, s-butyl, 1-chloro-cyclobutyl, 2,2-dimethylpropyl, i-propyl, 1-fluoropropyl, cyclobutyl, cyclopentyl, cyclohexyl, 1-cyclopropylethyl, 1-methylcyclobutyl, 1-methylcyclopentyl, C(CH$_3$)$_2$OCH$_3$, 1-methylcyclohexyl, 1-methoxyethyl, 1-methoxy-cyclopentyl, 1-methoxy-cyclobutyl, 1-methoxyl-cyclohexyl, 1-fluor-cyclopentyl, 1-fluor-cyclohexyl, 1-chlor-cyclopentyl, 1-chlor-cyclohexyl, 1-chlor-cyclobutyl, 2-methylpyrrolidin-1-yl, 2,2,2-trifluoroethoxy, azetidine, pyrrolidin-1-yl, piperidyl, methoxy(methyl)amino, 2-tetrahydrofuranyl, 2,4,6-tri-fluoro-phenyl, 2,6-difluoro-phenyl, 2-fluoro-phenyl or methoxy.

Examples of these compounds are those given in table B-1 to B-41.

Particular preference is given to diaminotriazine compounds of formula (I.b), which corresponds to diaminotriazines of formula (I) wherein $R^1$ and $R^2$ is hydrogen $R^{b1}$, $R^{b2}$, $R^{b3}$, $R^{A1}$, $R^{A2}$, $R^c$ are defined in table B.

Table B-1: Compounds of formula (I.b), where X is $CFCH_3CH_2CH_3$ and $R^{b1}$, $R^{b2}$, $R^{b3}$, $R^{A1}$, $R^{A2}$, $R^c$ are defined the rows of table B.

Table B-2: Compounds of formula (I.b), where X is $CF(CH_3)_2$ and $R^{b1}$, $R^{b2}$, $R^{b3}$, $R^{A1}$, $R^{A2}$, $R^c$ are defined the rows of table B.

Table B-3: Compounds of formula (I.b), where X is $CHFCH_3$ and $R^{b1}$, $R^{b2}$, $R^{b3}$, $R^{A1}$, $R^{A2}$, $R^c$ are defined the rows of table B.

Table B-4: Compounds of formula (I.b), where X is $CHFCH_2CH_3$ and $R^{b1}$, $R^{b2}$, $R^{b3}$, $R^{A1}$, $R^{A2}$, $R^c$ are defined the rows of table B.

Table B-5: Compounds of formula (I.b), where X is $CF(CH_2CH_3)_2$ and $R^{b1}$, $R^{b2}$, $R^{b3}$, $R^{A1}$, $R^{A2}$, $R^c$ are defined the rows of table B.

Table B-6: Compounds of formula (I.b), where X is $CF_2CH_3$ and $R^{b1}$, $R^{b2}$, $R^{b3}$, $R^{A1}$, $R^{A2}$, $R^c$ are defined the rows of table B.

Table B-7: Compounds of formula (I.b), where X is t-butyl and $R^{b1}$, $R^{b2}$, $R^{b3}$, $R^{A1}$, $R^{A2}$, $R^c$ are defined the rows of table B.

Table B-8: Compounds of formula (I.b), where X is i-butyl and $R^{b1}$, $R^{b2}$, $R^{b3}$, $R^{A1}$, $R^{A2}$, $R^c$ are defined the rows of table B.

Table B-9: Compounds of formula (I.b), where X is 2,2-dimethylpropyl and $R^{b1}$, $R^{b2}$, $R^{b3}$, $R^{A1}$, $R^{A2}$, $R^c$ are defined the rows of table B.

Table B-10: Compounds of formula (I.b), where X is i-propyl and $R^{b1}$, $R^{b2}$, $R^{b3}$, $R^{A1}$, $R^{A2}$, $R^c$ are defined the rows of table B.

Table B-11: Compounds of formula (I.b), where X is cyclobutyl and $R^{b1}$, $R^{b2}$, $R^{b3}$, $R^{A1}$, $R^{A2}$, $R^c$ are defined the rows of table B.

Table B-12: Compounds of formula (I.b), where X is cyclopentyl and $R^{b1}$, $R^{b2}$, $R^{b3}$, $R^{A1}$, $R^{A2}$, $R^c$ are defined the rows of table B.

Table B-13: Compounds of formula (I.b), where X is cyclohexyl and $R^{b1}$, $R^{b2}$, $R^{b3}$, $R^{A1}$, $R^{A2}$, $R^c$ are defined the rows of table B.

Table B-14: Compounds of formula (I.b), where X is 1-cyclopropylethyl and $R^{b1}$, $R^{b2}$, $R^{b3}$, $R^{A1}$, $R^{A2}$, $R^c$ are defined the rows of table B.

Table B-15: Compounds of formula (I.b), where X is 1-methylcyclobutyl and $R^{b1}$, $R^{b2}$, $R^{b3}$, $R^{A1}$, $R^{A2}$, $R^c$ are defined the rows of table B.

Table B-16: Compounds of formula (I.b), where X is 1-methylcyclopentyl and $R^{b1}$, $R^{b2}$, $R^{b3}$, $R^{A1}$, $R^{A2}$, $R^c$ are defined the rows of table B.

Table B-17: Compounds of formula (I.b), where X is $C(CH_3)_2OCH_3$ and $R^{b1}$, $R^{b2}$, $R^{b3}$, $R^{A1}$, $R^{A2}$, $R^c$ are defined the rows of table B.

Table B-18: Compounds of formula (I.b), where X is 1-methylcyclohexyl and $R^{b1}$, $R^{b2}$, $R^{b3}$, $R^{A1}$, $R^{A2}$, $R^c$ are defined the rows of table B.

Table B-19: Compounds of formula (I.b), where X is 1-methoxyethyl and $R^{b1}$, $R^{b2}$, $R^{b3}$, $RA^{A1}$ $R^{A2}$, $R^c$ are defined the rows of table B.

Table B-20: Compounds of formula (I.b), where X is 1-methoxy-cyclopentyl and $R^{b1}$, $R^{b2}$, $R^{b3}$, $R^{A1}R^{A2}$, $R^c$ are defined the rows of table B.

Table B-21: Compounds of formula (I.b), where X is 1-methoxy-cyclobutyl and $R^{b1}$, $R^{b2}$, $R^{b3}$, $RA^{A1}$, $R^{A2}$, $R^c$ are defined the rows of table B.

Table B-22: Compounds of formula (I.b), where X is 1-methoxyl-cyclohexyl and $R^{b1}$, $R^{b2}$, $R^{b3}$, $RA^{A1}$, $R^{A2}$, $R^c$ are defined the rows of table B.

Table B-23: Compounds of formula (I.b), where X is 1-fluor-cyclopentyl and $R^{b1}$, $R^{b2}$, $R^{b3}$, $RA^{A1}$, $R^{A2}$, $R^c$ are defined the rows of table B.

Table B-24: Compounds of formula (I.b), where X is 1-fluor-cyclohexyl and $R^{b1}$, $R^{b2}$, $R^{b3}$, $R^{A1}$, $R^{A2}$, $R^c$ are defined the rows of table B.

Table B-25: Compounds of formula (I.b), where X is 1-chlor-cyclopentyl and $R^{b1}$, $R^{b2}$, $R^{b3}$, $R^{A1}$, $R^{A2}$, $R^c$ are defined the rows of table B.

Table B-26: Compounds of formula (I.b), where X is 1-chlor-cyclohexyl and $R^{b1}$, $R^{b2}$, $R^{b3}$, $R^{A1}$, $R^{A2}$, $R^c$ are defined the rows of table B.

Table B-27: Compounds of formula (I.b), where X is 1-chlor-cyclobutyl and $R^{b1}$, $R^{b2}$, $R^{b3}$, $R^{A1}$, $R^{A2}$, $R^c$ are defined the rows of table B.

Table B-28: Compounds of formula (I.b), where X is 2-methylpyrrolidin-1-yl and $R^{b1}$, $R^{b2}$, $R^{b3}$, $R^{A1}$, $R^{A2}$, $R^c$ are defined the rows of table B.

Table B-29: Compounds of formula (I.b), where X is 2,2,2-trifluoroethoxy and $R^{b1}$, $R^{b2}$, $R^{b3}$, $R^{A1}$, $R^{A2}$, $R^c$ are defined the rows of table B.

Table B-30: Compounds of formula (I.b), where X is azitidine and $R^{b1}$, $R^{b2}$, $R^{b3}$, $R^{A1}$, $R^{A2}$, $R^c$ are defined the rows of table B.

Table B-31: Compounds of formula (I.b), where X is pyrrolidin-1-yl and $R^{b1}$, $R^{b2}$, $R^{b3}$, $R^{A1}$, $R^{A2}$, $R^c$ are defined the rows of table B.

Table B-32: Compounds of formula (I.b), where X is 2-tetrahydrofuranyl and $R^{b1}$, $R^{b2}$, $R^{b3}$, $R^{A1}$, $R^{A2}$, $R^c$ are defined the rows of table B.

Table B-33: Compounds of formula (I.b), where X is 2,4,6-tri-fluoro-phenyl and $R^{b1}$, $R^{b2}$, $R^{b3}$, $R^{A1}$, $R^{A2}$, $R^c$ are defined the rows of table B.

Table B-34: Compounds of formula (I.b), where X is 2,6-difluoro-phenyl and $R^{b1}$, $R^{b2}$, $R^{b3}$, $R^{A1}$, $R^{A2}$, $R^c$ are defined the rows of table B.

Table B-35: Compounds of formula (I.b), where X is 2-fluoro-phenyl and $R^{b1}$, $R^{b2}$, $R^{b3}$, $R^{A1}$, $R^{A2}$, $R^c$ are defined the rows of table B.

Table B-36: Compounds of formula (I.b), where X is 1-chlor-cyclobutyl and $R^{b1}$, $R^{b2}$, $R^{b3}$, $R^{A1}$, $R^{A2}$, $R^c$ are defined the rows of table B.

Table B-37: Compounds of formula (I.b), where X is s-butyl and $R^{b1}$, $R^{b2}$, $R^{b3}$, $R^{A1}$, $R^{A2}$, $R^c$ are defined the rows of table B.

Table B-38: Compounds of formula (I.b), where X is piperidyl and $R^{b1}$, $R^{b2}$, $R^{b3}$, $R^{A1}$, $R^{A2}$, $R^c$ are defined the rows of table B.

Table B-39: Compounds of formula (I.b), where X is methoxy(methyl)amino and $R^{b1}$, $R^{b2}$, $R^{b3}$, $R^{A1}$, $R^{A2}$, $R^c$ are defined the rows of table B.

Table B-40: Compounds of formula (I.b), where X is 1-fluoro-propyl and $R^{b1}$, $R^{b2}$, $R^{b3}$, $R^{A1}$, $R^{A2}$, $R^c$ are defined the rows of table B.

Table A-41: Compounds of formula (I.b), where X is methoxy and $R^{b1}$, $R^{b2}$, $R^{b3}$, $R^{A1}$, $R^{A2}$, $R^c$ are defined the rows of table B.

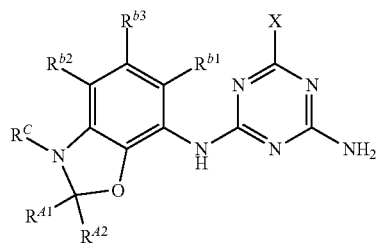

(I.b)

TABLE B

| no. | $R^{b1}$ | $R^{b3}$ | $R^{b2}$ | $R^{A1}$ | $R^{A2}$ | $R^c$ |
|---|---|---|---|---|---|---|
| B-1. | H | H | H | =O | | H |
| B-2. | F | H | H | =O | | H |
| B-3. | Cl | H | H | =O | | H |
| B-4. | Br | H | H | =O | | H |
| B-5. | I | H | H | =O | | H |
| B-6. | CH$_3$ | H | H | =O | | H |
| B-7. | CN | H | H | =O | | H |
| B-8. | H | F | H | =O | | H |
| B-9. | F | F | H | =O | | H |
| B-10. | Cl | F | H | =O | | H |
| B-11. | Br | F | H | =O | | H |
| B-12. | I | F | H | =O | | H |
| B-13. | CH$_3$ | F | H | =O | | H |
| B-14. | CN | F | H | =O | | H |
| B-15. | H | H | F | =O | | H |
| B-16. | F | H | F | =O | | H |
| B-17. | Cl | H | F | =O | | H |
| B-18. | Br | H | F | =O | | H |
| B-19. | I | H | F | =O | | H |
| B-20. | CH$_3$ | H | F | =O | | H |
| B-21. | CN | H | F | =O | | H |
| B-22. | H | F | F | =O | | H |
| B-23. | F | F | F | =O | | H |
| B-24. | Cl | F | F | =O | | H |
| B-25. | Br | F | F | =O | | H |
| B-26. | I | F | F | =O | | H |
| B-27. | CH$_3$ | F | F | =O | | H |
| B-28. | CN | F | F | =O | | H |
| B-29. | H | Cl | H | =O | | H |
| B-30. | Cl | Cl | H | =O | | H |
| B-31. | Cl | Cl | H | =O | | H |
| B-32. | Br | Cl | H | =O | | H |
| B-33. | I | Cl | H | =O | | H |
| B-34. | CH$_3$ | Cl | H | =O | | H |
| B-35. | CN | Cl | H | =O | | H |
| B-36. | H | H | Cl | =O | | H |
| B-37. | Cl | H | Cl | =O | | H |
| B-38. | Cl | H | Cl | =O | | H |
| B-39. | Br | H | Cl | =O | | H |
| B-40. | I | H | Cl | =O | | H |
| B-41. | CH$_3$ | H | Cl | =O | | H |
| B-42. | CN | H | Cl | =O | | H |
| B-43. | H | Cl | Cl | =O | | H |
| B-44. | Cl | Cl | Cl | =O | | H |
| B-45. | Cl | Cl | Cl | =O | | H |
| B-46. | Br | Cl | Cl | =O | | H |
| B-47. | I | Cl | Cl | =O | | H |
| B-48. | CH$_3$ | Cl | Cl | =O | | H |
| B-49. | CN | Cl | Cl | =O | | H |
| B-50. | H | Br | H | =O | | H |
| B-51. | F | Br | H | =O | | H |
| B-52. | Cl | Br | H | =O | | H |
| B-53. | Br | Br | H | =O | | H |
| B-54. | I | Br | H | =O | | H |
| B-55. | CH$_3$ | Br | H | =O | | H |
| B-56. | CN | Br | H | =O | | H |
| B-57. | H | H | Br | =O | | H |
| B-58. | F | H | Br | =O | | H |
| B-59. | Cl | H | Br | =O | | H |
| B-60. | Br | H | Br | =O | | H |
| B-61. | I | H | Br | =O | | H |
| B-62. | CH$_3$ | H | Br | =O | | H |
| B-63. | CN | H | Br | =O | | H |
| B-64. | H | Br | Br | =O | | H |
| B-65. | F | Br | Br | =O | | H |
| B-66. | Cl | Br | Br | =O | | H |
| B-67. | Br | Br | Br | =O | | H |
| B-68. | I | Br | Br | =O | | H |
| B-69. | CH$_3$ | Br | Br | =O | | H |
| B-70. | CN | Br | Br | =O | | H |
| B-71. | H | I | H | =O | | H |
| B-72. | F | I | H | =O | | H |
| B-73. | Cl | I | H | =O | | H |
| B-74. | Br | I | H | =O | | H |
| B-75. | I | I | H | =O | | H |
| B-76. | CH$_3$ | I | H | =O | | H |
| B-77. | CN | I | H | =O | | H |
| B-78. | H | H | I | =O | | H |
| B-79. | F | H | I | =O | | H |
| B-80. | Cl | H | I | =O | | H |
| B-81. | Br | H | I | =O | | H |
| B-82. | I | H | I | =O | | H |
| B-83. | CH$_3$ | H | I | =O | | H |
| B-84. | CN | H | I | =O | | H |
| B-85. | H | I | I | =O | | H |
| B-86. | F | I | I | =O | | H |
| B-87. | Cl | I | I | =O | | H |
| B-88. | Br | I | I | =O | | H |
| B-89. | I | I | I | =O | | H |
| B-90. | CH$_3$ | I | I | =O | | H |
| B-91. | CN | I | I | =O | | H |
| B-92. | H | F | Cl | =O | | H |
| B-93. | D | F | Cl | =O | | H |
| B-94. | F | F | Cl | =O | | H |
| B-95. | Cl | F | Cl | =O | | H |
| B-96. | Br | F | Cl | =O | | H |
| B-97. | I | F | Cl | =O | | H |
| B-98. | CH$_3$ | F | Cl | =O | | H |
| B-99. | CN | F | Cl | =O | | H |
| B-100. | H | F | Br | =O | | H |
| B-101. | F | F | Br | =O | | H |
| B-102. | Cl | F | Br | =O | | H |
| B-103. | Br | F | Br | =O | | H |
| B-104. | I | F | Br | =O | | H |
| B-105. | CH$_3$ | F | Br | =O | | H |
| B-106. | CN | F | Br | =O | | H |
| B-107. | H | F | I | =O | | H |
| B-108. | F | F | I | =O | | H |
| B-109. | Cl | F | I | =O | | H |
| B-110. | Br | F | I | =O | | H |
| B-111. | I | F | I | =O | | H |
| B-112. | CH$_3$ | F | I | =O | | H |
| B-113. | CN | F | I | =O | | H |
| B-114. | H | Cl | F | =O | | H |
| B-115. | F | Cl | F | =O | | H |
| B-116. | Cl | Cl | F | =O | | H |
| B-117. | Br | Cl | F | =O | | H |
| B-118. | I | Cl | F | =O | | H |
| B-119. | CH$_3$ | Cl | F | =O | | H |
| B-120. | CN | Cl | F | =O | | H |
| B-121. | H | Cl | Br | =O | | H |
| B-122. | F | Cl | Br | =O | | H |
| B-123. | Cl | Cl | Br | =O | | H |
| B-124. | Br | Cl | Br | =O | | H |
| B-125. | I | Cl | Br | =O | | H |
| B-126. | CH$_3$ | Cl | Br | =O | | H |
| B-127. | CN | Cl | Br | =O | | H |
| B-128. | H | Cl | I | =O | | H |
| B-129. | F | Cl | I | =O | | H |
| B-130. | Cl | Cl | I | =O | | H |
| B-131. | Br | Cl | I | =O | | H |

TABLE B-continued

| no. | $R^{b1}$ | $R^{b3}$ | $R^{b2}$ | $R^{A1}$ | $R^{A2}$ | $R^c$ |
|---|---|---|---|---|---|---|
| B-132. | I | Cl | I | =O | H | |
| B-133. | CH$_3$ | Cl | I | =O | H | |
| B-134. | CN | Cl | I | =O | H | |
| B-135. | H | Br | F | =O | H | |
| B-136. | F | Br | F | =O | H | |
| B-137. | Cl | Br | F | =O | H | |
| B-138. | Br | Br | F | =O | H | |
| B-139. | I | Br | F | =O | H | |
| B-140. | CH$_3$ | Br | F | =O | H | |
| B-141. | CN | Br | F | =O | H | |
| B-142. | H | Br | Cl | =O | H | |
| B-143. | F | Br | Cl | =O | H | |
| B-144. | Cl | Br | Cl | =O | H | |
| B-145. | Br | Br | Cl | =O | H | |
| B-146. | I | Br | Cl | =O | H | |
| B-147. | CH$_3$ | Br | Cl | =O | H | |
| B-148. | CN | Br | Cl | =O | H | |
| B-149. | H | Br | I | =O | H | |
| B-150. | F | Br | I | =O | H | |
| B-151. | Cl | Br | I | =O | H | |
| B-152. | Br | Br | I | =O | H | |
| B-153. | I | Br | I | =O | H | |
| B-154. | CH$_3$ | Br | I | =O | H | |
| B-155. | CN | Br | I | =O | H | |
| B-156. | H | I | F | =O | H | |
| B-157. | F | I | F | =O | H | |
| B-158. | Cl | I | F | =O | H | |
| B-159. | Br | I | F | =O | H | |
| B-160. | I | I | F | =O | H | |
| B-161. | CH$_3$ | I | F | =O | H | |
| B-162. | CN | I | F | =O | H | |
| B-163. | H | I | Cl | =O | H | |
| B-164. | F | I | Cl | =O | H | |
| B-165. | Cl | I | Cl | =O | H | |
| B-166. | Br | I | Cl | =O | H | |
| B-167. | I | I | Cl | =O | H | |
| B-168. | CH$_3$ | I | Cl | =O | H | |
| B-169. | CN | I | Cl | =O | H | |
| B-170. | H | I | Br | =O | H | |
| B-171. | F | I | Br | =O | H | |
| B-172. | Cl | I | Br | =O | H | |
| B-173. | Br | I | Br | =O | H | |
| B-174. | I | I | Br | =O | H | |
| B-175. | CH$_3$ | I | Br | =O | H | |
| B-176. | CN | I | Br | =O | H | |
| B-177. | H | H | H | =S | H | |
| B-178. | F | H | H | =S | H | |
| B-179. | Cl | H | H | =S | H | |
| B-180. | Br | H | H | =S | H | |
| B-181. | I | H | H | =S | H | |
| B-182. | CH$_3$ | H | H | =S | H | |
| B-183. | CN | H | H | =S | H | |
| B-184. | H | F | H | =S | H | |
| B-185. | F | F | H | =S | H | |
| B-186. | Cl | F | H | =S | H | |
| B-187. | Br | F | H | =S | H | |
| B-188. | I | F | H | =S | H | |
| B-189. | CH$_3$ | F | H | =S | H | |
| B-190. | CN | F | H | =S | H | |
| B-191. | H | H | F | =S | H | |
| B-192. | F | H | F | =S | H | |
| B-193. | Cl | H | F | =S | H | |
| B-194. | Br | H | F | =S | H | |
| B-195. | I | H | F | =S | H | |
| B-196. | CH$_3$ | H | F | =S | H | |
| B-197. | CN | H | F | =S | H | |
| B-198. | H | F | F | =S | H | |
| B-199. | F | F | F | =S | H | |
| B-200. | Cl | F | F | =S | H | |
| B-201. | Br | F | F | =S | H | |
| B-202. | I | F | F | =S | H | |
| B-203. | CH$_3$ | F | F | =S | H | |
| B-204. | CN | F | F | =S | H | |
| B-205. | H | Cl | H | =S | H | |
| B-206. | Cl | Cl | H | =S | H | |
| B-207. | Cl | Cl | H | =S | H | |
| B-208. | Br | Cl | H | =S | H | |
| B-209. | I | Cl | H | =S | H | |
| B-210. | CH$_3$ | Cl | H | =S | H | |
| B-211. | CN | Cl | H | =S | H | |
| B-212. | H | H | Cl | =S | H | |
| B-213. | Cl | H | Cl | =S | H | |
| B-214. | Cl | H | Cl | =S | H | |
| B-215. | Br | H | Cl | =S | H | |
| B-216. | I | H | Cl | =S | H | |
| B-217. | CH$_3$ | H | Cl | =S | H | |
| B-218. | CN | H | Cl | =S | H | |
| B-219. | H | Cl | Cl | =S | H | |
| B-220. | Cl | Cl | Cl | =S | H | |
| B-221. | Cl | Cl | Cl | =S | H | |
| B-222. | Br | Cl | Cl | =S | H | |
| B-223. | I | Cl | Cl | =S | H | |
| B-224. | CH$_3$ | Cl | Cl | =S | H | |
| B-225. | CN | Cl | Cl | =S | H | |
| B-226. | H | Br | H | =S | H | |
| B-227. | F | Br | H | =S | H | |
| B-228. | Cl | Br | H | =S | H | |
| B-229. | Br | Br | H | =S | H | |
| B-230. | I | Br | H | =S | H | |
| B-231. | CH$_3$ | Br | H | =S | H | |
| B-232. | CN | Br | H | =S | H | |
| B-233. | H | H | Br | =S | H | |
| B-234. | F | H | Br | =S | H | |
| B-235. | Cl | H | Br | =S | H | |
| B-236. | Br | H | Br | =S | H | |
| B-237. | I | H | Br | =S | H | |
| B-238. | CH$_3$ | H | Br | =S | H | |
| B-239. | CN | H | Br | =S | H | |
| B-240. | H | Br | Br | =S | H | |
| B-241. | F | Br | Br | =S | H | |
| B-242. | Cl | Br | Br | =S | H | |
| B-243. | Br | Br | Br | =S | H | |
| B-244. | I | Br | Br | =S | H | |
| B-245. | CH$_3$ | Br | Br | =S | H | |
| B-246. | CN | Br | Br | =S | H | |
| B-247. | H | I | H | =S | H | |
| B-248. | F | I | H | =S | H | |
| B-249. | Cl | I | H | =S | H | |
| B-250. | Br | I | H | =S | H | |
| B-251. | I | I | H | =S | H | |
| B-252. | CH$_3$ | I | H | =S | H | |
| B-253. | CN | I | H | =S | H | |
| B-254. | H | H | I | =S | H | |
| B-255. | F | H | I | =S | H | |
| B-256. | Cl | H | I | =S | H | |
| B-257. | Br | H | I | =S | H | |
| B-258. | I | H | I | =S | H | |
| B-259. | CH$_3$ | H | I | =S | H | |
| B-260. | CN | H | I | =S | H | |
| B-261. | H | I | I | =S | H | |
| B-262. | F | I | I | =S | H | |
| B-263. | Cl | I | I | =S | H | |
| B-264. | Br | I | I | =S | H | |
| B-265. | I | I | I | =S | H | |
| B-266. | CH$_3$ | I | I | =S | H | |
| B-267. | CN | I | I | =S | H | |
| B-268. | H | F | Cl | =S | H | |
| B-269. | D | F | Cl | =S | H | |
| B-270. | F | F | Cl | =S | H | |
| B-271. | Cl | F | Cl | =S | H | |
| B-272. | Br | F | Cl | =S | H | |
| B-273. | I | F | Cl | =S | H | |
| B-274. | CH$_3$ | F | Cl | =S | H | |
| B-275. | CN | F | Cl | =S | H | |
| B-276. | H | F | Br | =S | H | |
| B-277. | F | F | Br | =S | H | |
| B-278. | Cl | F | Br | =S | H | |
| B-279. | Br | F | Br | =S | H | |
| B-280. | I | F | Br | =S | H | |
| B-281. | CH$_3$ | F | Br | =S | H | |
| B-282. | CN | F | Br | =S | H | |
| B-283. | H | F | I | =S | H | |
| B-284. | F | F | I | =S | H | |
| B-285. | Cl | F | I | =S | H | |
| B-286. | Br | F | I | =S | H | |
| B-287. | I | F | I | =S | H | |

TABLE B-continued

| no. | $R^{b1}$ | $R^{b3}$ | $R^{b2}$ | $R^{A1}$ | $R^{A2}$ | $R^c$ |
|---|---|---|---|---|---|---|
| B-288. | CH$_3$ | F | I | =S | | H |
| B-289. | CN | F | I | =S | | H |
| B-290. | H | Cl | F | =S | | H |
| B-291. | F | Cl | F | =S | | H |
| B-292. | Cl | Cl | F | =S | | H |
| B-293. | Br | Cl | F | =S | | H |
| B-294. | I | Cl | F | =S | | H |
| B-295. | CH$_3$ | Cl | F | =S | | H |
| B-296. | CN | Cl | F | =S | | H |
| B-297. | H | Cl | Br | =S | | H |
| B-298. | F | Cl | Br | =S | | H |
| B-299. | Cl | Cl | Br | =S | | H |
| B-300. | Br | Cl | Br | =S | | H |
| B-301. | I | Cl | Br | =S | | H |
| B-302. | CH$_3$ | Cl | Br | =S | | H |
| B-303. | CN | Cl | Br | =S | | H |
| B-304. | H | Cl | I | =S | | H |
| B-305. | F | Cl | I | =S | | H |
| B-306. | Cl | Cl | I | =S | | H |
| B-307. | Br | Cl | I | =S | | H |
| B-308. | I | Cl | I | =S | | H |
| B-309. | CH$_3$ | Cl | I | =S | | H |
| B-310. | CN | Cl | I | =S | | H |
| B-311. | H | Br | F | =S | | H |
| B-312. | F | Br | F | =S | | H |
| B-313. | Cl | Br | F | =S | | H |
| B-314. | Br | Br | F | =S | | H |
| B-315. | I | Br | F | =S | | H |
| B-316. | CH$_3$ | Br | F | =S | | H |
| B-317. | CN | Br | F | =S | | H |
| B-318. | H | Br | Cl | =S | | H |
| B-319. | F | Br | Cl | =S | | H |
| B-320. | Cl | Br | Cl | =S | | H |
| B-321. | Br | Br | Cl | =S | | H |
| B-322. | I | Br | Cl | =S | | H |
| B-323. | CH$_3$ | Br | Cl | =S | | H |
| B-324. | CN | Br | Cl | =S | | H |
| B-325. | H | Br | I | =S | | H |
| B-326. | F | Br | I | =S | | H |
| B-327. | Cl | Br | I | =S | | H |
| B-328. | Br | Br | I | =S | | H |
| B-329. | I | Br | I | =S | | H |
| B-330. | CH$_3$ | Br | I | =S | | H |
| B-331. | CN | Br | I | =S | | H |
| B-332. | H | I | F | =S | | H |
| B-333. | F | I | F | =S | | H |
| B-334. | Cl | I | F | =S | | H |
| B-335. | Br | I | F | =S | | H |
| B-336. | I | I | F | =S | | H |
| B-337. | CH$_3$ | I | F | =S | | H |
| B-338. | CN | I | F | =S | | H |
| B-339. | H | I | Cl | =S | | H |
| B-340. | F | I | Cl | =S | | H |
| B-341. | Cl | I | Cl | =S | | H |
| B-342. | Br | I | Cl | =S | | H |
| B-343. | I | I | Cl | =S | | H |
| B-344. | CH$_3$ | I | Cl | =S | | H |
| B-345. | CN | I | Cl | =S | | H |
| B-346. | H | I | Br | =S | | H |
| B-347. | F | I | Br | =S | | H |
| B-348. | Cl | I | Br | =S | | H |
| B-349. | Br | I | Br | =S | | H |
| B-350. | I | I | Br | =S | | H |
| B-351. | CH$_3$ | I | Br | =S | | H |
| B-352. | CN | I | Br | =S | | H |
| B-353. | H | H | H | =O | | CH$_3$ |
| B-354. | F | H | H | =O | | CH$_3$ |
| B-355. | Cl | H | H | =O | | CH$_3$ |
| B-356. | Br | H | H | =O | | CH$_3$ |
| B-357. | I | H | H | =O | | CH$_3$ |
| B-358. | CH$_3$ | H | H | =O | | CH$_3$ |
| B-359. | CN | H | H | =O | | CH$_3$ |
| B-360. | H | F | H | =O | | CH$_3$ |
| B-361. | F | F | H | =O | | CH$_3$ |
| B-362. | Cl | F | H | =O | | CH$_3$ |
| B-363. | Br | F | H | =O | | CH$_3$ |
| B-364. | I | F | H | =O | | CH$_3$ |
| B-365. | CH$_3$ | F | H | =O | | CH$_3$ |
| B-366. | CN | F | H | =O | | CH$_3$ |
| B-367. | H | H | F | =O | | CH$_3$ |
| B-368. | F | H | F | =O | | CH$_3$ |
| B-369. | Cl | H | F | =O | | CH$_3$ |
| B-370. | Br | H | F | =O | | CH$_3$ |
| B-371. | I | H | F | =O | | CH$_3$ |
| B-372. | CH$_3$ | H | F | =O | | CH$_3$ |
| B-373. | CN | H | F | =O | | CH$_3$ |
| B-374. | H | F | F | =O | | CH$_3$ |
| B-375. | F | F | F | =O | | CH$_3$ |
| B-376. | Cl | F | F | =O | | CH$_3$ |
| B-377. | Br | F | F | =O | | CH$_3$ |
| B-378. | I | F | F | =O | | CH$_3$ |
| B-379. | CH$_3$ | F | F | =O | | CH$_3$ |
| B-380. | CN | F | F | =O | | CH$_3$ |
| B-381. | H | Cl | H | =O | | CH$_3$ |
| B-382. | Cl | Cl | H | =O | | CH$_3$ |
| B-383. | Cl | Cl | H | =O | | CH$_3$ |
| B-384. | Br | Cl | H | =O | | CH$_3$ |
| B-385. | I | Cl | H | =O | | CH$_3$ |
| B-386. | CH$_3$ | Cl | H | =O | | CH$_3$ |
| B-387. | CN | Cl | H | =O | | CH$_3$ |
| B-388. | H | H | Cl | =O | | CH$_3$ |
| B-389. | Cl | H | Cl | =O | | CH$_3$ |
| B-390. | Cl | H | Cl | =O | | CH$_3$ |
| B-391. | Br | H | Cl | =O | | CH$_3$ |
| B-392. | I | H | Cl | =O | | CH$_3$ |
| B-393. | CH$_3$ | H | Cl | =O | | CH$_3$ |
| B-394. | CN | H | Cl | =O | | CH$_3$ |
| B-395. | H | Cl | Cl | =O | | CH$_3$ |
| B-396. | Cl | Cl | Cl | =O | | CH$_3$ |
| B-397. | Cl | Cl | Cl | =O | | CH$_3$ |
| B-398. | Br | Cl | Cl | =O | | CH$_3$ |
| B-399. | I | Cl | Cl | =O | | CH$_3$ |
| B-400. | CH$_3$ | Cl | Cl | =O | | CH$_3$ |
| B-401. | CN | Cl | Cl | =O | | CH$_3$ |
| B-402. | H | Br | H | =O | | CH$_3$ |
| B-403. | F | Br | H | =O | | CH$_3$ |
| B-404. | Cl | Br | H | =O | | CH$_3$ |
| B-405. | Br | Br | H | =O | | CH$_3$ |
| B-406. | I | Br | H | =O | | CH$_3$ |
| B-407. | CH$_3$ | Br | H | =O | | CH$_3$ |
| B-408. | CN | Br | H | =O | | CH$_3$ |
| B-409. | H | H | Br | =O | | CH$_3$ |
| B-410. | F | H | Br | =O | | CH$_3$ |
| B-411. | Cl | H | Br | =O | | CH$_3$ |
| B-412. | Br | H | Br | =O | | CH$_3$ |
| B-413. | I | H | Br | =O | | CH$_3$ |
| B-414. | CH$_3$ | H | Br | =O | | CH$_3$ |
| B-415. | CN | H | Br | =O | | CH$_3$ |
| B-416. | H | Br | Br | =O | | CH$_3$ |
| B-417. | F | Br | Br | =O | | CH$_3$ |
| B-418. | Cl | Br | Br | =O | | CH$_3$ |
| B-419. | Br | Br | Br | =O | | CH$_3$ |
| B-420. | I | Br | Br | =O | | CH$_3$ |
| B-421. | CH$_3$ | Br | Br | =O | | CH$_3$ |
| B-422. | CN | Br | Br | =O | | CH$_3$ |
| B-423. | H | I | H | =O | | CH$_3$ |
| B-424. | F | I | H | =O | | CH$_3$ |
| B-425. | Cl | I | H | =O | | CH$_3$ |
| B-426. | Br | I | H | =O | | CH$_3$ |
| B-427. | I | I | H | =O | | CH$_3$ |
| B-428. | CH$_3$ | I | H | =O | | CH$_3$ |
| B-429. | CN | I | H | =O | | CH$_3$ |
| B-430. | H | H | I | =O | | CH$_3$ |
| B-431. | F | H | I | =O | | CH$_3$ |
| B-432. | Cl | H | I | =O | | CH$_3$ |
| B-433. | Br | H | I | =O | | CH$_3$ |
| B-434. | I | H | I | =O | | CH$_3$ |
| B-435. | CH$_3$ | H | I | =O | | CH$_3$ |
| B-436. | CN | H | I | =O | | CH$_3$ |
| B-437. | H | I | I | =O | | CH$_3$ |
| B-438. | F | I | I | =O | | CH$_3$ |
| B-439. | Cl | I | I | =O | | CH$_3$ |
| B-440. | Br | I | I | =O | | CH$_3$ |
| B-441. | I | I | I | =O | | CH$_3$ |
| B-442. | CH$_3$ | I | I | =O | | CH$_3$ |
| B-443. | CN | I | I | =O | | CH$_3$ |

TABLE B-continued

| no. | $R^{b1}$ | $R^{b3}$ | $R^{b2}$ | $R^{A1}$ | $R^{A2}$ | $R^c$ |
|---|---|---|---|---|---|---|
| B-444. | H | F | Cl | =O | | $CH_3$ |
| B-445. | D | F | Cl | =O | | $CH_3$ |
| B-446. | F | F | Cl | =O | | $CH_3$ |
| B-447. | Cl | F | Cl | =O | | $CH_3$ |
| B-448. | Br | F | Cl | =O | | $CH_3$ |
| B-449. | I | F | Cl | =O | | $CH_3$ |
| B-450. | $CH_3$ | F | Cl | =O | | $CH_3$ |
| B-451. | CN | F | Cl | =O | | $CH_3$ |
| B-452. | H | F | Br | =O | | $CH_3$ |
| B-453. | F | F | Br | =O | | $CH_3$ |
| B-454. | Cl | F | Br | =O | | $CH_3$ |
| B-455. | Br | F | Br | =O | | $CH_3$ |
| B-456. | I | F | Br | =O | | $CH_3$ |
| B-457. | $CH_3$ | F | Br | =O | | $CH_3$ |
| B-458. | CN | F | Br | =O | | $CH_3$ |
| B-459. | H | F | I | =O | | $CH_3$ |
| B-460. | F | F | I | =O | | $CH_3$ |
| B-461. | Cl | F | I | =O | | $CH_3$ |
| B-462. | Br | F | I | =O | | $CH_3$ |
| B-463. | I | F | I | =O | | $CH_3$ |
| B-464. | $CH_3$ | F | I | =O | | $CH_3$ |
| B-465. | CN | F | I | =O | | $CH_3$ |
| B-466. | H | Cl | F | =O | | $CH_3$ |
| B-467. | F | Cl | F | =O | | $CH_3$ |
| B-468. | Cl | Cl | F | =O | | $CH_3$ |
| B-469. | Br | Cl | F | =O | | $CH_3$ |
| B-470. | I | Cl | F | =O | | $CH_3$ |
| B-471. | $CH_3$ | Cl | F | =O | | $CH_3$ |
| B-472. | CN | Cl | F | =O | | $CH_3$ |
| B-473. | H | Cl | Br | =O | | $CH_3$ |
| B-474. | F | Cl | Br | =O | | $CH_3$ |
| B-475. | Cl | Cl | Br | =O | | $CH_3$ |
| B-476. | Br | Cl | Br | =O | | $CH_3$ |
| B-477. | I | Cl | Br | =O | | $CH_3$ |
| B-478. | $CH_3$ | Cl | Br | =O | | $CH_3$ |
| B-479. | CN | Cl | Br | =O | | $CH_3$ |
| B-480. | H | Cl | I | =O | | $CH_3$ |
| B-481. | F | Cl | I | =O | | $CH_3$ |
| B-482. | Cl | Cl | I | =O | | $CH_3$ |
| B-483. | Br | Cl | I | =O | | $CH_3$ |
| B-484. | I | Cl | I | =O | | $CH_3$ |
| B-485. | $CH_3$ | Cl | I | =O | | $CH_3$ |
| B-486. | CN | Cl | I | =O | | $CH_3$ |
| B-487. | H | Br | F | =O | | $CH_3$ |
| B-488. | F | Br | F | =O | | $CH_3$ |
| B-489. | Cl | Br | F | =O | | $CH_3$ |
| B-490. | Br | Br | F | =O | | $CH_3$ |
| B-491. | I | Br | F | =O | | $CH_3$ |
| B-492. | $CH_3$ | Br | F | =O | | $CH_3$ |
| B-493. | CN | Br | F | =O | | $CH_3$ |
| B-494. | H | Br | Cl | =O | | $CH_3$ |
| B-495. | F | Br | Cl | =O | | $CH_3$ |
| B-496. | Cl | Br | Cl | =O | | $CH_3$ |
| B-497. | Br | Br | Cl | =O | | $CH_3$ |
| B-498. | I | Br | Cl | =O | | $CH_3$ |
| B-499. | $CH_3$ | Br | Cl | =O | | $CH_3$ |
| B-500. | CN | Br | Cl | =O | | $CH_3$ |
| B-501. | H | Br | I | =O | | $CH_3$ |
| B-502. | F | Br | I | =O | | $CH_3$ |
| B-503. | Cl | Br | I | =O | | $CH_3$ |
| B-504. | Br | Br | I | =O | | $CH_3$ |
| B-505. | I | Br | I | =O | | $CH_3$ |
| B-506. | $CH_3$ | Br | I | =O | | $CH_3$ |
| B-507. | CN | Br | I | =O | | $CH_3$ |
| B-508. | H | I | F | =O | | $CH_3$ |
| B-509. | F | I | F | =O | | $CH_3$ |
| B-510. | Cl | I | F | =O | | $CH_3$ |
| B-511. | Br | I | F | =O | | $CH_3$ |
| B-512. | I | I | F | =O | | $CH_3$ |
| B-513. | $CH_3$ | I | F | =O | | $CH_3$ |
| B-514. | CN | I | F | =O | | $CH_3$ |
| B-515. | H | I | Cl | =O | | $CH_3$ |
| B-516. | F | I | Cl | =O | | $CH_3$ |
| B-517. | Cl | I | Cl | =O | | $CH_3$ |
| B-518. | Br | I | Cl | =O | | $CH_3$ |
| B-519. | I | I | Cl | =O | | $CH_3$ |
| B-520. | $CH_3$ | I | Cl | =O | | $CH_3$ |
| B-521. | CN | I | Cl | =O | | $CH_3$ |
| B-522. | H | I | Br | =O | | $CH_3$ |
| B-523. | F | I | Br | =O | | $CH_3$ |
| B-524. | Cl | I | Br | =O | | $CH_3$ |
| B-525. | Br | I | Br | =O | | $CH_3$ |
| B-526. | I | I | Br | =O | | $CH_3$ |
| B-527. | $CH_3$ | I | Br | =O | | $CH_3$ |
| B-528. | CN | I | Br | =O | | $CH_3$ |
| B-529. | H | H | H | =S | | $CH_3$ |
| B-530. | F | H | H | =S | | $CH_3$ |
| B-531. | Cl | H | H | =S | | $CH_3$ |
| B-532. | Br | H | H | =S | | $CH_3$ |
| B-533. | I | H | H | =S | | $CH_3$ |
| B-534. | $CH_3$ | H | H | =S | | $CH_3$ |
| B-535. | CN | H | H | =S | | $CH_3$ |
| B-536. | H | F | H | =S | | $CH_3$ |
| B-537. | F | F | H | =S | | $CH_3$ |
| B-538. | Cl | F | H | =S | | $CH_3$ |
| B-539. | Br | F | H | =S | | $CH_3$ |
| B-540. | I | F | H | =S | | $CH_3$ |
| B-541. | $CH_3$ | F | H | =S | | $CH_3$ |
| B-542. | CN | F | H | =S | | $CH_3$ |
| B-543. | H | H | F | =S | | $CH_3$ |
| B-544. | F | H | F | =S | | $CH_3$ |
| B-545. | Cl | H | F | =S | | $CH_3$ |
| B-546. | Br | H | F | =S | | $CH_3$ |
| B-547. | I | H | F | =S | | $CH_3$ |
| B-548. | $CH_3$ | H | F | =S | | $CH_3$ |
| B-549. | CN | H | F | =S | | $CH_3$ |
| B-550. | H | F | F | =S | | $CH_3$ |
| B-551. | F | F | F | =S | | $CH_3$ |
| B-552. | Cl | F | F | =S | | $CH_3$ |
| B-553. | Br | F | F | =S | | $CH_3$ |
| B-554. | I | F | F | =S | | $CH_3$ |
| B-555. | $CH_3$ | F | F | =S | | $CH_3$ |
| B-556. | CN | F | F | =S | | $CH_3$ |
| B-557. | H | Cl | H | =S | | $CH_3$ |
| B-558. | Cl | Cl | H | =S | | $CH_3$ |
| B-559. | Cl | Cl | H | =S | | $CH_3$ |
| B-560. | Br | Cl | H | =S | | $CH_3$ |
| B-561. | I | Cl | H | =S | | $CH_3$ |
| B-562. | $CH_3$ | Cl | H | =S | | $CH_3$ |
| B-563. | CN | Cl | H | =S | | $CH_3$ |
| B-564. | H | H | Cl | =S | | $CH_3$ |
| B-565. | Cl | H | Cl | =S | | $CH_3$ |
| B-566. | Cl | H | Cl | =S | | $CH_3$ |
| B-567. | Br | H | Cl | =S | | $CH_3$ |
| B-568. | I | H | Cl | =S | | $CH_3$ |
| B-569. | $CH_3$ | H | Cl | =S | | $CH_3$ |
| B-570. | CN | H | Cl | =S | | $CH_3$ |
| B-571. | H | Cl | Cl | =S | | $CH_3$ |
| B-572. | Cl | Cl | Cl | =S | | $CH_3$ |
| B-573. | Cl | Cl | Cl | =S | | $CH_3$ |
| B-574. | Br | Cl | Cl | =S | | $CH_3$ |
| B-575. | I | Cl | Cl | =S | | $CH_3$ |
| B-576. | $CH_3$ | Cl | Cl | =S | | $CH_3$ |
| B-577. | CN | Cl | Cl | =S | | $CH_3$ |
| B-578. | H | Br | H | =S | | $CH_3$ |
| B-579. | F | Br | H | =S | | $CH_3$ |
| B-580. | Cl | Br | H | =S | | $CH_3$ |
| B-581. | Br | Br | H | =S | | $CH_3$ |
| B-582. | I | Br | H | =S | | $CH_3$ |
| B-583. | $CH_3$ | Br | H | =S | | $CH_3$ |
| B-584. | CN | Br | H | =S | | $CH_3$ |
| B-585. | H | H | Br | =S | | $CH_3$ |
| B-586. | F | H | Br | =S | | $CH_3$ |
| B-587. | Cl | H | Br | =S | | $CH_3$ |
| B-588. | Br | H | Br | =S | | $CH_3$ |
| B-589. | I | H | Br | =S | | $CH_3$ |
| B-590. | $CH_3$ | H | Br | =S | | $CH_3$ |
| B-591. | CN | H | Br | =S | | $CH_3$ |
| B-592. | H | Br | Br | =S | | $CH_3$ |
| B-593. | F | Br | Br | =S | | $CH_3$ |
| B-594. | Cl | Br | Br | =S | | $CH_3$ |
| B-595. | Br | Br | Br | =S | | $CH_3$ |
| B-596. | I | Br | Br | =S | | $CH_3$ |
| B-597. | $CH_3$ | Br | Br | =S | | $CH_3$ |
| B-598. | CN | Br | Br | =S | | $CH_3$ |
| B-599. | H | I | H | =S | | $CH_3$ |

TABLE B-continued

| no. | $R^{b1}$ | $R^{b3}$ | $R^{b2}$ | $R^{A1}$ | $R^{A2}$ | $R^c$ |
|---|---|---|---|---|---|---|
| B-600. | F | I | H | =S | | $CH_3$ |
| B-601. | Cl | I | H | =S | | $CH_3$ |
| B-602. | Br | I | H | =S | | $CH_3$ |
| B-603. | I | I | H | =S | | $CH_3$ |
| B-604. | $CH_3$ | I | H | =S | | $CH_3$ |
| B-605. | CN | I | H | =S | | $CH_3$ |
| B-606. | H | H | I | =S | | $CH_3$ |
| B-607. | F | H | I | =S | | $CH_3$ |
| B-608. | Cl | H | I | =S | | $CH_3$ |
| B-609. | Br | H | I | =S | | $CH_3$ |
| B-610. | I | H | I | =S | | $CH_3$ |
| B-611. | $CH_3$ | H | I | =S | | $CH_3$ |
| B-612. | CN | H | I | =S | | $CH_3$ |
| B-613. | H | I | I | =S | | $CH_3$ |
| B-614. | F | I | I | =S | | $CH_3$ |
| B-615. | Cl | I | I | =S | | $CH_3$ |
| B-616. | Br | I | I | =S | | $CH_3$ |
| B-617. | I | I | I | =S | | $CH_3$ |
| B-618. | $CH_3$ | I | I | =S | | $CH_3$ |
| B-619. | CN | I | I | =S | | $CH_3$ |
| B-620. | H | F | Cl | =S | | $CH_3$ |
| B-621. | D | F | Cl | =S | | $CH_3$ |
| B-622. | F | F | Cl | =S | | $CH_3$ |
| B-623. | Cl | F | Cl | =S | | $CH_3$ |
| B-624. | Br | F | Cl | =S | | $CH_3$ |
| B-625. | I | F | Cl | =S | | $CH_3$ |
| B-626. | $CH_3$ | F | Cl | =S | | $CH_3$ |
| B-627. | CN | F | Cl | =S | | $CH_3$ |
| B-628. | H | F | Br | =S | | $CH_3$ |
| B-629. | F | F | Br | =S | | $CH_3$ |
| B-630. | Cl | F | Br | =S | | $CH_3$ |
| B-631. | Br | F | Br | =S | | $CH_3$ |
| B-632. | I | F | Br | =S | | $CH_3$ |
| B-633. | $CH_3$ | F | Br | =S | | $CH_3$ |
| B-634. | CN | F | Br | =S | | $CH_3$ |
| B-635. | H | F | I | =S | | $CH_3$ |
| B-636. | F | F | I | =S | | $CH_3$ |
| B-637. | Cl | F | I | =S | | $CH_3$ |
| B-638. | Br | F | I | =S | | $CH_3$ |
| B-639. | I | F | I | =S | | $CH_3$ |
| B-640. | $CH_3$ | F | I | =S | | $CH_3$ |
| B-641. | CN | F | I | =S | | $CH_3$ |
| B-642. | H | Cl | F | =S | | $CH_3$ |
| B-643. | F | Cl | F | =S | | $CH_3$ |
| B-644. | Cl | Cl | F | =S | | $CH_3$ |
| B-645. | Br | Cl | F | =S | | $CH_3$ |
| B-646. | I | Cl | F | =S | | $CH_3$ |
| B-647. | $CH_3$ | Cl | F | =S | | $CH_3$ |
| B-648. | CN | Cl | F | =S | | $CH_3$ |
| B-649. | H | Cl | Br | =S | | $CH_3$ |
| B-650. | F | Cl | Br | =S | | $CH_3$ |
| B-651. | Cl | Cl | Br | =S | | $CH_3$ |
| B-652. | Br | Cl | Br | =S | | $CH_3$ |
| B-653. | I | Cl | Br | =S | | $CH_3$ |
| B-654. | $CH_3$ | Cl | Br | =S | | $CH_3$ |
| B-655. | CN | Cl | Br | =S | | $CH_3$ |
| B-656. | H | Cl | I | =S | | $CH_3$ |
| B-657. | F | Cl | I | =S | | $CH_3$ |
| B-658. | Cl | Cl | I | =S | | $CH_3$ |
| B-659. | Br | Cl | I | =S | | $CH_3$ |
| B-660. | I | Cl | I | =S | | $CH_3$ |
| B-661. | $CH_3$ | Cl | I | =S | | $CH_3$ |
| B-662. | CN | Cl | I | =S | | $CH_3$ |
| B-663. | H | Br | F | =S | | $CH_3$ |
| B-664. | F | Br | F | =S | | $CH_3$ |
| B-665. | Cl | Br | F | =S | | $CH_3$ |
| B-666. | Br | Br | F | =S | | $CH_3$ |
| B-667. | I | Br | F | =S | | $CH_3$ |
| B-668. | $CH_3$ | Br | F | =S | | $CH_3$ |
| B-669. | CN | Br | F | =S | | $CH_3$ |
| B-670. | H | Br | Cl | =S | | $CH_3$ |
| B-671. | F | Br | Cl | =S | | $CH_3$ |
| B-672. | Cl | Br | Cl | =S | | $CH_3$ |
| B-673. | Br | Br | Cl | =S | | $CH_3$ |
| B-674. | I | Br | Cl | =S | | $CH_3$ |
| B-675. | $CH_3$ | Br | Cl | =S | | $CH_3$ |
| B-676. | CN | Br | Cl | =S | | $CH_3$ |
| B-677. | H | Br | I | =S | | $CH_3$ |
| B-678. | F | Br | I | =S | | $CH_3$ |
| B-679. | Cl | Br | I | =S | | $CH_3$ |
| B-680. | Br | Br | I | =S | | $CH_3$ |
| B-681. | I | Br | I | =S | | $CH_3$ |
| B-682. | $CH_3$ | Br | I | =S | | $CH_3$ |
| B-683. | CN | Br | I | =S | | $CH_3$ |
| B-684. | H | I | F | =S | | $CH_3$ |
| B-685. | F | I | F | =S | | $CH_3$ |
| B-686. | Cl | I | F | =S | | $CH_3$ |
| B-687. | Br | I | F | =S | | $CH_3$ |
| B-688. | I | I | F | =S | | $CH_3$ |
| B-689. | $CH_3$ | I | F | =S | | $CH_3$ |
| B-690. | CN | I | F | =S | | $CH_3$ |
| B-691. | H | I | Cl | =S | | $CH_3$ |
| B-692. | F | I | Cl | =S | | $CH_3$ |
| B-693. | Cl | I | Cl | =S | | $CH_3$ |
| B-694. | Br | I | Cl | =S | | $CH_3$ |
| B-695. | I | I | Cl | =S | | $CH_3$ |
| B-696. | $CH_3$ | I | Cl | =S | | $CH_3$ |
| B-697. | CN | I | Cl | =S | | $CH_3$ |
| B-698. | H | I | Br | =S | | $CH_3$ |
| B-699. | F | I | Br | =S | | $CH_3$ |
| B-700. | Cl | I | Br | =S | | $CH_3$ |
| B-701. | Br | I | Br | =S | | $CH_3$ |
| B-702. | I | I | Br | =S | | $CH_3$ |
| B-703. | $CH_3$ | I | Br | =S | | $CH_3$ |
| B-704. | CN | I | Br | =S | | $CH_3$ |

Particularly preferred is given to diaminotriazine compounds of formula (I.c), which corresponds to formula (I), wherein $R^1$ is hydrogen, $R^2$ is hydrogen and $R^{b1}$, $R^{b2}$, $R^{b3}$ are given in table C, and wherein X is as defined above and in particular X is selected from the group consisting of $CF(CH_3)_2$, $CFCH_3CH_2CH_3$, $CHFCH_3$, $CHFCH_2CH_3$, $CF(CH_2CH_3)_2$, $CF_2CH_3$, t-butyl, i-butyl, s-butyl, 1-chloro-cyclobutyl, 2,2-dimethylpropyl, i-propyl, 1-fluoropropyl, cyclobutyl, cyclopentyl, cyclohexyl, 1-cyclopropylethyl, 1-methylcyclobutyl, 1-methylcyclopentyl, $C(CH_3)_2OCH_3$, 1-methylcyclohexyl, 1-methoxyethyl, 1-methoxy-cyclopentyl, 1-methoxy-cyclobutyl, 1-methoxyl-cyclohexyl, 1-fluor-cyclopentyl, 1-fluor-cyclohexyl, 1-chlor-cyclopentyl, 1-chlor-cyclohexyl, 1-chlor-cyclobutyl, 2-methylpyrrolidin-1-yl, 2,2,2-trifluoroethoxy, azetidine, pyrrolidin-1-yl, piperidyl, methoxy(methyl)amino, 2-tetrahydrofuranyl, 2,4,6-trifluoro-phenyl, 2,6-difluoro-phenyl, 2-fluoro-phenyl or methoxy.

Examples of these compounds are those given in table C-1 to C-41.

Particular preference is given to diaminotriazine compounds of formula (I.c), which corresponds to diaminotriazines of formula (I) wherein $R^1$ and $R^2$ is hydrogen $R^{b1}$, $R^{b2}$, $R^{b3}$ are defined in table C.

Table C-1: Compounds of formula (I.c), where X is $CFCH_3CH_2CH_3$ and $R^{b1}$, $R^2$, $R^{b3}$, are defined the rows of table C.

Table C-2: Compounds of formula (I.c), where X is $CF(CH_3)_2$ and $R^{b1}$, $R^2$, $R^{b3}$ are defined the rows of table C.

Table C-3: Compounds of formula (I.c), where X is $CHFCH_3$ and $R^{b1}$, $R^{b2}$, $R^{b3}$ are defined the rows of table C.

Table C-4: Compounds of formula (I.c), where X is $CHFCH_2CH_3$ and $R^{b1}$, $R^{b2}$, $R^{b3}$ are defined the rows of table C.

Table C-5: Compounds of formula (I.c), where X is $CF(CH_2CH_3)_2$ and $R^{b1}$, $R^{b2}$, $R^{b3}$ are defined the rows of table C.

Table C-6: Compounds of formula (I.c), where X is $CF_2CH_3$ and $R^{b1}$, $R^{b2}$, $R^{b3}$ are defined the rows of table C.

Table C-7: Compounds of formula (I.c), where X is t-butyl and $R^{b1}$, $R^{b2}$, $R^{b3}$ are defined the rows of table C.

Table C-8: Compounds of formula (I.c), where X is i-butyl and $R^{b1}$, $R^{b2}$, $R^{b3}$ are defined the rows of table C.

Table C-9: Compounds of formula (I.c), where X is 2,2-dimethylpropyl and $R^{b1}$, $R^{b2}$, $R^{b3}$ are defined the rows of table C.

Table C-10: Compounds of formula (I.c), where X is i-propyl and $R^{b1}$, $R^{b2}$, $R^{b3}$ are defined the rows of table C.

Table C-11: Compounds of formula (I.c), where X is cyclobutyl and $R^{b1}$, $R^{b2}$, $R^{b3}$ are defined the rows of table C.

Table C-12: Compounds of formula (I.c), where X is cyclopentyl and $R^{b1}$, $R^{b2}$, $R^{b3}$ are defined the rows of table C.

Table C-13: Compounds of formula (I.c), where X is cyclohexyl and $R^{b1}$, $R^{b2}$, $R^{b3}$ are defined the rows of table C.

Table C-14: Compounds of formula (I.c), where X is 1-cyclopropylethyl and $R^{b1}$, $R^{b2}$, $R^{b3}$ are defined the rows of table C.

Table C-15: Compounds of formula (I.c), where X is 1-methylcyclobutyl and $R^{b1}$, $R^{b2}$, $R^{b3}$ are defined the rows of table C.

Table C-16: Compounds of formula (I.c), where X is 1-methylcyclopentyl and $R^{b1}$, $R^{b2}$, $R^{b3}$ are defined the rows of table C.

Table C-17: Compounds of formula (I.c), where X is $C(CH_3)_2OCH_3$ and $R^{b1}$, $R^{b2}$, $R^{b3}$ are defined the rows of table C.

Table C-18: Compounds of formula (I.c), where X is 1-methylcyclohexyl and $R^{b1}$, $R^{b2}$, $R^{b3}$ are defined the rows of table C.

Table C-19: Compounds of formula (I.c), where X is 1-methoxyethyl and $R^{b1}$, $R^{b2}$, $R^{b3}$, are defined the rows of table C.

Table C-20: Compounds of formula (I.c), where X is 1-methoxy-cyclopentyl and $R^{b1}$, $R^{b2}$, $R^{b3}$ are defined the rows of table C.

Table C-21: Compounds of formula (I.c), where X is 1-methoxy-cyclobutyl and $R^{b1}$, $R^{b2}$, $R^{b3}$ are defined the rows of table C.

Table C-22: Compounds of formula (I.c), where X is 1-methoxyl-cyclohexyl and $R^{b1}$, $R^{b2}$, $R^{b3}$ are defined the rows of table C.

Table C-23: Compounds of formula (I.c), where X is 1-fluor-cyclopentyl and $R^{b1}$, $R^{b2}$, $R^{b3}$ are defined the rows of table C.

Table C-24: Compounds of formula (I.c), where X is 1-fluor-cyclohexyl and $R^{b1}$, $R^{b2}$, $R^{b3}$ are defined the rows of table C.

Table C-25: Compounds of formula (I.c), where X is 1-chlor-cyclopentyl and $R^{b1}$, $R^{b2}$, $R^{b3}$ are defined the rows of table C.

Table C-26: Compounds of formula (I.c), where X is 1-chlor-cyclohexyl and $R^{b1}$, $R^{b2}$, $R^{b3}$ are defined the rows of table C.

Table C-27: Compounds of formula (I.c), where X is 1-chlor-cyclobutyl and $R^{b1}$, $R^{b2}$, $R^{b3}$ are defined the rows of table C.

Table C-28: Compounds of formula (I.c), where X is 2-methylpyrrolidin-1-yl and $R^{b1}$, $R^{b2}$, $R^{b3}$ are defined the rows of table C.

Table C-29: Compounds of formula (I.c), where X is 2,2,2-trifluoroethoxy and $R^{b1}$, $R^{b2}$, $R^{b3}$ are defined the rows of table C.

Table C-30: Compounds of formula (I.c), where X is azitidine and $R^{b1}$, $R^{b2}$, $R^{b3}$ are defined the rows of table C.

Table C-31: Compounds of formula (I.c), where X is pyrrolidin-1-yl and $R^{b1}$, $R^{b2}$, $R^{b3}$, are defined the rows of table C.

Table C-32: Compounds of formula (I.c), where X is 2-tetrahydrofuranyl and $R^{b1}$, $R^{b2}$, $R^{b3}$ are defined the rows of table C.

Table C-33: Compounds of formula (I.c), where X is 2,4,6-tri-fluoro-phenyl and $R^{b1}$, $R^{b2}$, $R^{b3}$ are defined the rows of table C.

Table C-34: Compounds of formula (I.c), where X is 2,6-difluoro-phenyl and $R^{b1}$, $R^{b2}$, $R^{b3}$ are defined the rows of table C.

Table C-35: Compounds of formula (I.c), where X is 2-fluoro-phenyl and $R^{b1}$, $R^{b2}$, $R^{b3}$ are defined the rows of table C.

Table C-36: Compounds of formula (I.c), where X is 1-chlor-cyclobutyl and $R^{b1}$, $R^{b2}$, $R^{b3}$ are defined the rows of table C.

Table C-37: Compounds of formula (I.c), where X is s-butyl and $R^{b1}$, $R^{b2}$, $R^{b3}$ are defined the rows of table C.

Table C-38: Compounds of formula (I.c), where X is piperidyl and $R^{b1}$, $R^{b2}$, $R^{b3}$ are defined the rows of table C.

Table C-39: Compounds of formula (I.c), where X is methoxy(methyl)amino and $R^{b1}$, $R^{b2}$, $R^{b3}$ are defined the rows of table C.

Table C-40: Compounds of formula (I.c), where X is 1-fluoro-propyl and $R^{b1}$, $R^{b2}$, $R^{b3}$ are defined the rows of table C.

Table C-41: Compounds of formula (I.c), where X is methoxy and $R^{b1}$, $R^{b2}$, $R^{b3}$ are defined the rows of table C.

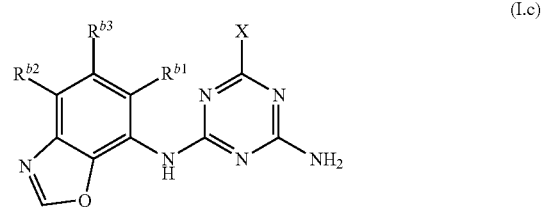

(I.c)

Particularly preferred is given to diaminotriazine compounds of formula (I.d), which corresponds to formula (I), wherein $R^1$ is hydrogen, $R^2$ is hydrogen and $R^{b1}$, $R^{b2}$, $R^{b3}$ are given in table C, and wherein X is as defined above and in particular X is selected from the group consisting of $CF(CH_3)_2$, $CFCH_3CH_2CH_3$, $CHFCH_3$, $CHFCH_2CH_3$, $CF(CH_2CH_3)_2$, $CF_2CH_3$, t-butyl, i-butyl, s-butyl, 1-chloro-cyclobutyl, 2,2-dimethylpropyl, i-propyl, 1-fluoropropyl, cyclobutyl, cyclopentyl, cyclohexyl, 1-cyclopropylethyl, 1-methylcyclobutyl, 1-methylcyclopentyl, $C(CH_3)_2OCH_3$, 1-methylcyclohexyl, 1-methoxyethyl, 1-methoxy-cyclopentyl, 1-methoxy-cyclobutyl, 1-methoxyl-cyclohexyl, 1-fluor-cyclopentyl, 1-fluor-cyclohexyl, 1-chlor-cyclopentyl, 1-chlor-cyclohexyl, 1-chlor-cyclobutyl, 2-methylpyrrolidin-1-yl, 2,2,2-trifluoroethoxy, azetidine, pyrrolidin-1-yl, piperidyl, methoxy(methyl)amino, 2-tetrahydrofuranyl, 2,4,6-tri-fluoro-phenyl, 2,6-difluoro-phenyl, 2-fluoro-phenyl or methoxy.

Examples of these compounds are those given in table D-1 to D-41.

Particular preference is given to diaminotriazine compounds of formula (I.d), which corresponds to diaminotriazines of formula (I) wherein $R^1$ and $R^2$ is hydrogen $R^{b1}$, $R^{b2}$, $R^{b3}$ are defined in table C.

Table D-1: Compounds of formula (I.d), where X is CFCH₃CH₂CH₃ and $R^{b1}$, $R^{b2}$, $R^{b3}$, are defined the rows of table C.
Table D-2: Compounds of formula (I.d), where X is CF(CH₃)₂ and $R^{b1}$, $R^{b2}$, $R^{b3}$ are defined the rows of table C.
Table D-3: Compounds of formula (I.d), where X is CHFCH₃ and $R^{b1}$, $R^{b2}$, $R^{b3}$ are defined the rows of table C.
Table D-4: Compounds of formula (I.d), where X is CHFCH₂CH₃ and $R^{b1}$, $R^{b2}$, $R^{b3}$, are defined the rows of table C.
Table D-5: Compounds of formula (I.d), where X is CF(CH₂CH₃)₂ and $R^{b1}$, $R^{b2}$, $R^{b3}$ are defined the rows of table C.
Table D-6: Compounds of formula (I.d), where X is CF₂CH₃ and $R^{b1}$, $R^{b2}$, $R^{b3}$ are defined the rows of table C.
Table D-7: Compounds of formula (I.d), where X is t-butyl and $R^{b1}$, $R^{b2}$, $R^{b3}$ are defined the rows of table C.
Table D-8: Compounds of formula (I.d), where X is i-butyl and $R^{b1}$, $R^{b2}$, $R^{b3}$ are defined the rows of table C.
Table D-9: Compounds of formula (I.d), where X is 2,2-dimethylpropyl and $R^{b1}$, $R^{b2}$, $R^{b3}$ are defined the rows of table C.
Table D-10: Compounds of formula (I.d), where X is i-propyl and $R^{b1}$, $R^{b2}$, $R^{b3}$ are defined the rows of table C.
Table D-11: Compounds of formula (I.d), where X is cyclobutyl and $R^{b1}$, $R^{b2}$, $R^{b3}$ are defined the rows of table C.
Table D-12: Compounds of formula (I.d), where X is cyclopentyl and $R^{b1}$, $R^{b2}$, $R^{b3}$ are defined the rows of table C.
Table D-13: Compounds of formula (I.d), where X is cyclohexyl and $R^{b1}$, $R^{b2}$, $R^{b3}$ are defined the rows of table C.
Table D-14: Compounds of formula (I.d), where X is 1-cyclopropylethyl and $R^{b1}$, $R^{b2}$, $R^{b3}$ are defined the rows of table C.
Table D-15: Compounds of formula (I.d), where X is 1-methylcyclobutyl and $R^{b1}$, $R^{b2}$, $R^{b3}$ are defined the rows of table C.
Table D-16: Compounds of formula (I.d), where X is 1-methylcyclopentyl and $R^{b1}$, $R^{b2}$, $R^{b3}$ are defined the rows of table C.
Table D-17: Compounds of formula (I.d), where X is C(CH₃)₂OCH₃ and $R^{b1}$, $R^{b2}$, $R^{b3}$, $R^{A1}$, $R^{A2}$, $R^c$ are defined the rows of table C.
Table D-18: Compounds of formula (I.d), where X is 1-methylcyclohexyl and $R^{b1}$, $R^{b2}$, $R^{b3}$ are defined the rows of table C.
Table D-19: Compounds of formula (I.d), where X is 1-methoxyethyl and $R^{b1}$, $R^{b2}$, $R^{b3}$, are defined the rows of table C.
Table D-20: Compounds of formula (I.d), where X is 1-methoxy-cyclopentyl and $R^{b1}$, $R^{b2}$, $R^{b3}$ are defined the rows of table C.
Table D-21: Compounds of formula (I.d), where X is 1-methoxy-cyclobutyl and $R^{b1}$, $R^{b2}$, $R^{b3}$ are defined the rows of table C.
Table D-22: Compounds of formula (I.d), where X is 1-methoxyl-cyclohexyl and $R^{b1}$, $R^{b2}$, $R^{b3}$ are defined the rows of table C.
Table D-23: Compounds of formula (I.d), where X is 1-fluor-cyclopentyl and $R^{b1}$, $R^{b2}$, $R^{b3}$ are defined the rows of table C.
Table D-24: Compounds of formula (I.d), where X is 1-fluor-cyclohexyl and $R^{b1}$, $R^{b2}$, $R^{b3}$ are defined the rows of table C.
Table D-25: Compounds of formula (I.d), where X is 1-chlor-cyclopentyl and $R^{b1}$, $R^{b2}$, $R^{b3}$ are defined the rows of table C.
Table D-26: Compounds of formula (I.d), where X is 1-chlor-cyclohexyl and $R^{b1}$, $R^{b2}$, $R^{b3}$, $R^{A1}$, $R^{A2}$, $R^c$ are defined the rows of table C.
Table D-27: Compounds of formula (I.d), where X is 1-chlor-cyclobutyl and $R^{b1}$, $R^{b2}$, $R^{b3}$ are defined the rows of table C.
Table D-28: Compounds of formula (I.d), where X is 2-methylpyrrolidin-1-yl and $R^{b1}$, $R^{b2}$, $R^{b3}$ are defined the rows of table C.
Table D-29: Compounds of formula (I.d), where X is 2,2,2-trifluoroethoxy and $R^{b1}$, $R^{b2}$, $R^{b3}$ are defined the rows of table C.
Table D-30: Compounds of formula (I.d), where X is azitidine and $R^{b1}$, $R^{b2}$, $R^{b3}$ are defined the rows of table C.
Table D-31: Compounds of formula (I.d), where X is pyrrolidin-1-yl and $R^{b1}$, $R^{b2}$, $R^{b3}$, are defined the rows of table C.
Table D-32: Compounds of formula (I.d), where X is 2-tetrahydrofuranyl and $R^{b1}$, $R^{b2}$, $R^{b3}$ are defined the rows of table C.
Table D-33: Compounds of formula (I.d), where X is 2,4,6-tri-fluoro-phenyl and $R^{b1}$, $R^{b2}$, $R^{b3}$ are defined the rows of table C.
Table D-34: Compounds of formula (I.d), where X is 2,6-difluoro-phenyl and $R^{b1}$, $R^{b2}$, $R^{b3}$ are defined the rows of table C.
Table D-35: Compounds of formula (I.d), where X is 2-fluoro-phenyl and $R^{b1}$, $R^{b2}$, $R^{b3}$ are defined the rows of table C.
Table D-36: Compounds of formula (I.d), where X is 1-chlor-cyclobutyl and $R^{b1}$, $R^{b2}$, $R^{b3}$ are defined the rows of table C.
Table D-37: Compounds of formula (I.d), where X is s-butyl and $R^{b1}$, $R^{b2}$, $R^{b3}$ defined the rows of table C.
Table D-38: Compounds of formula (I.d), where X is piperidyl and $R^{b1}$, $R^{b2}$, $R^{b3}$ are defined the rows of table C.
Table D-39: Compounds of formula (I.d), where X is methoxy(methyl)amino and $R^{b1}$, $R^{b2}$, $R^{b3}$ are defined the rows of table C.
Table D-40: Compounds of formula (I.d), where X is 1-fluoro-propyl and $R^{b1}$, $R^{b2}$, $R^{b3}$ are defined the rows of table C.
Table C-41: Compounds of formula (I.d), where X is methoxy and $R^{b1}$, $R^{b2}$, $R^{b3}$ are defined the rows of table C.

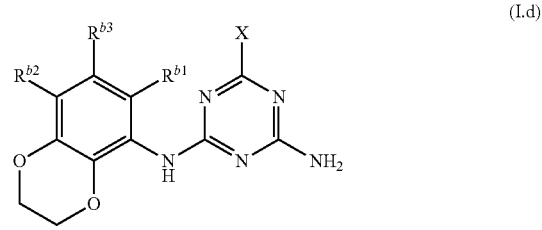

(I.d)

Particularly preferred is given to diaminotriazine compounds of formula (I.e), which corresponds to formula (I), wherein $R^1$ is hydrogen, $R^2$ is hydrogen and $R^{b1}$, $R^{b2}$, $R^{b3}$ are given in table C, and wherein X is as defined above and in particular X is selected from the group consisting of CF(CH₃)₂, CFCH₃CH₂CH₃, CHFCH₃, CHFCH₂CH₃, CF(CH₂CH₃)₂, CF₂CH₃, t-butyl, i-butyl, s-butyl, 1-chloro-cyclobutyl, 2,2-dimethylpropyl, i-propyl, 1-fluoropropyl, cyclobutyl, cyclopentyl, cyclohexyl, 1-cyclopropylethyl, 1-methylcyclobutyl, 1-methylcyclopentyl, $C(CH_3)_2OCH_3$, 1-methylcyclohexyl, 1-methoxy-ethyl, 1-methoxy-cyclopentyl, 1-methoxy-cyclobutyl, 1-methoxyl-cyclohexyl, 1-fluor-cyclopentyl, 1-fluor-cyclohexyl, 1-chlor-cyclopentyl, 1-chlor-cyclohexyl, 1-chlor-cyclobutyl, 2-methylpyrrolidin-1-yl, 2,2,2-trifluoroethoxy, azetidine, pyrrolidin-1-yl, piperidyl, methoxy(methyl)amino, 2-tetrahydrofuranyl, 2,4,6-trifluoro-phenyl, 2,6-difluoro-phenyl, 2-fluoro-phenyl or methoxy.

Examples of these compounds are those given in table E-1 to E-41.

Particular preference is given to diaminotriazine compounds of formula (I.e), which corresponds to diaminotriazines of formula (I) wherein $R^1$ and $R^2$ is hydrogen $R^{b1}$, $R^{b2}$, $R^{b3}$ are defined in table C.

Table E-1: Compounds of formula (I.e), where X is $CFCH_3CH_2CH_3$ and $R^{b1}$, $R^{b2}$, $R^{b3}$, are defined the rows of table C.

Table E-2: Compounds of formula (I.e), where X is $CF(CH_3)_2$ and $R^{b1}$, $R^{b2}$, $R^{b3}$ are defined the rows of table C.

Table E-3: Compounds of formula (I.e), where X is $CHFCH_3$ and $R^{b1}$, $R^{b2}$, $R^{b3}$ are defined the rows of table C.

Table E-4: Compounds of formula (I.e), where X is $CHFCH_2CH_3$ and $R^{b1}$, $R^{b2}$, $R^{b3}$, are defined the rows of table C.

Table E-5: Compounds of formula (I.e), where X is $CF(CH_2CH_3)_2$ and $R^{b1}$, $R^{b2}$, $R^{b3}$ are defined the rows of table C.

Table E-6: Compounds of formula (I.e), where X is $CF_2CH_3$ and $R^{b1}$, $R^{b2}$, $R^{b3}$ are defined the rows of table C.

Table E-7: Compounds of formula (I.e), where X is t-butyl and $R^{b1}$, $R^{b2}$, $R^{b3}$ are defined the rows of table C.

Table E-8: Compounds of formula (I.e), where X is i-butyl and $R^{b1}$, $R^{b2}$, $R^{b3}$ are defined the rows of table C.

Table E-9: Compounds of formula (I.e), where X is 2,2-dimethylpropyl and $R^{b1}$, $R^{b2}$, $R^{b3}$ are defined the rows of table C.

Table E-10: Compounds of formula (I.e), where X is i-propyl and $R^{b1}$, $R^{b2}$, $R^{b3}$ are defined the rows of table C.

Table E-11: Compounds of formula (I.e), where X is cyclobutyl and $R^{b1}$, $R^{b2}$, $R^{b3}$ are defined the rows of table C.

Table E-12: Compounds of formula (I.e), where X is cyclopentyl and $R^{b1}$, $R^{b2}$, $R^{b3}$ are defined the rows of table C.

Table E-13: Compounds of formula (I.e), where X is cyclohexyl and $R^{b1}$, $R^{b2}$, $R^{b3}$ are defined the rows of table C.

Table E-14: Compounds of formula (I.e), where X is 1-cyclopropylethyl and $R^{b1}$, $R^{b2}$, $R^{b3}$ are defined the rows of table C.

Table E-15: Compounds of formula (I.e), where X is 1-methylcyclobutyl and $R^{b1}$, $R^{b2}$, $R^{b3}$ are defined the rows of table C.

Table E-16: Compounds of formula (I.e), where X is 1-methylcyclopentyl and $R^{b1}$, $R^{b2}$, $R^{b3}$ are defined the rows of table C.

Table E-17: Compounds of formula (I.e), where X is $C(CH_3)_2OCH_3$ and $R^{b1}$, $R^{b2}$, $R^{b3}$ are defined the rows of table C.

Table E-18: Compounds of formula (I.e), where X is 1-methylcyclohexyl and $R^{b1}$, $R^{b2}$, $R^{b3}$ are defined the rows of table C.

Table E-19: Compounds of formula (I.e), where X is 1-methoxyethyl and $R^{b1}$, $R^{b2}$, $R^{b3}$, are defined the rows of table C.

Table E-20: Compounds of formula (I.e), where X is 1-methoxy-cyclopentyl and $R^{b1}$, $R^{b2}$, $R^{b3}$ are defined the rows of table C.

Table E-21: Compounds of formula (I.e), where X is 1-methoxy-cyclobutyl and $R^{b1}$, $R^{b2}$, $R^{b3}$ are defined the rows of table C.

Table E-22: Compounds of formula (I.e), where X is 1-methoxyl-cyclohexyl and $R^{b1}$, $R^{b2}$, $R^{b3}$ are defined the rows of table C.

Table E-23: Compounds of formula (I.e), where X is 1-fluor-cyclopentyl and $R^{b1}$, $R^{b2}$, $R^{b3}$ are defined the rows of table C.

Table E-24: Compounds of formula (I.e), where X is 1-fluor-cyclohexyl and $R^{b1}$, $R^{b2}$, $R^{b3}$ are defined the rows of table C.

Table E-25: Compounds of formula (I.e), where X is 1-chlor-cyclopentyl and $R^{b1}$, $R^{b2}$, $R^{b3}$ are defined the rows of table C.

Table E-26: Compounds of formula (I.e), where X is 1-chlor-cyclohexyl and $R^{b1}$, $R^{b2}$, $R^{b3}$ are defined the rows of table C.

Table E-27: Compounds of formula (I.e), where X is 1-chlor-cyclobutyl and $R^{b1}$, $R^{b2}$, $R^{b3}$ are defined the rows of table C.

Table E-28: Compounds of formula (I.e), where X is 2-methylpyrrolidin-1-yl and $R^{b1}$, $R^{b2}$, $R^{b3}$ are defined the rows of table C.

Table E-29: Compounds of formula (I.e), where X is 2,2,2-trifluoroethoxy and $R^{b1}$, $R^{b2}$, $R^{b3}$ are defined the rows of table C.

Table E-30: Compounds of formula (I.e), where X is azitidine and $R^{b1}$, $R^{b2}$, $R^{b3}$ are defined the rows of table C.

Table E-31: Compounds of formula (I.e), where X is pyrrolidin-1-yl and $R^{b1}$, $R^{b2}$, $R^{b3}$, are defined the rows of table C.

Table E-32: Compounds of formula (I.e), where X is 2-tetrahydrofuranyl and $R^{b1}$, $R^{b2}$, $R^{b3}$ are defined the rows of table C.

Table E-33: Compounds of formula (I.e), where X is 2,4,6-tri-fluoro-phenyl and $R^{b1}$, $R^{b2}$, $R^{b3}$ are defined the rows of table C.

Table E-34: Compounds of formula (I.e), where X is 2,6-difluoro-phenyl and $R^{b1}$, $R^{b2}$, $R^{b3}$ are defined the rows of table C.

Table E-35: Compounds of formula (I.e), where X is 2-fluoro-phenyl and $R^{b1}$, $R^{b2}$, $R^{b3}$ are defined the rows of table C.

Table E-36: Compounds of formula (I.e), where X is 1-chlor-cyclobutyl and $R^{b1}$, $R^{b2}$, $R^{b3}$ are defined the rows of table C.

Table E-37: Compounds of formula (I.e), where X is s-butyl and $R^{b1}$, $R^{b2}$, $R^{b3}$ defined the rows of table C.

Table E-38: Compounds of formula (I.e), where X is piperidyl and $R^{b1}$, $R^{b2}$, $R^{b3}$ are defined the rows of table C.

Table E-39: Compounds of formula (I.e), where X is methoxy(methyl)amino and $R^{b1}$, $R^{b2}$, $R^{b3}$ are defined the rows of table C.

Table E-40: Compounds of formula (I.e), where X is 1-fluoro-propyl and $R^{b1}$, $R^{b2}$, $R^{b3}$ are defined the rows of table C.

Table E-41: Compounds of formula (I.e), where X is methoxy and $R^{b1}$, $R^{b2}$, $R^{b3}$ are defined the rows of table C.

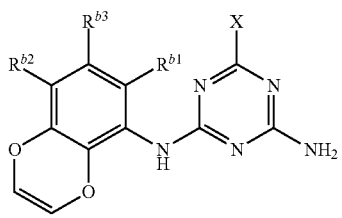

(I.e)

Particularly preferred is given to diaminotriazine compounds of formula (I.f), which corresponds to formula (I), wherein $R^1$ is hydrogen, $R^2$ is hydrogen and $R^{b1}$, $R^{b2}$, $R^{b3}$ are given in table C, and wherein X is as defined above and in particular X is selected from the group consisting of $CF(CH_3)_2$, $CFCH_3CH_2CH_3$, $CHFCH_3$, $CHFCH_2CH_3$, $CF(CH_2CH_3)_2$, $CF_2CH_3$, t-butyl, i-butyl, s-butyl, 1-chloro-cyclobutyl, 2,2-dimethylpropyl, i-propyl, 1-fluoropropyl, cyclobutyl, cyclopentyl, cyclohexyl, 1-cyclopropylethyl, 1-methylcyclobutyl, 1-methylcyclopentyl, $C(CH_3)_2OCH_3$, 1-methylcyclohexyl, 1-methoxyethyl, 1-methoxy-cyclopentyl, 1-methoxy-cyclobutyl, 1-methoxyl-cyclohexyl, 1-fluor-cyclopentyl, 1-fluor-cyclohexyl, 1-chlor-cyclopentyl, 1-chlor-cyclohexyl, 1-chlor-cyclobutyl, 2-methylpyrrolidin-1-yl, 2,2,2-trifluoroethoxy, azetidine, pyrrolidin-1-yl, piperidyl, methoxy(methyl)amino, 2-tetrahydrofuranyl, 2,4,6-trifluoro-phenyl, 2,6-difluoro-phenyl, 2-fluoro-phenyl or methoxy.

Examples of these compounds are those given in table F-1 to F-41.

Particular preference is given to diaminotriazine compounds of formula (I.f), which corresponds to diaminotriazines of formula (I) wherein $R^1$ and $R^2$ is hydrogen $R^{b1}$, $R^{b2}$, $R^{b3}$ are defined in table C.

Table F-1: Compounds of formula (I.f), where X is $CFCH_3CH_2CH_3$ and $R^{b1}$, $R^{b2}$, $R^{b3}$, are defined the rows of table C.

Table F-2: Compounds of formula (I.f), where X is $CF(CH_3)_2$ and $R^{b1}$, $R^{b2}$, $R^{b3}$ are defined the rows of table C.

Table F-3: Compounds of formula (I.f), where X is $CHFCH_3$ and $R^{b1}$, $R^{b2}$, $R^{b3}$ are defined the rows of table C.

Table F-4: Compounds of formula (I.f), where X is $CHFCH_2CH_3$ and $R^{b1}$, $R^{b2}$, $R^{b3}$ are defined the rows of table C.

Table F-5: Compounds of formula (I.f), where X is $CF(CH_2CH_3)_2$ and $R^{b1}$, $R^{b2}$, $R^{b3}$ are defined the rows of table C.

Table F-6: Compounds of formula (I.f), where X is $CF_2CH_3$ and $R^{b1}$, $R^{b2}$, $R^{b3}$ are defined the rows of table C.

Table F-7: Compounds of formula (I.f), where X is t-butyl and $R^{b1}$, $R^{b2}$, $R^{b3}$ are defined the rows of table C.

Table F-8: Compounds of formula (I.f), where X is i-butyl and $R^{b1}$, $R^{b2}$, $R^{b3}$ are defined the rows of table C.

Table F-9: Compounds of formula (I.f), where X is 2,2-dimethylpropyl and $R^{b1}$, $R^{b2}$, $R^{b3}$ are defined the rows of table C.

Table F-10: Compounds of formula (I.f), where X is i-propyl and $R^{b1}$, $R^{b2}$, $R^{b3}$ are defined the rows of table C.

Table F-11: Compounds of formula (I.f), where X is cyclobutyl and $R^{b1}$, $R^{b2}$, $R^{b3}$ are defined the rows of table C.

Table F-12: Compounds of formula (I.f), where X is cyclopentyl and $R^{b1}$, $R^{b2}$, $R^{b3}$ are defined the rows of table C.

Table F-13: Compounds of formula (I.f), where X is cyclohexyl and $R^{b1}$, $R^{b2}$, $R^{b3}$ are defined the rows of table C.

Table F-14: Compounds of formula (I.f), where X is 1-cyclopropylethyl and $R^{b1}$, $R^{b2}$, $R^{b3}$ are defined the rows of table C.

Table F-15: Compounds of formula (I.f), where X is 1-methylcyclobutyl and $R^{b1}$, $R^{b2}$, $R^{b3}$ are defined the rows of table C.

Table F-16: Compounds of formula (I.f), where X is 1-methylcyclopentyl and $R^{b1}$, $R^{b2}$, $R^{b3}$ are defined the rows of table C.

Table F-17: Compounds of formula (I.f), where X is $C(CH_3)_2OCH_3$ and $R^{b1}$, $R^{b2}$, $R^{b3}$ are defined the rows of table C.

Table F-18: Compounds of formula (I.f), where X is 1-methylcyclohexyl and $R^{b1}$, $R^{b2}$, $R^{b3}$ are defined the rows of table C.

Table F-19: Compounds of formula (I.f), where X is 1-methoxyethyl and $R^{b1}$, $R^{b2}$, $R^{b3}$, are defined the rows of table C.

Table F-20: Compounds of formula (I.f), where X is 1-methoxy-cyclopentyl and $R^{b1}$, $R^{b2}$, $R^{b3}$ are defined the rows of table C.

Table F-21: Compounds of formula (I.f), where X is 1-methoxy-cyclobutyl and $R^{b1}$, $R^{b2}$, $R^{b3}$ are defined the rows of table C.

Table F-22: Compounds of formula (I.f), where X is 1-methoxyl-cyclohexyl and $R^{b1}$, $R^{b2}$, $R^{b3}$ are defined the rows of table C.

Table F-23: Compounds of formula (I.f), where X is 1-fluor-cyclopentyl and $R^{b1}$, $R^{b2}$, $R^{b3}$ are defined the rows of table C.

Table F-24: Compounds of formula (I.f), where X is 1-fluor-cyclohexyl and $R^{b1}$, $R^{b2}$, $R^{b3}$ are defined the rows of table C.

Table F-25: Compounds of formula (I.f), where X is 1-chlor-cyclopentyl and $R^{b1}$, $R^{b2}$, $R^{b3}$ are defined the rows of table C.

Table F-26: Compounds of formula (I.f), where X is 1-chlor-cyclohexyl and $R^{b1}$, $R^{b2}$, $R^{b3}$ are defined the rows of table C.

Table F-27: Compounds of formula (I.f), where X is 1-chlor-cyclobutyl and $R^{b1}$, $R^{b2}$, $R^{b3}$ are defined the rows of table C.

Table F-28: Compounds of formula (I.f), where X is 2-methylpyrrolidin-1-yl and $R^{b1}$, $R^{b2}$, $R^{b3}$ are defined the rows of table C.

Table F-29: Compounds of formula (I.f), where X is 2,2,2-trifluoroethoxy and $R^{b1}$, $R^{b2}$, $R^{b3}$ are defined the rows of table C.

Table F-30: Compounds of formula (I.f), where X is azitidine and $R^{b1}$, $R^{b2}$, $R^{b3}$ are defined the rows of table C.

Table F-31: Compounds of formula (I.f), where X is pyrrolidin-1-yl and $R^{b1}$, $R^{b2}$, $R^{b3}$, are defined the rows of table C.

Table F-32: Compounds of formula (I.f), where X is 2-tetrahydrofuranyl and $R^{b1}$, $R^{b2}$, $R^{b3}$ are defined the rows of table C.

Table F-33: Compounds of formula (I.f), where X is 2,4,6-tri-fluoro-phenyl and $R^{b1}$, $R^{b2}$, $R^{b3}$ are defined the rows of table C.

Table F-34: Compounds of formula (I.f), where X is 2,6-difluoro-phenyl and $R^{b1}$, $R^{b2}$, $R^{b3}$ are defined the rows of table C.

Table F-35: Compounds of formula (I.f), where X is 2-fluoro-phenyl and $R^{b1}$, $R^{b2}$, $R^{b3}$ are defined the rows of table C.

Table F-36: Compounds of formula (I.f), where X is 1-chlorcyclobutyl and $R^{b1}$, $R^{b2}$, $R^{b3}$ are defined the rows of table C.

Table F-37: Compounds of formula (I.f), where X is s-butyl and $R^{b1}$, $R^{b2}$, $R^{b3}$ are defined the rows of table C.

Table F-38: Compounds of formula (I.f), where X is piperidyl and $R^{b1}$, $R^{b2}$, $R^{b3}$ are defined the rows of table C.

Table F-39: Compounds of formula (I.f), where X is methoxy(methyl)amino and $R^{b1}$, $R^{b2}$, $R^{b3}$ are defined the rows of table C.

Table F-40: Compounds of formula (I.f), where X is 1-fluoro-propyl and $R^{b1}$, $R^{b2}$, $R^{b3}$ are defined the rows of table C.

Table F-41: Compounds of formula (I.f), where X is methoxy and $R^{b1}$, $R^{b2}$, $R^{b3}$ are defined the rows of table C.

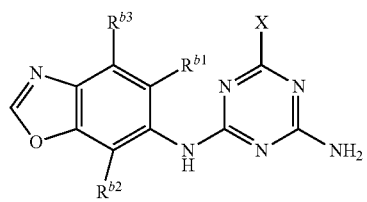

(I.f)

TABLE C

| | $R^{b1}$ | $R^{b3}$ | $R^{b2}$ |
|---|---|---|---|
| C-1. | H | H | H |
| C-2. | F | H | H |
| C-3. | Cl | H | H |
| C-4. | Br | H | H |
| C-5. | I | H | H |
| C-6. | CH$_3$ | H | H |
| C-7. | CN | H | H |
| C-8. | H | F | H |
| C-9. | F | F | H |
| C-10. | Cl | F | H |
| C-11. | Br | F | H |
| C-12. | I | F | H |
| C-13. | CH$_3$ | F | H |
| C-14. | CN | F | H |
| C-15. | H | H | F |
| C-16. | F | H | F |
| C-17. | Cl | H | F |
| C-18. | Br | H | F |
| C-19. | I | H | F |
| C-20. | CH$_3$ | H | F |
| C-21. | CN | H | F |
| C-22. | H | F | F |
| C-23. | F | F | F |
| C-24. | Cl | F | F |
| C-25. | Br | F | F |
| C-26. | I | F | F |
| C-27. | CH$_3$ | F | F |
| C-28. | CN | F | F |
| C-29. | H | Cl | H |
| C-30. | Cl | Cl | H |
| C-31. | Cl | Cl | H |
| C-32. | Br | Cl | H |
| C-33. | I | Cl | H |
| C-34. | CH$_3$ | Cl | H |
| C-35. | CN | Cl | H |
| C-36. | H | H | Cl |
| C-37. | Cl | H | Cl |
| C-38. | Cl | H | Cl |
| C-39. | Br | H | Cl |
| C-40. | I | H | Cl |
| C-41. | CH$_3$ | H | Cl |
| C-42. | CN | H | Cl |

TABLE C-continued

| | $R^{b1}$ | $R^{b3}$ | $R^{b2}$ |
|---|---|---|---|
| C-43. | H | Cl | Cl |
| C-44. | Cl | Cl | Cl |
| C-45. | Cl | Cl | Cl |
| C-46. | Br | Cl | Cl |
| C-47. | I | Cl | Cl |
| C-48. | CH$_3$ | Cl | Cl |
| C-49. | CN | Cl | Cl |
| C-50. | H | Br | H |
| C-51. | F | Br | H |
| C-52. | Cl | Br | H |
| C-53. | Br | Br | H |
| C-54. | I | Br | H |
| C-55. | CH$_3$ | Br | H |
| C-56. | CN | Br | H |
| C-57. | H | H | Br |
| C-58. | F | H | Br |
| C-59. | Cl | H | Br |
| C-60. | Br | H | Br |
| C-61. | I | H | Br |
| C-62. | CH$_3$ | H | Br |
| C-63. | CN | H | Br |
| C-64. | H | Br | Br |
| C-65. | F | Br | Br |
| C-66. | Cl | Br | Br |
| C-67. | Br | Br | Br |
| C-68. | I | Br | Br |
| C-69. | CH$_3$ | Br | Br |
| C-70. | CN | H | Br |
| C-71. | H | I | H |
| C-72. | F | I | H |
| C-73. | Cl | I | H |
| C-74. | Br | I | H |
| C-75. | I | I | H |
| C-76. | CH$_3$ | I | H |
| C-77. | CN | I | H |
| C-78. | H | H | I |
| C-79. | F | H | I |
| C-80. | Cl | H | I |
| C-81. | Br | H | I |
| C-82. | I | H | I |
| C-83. | CH$_3$ | H | I |
| C-84. | CN | H | I |
| C-85. | H | I | I |
| C-86. | F | I | I |
| C-87. | Cl | I | I |
| C-88. | Br | I | I |
| C-89. | I | I | I |
| C-90. | CH$_3$ | I | I |
| C-91. | CN | I | I |
| C-92. | H | F | Cl |
| C-93. | D | F | Cl |
| C-94. | F | F | Cl |
| C-95. | Cl | F | Cl |
| C-96. | Br | F | Cl |
| C-97. | I | F | Cl |
| C-98. | CH$_3$ | F | Cl |
| C-99. | CN | F | Cl |
| C-100. | H | F | Br |
| C-101. | F | F | Br |
| C-102. | Cl | F | Br |
| C-103. | Br | F | Br |
| C-104. | I | F | Br |
| C-105. | CH$_3$ | F | Br |
| C-106. | CN | F | Br |
| C-107. | H | F | I |
| C-108. | F | F | I |
| C-109. | Cl | F | I |
| C-110. | Br | F | I |
| C-111. | I | F | I |
| C-112. | CH$_3$ | F | I |
| C-113. | CN | F | I |
| C-114. | H | Cl | F |
| C-115. | F | Cl | F |
| C-116. | Cl | Cl | F |
| C-117. | Br | Cl | F |
| C-118. | I | Cl | F |
| C-119. | CH$_3$ | Cl | F |
| C-120. | CN | Cl | F |

TABLE C-continued

| | $R^{b1}$ | $R^{b3}$ | $R^{b2}$ |
|---|---|---|---|
| C-121. | H | Cl | Br |
| C-122. | F | Cl | Br |
| C-123. | Cl | Cl | Br |
| C-124. | Br | Cl | Br |
| C-125. | I | Cl | Br |
| C-126. | CH$_3$ | Cl | Br |
| C-127. | CN | Cl | Br |
| C-128. | H | Cl | I |
| C-129. | F | Cl | I |
| C-130. | Cl | Cl | I |
| C-131. | Br | Cl | I |
| C-132. | I | Cl | I |
| C-133. | CH$_3$ | Cl | I |
| C-134. | CN | Cl | I |
| C-135. | H | Br | F |
| C-136. | F | Br | F |
| C-137. | Cl | Br | F |
| C-138. | Br | Br | F |
| C-139. | I | Br | F |
| C-140. | CH$_3$ | Br | F |
| C-141. | CN | Br | F |
| C-142. | H | Br | Cl |
| C-143. | F | Br | Cl |
| C-144. | Cl | Br | Cl |
| C-145. | Br | Br | Cl |
| C-146. | I | Br | Cl |
| C-147. | CH$_3$ | Br | Cl |
| C-148. | CN | Br | Cl |
| C-149. | H | Br | I |
| C-150. | F | Br | I |
| C-151. | Cl | Br | I |
| C-152. | Br | Br | I |
| C-153. | I | Br | I |
| C-154. | CH$_3$ | Br | I |
| C-155. | CN | Br | I |
| C-156. | H | I | F |
| C-157. | F | I | F |
| C-158. | Cl | I | F |
| C-159. | Br | I | F |
| C-160. | I | I | F |
| C-161. | CH$_3$ | I | F |
| C-162. | CN | I | F |
| C-163. | H | I | Cl |
| C-164. | F | I | Cl |
| C-165. | Cl | I | Cl |
| C-166. | Br | I | Cl |
| C-167. | I | I | Cl |
| C-168. | CH$_3$ | I | Cl |
| C-169. | CN | I | Cl |
| C-170. | H | I | Br |
| C-171. | F | I | Br |
| C-172. | Cl | I | Br |
| C-173. | Br | I | Br |
| C-174. | I | I | Br |
| C-175. | CH$_3$ | I | Br |
| C-176. | CN | I | Br |

Particularly preferred is given to diaminotriazine compounds of formula (I.g), which corresponds to formula (I), wherein A is 1,3-dioxolan-yl, $R^b$ is F and $R^1$ and $R^2$ are given in table D, and wherein X is as defined above and in particular X is selected from the group consisting of CF(CH$_3$)$_2$, CFCH$_3$CH$_2$CH$_3$, CHFCH$_3$, CHFCH$_2$CH$_3$, CF(CH$_2$CH$_3$)$_2$, CF$_2$CH$_3$, t-butyl, i-butyl, s-butyl, 1-chloro-cyclobutyl, 2,2-dimethylpropyl, i-propyl, 1-fluoropropyl, cyclobutyl, cyclopentyl, cyclohexyl, 1-cyclopropylethyl, 1-methylcyclobutyl, 1-methylcyclopentyl, C(CH$_3$)$_2$OCH$_3$, 1-methylcyclohexyl, 1-methoxyethyl, 1-methoxy-cyclopentyl, 1-methoxy-cyclobutyl, 1-methoxyl-cyclohexyl, 1-fluor-cyclopentyl, 1-fluor-cyclohexyl, 1-chlor-cyclopentyl, 1-chlor-cyclohexyl, 1-chlor-cyclobutyl, 2-methylpyrrolidin-1-yl, 2,2,2-trifluoroethoxy, azetidine, pyrrolidin-1-yl, piperidyl, methoxy(methyl)amino, 2-tetrahydrofuranyl, 2,4,6-trifluoro-phenyl, 2,6-difluoro-phenyl, 2-fluoro-phenyl or methoxy.

Examples of these compounds are those given in table G-1 to G-41.

Particular preference is given to diaminotriazine compounds of formula (I.g), which corresponds to diaminotriazines of formula (I) wherein A is 1,3-dioxolan-yl $R^b$ is F and $R^1$ and $R^2$ are given in table D.

Table G-1: Compounds of formula (I.g), where X is CFCH$_3$CH$_2$CH$_3$ and $R^1$, $R^2$ are defined the rows of table D.

Table G-2: Compounds of formula (I.g), where X is CF(CH$_3$)$_2$ and $R^{b1}$, and $R^1$, $R^2$ are defined the rows of table D.

Table G-3: Compounds of formula (I.g), where X is CHFCH$_3$ and $R^1$, $R^2$ are defined the rows of table D.

Table G-4: Compounds of formula (I.g), where X is CHFCH$_2$CH$_3$ and and $R^1$, $R^2$ are defined the rows of table D.

Table G-5: Compounds of formula (I.g), where X is CF(CH$_2$CH$_3$)$_2$ and $R^1$, $R^2$ are defined the rows of table D.

Table G-6: Compounds of formula (I.g), where X is CF$_2$CH$_3$ and $R^1$, $R^2$ are defined the rows of table D.

Table G-7: Compounds of formula (I.g), where X is t-butyl and $R^1$, $R^2$ are defined the rows of table D.

Table G-8: Compounds of formula (I.g), where X is i-butyl and and $R^1$, $R^2$ are defined the rows of table D.

Table G-9: Compounds of formula (I.g), where X is 2,2-dimethylpropyl and $R^1$, $R^2$ are defined the rows of table C.

Table G-10: Compounds of formula (I.g), where X is i-propyl and and $R^1$, $R^2$ are defined the rows of table D.

Table G-11: Compounds of formula (I.g), where X is cyclobutyl and $R^1$, $R^2$ are defined the rows of table D.

Table G-12: Compounds of formula (I.g), where X is cyclopentyl and $R^1$, $R^2$ are defined the rows of table D.

Table G-13: Compounds of formula (I.g), where X is cyclohexyl and and $R^1$, $R^2$ are defined the rows of table D.

Table G-14: Compounds of formula (I.g), where X is 1-cyclopropylethyl and $R^1$, $R^2$ are defined the rows of table D.

Table G-15: Compounds of formula (I.g), where X is 1-methylcyclobutyl and $R^1$, $R^2$ are defined the rows of table D.

Table G-16: Compounds of formula (I.g), where X is 1-methylcyclopentyl and $R^1$, $R^2$ are defined the rows of table D.

Table G-17: Compounds of formula (I.g), where X is C(CH$_3$)$_2$OCH$_3$ and $R^1$, $R^2$ are defined the rows of table D.

Table G-18: Compounds of formula (I.g), where X is 1-methylcyclohexyl and $R^1$, $R^2$ are defined the rows of table D.

Table G-19: Compounds of formula (I.g), where X is 1-methoxyethyl and $R^1$, $R^2$ are defined the rows of table D.

Table G-20: Compounds of formula (I.g), where X is 1-methoxy-cyclopentyl and $R^1$, $R^2$ are defined the rows of table D.

Table G-21: Compounds of formula (I.g), where X is 1-methoxy-cyclobutyl and $R^1$, $R^2$ are defined the rows of table D.

Table G-22: Compounds of formula (I.g), where X is 1-methoxyl-cyclohexyl and $R^1$, $R^2$ are defined the rows of table D.

Table G-23: Compounds of formula (I.g), where X is 1-fluor-cyclopentyl and $R^1$, $R^2$ are defined the rows of table D.

121

Table G-24: Compounds of formula (I.g), where X is 1-fluor-cyclohexyl and $R^1$, $R^2$ are defined the rows of table D.

Table G-25: Compounds of formula (I.g), where X is 1-chlor-cyclopentyl and $R^1$, $R^2$ are defined the rows of table D.

Table G-26: Compounds of formula (I.g), where X is 1-chlor-cyclohexyl and $R^1$, $R^2$ are defined the rows of table D.

Table G-27: Compounds of formula (I.g), where X is 1-chlor-cyclobutyl and $R^1$, $R^2$ are defined the rows of table D.

Table G-28: Compounds of formula (I.g), where X is 2-methylpyrrolidin-1-yl and $R^1$, $R^2$ are defined the rows of table D.

Table G-29: Compounds of formula (I.g), where X is 2,2,2-trifluoroethoxy and $R^1$, $R^2$ are defined the rows of table D.

Table G-30: Compounds of formula (I.g), where X is azitidine and $R^1$, $R^2$ are defined the rows of table D.

Table G-31: Compounds of formula (I.g), where X is pyrrolidin-1-yl and $R^1$, $R^2$ are defined the rows of table D.

Table G-32: Compounds of formula (I.g), where X is 2-tetrahydrofuranyl and $R^1$, $R^2$ are defined the rows of table D.

Table G-33: Compounds of formula (I.g), where X is 2,4,6-tri-fluoro-phenyl and $R^1$, $R^2$ are defined the rows of table D.

Table G-34: Compounds of formula (I.g), where X is 2,6-difluoro-phenyl and $R^1$, $R^2$ are defined the rows of table D.

Table G-35: Compounds of formula (I.g), where X is 2-fluoro-phenyl and $R^1$, $R^2$ are defined the rows of table D.

Table G-36: Compounds of formula (I.g), where X is 1-chlor-cyclobutyl and $R^1$, $R^2$ are defined the rows of table D.

Table G-37: Compounds of formula (I.g), where X is s-butyl and $R^1$, $R^2$ are defined the rows of table D.

Table G-38: Compounds of formula (I.g), where X is piperidyl and $R^1$, $R^2$ are defined the rows of table D.

Table G-39: Compounds of formula (I.g), where X is methoxy(methyl)amino and $R^1$, $R^2$ are defined the rows of table D.

Table G-40: Compounds of formula (I.g), where X is 1-fluoro-propyl and $R^1$, $R^2$ are defined the rows of table D.

Table G-41: Compounds of formula (I.g), where X is methoxy and $R^1$, $R^2$ are defined the rows of table D.

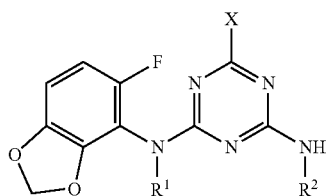

(I.g)

TABLE D

| no | $R^1$ | $R^2$ |
|---|---|---|
| D-1. | H | H |
| D-2. | $CH_3$ | H |
| D-3. | H | $CH_3$ |
| D-4. | $CH_3$ | $CH_3$ |

TABLE D-continued

| no | $R^1$ | $R^2$ |
|---|---|---|
| D-5. | $C(=O)CH_3$ | H |
| D-6. | H | $C(=O)CH_3$ |
| D-7. | $C(=O)CH_3$ | $C(=O)CH_3$ |
| D-8. | $C(=O)CH_3$ | $CH_3$ |
| D-9. | $CH_3$ | $C(=O)CH_3$ |

The diaminotriazine compounds of formula (I) according to the invention can be prepared by standard processes of organic chemistry, for example by the following processes:

Process A)

The diaminotriazine compounds of formula (I), wherein $R^2$ is as defined above and in particular H, $C_1$-$C_6$-alkyl or ($C_1$-$C_6$-alkoxy)-$C_1$-$C_6$-alkyl, can be prepared by reacting halotriazines of formula (II) with amines of formula (III) in the presence of a base and a catalyst as depicted in the following scheme 1:

Scheme 1:

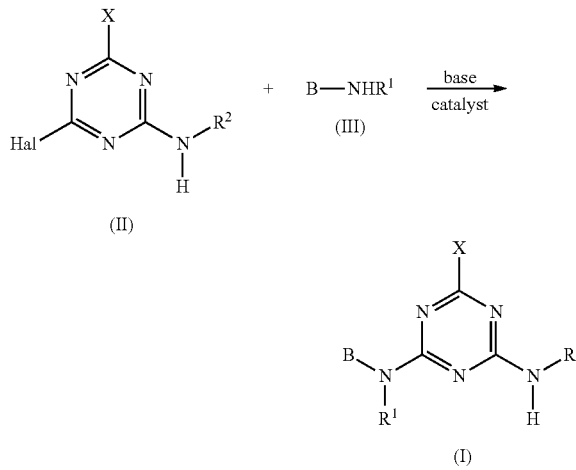

In scheme 1, the variable B is a radical

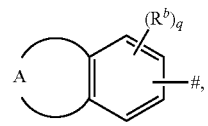

donates the bond to the remainder molecule, the variables $R^1$, $R^2$, $R^b$, q A and X have the above meanings while Hal is halogen, in particular bromine or chlorine and especially chlorine.

Compounds of formula (II) are novel and valuable intermediates in the production of the diaminotriazine compounds of formula (I) and therefore form part of the present invention.

Particular embodiments of the halotriazines of formual (II) relate to compounds, where the variables Hal, $R^1$, $R^2$ and X have in particular the following meanings:

Hal preferably Cl or Br, especially Cl;

$R^2$ is in particular H, $C_1$-$C_6$-alkyl, ($C_1$-$C_6$-alkoxy)-$C_1$-$C_6$-alkyl;

more particularly H, $C_1$-$C_4$-alkoxy-$C_1$-$C_4$-alkyl, such as CH2OCH3;
especially hydrogen;
X is as defined above and in particular as defined in embodiments groups.

Particular embodiments relate to the halotriazines of formula (II.a), which correspond to the halotriazines of formula (II) wherein $R^2$ is hydrogen and Hal is Cl. Further particular embodiments relate to the halotriazines of formula (II.b), which correspond to the halotriazines of formula (II) wherein $R^2$ is hydrogen and Hal is Br:

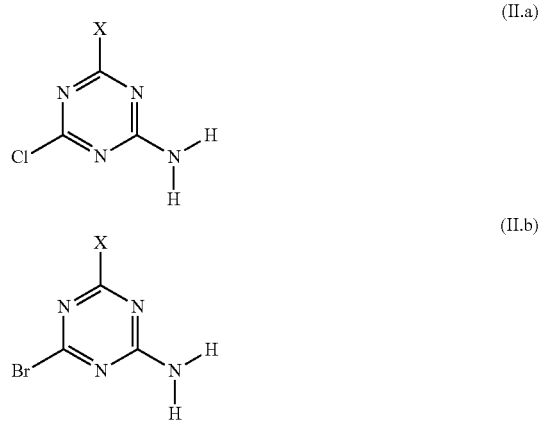

(II.a)

(II.b)

Particular examples of the compounds of formulae (II.a) and (II.b) are those, wherein X is as defined in the table A.

In formula (III)
$R^1$ is in particular H, $C_1$-$C_6$-alkyl, ($C_1$-$C_6$-alkoxy)-$C_1$-$C_6$-alkyl;
more particularly H, ($C_1$-$C_4$-alkoxy)-$C_1$-$C_4$-alkyl, such as $CH_2OCH_3$;
especially hydrogen; and
A is as defined above.

The reaction of the halotriazines of formula (II) with the amines of formula (III) is usually carried out at temperatures in the range from from 50° C. to the boiling point of the reaction mixture, preferably from 50° C. to 150° C., particularly preferably from 60° C. to 100° C., in an inert organic solvent (e.g. P. Dao et al., Tetrahedron 2012, 68, 3856-3860).

The reaction can be carried out at atmospheric pressure or under elevated pressure, if appropriate, under an inert gas, continuously or batchwise.

In one embodiment of the process according to the invention, the halotriazines of formula (II) and the amines of formula (III) are used in equimolar amounts.

In another embodiment of the process according to the invention, the amines of formula (III) are used in excess with regard to the halotriazines of formula (II).

Preferably the molar ratio of the amines of formula (III) to the halotriazines of formula (II) is in the range from 2:1 to 1:1, preferably 1.5:1 to 1:1, especially preferred 1.2:1.

The reaction of the halotriazines of formula (II) with the amines of formula (III) is usually carried out in an organic solvent. Suitable in principle are all solvents which are capable of dissolving the halotriazines of formula (II) and the amines of formula (II) at least partly and preferably fully under reaction conditions. Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP). Preferred solvents are ethers as defined above. The term solvent as used herein also includes mixtures of two or more of the above compounds.

The reaction of the halotriazines of formula (II) with the amines of formula (III) is usually carried out in the presence of a base. Examples of suitable bases include metal-containing bases and nitrogen-containing bases. Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal and alkaline earth metal formates, acetates and other metal salts of carboxylic acids, such as sodium formate, sodium benzoate, lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and also bicyclic amines such as 1,8-diazabicyclo[5.4.0]undec-7-ene (DBU) or 1,5-diazabicyclo[4.3.0]non-5-ene (DBN). Preferred bases are alkali metal and alkaline earth metal alkoxides as defined above. The term base as used herein also includes mixtures of two or more, preferably two of the above compounds. Particular preference is given to the use of one base. The bases can be used in excess, preferably from 1 to 10, especially preferred from 2 to 4 base equivalents based on the halotriazines of formula (II), and they may also be used as the solvent.

The reaction of the halotriazines of formula (II) with the amines of formula (III) may be carried out in the presence of a catalyst. Examples of suitable catalysts include for example, palladium based catalysts like, for example, Palladium(II)acetate, tetrakis(triphenylphosphine)palladium (0), bis(triphenylphosphine)palladium(II)chloride or (1,1,-bis(diphenylphosphino)ferrocene)-dichloropalladium(II), and optionally suitable additives such as, for example, phosphines like, for example, P(o-tolyl)$_3$, triphenylphosphine or BINAP (2,2'-Bis(diphenylphospino)-1,1'-binaphthyl). The amount of catalyst is usually 10 to 20 mol % (0.1 to 0.2 equivalents) based on the halotriazines of formula (II).

The end of the reaction can easily be determined by the skilled worker by means of routine methods.

The reaction mixtures are worked up in a customary manner, for example by mixing with water, separation of the phases and, if appropriate, chromatographic purification of the crude product.

The amines of formula (III) used for the preparation of diaminotriazine compounds of formula (I), wherein $R^1$ is H, $C_1$-$C_6$-alkyl, ($C_1$-$C_6$-alkoxy)-$C_1$-$C_6$-alkyl or $C_1$-$C_6$-alkoxy, are commercially available and/or can be prepared by analogy to known literature.

The halotriazines of formula (II) required for the preparation of diaminotriazine compounds of formula (I), wherein $R^2$ is H, $C_1$-$C_6$-alkyl, ($C_1$-$C_6$-alkoxy)-$C_1$-$C_6$-alkyl or $C_1$-$C_6$-alkoxy, can be prepared by analogy (e.g. J. K. Chakrabarti et al., Tetrahedron 1975, 31, 1879-1882) by reacting thiotriazines of formula (IV) with a halogen, as depicted in scheme 2:

Scheme 2:

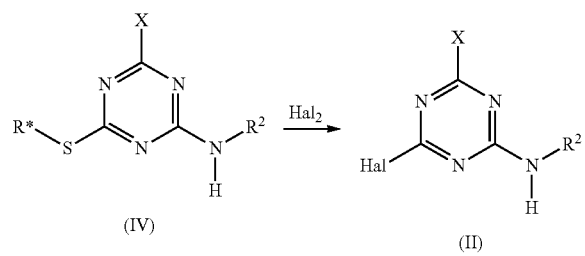

(IV)　　　　　　　(II)

The variable X in formulae (II) and (VI) has the meanings, in particular the preferred meanings, as defined above in context of formula (I).

R* is $C_1$-$C_6$-alkyl, $C_2$-$C_6$-haloalkyl or phenyl;
　in particular $C_1$-$C_4$-alkyl or $C_2$-$C_4$-haloalkyl;
　more particularly $C_1$-$C_4$-alkyl;
　especially CH$_3$; and Compounds of formula (IV) are novel and valuable intermediates in the production of the diaminotriazine compounds of formula (I) and therefore also form part of the present invention.

Particular embodiments of the compounds of formual (IV) relate to compounds, where the variables R*, $R^2$ and X have in particular the following meanings:

R* is $C_1$-$C_6$-alkyl, $C_2$-$C_6$-haloalkyl or phenyl;
　in particular $C_1$-$C_4$-alkyl or $C_2$-$C_4$-haloalkyl;
　more particularly $C_1$-$C_4$-alkyl;
　especially CH$_3$; and $R^2$ is in particular H, $C_1$-$C_6$-alkyl, ($C_1$-$C_6$-alkoxy)-$C_1$-$C_6$-alkyl;
　more particularly H, ($C_1$-$C_4$-alkoxy)-$C_1$-$C_4$-alkyl, such as CH$_2$OCH$_3$;
　especially hydrogen;

X is as defined above and in particular as defined in the embodiments groups.

Particular embodiments relate to the compounds of formula (IV.a), which correspond to the compounds of formula (IV) wherein $R^2$ is hydrogen and R* is CH$_3$.

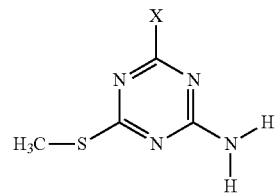

(IV.a)

Particular examples of the compounds of formulae (IV.a) are those, wherein X is as defined in the table B above.

The reaction of the thiotriazines of formula (IV) with the halogen is usually carried out from 0° C. to the boiling point of the reaction mixture, preferably from 15° C. to the boiling point of the reaction mixture, particularly preferably from 15° C. to 40° C., in an inert organic solvent (e.g. J. K. Chakrabarti et al., Tetrahedron 1975, 31, 1879-1882).

The reaction can be carried out at atmospheric pressure or under elevated pressure, if appropriate under an inert gas, continuously or batchwise.

In the reaction of the thiotriazines of formula (IV) with, halogen is generally used in excess with regard to the thiotriazines of formula (IV).

The reaction of the thiotriazines of formula (IV) with the halogen is usually carried out in an organic solvent.

Suitable in principle are all solvents which are capable of dissolving the thiotriazines of formula (IV) and the halogen at least partly and preferably fully under reaction conditions. Examples of suitable solvents are aliphatic hydrocarbons such as pentane, hexane, cyclohexane and mixtures of $C_5$-$C_8$-alkanes, halogenated hydrocarbons such as dichloromethane, 1,2-dichloroethane, chloroform and carbon tetrachloride; ethers such as diethyl ether, diisopropyl ether, tert.-butyl methylether (TBME), dioxane, anisole and tetrahydrofuran (THF), alcohols such as methanol, ethanol, n-propanol, isopropanol, n-butanol and tert.-butanol, as well as organic acids like formic acid, acetic acid, propionic acid, oxalic acid, citric acid, trifluoroacetic acid. Preferred solvents are halogenated hydrocarbons and organic acids as defined above. The term solvent as used herein also includes mixtures of two or more of the above compounds. The end of the reaction can easily be determined by the skilled worker by means of routine methods. The reaction mixtures are worked up in a customary manner, for example by mixing with water, separation of the phases and, if appropriate, chromatographic purification of the crude product.

The halotriazines of formula (II) required for the preparation of diaminotriazine compounds of formula (I), wherein $R^2$ is H, $C_1$-$C_6$-alkyl, ($C_1$-$C_6$-alkoxy)-$C_1$-$C_6$-alkyl, can also be prepared by reacting 2,4-dichlorotriazines of formula (VII) with a an amine H$_2$N-$R^2$, in particular with ammonia, as depicted in scheme 3:

Scheme 3:

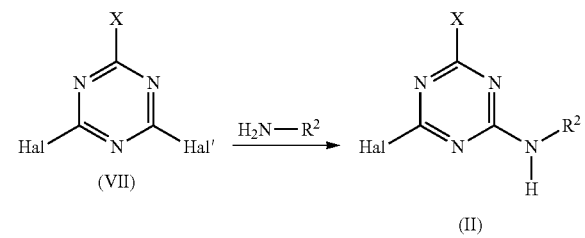

(VII)　　　　　　　(II)

The variable X in formulae (II) and (VII) has the meanings, in particular the preferred meanings, as defined above in context of formula (I).

Hal and Hal' are each, independently, halogen, in particular bromine or chlorine, especially chlorine.

The reaction depicted in scheme 3 can be performed by simply mixing the required amounts of the compound of formula (VII) with the amine $H_2N$—$R^2$ or by analogy to the reaction depicted in step 1.

Preferably the molar ratio of the amine to the halotriazines of formula (II) is in the range from 10:1 to 1:1, preferably 5:1 to 1:1. Compound (IV) can be obtained by reaction of compound (II) with mercaptan R*—SH.

The reaction depicted in scheme 3 is preferably carried out in an inert solvent. Examples of suitable solvents are nitromethane, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP) and mixtures thereof with with water or with aliphatic hydrocarbons such as pentane, hexane, cyclohexane or with mixtures of $C_5$-$C_8$-alkane. Preferred solvents are ethers as defined above and mixtures thereof with water. The term solvent as used herein also includes mixtures of two or more of the above compounds.

The reaction depicted in scheme 1 may be performed in the presence of an auxiliary base. Suitable bases are those mentioned in context with the reaction depicted in scheme 1. However, the amine $H_2N$—$R^2$ may itself serve as an auxiliary base. In this case, usually an excess of the amine $H_2N$—$R^2$ is used.

Process B)

The diaminotriazine compounds of formula (I), wherein $R^2$ is different from hydrogen, e.g. $C_1$-$C_6$-alkyl, ($C_1$-$C_6$-alkoxy)-$C_1$-$C_6$-alkyl, CN, ($C_1$-$C_6$-alkyl)carbonyl, ($C_1$-$C_6$-alkoxy)carbonyl, ($C_1$-$C_6$-alkyl)sulfonyl, phenylsulfonyl, phenyl, phenyl-$C_1$-C6 alkyl, phenylcarbonyl or phenoxycarbonyl,
  wherein the phenyl is unsubstituted or substituted as defined above for the respective radicals in formula (I);
  can be prepared by reacting azines of formula (I), wherein $R^2$ is hydrogen with a compound of formula (V) as depicted in scheme 4:

Scheme 4:

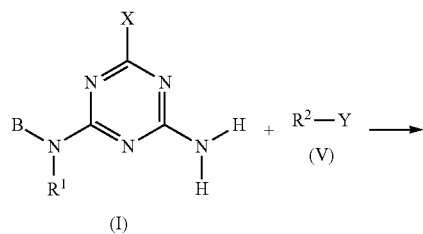

(I)

-continued

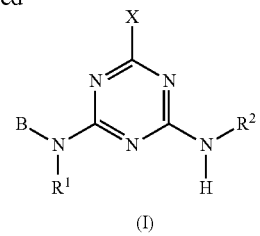

(I)

wherein $R^2$ in hydrogen

The variable B is a radical

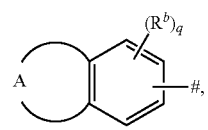

donates the bond to the remainder molecule, the variables A, $R^b$, q, $R^1$ and X have the meanings, in particular the preferred meanings, as in formula (I) mentioned above,
$R^2$ is different from hydrogen, e.g. $C_1$-$C_6$-alkyl, ($C_1$-$C_6$-alkoxy)-$C_1$-$C_6$-alkyl, CN, ($C_1$-$C_6$-alkyl)carbonyl, ($C_1$-$C_6$-alkoxy)carbonyl, ($C_1$-$C_6$-alkyl)sulfonyl, phenylsulfonyl, phenyl, phenyl-$C_1$-$C_6$ alkyl, phenylcarbonyl or phenoxycarbonyl,
  wherein the phenyl is unsubstituted or substituted as defined above for the respective radicals in formula (I);
  in particular $C_1$-$C_4$-alkyl, ON, ($C_1$-$C_6$-alkyl)carbonyl, ($C_1$-$C_6$-alkoxy)carbonyl or ($C_1$-$C_6$-alkyl)sulfonyl;
  especially CN, $COCH_3$, $COOCH_3$ or $SO_2CH_3$; and
Y is halogen or oxycarbonyl-$C_1$-$C_6$-alkyl;
  in particular halogen;
  especially Cl, I or Br.

Process C)

The diaminotriazine compounds of formula (I), wherein $R^1$ is is different from hydrogen, e.g. $C_1$-$C_6$-alkyl, ($C_1$-$C_6$-alkoxy)-$C_1$-$C_6$-alkyl, CN, ($C_1$-$C_6$-alkyl)carbonyl, ($C_1$-$C_6$-alkoxy)carbonyl, ($C_1$-$C_6$-alkyl)sulfonyl, phenylsulfonyl, phenyl, phenyl-$C_1$-C6 alkyl, phenylcarbonyl or phenoxycarbonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;
  can be prepared by reacting azines of formula (I), wherein $R^1$ is hydrogen with a compound of formula (VI), as depecited in scheme 5:

Scheme 5

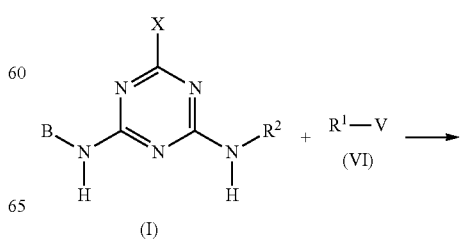

(I)

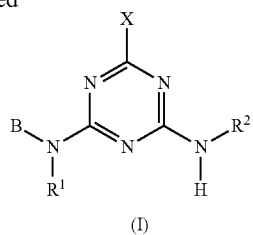

(I)

wherein $R^1$ in hydrogen

The variable B is a radical

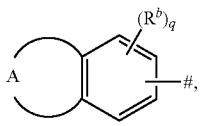

donates the bond to the remainder molecule, the variables A, $R^b$, q, $R^2$ and X have the meanings, in particular the preferred meanings, as in formula (I) mentioned above,
$R^1$ is different from hydrogen, e.g. $C_1$-$C_6$-alkyl, ($C_1$-$C_6$-alkoxy)-$C_1$-$C_6$-alkyl, CN, ($C_1$-$C_6$-alkyl)carbonyl, ($C_1$-$C_6$-alkoxy)carbonyl, ($C_1$-$C_6$-alkyl)sulfonyl, phenylsulfonyl, phenyl, phenyl-$C_1$-C6 alkyl, phenylcarbonyl or phenoxycarbonyl,
  wherein the phenyl is unsubstituted or substituted as defined above for the respective radicals in formula (I);
  in particular $C_1$-$C_4$-alkyl, ON, ($C_1$-$C_6$-alkyl)carbonyl, ($C_1$-$C_6$-alkoxy)carbonyl or ($C_1$-$C_6$-alkyl)sulfonyl;
  especially ON, $COCH_3$, $COOCH_3$ or $SO_2CH_3$; and
V is halogen or oxycarbonyl-$C_1$-$C_6$-alkyl;
  in particular halogen;
  especially Cl, I or Br.

Both processes B and C independently of one another usually carried out at from 0° C. to the boiling point of the reaction mixture, preferably from 23° C. to 130° C., particularly preferably from 23° C. to 100° C., (e.g. Y. Yuki et al., Polym. J. 1992, 24, 791-799).

Both processes B and C independently of one another can be carried out at atmospheric pressure or under elevated pressure, if appropriate under an inert gas, continuously or batchwise.

In one embodiment of processes B and C according to the invention independently of one another, the diaminotriazine compounds of formula (I), wherein $R^2$, or $R^1$ respectively, is hydrogen are used in excess with regard to the compound of formula (V), or (VI) respectively.

In another embodiment of processes B and C according to the invention independently of one another, the diaminotriazine compounds of formula (I), wherein $R^2$, or $R^1$ respectively, is hydrogen and the compound of formula (V), or (VI) respectively, are used in equimolar amounts.

Preferably the molar ratio of the diaminotriazine compounds of formula (I), wherein $R^2$, or $R^1$ respectively, is hydrogen to the compound of formula (V), or (VI) respectively is in the range from 1:1.5 to 1:1, preferably 1:1.2 to 1:1, especially preferred 1:1.

Both processes B and C independently of one another are usually carried out in an organic solvent. Suitable in principle are all solvents which are capable of dissolving the diaminotriazine compounds of formula (I), wherein $R^2$, or $R^1$ respectively, is hydrogen and the compound of formula (V), or (VI) respectively, at least partly and preferably fully under reaction conditions.

Examples of suitable solvents are halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); nitriles such as acetonitrile and propionitrile; alcohols such as methanol, ethanol, n-propanol, isopropanol, n-butanol and tert.-butanol; organic acids like formic acid, acetic acid, propionic acid, oxalic acid, methylbenzenesulfonic acid, benzenesulfonic acid, camphorsulfonic acid, citric acid, trifluoroacetic acid as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP). Preferred solvents are halogenated hydrocarbons, ethers and dipolar aprotic solvents as mentioned above. More preferred solvents are dichloromethane or dioxane. It is also possible to use mixtures of the solvents mentioned.

The term solvent as used herein also includes mixtures of two or more of the above compounds.

Both processes B and C independently of one another are optionally carried out in the presence of a base. Examples of suitable bases include metal-containing bases and nitrogen-containing bases. Examples of suitable metal-containing bases are inorganic compounds such as alkali metal and alkaline earth metal hydrides such as lithium hydride, sodium hydride, potassium hydride and calcium hydride, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN). Preferred bases are organic bases and alkali metal carbonates as mentioned above. Especially preferred bases are organic bases as mentioned above. The term base as used herein also includes mixtures of two or more, preferably two of the above compounds. The bases are generally employed in excess; however they can also be employed in equimolar amounts, or, if appropriate, can be used as solvent. Preferably from 1 to 5 base equivalents, particularly preferred 3 base equivalents of base are used, based on the diaminotriazine compounds of formula (I).

Work-up of the reaction mixture is performed by standard procedures.

The compounds of formula (V), or (VI) respectively, are known compounds. They are commercially available or can be prepared in analogy to known methods.

Process D)

The diaminotrazine compounds of formula (I), wherein $R^1$ and $R^2$ are defined above, can be prepared by reacting biguanidines of formula (VII) with carbonyl compounds of formula (VIII) in the presence of a base:

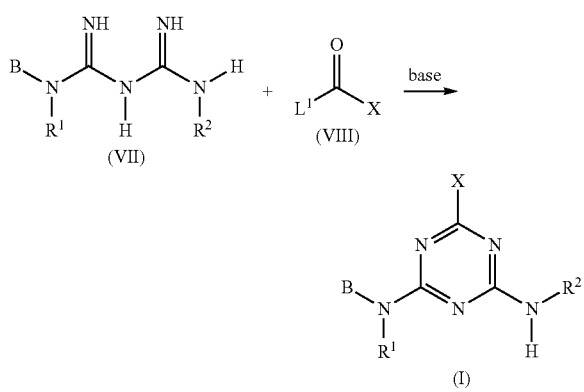

The variable B is a radical

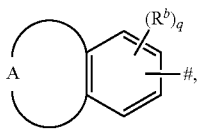

donates the bond to the remainder molecule, the variables A, $R^b$, q and X have the meanings, in particular the preferred meanings, as in formula (I) mentioned above, and $L^1$ is a nucleophilically displaceable leaving group such as halogen, CN, $C_1$-$C_6$-alkoxy, $C_1$-$C_6$-alkoxycarbonyl, $C_1$-$C_6$-alkylcarbonyloxy or $C_1$-$C_6$-alkoxycarbonyloxy;
preferably halogen or $C_1$-$C_6$-alkoxy;
particularly preferred Cl or $C_1$-$C_6$-alkoxy,
also particularly preferred halogen;
especially preferred Cl.

The reaction of biguanidines of formula (VII) with carbonyl compounds of formula (VIII) is usually carried out at temperatures from 50° C. to the boiling point of the reaction mixture, preferably from 50° C. to 200°C (e.g. R. Sathunuru et al., J. Heterocycl. Chem. 2008, 45, 1673-1678).

The reaction can be carried out at atmospheric pressure or under elevated pressure, if appropriate under an inert gas, continuously or batchwise.

In one embodiment of the process according to the invention, the biguanidines of formula (VII) and the carbonyl compounds of formula (VIII) are used in equimolar amounts.

In another embodiment of the process according to the invention, the carbonyl compounds of formula (VIII) are used in excess with regard to the biguanidines of formula (VII).

Preferably the molar ratio of the carbonyl compounds of formula (VIII) to the biguanidines of formula (VII) is in the range from 1.5:1 to 1:1, preferably 1.2:1 to 1:1, especially preferred 1.2:1, also especially preferred 1:1.

The reaction of the biguanidines of formula (VII) with the carbonyl compounds of formula (VIII) is carried out in an organic solvent.

Suitable in principle are all solvents which are capable of dissolving the biguanidines of formula (VII) and the carbonyl compounds of formula (VIII) at least partly and preferably fully under reaction conditions.

Examples of suitable solvents are
aliphatic hydrocarbons such as pentane, hexane, cyclohexane, nitromethane and mixtures of $C_5$-$C_8$-alkanes; romatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as defined above.

More preferred solvents are ethers as defined above.

The term solvent as used herein also includes mixtures of two or more of the above compounds.

The reaction of the biguanidines of formula (VII) with the carbonyl compounds of formula (VIII) is carried out in the presence of a base.

Examples of suitable bases include metal-containing bases and nitrogen-containing bases. Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-$C_1$-$C_6$-alkylamines, for example triethylamine, trimethylamine, N-ethyldiisopropylamine, and N-methyl-piperidine, pyridine, substituted pyridines such as collidine, lutidine, N-methylmorpholine and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines as defined above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the biguanidines of formula (VII).

The end of the reaction can easily be determined by the skilled worker by means of routine methods.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature.

If the intermediates and the end products are obtained as solid, purification can also be carried out by recrystallisation or digestion.

The carbonyl compounds of formula (VIII) required for the preparation of azines of formula (I) are known in the art or they can be prepared in accordance and/or are commercially available.

The biguanidines of formula (VII) required for the preparation of azines of formula (I), wherein $R^1$ and $R^2$ are defined above, can be prepared by reacting guanidines of formula (IX) with amines of formula (X) in the presence of an acid:

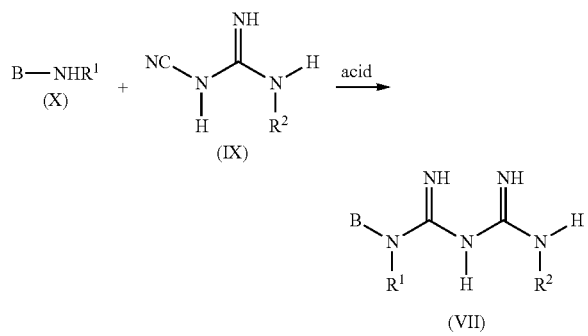

The variable B is a radical

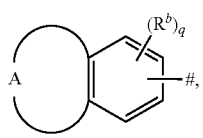

donates the bond to the remainder molecule, the variables A, $R^b$ and q have the meanings, in particular the preferred meanings, as in formula (I) mentioned above.

The reaction of guanidines of formula (IX) with amines of formula (X) is usually carried out from 50° C. to 150° C., preferably from 80° C. to 130° C.

Microwave-Technology was used where applicable (e.g. C. O. Kappe, A. Stadler, Microwaves in Organic and Medicinal Chemistry, Weinheim 2012).

The reaction can be carried out at atmospheric pressure or under elevated pressure, if appropriate under an inert gas, continuously or batchwise.

In one embodiment of the process according to the invention, the guanidines of formula (IX) and the amines of formula (X) are used in equimolar amounts.

In another embodiment of the process according to the invention, the amines of formula (X) are used in excess with regard to the guanidines of formula (IX).

Preferably the molar ratio of the amines of formula (X) to the guanidines of formula (IX) is in the range from 2:1 to 1:1, preferably 1.5:1 to 1:1, especially preferred 1:1.

The reaction of the guanidines of formula (IX) with the amines of formula (X) is carried out in an organic solvent.

Suitable in principle are all solvents which are capable of dissolving the guanidines of formula (IX) and the amines of formula (X) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, nitriles and dipolar aprotic solvents as defined above.

More preferred solvents are nitriles as defined above.

The term solvent as used herein also includes mixtures of two or more of the above compounds.

The reaction of the guanidines of formula (IX) with the amines of formula (X) is carried out in the presence of an acid.

As acids and acidic catalysts inorganic acids like hydrofluoric acid, hydrochloric acid, hydrobromic acid, hydroiodic acid, phosphoric acid, sulfuric acid; mineral acids like hydrochloric acid, sulfuric acid, phosphoric acid, Lewis acids like boron trifluoride, aluminium chloride, ferric-III-chloride, tin-IV-chloride, titanium-IV-chloride and zinc-II-chloride, as well as organic acids like formic acid, acetic acid, propionic acid, oxalic acid, methylbenzenesulfonic acid, benzenesulfonic acid, camphorsulfonic acid, citric acid, trifluoroacetic acid, can be used.

The acids are generally employed in excess or, if appropriate, can be used as solvent.

Work up can be carried out in a known manner.

The guanidines of formula (IX) required for the preparation of biguanidines of formula (VII) are commercially available or can be prepared in accordance with literature procedures (e.g. J. L. LaMattina et al., J. Med. Chem. 1990, 33, 543-552; A. Perez-Medrano et al., J. Med. Chem. 2009, 52, 3366-3376).

The amines of formula (X) required for the preparation of biguanidines of formula (VII) are commercially available.

The compounds of formula (I) have herbicidal activity. Therefore, they can be used for controlling unwanted or undesired plants or vegetation. They can also be used in a method for controlling unwanted or undesired plants or vegetation, which method comprises allowing at least one compound of formula (I) or a salt thereof to act on plants, their environment or on seed. In order to allow the compound of formula (I) or a salt thereof to act on plants, their environment or on seed the compounds of the invention are applied to the plants, their environment or to the seed of said plants.

To widen the spectrum of action and to achieve synergistic effects, the diaminotriazine compounds of formula (I) may be mixed with a large number of representatives of other herbicidal or growth-regulating active ingredient groups and then applied concomitantly.

Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

The invention also relates to combinations of diaminotriazine compounds of formula (I) with at least one further herbicide B and/or at least one safener C).

The further herbicidal compound B (component B) is in particular selected from the herbicides of class b1) to b15):
- b1) lipid biosynthesis inhibitors;
- b2) acetolactate synthase inhibitors (ALS inhibitors);
- b3) photosynthesis inhibitors;
- b4) protoporphyrinogen-IX oxidase inhibitors,
- b5) bleacher herbicides;
- b6) enolpyruvyl shikimate 3-phosphate synthase inhibitors (EPSP inhibitors);
- b7) glutamine synthetase inhibitors;
- b8) 7,8-dihydropteroate synthase inhibitors (DHP inhibitors);
- b9) mitosis inhibitors;
- b10) inhibitors of the synthesis of very long chain fatty acids (VLCFA inhibitors);
- b11) cellulose biosynthesis inhibitors;
- b12) decoupler herbicides;
- b13) auxinic herbicides;
- b14) auxin transport inhibitors; and
- b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

including their agriculturally acceptable salts or derivatives such as ethers, esters or amides.

In one embodiment of the present invention the compositions according to the present invention comprise at least one diaminotriazine compound of formula (I) and at least one further active compound B (herbicide B).

According to a further embodiment of the invention the compositions contain at least one inhibitor of the lipid biosynthesis (herbicide b1). These are compounds that inhibit lipid biosynthesis. Inhibition of the lipid biosynthesis can be affected either through inhibition of acetylCoA carboxylase (hereinafter termed ACC herbicides) or through a different mode of action (hereinafter termed non-ACC herbicides). The ACC herbicides belong to the group A of the HRAC classification system whereas the non-ACC herbicides belong to the group N of the HRAC classification.

According to a further embodiment of the invention the compositions contain at least one ALS inhibitor (herbicide b2). The herbicidal activity of these compounds is based on the inhibition of acetolactate synthase and thus on the inhibition of the branched chain amino acid biosynthesis. These inhibitors belong to the group B of the HRAC classification system.

According to a further embodiment of the invention the compositions contain at least one inhibitor of photosynthesis (herbicide b3). The herbicidal activity of these compounds is based either on the inhibition of the photosystem 11 in plants (so-called PSII inhibitors, groups C1, C2 and C3 of HRAC classification) or on diverting the electron transfer in photosystem 1 in plants (so-called PSI inhibitors, group D of HRAC classification) and thus on an inhibition of photosynthesis. Amongst these, PSII inhibitors are preferred.

According to a further embodiment of the invention the compositions contain at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

According to a further embodiment of the invention the compositions contain at least one bleacher-herbicide (herbicide b5). The herbicidal activity of these compounds is based on the inhibition of the carotenoid biosynthesis. These include compounds which inhibit carotenoid biosynthesis by inhibition of phytoene desaturase (so-called PDS inhibitors, group F1 of HRAC classification), compounds that inhibit the 4-hydroxyphenyl-pyruvate-dioxygenase (HPPD inhibitors, group F2 of HRAC classification), compounds that inhibit DOXsynthase (group F4 of HRAC class) and compounds which inhibit carotenoid biosynthesis by an unknown mode of action (bleacher—unknown target, group F3 of HRAC classification).

According to a further embodiment of the invention the compositions contain at least one EPSP synthase inhibitor (herbicide b6). The herbicidal activity of these compounds is based on the inhibition of enolpyruvyl shikimate 3-phosphate synthase, and thus on the inhibition of the amino acid biosynthesis in plants. These inhibitors belong to the group G of the HRAC classification system.

According to a further embodiment of the invention the compositions contain at least one glutamine synthetase inhibitor (herbicide b7). The herbicidal activity of these compounds is based on the inhibition of glutamine synthetase, and thus on the inhibition of the aminoacid biosynthesis in plants. These inhibitors belong to the group H of the HRAC classification system.

According to an further embodiment of the invention the compositions contain at least one DHP synthase inhibitor (herbicide b8). The herbicidal activity of these compounds is based on the inhibition of 7,8-dihydropteroate synthase. These inhibitors belong to the group I of the HRAC classification system.

According to a further embodiment of the invention the compositions contain at least one mitosis inhibitor (herbicide b9). The herbicidal activity of these compounds is based on the disturbance or inhibition of microtubule formation or organization, and thus on the inhibition of mitosis. These inhibitors belong to the groups K1 and K2 of the HRAC classification system. Among these, compounds of the group K1, in particular dinitroanilines, are preferred.

According to a further embodiment of the invention the compositions contain at least one VLCFA inhibitor (herbicide b10). The herbicidal activity of these compounds is based on the inhibition of the synthesis of very long chain fatty acids and thus on the disturbance or inhibition of cell division in plants. These inhibitors belong to the group K3 of the HRAC classification system.

According to an further embodiment of the invention the compositions contain at least one cellulose biosynthesis inhibitor (herbicide b11). The herbicidal activity of these compounds is based on the inhibition of the biosynthesis of cellulose and thus on the inhibition of the synthesis of cell walls in plants. These inhibitors belong to the group L of the HRAC classification system.

According to a further embodiment of the invention the compositions contain at least one decoupler herbicide (herbicide b12). The herbicidal activity of these compounds is based on the disruption of the cell membrane. These inhibitors belong to the group M of the HRAC classification system.

According to a further embodiment of the invention the compositions contain at least one auxinic herbicide (herbicide b13). These include compounds that mimic auxins, i.e. plant hormones, and affect the growth of the plants. These compounds belong to the group O of the HRAC classification system.

According to a further embodiment of the invention the compositions contain at least one auxin transport inhibitor (herbicide b14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http://www.plantprotection.org/hrac/MOA.html).

Preference is given to those compositions according to the present invention comprising at least one herbicide B selected from herbicides of class b1, b6, b9, b10 and b11.

Preference is also given to those compositions according to the present invention comprising at least one herbicide B selected from herbicides of class b2, b3, b4, b5, b6, b9 and b10.

Specific preference is given to those compositions according to the present invention which comprise at least one herbicide B selected from the herbicides of class b4, b6 b9 and b10.

Particular preference is given to those compositions according to the present invention which comprise at least one herbicide B selected from the herbicides of class b4, b6 and b10.

Examples of herbicides B which can be used in combination with the diaminitriazine compounds of formula (I) according to the present invention are:

b1) from the group of the lipid biosynthesis inhibitors:

ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2",4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2",4'-Dichloro -4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;
among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100; Sumitomo; LS 5296489), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 4061013), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (LS 567 0033=F2-Flumioxazin), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0) (LS 568 1323=Uracil-F2-PPO), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3) (Isagro, IR6396), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4) (FMC Trifluoromethyluracil);

b5) from the group of the bleacher herbicides:
PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquintrione, isoxaflutole, mesotrione, pyrasulfotole, pyrazolynate, pyrazoxyfen, sulcotrione, tefuryltrione, tembotrione, tolpyralate, topramezone, bleacher, unknown target: aclonifen, amitrole and flumeturon;

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II..1, II.2, II.3, II.4, II.5, II.6, II.7, II.8 and II.9

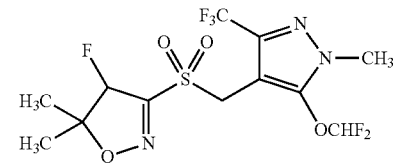

II.1

-continued

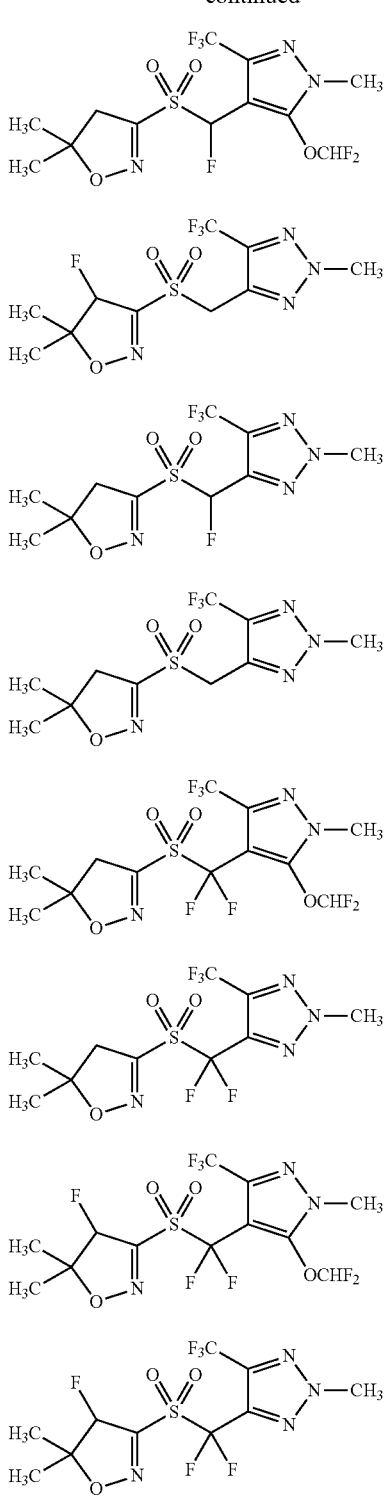

the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:
chlorthiamid, dichlobenil, flupoxam, indaziflam, isoxaben, triaziflam and 1-cyclohexyl-5-pentafluorphenyloxy-1⁴-[1,2,4,6]thiatriazin-3-ylamine (CAS 175899-01-1);

b12) from the group of the decoupler herbicides:
dinoseb, dinoterb and DNOC and its salts;

b13) from the group of the auxinic herbicides:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8 DOW, LS 566509); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor");

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3 Mitsui; SW-065; H-965) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preferred herbicides B that can be used in combination with the diaminotriazine compounds of the formula (I) according to the present invention are:

b1) from the group of the lipid biosynthesis inhibitors:
clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1¹-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2",4'-dichloro-4-cyclopropyl-[1,1'- biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-ylcarbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-ylcarbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-ylcarbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-ylcarbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:
ametryn, amicarbazone, atrazine, bentazon, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors:
acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen, pyraflufen-ethyl, saflufenacil, sulfentrazone, tiafenacil, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100; Sumitomo; LS 5296489), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7) (LS 4061013), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (LS 567 0033=F2-Flumioxazin); 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0) (LS 568 1323=Uracil-F2-PPO), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4) (FMC Trifluoromethyluracil);

b5) from the group of the bleacher herbicides:
aclonifen, amitrole, beflubutamid, benzobicyclon, bicyclopyrone, clomazone, diflufenican, fenquintrione, flumeturon, flurochloridone, flurtamone, isoxaflutole, mesotrione, norflurazon, picolinafen, pyrasulfotole, pyrazolynate, sulcotrione, tefuryltrione, tembotrione, tolpyralate, topramezone and 4-(3-trifluoromethylphenoxy)-2-(4-trifluoromethylphenyl)pyrimidine (CAS 180608-33-7);

b6) from the group of the EPSP synthase inhibitors:
glyphosate, glyphosate-isopropylammonium, glyphosate-potassium and glyphosate-trimesium (sulfosate);

b7) from the group of the glutamine synthase inhibitors:
glufosinate, glufosinate-P, glufosinate-ammonium;

b8) from the group of the DHP synthase inhibitors:
asulam;

b9) from the group of the mitosis inhibitors:
benfluralin, dithiopyr, ethalfluralin, flamprop, flamprop-isopropyl, flamprop-methyl, flamprop-M-isopropyl, flamprop-M-methyl, oryzalin, pendimethalin, thiazopyr and trifluralin;

b10) from the group of the VLCFA inhibitors:
acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b13) from the group of the auxinic herbicides:
2,4-D and its salts and esters, aminocyclopyrachlor and its salts and esters, aminopyralid and its salts such as aminopyralid-dimethylammonium, aminopyralid-tris (2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8 DOW, LS 566509), MCPA and its salts and esters, MCPB and its salts and esters, mecoprop-P and its salts and esters, picloram and its salts and esters, quinclorac, quinmerac, triclopyr and its salts and esters, 4-amino- 3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor");

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3 Mitsui; SW-065; H-965) and its salts and esters, dalapon, difenzoquat, difenzoquat-metilsulfate, DSMA, dymron (=daimuron), indanofan, metam, methylbromide, MSMA, oxaziclomefone, pyributicarb and tridiphane.

Particularly preferred herbicides B that can be used in combination with the diaminotriazine compounds of the formula (I) according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2'',4'-Dichloro -4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: flumioxazin, oxyfluorfen, pyraflufen, pyraflufen-ethyl, saflufenacil, sulfentrazone, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy] acetate (CAS 353292-31-6; S-3100; Sumitomo; LS 5296489), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7) (LS 4061013) , 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (LS 567 0033=F2-Flumioxazin), and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0) (LS 568 1323=Uracil-F2-PPO);

b5) from the group of the bleacher herbicides: amitrole, bicyclopyrone, clomazone, diflufenican, fenquintrione, flumeturon, flurochloridone, isoxaflutole, mesotrione, picolinafen, sulcotrione, tefuryltrione, tembotrione, tolpyralate and topramezone;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: indaziflam, isoxaben and triaziflam;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, halauxifen, halauxifen-methyl, quinclorac, quinmerac, 4-amino-3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor");

b14) from the group of the auxin transport inhibitors: diflufenzopyr and diflufenzopyr-sodium, b15) from the group of the other herbicides: dymron (=daimuron), indanofan, oxaziclomefone.

Particularly preferred herbicides B are the herbicides B as defined above; in particular the herbicides B.1-B.196 listed below in table B:

TABLE B

| | Herbicide B |
|---|---|
| B.1 | clethodim |
| B.2 | clodinafop-propargyl |
| B.3 | cycloxydim |

TABLE B-continued

Herbicide B

| | | |
|---|---|---|
| B.4 | cyhalofop-butyl | |
| B.5 | fenoxaprop-ethyl | |
| B.6 | fenoxaprop-P-ethyl | |
| B.7 | metamifop | |
| B.8 | pinoxaden | |
| B.9 | profoxydim | |
| B.10 | sethoxydim | |
| B.11 | tepraloxydim | |
| B.12 | tralkoxydim | |
| B.13 | esprocarb | |
| B.14 | ethofumesate | |
| B.15 | molinate | |
| B.16 | prosulfocarb | |
| B.17 | thiobencarb | |
| B.18 | triallate | |
| B.19 | bensulfuron-methyl | |
| B.20 | bispyribac-sodium | |
| B.21 | cloransulam-methyl | |
| B.22 | chlorsulfuron | |
| B.23 | clorimuron | |
| B.24 | cyclosulfamuron | |
| B.25 | diclosulam | |
| B.26 | florasulam | |
| B.27 | flumetsulam | |
| B.28 | flupyrsulfuron-methyl-sodium | |
| B.29 | foramsulfuron | |
| B.30 | imazamox | |
| B.31 | imazamox-ammonium | |
| B.32 | imazapic | |
| B.33 | imazapic-ammonium | |
| B.34 | imazapic-isopropylammonium | |
| B.35 | imazapyr | |
| B.36 | imazapyr-ammonium | |
| B.37 | imazapyr-isopropylammonium | |
| B.38 | imazaquin | |
| B.39 | imazaquin-ammonium | |
| B.40 | imazethapyr | |
| B.41 | imazethapyr-ammonium | |
| B.42 | imazethapyr-isopropylammonium | |
| B.43 | imazosulfuron | |
| B.44 | iodosulfuron-methyl-sodium | |
| B.45 | iofensulfuron | |
| B.46 | iofensulfuron-sodium | |
| B.47 | mesosulfuron-methyl | |
| B.48 | metazosulfuron | |
| B.49 | metsulfuron-methyl | |
| B.50 | metosulam | |
| B.51 | nicosulfuron | |
| B.52 | penoxsulam | |
| B.53 | propoxycarbazon-sodium | |
| B.54 | pyrazosulfuron-ethyl | |
| B.55 | pyribenzoxim | |
| B.56 | pyriftalid | |
| B.57 | pyroxsulam | |
| B.58 | propyrisulfuron | |
| B.59 | rimsulfuron | |
| B.60 | sulfosulfuron | |
| B.61 | thiencarbazone-methyl | |
| B.62 | thifensulfuron-methyl | |
| B.63 | tribenuron-methyl | |
| B.64 | tritosulfuron | |
| B.65 | triafamone | |
| B.66 | ametryne | |
| B.67 | atrazine | |
| B.68 | bentazon | |
| B.69 | bromoxynil | |
| B.70 | bromoxynil-octanoate | |
| B.71 | bromoxynil-heptanoate | |
| B.72 | bromoxynil-potassium | |
| B.73 | diuron | |
| B.74 | fluometuron | |
| B.75 | hexazinone | |
| B.76 | isoproturon | |
| B.77 | linuron | |
| B.78 | metamitron | |
| B.79 | metribuzin | |
| B.80 | propanil | |
| B.81 | simazin | |
| B.82 | terbuthylazine | |
| B.83 | terbutryn | |
| B.84 | paraquat-dichloride | |
| B.85 | acifluorfen | |
| B.86 | butafenacil | |
| B.87 | carfentrazone-ethyl | |
| B.88 | flumioxazin | |
| B.89 | fomesafen | |
| B.90 | oxadiargyl | |
| B.91 | oxyfluorfen | |
| B.92 | pyraflufen | |
| B.93 | pyraflufen-ethyl | |
| B.94 | saflufenacil | |
| B.95 | sulfentrazone | |
| B.96 | trifludimoxazin (BAS 850 H) | |
| B.97 | ethyl [3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetate (CAS 353292-31-6) Sumitomo; LS 5296489 | |
| B.98 | benzobicyclon | |
| B.99 | bicyclopyrone | |
| B.100 | clomazone | |
| B.101 | diflufenican | |
| B.102 | flurochloridone | |
| B.103 | isoxaflutole | |
| B.104 | mesotrione | |
| B.105 | norflurazone | |
| B.106 | picolinafen | |
| B.107 | sulcotrione | |
| B.108 | tefuryltrione | |
| B.109 | tembotrione | |
| B.110 | tolpyralate | |
| B.111 | topramezone | |
| B.112 | topramezone-sodium | |
| B.113 | amitrole | |
| B.114 | fluometuron | |
| B.115 | fenquintrione | |
| B.116 | glyphosate | |
| B.117 | glyphosate-ammonium | |
| B.118 | glyphosate-dimethylammonium | |
| B.119 | glyphosate-isopropylammonium | |
| B.120 | glyphosate-trimesium (sulfosate) | |
| B.121 | glyphosate-potassium | |
| B.122 | glufosinate | |
| B.123 | glufosinate-ammonium | |
| B.124 | glufosinate-P | |
| B.125 | glufosinate-P-ammonium | |
| B.126 | pendimethalin | |
| B.127 | trifluralin | |
| B.128 | acetochlor | |
| B.129 | butachlor | |
| B.130 | cafenstrole | |
| B.131 | dimethenamid-P | |
| B.132 | fentrazamide | |
| B.133 | flufenacet | |
| B.134 | mefenacet | |
| B.135 | metazachlor | |
| B.136 | metolachlor | |
| B.137 | S-metolachlor | |
| B.138 | pretilachlor | |
| B.139 | fenoxasulfone | |
| B.140 | indaziflam | |
| B.141 | isoxaben | |
| B.142 | triaziflam | |
| B.143 | ipfencarbazone | |
| B.144 | pyroxsulfone | |
| B.145 | 2,4-D | |
| B.146 | 2,4-D-isobutyl | |
| B.147 | 2,4-D-dimethylammonium | |
| B.148 | 2,4-D-N,N-trimethylethanolammonium | |
| B.149 | aminopyralid | |
| B.150 | aminopyralid-methyl | |
| B.151 | aminopyralid-dimethyl-ammonium | |
| B.152 | aminopyralid-tris(2-hydroxypropyl)ammonium | |
| B.153 | clopyralid | |
| B.154 | clopyralid-methyl | |
| B.155 | clopyralid-olamine | |
| B.156 | dicamba | |

TABLE B-continued

| | Herbicide B |
|---|---|
| B.157 | dicamba-butotyl |
| B.158 | dicamba-diglycolamine |
| B.159 | dicamba-dimethylammonium |
| B.160 | dicamba-diolamine |
| B.161 | dicamba-isopropylammonium |
| B.162 | dicamba-potassium |
| B.163 | dicamba-sodium |
| B.164 | dicamba-trolamine |
| B.165 | dicamba-N,N-bis-(3-aminopropyl)methylamine |
| B.166 | dicamba-diethylenetriamine |
| B.167 | fluroxypyr |
| B.168 | fluroxypyr-meptyl |
| B.169 | halauxifen |
| B.170 | halauxifen-methyl |
| B.171 | MCPA |
| B.172 | MCPA-2-ethylhexyl |
| B.173 | MCPA-dimethylammonium |
| B.174 | quinclorac |
| B.175 | quinclorac-dimethylammonium |
| B.176 | quinmerac |
| B.177 | quinmerac-dimethylammonium |
| B.178 | 4-amino-3-chloro-6-(4-chloro-2-fluoro-3-methoxyphenyl)-5-fluoropyridine-2-carboxylic acid (DOW, "Rinskor-acid") |
| B.179 | benzyl 4-amino-3-chloro-6-(4-chloro-2-fluoro-3-methoxy-phenyl)-5-fluoropyridine-2-carboxylate (CAS 1390661-72-9) (DOW, "Rinskor") |
| B.180 | aminocyclopyrachlor |
| B.181 | aminocyclopyrachlor-potassium |
| B.182 | aminocyclopyrachlor-methyl |
| B.183 | diflufenzopyr |
| B.184 | diflufenzopyr-sodium |
| B.185 | dymron |
| B.186 | indanofan |
| B.187 | oxaziclomefone |
| B.188 | II.1 |
| B.189 | II.2 |
| B.190 | II.3 |
| B.191 | II.4 |
| B.192 | II.5 |
| B.193 | II.6 |
| B.194 | II.7 |
| B.195 | II.8 |
| B.196 | II.9 |

In another embodiment of the present invention the compositions according to the present invention comprise at least one diaminotriazine compound of formula (I) and at least one safener C.

Safeners are chemical compounds which prevent or reduce damage on useful plants without having a major impact on the herbicidal action of the herbicidal active components of the present compositions towards unwanted plants. They can be applied either before sowings (e.g. on seed treatments, shoots or seedlings) or in the pre-emergence application or post-emergence application of the useful plant. The safeners and the diaminotriazine compound of formula (I) and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro-[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C are benoxacor, cloquintocet, cyprosulfamide, dichlormid, fenchlorazole, fenclorim, furilazole, isoxadifen, mefenpyr, naphtalic anhydride, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | N-(2-Methoxybenzoyl)-4-[(methylaminocarbonyl)amino]benzenesulfonamide (CAS 129531-12-0) |

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)-ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl)ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinmerac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises at least one, preferably exactly one compound of formula (I) and as component B at least one, preferably exactly one, herbicide B.

According to another preferred embodiment of the invention, the composition comprises at least one, preferably exactly one compound of formula (I) and at least two, preferably exactly two, herbicides B different from each other.

According to another preferred embodiment of the invention, the composition comprises at least one, preferably exactly one compound of formula (I) and at least three, preferably exactly three, herbicides B different from each other.

According to another preferred embodiment of the invention, the composition comprises at least one, preferably exactly one compound of formula (I) and as component C at least one, preferably exactly one, safener C.

According to another preferred embodiment of the invention, the composition comprises at least one, preferably exactly one compound of formula (I) as component B at least one, preferably exactly one, herbicide B, and as component C at least one, preferably exactly one safener C.

According to another preferred embodiment of the invention, the composition comprises at least one, preferably exactly one compound of formula (I), at least two, preferably exactly two herbicides B different from each other, and as component C at least one, preferably exactly one, safener C.

According to another preferred embodiment of the invention, the composition comprises at least one, preferably exactly one compound of formula (I) at least three, preferably exactly three herbicides B different from each other, and as component C at least one, preferably exactly one, safener C.

According to another preferred embodiment of the invention, the composition comprises, in addition to a compounds of formula (I), at least one and especially exactly one herbicidally active compound from group b1), in particular selected from the group consisting of clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate.

According to another preferred embodiment of the invention, the composition comprises, in addition to a compounds of formula (I), at least one and especially exactly one herbicidally active compound from group b2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

According to another preferred embodiment of the invention, the composition comprises, in addition to a compounds of formula (I), at least one and especially exactly one herbicidally active compound from group b3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

According to another preferred embodiment of the invention, the composition comprises, in addition to a compounds of formula (I), at least one and especially exactly one herbicidally active compound from group b4), in particular selected from the group consisting of flumioxazin, oxyfluorfen, pyraflufen, pyraflufen-ethyl, saflufenacil, sulfentrazone, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100; Sumitomo; LS 5296489) , 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7) LS 4061013), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (L5567 0033 =F2-Flumioxazin) and 1-methyl-6-trifluoro-methyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0) (LS 568 1323 =Uracil-F2-PPO).

According to another preferred embodiment of the invention, the composition comprises, in addition to a compounds of formula (I), at least one and especially exactly one herbicidally active compound from group b5), in particular selected from flurochloridone, isoxaflutole, mesotrione, picolinafen, sulcotrione, tefuryltrione, tembotrione, tolpyralate and topramezone.

According to another preferred embodiment of the invention, the composition comprises, in addition to a compounds of formula (I), at least one and especially exactly one herbicidally active compound from group b6), in particular selected from the group consisting of glyphosate, glyphosate-isopropylammonium and glyphosate-trimesium (sulfosate).

According to another preferred embodiment of the invention, the composition comprises, in addition to a compounds of formula (I), at least one and especially exactly one herbicidally active compound from group b7), in particular selected from the group consisting of glufosinate, glufosinate-P and glufosinate-ammonium.

According to another preferred embodiment of the invention, the composition comprises, in addition to a compounds of formula (I), at least one and especially exactly one herbicidally active compound from group b9), in particular selected from the group consisting of pendimethalin and trifluralin.

According to another preferred embodiment of the invention, the composition comprises, in addition to a compounds of formula (I), at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone. Likewise, preference is given to compositions comprising in addition to a compounds of formula (I), at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to a compounds of formula (I), at least one and especially exactly one herbicidally active compound from group b11), in particular indaziflam, isoxaben and triaziflam.

According to another preferred embodiment of the invention, the composition comprises, in addition to a compounds of formula (I), at least one and especially exactly one herbicidally active compound from group b13), in particular selected from the group consisting of 2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, fluroxypyr-meptyl, halauxifen, halauxifen-methyl, quinclorac, quinmerac, 4-amino-3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor").

According to another preferred embodiment of the invention, the composition comprises, in addition to a compounds of formula (I), at least one and especially exactly one herbicidally active compound from group b14), in particular selected from the group consisting of diflufenzopyr and diflufenzopyr-sodium.

According to another preferred embodiment of the invention, the composition comprises, in addition to a compounds of formula (I), at least one and especially exactly one herbicidally active compound from group b15), in particular selected from the group consisting of dymron (=daimuron), indanofan and oxaziclomefone.

According to another preferred embodiment of the invention, the composition comprises, in addition to a compounds of formula (I), at least one and especially exactly one safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Further preferred embodiments relate to ternary compositions which correspond to the binary compositions mentioned above and additionally comprise a safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, for example 1, 2 or 3, active compounds of the formula (I) and either one or more, for example 1, 2 or 3, herbicides B or one or more safeners C.

Correspondingly, the term "ternary compositions" includes compositions comprising one or more, for example 1, 2 or 3, active compounds of the formula (I), one or more, for example 1, 2 or 3, herbicides B and one or more, for example 1, 2 or 3, safeners C.

In binary compositions comprising at least one compound of the formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one compound of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given above, in particular within the preferred limits. Particularly preferred are the compositions mentioned below comprising the compounds of formula (I) as defined and the substance(s) as defined in the respective row of table 1;

especially preferred comprising as only herbicidal active compounds the compounds of formula (I) as defined and the substance(s) as defined in the respective row of table 1;

most preferably comprising as only active compounds the compounds of formula I as defined and the substance(s) as defined in the respective row of table 1.

Particularly preferred are compositions 1.1 to 1.3545, comprising the compounds of formula (I) and the substance(s) as defined in the respective row of table 1:

The following combinations indicated by the code A-X.Y.Z represent particular embodiments of the invention:
A-1.1.1 to A-1.3344.3545, A-14.1.1 to A-14.3344.3545,
A-2.1.1 to A-2.3344.3545, A-15.1.1 to A-15.3344.3545,
A-3.1.1 to A-3.3344.3545, A-16.1.1 to A-16.3344.3545,
A-4.1.1 to A-4.3344.3545, A-17.1.1 to A-17.3344.3545,
A-5.1.1 to A-5.3344.3545, A-18.1.1 to A-18.3344.3545,
A-6.1.1 to A-6.3344.3545, A-19.1.1 to A-19.3344.3545,
A-7.1.1 to A-7.3344.3545, A-20.1.1 to A-20.3344.3545,
A-8.1.1 to A-8.3344.3545, A-21.1.1 to A-21.3344.3545, A-9.1.1 to A-9.3344.3545, A-22.1.1 to A-22.3344.3545,
A-10.1.1 to A-10.3344.3545, A-23.1.1 to A-23.3344.3545,
A-11.1.1 to A-11.3344.3545, A-24.1.1 to A-24.3344.3545,
A-12.1.1 to A-12.3344.3545, A-25.1.1 to A-25.3344.3545,
A-13.1.1 to A-13.3344.3545, A-26.1.1 to A-26.3344.3545,
A-27.1.1 to A-27.3344.3545, A-35.1.1 to A-35.3344.3545,
A-28.1.1 to A-28.3344.3545, A-36.1.1 to A-35.3344.3545,
A-29.1.1 to A-29.3344.3545, A-37.1.1 to A-37.3344.3545,
A-30.1.1 to A-30.3344.3545, A-38.1.1 to A-38.3344.3545,
A-31.1.1 to A-31.3344.3545, A-39.1.1 to A-39.3344.3545,
A-32.1.1 to A-32.3344.3545, A-40.1.1 to A-40.3344.3545,
A-33.1.1 to A-33.3344.3545, A-41.1.1 to A-40.3344.3545.
A-34.1.1 to A-34.3344.3545, In the above codes A-X refers to the numbers of tables A-1 to A.41. The integer Y refers to the row of table A, while the integer Z refers to the row of table 1 below. Hence, the code A-1.1.1 refers to the combination of the compound of formula I.a of table A-1, wherein $R^{b1}$, $R^{b2}$, $R^{b3}$, $R^{A1}$, $R^{A2}$ $Y^1$ and $Y^2$ are as defined in row 1 of table A, with the combination of the herbicide B and and the safener C are as defined in combination no. 1.1 of table 1.

The code A-12.2.41 refers to the combination of the compound of formula I.a of table A-12, wherein $R^{b1}$, $R^{b2}$, $R^{b3}$, $R^{A1}$, $R^{A2}$ $Y^1$ and $Y^2$ are as defined in row 2 of table A, with the combination of the herbicide B and and the safener C are as defined in combination no. 1.41 of table 1.

The code A-41.300. 3545 refers to the combination of the compound of formula I.a of table A-41, wherein $R^{b1}$, $R^{b2}$, $R^{b3}$, $R^{A1}$, $R^{A2}$ $Y^1$ and $Y^2$ are as defined in row 300 of table A, with the combination of the herbicide B and and the safener C are as defined in combination no. 1. 3545 of table 1.

Likewise the following combinations indicated by the code B-X.Y.Z represent particular embodiments of the invention:
B-1.1.1 to B-1.704.3545, B-17.1.1 to B-17.704.3545,
B-2.1.1 to B-2.704.3545, B-18.1.1 to B-18.704.3545,
B-3.1.1 to B-3.704.3545, B-19.1.1 to B-19.704.3545,
B-4.1.1 to B-4.704.3545, B-20.1.1 to B-20.704.3545,
B-5.1.1 to B-5.704.3545, B-21.1.1 to B-21.704.3545,
B-6.1.1 to B-6.704.3545, B-22.1.1 to B-22.704.3545,
B-7.1.1 to B-7.704.3545, B-23.1.1 to B-23.704.3545,
B-8.1.1 to B-8.704.3545, B-24.1.1 to B-24.704.3545,
B-9.1.1 to B-9.704.3545, B-25.1.1 to B-25.704.3545,
B-10.1.1 to B-10.704.3545, B-26.1.1 to B-26.704.3545,
B-11.1.1 to B-11.704.3545, B-27.1.1 to B-27.704.3545,
B-12.1.1 to B-12.704.3545, B-28.1.1 to B-28.704.3545,
B-13.1.1 to B-13.704.3545, B-29.1.1 to B-29.704.3545,
B-14.1.1 to B-14.704.3545, B-30.1.1 to B-30.704.3545,
B-15.1.1 to B-15.704.3545, B-31.1.1 to B-31.704.3545,
B-16.1.1 to B-16.704.3545, B-32.1.1 to B-32.704.3545,
B-33.1.1 to B-33.704.3545, B-39.1.1 to B-39.704.3545,
B-34.1.1 to B-34.704.3545, B-40.1.1 to B-40.704.3545,
B-35.1.1 to B-35.704.3545, B-41.1.1 to B-41.704.3545,
B-36.1.1 to B-35.704.3545,
B-37.1.1 to B-37.704.3545,
B-38.1.1 to B-38.704.3545, In the above codes B-X refers to the numbers of tables B-1 to B.41. The integer Y refers to the row of table B, while the integer Z refers to the row of table 1 below. Hence, the code B-1.1.1 refers to the combination of the compound of formula I.b of table B-1, wherein $R^{b1}$, $R^{b2}$, $R^{b3}$, $R^{A1}$, $R^{A2}$ and $R^c$ are as defined in row 1 of table B, with the combination of the herbicide B and and the safener C are as defined in combination no. 1.1 of table 1. The code B-12.2.41 refers to the combination of the compound of formula I.b of table B-12, wherein $R^{b1}$, $R^{b2}$, $R^{b3}$, $R^{A1}$, $R^{A2}$ and $R^c$ are as defined in row 2 of table B, with the combination of the herbicide B and and the safener C are as defined in combination no. 1.41 of table 1. The code B-41.300. 3545 refers to the combination of the compound of formula I.b of table B-41, wherein $R^{b1}$, $R^{b2}$, $R^{b3}$, $R^{A1}$, $R^{A2}$ and $R^c$ are as defined in row 300 of table B, with the combination of the herbicide B and and the safener C are as defined in combination no. 1. 3545 of table 1.

Likewise the following combinations indicated by the code C-X.Y.Z represent particular embodiments of the invention:
C-1.1.1 to C-1.176.3545, C-21.1.1 to C-21.176.3545,
C-2.1.1 to C-2.176.3545, C-22.1.1 to C-22.176.3545,
C-3.1.1 to C-3.176.3545, C-23.1.1 to C-23.176.3545,
C-4.1.1 to C-4.176.3545, C-24.1.1 to C-24.176.3545,
C-5.1.1 to C-5.176.3545, C-25.1.1 to C-25.176.3545,
C-6.1.1 to C-6.176.3545, C-26.1.1 to C-26.176.3545,
C-7.1.1 to C-7.176.3545, C-27.1.1 to C-27.176.3545,
C-8.1.1 to C-8.176.3545, C-28.1.1 to C-28.176.3545,
C-9.1.1 to C-9.176.3545, C-29.1.1 to C-29.176.3545,
C-10.1.1 to C-10.176.3545, C-30.1.1 to C-30.176.3545,
C-11.1.1 to C-11.176.3545, C-31.1.1 to C-31.176.3545,
C-12.1.1 to C-12.176.3545, C-32.1.1 to C-32.176.3545,
C-13.1.1 to C-13.176.3545, C-33.1.1 to C-33.176.3545,
C-14.1.1 to C-14.176.3545, C-34.1.1 to C-34.176.3545,
C-15.1.1 to C-15.176.3545, C-35.1.1 to C-35.176.3545,
C-16.1.1 to C-16.176.3545, C-36.1.1 to C-35.176.3545,
C-17.1.1 to C-17.176.3545, C-37.1.1 to C-37.176.3545,
C-18.1.1 to C-18.176.3545, C-38.1.1 to C-38.176.3545,
C-19.1.1 to C-19.176.3545, C-39.1.1 to C-39.176.3545,
C-20.1.1 to C-20.176.3545, C-40.1.1 to C-40.176.3545,
C-41.1.1 to C-41.176.3545.

In the above codes C-X refers to the numbers of tables C-1 to C-41. The integer Y refers to the row of table C, while the integer Z refers to the row of table 1 below. Hence, the code C-1.1.1 refers to the combination of the compound of formula I.c of table C-1, wherein $R^{b1}$, $R^{b2}$ and $R^{b3}$ are as defined in row 1 of table C, with the combination of the herbicide B and and the safener C are as defined in combination no. 1.1 of table 1. The code C-12.2.41 refers to the combination of the compound of formula I.c of table C-12, wherein $R^{b1}$, $R^{b2}$ and $R^{b3}$ are as defined in row 2 of table C, with the combination of the herbicide B and and the safener C are as defined in combination no. 1.41 of table 1. The code C-41.176. 3545 refers to the combination of the compound of formula I.c of table C-41, wherein $R^{b1}$, $R^{b2}$ and $R^{b3}$ are as defined in row 176 of table C, with the combination of the herbicide B and and the safener C are as defined in combination no. 1. 3545 of table 1.

Likewise the following combinations indicated by the code D-X.Y.Z represent particular embodiments of the invention:
D-1.1.1 to D-1.176.3545, D-23.1.1 to D-23.176.3545,
D-2.1.1 to D-2.176.3545, D-24.1.1 to D-24.176.3545,
D-3.1.1 to D-3.176.3545, D-25.1.1 to D-25.176.3545,
D-4.1.1 to D-4.176.3545, D-26.1.1 to D-26.176.3545,
D-5.1.1 to D-5.176.3545, D-27.1.1 to D-27.176.3545,
D-6.1.1 to D-6.176.3545, D-28.1.1 to D-28.176.3545,
D-7.1.1 to D-7.176.3545, D-29.1.1 to D-29.176.3545,
D-8.1.1 to D-8.176.3545, D-30.1.1 to D-30.176.3545,
D-9.1.1 to D-9.176.3545, D-31.1.1 to D-31.176.3545,
D-10.1.1 to D-10.176.3545, D-32.1.1 to D-32.176.3545,
D-11.1.1 to D-11.176.3545, D-33.1.1 to D-33.176.3545,
D-12.1.1 to D-12.176.3545, D-34.1.1 to D-34.176.3545,
D-13.1.1 to D-13.176.3545, D-35.1.1 to D-35.176.3545,
D-14.1.1 to D-14.176.3545, D-36.1.1 to D-35.176.3545,
D-15.1.1 to D-15.176.3545, D-37.1.1 to D-37.176.3545, D-16.1.1 to D-16.176.3545, D-38.1.1 to D-38.176.3545,
D-17.1.1 to D-17.176.3545, D-39.1.1 to D-39.176.3545,
D-18.1.1 to D-18.176.3545, D-40.1.1 to D-40.176.3545,
D-19.1.1 to D-19.176.3545, D-41.1.1 to D-41.176.3545,
D-20.1.1 to D-20.176.3545,
D-21.1.1 to D-21.176.3545,
D-22.1.1 to D-22.176.3545, In the above codes D-X refers to the numbers of tables D-1 to D-41. The integer Y refers to the row of table C, while the integer Z refers to the row of table 1 below.

Hence, the code D-1.1.1 refers to the combination of the compound of formula I.d of table D-1, wherein $R^{b1}$, $R^{b2}$ and $R^{b3}$ are as defined in row 1 of table C, with the combination of the herbicide B and and the safener C are as defined in combination no. 1.1 of table 1. The code D-12.2.41 refers to the combination of the compound of formula I.d of table D-12, wherein $R^{b1}$, $R^{b2}$ and $R^{b3}$ are as defined in row 2 of table C, with the combination of the herbicide B and and the safener C are as defined in combination no. 1.41 of table 1.The code D-41.176.3545 refers to the combination of the compound of formula I.d of table D-41, wherein $R^{b1}$, $R^{b2}$ and $R^{b3}$ are as defined in row 176 of table C, with the combination of the herbicide B and and the safener C are as defined in combination no. 1. 3545 of table 1.

Likewise the following combinations indicated by the code E-X.Y.Z represent particular embodiments of the invention:
E-1.1.1 to E-1.176.3545, E-23.1.1 to E-23.176.3545,
E-2.1.1 to E-2.176.3545, E-24.1.1 to E-24.176.3545,
E-3.1.1 to E-3.176.3545, E-25.1.1 to E-25.176.3545,
E-4.1.1 to E-4.176.3545, E-26.1.1 to E-26.176.3545,
E-5.1.1 to E-5.176.3545, E-27.1.1 to E-27.176.3545,
E-6.1.1 to E-6.176.3545, E-28.1.1 to E-28.176.3545,
E-7.1.1 to E-7.176.3545, E-29.1.1 to E-29.176.3545,
E-8.1.1 to E-8.176.3545, E-30.1.1 to E-30.176.3545,
E-9.1.1 to E-9.176.3545, E-31.1.1 to E-31.176.3545,
E-10.1.1 to E-10.176.3545, E-32.1.1 to E-32.176.3545,
E-11.1.1 to E-11.176.3545, E-33.1.1 to E-33.176.3545,
E-12.1.1 to E-12.176.3545, E-34.1.1 to E-34.176.3545,
E-13.1.1 to E-13.176.3545, E-35.1.1 to E-35.176.3545,
E-14.1.1 to E-14.176.3545, E-36.1.1 to E-35.176.3545,
E-15.1.1 to E-15.176.3545, E-37.1.1 to E-37.176.3545,
E-16.1.1 to E-16.176.3545, E-38.1.1 to E-38.176.3545,
E-17.1.1 to E-17.176.3545, E-39.1.1 to E-39.176.3545,
E-18.1.1 to E-18.176.3545, E-40.1.1 to E-40.176.3545,
E-19.1.1 to E-19.176.3545, E-41.1.1 to E-41.176.3545,
E-20.1.1 to E-20.176.3545,
E-21.1.1 to E-21.176.3545,
E-22.1.1 to E-22.176.3545, In the above codes E-X refers to the numbers of tables E-1 to E-41. The integer Y refers to the row of table C, while the integer Z refers to the row of table 1 below. Hence, the code E-1.1.1 refers to the combination of the compound of formula I.e of table E-1, wherein $R^{b1}$, $R^{b2}$ and $R^{b3}$ are as defined in row 1 of table C, with the combination of the herbicide B and and the safener C are as defined in combination no. 1.1 of table 1. The code E-12.2.41 refers to the combination of the compound of formula I.e of table E-12, wherein $R^{b1}$, $R^{b2}$ and $R^{b3}$ are as defined in row 2 of table C, with the combination of the herbicide B and and the safener C are as defined in combination no. 1.41 of table 1. The code E-41.176. 3545 refers to the combination of the compound of formula I.e of table E-41, wherein $R^{b1}$, $R^{b2}$ and $R^{b3}$ are as defined in row 176 of table C, with the combination of the herbicide B and and the safener C are as defined in combination no. 1. 3545 of table 1.

Likewise the following combinations indicated by the code F-X.Y.Z represent particular embodiments of the invention:
F-1.1.1 to F-1.176.3545, F-23.1.1 to F-23.176.3545,
F-2.1.1 to F-2.176.3545, F-24.1.1 to F-24.176.3545,
F-3.1.1 to F-3.176.3545, F-25.1.1 to F-25.176.3545,
F-4.1.1 to F-4.176.3545, F-26.1.1 to F-26.176.3545,
F-5.1.1 to F-5.176.3545, F-27.1.1 to F-27.176.3545,
F-6.1.1 to F-6.176.3545, F-28.1.1 to F-28.176.3545,
F-7.1.1 to F-7.176.3545, F-29.1.1 to F-29.176.3545,
F-8.1.1 to F-8.176.3545, F-30.1.1 to F-30.176.3545,
F-9.1.1 to F-9.176.3545, F-31.1.1 to F-31.176.3545,
F-10.1.1 to F-10.176.3545, F-32.1.1 to F-32.176.3545,
F-11.1.1 to F-11.176.3545, F-33.1.1 to F-33.176.3545,
F-12.1.1 to F-12.176.3545, F-34.1.1 to F-34.176.3545,
F-13.1.1 to F-13.176.3545, F-35.1.1 to F-35.176.3545,
F-14.1.1 to F-14.176.3545, F-36.1.1 to F-35.176.3545,
F-15.1.1 to F-15.176.3545, F-37.1.1 to F-37.176.3545,
F-16.1.1 to F-16.176.3545, F-38.1.1 to F-38.176.3545,
F-17.1.1 to F-17.176.3545, F-39.1.1 to F-39.176.3545,
F-18.1.1 to F-18.176.3545, F-40.1.1 to F-40.176.3545,
F-19.1.1 to F-19.176.3545, F-41.1.1 to F-41.176.3545,
F-20.1.1 to F-20.176.3545,
F-21.1.1 to F-21.176.3545,
F-22.1.1 to F-22.176.3545, In the above codes F-X refers to the numbers of tables F-1 to F-41. The integer Y refers to the row of table C, while the integer Z refers to the row of table 1 below. Hence, the code F-1.1.1 refers to the combination of the compound of formula I.e of table F-1, wherein $R^{b1}$, $R^{b2}$ and $R^{b3}$ are as defined in row 1 of table C, with the combination of the herbicide B and and the safener C are as defined in combination no. 1.1 of table 1. The code F-12.2.41 refers to the combination of the compound of formula I.e of table F-12, wherein $R^{b1}$, $R^{b2}$ and $R^{b3}$ are as defined in row 2 of table C, with the combination of the herbicide B and and the safener C are as defined in combination no. 1.41 of table 1. The code F-41.176. 3545 refers to the combination of the compound of formula I.e of table F-41, wherein $R^{b1}$, $R^{b2}$ and $R^{b3}$ are as defined in row 176 of table C, with the combination of the herbicide B and and the safener C are as defined in combination no. 1. 3545 of table 1.

Likewise the following combinations indicated by the code G-X.Y.Z represent particular embodiments of the invention:
G-1.1.1 to G-1.9.3545, G-23.1.1 to G-23.9.3545,
G-2.1.1 to G-2.9.3545, G-24.1.1 to G-24.9.3545,
G-3.1.1 to G-3.9.3545, G-25.1.1 to G-25.9.3545,
G-4.1.1 to G-4.9.3545, G-26.1.1 to G-26.9.3545,
G-5.1.1 to G-5.9.3545, G-27.1.1 to G-27.9.3545,
G-6.1.1 to G-6.9.3545, G-28.1.1 to G-28.9.3545,
G-7.1.1 to G-7.9.3545, G-29.1.1 to G-29.9.3545,
G-8.1.1 to G-8.9.3545, G-30.1.1 to G-30.9.3545,
G-9.1.1 to G-9.9.3545, G-31.1.1 to G-31.9.3545,
G-10.1.1 to G-10.9.3545, G-32.1.1 to G-32.9.3545,
G-11.1.1 to G-11.9.3545, G-33.1.1 to G-33.9.3545,
G-12.1.1 to G-12.9.3545, G-34.1.1 to G-34.9.3545,
G-13.1.1 to G-13.9.3545, G-35.1.1 to G-35.9.3545,
G-14.1.1 to G-14.9.3545, G-36.1.1 to G-35.9.3545,
G-15.1.1 to G-15.9.3545, G-37.1.1 to G-37.9.3545,
G-16.1.1 to G-16.9.3545, G-38.1.1 to G-38.9.3545,
G-17.1.1 to G-17.9.3545, G-39.1.1 to G-39.9.3545,
G-18.1.1 to G-18.9.3545, G-40.1.1 to G-40.9.3545,
G-19.1.1 to G-19.9.3545, G-41.1.1 to G-41.9.3545,
G-20.1.1 to G-20.9.3545,
G-21.1.1 to G-21.9.3545,
G-22.1.1 to G-22.9.3545, In the above codes G-X refers to the numbers of tables G-1 to G-41. The integer Y refers to the row of table D, while the integer Z refers to the row of table 1 below. Hence, the code G-1.1.1 refers to the combination of the compound of formula I.f of table G-1, wherein $R^1$ and $R^2$ are as defined in row 1 of table D, with the combination of the herbicide B and and the safener C are as defined in combination no. 1.1 of table 1.

The code G-9.2.41 refers to the combination of the compound of formula I.f of table G-9, wherein $R^1$ and $R^2$ are as defined in row 2 of table D, with the combination of the herbicide B and and the safener C are as defined in combination no. 1.41 of table 1.

The code G-41.9. 3545 refers to the combination of the compound of formula I.f of table G-41, wherein $R^1$ and $R^2$ are as defined in row 9 of table D, with the combination of the herbicide B and and the safener C are as defined in combination no. 1. 3545 of table 1.

TABLE 1

(compositions 1.1 to 1.3545):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |

TABLE 1-continued (compositions 1.1 to 1.3545):

| comp. no. | herbicide B | safener C |
|---|---|---|
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |

TABLE 1-continued (compositions 1.1 to 1.3545):

| comp. no. | herbicide B | safener C |
|---|---|---|
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | |
| 1.191 | B.191 | |
| 1.192 | B.192 | |
| 1.193 | B.193 | |
| 1.194 | B.194 | |
| 1.195 | B.195 | |
| 1.196 | B.196 | |
| 1.197 | B.1 | C.1 |
| 1.198 | B.2 | C.1 |
| 1.199 | B.3 | C.1 |
| 1.200 | B.4 | C.1 |
| 1.201 | B.5 | C.1 |
| 1.202 | B.6 | C.1 |
| 1.203 | B.7 | C.1 |
| 1.204 | B.8 | C.1 |
| 1.205 | B.9 | C.1 |
| 1.206 | B.10 | C.1 |
| 1.207 | B.11 | C.1 |
| 1.208 | B.12 | C.1 |
| 1.209 | B.13 | C.1 |
| 1.210 | B.14 | C.1 |
| 1.211 | B.15 | C.1 |
| 1.212 | B.16 | C.1 |
| 1.213 | B.17 | C.1 |
| 1.214 | B.18 | C.1 |
| 1.215 | B.19 | C.1 |
| 1.216 | B.20 | C.1 |
| 1.217 | B.21 | C.1 |
| 1.218 | B.22 | C.1 |
| 1.219 | B.23 | C.1 |
| 1.220 | B.24 | C.1 |
| 1.221 | B.25 | C.1 |
| 1.222 | B.26 | C.1 |
| 1.223 | B.27 | C.1 |
| 1.224 | B.28 | C.1 |
| 1.225 | B.29 | C.1 |
| 1.226 | B.30 | C.1 |
| 1.227 | B.31 | C.1 |
| 1.228 | B.32 | C.1 |
| 1.229 | B.33 | C.1 |
| 1.230 | B.34 | C.1 |
| 1.231 | B.35 | C.1 |
| 1.232 | B.36 | C.1 |
| 1.233 | B.37 | C.1 |
| 1.234 | B.38 | C.1 |
| 1.235 | B.39 | C.1 |
| 1.236 | B.40 | C.1 |
| 1.237 | B.41 | C.1 |
| 1.238 | B.42 | C.1 |
| 1.239 | B.43 | C.1 |
| 1.240 | B.44 | C.1 |
| 1.241 | B.45 | C.1 |
| 1.242 | B.46 | C.1 |
| 1.243 | B.47 | C.1 |
| 1.244 | B.48 | C.1 |
| 1.245 | B.49 | C.1 |
| 1.246 | B.50 | C.1 |
| 1.247 | B.51 | C.1 |
| 1.248 | B.52 | C.1 |
| 1.249 | B.53 | C.1 |
| 1.250 | B.54 | C.1 |
| 1.251 | B.55 | C.1 |
| 1.252 | B.56 | C.1 |
| 1.253 | B.57 | C.1 |
| 1.254 | B.58. | C.1 |
| 1.255 | B.59 | C.1 |
| 1.256 | B.60 | C.1 |
| 1.257 | B.61 | C.1 |
| 1.258 | B.62 | C.1 |
| 1.259 | B.63 | C.1 |
| 1.260 | B.64 | C.1 |
| 1.261 | B.65 | C.1 |
| 1.262 | B.66 | C.1 |
| 1.263 | B.67 | C.1 |
| 1.264 | B.68 | C.1 |
| 1.265 | B.69 | C.1 |
| 1.266 | B.70 | C.1 |
| 1.267 | B.71 | C.1 |
| 1.268 | B.72 | C.1 |
| 1.269 | B.73 | C.1 |
| 1.270 | B.74 | C.1 |
| 1.271 | B.75 | C.1 |
| 1.272 | B.76 | C.1 |
| 1.273 | B.77 | C.1 |
| 1.274 | B.78 | C.1 |
| 1.275 | B.79 | C.1 |
| 1.276 | B.80 | C.1 |
| 1.277 | B.81 | C.1 |
| 1.278 | B.82 | C.1 |
| 1.279 | B.83 | C.1 |
| 1.280 | B.84 | C.1 |

TABLE 1-continued (compositions 1.1 to 1.3545):

| comp. no. | herbicide B | safener C |
|---|---|---|
| 1.281 | B.85 | C.1 |
| 1.282 | B.86 | C.1 |
| 1.283 | B.87 | C.1 |
| 1.284 | B.88 | C.1 |
| 1.285 | B.89 | C.1 |
| 1.286 | B.90 | C.1 |
| 1.287 | B.91 | C.1 |
| 1.288 | B.92 | C.1 |
| 1.289 | B.93 | C.1 |
| 1.290 | B.94 | C.1 |
| 1.291 | B.95 | C.1 |
| 1.292 | B.96 | C.1 |
| 1.293 | B.97 | C.1 |
| 1.294 | B.98 | C.1 |
| 1.295 | B.99 | C.1 |
| 1.296 | B.100 | C.1 |
| 1.297 | B.101 | C.1 |
| 1.298 | B.102 | C.1 |
| 1.299 | B.103 | C.1 |
| 1.300 | B.104 | C.1 |
| 1.301 | B.105 | C.1 |
| 1.302 | B.106 | C.1 |
| 1.303 | B.107 | C.1 |
| 1.304 | B.108 | C.1 |
| 1.305 | B.109 | C.1 |
| 1.306 | B.110 | C.1 |
| 1.307 | B.111 | C.1 |
| 1.308 | B.112 | C.1 |
| 1.309 | B.113 | C.1 |
| 1.310 | B.114 | C.1 |
| 1.311 | B.115 | C.1 |
| 1.312 | B.116 | C.1 |
| 1.313 | B.117 | C.1 |
| 1.314 | B.118 | C.1 |
| 1.315 | B.119 | C.1 |
| 1.316 | B.120 | C.1 |
| 1.317 | B.121 | C.1 |
| 1.318 | B.122 | C.1 |
| 1.319 | B.123 | C.1 |
| 1.320 | B.124 | C.1 |
| 1.321 | B.125 | C.1 |
| 1.322 | B.126 | C.1 |
| 1.323 | B.127 | C.1 |
| 1.324 | B.128 | C.1 |
| 1.325 | B.129 | C.1 |
| 1.326 | B.130 | C.1 |
| 1.327 | B.131 | C.1 |
| 1.328 | B.132 | C.1 |
| 1.329 | B.133 | C.1 |
| 1.330 | B.134 | C.1 |
| 1.331 | B.135 | C.1 |
| 1.332 | B.136 | C.1 |
| 1.333 | B.137 | C.1 |
| 1.334 | B.138 | C.1 |
| 1.335 | B.139 | C.1 |
| 1.336 | B.140 | C.1 |
| 1.337 | B.141 | C.1 |
| 1.338 | B.142 | C.1 |
| 1.339 | B.143 | C.1 |
| 1.340 | B.144 | C.1 |
| 1.341 | B.145 | C.1 |
| 1.342 | B.146 | C.1 |
| 1.343 | B.147 | C.1 |
| 1.344 | B.148 | C.1 |
| 1.345 | B.149 | C.1 |
| 1.346 | B.150 | C.1 |
| 1.347 | B.151 | C.1 |
| 1.348 | B.152 | C.1 |
| 1.349 | B.153 | C.1 |
| 1.350 | B.154 | C.1 |
| 1.351 | B.155 | C.1 |
| 1.352 | B.156 | C.1 |
| 1.353 | B.157 | C.1 |
| 1.354 | B.158 | C.1 |
| 1.355 | B.159 | C.1 |
| 1.356 | B.160 | C.1 |
| 1.357 | B.161 | C.1 |
| 1.358 | B.162 | C.1 |
| 1.359 | B.163 | C.1 |
| 1.360 | B.164 | C.1 |
| 1.361 | B.165 | C.1 |
| 1.362 | B.166 | C.1 |
| 1.363 | B.167 | C.1 |
| 1.364 | B.168 | C.1 |
| 1.365 | B.169 | C.1 |
| 1.366 | B.170 | C.1 |
| 1.367 | B.171 | C.1 |
| 1.368 | B.172 | C.1 |
| 1.369 | B.173 | C.1 |
| 1.370 | B.174 | C.1 |
| 1.371 | B.175 | C.1 |
| 1.372 | B.176 | C.1 |
| 1.373 | B.177 | C.1 |
| 1.374 | B.178 | C.1 |
| 1.375 | B.179 | C.1 |
| 1.376 | B.180 | C.1 |
| 1.377 | B.181 | C.1 |
| 1.378 | B.182 | C.1 |
| 1.379 | B.183 | C.1 |
| 1.380 | B.184 | C.1 |
| 1.381 | B.185 | C.1 |
| 1.382 | B.186 | C.1 |
| 1.383 | B.187 | C.1 |
| 1.384 | B.188 | C.1 |
| 1.385 | B.189 | C.1 |
| 1.386 | B.190 | C.1 |
| 1.387 | B.191 | C.1 |
| 1.388 | B.192 | C.1 |
| 1.389 | B.193 | C.1 |
| 1.390 | B.194 | C.1 |
| 1.391 | B.195 | C.1 |
| 1.392 | B.196 | C.1 |
| 1.393 | B.1 | C.2 |
| 1.394 | B.2 | C.2 |
| 1.395 | B.3 | C.2 |
| 1.396 | B.4 | C.2 |
| 1.397 | B.5 | C.2 |
| 1.398 | B.6 | C.2 |
| 1.399 | B.7 | C.2 |
| 1.400 | B.8 | C.2 |
| 1.401 | B.9 | C.2 |
| 1.402 | B.10 | C.2 |
| 1.403 | B.11 | C.2 |
| 1.404 | B.12 | C.2 |
| 1.405 | B.13 | C.2 |
| 1.406 | B.14 | C.2 |
| 1.407 | B.15 | C.2 |
| 1.408 | B.16 | C.2 |
| 1.409 | B.17 | C.2 |
| 1.410 | B.18 | C.2 |
| 1.411 | B.19 | C.2 |
| 1.412 | B.20 | C.2 |
| 1.413 | B.21 | C.2 |
| 1.414 | B.22 | C.2 |
| 1.415 | B.23 | C.2 |
| 1.416 | B.24 | C.2 |
| 1.417 | B.25 | C.2 |
| 1.418 | B.26 | C.2 |
| 1.419 | B.27 | C.2 |
| 1.420 | B.28 | C.2 |
| 1.421 | B.29 | C.2 |
| 1.422 | B.30 | C.2 |
| 1.423 | B.31 | C.2 |
| 1.424 | B.32 | C.2 |
| 1.425 | B.33 | C.2 |
| 1.426 | B.34 | C.2 |
| 1.427 | B.35 | C.2 |
| 1.428 | B.36 | C.2 |
| 1.429 | B.37 | C.2 |
| 1.430 | B.38 | C.2 |
| 1.431 | B.39 | C.2 |
| 1.432 | B.40 | C.2 |

TABLE 1-continued (compositions 1.1 to 1.3545):

| comp. no. | herbicide B | safener C |
|---|---|---|
| 1.433 | B.41 | C.2 |
| 1.434 | B.42 | C.2 |
| 1.435 | B.43 | C.2 |
| 1.436 | B.44 | C.2 |
| 1.437 | B.45 | C.2 |
| 1.438 | B.46 | C.2 |
| 1.439 | B.47 | C.2 |
| 1.440 | B.48 | C.2 |
| 1.441 | B.49 | C.2 |
| 1.442 | B.50 | C.2 |
| 1.443 | B.51 | C.2 |
| 1.444 | B.52 | C.2 |
| 1.445 | B.53 | C.2 |
| 1.446 | B.54 | C.2 |
| 1.447 | B.55 | C.2 |
| 1.448 | B.56 | C.2 |
| 1.449 | B.57 | C.2 |
| 1.450 | B.58. | C.2 |
| 1.451 | B.59 | C.2 |
| 1.452 | B.60 | C.2 |
| 1.453 | B.61 | C.2 |
| 1.454 | B.62 | C.2 |
| 1.455 | B.63 | C.2 |
| 1.456 | B.64 | C.2 |
| 1.457 | B.65 | C.2 |
| 1.458 | B.66 | C.2 |
| 1.459 | B.67 | C.2 |
| 1.460 | B.68 | C.2 |
| 1.461 | B.69 | C.2 |
| 1.462 | B.70 | C.2 |
| 1.463 | B.71 | C.2 |
| 1.464 | B.72 | C.2 |
| 1.465 | B.73 | C.2 |
| 1.466 | B.74 | C.2 |
| 1.467 | B.75 | C.2 |
| 1.468 | B.76 | C.2 |
| 1.469 | B.77 | C.2 |
| 1.470 | B.78 | C.2 |
| 1.471 | B.79 | C.2 |
| 1.472 | B.80 | C.2 |
| 1.473 | B.81 | C.2 |
| 1.474 | B.82 | C.2 |
| 1.475 | B.83 | C.2 |
| 1.476 | B.84 | C.2 |
| 1.477 | B.85 | C.2 |
| 1.478 | B.86 | C.2 |
| 1.479 | B.87 | C.2 |
| 1.480 | B.88 | C.2 |
| 1.481 | B.89 | C.2 |
| 1.482 | B.90 | C.2 |
| 1.483 | B.91 | C.2 |
| 1.484 | B.92 | C.2 |
| 1.485 | B.93 | C.2 |
| 1.486 | B.94 | C.2 |
| 1.487 | B.95 | C.2 |
| 1.488 | B.96 | C.2 |
| 1.489 | B.97 | C.2 |
| 1.490 | B.98 | C.2 |
| 1.491 | B.99 | C.2 |
| 1.492 | B.100 | C.2 |
| 1.493 | B.101 | C.2 |
| 1.494 | B.102 | C.2 |
| 1.495 | B.103 | C.2 |
| 1.496 | B.104 | C.2 |
| 1.497 | B.105 | C.2 |
| 1.498 | B.106 | C.2 |
| 1.499 | B.107 | C.2 |
| 1.500 | B.108 | C.2 |
| 1.501 | B.109 | C.2 |
| 1.502 | B.110 | C.2 |
| 1.503 | B.111 | C.2 |
| 1.504 | B.112 | C.2 |
| 1.505 | B.113 | C.2 |
| 1.506 | B.114 | C.2 |
| 1.507 | B.115 | C.2 |
| 1.508 | B.116 | C.2 |
| 1.509 | B.117 | C.2 |
| 1.510 | B.118 | C.2 |
| 1.511 | B.119 | C.2 |
| 1.512 | B.120 | C.2 |
| 1.513 | B.121 | C.2 |
| 1.514 | B.122 | C.2 |
| 1.515 | B.123 | C.2 |
| 1.516 | B.124 | C.2 |
| 1.517 | B.125 | C.2 |
| 1.518 | B.126 | C.2 |
| 1.519 | B.127 | C.2 |
| 1.520 | B.128 | C.2 |
| 1.521 | B.129 | C.2 |
| 1.522 | B.130 | C.2 |
| 1.523 | B.131 | C.2 |
| 1.524 | B.132 | C.2 |
| 1.525 | B.133 | C.2 |
| 1.526 | B.134 | C.2 |
| 1.527 | B.135 | C.2 |
| 1.528 | B.136 | C.2 |
| 1.529 | B.137 | C.2 |
| 1.530 | B.138 | C.2 |
| 1.531 | B.139 | C.2 |
| 1.532 | B.140 | C.2 |
| 1.533 | B.141 | C.2 |
| 1.534 | B.142 | C.2 |
| 1.535 | B.143 | C.2 |
| 1.536 | B.144 | C.2 |
| 1.537 | B.145 | C.2 |
| 1.538 | B.146 | C.2 |
| 1.539 | B.147 | C.2 |
| 1.540 | B.148 | C.2 |
| 1.541 | B.149 | C.2 |
| 1.542 | B.150 | C.2 |
| 1.543 | B.151 | C.2 |
| 1.544 | B.152 | C.2 |
| 1.545 | B.153 | C.2 |
| 1.546 | B.154 | C.2 |
| 1.547 | B.155 | C.2 |
| 1.548 | B.156 | C.2 |
| 1.549 | B.157 | C.2 |
| 1.550 | B.158 | C.2 |
| 1.551 | B.159 | C.2 |
| 1.552 | B.160 | C.2 |
| 1.553 | B.161 | C.2 |
| 1.554 | B.162 | C.2 |
| 1.555 | B.163 | C.2 |
| 1.556 | B.164 | C.2 |
| 1.557 | B.165 | C.2 |
| 1.558 | B.166 | C.2 |
| 1.559 | B.167 | C.2 |
| 1.560 | B.168 | C.2 |
| 1.561 | B.169 | C.2 |
| 1.562 | B.170 | C.2 |
| 1.563 | B.171 | C.2 |
| 1.564 | B.172 | C.2 |
| 1.565 | B.173 | C.2 |
| 1.566 | B.174 | C.2 |
| 1.567 | B.175 | C.2 |
| 1.568 | B.176 | C.2 |
| 1.569 | B.177 | C.2 |
| 1.570 | B.178 | C.2 |
| 1.571 | B.179 | C.2 |
| 1.572 | B.180 | C.2 |
| 1.573 | B.181 | C.2 |
| 1.574 | B.182 | C.2 |
| 1.575 | B.183 | C.2 |
| 1.576 | B.184 | C.2 |
| 1.577 | B.185 | C.2 |
| 1.578 | B.186 | C.2 |
| 1.579 | B.187 | C.2 |
| 1.580 | B.188 | C.2 |
| 1.581 | B.189 | C.2 |
| 1.582 | B.190 | C.2 |
| 1.583 | B.191 | C.2 |
| 1.584 | B.192 | C.2 |

TABLE 1-continued (compositions 1.1 to 1.3545):

| comp. no. | herbicide B | safener C |
|---|---|---|
| 1.585 | B.193 | C.2 |
| 1.586 | B.194 | C.2 |
| 1.587 | B.195 | C.2 |
| 1.588 | B.196 | C.2 |
| 1.589 | B.1 | C.3 |
| 1.590 | B.2 | C.3 |
| 1.591 | B.3 | C.3 |
| 1.592 | B.4 | C.3 |
| 1.593 | B.5 | C.3 |
| 1.594 | B.6 | C.3 |
| 1.595 | B.7 | C.3 |
| 1.596 | B.8 | C.3 |
| 1.597 | B.9 | C.3 |
| 1.598 | B.10 | C.3 |
| 1.599 | B.11 | C.3 |
| 1.600 | B.12 | C.3 |
| 1.601 | B.13 | C.3 |
| 1.602 | B.14 | C.3 |
| 1.603 | B.15 | C.3 |
| 1.604 | B.16 | C.3 |
| 1.605 | B.17 | C.3 |
| 1.606 | B.18 | C.3 |
| 1.607 | B.19 | C.3 |
| 1.608 | B.20 | C.3 |
| 1.609 | B.21 | C.3 |
| 1.610 | B.22 | C.3 |
| 1.611 | B.23 | C.3 |
| 1.612 | B.24 | C.3 |
| 1.613 | B.25 | C.3 |
| 1.614 | B.26 | C.3 |
| 1.615 | B.27 | C.3 |
| 1.616 | B.28 | C.3 |
| 1.617 | B.29 | C.3 |
| 1.618 | B.30 | C.3 |
| 1.619 | B.31 | C.3 |
| 1.620 | B.32 | C.3 |
| 1.621 | B.33 | C.3 |
| 1.622 | B.34 | C.3 |
| 1.623 | B.35 | C.3 |
| 1.624 | B.36 | C.3 |
| 1.625 | B.37 | C.3 |
| 1.626 | B.38 | C.3 |
| 1.627 | B.39 | C.3 |
| 1.628 | B.40 | C.3 |
| 1.629 | B.41 | C.3 |
| 1.630 | B.42 | C.3 |
| 1.631 | B.43 | C.3 |
| 1.632 | B.44 | C.3 |
| 1.633 | B.45 | C.3 |
| 1.634 | B.46 | C.3 |
| 1.635 | B.47 | C.3 |
| 1.636 | B.48 | C.3 |
| 1.637 | B.49 | C.3 |
| 1.638 | B.50 | C.3 |
| 1.639 | B.51 | C.3 |
| 1.640 | B.52 | C.3 |
| 1.641 | B.53 | C.3 |
| 1.642 | B.54 | C.3 |
| 1.643 | B.55 | C.3 |
| 1.644 | B.56 | C.3 |
| 1.645 | B.57 | C.3 |
| 1.646 | B.58. | C.3 |
| 1.647 | B.59 | C.3 |
| 1.648 | B.60 | C.3 |
| 1.649 | B.61 | C.3 |
| 1.650 | B.62 | C.3 |
| 1.651 | B.63 | C.3 |
| 1.652 | B.64 | C.3 |
| 1.653 | B.65 | C.3 |
| 1.654 | B.66 | C.3 |
| 1.655 | B.67 | C.3 |
| 1.656 | B.68 | C.3 |
| 1.657 | B.69 | C.3 |
| 1.658 | B.70 | C.3 |
| 1.659 | B.71 | C.3 |
| 1.660 | B.72 | C.3 |
| 1.661 | B.73 | C.3 |
| 1.662 | B.74 | C.3 |
| 1.663 | B.75 | C.3 |
| 1.664 | B.76 | C.3 |
| 1.665 | B.77 | C.3 |
| 1.666 | B.78 | C.3 |
| 1.667 | B.79 | C.3 |
| 1.668 | B.80 | C.3 |
| 1.669 | B.81 | C.3 |
| 1.670 | B.82 | C.3 |
| 1.671 | B.83 | C.3 |
| 1.672 | B.84 | C.3 |
| 1.673 | B.85 | C.3 |
| 1.674 | B.86 | C.3 |
| 1.675 | B.87 | C.3 |
| 1.676 | B.88 | C.3 |
| 1.677 | B.89 | C.3 |
| 1.678 | B.90 | C.3 |
| 1.679 | B.91 | C.3 |
| 1.680 | B.92 | C.3 |
| 1.681 | B.93 | C.3 |
| 1.682 | B.94 | C.3 |
| 1.683 | B.95 | C.3 |
| 1.684 | B.96 | C.3 |
| 1.685 | B.97 | C.3 |
| 1.686 | B.98 | C.3 |
| 1.687 | B.99 | C.3 |
| 1.688 | B.100 | C.3 |
| 1.689 | B.101 | C.3 |
| 1.690 | B.102 | C.3 |
| 1.691 | B.103 | C.3 |
| 1.692 | B.104 | C.3 |
| 1.693 | B.105 | C.3 |
| 1.694 | B.106 | C.3 |
| 1.695 | B.107 | C.3 |
| 1.696 | B.108 | C.3 |
| 1.697 | B.109 | C.3 |
| 1.698 | B.110 | C.3 |
| 1.699 | B.111 | C.3 |
| 1.700 | B.112 | C.3 |
| 1.701 | B.113 | C.3 |
| 1.702 | B.114 | C.3 |
| 1.703 | B.115 | C.3 |
| 1.704 | B.116 | C.3 |
| 1.705 | B.117 | C.3 |
| 1.706 | B.118 | C.3 |
| 1.707 | B.119 | C.3 |
| 1.708 | B.120 | C.3 |
| 1.709 | B.121 | C.3 |
| 1.710 | B.122 | C.3 |
| 1.711 | B.123 | C.3 |
| 1.712 | B.124 | C.3 |
| 1.713 | B.125 | C.3 |
| 1.714 | B.126 | C.3 |
| 1.715 | B.127 | C.3 |
| 1.716 | B.128 | C.3 |
| 1.717 | B.129 | C.3 |
| 1.718 | B.130 | C.3 |
| 1.719 | B.131 | C.3 |
| 1.720 | B.132 | C.3 |
| 1.721 | B.133 | C.3 |
| 1.722 | B.134 | C.3 |
| 1.723 | B.135 | C.3 |
| 1.724 | B.136 | C.3 |
| 1.725 | B.137 | C.3 |
| 1.726 | B.138 | C.3 |
| 1.727 | B.139 | C.3 |
| 1.728 | B.140 | C.3 |
| 1.729 | B.141 | C.3 |
| 1.730 | B.142 | C.3 |
| 1.731 | B.143 | C.3 |
| 1.732 | B.144 | C.3 |
| 1.733 | B.145 | C.3 |
| 1.734 | B.146 | C.3 |
| 1.735 | B.147 | C.3 |
| 1.736 | B.148 | C.3 |

TABLE 1-continued (compositions 1.1 to 1.3545):

| comp. no. | herbicide B | safener C |
|---|---|---|
| 1.737 | B.149 | C.3 |
| 1.738 | B.150 | C.3 |
| 1.739 | B.151 | C.3 |
| 1.740 | B.152 | C.3 |
| 1.741 | B.153 | C.3 |
| 1.742 | B.154 | C.3 |
| 1.743 | B.155 | C.3 |
| 1.744 | B.156 | C.3 |
| 1.745 | B.157 | C.3 |
| 1.746 | B.158 | C.3 |
| 1.747 | B.159 | C.3 |
| 1.748 | B.160 | C.3 |
| 1.749 | B.161 | C.3 |
| 1.750 | B.162 | C.3 |
| 1.751 | B.163 | C.3 |
| 1.752 | B.164 | C.3 |
| 1.753 | B.165 | C.3 |
| 1.754 | B.166 | C.3 |
| 1.755 | B.167 | C.3 |
| 1.756 | B.168 | C.3 |
| 1.757 | B.169 | C.3 |
| 1.758 | B.170 | C.3 |
| 1.759 | B.171 | C.3 |
| 1.760 | B.172 | C.3 |
| 1.761 | B.173 | C.3 |
| 1.762 | B.174 | C.3 |
| 1.763 | B.175 | C.3 |
| 1.764 | B.176 | C.3 |
| 1.765 | B.177 | C.3 |
| 1.766 | B.178 | C.3 |
| 1.767 | B.179 | C.3 |
| 1.768 | B.180 | C.3 |
| 1.769 | B.181 | C.3 |
| 1.770 | B.182 | C.3 |
| 1.771 | B.183 | C.3 |
| 1.772 | B.184 | C.3 |
| 1.773 | B.185 | C.3 |
| 1.774 | B.186 | C.3 |
| 1.775 | B.187 | C.3 |
| 1.776 | B.188 | C.3 |
| 1.777 | B.189 | C.3 |
| 1.778 | B.190 | C.3 |
| 1.779 | B.191 | C.3 |
| 1.780 | B.192 | C.3 |
| 1.781 | B.193 | C.3 |
| 1.782 | B.194 | C.3 |
| 1.783 | B.195 | C.3 |
| 1.784 | B.196 | C.3 |
| 1.785 | B.1 | C.4 |
| 1.786 | B.2 | C.4 |
| 1.787 | B.3 | C.4 |
| 1.788 | B.4 | C.4 |
| 1.789 | B.5 | C.4 |
| 1.790 | B.6 | C.4 |
| 1.791 | B.7 | C.4 |
| 1.792 | B.8 | C.4 |
| 1.793 | B.9 | C.4 |
| 1.794 | B.10 | C.4 |
| 1.795 | B.11 | C.4 |
| 1.796 | B.12 | C.4 |
| 1.797 | B.13 | C.4 |
| 1.798 | B.14 | C.4 |
| 1.799 | B.15 | C.4 |
| 1.800 | B.16 | C.4 |
| 1.801 | B.17 | C.4 |
| 1.802 | B.18 | C.4 |
| 1.803 | B.19 | C.4 |
| 1.804 | B.20 | C.4 |
| 1.805 | B.21 | C.4 |
| 1.806 | B.22 | C.4 |
| 1.807 | B.23 | C.4 |
| 1.808 | B.24 | C.4 |
| 1.809 | B.25 | C.4 |
| 1.810 | B.26 | C.4 |
| 1.811 | B.27 | C.4 |
| 1.812 | B.28 | C.4 |
| 1.813 | B.29 | C.4 |
| 1.814 | B.30 | C.4 |
| 1.815 | B.31 | C.4 |
| 1.816 | B.32 | C.4 |
| 1.817 | B.33 | C.4 |
| 1.818 | B.34 | C.4 |
| 1.819 | B.35 | C.4 |
| 1.820 | B.36 | C.4 |
| 1.821 | B.37 | C.4 |
| 1.822 | B.38 | C.4 |
| 1.823 | B.39 | C.4 |
| 1.824 | B.40 | C.4 |
| 1.825 | B.41 | C.4 |
| 1.826 | B.42 | C.4 |
| 1.827 | B.43 | C.4 |
| 1.828 | B.44 | C.4 |
| 1.829 | B.45 | C.4 |
| 1.830 | B.46 | C.4 |
| 1.831 | B.47 | C.4 |
| 1.832 | B.48 | C.4 |
| 1.833 | B.49 | C.4 |
| 1.834 | B.50 | C.4 |
| 1.835 | B.51 | C.4 |
| 1.836 | B.52 | C.4 |
| 1.837 | B.53 | C.4 |
| 1.838 | B.54 | C.4 |
| 1.839 | B.55 | C.4 |
| 1.840 | B.56 | C.4 |
| 1.841 | B.57 | C.4 |
| 1.842 | B.58. | C.4 |
| 1.843 | B.59 | C.4 |
| 1.844 | B.60 | C.4 |
| 1.845 | B.61 | C.4 |
| 1.846 | B.62 | C.4 |
| 1.847 | B.63 | C.4 |
| 1.848 | B.64 | C.4 |
| 1.849 | B.65 | C.4 |
| 1.850 | B.66 | C.4 |
| 1.851 | B.67 | C.4 |
| 1.852 | B.68 | C.4 |
| 1.853 | B.69 | C.4 |
| 1.854 | B.70 | C.4 |
| 1.855 | B.71 | C.4 |
| 1.856 | B.72 | C.4 |
| 1.857 | B.73 | C.4 |
| 1.858 | B.74 | C.4 |
| 1.859 | B.75 | C.4 |
| 1.860 | B.76 | C.4 |
| 1.861 | B.77 | C.4 |
| 1.862 | B.78 | C.4 |
| 1.863 | B.79 | C.4 |
| 1.864 | B.80 | C.4 |
| 1.865 | B.81 | C.4 |
| 1.866 | B.82 | C.4 |
| 1.867 | B.83 | C.4 |
| 1.868 | B.84 | C.4 |
| 1.869 | B.85 | C.4 |
| 1.870 | B.86 | C.4 |
| 1.871 | B.87 | C.4 |
| 1.872 | B.88 | C.4 |
| 1.873 | B.89 | C.4 |
| 1.874 | B.90 | C.4 |
| 1.875 | B.91 | C.4 |
| 1.876 | B.92 | C.4 |
| 1.877 | B.93 | C.4 |
| 1.878 | B.94 | C.4 |
| 1.879 | B.95 | C.4 |
| 1.880 | B.96 | C.4 |
| 1.881 | B.97 | C.4 |
| 1.882 | B.98 | C.4 |
| 1.883 | B.99 | C.4 |
| 1.884 | B.100 | C.4 |
| 1.885 | B.101 | C.4 |
| 1.886 | B.102 | C.4 |
| 1.887 | B.103 | C.4 |
| 1.888 | B.104 | C.4 |

TABLE 1-continued (compositions 1.1 to 1.3545):

| comp. no. | herbicide B | safener C |
|---|---|---|
| 1.889 | B.105 | C.4 |
| 1.890 | B.106 | C.4 |
| 1.891 | B.107 | C.4 |
| 1.892 | B.108 | C.4 |
| 1.893 | B.109 | C.4 |
| 1.894 | B.110 | C.4 |
| 1.895 | B.111 | C.4 |
| 1.896 | B.112 | C.4 |
| 1.897 | B.113 | C.4 |
| 1.898 | B.114 | C.4 |
| 1.899 | B.115 | C.4 |
| 1.900 | B.116 | C.4 |
| 1.901 | B.117 | C.4 |
| 1.902 | B.118 | C.4 |
| 1.903 | B.119 | C.4 |
| 1.904 | B.120 | C.4 |
| 1.905 | B.121 | C.4 |
| 1.906 | B.122 | C.4 |
| 1.907 | B.123 | C.4 |
| 1.908 | B.124 | C.4 |
| 1.909 | B.125 | C.4 |
| 1.910 | B.126 | C.4 |
| 1.911 | B.127 | C.4 |
| 1.912 | B.128 | C.4 |
| 1.913 | B.129 | C.4 |
| 1.914 | B.130 | C.4 |
| 1.915 | B.131 | C.4 |
| 1.916 | B.132 | C.4 |
| 1.917 | B.133 | C.4 |
| 1.918 | B.134 | C.4 |
| 1.919 | B.135 | C.4 |
| 1.920 | B.136 | C.4 |
| 1.921 | B.137 | C.4 |
| 1.922 | B.138 | C.4 |
| 1.923 | B.139 | C.4 |
| 1.924 | B.140 | C.4 |
| 1.925 | B.141 | C.4 |
| 1.926 | B.142 | C.4 |
| 1.927 | B.143 | C.4 |
| 1.928 | B.144 | C.4 |
| 1.929 | B.145 | C.4 |
| 1.930 | B.146 | C.4 |
| 1.931 | B.147 | C.4 |
| 1.932 | B.148 | C.4 |
| 1.933 | B.149 | C.4 |
| 1.934 | B.150 | C.4 |
| 1.935 | B.151 | C.4 |
| 1.936 | B.152 | C.4 |
| 1.937 | B.153 | C.4 |
| 1.938 | B.154 | C.4 |
| 1.939 | B.155 | C.4 |
| 1.940 | B.156 | C.4 |
| 1.941 | B.157 | C.4 |
| 1.942 | B.158 | C.4 |
| 1.943 | B.159 | C.4 |
| 1.944 | B.160 | C.4 |
| 1.945 | B.161 | C.4 |
| 1.946 | B.162 | C.4 |
| 1.947 | B.163 | C.4 |
| 1.948 | B.164 | C.4 |
| 1.949 | B.165 | C.4 |
| 1.950 | B.166 | C.4 |
| 1.951 | B.167 | C.4 |
| 1.952 | B.168 | C.4 |
| 1.953 | B.169 | C.4 |
| 1.954 | B.170 | C.4 |
| 1.955 | B.171 | C.4 |
| 1.956 | B.172 | C.4 |
| 1.957 | B.173 | C.4 |
| 1.958 | B.174 | C.4 |
| 1.959 | B.175 | C.4 |
| 1.960 | B.176 | C.4 |
| 1.961 | B.177 | C.4 |
| 1.962 | B.178 | C.4 |
| 1.963 | B.179 | C.4 |
| 1.964 | B.180 | C.4 |
| 1.965 | B.181 | C.4 |
| 1.966 | B.182 | C.4 |
| 1.967 | B.183 | C.4 |
| 1.968 | B.184 | C.4 |
| 1.969 | B.185 | C.4 |
| 1.970 | B.186 | C.4 |
| 1.971 | B.187 | C.4 |
| 1.972 | B.188 | C.4 |
| 1.973 | B.189 | C.4 |
| 1.974 | B.190 | C.4 |
| 1.975 | B.191 | C.4 |
| 1.976 | B.192 | C.4 |
| 1.977 | B.193 | C.4 |
| 1.978 | B.194 | C.4 |
| 1.979 | B.195 | C.4 |
| 1.980 | B.196 | C.4 |
| 1.981 | B.1 | C.5 |
| 1.982 | B.2 | C.5 |
| 1.983 | B.3 | C.5 |
| 1.984 | B.4 | C.5 |
| 1.985 | B.5 | C.5 |
| 1.986 | B.6 | C.5 |
| 1.987 | B.7 | C.5 |
| 1.988 | B.8 | C.5 |
| 1.989 | B.9 | C.5 |
| 1.990 | B.10 | C.5 |
| 1.991 | B.11 | C.5 |
| 1.992 | B.12 | C.5 |
| 1.993 | B.13 | C.5 |
| 1.994 | B.14 | C.5 |
| 1.995 | B.15 | C.5 |
| 1.996 | B.16 | C.5 |
| 1.997 | B.17 | C.5 |
| 1.998 | B.18 | C.5 |
| 1.999 | B.19 | C.5 |
| 1.1000 | B.20 | C.5 |
| 1.1001 | B.21 | C.5 |
| 1.1002 | B.22 | C.5 |
| 1.1003 | B.23 | C.5 |
| 1.1004 | B.24 | C.5 |
| 1.1005 | B.25 | C.5 |
| 1.1006 | B.26 | C.5 |
| 1.1007 | B.27 | C.5 |
| 1.1008 | B.28 | C.5 |
| 1.1009 | B.29 | C.5 |
| 1.1010 | B.30 | C.5 |
| 1.1011 | B.31 | C.5 |
| 1.1012 | B.32 | C.5 |
| 1.1013 | B.33 | C.5 |
| 1.1014 | B.34 | C.5 |
| 1.1015 | B.35 | C.5 |
| 1.1016 | B.36 | C.5 |
| 1.1017 | B.37 | C.5 |
| 1.1018 | B.38 | C.5 |
| 1.1019 | B.39 | C.5 |
| 1.1020 | B.40 | C.5 |
| 1.1021 | B.41 | C.5 |
| 1.1022 | B.42 | C.5 |
| 1.1023 | B.43 | C.5 |
| 1.1024 | B.44 | C.5 |
| 1.1025 | B.45 | C.5 |
| 1.1026 | B.46 | C.5 |
| 1.1027 | B.47 | C.5 |
| 1.1028 | B.48 | C.5 |
| 1.1029 | B.49 | C.5 |
| 1.1030 | B.50 | C.5 |
| 1.1031 | B.51 | C.5 |
| 1.1032 | B.52 | C.5 |
| 1.1033 | B.53 | C.5 |
| 1.1034 | B.54 | C.5 |
| 1.1035 | B.55 | C.5 |
| 1.1036 | B.56 | C.5 |
| 1.1037 | B.57 | C.5 |
| 1.1038 | B.58. | C.5 |
| 1.1039 | B.59 | C.5 |
| 1.1040 | B.60 | C.5 |

TABLE 1-continued (compositions 1.1 to 1.3545):

| comp. no. | herbicide B | safener C |
|---|---|---|
| 1.1041 | B.61 | C.5 |
| 1.1042 | B.62 | C.5 |
| 1.1043 | B.63 | C.5 |
| 1.1044 | B.64 | C.5 |
| 1.1045 | B.65 | C.5 |
| 1.1046 | B.66 | C.5 |
| 1.1047 | B.67 | C.5 |
| 1.1048 | B.68 | C.5 |
| 1.1049 | B.69 | C.5 |
| 1.1050 | B.70 | C.5 |
| 1.1051 | B.71 | C.5 |
| 1.1052 | B.72 | C.5 |
| 1.1053 | B.73 | C.5 |
| 1.1054 | B.74 | C.5 |
| 1.1055 | B.75 | C.5 |
| 1.1056 | B.76 | C.5 |
| 1.1057 | B.77 | C.5 |
| 1.1058 | B.78 | C.5 |
| 1.1059 | B.79 | C.5 |
| 1.1060 | B.80 | C.5 |
| 1.1061 | B.81 | C.5 |
| 1.1062 | B.82 | C.5 |
| 1.1063 | B.83 | C.5 |
| 1.1064 | B.84 | C.5 |
| 1.1065 | B.85 | C.5 |
| 1.1066 | B.86 | C.5 |
| 1.1067 | B.87 | C.5 |
| 1.1068 | B.88 | C.5 |
| 1.1069 | B.89 | C.5 |
| 1.1070 | B.90 | C.5 |
| 1.1071 | B.91 | C.5 |
| 1.1072 | B.92 | C.5 |
| 1.1073 | B.93 | C.5 |
| 1.1074 | B.94 | C.5 |
| 1.1075 | B.95 | C.5 |
| 1.1076 | B.96 | C.5 |
| 1.1077 | B.97 | C.5 |
| 1.1078 | B.98 | C.5 |
| 1.1079 | B.99 | C.5 |
| 1.1080 | B.100 | C.5 |
| 1.1081 | B.101 | C.5 |
| 1.1082 | B.102 | C.5 |
| 1.1083 | B.103 | C.5 |
| 1.1084 | B.104 | C.5 |
| 1.1085 | B.105 | C.5 |
| 1.1086 | B.106 | C.5 |
| 1.1087 | B.107 | C.5 |
| 1.1088 | B.108 | C.5 |
| 1.1089 | B.109 | C.5 |
| 1.1090 | B.110 | C.5 |
| 1.1091 | B.111 | C.5 |
| 1.1092 | B.112 | C.5 |
| 1.1093 | B.113 | C.5 |
| 1.1094 | B.114 | C.5 |
| 1.1095 | B.115 | C.5 |
| 1.1096 | B.116 | C.5 |
| 1.1097 | B.117 | C.5 |
| 1.1098 | B.118 | C.5 |
| 1.1099 | B.119 | C.5 |
| 1.1100 | B.120 | C.5 |
| 1.1101 | B.121 | C.5 |
| 1.1102 | B.122 | C.5 |
| 1.1103 | B.123 | C.5 |
| 1.1104 | B.124 | C.5 |
| 1.1105 | B.125 | C.5 |
| 1.1106 | B.126 | C.5 |
| 1.1107 | B.127 | C.5 |
| 1.1108 | B.128 | C.5 |
| 1.1109 | B.129 | C.5 |
| 1.1110 | B.130 | C.5 |
| 1.1111 | B.131 | C.5 |
| 1.1112 | B.132 | C.5 |
| 1.1113 | B.133 | C.5 |
| 1.1114 | B.134 | C.5 |
| 1.1115 | B.135 | C.5 |
| 1.1116 | B.136 | C.5 |
| 1.1117 | B.137 | C.5 |
| 1.1118 | B.138 | C.5 |
| 1.1119 | B.139 | C.5 |
| 1.1120 | B.140 | C.5 |
| 1.1121 | B.141 | C.5 |
| 1.1122 | B.142 | C.5 |
| 1.1123 | B.143 | C.5 |
| 1.1124 | B.144 | C.5 |
| 1.1125 | B.145 | C.5 |
| 1.1126 | B.146 | C.5 |
| 1.1127 | B.147 | C.5 |
| 1.1128 | B.148 | C.5 |
| 1.1129 | B.149 | C.5 |
| 1.1130 | B.150 | C.5 |
| 1.1131 | B.151 | C.5 |
| 1.1132 | B.152 | C.5 |
| 1.1133 | B.153 | C.5 |
| 1.1134 | B.154 | C.5 |
| 1.1135 | B.155 | C.5 |
| 1.1136 | B.156 | C.5 |
| 1.1137 | B.157 | C.5 |
| 1.1138 | B.158 | C.5 |
| 1.1139 | B.159 | C.5 |
| 1.1140 | B.160 | C.5 |
| 1.1141 | B.161 | C.5 |
| 1.1142 | B.162 | C.5 |
| 1.1143 | B.163 | C.5 |
| 1.1144 | B.164 | C.5 |
| 1.1145 | B.165 | C.5 |
| 1.1146 | B.166 | C.5 |
| 1.1147 | B.167 | C.5 |
| 1.1148 | B.168 | C.5 |
| 1.1149 | B.169 | C.5 |
| 1.1150 | B.170 | C.5 |
| 1.1151 | B.171 | C.5 |
| 1.1152 | B.172 | C.5 |
| 1.1153 | B.173 | C.5 |
| 1.1154 | B.174 | C.5 |
| 1.1155 | B.175 | C.5 |
| 1.1156 | B.176 | C.5 |
| 1.1157 | B.177 | C.5 |
| 1.1158 | B.178 | C.5 |
| 1.1159 | B.179 | C.5 |
| 1.1160 | B.180 | C.5 |
| 1.1161 | B.181 | C.5 |
| 1.1162 | B.182 | C.5 |
| 1.1163 | B.183 | C.5 |
| 1.1164 | B.184 | C.5 |
| 1.1165 | B.185 | C.5 |
| 1.1166 | B.186 | C.5 |
| 1.1167 | B.187 | C.5 |
| 1.1168 | B.188 | C.5 |
| 1.1169 | B.189 | C.5 |
| 1.1170 | B.190 | C.5 |
| 1.1171 | B.191 | C.5 |
| 1.1172 | B.192 | C.5 |
| 1.1173 | B.193 | C.5 |
| 1.1174 | B.194 | C.5 |
| 1.1175 | B.195 | C.5 |
| 1.1176 | B.196 | C.5 |
| 1.1177 | B.1 | C.6 |
| 1.1178 | B.2 | C.6 |
| 1.1179 | B.3 | C.6 |
| 1.1180 | B.4 | C.6 |
| 1.1181 | B.5 | C.6 |
| 1.1182 | B.6 | C.6 |
| 1.1183 | B.7 | C.6 |
| 1.1184 | B.8 | C.6 |
| 1.1185 | B.9 | C.6 |
| 1.1186 | B.10 | C.6 |
| 1.1187 | B.11 | C.6 |
| 1.1188 | B.12 | C.6 |
| 1.1189 | B.13 | C.6 |
| 1.1190 | B.14 | C.6 |
| 1.1191 | B.15 | C.6 |
| 1.1192 | B.16 | C.6 |

TABLE 1-continued (compositions 1.1 to 1.3545):

| comp. no. | herbicide B | safener C |
|---|---|---|
| 1.1193 | B.17 | C.6 |
| 1.1194 | B.18 | C.6 |
| 1.1195 | B.19 | C.6 |
| 1.1196 | B.20 | C.6 |
| 1.1197 | B.21 | C.6 |
| 1.1198 | B.22 | C.6 |
| 1.1199 | B.23 | C.6 |
| 1.1200 | B.24 | C.6 |
| 1.1201 | B.25 | C.6 |
| 1.1202 | B.26 | C.6 |
| 1.1203 | B.27 | C.6 |
| 1.1204 | B.28 | C.6 |
| 1.1205 | B.29 | C.6 |
| 1.1206 | B.30 | C.6 |
| 1.1207 | B.31 | C.6 |
| 1.1208 | B.32 | C.6 |
| 1.1209 | B.33 | C.6 |
| 1.1210 | B.34 | C.6 |
| 1.1211 | B.35 | C.6 |
| 1.1212 | B.36 | C.6 |
| 1.1213 | B.37 | C.6 |
| 1.1214 | B.38 | C.6 |
| 1.1215 | B.39 | C.6 |
| 1.1216 | B.40 | C.6 |
| 1.1217 | B.41 | C.6 |
| 1.1218 | B.42 | C.6 |
| 1.1219 | B.43 | C.6 |
| 1.1220 | B.44 | C.6 |
| 1.1221 | B.45 | C.6 |
| 1.1222 | B.46 | C.6 |
| 1.1223 | B.47 | C.6 |
| 1.1224 | B.48 | C.6 |
| 1.1225 | B.49 | C.6 |
| 1.1226 | B.50 | C.6 |
| 1.1227 | B.51 | C.6 |
| 1.1228 | B.52 | C.6 |
| 1.1229 | B.53 | C.6 |
| 1.1230 | B.54 | C.6 |
| 1.1231 | B.55 | C.6 |
| 1.1232 | B.56 | C.6 |
| 1.1233 | B.57 | C.6 |
| 1.1234 | B.58. | C.6 |
| 1.1235 | B.59 | C.6 |
| 1.1236 | B.60 | C.6 |
| 1.1237 | B.61 | C.6 |
| 1.1238 | B.62 | C.6 |
| 1.1239 | B.63 | C.6 |
| 1.1240 | B.64 | C.6 |
| 1.1241 | B.65 | C.6 |
| 1.1242 | B.66 | C.6 |
| 1.1243 | B.67 | C.6 |
| 1.1244 | B.68 | C.6 |
| 1.1245 | B.69 | C.6 |
| 1.1246 | B.70 | C.6 |
| 1.1247 | B.71 | C.6 |
| 1.1248 | B.72 | C.6 |
| 1.1249 | B.73 | C.6 |
| 1.1250 | B.74 | C.6 |
| 1.1251 | B.75 | C.6 |
| 1.1252 | B.76 | C.6 |
| 1.1253 | B.77 | C.6 |
| 1.1254 | B.78 | C.6 |
| 1.1255 | B.79 | C.6 |
| 1.1256 | B.80 | C.6 |
| 1.1257 | B.81 | C.6 |
| 1.1258 | B.82 | C.6 |
| 1.1259 | B.83 | C.6 |
| 1.1260 | B.84 | C.6 |
| 1.1261 | B.85 | C.6 |
| 1.1262 | B.86 | C.6 |
| 1.1263 | B.87 | C.6 |
| 1.1264 | B.88 | C.6 |
| 1.1265 | B.89 | C.6 |
| 1.1266 | B.90 | C.6 |
| 1.1267 | B.91 | C.6 |
| 1.1268 | B.92 | C.6 |
| 1.1269 | B.93 | C.6 |
| 1.1270 | B.94 | C.6 |
| 1.1271 | B.95 | C.6 |
| 1.1272 | B.96 | C.6 |
| 1.1273 | B.97 | C.6 |
| 1.1274 | B.98 | C.6 |
| 1.1275 | B.99 | C.6 |
| 1.1276 | B.100 | C.6 |
| 1.1277 | B.101 | C.6 |
| 1.1278 | B.102 | C.6 |
| 1.1279 | B.103 | C.6 |
| 1.1280 | B.104 | C.6 |
| 1.1281 | B.105 | C.6 |
| 1.1282 | B.106 | C.6 |
| 1.1283 | B.107 | C.6 |
| 1.1284 | B.108 | C.6 |
| 1.1285 | B.109 | C.6 |
| 1.1286 | B.110 | C.6 |
| 1.1287 | B.111 | C.6 |
| 1.1288 | B.112 | C.6 |
| 1.1289 | B.113 | C.6 |
| 1.1290 | B.114 | C.6 |
| 1.1291 | B.115 | C.6 |
| 1.1292 | B.116 | C.6 |
| 1.1293 | B.117 | C.6 |
| 1.1294 | B.118 | C.6 |
| 1.1295 | B.119 | C.6 |
| 1.1296 | B.120 | C.6 |
| 1.1297 | B.121 | C.6 |
| 1.1298 | B.122 | C.6 |
| 1.1299 | B.123 | C.6 |
| 1.1300 | B.124 | C.6 |
| 1.1301 | B.125 | C.6 |
| 1.1302 | B.126 | C.6 |
| 1.1303 | B.127 | C.6 |
| 1.1304 | B.128 | C.6 |
| 1.1305 | B.129 | C.6 |
| 1.1306 | B.130 | C.6 |
| 1.1307 | B.131 | C.6 |
| 1.1308 | B.132 | C.6 |
| 1.1309 | B.133 | C.6 |
| 1.1310 | B.134 | C.6 |
| 1.1311 | B.135 | C.6 |
| 1.1312 | B.136 | C.6 |
| 1.1313 | B.137 | C.6 |
| 1.1314 | B.138 | C.6 |
| 1.1315 | B.139 | C.6 |
| 1.1316 | B.140 | C.6 |
| 1.1317 | B.141 | C.6 |
| 1.1318 | B.142 | C.6 |
| 1.1319 | B.143 | C.6 |
| 1.1320 | B.144 | C.6 |
| 1.1321 | B.145 | C.6 |
| 1.1322 | B.146 | C.6 |
| 1.1323 | B.147 | C.6 |
| 1.1324 | B.148 | C.6 |
| 1.1325 | B.149 | C.6 |
| 1.1326 | B.150 | C.6 |
| 1.1327 | B.151 | C.6 |
| 1.1328 | B.152 | C.6 |
| 1.1329 | B.153 | C.6 |
| 1.1330 | B.154 | C.6 |
| 1.1331 | B.155 | C.6 |
| 1.1332 | B.156 | C.6 |
| 1.1333 | B.157 | C.6 |
| 1.1334 | B.158 | C.6 |
| 1.1335 | B.159 | C.6 |
| 1.1336 | B.160 | C.6 |
| 1.1337 | B.161 | C.6 |
| 1.1338 | B.162 | C.6 |
| 1.1339 | B.163 | C.6 |
| 1.1340 | B.164 | C.6 |
| 1.1341 | B.165 | C.6 |
| 1.1342 | B.166 | C.6 |
| 1.1343 | B.167 | C.6 |
| 1.1344 | B.168 | C.6 |

TABLE 1-continued (compositions 1.1 to 1.3545):

| comp. no. | herbicide B | safener C |
|---|---|---|
| 1.1345 | B.169 | C.6 |
| 1.1346 | B.170 | C.6 |
| 1.1347 | B.171 | C.6 |
| 1.1348 | B.172 | C.6 |
| 1.1349 | B.173 | C.6 |
| 1.1350 | B.174 | C.6 |
| 1.1351 | B.175 | C.6 |
| 1.1352 | B.176 | C.6 |
| 1.1353 | B.177 | C.6 |
| 1.1354 | B.178 | C.6 |
| 1.1355 | B.179 | C.6 |
| 1.1356 | B.180 | C.6 |
| 1.1357 | B.181 | C.6 |
| 1.1358 | B.182 | C.6 |
| 1.1359 | B.183 | C.6 |
| 1.1360 | B.184 | C.6 |
| 1.1361 | B.185 | C.6 |
| 1.1362 | B.186 | C.6 |
| 1.1363 | B.187 | C.6 |
| 1.1364 | B.188 | C.6 |
| 1.1365 | B.189 | C.6 |
| 1.1366 | B.190 | C.6 |
| 1.1367 | B.191 | C.6 |
| 1.1368 | B.192 | C.6 |
| 1.1369 | B.193 | C.6 |
| 1.1370 | B.194 | C.6 |
| 1.1371 | B.195 | C.6 |
| 1.1372 | B.196 | C.6 |
| 1.1373 | B.1 | C.7 |
| 1.1374 | B.2 | C.7 |
| 1.1375 | B.3 | C.7 |
| 1.1376 | B.4 | C.7 |
| 1.1377 | B.5 | C.7 |
| 1.1378 | B.6 | C.7 |
| 1.1379 | B.7 | C.7 |
| 1.1380 | B.8 | C.7 |
| 1.1381 | B.9 | C.7 |
| 1.1382 | B.10 | C.7 |
| 1.1383 | B.11 | C.7 |
| 1.1384 | B.12 | C.7 |
| 1.1385 | B.13 | C.7 |
| 1.1386 | B.14 | C.7 |
| 1.1387 | B.15 | C.7 |
| 1.1388 | B.16 | C.7 |
| 1.1389 | B.17 | C.7 |
| 1.1390 | B.18 | C.7 |
| 1.1391 | B.19 | C.7 |
| 1.1392 | B.20 | C.7 |
| 1.1393 | B.21 | C.7 |
| 1.1394 | B.22 | C.7 |
| 1.1395 | B.23 | C.7 |
| 1.1396 | B.24 | C.7 |
| 1.1397 | B.25 | C.7 |
| 1.1398 | B.26 | C.7 |
| 1.1399 | B.27 | C.7 |
| 1.1400 | B.28 | C.7 |
| 1.1401 | B.29 | C.7 |
| 1.1402 | B.30 | C.7 |
| 1.1403 | B.31 | C.7 |
| 1.1404 | B.32 | C.7 |
| 1.1405 | B.33 | C.7 |
| 1.1406 | B.34 | C.7 |
| 1.1407 | B.35 | C.7 |
| 1.1408 | B.36 | C.7 |
| 1.1409 | B.37 | C.7 |
| 1.1410 | B.38 | C.7 |
| 1.1411 | B.39 | C.7 |
| 1.1412 | B.40 | C.7 |
| 1.1413 | B.41 | C.7 |
| 1.1414 | B.42 | C.7 |
| 1.1415 | B.43 | C.7 |
| 1.1416 | B.44 | C.7 |
| 1.1417 | B.45 | C.7 |
| 1.1418 | B.46 | C.7 |
| 1.1419 | B.47 | C.7 |
| 1.1420 | B.48 | C.7 |
| 1.1421 | B.49 | C.7 |
| 1.1422 | B.50 | C.7 |
| 1.1423 | B.51 | C.7 |
| 1.1424 | B.52 | C.7 |
| 1.1425 | B.53 | C.7 |
| 1.1426 | B.54 | C.7 |
| 1.1427 | B.55 | C.7 |
| 1.1428 | B.56 | C.7 |
| 1.1429 | B.57 | C.7 |
| 1.1430 | B.58. | C.7 |
| 1.1431 | B.59 | C.7 |
| 1.1432 | B.60 | C.7 |
| 1.1433 | B.61 | C.7 |
| 1.1434 | B.62 | C.7 |
| 1.1435 | B.63 | C.7 |
| 1.1436 | B.64 | C.7 |
| 1.1437 | B.65 | C.7 |
| 1.1438 | B.66 | C.7 |
| 1.1439 | B.67 | C.7 |
| 1.1440 | B.68 | C.7 |
| 1.1441 | B.69 | C.7 |
| 1.1442 | B.70 | C.7 |
| 1.1443 | B.71 | C.7 |
| 1.1444 | B.72 | C.7 |
| 1.1445 | B.73 | C.7 |
| 1.1446 | B.74 | C.7 |
| 1.1447 | B.75 | C.7 |
| 1.1448 | B.76 | C.7 |
| 1.1449 | B.77 | C.7 |
| 1.1450 | B.78 | C.7 |
| 1.1451 | B.79 | C.7 |
| 1.1452 | B.80 | C.7 |
| 1.1453 | B.81 | C.7 |
| 1.1454 | B.82 | C.7 |
| 1.1455 | B.83 | C.7 |
| 1.1456 | B.84 | C.7 |
| 1.1457 | B.85 | C.7 |
| 1.1458 | B.86 | C.7 |
| 1.1459 | B.87 | C.7 |
| 1.1460 | B.88 | C.7 |
| 1.1461 | B.89 | C.7 |
| 1.1462 | B.90 | C.7 |
| 1.1463 | B.91 | C.7 |
| 1.1464 | B.92 | C.7 |
| 1.1465 | B.93 | C.7 |
| 1.1466 | B.94 | C.7 |
| 1.1467 | B.95 | C.7 |
| 1.1468 | B.96 | C.7 |
| 1.1469 | B.97 | C.7 |
| 1.1470 | B.98 | C.7 |
| 1.1471 | B.99 | C.7 |
| 1.1472 | B.100 | C.7 |
| 1.1473 | B.101 | C.7 |
| 1.1474 | B.102 | C.7 |
| 1.1475 | B.103 | C.7 |
| 1.1476 | B.104 | C.7 |
| 1.1477 | B.105 | C.7 |
| 1.1478 | B.106 | C.7 |
| 1.1479 | B.107 | C.7 |
| 1.1480 | B.108 | C.7 |
| 1.1481 | B.109 | C.7 |
| 1.1482 | B.110 | C.7 |
| 1.1483 | B.111 | C.7 |
| 1.1484 | B.112 | C.7 |
| 1.1485 | B.113 | C.7 |
| 1.1486 | B.114 | C.7 |
| 1.1487 | B.115 | C.7 |
| 1.1488 | B.116 | C.7 |
| 1.1489 | B.117 | C.7 |
| 1.1490 | B.118 | C.7 |
| 1.1491 | B.119 | C.7 |
| 1.1492 | B.120 | C.7 |
| 1.1493 | B.121 | C.7 |
| 1.1494 | B.122 | C.7 |
| 1.1495 | B.123 | C.7 |
| 1.1496 | B.124 | C.7 |

TABLE 1-continued (compositions 1.1 to 1.3545):

| comp. no. | herbicide B | safener C |
|---|---|---|
| 1.1497 | B.125 | C.7 |
| 1.1498 | B.126 | C.7 |
| 1.1499 | B.127 | C.7 |
| 1.1500 | B.128 | C.7 |
| 1.1501 | B.129 | C.7 |
| 1.1502 | B.130 | C.7 |
| 1.1503 | B.131 | C.7 |
| 1.1504 | B.132 | C.7 |
| 1.1505 | B.133 | C.7 |
| 1.1506 | B.134 | C.7 |
| 1.1507 | B.135 | C.7 |
| 1.1508 | B.136 | C.7 |
| 1.1509 | B.137 | C.7 |
| 1.1510 | B.138 | C.7 |
| 1.1511 | B.139 | C.7 |
| 1.1512 | B.140 | C.7 |
| 1.1513 | B.141 | C.7 |
| 1.1514 | B.142 | C.7 |
| 1.1515 | B.143 | C.7 |
| 1.1516 | B.144 | C.7 |
| 1.1517 | B.145 | C.7 |
| 1.1518 | B.146 | C.7 |
| 1.1519 | B.147 | C.7 |
| 1.1520 | B.148 | C.7 |
| 1.1521 | B.149 | C.7 |
| 1.1522 | B.150 | C.7 |
| 1.1523 | B.151 | C.7 |
| 1.1524 | B.152 | C.7 |
| 1.1525 | B.153 | C.7 |
| 1.1526 | B.154 | C.7 |
| 1.1527 | B.155 | C.7 |
| 1.1528 | B.156 | C.7 |
| 1.1529 | B.157 | C.7 |
| 1.1530 | B.158 | C.7 |
| 1.1531 | B.159 | C.7 |
| 1.1532 | B.160 | C.7 |
| 1.1533 | B.161 | C.7 |
| 1.1534 | B.162 | C.7 |
| 1.1535 | B.163 | C.7 |
| 1.1536 | B.164 | C.7 |
| 1.1537 | B.165 | C.7 |
| 1.1538 | B.166 | C.7 |
| 1.1539 | B.167 | C.7 |
| 1.1540 | B.168 | C.7 |
| 1.1541 | B.169 | C.7 |
| 1.1542 | B.170 | C.7 |
| 1.1543 | B.171 | C.7 |
| 1.1544 | B.172 | C.7 |
| 1.1545 | B.173 | C.7 |
| 1.1546 | B.174 | C.7 |
| 1.1547 | B.175 | C.7 |
| 1.1548 | B.176 | C.7 |
| 1.1549 | B.177 | C.7 |
| 1.1550 | B.178 | C.7 |
| 1.1551 | B.179 | C.7 |
| 1.1552 | B.180 | C.7 |
| 1.1553 | B.181 | C.7 |
| 1.1554 | B.182 | C.7 |
| 1.1555 | B.183 | C.7 |
| 1.1556 | B.184 | C.7 |
| 1.1557 | B.185 | C.7 |
| 1.1558 | B.186 | C.7 |
| 1.1559 | B.187 | C.7 |
| 1.1560 | B.188 | C.7 |
| 1.1561 | B.189 | C.7 |
| 1.1562 | B.190 | C.7 |
| 1.1563 | B.191 | C.7 |
| 1.1564 | B.192 | C.7 |
| 1.1565 | B.193 | C.7 |
| 1.1566 | B.194 | C.7 |
| 1.1567 | B.195 | C.7 |
| 1.1568 | B.196 | C.7 |
| 1.1569 | B.1 | C.8 |
| 1.1570 | B.2 | C.8 |
| 1.1571 | B.3 | C.8 |
| 1.1572 | B.4 | C.8 |
| 1.1573 | B.5 | C.8 |
| 1.1574 | B.6 | C.8 |
| 1.1575 | B.7 | C.8 |
| 1.1576 | B.8 | C.8 |
| 1.1577 | B.9 | C.8 |
| 1.1578 | B.10 | C.8 |
| 1.1579 | B.11 | C.8 |
| 1.1580 | B.12 | C.8 |
| 1.1581 | B.13 | C.8 |
| 1.1582 | B.14 | C.8 |
| 1.1583 | B.15 | C.8 |
| 1.1584 | B.16 | C.8 |
| 1.1585 | B.17 | C.8 |
| 1.1586 | B.18 | C.8 |
| 1.1587 | B.19 | C.8 |
| 1.1588 | B.20 | C.8 |
| 1.1589 | B.21 | C.8 |
| 1.1590 | B.22 | C.8 |
| 1.1591 | B.23 | C.8 |
| 1.1592 | B.24 | C.8 |
| 1.1593 | B.25 | C.8 |
| 1.1594 | B.26 | C.8 |
| 1.1595 | B.27 | C.8 |
| 1.1596 | B.28 | C.8 |
| 1.1597 | B.29 | C.8 |
| 1.1598 | B.30 | C.8 |
| 1.1599 | B.31 | C.8 |
| 1.1600 | B.32 | C.8 |
| 1.1601 | B.33 | C.8 |
| 1.1602 | B.34 | C.8 |
| 1.1603 | B.35 | C.8 |
| 1.1604 | B.36 | C.8 |
| 1.1605 | B.37 | C.8 |
| 1.1606 | B.38 | C.8 |
| 1.1607 | B.39 | C.8 |
| 1.1608 | B.40 | C.8 |
| 1.1609 | B.41 | C.8 |
| 1.1610 | B.42 | C.8 |
| 1.1611 | B.43 | C.8 |
| 1.1612 | B.44 | C.8 |
| 1.1613 | B.45 | C.8 |
| 1.1614 | B.46 | C.8 |
| 1.1615 | B.47 | C.8 |
| 1.1616 | B.48 | C.8 |
| 1.1617 | B.49 | C.8 |
| 1.1618 | B.50 | C.8 |
| 1.1619 | B.51 | C.8 |
| 1.1620 | B.52 | C.8 |
| 1.1621 | B.53 | C.8 |
| 1.1622 | B.54 | C.8 |
| 1.1623 | B.55 | C.8 |
| 1.1624 | B.56 | C.8 |
| 1.1625 | B.57 | C.8 |
| 1.1626 | B.58. | C.8 |
| 1.1627 | B.59 | C.8 |
| 1.1628 | B.60 | C.8 |
| 1.1629 | B.61 | C.8 |
| 1.1630 | B.62 | C.8 |
| 1.1631 | B.63 | C.8 |
| 1.1632 | B.64 | C.8 |
| 1.1633 | B.65 | C.8 |
| 1.1634 | B.66 | C.8 |
| 1.1635 | B.67 | C.8 |
| 1.1636 | B.68 | C.8 |
| 1.1637 | B.69 | C.8 |
| 1.1638 | B.70 | C.8 |
| 1.1639 | B.71 | C.8 |
| 1.1640 | B.72 | C.8 |
| 1.1641 | B.73 | C.8 |
| 1.1642 | B.74 | C.8 |
| 1.1643 | B.75 | C.8 |
| 1.1644 | B.76 | C.8 |
| 1.1645 | B.77 | C.8 |
| 1.1646 | B.78 | C.8 |
| 1.1647 | B.79 | C.8 |
| 1.1648 | B.80 | C.8 |

TABLE 1-continued (compositions 1.1 to 1.3545):

| comp. no. | herbicide B | safener C |
|---|---|---|
| 1.1649 | B.81 | C.8 |
| 1.1650 | B.82 | C.8 |
| 1.1651 | B.83 | C.8 |
| 1.1652 | B.84 | C.8 |
| 1.1653 | B.85 | C.8 |
| 1.1654 | B.86 | C.8 |
| 1.1655 | B.87 | C.8 |
| 1.1656 | B.88 | C.8 |
| 1.1657 | B.89 | C.8 |
| 1.1658 | B.90 | C.8 |
| 1.1659 | B.91 | C.8 |
| 1.1660 | B.92 | C.8 |
| 1.1661 | B.93 | C.8 |
| 1.1662 | B.94 | C.8 |
| 1.1663 | B.95 | C.8 |
| 1.1664 | B.96 | C.8 |
| 1.1665 | B.97 | C.8 |
| 1.1666 | B.98 | C.8 |
| 1.1667 | B.99 | C.8 |
| 1.1668 | B.100 | C.8 |
| 1.1669 | B.101 | C.8 |
| 1.1670 | B.102 | C.8 |
| 1.1671 | B.103 | C.8 |
| 1.1672 | B.104 | C.8 |
| 1.1673 | B.105 | C.8 |
| 1.1674 | B.106 | C.8 |
| 1.1675 | B.107 | C.8 |
| 1.1676 | B.108 | C.8 |
| 1.1677 | B.109 | C.8 |
| 1.1678 | B.110 | C.8 |
| 1.1679 | B.111 | C.8 |
| 1.1680 | B.112 | C.8 |
| 1.1681 | B.113 | C.8 |
| 1.1682 | B.114 | C.8 |
| 1.1683 | B.115 | C.8 |
| 1.1684 | B.116 | C.8 |
| 1.1685 | B.117 | C.8 |
| 1.1686 | B.118 | C.8 |
| 1.1687 | B.119 | C.8 |
| 1.1688 | B.120 | C.8 |
| 1.1689 | B.121 | C.8 |
| 1.1690 | B.122 | C.8 |
| 1.1691 | B.123 | C.8 |
| 1.1692 | B.124 | C.8 |
| 1.1693 | B.125 | C.8 |
| 1.1694 | B.126 | C.8 |
| 1.1695 | B.127 | C.8 |
| 1.1696 | B.128 | C.8 |
| 1.1697 | B.129 | C.8 |
| 1.1698 | B.130 | C.8 |
| 1.1699 | B.131 | C.8 |
| 1.1700 | B.132 | C.8 |
| 1.1701 | B.133 | C.8 |
| 1.1702 | B.134 | C.8 |
| 1.1703 | B.135 | C.8 |
| 1.1704 | B.136 | C.8 |
| 1.1705 | B.137 | C.8 |
| 1.1706 | B.138 | C.8 |
| 1.1707 | B.139 | C.8 |
| 1.1708 | B.140 | C.8 |
| 1.1709 | B.141 | C.8 |
| 1.1710 | B.142 | C.8 |
| 1.1711 | B.143 | C.8 |
| 1.1712 | B.144 | C.8 |
| 1.1713 | B.145 | C.8 |
| 1.1714 | B.146 | C.8 |
| 1.1715 | B.147 | C.8 |
| 1.1716 | B.148 | C.8 |
| 1.1717 | B.149 | C.8 |
| 1.1718 | B.150 | C.8 |
| 1.1719 | B.151 | C.8 |
| 1.1720 | B.152 | C.8 |
| 1.1721 | B.153 | C.8 |
| 1.1722 | B.154 | C.8 |
| 1.1723 | B.155 | C.8 |
| 1.1724 | B.156 | C.8 |
| 1.1725 | B.157 | C.8 |
| 1.1726 | B.158 | C.8 |
| 1.1727 | B.159 | C.8 |
| 1.1728 | B.160 | C.8 |
| 1.1729 | B.161 | C.8 |
| 1.1730 | B.162 | C.8 |
| 1.1731 | B.163 | C.8 |
| 1.1732 | B.164 | C.8 |
| 1.1733 | B.165 | C.8 |
| 1.1734 | B.166 | C.8 |
| 1.1735 | B.167 | C.8 |
| 1.1736 | B.168 | C.8 |
| 1.1737 | B.169 | C.8 |
| 1.1738 | B.170 | C.8 |
| 1.1739 | B.171 | C.8 |
| 1.1740 | B.172 | C.8 |
| 1.1741 | B.173 | C.8 |
| 1.1742 | B.174 | C.8 |
| 1.1743 | B.175 | C.8 |
| 1.1744 | B.176 | C.8 |
| 1.1745 | B.177 | C.8 |
| 1.1746 | B.178 | C.8 |
| 1.1747 | B.179 | C.8 |
| 1.1748 | B.180 | C.8 |
| 1.1749 | B.181 | C.8 |
| 1.1750 | B.182 | C.8 |
| 1.1751 | B.183 | C.8 |
| 1.1752 | B.184 | C.8 |
| 1.1753 | B.185 | C.8 |
| 1.1754 | B.186 | C.8 |
| 1.1755 | B.187 | C.8 |
| 1.1756 | B.188 | C.8 |
| 1.1757 | B.189 | C.8 |
| 1.1758 | B.190 | C.8 |
| 1.1759 | B.191 | C.8 |
| 1.1760 | B.192 | C.8 |
| 1.1761 | B.193 | C.8 |
| 1.1762 | B.194 | C.8 |
| 1.1763 | B.195 | C.8 |
| 1.1764 | B.196 | C.8 |
| 1.1765 | B.1 | C.9 |
| 1.1766 | B.2 | C.9 |
| 1.1767 | B.3 | C.9 |
| 1.1768 | B.4 | C.9 |
| 1.1769 | B.5 | C.9 |
| 1.1770 | B.6 | C.9 |
| 1.1771 | B.7 | C.9 |
| 1.1772 | B.8 | C.9 |
| 1.1773 | B.9 | C.9 |
| 1.1774 | B.10 | C.9 |
| 1.1775 | B.11 | C.9 |
| 1.1776 | B.12 | C.9 |
| 1.1777 | B.13 | C.9 |
| 1.1778 | B.14 | C.9 |
| 1.1779 | B.15 | C.9 |
| 1.1780 | B.16 | C.9 |
| 1.1781 | B.17 | C.9 |
| 1.1782 | B.18 | C.9 |
| 1.1783 | B.19 | C.9 |
| 1.1784 | B.20 | C.9 |
| 1.1785 | B.21 | C.9 |
| 1.1786 | B.22 | C.9 |
| 1.1787 | B.23 | C.9 |
| 1.1788 | B.24 | C.9 |
| 1.1789 | B.25 | C.9 |
| 1.1790 | B.26 | C.9 |
| 1.1791 | B.27 | C.9 |
| 1.1792 | B.28 | C.9 |
| 1.1793 | B.29 | C.9 |
| 1.1794 | B.30 | C.9 |
| 1.1795 | B.31 | C.9 |
| 1.1796 | B.32 | C.9 |
| 1.1797 | B.33 | C.9 |
| 1.1798 | B.34 | C.9 |
| 1.1799 | B.35 | C.9 |
| 1.1800 | B.36 | C.9 |

TABLE 1-continued (compositions 1.1 to 1.3545):

| comp. no. | herbicide B | safener C |
|---|---|---|
| 1.1801 | B.37 | C.9 |
| 1.1802 | B.38 | C.9 |
| 1.1803 | B.39 | C.9 |
| 1.1804 | B.40 | C.9 |
| 1.1805 | B.41 | C.9 |
| 1.1806 | B.42 | C.9 |
| 1.1807 | B.43 | C.9 |
| 1.1808 | B.44 | C.9 |
| 1.1809 | B.45 | C.9 |
| 1.1810 | B.46 | C.9 |
| 1.1811 | B.47 | C.9 |
| 1.1812 | B.48 | C.9 |
| 1.1813 | B.49 | C.9 |
| 1.1814 | B.50 | C.9 |
| 1.1815 | B.51 | C.9 |
| 1.1816 | B.52 | C.9 |
| 1.1817 | B.53 | C.9 |
| 1.1818 | B.54 | C.9 |
| 1.1819 | B.55 | C.9 |
| 1.1820 | B.56 | C.9 |
| 1.1821 | B.57 | C.9 |
| 1.1822 | B.58. | C.9 |
| 1.1823 | B.59 | C.9 |
| 1.1824 | B.60 | C.9 |
| 1.1825 | B.61 | C.9 |
| 1.1826 | B.62 | C.9 |
| 1.1827 | B.63 | C.9 |
| 1.1828 | B.64 | C.9 |
| 1.1829 | B.65 | C.9 |
| 1.1830 | B.66 | C.9 |
| 1.1831 | B.67 | C.9 |
| 1.1832 | B.68 | C.9 |
| 1.1833 | B.69 | C.9 |
| 1.1834 | B.70 | C.9 |
| 1.1835 | B.71 | C.9 |
| 1.1836 | B.72 | C.9 |
| 1.1837 | B.73 | C.9 |
| 1.1838 | B.74 | C.9 |
| 1.1839 | B.75 | C.9 |
| 1.1840 | B.76 | C.9 |
| 1.1841 | B.77 | C.9 |
| 1.1842 | B.78 | C.9 |
| 1.1843 | B.79 | C.9 |
| 1.1844 | B.80 | C.9 |
| 1.1845 | B.81 | C.9 |
| 1.1846 | B.82 | C.9 |
| 1.1847 | B.83 | C.9 |
| 1.1848 | B.84 | C.9 |
| 1.1849 | B.85 | C.9 |
| 1.1850 | B.86 | C.9 |
| 1.1851 | B.87 | C.9 |
| 1.1852 | B.88 | C.9 |
| 1.1853 | B.89 | C.9 |
| 1.1854 | B.90 | C.9 |
| 1.1855 | B.91 | C.9 |
| 1.1856 | B.92 | C.9 |
| 1.1857 | B.93 | C.9 |
| 1.1858 | B.94 | C.9 |
| 1.1859 | B.95 | C.9 |
| 1.1860 | B.96 | C.9 |
| 1.1861 | B.97 | C.9 |
| 1.1862 | B.98 | C.9 |
| 1.1863 | B.99 | C.9 |
| 1.1864 | B.100 | C.9 |
| 1.1865 | B.101 | C.9 |
| 1.1866 | B.102 | C.9 |
| 1.1867 | B.103 | C.9 |
| 1.1868 | B.104 | C.9 |
| 1.1869 | B.105 | C.9 |
| 1.1870 | B.106 | C.9 |
| 1.1871 | B.107 | C.9 |
| 1.1872 | B.108 | C.9 |
| 1.1873 | B.109 | C.9 |
| 1.1874 | B.110 | C.9 |
| 1.1875 | B.111 | C.9 |
| 1.1876 | B.112 | C.9 |
| 1.1877 | B.113 | C.9 |
| 1.1878 | B.114 | C.9 |
| 1.1879 | B.115 | C.9 |
| 1.1880 | B.116 | C.9 |
| 1.1881 | B.117 | C.9 |
| 1.1882 | B.118 | C.9 |
| 1.1883 | B.119 | C.9 |
| 1.1884 | B.120 | C.9 |
| 1.1885 | B.121 | C.9 |
| 1.1886 | B.122 | C.9 |
| 1.1887 | B.123 | C.9 |
| 1.1888 | B.124 | C.9 |
| 1.1889 | B.125 | C.9 |
| 1.1890 | B.126 | C.9 |
| 1.1891 | B.127 | C.9 |
| 1.1892 | B.128 | C.9 |
| 1.1893 | B.129 | C.9 |
| 1.1894 | B.130 | C.9 |
| 1.1895 | B.131 | C.9 |
| 1.1896 | B.132 | C.9 |
| 1.1897 | B.133 | C.9 |
| 1.1898 | B.134 | C.9 |
| 1.1899 | B.135 | C.9 |
| 1.1900 | B.136 | C.9 |
| 1.1901 | B.137 | C.9 |
| 1.1902 | B.138 | C.9 |
| 1.1903 | B.139 | C.9 |
| 1.1904 | B.140 | C.9 |
| 1.1905 | B.141 | C.9 |
| 1.1906 | B.142 | C.9 |
| 1.1907 | B.143 | C.9 |
| 1.1908 | B.144 | C.9 |
| 1.1909 | B.145 | C.9 |
| 1.1910 | B.146 | C.9 |
| 1.1911 | B.147 | C.9 |
| 1.1912 | B.148 | C.9 |
| 1.1913 | B.149 | C.9 |
| 1.1914 | B.150 | C.9 |
| 1.1915 | B.151 | C.9 |
| 1.1916 | B.152 | C.9 |
| 1.1917 | B.153 | C.9 |
| 1.1918 | B.154 | C.9 |
| 1.1919 | B.155 | C.9 |
| 1.1920 | B.156 | C.9 |
| 1.1921 | B.157 | C.9 |
| 1.1922 | B.158 | C.9 |
| 1.1923 | B.159 | C.9 |
| 1.1924 | B.160 | C.9 |
| 1.1925 | B.161 | C.9 |
| 1.1926 | B.162 | C.9 |
| 1.1927 | B.163 | C.9 |
| 1.1928 | B.164 | C.9 |
| 1.1929 | B.165 | C.9 |
| 1.1930 | B.166 | C.9 |
| 1.1931 | B.167 | C.9 |
| 1.1932 | B.168 | C.9 |
| 1.1933 | B.169 | C.9 |
| 1.1934 | B.170 | C.9 |
| 1.1935 | B.171 | C.9 |
| 1.1936 | B.172 | C.9 |
| 1.1937 | B.173 | C.9 |
| 1.1938 | B.174 | C.9 |
| 1.1939 | B.175 | C.9 |
| 1.1940 | B.176 | C.9 |
| 1.1941 | B.177 | C.9 |
| 1.1942 | B.178 | C.9 |
| 1.1943 | B.179 | C.9 |
| 1.1944 | B.180 | C.9 |
| 1.1945 | B.181 | C.9 |
| 1.1946 | B.182 | C.9 |
| 1.1947 | B.183 | C.9 |
| 1.1948 | B.184 | C.9 |
| 1.1949 | B.185 | C.9 |
| 1.1950 | B.186 | C.9 |
| 1.1951 | B.187 | C.9 |
| 1.1952 | B.188 | C.9 |

TABLE 1-continued (compositions 1.1 to 1.3545):

| comp. no. | herbicide B | safener C |
|---|---|---|
| 1.1953 | B.189 | C.9 |
| 1.1954 | B.190 | C.9 |
| 1.1955 | B.191 | C.9 |
| 1.1956 | B.192 | C.9 |
| 1.1957 | B.193 | C.9 |
| 1.1958 | B.194 | C.9 |
| 1.1959 | B.195 | C.9 |
| 1.1960 | B.196 | C.9 |
| 1.1961 | B.1 | C.10 |
| 1.1962 | B.2 | C.10 |
| 1.1963 | B.3 | C.10 |
| 1.1964 | B.4 | C.10 |
| 1.1965 | B.5 | C.10 |
| 1.1966 | B.6 | C.10 |
| 1.1967 | B.7 | C.10 |
| 1.1968 | B.8 | C.10 |
| 1.1969 | B.9 | C.10 |
| 1.1970 | B.10 | C.10 |
| 1.1971 | B.11 | C.10 |
| 1.1972 | B.12 | C.10 |
| 1.1973 | B.13 | C.10 |
| 1.1974 | B.14 | C.10 |
| 1.1975 | B.15 | C.10 |
| 1.1976 | B.16 | C.10 |
| 1.1977 | B.17 | C.10 |
| 1.1978 | B.18 | C.10 |
| 1.1979 | B.19 | C.10 |
| 1.1980 | B.20 | C.10 |
| 1.1981 | B.21 | C.10 |
| 1.1982 | B.22 | C.10 |
| 1.1983 | B.23 | C.10 |
| 1.1984 | B.24 | C.10 |
| 1.1985 | B.25 | C.10 |
| 1.1986 | B.26 | C.10 |
| 1.1987 | B.27 | C.10 |
| 1.1988 | B.28 | C.10 |
| 1.1989 | B.29 | C.10 |
| 1.1990 | B.30 | C.10 |
| 1.1991 | B.31 | C.10 |
| 1.1992 | B.32 | C.10 |
| 1.1993 | B.33 | C.10 |
| 1.1994 | B.34 | C.10 |
| 1.1995 | B.35 | C.10 |
| 1.1996 | B.36 | C.10 |
| 1.1997 | B.37 | C.10 |
| 1.1998 | B.38 | C.10 |
| 1.1999 | B.39 | C.10 |
| 1.2000 | B.40 | C.10 |
| 1.2001 | B.41 | C.10 |
| 1.2002 | B.42 | C.10 |
| 1.2003 | B.43 | C.10 |
| 1.2004 | B.44 | C.10 |
| 1.2005 | B.45 | C.10 |
| 1.2006 | B.46 | C.10 |
| 1.2007 | B.47 | C.10 |
| 1.2008 | B.48 | C.10 |
| 1.2009 | B.49 | C.10 |
| 1.2010 | B.50 | C.10 |
| 1.2011 | B.51 | C.10 |
| 1.2012 | B.52 | C.10 |
| 1.2013 | B.53 | C.10 |
| 1.2014 | B.54 | C.10 |
| 1.2015 | B.55 | C.10 |
| 1.2016 | B.56 | C.10 |
| 1.2017 | B.57 | C.10 |
| 1.2018 | B.58. | C.10 |
| 1.2019 | B.59 | C.10 |
| 1.2020 | B.60 | C.10 |
| 1.2021 | B.61 | C.10 |
| 1.2022 | B.62 | C.10 |
| 1.2023 | B.63 | C.10 |
| 1.2024 | B.64 | C.10 |
| 1.2025 | B.65 | C.10 |
| 1.2026 | B.66 | C.10 |
| 1.2027 | B.67 | C.10 |
| 1.2028 | B.68 | C.10 |
| 1.2029 | B.69 | C.10 |
| 1.2030 | B.70 | C.10 |
| 1.2031 | B.71 | C.10 |
| 1.2032 | B.72 | C.10 |
| 1.2033 | B.73 | C.10 |
| 1.2034 | B.74 | C.10 |
| 1.2035 | B.75 | C.10 |
| 1.2036 | B.76 | C.10 |
| 1.2037 | B.77 | C.10 |
| 1.2038 | B.78 | C.10 |
| 1.2039 | B.79 | C.10 |
| 1.2040 | B.80 | C.10 |
| 1.2041 | B.81 | C.10 |
| 1.2042 | B.82 | C.10 |
| 1.2043 | B.83 | C.10 |
| 1.2044 | B.84 | C.10 |
| 1.2045 | B.85 | C.10 |
| 1.2046 | B.86 | C.10 |
| 1.2047 | B.87 | C.10 |
| 1.2048 | B.88 | C.10 |
| 1.2049 | B.89 | C.10 |
| 1.2050 | B.90 | C.10 |
| 1.2051 | B.91 | C.10 |
| 1.2052 | B.92 | C.10 |
| 1.2053 | B.93 | C.10 |
| 1.2054 | B.94 | C.10 |
| 1.2055 | B.95 | C.10 |
| 1.2056 | B.96 | C.10 |
| 1.2057 | B.97 | C.10 |
| 1.2058 | B.98 | C.10 |
| 1.2059 | B.99 | C.10 |
| 1.2060 | B.100 | C.10 |
| 1.2061 | B.101 | C.10 |
| 1.2062 | B.102 | C.10 |
| 1.2063 | B.103 | C.10 |
| 1.2064 | B.104 | C.10 |
| 1.2065 | B.105 | C.10 |
| 1.2066 | B.106 | C.10 |
| 1.2067 | B.107 | C.10 |
| 1.2068 | B.108 | C.10 |
| 1.2069 | B.109 | C.10 |
| 1.2070 | B.110 | C.10 |
| 1.2071 | B.111 | C.10 |
| 1.2072 | B.112 | C.10 |
| 1.2073 | B.113 | C.10 |
| 1.2074 | B.114 | C.10 |
| 1.2075 | B.115 | C.10 |
| 1.2076 | B.116 | C.10 |
| 1.2077 | B.117 | C.10 |
| 1.2078 | B.118 | C.10 |
| 1.2079 | B.119 | C.10 |
| 1.2080 | B.120 | C.10 |
| 1.2081 | B.121 | C.10 |
| 1.2082 | B.122 | C.10 |
| 1.2083 | B.123 | C.10 |
| 1.2084 | B.124 | C.10 |
| 1.2085 | B.125 | C.10 |
| 1.2086 | B.126 | C.10 |
| 1.2087 | B.127 | C.10 |
| 1.2088 | B.128 | C.10 |
| 1.2089 | B.129 | C.10 |
| 1.2090 | B.130 | C.10 |
| 1.2091 | B.131 | C.10 |
| 1.2092 | B.132 | C.10 |
| 1.2093 | B.133 | C.10 |
| 1.2094 | B.134 | C.10 |
| 1.2095 | B.135 | C.10 |
| 1.2096 | B.136 | C.10 |
| 1.2097 | B.137 | C.10 |
| 1.2098 | B.138 | C.10 |
| 1.2099 | B.139 | C.10 |
| 1.2100 | B.140 | C.10 |
| 1.2101 | B.141 | C.10 |
| 1.2102 | B.142 | C.10 |
| 1.2103 | B.143 | C.10 |
| 1.2104 | B.144 | C.10 |

TABLE 1-continued (compositions 1.1 to 1.3545):

| comp. no. | herbicide B | safener C |
|---|---|---|
| 1.2105 | B.145 | C.10 |
| 1.2106 | B.146 | C.10 |
| 1.2107 | B.147 | C.10 |
| 1.2108 | B.148 | C.10 |
| 1.2109 | B.149 | C.10 |
| 1.2110 | B.150 | C.10 |
| 1.2111 | B.151 | C.10 |
| 1.2112 | B.152 | C.10 |
| 1.2113 | B.153 | C.10 |
| 1.2114 | B.154 | C.10 |
| 1.2115 | B.155 | C.10 |
| 1.2116 | B.156 | C.10 |
| 1.2117 | B.157 | C.10 |
| 1.2118 | B.158 | C.10 |
| 1.2119 | B.159 | C.10 |
| 1.2120 | B.160 | C.10 |
| 1.2121 | B.161 | C.10 |
| 1.2122 | B.162 | C.10 |
| 1.2123 | B.163 | C.10 |
| 1.2124 | B.164 | C.10 |
| 1.2125 | B.165 | C.10 |
| 1.2126 | B.166 | C.10 |
| 1.2127 | B.167 | C.10 |
| 1.2128 | B.168 | C.10 |
| 1.2129 | B.169 | C.10 |
| 1.2130 | B.170 | C.10 |
| 1.2131 | B.171 | C.10 |
| 1.2132 | B.172 | C.10 |
| 1.2133 | B.173 | C.10 |
| 1.2134 | B.174 | C.10 |
| 1.2135 | B.175 | C.10 |
| 1.2136 | B.176 | C.10 |
| 1.2137 | B.177 | C.10 |
| 1.2138 | B.178 | C.10 |
| 1.2139 | B.179 | C.10 |
| 1.2140 | B.180 | C.10 |
| 1.2141 | B.181 | C.10 |
| 1.2142 | B.182 | C.10 |
| 1.2143 | B.183 | C.10 |
| 1.2144 | B.184 | C.10 |
| 1.2145 | B.185 | C.10 |
| 1.2146 | B.186 | C.10 |
| 1.2147 | B.187 | C.10 |
| 1.2148 | B.188 | C.10 |
| 1.2149 | B.189 | C.10 |
| 1.2150 | B.190 | C.10 |
| 1.2151 | B.191 | C.10 |
| 1.2152 | B.192 | C.10 |
| 1.2153 | B.193 | C.10 |
| 1.2154 | B.194 | C.10 |
| 1.2155 | B.195 | C.10 |
| 1.2156 | B.196 | C.10 |
| 1.2157 | B.1 | C.11 |
| 1.2158 | B.2 | C.11 |
| 1.2159 | B.3 | C.11 |
| 1.2160 | B.4 | C.11 |
| 1.2161 | B.5 | C.11 |
| 1.2162 | B.6 | C.11 |
| 1.2163 | B.7 | C.11 |
| 1.2164 | B.8 | C.11 |
| 1.2165 | B.9 | C.11 |
| 1.2166 | B.10 | C.11 |
| 1.2167 | B.11 | C.11 |
| 1.2168 | B.12 | C.11 |
| 1.2169 | B.13 | C.11 |
| 1.2170 | B.14 | C.11 |
| 1.2171 | B.15 | C.11 |
| 1.2172 | B.16 | C.11 |
| 1.2173 | B.17 | C.11 |
| 1.2174 | B.18 | C.11 |
| 1.2175 | B.19 | C.11 |
| 1.2176 | B.20 | C.11 |
| 1.2177 | B.21 | C.11 |
| 1.2178 | B.22 | C.11 |
| 1.2179 | B.23 | C.11 |
| 1.2180 | B.24 | C.11 |
| 1.2181 | B.25 | C.11 |
| 1.2182 | B.26 | C.11 |
| 1.2183 | B.27 | C.11 |
| 1.2184 | B.28 | C.11 |
| 1.2185 | B.29 | C.11 |
| 1.2186 | B.30 | C.11 |
| 1.2187 | B.31 | C.11 |
| 1.2188 | B.32 | C.11 |
| 1.2189 | B.33 | C.11 |
| 1.2190 | B.34 | C.11 |
| 1.2191 | B.35 | C.11 |
| 1.2192 | B.36 | C.11 |
| 1.2193 | B.37 | C.11 |
| 1.2194 | B.38 | C.11 |
| 1.2195 | B.39 | C.11 |
| 1.2196 | B.40 | C.11 |
| 1.2197 | B.41 | C.11 |
| 1.2198 | B.42 | C.11 |
| 1.2199 | B.43 | C.11 |
| 1.2200 | B.44 | C.11 |
| 1.2201 | B.45 | C.11 |
| 1.2202 | B.46 | C.11 |
| 1.2203 | B.47 | C.11 |
| 1.2204 | B.48 | C.11 |
| 1.2205 | B.49 | C.11 |
| 1.2206 | B.50 | C.11 |
| 1.2207 | B.51 | C.11 |
| 1.2208 | B.52 | C.11 |
| 1.2209 | B.53 | C.11 |
| 1.2210 | B.54 | C.11 |
| 1.2211 | B.55 | C.11 |
| 1.2212 | B.56 | C.11 |
| 1.2213 | B.57 | C.11 |
| 1.2214 | B.58. | C.11 |
| 1.2215 | B.59 | C.11 |
| 1.2216 | B.60 | C.11 |
| 1.2217 | B.61 | C.11 |
| 1.2218 | B.62 | C.11 |
| 1.2219 | B.63 | C.11 |
| 1.2220 | B.64 | C.11 |
| 1.2221 | B.65 | C.11 |
| 1.2222 | B.66 | C.11 |
| 1.2223 | B.67 | C.11 |
| 1.2224 | B.68 | C.11 |
| 1.2225 | B.69 | C.11 |
| 1.2226 | B.70 | C.11 |
| 1.2227 | B.71 | C.11 |
| 1.2228 | B.72 | C.11 |
| 1.2229 | B.73 | C.11 |
| 1.2230 | B.74 | C.11 |
| 1.2231 | B.75 | C.11 |
| 1.2232 | B.76 | C.11 |
| 1.2233 | B.77 | C.11 |
| 1.2234 | B.78 | C.11 |
| 1.2235 | B.79 | C.11 |
| 1.2236 | B.80 | C.11 |
| 1.2237 | B.81 | C.11 |
| 1.2238 | B.82 | C.11 |
| 1.2239 | B.83 | C.11 |
| 1.2240 | B.84 | C.11 |
| 1.2241 | B.85 | C.11 |
| 1.2242 | B.86 | C.11 |
| 1.2243 | B.87 | C.11 |
| 1.2244 | B.88 | C.11 |
| 1.2245 | B.89 | C.11 |
| 1.2246 | B.90 | C.11 |
| 1.2247 | B.91 | C.11 |
| 1.2248 | B.92 | C.11 |
| 1.2249 | B.93 | C.11 |
| 1.2250 | B.94 | C.11 |
| 1.2251 | B.95 | C.11 |
| 1.2252 | B.96 | C.11 |
| 1.2253 | B.97 | C.11 |
| 1.2254 | B.98 | C.11 |
| 1.2255 | B.99 | C.11 |
| 1.2256 | B.100 | C.11 |

TABLE 1-continued (compositions 1.1 to 1.3545):

| comp. no. | herbicide B | safener C |
|---|---|---|
| 1.2257 | B.101 | C.11 |
| 1.2258 | B.102 | C.11 |
| 1.2259 | B.103 | C.11 |
| 1.2260 | B.104 | C.11 |
| 1.2261 | B.105 | C.11 |
| 1.2262 | B.106 | C.11 |
| 1.2263 | B.107 | C.11 |
| 1.2264 | B.108 | C.11 |
| 1.2265 | B.109 | C.11 |
| 1.2266 | B.110 | C.11 |
| 1.2267 | B.111 | C.11 |
| 1.2268 | B.112 | C.11 |
| 1.2269 | B.113 | C.11 |
| 1.2270 | B.114 | C.11 |
| 1.2271 | B.115 | C.11 |
| 1.2272 | B.116 | C.11 |
| 1.2273 | B.117 | C.11 |
| 1.2274 | B.118 | C.11 |
| 1.2275 | B.119 | C.11 |
| 1.2276 | B.120 | C.11 |
| 1.2277 | B.121 | C.11 |
| 1.2278 | B.122 | C.11 |
| 1.2279 | B.123 | C.11 |
| 1.2280 | B.124 | C.11 |
| 1.2281 | B.125 | C.11 |
| 1.2282 | B.126 | C.11 |
| 1.2283 | B.127 | C.11 |
| 1.2284 | B.128 | C.11 |
| 1.2285 | B.129 | C.11 |
| 1.2286 | B.130 | C.11 |
| 1.2287 | B.131 | C.11 |
| 1.2288 | B.132 | C.11 |
| 1.2289 | B.133 | C.11 |
| 1.2290 | B.134 | C.11 |
| 1.2291 | B.135 | C.11 |
| 1.2292 | B.136 | C.11 |
| 1.2293 | B.137 | C.11 |
| 1.2294 | B.138 | C.11 |
| 1.2295 | B.139 | C.11 |
| 1.2296 | B.140 | C.11 |
| 1.2297 | B.141 | C.11 |
| 1.2298 | B.142 | C.11 |
| 1.2299 | B.143 | C.11 |
| 1.2300 | B.144 | C.11 |
| 1.2301 | B.145 | C.11 |
| 1.2302 | B.146 | C.11 |
| 1.2303 | B.147 | C.11 |
| 1.2304 | B.148 | C.11 |
| 1.2305 | B.149 | C.11 |
| 1.2306 | B.150 | C.11 |
| 1.2307 | B.151 | C.11 |
| 1.2308 | B.152 | C.11 |
| 1.2309 | B.153 | C.11 |
| 1.2310 | B.154 | C.11 |
| 1.2311 | B.155 | C.11 |
| 1.2312 | B.156 | C.11 |
| 1.2313 | B.157 | C.11 |
| 1.2314 | B.158 | C.11 |
| 1.2315 | B.159 | C.11 |
| 1.2316 | B.160 | C.11 |
| 1.2317 | B.161 | C.11 |
| 1.2318 | B.162 | C.11 |
| 1.2319 | B.163 | C.11 |
| 1.2320 | B.164 | C.11 |
| 1.2321 | B.165 | C.11 |
| 1.2322 | B.166 | C.11 |
| 1.2323 | B.167 | C.11 |
| 1.2324 | B.168 | C.11 |
| 1.2325 | B.169 | C.11 |
| 1.2326 | B.170 | C.11 |
| 1.2327 | B.171 | C.11 |
| 1.2328 | B.172 | C.11 |
| 1.2329 | B.173 | C.11 |
| 1.2330 | B.174 | C.11 |
| 1.2331 | B.175 | C.11 |
| 1.2332 | B.176 | C.11 |
| 1.2333 | B.177 | C.11 |
| 1.2334 | B.178 | C.11 |
| 1.2335 | B.179 | C.11 |
| 1.2336 | B.180 | C.11 |
| 1.2337 | B.181 | C.11 |
| 1.2338 | B.182 | C.11 |
| 1.2339 | B.183 | C.11 |
| 1.2340 | B.184 | C.11 |
| 1.2341 | B.185 | C.11 |
| 1.2342 | B.186 | C.11 |
| 1.2343 | B.187 | C.11 |
| 1.2344 | B.188 | C.11 |
| 1.2345 | B.189 | C.11 |
| 1.2346 | B.190 | C.11 |
| 1.2347 | B.191 | C.11 |
| 1.2348 | B.192 | C.11 |
| 1.2349 | B.193 | C.11 |
| 1.2350 | B.194 | C.11 |
| 1.2351 | B.195 | C.11 |
| 1.2352 | B.196 | C.11 |
| 1.2353 | B.1 | C.12 |
| 1.2354 | B.2 | C.12 |
| 1.2355 | B.3 | C.12 |
| 1.2356 | B.4 | C.12 |
| 1.2357 | B.5 | C.12 |
| 1.2358 | B.6 | C.12 |
| 1.2359 | B.7 | C.12 |
| 1.2360 | B.8 | C.12 |
| 1.2361 | B.9 | C.12 |
| 1.2362 | B.10 | C.12 |
| 1.2363 | B.11 | C.12 |
| 1.2364 | B.12 | C.12 |
| 1.2365 | B.13 | C.12 |
| 1.2366 | B.14 | C.12 |
| 1.2367 | B.15 | C.12 |
| 1.2368 | B.16 | C.12 |
| 1.2369 | B.17 | C.12 |
| 1.2370 | B.18 | C.12 |
| 1.2371 | B.19 | C.12 |
| 1.2372 | B.20 | C.12 |
| 1.2373 | B.21 | C.12 |
| 1.2374 | B.22 | C.12 |
| 1.2375 | B.23 | C.12 |
| 1.2376 | B.24 | C.12 |
| 1.2377 | B.25 | C.12 |
| 1.2378 | B.26 | C.12 |
| 1.2379 | B.27 | C.12 |
| 1.2380 | B.28 | C.12 |
| 1.2381 | B.29 | C.12 |
| 1.2382 | B.30 | C.12 |
| 1.2383 | B.31 | C.12 |
| 1.2384 | B.32 | C.12 |
| 1.2385 | B.33 | C.12 |
| 1.2386 | B.34 | C.12 |
| 1.2387 | B.35 | C.12 |
| 1.2388 | B.36 | C.12 |
| 1.2389 | B.37 | C.12 |
| 1.2390 | B.38 | C.12 |
| 1.2391 | B.39 | C.12 |
| 1.2392 | B.40 | C.12 |
| 1.2393 | B.41 | C.12 |
| 1.2394 | B.42 | C.12 |
| 1.2395 | B.43 | C.12 |
| 1.2396 | B.44 | C.12 |
| 1.2397 | B.45 | C.12 |
| 1.2398 | B.46 | C.12 |
| 1.2399 | B.47 | C.12 |
| 1.2400 | B.48 | C.12 |
| 1.2401 | B.49 | C.12 |
| 1.2402 | B.50 | C.12 |
| 1.2403 | B.51 | C.12 |
| 1.2404 | B.52 | C.12 |
| 1.2405 | B.53 | C.12 |
| 1.2406 | B.54 | C.12 |
| 1.2407 | B.55 | C.12 |
| 1.2408 | B.56 | C.12 |

TABLE 1-continued (compositions 1.1 to 1.3545):

| comp. no. | herbicide B | safener C |
|---|---|---|
| 1.2409 | B.57 | C.12 |
| 1.2410 | B.58. | C.12 |
| 1.2411 | B.59 | C.12 |
| 1.2412 | B.60 | C.12 |
| 1.2413 | B.61 | C.12 |
| 1.2414 | B.62 | C.12 |
| 1.2415 | B.63 | C.12 |
| 1.2416 | B.64 | C.12 |
| 1.2417 | B.65 | C.12 |
| 1.2418 | B.66 | C.12 |
| 1.2419 | B.67 | C.12 |
| 1.2420 | B.68 | C.12 |
| 1.2421 | B.69 | C.12 |
| 1.2422 | B.70 | C.12 |
| 1.2423 | B.71 | C.12 |
| 1.2424 | B.72 | C.12 |
| 1.2425 | B.73 | C.12 |
| 1.2426 | B.74 | C.12 |
| 1.2427 | B.75 | C.12 |
| 1.2428 | B.76 | C.12 |
| 1.2429 | B.77 | C.12 |
| 1.2430 | B.78 | C.12 |
| 1.2431 | B.79 | C.12 |
| 1.2432 | B.80 | C.12 |
| 1.2433 | B.81 | C.12 |
| 1.2434 | B.82 | C.12 |
| 1.2435 | B.83 | C.12 |
| 1.2436 | B.84 | C.12 |
| 1.2437 | B.85 | C.12 |
| 1.2438 | B.86 | C.12 |
| 1.2439 | B.87 | C.12 |
| 1.2440 | B.88 | C.12 |
| 1.2441 | B.89 | C.12 |
| 1.2442 | B.90 | C.12 |
| 1.2443 | B.91 | C.12 |
| 1.2444 | B.92 | C.12 |
| 1.2445 | B.93 | C.12 |
| 1.2446 | B.94 | C.12 |
| 1.2447 | B.95 | C.12 |
| 1.2448 | B.96 | C.12 |
| 1.2449 | B.97 | C.12 |
| 1.2450 | B.98 | C.12 |
| 1.2451 | B.99 | C.12 |
| 1.2452 | B.100 | C.12 |
| 1.2453 | B.101 | C.12 |
| 1.2454 | B.102 | C.12 |
| 1.2455 | B.103 | C.12 |
| 1.2456 | B.104 | C.12 |
| 1.2457 | B.105 | C.12 |
| 1.2458 | B.106 | C.12 |
| 1.2459 | B.107 | C.12 |
| 1.2460 | B.108 | C.12 |
| 1.2461 | B.109 | C.12 |
| 1.2462 | B.110 | C.12 |
| 1.2463 | B.111 | C.12 |
| 1.2464 | B.112 | C.12 |
| 1.2465 | B.113 | C.12 |
| 1.2466 | B.114 | C.12 |
| 1.2467 | B.115 | C.12 |
| 1.2468 | B.116 | C.12 |
| 1.2469 | B.117 | C.12 |
| 1.2470 | B.118 | C.12 |
| 1.2471 | B.119 | C.12 |
| 1.2472 | B.120 | C.12 |
| 1.2473 | B.121 | C.12 |
| 1.2474 | B.122 | C.12 |
| 1.2475 | B.123 | C.12 |
| 1.2476 | B.124 | C.12 |
| 1.2477 | B.125 | C.12 |
| 1.2478 | B.126 | C.12 |
| 1.2479 | B.127 | C.12 |
| 1.2480 | B.128 | C.12 |
| 1.2481 | B.129 | C.12 |
| 1.2482 | B.130 | C.12 |
| 1.2483 | B.131 | C.12 |
| 1.2484 | B.132 | C.12 |
| 1.2485 | B.133 | C.12 |
| 1.2486 | B.134 | C.12 |
| 1.2487 | B.135 | C.12 |
| 1.2488 | B.136 | C.12 |
| 1.2489 | B.137 | C.12 |
| 1.2490 | B.138 | C.12 |
| 1.2491 | B.139 | C.12 |
| 1.2492 | B.140 | C.12 |
| 1.2493 | B.141 | C.12 |
| 1.2494 | B.142 | C.12 |
| 1.2495 | B.143 | C.12 |
| 1.2496 | B.144 | C.12 |
| 1.2497 | B.145 | C.12 |
| 1.2498 | B.146 | C.12 |
| 1.2499 | B.147 | C.12 |
| 1.2500 | B.148 | C.12 |
| 1.2501 | B.149 | C.12 |
| 1.2502 | B.150 | C.12 |
| 1.2503 | B.151 | C.12 |
| 1.2504 | B.152 | C.12 |
| 1.2505 | B.153 | C.12 |
| 1.2506 | B.154 | C.12 |
| 1.2507 | B.155 | C.12 |
| 1.2508 | B.156 | C.12 |
| 1.2509 | B.157 | C.12 |
| 1.2510 | B.158 | C.12 |
| 1.2511 | B.159 | C.12 |
| 1.2512 | B.160 | C.12 |
| 1.2513 | B.161 | C.12 |
| 1.2514 | B.162 | C.12 |
| 1.2515 | B.163 | C.12 |
| 1.2516 | B.164 | C.12 |
| 1.2517 | B.165 | C.12 |
| 1.2518 | B.166 | C.12 |
| 1.2519 | B.167 | C.12 |
| 1.2520 | B.168 | C.12 |
| 1.2521 | B.169 | C.12 |
| 1.2522 | B.170 | C.12 |
| 1.2523 | B.171 | C.12 |
| 1.2524 | B.172 | C.12 |
| 1.2525 | B.173 | C.12 |
| 1.2526 | B.174 | C.12 |
| 1.2527 | B.175 | C.12 |
| 1.2528 | B.176 | C.12 |
| 1.2529 | B.177 | C.12 |
| 1.2530 | B.178 | C.12 |
| 1.2531 | B.179 | C.12 |
| 1.2532 | B.180 | C.12 |
| 1.2533 | B.181 | C.12 |
| 1.2534 | B.182 | C.12 |
| 1.2535 | B.183 | C.12 |
| 1.2536 | B.184 | C.12 |
| 1.2537 | B.185 | C.12 |
| 1.2538 | B.186 | C.12 |
| 1.2539 | B.187 | C.12 |
| 1.2540 | B.188 | C.12 |
| 1.2541 | B.189 | C.12 |
| 1.2542 | B.190 | C.12 |
| 1.2543 | B.191 | C.12 |
| 1.2544 | B.192 | C.12 |
| 1.2545 | B.193 | C.12 |
| 1.2546 | B.194 | C.12 |
| 1.2547 | B.195 | C.12 |
| 1.2548 | B.196 | C.12 |
| 1.2549 | B.1 | C.13 |
| 1.2550 | B.2 | C.13 |
| 1.2551 | B.3 | C.13 |
| 1.2552 | B.4 | C.13 |
| 1.2553 | B.5 | C.13 |
| 1.2554 | B.6 | C.13 |
| 1.2555 | B.7 | C.13 |
| 1.2556 | B.8 | C.13 |
| 1.2557 | B.9 | C.13 |
| 1.2558 | B.10 | C.13 |
| 1.2559 | B.11 | C.13 |
| 1.2560 | B.12 | C.13 |

TABLE 1-continued (compositions 1.1 to 1.3545):

| comp. no. | herbicide B | safener C |
|---|---|---|
| 1.2561 | B.13 | C.13 |
| 1.2562 | B.14 | C.13 |
| 1.2563 | B.15 | C.13 |
| 1.2564 | B.16 | C.13 |
| 1.2565 | B.17 | C.13 |
| 1.2566 | B.18 | C.13 |
| 1.2567 | B.19 | C.13 |
| 1.2568 | B.20 | C.13 |
| 1.2569 | B.21 | C.13 |
| 1.2570 | B.22 | C.13 |
| 1.2571 | B.23 | C.13 |
| 1.2572 | B.24 | C.13 |
| 1.2573 | B.25 | C.13 |
| 1.2574 | B.26 | C.13 |
| 1.2575 | B.27 | C.13 |
| 1.2576 | B.28 | C.13 |
| 1.2577 | B.29 | C.13 |
| 1.2578 | B.30 | C.13 |
| 1.2579 | B.31 | C.13 |
| 1.2580 | B.32 | C.13 |
| 1.2581 | B.33 | C.13 |
| 1.2582 | B.34 | C.13 |
| 1.2583 | B.35 | C.13 |
| 1.2584 | B.36 | C.13 |
| 1.2585 | B.37 | C.13 |
| 1.2586 | B.38 | C.13 |
| 1.2587 | B.39 | C.13 |
| 1.2588 | B.40 | C.13 |
| 1.2589 | B.41 | C.13 |
| 1.2590 | B.42 | C.13 |
| 1.2591 | B.43 | C.13 |
| 1.2592 | B.44 | C.13 |
| 1.2593 | B.45 | C.13 |
| 1.2594 | B.46 | C.13 |
| 1.2595 | B.47 | C.13 |
| 1.2596 | B.48 | C.13 |
| 1.2597 | B.49 | C.13 |
| 1.2598 | B.50 | C.13 |
| 1.2599 | B.51 | C.13 |
| 1.2600 | B.52 | C.13 |
| 1.2601 | B.53 | C.13 |
| 1.2602 | B.54 | C.13 |
| 1.2603 | B.55 | C.13 |
| 1.2604 | B.56 | C.13 |
| 1.2605 | B.57 | C.13 |
| 1.2606 | B.58. | C.13 |
| 1.2607 | B.59 | C.13 |
| 1.2608 | B.60 | C.13 |
| 1.2609 | B.61 | C.13 |
| 1.2610 | B.62 | C.13 |
| 1.2611 | B.63 | C.13 |
| 1.2612 | B.64 | C.13 |
| 1.2613 | B.65 | C.13 |
| 1.2614 | B.66 | C.13 |
| 1.2615 | B.67 | C.13 |
| 1.2616 | B.68 | C.13 |
| 1.2617 | B.69 | C.13 |
| 1.2618 | B.70 | C.13 |
| 1.2619 | B.71 | C.13 |
| 1.2620 | B.72 | C.13 |
| 1.2621 | B.73 | C.13 |
| 1.2622 | B.74 | C.13 |
| 1.2623 | B.75 | C.13 |
| 1.2624 | B.76 | C.13 |
| 1.2625 | B.77 | C.13 |
| 1.2626 | B.78 | C.13 |
| 1.2627 | B.79 | C.13 |
| 1.2628 | B.80 | C.13 |
| 1.2629 | B.81 | C.13 |
| 1.2630 | B.82 | C.13 |
| 1.2631 | B.83 | C.13 |
| 1.2632 | B.84 | C.13 |
| 1.2633 | B.85 | C.13 |
| 1.2634 | B.86 | C.13 |
| 1.2635 | B.87 | C.13 |
| 1.2636 | B.88 | C.13 |
| 1.2637 | B.89 | C.13 |
| 1.2638 | B.90 | C.13 |
| 1.2639 | B.91 | C.13 |
| 1.2640 | B.92 | C.13 |
| 1.2641 | B.93 | C.13 |
| 1.2642 | B.94 | C.13 |
| 1.2643 | B.95 | C.13 |
| 1.2644 | B.96 | C.13 |
| 1.2645 | B.97 | C.13 |
| 1.2646 | B.98 | C.13 |
| 1.2647 | B.99 | C.13 |
| 1.2648 | B.100 | C.13 |
| 1.2649 | B.101 | C.13 |
| 1.2650 | B.102 | C.13 |
| 1.2651 | B.103 | C.13 |
| 1.2652 | B.104 | C.13 |
| 1.2653 | B.105 | C.13 |
| 1.2654 | B.106 | C.13 |
| 1.2655 | B.107 | C.13 |
| 1.2656 | B.108 | C.13 |
| 1.2657 | B.109 | C.13 |
| 1.2658 | B.110 | C.13 |
| 1.2659 | B.111 | C.13 |
| 1.2660 | B.112 | C.13 |
| 1.2661 | B.113 | C.13 |
| 1.2662 | B.114 | C.13 |
| 1.2663 | B.115 | C.13 |
| 1.2664 | B.116 | C.13 |
| 1.2665 | B.117 | C.13 |
| 1.2666 | B.118 | C.13 |
| 1.2667 | B.119 | C.13 |
| 1.2668 | B.120 | C.13 |
| 1.2669 | B.121 | C.13 |
| 1.2670 | B.122 | C.13 |
| 1.2671 | B.123 | C.13 |
| 1.2672 | B.124 | C.13 |
| 1.2673 | B.125 | C.13 |
| 1.2674 | B.126 | C.13 |
| 1.2675 | B.127 | C.13 |
| 1.2676 | B.128 | C.13 |
| 1.2677 | B.129 | C.13 |
| 1.2678 | B.130 | C.13 |
| 1.2679 | B.131 | C.13 |
| 1.2680 | B.132 | C.13 |
| 1.2681 | B.133 | C.13 |
| 1.2682 | B.134 | C.13 |
| 1.2683 | B.135 | C.13 |
| 1.2684 | B.136 | C.13 |
| 1.2685 | B.137 | C.13 |
| 1.2686 | B.138 | C.13 |
| 1.2687 | B.139 | C.13 |
| 1.2688 | B.140 | C.13 |
| 1.2689 | B.141 | C.13 |
| 1.2690 | B.142 | C.13 |
| 1.2691 | B.143 | C.13 |
| 1.2692 | B.144 | C.13 |
| 1.2693 | B.145 | C.13 |
| 1.2694 | B.146 | C.13 |
| 1.2695 | B.147 | C.13 |
| 1.2696 | B.148 | C.13 |
| 1.2697 | B.149 | C.13 |
| 1.2698 | B.150 | C.13 |
| 1.2699 | B.151 | C.13 |
| 1.2700 | B.152 | C.13 |
| 1.2701 | B.153 | C.13 |
| 1.2702 | B.154 | C.13 |
| 1.2703 | B.155 | C.13 |
| 1.2704 | B.156 | C.13 |
| 1.2705 | B.157 | C.13 |
| 1.2706 | B.158 | C.13 |
| 1.2707 | B.159 | C.13 |
| 1.2708 | B.160 | C.13 |
| 1.2709 | B.161 | C.13 |
| 1.2710 | B.162 | C.13 |
| 1.2711 | B.163 | C.13 |
| 1.2712 | B.164 | C.13 |

TABLE 1-continued (compositions 1.1 to 1.3545):

| comp. no. | herbicide B | safener C |
|---|---|---|
| 1.2713 | B.165 | C.13 |
| 1.2714 | B.166 | C.13 |
| 1.2715 | B.167 | C.13 |
| 1.2716 | B.168 | C.13 |
| 1.2717 | B.169 | C.13 |
| 1.2718 | B.170 | C.13 |
| 1.2719 | B.171 | C.13 |
| 1.2720 | B.172 | C.13 |
| 1.2721 | B.173 | C.13 |
| 1.2722 | B.174 | C.13 |
| 1.2723 | B.175 | C.13 |
| 1.2724 | B.176 | C.13 |
| 1.2725 | B.177 | C.13 |
| 1.2726 | B.178 | C.13 |
| 1.2727 | B.179 | C.13 |
| 1.2728 | B.180 | C.13 |
| 1.2729 | B.181 | C.13 |
| 1.2730 | B.182 | C.13 |
| 1.2731 | B.183 | C.13 |
| 1.2732 | B.184 | C.13 |
| 1.2733 | B.185 | C.13 |
| 1.2734 | B.186 | C.13 |
| 1.2735 | B.187 | C.13 |
| 1.2736 | B.188 | C.13 |
| 1.2737 | B.189 | C.13 |
| 1.2738 | B.190 | C.13 |
| 1.2739 | B.191 | C.13 |
| 1.2740 | B.192 | C.13 |
| 1.2741 | B.193 | C.13 |
| 1.2742 | B.194 | C.13 |
| 1.2743 | B.195 | C.13 |
| 1.2744 | B.196 | C.13 |
| 1.2745 | B.1 | C.14 |
| 1.2746 | B.2 | C.14 |
| 1.2747 | B.3 | C.14 |
| 1.2748 | B.4 | C.14 |
| 1.2749 | B.5 | C.14 |
| 1.2750 | B.6 | C.14 |
| 1.2751 | B.7 | C.14 |
| 1.2752 | B.8 | C.14 |
| 1.2753 | B.9 | C.14 |
| 1.2754 | B.10 | C.14 |
| 1.2755 | B.11 | C.14 |
| 1.2756 | B.12 | C.14 |
| 1.2757 | B.13 | C.14 |
| 1.2758 | B.14 | C.14 |
| 1.2759 | B.15 | C.14 |
| 1.2760 | B.16 | C.14 |
| 1.2761 | B.17 | C.14 |
| 1.2762 | B.18 | C.14 |
| 1.2763 | B.19 | C.14 |
| 1.2764 | B.20 | C.14 |
| 1.2765 | B.21 | C.14 |
| 1.2766 | B.22 | C.14 |
| 1.2767 | B.23 | C.14 |
| 1.2768 | B.24 | C.14 |
| 1.2769 | B.25 | C.14 |
| 1.2770 | B.26 | C.14 |
| 1.2771 | B.27 | C.14 |
| 1.2772 | B.28 | C.14 |
| 1.2773 | B.29 | C.14 |
| 1.2774 | B.30 | C.14 |
| 1.2775 | B.31 | C.14 |
| 1.2776 | B.32 | C.14 |
| 1.2777 | B.33 | C.14 |
| 1.2778 | B.34 | C.14 |
| 1.2779 | B.35 | C.14 |
| 1.2780 | B.36 | C.14 |
| 1.2781 | B.37 | C.14 |
| 1.2782 | B.38 | C.14 |
| 1.2783 | B.39 | C.14 |
| 1.2784 | B.40 | C.14 |
| 1.2785 | B.41 | C.14 |
| 1.2786 | B.42 | C.14 |
| 1.2787 | B.43 | C.14 |
| 1.2788 | B.44 | C.14 |
| 1.2789 | B.45 | C.14 |
| 1.2790 | B.46 | C.14 |
| 1.2791 | B.47 | C.14 |
| 1.2792 | B.48 | C.14 |
| 1.2793 | B.49 | C.14 |
| 1.2794 | B.50 | C.14 |
| 1.2795 | B.51 | C.14 |
| 1.2796 | B.52 | C.14 |
| 1.2797 | B.53 | C.14 |
| 1.2798 | B.54 | C.14 |
| 1.2799 | B.55 | C.14 |
| 1.2800 | B.56 | C.14 |
| 1.2801 | B.57 | C.14 |
| 1.2802 | B.58. | C.14 |
| 1.2803 | B.59 | C.14 |
| 1.2804 | B.60 | C.14 |
| 1.2805 | B.61 | C.14 |
| 1.2806 | B.62 | C.14 |
| 1.2807 | B.63 | C.14 |
| 1.2808 | B.64 | C.14 |
| 1.2809 | B.65 | C.14 |
| 1.2810 | B.66 | C.14 |
| 1.2811 | B.67 | C.14 |
| 1.2812 | B.68 | C.14 |
| 1.2813 | B.69 | C.14 |
| 1.2814 | B.70 | C.14 |
| 1.2815 | B.71 | C.14 |
| 1.2816 | B.72 | C.14 |
| 1.2817 | B.73 | C.14 |
| 1.2818 | B.74 | C.14 |
| 1.2819 | B.75 | C.14 |
| 1.2820 | B.76 | C.14 |
| 1.2821 | B.77 | C.14 |
| 1.2822 | B.78 | C.14 |
| 1.2823 | B.79 | C.14 |
| 1.2824 | B.80 | C.14 |
| 1.2825 | B.81 | C.14 |
| 1.2826 | B.82 | C.14 |
| 1.2827 | B.83 | C.14 |
| 1.2828 | B.84 | C.14 |
| 1.2829 | B.85 | C.14 |
| 1.2830 | B.86 | C.14 |
| 1.2831 | B.87 | C.14 |
| 1.2832 | B.88 | C.14 |
| 1.2833 | B.89 | C.14 |
| 1.2834 | B.90 | C.14 |
| 1.2835 | B.91 | C.14 |
| 1.2836 | B.92 | C.14 |
| 1.2837 | B.93 | C.14 |
| 1.2838 | B.94 | C.14 |
| 1.2839 | B.95 | C.14 |
| 1.2840 | B.96 | C.14 |
| 1.2841 | B.97 | C.14 |
| 1.2842 | B.98 | C.14 |
| 1.2843 | B.99 | C.14 |
| 1.2844 | B.100 | C.14 |
| 1.2845 | B.101 | C.14 |
| 1.2846 | B.102 | C.14 |
| 1.2847 | B.103 | C.14 |
| 1.2848 | B.104 | C.14 |
| 1.2849 | B.105 | C.14 |
| 1.2850 | B.106 | C.14 |
| 1.2851 | B.107 | C.14 |
| 1.2852 | B.108 | C.14 |
| 1.2853 | B.109 | C.14 |
| 1.2854 | B.110 | C.14 |
| 1.2855 | B.111 | C.14 |
| 1.2856 | B.112 | C.14 |
| 1.2857 | B.113 | C.14 |
| 1.2858 | B.114 | C.14 |
| 1.2859 | B.115 | C.14 |
| 1.2860 | B.116 | C.14 |
| 1.2861 | B.117 | C.14 |
| 1.2862 | B.118 | C.14 |
| 1.2863 | B.119 | C.14 |
| 1.2864 | B.120 | C.14 |

TABLE 1-continued (compositions 1.1 to 1.3545):

| comp. no. | herbicide B | safener C |
|---|---|---|
| 1.2865 | B.121 | C.14 |
| 1.2866 | B.122 | C.14 |
| 1.2867 | B.123 | C.14 |
| 1.2868 | B.124 | C.14 |
| 1.2869 | B.125 | C.14 |
| 1.2870 | B.126 | C.14 |
| 1.2871 | B.127 | C.14 |
| 1.2872 | B.128 | C.14 |
| 1.2873 | B.129 | C.14 |
| 1.2874 | B.130 | C.14 |
| 1.2875 | B.131 | C.14 |
| 1.2876 | B.132 | C.14 |
| 1.2877 | B.133 | C.14 |
| 1.2878 | B.134 | C.14 |
| 1.2879 | B.135 | C.14 |
| 1.2880 | B.136 | C.14 |
| 1.2881 | B.137 | C.14 |
| 1.2882 | B.138 | C.14 |
| 1.2883 | B.139 | C.14 |
| 1.2884 | B.140 | C.14 |
| 1.2885 | B.141 | C.14 |
| 1.2886 | B.142 | C.14 |
| 1.2887 | B.143 | C.14 |
| 1.2888 | B.144 | C.14 |
| 1.2889 | B.145 | C.14 |
| 1.2890 | B.146 | C.14 |
| 1.2891 | B.147 | C.14 |
| 1.2892 | B.148 | C.14 |
| 1.2893 | B.149 | C.14 |
| 1.2894 | B.150 | C.14 |
| 1.2895 | B.151 | C.14 |
| 1.2896 | B.152 | C.14 |
| 1.2897 | B.153 | C.14 |
| 1.2898 | B.154 | C.14 |
| 1.2899 | B.155 | C.14 |
| 1.2900 | B.156 | C.14 |
| 1.2901 | B.157 | C.14 |
| 1.2902 | B.158 | C.14 |
| 1.2903 | B.159 | C.14 |
| 1.2904 | B.160 | C.14 |
| 1.2905 | B.161 | C.14 |
| 1.2906 | B.162 | C.14 |
| 1.2907 | B.163 | C.14 |
| 1.2908 | B.164 | C.14 |
| 1.2909 | B.165 | C.14 |
| 1.2910 | B.166 | C.14 |
| 1.2911 | B.167 | C.14 |
| 1.2912 | B.168 | C.14 |
| 1.2913 | B.169 | C.14 |
| 1.2914 | B.170 | C.14 |
| 1.2915 | B.171 | C.14 |
| 1.2916 | B.172 | C.14 |
| 1.2917 | B.173 | C.14 |
| 1.2918 | B.174 | C.14 |
| 1.2919 | B.175 | C.14 |
| 1.2920 | B.176 | C.14 |
| 1.2921 | B.177 | C.14 |
| 1.2922 | B.178 | C.14 |
| 1.2923 | B.179 | C.14 |
| 1.2924 | B.180 | C.14 |
| 1.2925 | B.181 | C.14 |
| 1.2926 | B.182 | C.14 |
| 1.2927 | B.183 | C.14 |
| 1.2928 | B.184 | C.14 |
| 1.2929 | B.185 | C.14 |
| 1.2930 | B.186 | C.14 |
| 1.2931 | B.187 | C.14 |
| 1.2932 | B.188 | C.14 |
| 1.2933 | B.189 | C.14 |
| 1.2934 | B.190 | C.14 |
| 1.2935 | B.191 | C.14 |
| 1.2936 | B.192 | C.14 |
| 1.2937 | B.193 | C.14 |
| 1.2938 | B.194 | C.14 |
| 1.2939 | B.195 | C.14 |
| 1.2940 | B.196 | C.14 |
| 1.2941 | B.1 | C.15 |
| 1.2942 | B.2 | C.15 |
| 1.2943 | B.3 | C.15 |
| 1.2944 | B.4 | C.15 |
| 1.2945 | B.5 | C.15 |
| 1.2946 | B.6 | C.15 |
| 1.2947 | B.7 | C.15 |
| 1.2948 | B.8 | C.15 |
| 1.2949 | B.9 | C.15 |
| 1.2950 | B.10 | C.15 |
| 1.2951 | B.11 | C.15 |
| 1.2952 | B.12 | C.15 |
| 1.2953 | B.13 | C.15 |
| 1.2954 | B.14 | C.15 |
| 1.2955 | B.15 | C.15 |
| 1.2956 | B.16 | C.15 |
| 1.2957 | B.17 | C.15 |
| 1.2958 | B.18 | C.15 |
| 1.2959 | B.19 | C.15 |
| 1.2960 | B.20 | C.15 |
| 1.2961 | B.21 | C.15 |
| 1.2962 | B.22 | C.15 |
| 1.2963 | B.23 | C.15 |
| 1.2964 | B.24 | C.15 |
| 1.2965 | B.25 | C.15 |
| 1.2966 | B.26 | C.15 |
| 1.2967 | B.27 | C.15 |
| 1.2968 | B.28 | C.15 |
| 1.2969 | B.29 | C.15 |
| 1.2970 | B.30 | C.15 |
| 1.2971 | B.31 | C.15 |
| 1.2972 | B.32 | C.15 |
| 1.2973 | B.33 | C.15 |
| 1.2974 | B.34 | C.15 |
| 1.2975 | B.35 | C.15 |
| 1.2976 | B.36 | C.15 |
| 1.2977 | B.37 | C.15 |
| 1.2978 | B.38 | C.15 |
| 1.2979 | B.39 | C.15 |
| 1.2980 | B.40 | C.15 |
| 1.2981 | B.41 | C.15 |
| 1.2982 | B.42 | C.15 |
| 1.2983 | B.43 | C.15 |
| 1.2984 | B.44 | C.15 |
| 1.2985 | B.45 | C.15 |
| 1.2986 | B.46 | C.15 |
| 1.2987 | B.47 | C.15 |
| 1.2988 | B.48 | C.15 |
| 1.2989 | B.49 | C.15 |
| 1.2990 | B.50 | C.15 |
| 1.2991 | B.51 | C.15 |
| 1.2992 | B.52 | C.15 |
| 1.2993 | B.53 | C.15 |
| 1.2994 | B.54 | C.15 |
| 1.2995 | B.55 | C.15 |
| 1.2996 | B.56 | C.15 |
| 1.2997 | B.57 | C.15 |
| 1.2998 | B.58 | C.15 |
| 1.2999 | B.59 | C.15 |
| 1.3000 | B.60 | C.15 |
| 1.3001 | B.61 | C.15 |
| 1.3002 | B.62 | C.15 |
| 1.3003 | B.63 | C.15 |
| 1.3004 | B.64 | C.15 |
| 1.3005 | B.65 | C.15 |
| 1.3006 | B.66 | C.15 |
| 1.3007 | B.67 | C.15 |
| 1.3008 | B.68 | C.15 |
| 1.3009 | B.69 | C.15 |
| 1.3010 | B.70 | C.15 |
| 1.3011 | B.71 | C.15 |
| 1.3012 | B.72 | C.15 |
| 1.3013 | B.73 | C.15 |
| 1.3014 | B.74 | C.15 |
| 1.3015 | B.75 | C.15 |
| 1.3016 | B.76 | C.15 |

TABLE 1-continued (compositions 1.1 to 1.3545):

| comp. no. | herbicide B | safener C |
|---|---|---|
| 1.3017 | B.77 | C.15 |
| 1.3018 | B.78 | C.15 |
| 1.3019 | B.79 | C.15 |
| 1.3020 | B.80 | C.15 |
| 1.3021 | B.81 | C.15 |
| 1.3022 | B.82 | C.15 |
| 1.3023 | B.83 | C.15 |
| 1.3024 | B.84 | C.15 |
| 1.3025 | B.85 | C.15 |
| 1.3026 | B.86 | C.15 |
| 1.3027 | B.87 | C.15 |
| 1.3028 | B.88 | C.15 |
| 1.3029 | B.89 | C.15 |
| 1.3030 | B.90 | C.15 |
| 1.3031 | B.91 | C.15 |
| 1.3032 | B.92 | C.15 |
| 1.3033 | B.93 | C.15 |
| 1.3034 | B.94 | C.15 |
| 1.3035 | B.95 | C.15 |
| 1.3036 | B.96 | C.15 |
| 1.3037 | B.97 | C.15 |
| 1.3038 | B.98 | C.15 |
| 1.3039 | B.99 | C.15 |
| 1.3040 | B.100 | C.15 |
| 1.3041 | B.101 | C.15 |
| 1.3042 | B.102 | C.15 |
| 1.3043 | B.103 | C.15 |
| 1.3044 | B.104 | C.15 |
| 1.3045 | B.105 | C.15 |
| 1.3046 | B.106 | C.15 |
| 1.3047 | B.107 | C.15 |
| 1.3048 | B.108 | C.15 |
| 1.3049 | B.109 | C.15 |
| 1.3050 | B.110 | C.15 |
| 1.3051 | B.111 | C.15 |
| 1.3052 | B.112 | C.15 |
| 1.3053 | B.113 | C.15 |
| 1.3054 | B.114 | C.15 |
| 1.3055 | B.115 | C.15 |
| 1.3056 | B.116 | C.15 |
| 1.3057 | B.117 | C.15 |
| 1.3058 | B.118 | C.15 |
| 1.3059 | B.119 | C.15 |
| 1.3060 | B.120 | C.15 |
| 1.3061 | B.121 | C.15 |
| 1.3062 | B.122 | C.15 |
| 1.3063 | B.123 | C.15 |
| 1.3064 | B.124 | C.15 |
| 1.3065 | B.125 | C.15 |
| 1.3066 | B.126 | C.15 |
| 1.3067 | B.127 | C.15 |
| 1.3068 | B.128 | C.15 |
| 1.3069 | B.129 | C.15 |
| 1.3070 | B.130 | C.15 |
| 1.3071 | B.131 | C.15 |
| 1.3072 | B.132 | C.15 |
| 1.3073 | B.133 | C.15 |
| 1.3074 | B.134 | C.15 |
| 1.3075 | B.135 | C.15 |
| 1.3076 | B.136 | C.15 |
| 1.3077 | B.137 | C.15 |
| 1.3078 | B.138 | C.15 |
| 1.3079 | B.139 | C.15 |
| 1.3080 | B.140 | C.15 |
| 1.3081 | B.141 | C.15 |
| 1.3082 | B.142 | C.15 |
| 1.3083 | B.143 | C.15 |
| 1.3084 | B.144 | C.15 |
| 1.3085 | B.145 | C.15 |
| 1.3086 | B.146 | C.15 |
| 1.3087 | B.147 | C.15 |
| 1.3088 | B.148 | C.15 |
| 1.3089 | B.149 | C.15 |
| 1.3090 | B.150 | C.15 |
| 1.3091 | B.151 | C.15 |
| 1.3092 | B.152 | C.15 |
| 1.3093 | B.153 | C.15 |
| 1.3094 | B.154 | C.15 |
| 1.3095 | B.155 | C.15 |
| 1.3096 | B.156 | C.15 |
| 1.3097 | B.157 | C.15 |
| 1.3098 | B.158 | C.15 |
| 1.3099 | B.159 | C.15 |
| 1.3100 | B.160 | C.15 |
| 1.3101 | B.161 | C.15 |
| 1.3102 | B.162 | C.15 |
| 1.3103 | B.163 | C.15 |
| 1.3104 | B.164 | C.15 |
| 1.3105 | B.165 | C.15 |
| 1.3106 | B.166 | C.15 |
| 1.3107 | B.167 | C.15 |
| 1.3108 | B.168 | C.15 |
| 1.3109 | B.169 | C.15 |
| 1.3110 | B.170 | C.15 |
| 1.3111 | B.171 | C.15 |
| 1.3112 | B.172 | C.15 |
| 1.3113 | B.173 | C.15 |
| 1.3114 | B.174 | C.15 |
| 1.3115 | B.175 | C.15 |
| 1.3116 | B.176 | C.15 |
| 1.3117 | B.177 | C.15 |
| 1.3118 | B.178 | C.15 |
| 1.3119 | B.179 | C.15 |
| 1.3120 | B.180 | C.15 |
| 1.3121 | B.181 | C.15 |
| 1.3122 | B.182 | C.15 |
| 1.3123 | B.183 | C.15 |
| 1.3124 | B.184 | C.15 |
| 1.3125 | B.185 | C.15 |
| 1.3126 | B.186 | C.15 |
| 1.3127 | B.187 | C.15 |
| 1.3128 | B.188 | C.15 |
| 1.3129 | B.189 | C.15 |
| 1.3130 | B.190 | C.15 |
| 1.3131 | B.191 | C.15 |
| 1.3132 | B.192 | C.15 |
| 1.3133 | B.193 | C.15 |
| 1.3134 | B.194 | C.15 |
| 1.3135 | B.195 | C.15 |
| 1.3136 | B.196 | C.15 |
| 1.3137 | B.1 | C.16 |
| 1.3138 | B.2 | C.16 |
| 1.3139 | B.3 | C.16 |
| 1.3140 | B.4 | C.16 |
| 1.3141 | B.5 | C.16 |
| 1.3142 | B.6 | C.16 |
| 1.3143 | B.7 | C.16 |
| 1.3144 | B.8 | C.16 |
| 1.3145 | B.9 | C.16 |
| 1.3146 | B.10 | C.16 |
| 1.3147 | B.11 | C.16 |
| 1.3148 | B.12 | C.16 |
| 1.3149 | B.13 | C.16 |
| 1.3150 | B.14 | C.16 |
| 1.3151 | B.15 | C.16 |
| 1.3152 | B.16 | C.16 |
| 1.3153 | B.17 | C.16 |
| 1.3154 | B.18 | C.16 |
| 1.3155 | B.19 | C.16 |
| 1.3156 | B.20 | C.16 |
| 1.3157 | B.21 | C.16 |
| 1.3158 | B.22 | C.16 |
| 1.3159 | B.23 | C.16 |
| 1.3160 | B.24 | C.16 |
| 1.3161 | B.25 | C.16 |
| 1.3162 | B.26 | C.16 |
| 1.3163 | B.27 | C.16 |
| 1.3164 | B.28 | C.16 |
| 1.3165 | B.29 | C.16 |
| 1.3166 | B.30 | C.16 |
| 1.3167 | B.31 | C.16 |
| 1.3168 | B.32 | C.16 |

TABLE 1-continued (compositions 1.1 to 1.3545):

| comp. no. | herbicide B | safener C |
|---|---|---|
| 1.3169 | B.33 | C.16 |
| 1.3170 | B.34 | C.16 |
| 1.3171 | B.35 | C.16 |
| 1.3172 | B.36 | C.16 |
| 1.3173 | B.37 | C.16 |
| 1.3174 | B.38 | C.16 |
| 1.3175 | B.39 | C.16 |
| 1.3176 | B.40 | C.16 |
| 1.3177 | B.41 | C.16 |
| 1.3178 | B.42 | C.16 |
| 1.3179 | B.43 | C.16 |
| 1.3180 | B.44 | C.16 |
| 1.3181 | B.45 | C.16 |
| 1.3182 | B.46 | C.16 |
| 1.3183 | B.47 | C.16 |
| 1.3184 | B.48 | C.16 |
| 1.3185 | B.49 | C.16 |
| 1.3186 | B.50 | C.16 |
| 1.3187 | B.51 | C.16 |
| 1.3188 | B.52 | C.16 |
| 1.3189 | B.53 | C.16 |
| 1.3190 | B.54 | C.16 |
| 1.3191 | B.55 | C.16 |
| 1.3192 | B.56 | C.16 |
| 1.3193 | B.57 | C.16 |
| 1.3194 | B.58. | C.16 |
| 1.3195 | B.59 | C.16 |
| 1.3196 | B.60 | C.16 |
| 1.3197 | B.61 | C.16 |
| 1.3198 | B.62 | C.16 |
| 1.3199 | B.63 | C.16 |
| 1.3200 | B.64 | C.16 |
| 1.3201 | B.65 | C.16 |
| 1.3202 | B.66 | C.16 |
| 1.3203 | B.67 | C.16 |
| 1.3204 | B.68 | C.16 |
| 1.3205 | B.69 | C.16 |
| 1.3206 | B.70 | C.16 |
| 1.3207 | B.71 | C.16 |
| 1.3208 | B.72 | C.16 |
| 1.3209 | B.73 | C.16 |
| 1.3210 | B.74 | C.16 |
| 1.3211 | B.75 | C.16 |
| 1.3212 | B.76 | C.16 |
| 1.3213 | B.77 | C.16 |
| 1.3214 | B.78 | C.16 |
| 1.3215 | B.79 | C.16 |
| 1.3216 | B.80 | C.16 |
| 1.3217 | B.81 | C.16 |
| 1.3218 | B.82 | C.16 |
| 1.3219 | B.83 | C.16 |
| 1.3220 | B.84 | C.16 |
| 1.3221 | B.85 | C.16 |
| 1.3222 | B.86 | C.16 |
| 1.3223 | B.87 | C.16 |
| 1.3224 | B.88 | C.16 |
| 1.3225 | B.89 | C.16 |
| 1.3226 | B.90 | C.16 |
| 1.3227 | B.91 | C.16 |
| 1.3228 | B.92 | C.16 |
| 1.3229 | B.93 | C.16 |
| 1.3230 | B.94 | C.16 |
| 1.3231 | B.95 | C.16 |
| 1.3232 | B.96 | C.16 |
| 1.3233 | B.97 | C.16 |
| 1.3234 | B.98 | C.16 |
| 1.3235 | B.99 | C.16 |
| 1.3236 | B.100 | C.16 |
| 1.3237 | B.101 | C.16 |
| 1.3238 | B.102 | C.16 |
| 1.3239 | B.103 | C.16 |
| 1.3240 | B.104 | C.16 |
| 1.3241 | B.105 | C.16 |
| 1.3242 | B.106 | C.16 |
| 1.3243 | B.107 | C.16 |
| 1.3244 | B.108 | C.16 |
| 1.3245 | B.109 | C.16 |
| 1.3246 | B.110 | C.16 |
| 1.3247 | B.111 | C.16 |
| 1.3248 | B.112 | C.16 |
| 1.3249 | B.113 | C.16 |
| 1.3250 | B.114 | C.16 |
| 1.3251 | B.115 | C.16 |
| 1.3252 | B.116 | C.16 |
| 1.3253 | B.117 | C.16 |
| 1.3254 | B.118 | C.16 |
| 1.3255 | B.119 | C.16 |
| 1.3256 | B.120 | C.16 |
| 1.3257 | B.121 | C.16 |
| 1.3258 | B.122 | C.16 |
| 1.3259 | B.123 | C.16 |
| 1.3260 | B.124 | C.16 |
| 1.3261 | B.125 | C.16 |
| 1.3262 | B.126 | C.16 |
| 1.3263 | B.127 | C.16 |
| 1.3264 | B.128 | C.16 |
| 1.3265 | B.129 | C.16 |
| 1.3266 | B.130 | C.16 |
| 1.3267 | B.131 | C.16 |
| 1.3268 | B.132 | C.16 |
| 1.3269 | B.133 | C.16 |
| 1.3270 | B.134 | C.16 |
| 1.3271 | B.135 | C.16 |
| 1.3272 | B.136 | C.16 |
| 1.3273 | B.137 | C.16 |
| 1.3274 | B.138 | C.16 |
| 1.3275 | B.139 | C.16 |
| 1.3276 | B.140 | C.16 |
| 1.3277 | B.141 | C.16 |
| 1.3278 | B.142 | C.16 |
| 1.3279 | B.143 | C.16 |
| 1.3280 | B.144 | C.16 |
| 1.3281 | B.145 | C.16 |
| 1.3282 | B.146 | C.16 |
| 1.3283 | B.147 | C.16 |
| 1.3284 | B.148 | C.16 |
| 1.3285 | B.149 | C.16 |
| 1.3286 | B.150 | C.16 |
| 1.3287 | B.151 | C.16 |
| 1.3288 | B.152 | C.16 |
| 1.3289 | B.153 | C.16 |
| 1.3290 | B.154 | C.16 |
| 1.3291 | B.155 | C.16 |
| 1.3292 | B.156 | C.16 |
| 1.3293 | B.157 | C.16 |
| 1.3294 | B.158 | C.16 |
| 1.3295 | B.159 | C.16 |
| 1.3296 | B.160 | C.16 |
| 1.3297 | B.161 | C.16 |
| 1.3298 | B.162 | C.16 |
| 1.3299 | B.163 | C.16 |
| 1.3300 | B.164 | C.16 |
| 1.3301 | B.165 | C.16 |
| 1.3302 | B.166 | C.16 |
| 1.3303 | B.167 | C.16 |
| 1.3304 | B.168 | C.16 |
| 1.3305 | B.169 | C.16 |
| 1.3306 | B.170 | C.16 |
| 1.3307 | B.171 | C.16 |
| 1.3308 | B.172 | C.16 |
| 1.3309 | B.173 | C.16 |
| 1.3310 | B.174 | C.16 |
| 1.3311 | B.175 | C.16 |
| 1.3312 | B.176 | C.16 |
| 1.3313 | B.177 | C.16 |
| 1.3314 | B.178 | C.16 |
| 1.3315 | B.179 | C.16 |
| 1.3316 | B.180 | C.16 |
| 1.3317 | B.181 | C.16 |
| 1.3318 | B.182 | C.16 |
| 1.3319 | B.183 | C.16 |
| 1.3320 | B.184 | C.16 |

TABLE 1-continued (compositions 1.1 to 1.3545):

| comp. no. | herbicide B | safener C |
|---|---|---|
| 1.3321 | B.185 | C.16 |
| 1.3322 | B.186 | C.16 |
| 1.3323 | B.187 | C.16 |
| 1.3324 | B.188 | C.16 |
| 1.3325 | B.189 | C.16 |
| 1.3326 | B.190 | C.16 |
| 1.3327 | B.191 | C.16 |
| 1.3328 | B.192 | C.16 |
| 1.3329 | B.193 | C.16 |
| 1.3330 | B.194 | C.16 |
| 1.3331 | B.195 | C.16 |
| 1.3332 | B.196 | C.16 |
| 1.3333 | B.1 | C.17 |
| 1.3334 | B.2 | C.17 |
| 1.3335 | B.3 | C.17 |
| 1.3336 | B.4 | C.17 |
| 1.3337 | B.5 | C.17 |
| 1.3338 | B.6 | C.17 |
| 1.3339 | B.7 | C.17 |
| 1.3340 | B.8 | C.17 |
| 1.3341 | B.9 | C.17 |
| 1.3342 | B.10 | C.17 |
| 1.3343 | B.11 | C.17 |
| 1.3344 | B.12 | C.17 |
| 1.3345 | B.13 | C.17 |
| 1.3346 | B.14 | C.17 |
| 1.3347 | B.15 | C.17 |
| 1.3348 | B.16 | C.17 |
| 1.3349 | B.17 | C.17 |
| 1.3350 | B.18 | C.17 |
| 1.3351 | B.19 | C.17 |
| 1.3352 | B.20 | C.17 |
| 1.3353 | B.21 | C.17 |
| 1.3354 | B.22 | C.17 |
| 1.3355 | B.23 | C.17 |
| 1.3356 | B.24 | C.17 |
| 1.3357 | B.25 | C.17 |
| 1.3358 | B.26 | C.17 |
| 1.3359 | B.27 | C.17 |
| 1.3360 | B.28 | C.17 |
| 1.3361 | B.29 | C.17 |
| 1.3362 | B.30 | C.17 |
| 1.3363 | B.31 | C.17 |
| 1.3364 | B.32 | C.17 |
| 1.3365 | B.33 | C.17 |
| 1.3366 | B.34 | C.17 |
| 1.3367 | B.35 | C.17 |
| 1.3368 | B.36 | C.17 |
| 1.3369 | B.37 | C.17 |
| 1.3370 | B.38 | C.17 |
| 1.3371 | B.39 | C.17 |
| 1.3372 | B.40 | C.17 |
| 1.3373 | B.41 | C.17 |
| 1.3374 | B.42 | C.17 |
| 1.3375 | B.43 | C.17 |
| 1.3376 | B.44 | C.17 |
| 1.3377 | B.45 | C.17 |
| 1.3378 | B.46 | C.17 |
| 1.3379 | B.47 | C.17 |
| 1.3380 | B.48 | C.17 |
| 1.3381 | B.49 | C.17 |
| 1.3382 | B.50 | C.17 |
| 1.3383 | B.51 | C.17 |
| 1.3384 | B.52 | C.17 |
| 1.3385 | B.53 | C.17 |
| 1.3386 | B.54 | C.17 |
| 1.3387 | B.55 | C.17 |
| 1.3388 | B.56 | C.17 |
| 1.3389 | B.57 | C.17 |
| 1.3390 | B.58. | C.17 |
| 1.3391 | B.59 | C.17 |
| 1.3392 | B.60 | C.17 |
| 1.3393 | B.61 | C.17 |
| 1.3394 | B.62 | C.17 |
| 1.3395 | B.63 | C.17 |
| 1.3396 | B.64 | C.17 |
| 1.3397 | B.65 | C.17 |
| 1.3398 | B.66 | C.17 |
| 1.3399 | B.67 | C.17 |
| 1.3400 | B.68 | C.17 |
| 1.3401 | B.69 | C.17 |
| 1.3402 | B.70 | C.17 |
| 1.3403 | B.71 | C.17 |
| 1.3404 | B.72 | C.17 |
| 1.3405 | B.73 | C.17 |
| 1.3406 | B.74 | C.17 |
| 1.3407 | B.75 | C.17 |
| 1.3408 | B.76 | C.17 |
| 1.3409 | B.77 | C.17 |
| 1.3410 | B.78 | C.17 |
| 1.3411 | B.79 | C.17 |
| 1.3412 | B.80 | C.17 |
| 1.3413 | B.81 | C.17 |
| 1.3414 | B.82 | C.17 |
| 1.3415 | B.83 | C.17 |
| 1.3416 | B.84 | C.17 |
| 1.3417 | B.85 | C.17 |
| 1.3418 | B.86 | C.17 |
| 1.3419 | B.87 | C.17 |
| 1.3420 | B.88 | C.17 |
| 1.3421 | B.89 | C.17 |
| 1.3422 | B.90 | C.17 |
| 1.3423 | B.91 | C.17 |
| 1.3424 | B.92 | C.17 |
| 1.3425 | B.93 | C.17 |
| 1.3426 | B.94 | C.17 |
| 1.3427 | B.95 | C.17 |
| 1.3428 | B.96 | C.17 |
| 1.3429 | B.97 | C.17 |
| 1.3430 | B.98 | C.17 |
| 1.3431 | B.99 | C.17 |
| 1.3432 | B.100 | C.17 |
| 1.3433 | B.101 | C.17 |
| 1.3434 | B.102 | C.17 |
| 1.3435 | B.103 | C.17 |
| 1.3436 | B.104 | C.17 |
| 1.3437 | B.105 | C.17 |
| 1.3438 | B.106 | C.17 |
| 1.3439 | B.107 | C.17 |
| 1.3440 | B.108 | C.17 |
| 1.3441 | B.109 | C.17 |
| 1.3442 | B.110 | C.17 |
| 1.3443 | B.111 | C.17 |
| 1.3444 | B.112 | C.17 |
| 1.3445 | B.113 | C.17 |
| 1.3446 | B.114 | C.17 |
| 1.3447 | B.115 | C.17 |
| 1.3448 | B.116 | C.17 |
| 1.3449 | B.117 | C.17 |
| 1.3450 | B.118 | C.17 |
| 1.3451 | B.119 | C.17 |
| 1.3452 | B.120 | C.17 |
| 1.3453 | B.121 | C.17 |
| 1.3454 | B.122 | C.17 |
| 1.3455 | B.123 | C.17 |
| 1.3456 | B.124 | C.17 |
| 1.3457 | B.125 | C.17 |
| 1.3458 | B.126 | C.17 |
| 1.3459 | B.127 | C.17 |
| 1.3460 | B.128 | C.17 |
| 1.3461 | B.129 | C.17 |
| 1.3462 | B.130 | C.17 |
| 1.3463 | B.131 | C.17 |
| 1.3464 | B.132 | C.17 |
| 1.3465 | B.133 | C.17 |
| 1.3466 | B.134 | C.17 |
| 1.3467 | B.135 | C.17 |
| 1.3468 | B.136 | C.17 |
| 1.3469 | B.137 | C.17 |
| 1.3470 | B.138 | C.17 |
| 1.3471 | B.139 | C.17 |
| 1.3472 | B.140 | C.17 |

TABLE 1-continued (compositions 1.1 to 1.3545):

| comp. no. | herbicide B | safener C |
|---|---|---|
| 1.3473 | B.141 | C.17 |
| 1.3474 | B.142 | C.17 |
| 1.3475 | B.143 | C.17 |
| 1.3476 | B.144 | C.17 |
| 1.3477 | B.145 | C.17 |
| 1.3478 | B.146 | C.17 |
| 1.3479 | B.147 | C.17 |
| 1.3480 | B.148 | C.17 |
| 1.3481 | B.149 | C.17 |
| 1.3482 | B.150 | C.17 |
| 1.3483 | B.151 | C.17 |
| 1.3484 | B.152 | C.17 |
| 1.3485 | B.153 | C.17 |
| 1.3486 | B.154 | C.17 |
| 1.3487 | B.155 | C.17 |
| 1.3488 | B.156 | C.17 |
| 1.3489 | B.157 | C.17 |
| 1.3490 | B.158 | C.17 |
| 1.3491 | B.159 | C.17 |
| 1.3492 | B.160 | C.17 |
| 1.3493 | B.161 | C.17 |
| 1.3494 | B.162 | C.17 |
| 1.3495 | B.163 | C.17 |
| 1.3496 | B.164 | C.17 |
| 1.3497 | B.165 | C.17 |
| 1.3498 | B.166 | C.17 |
| 1.3499 | B.167 | C.17 |
| 1.3500 | B.168 | C.17 |
| 1.3501 | B.169 | C.17 |
| 1.3502 | B.170 | C.17 |
| 1.3503 | B.171 | C.17 |
| 1.3504 | B.172 | C.17 |
| 1.3505 | B.173 | C.17 |
| 1.3506 | B.174 | C.17 |
| 1.3507 | B.175 | C.17 |
| 1.3508 | B.176 | C.17 |
| 1.3509 | B.177 | C.17 |
| 1.3510 | B.178 | C.17 |
| 1.3511 | B.179 | C.17 |
| 1.3512 | B.180 | C.17 |
| 1.3513 | B.181 | C.17 |
| 1.3514 | B.182 | C.17 |
| 1.3515 | B.183 | C.17 |
| 1.3516 | B.184 | C.17 |
| 1.3517 | B.185 | C.17 |
| 1.3518 | B.186 | C.17 |
| 1.3519 | B.187 | C.17 |
| 1.3520 | B.188 | C.17 |
| 1.3521 | B.189 | C.17 |
| 1.3522 | B.190 | C.17 |
| 1.3523 | B.191 | C.17 |
| 1.3524 | B.192 | C.17 |
| 1.3525 | B.193 | C.17 |
| 1.3526 | B.194 | C.17 |
| 1.3527 | B.195 | C.17 |
| 1.3528 | B.196 | C.17 |
| 1.3529 | — | C.1 |
| 1.3530 | — | C.2 |
| 1.3531 | — | C.3 |
| 1.3532 | — | C.4 |
| 1.3533 | — | C.5 |
| 1.3534 | — | C.6 |
| 1.3535 | — | C.7 |
| 1.3536 | — | C.8 |
| 1.3537 | — | C.9 |
| 1.3538 | — | C.10 |
| 1.3539 | — | C.11 |
| 1.3540 | — | C.12 |
| 1.3541 | — | C.13 |
| 1.3542 | — | C.14 |
| 1.3543 | — | C.15 |
| 1.3544 | — | C.16 |
| 1.3545 | — | C.17 |

The specific number for each single composition is deductible as follows: Composition 1.200 for example comprises compounds of formula (I) cyhalofop-butyl (B.4) and benoxacor (C.1).

Composition 2.200 for example comprises the compounds of formula (I) (see the definition for compositions 21 to 2.3545 below), cyhalofop-butyl (B.4) and benoxacor (C.1).

Composition 7.200 for example comprises compounds of formula (I) imazapyr (B.35), cyhalofop-butyl (B.4) and benoxacor (C.1.

Also especially preferred are compositions 2.1. to 2.3545 which differ from the corresponding compositions 1.1 to 1.3545 only in that they comprise as the active compound A the compounds of formula (Ia).

Also especially preferred are compositions 3.1. to 3.3545 which differ from the corresponding compositions 1.1 to 1.3545 only in that they additionally comprise B.2 clodinafop-propargyl as further herbicide B.

Also especially preferred are compositions 4.1. to 4.3545 which differ from the corresponding compositions 1.1 to 1.3545 only in that they additionally comprise B.8 pinoxaden as further herbicide B.

Also especially preferred are compositions 5.1. to 5.3545 which differ from the corresponding compositions 1.1 to 1.3545 only in that they additionally comprise B.30 imazamox as further herbicide B.

Also especially preferred are compositions 6.1. to 6.3545 which differ from the corresponding compositions 1.1 to 1.3545 only in that they additionally comprise B.32 imazapic as further herbicide B.

Also especially preferred are compositions 7.1. to 7.3545 which differ from the corresponding compositions 1.1 to 1.3545 only in that they additionally comprise B.35 imazapyr as further herbicide B.

Also especially preferred are compositions 8.1. to 8.3545 which differ from the corresponding compositions 1.1 to 1.3545 only in that they additionally comprise B.38 imazaquin as further herbicide B.

Also especially preferred are compositions 9.1. to 9.3545 which differ from the corresponding compositions 1.1 to 1.3545 only in that they additionally comprise B.40 imazethapyr as further herbicide B.

Also especially preferred are compositions 10.1. to 10.3545 which differ from the corresponding compositions 1.1 to 1.3545 only in that they additionally comprise B.51 nicosulfuron as further herbicide B.

Also especially preferred are compositions 11.1. to 11.3545 which differ from the corresponding compositions 1.1 to 1.3545 only in that they additionally comprise B.55 pyribenzoxim as further herbicide B.

Also especially preferred are compositions 12.1. to 12.3545 which differ from the corresponding compositions 1.1 to 1.3545 only in that they additionally comprise B.56 pyriftalid as further herbicide B.

Also especially preferred are compositions 13.1. to 13.3545 which differ from the corresponding compositions 1.1 to 1.3545 only in that they additionally comprise B.64 tritosulfuron as further herbicide B.

Also especially preferred are compositions 14.1. to 14.3545 which differ from the corresponding compositions 1.1 to 1.3545 only in that they additionally comprise B.66 ametryne as further herbicide B.

Also especially preferred are compositions 15.1. to 15.3545 which differ from the corresponding compositions 1.1 to 1.3545 only in that they additionally comprise B.67 atrazine as further herbicide B.

Also especially preferred are compositions 16.1. to 16.3545 which differ from the corresponding compositions 1.1 to 1.3545 only in that they additionally comprise B.68 bentazon as further herbicide B.

Also especially preferred are compositions 17.1. to 17.3545 which differ from the corresponding compositions 1.1 to 1.3545 only in that they additionally comprise B.69 bromoxynil as further herbicide B.

Also especially preferred are compositions 18.1. to 18.3545 which differ from the corresponding compositions 1.1 to 1.3545 only in that they additionally comprise B.73 diuron as further herbicide B.

Also especially preferred are compositions 19.1. to 19.3545 which differ from the corresponding compositions 1.1 to 1.3545 only in that they additionally comprise B.76 isoproturon as further herbicide B.

Also especially preferred are compositions 20.1. to 20.3545 which differ from the corresponding compositions 1.1 to 1.3545 only in that they additionally comprise B.81 simazin as further herbicide B.

Also especially preferred are compositions 21.1. to 21.3545 which differ from the corresponding compositions 1.1 to 1.3545 only in that they additionally comprise B.82 terbuthylazin as further herbicide B.

Also especially preferred are compositions 22.1. to 22.3545 which differ from the corresponding compositions 1.1 to 1.3545 only in that they additionally comprise B.85 acifluorfen as further herbicide B.

Also especially preferred are compositions 23.1. to 23.3545 which differ from the corresponding compositions 1.1 to 1.3545 only in that they additionally comprise B.88 flumioxazin as further herbicide B.

Also especially preferred are compositions 24.1. to 24.3545 which differ from the corresponding compositions 1.1 to 1.3545 only in that they additionally comprise B.89 fomesafen as further herbicide B.

Also especially preferred are compositions 25.1. to 25.3545 which differ from the corresponding compositions 1.1 to 1.3545 only in that they additionally comprise B.94 saflufenacil as further herbicide B.

Also especially preferred are compositions 26.1. to 26.3545 which differ from the corresponding compositions 1.1 to 1.3545 only in that they additionally comprise B.95 sulfentrazone as further herbicide B.

Also especially preferred are compositions 27.1. to 27.3545 which differ from the corresponding compositions 1.1 to 1.3545 only in that they additionally comprise B.98 benzbicyclone as further herbicide B.

Also especially preferred are compositions 28.1. to 28.3545 which differ from the corresponding compositions 1.1 to 1.3545 only in that they additionally comprise B.100 clomazone as further herbicide B.

Also especially preferred are compositions 29.1. to 29.3545 which differ from the corresponding compositions 1.1 to 1.3545 only in that they additionally comprise B.103 isoxaflutole as further herbicide B.

Also especially preferred are compositions 30.1. to 30.3545 which differ from the corresponding compositions 1.1 to 1.3545 only in that they additionally comprise B.103 isoxaflutole and B.67 atrazine as further herbicides B.

Also especially preferred are compositions 31.1. to 31.3545 which differ from the corresponding compositions 1.1 to 1.3545 only in that they additionally comprise B.103 isoxaflutole and B.76 isoproturon as further herbicides B.

Also especially preferred are compositions 32.1. to 32.3545 which differ from the corresponding compositions 1.1 to 1.3545 only in that they additionally comprise B.103 isoxaflutole and B.82 terbutylazin as further herbicides B.

Also especially preferred are compositions 33.1. to 33.3545 which differ from the corresponding compositions 1.1 to 1.3545 only in that they additionally comprise B.104 mesotrione as further herbicide B.

Also especially preferred are compositions 34.1. to 34.3545 which differ from the corresponding compositions 1.1 to 1.3545 only in that they additionally comprise B.104 mesotrione and B.67 atrazine as further herbicides B.

Also especially preferred are compositions 35.1. to 35.3545 which differ from the corresponding compositions 1.1 to 1.3545 only in that they additionally comprise B.104 mesotrione and B.76 isoproturon as further herbicides B.

Also especially preferred are compositions 36.1. to 36.3545 which differ from the corresponding compositions 1.1 to 1.3545 only in that they additionally comprise B.104 mesotrione and B.82 terbutylazin as further herbicides B.

Also especially preferred are compositions 37.1. to 37.3545 which differ from the corresponding compositions 1.1 to 1.3545 only in that they additionally comprise B.106 picolinafen as further herbicide B.

Also especially preferred are compositions 38.1. to 38.3545 which differ from the corresponding compositions 1.1 to 1.3545 only in that they additionally comprise B.107 sulcotrione as further herbicide B.

Also especially preferred are compositions 39.1. to 39.3545 which differ from the corresponding compositions 1.1 to 1.3545 only in that they additionally comprise B. 107 sulcotrione and B.67 atrazine as further herbicides B.

Also especially preferred are compositions 40.1. to 40.3545 which differ from the corresponding compositions 1.1 to 1.3545 only in that they additionally comprise B. 107 sulcotrione and B.76 isoproturon as further herbicides B.

Also especially preferred are compositions 41.1. to 41.3545 which differ from the corresponding compositions 1.1 to 1.3545 only in that they additionally comprise B. 107 sulcotrione and B.82 terbutylazin as further herbicides B.

Also especially preferred are compositions 42.1. to 42.3545 which differ from the corresponding compositions 1.1 to 1.3545 only in that they additionally comprise B.109 tembotrione as further herbicide B.

Also especially preferred are compositions 43.1. to 43.3545 which differ from the corresponding compositions 1.1 to 1.3545 only in that they additionally comprise B.111 topramezone as further herbicide B.

Also especially preferred are compositions 44.1. to 44.3545 which differ from the corresponding compositions 1.1 to 1.3545 only in that they additionally comprise B.111 topramezone and B.67 atrazine as further herbicides B.

Also especially preferred are compositions 45.1. to 45.3545 which differ from the corresponding compositions 1.1 to 1.3545 only in that they additionally comprise B.111 topramezone and B.76 isoproturon as further herbicides B.

Also especially preferred are compositions 46.1. to 46.3545 which differ from the corresponding compositions 1.1 to 1.3545 only in that they additionally comprise B.111 topramezone and B.82 terbutylazin as further herbicides B.

Also especially preferred are compositions 47.1. to 47.3545 which differ from the corresponding compositions 1.1 to 1.3545 only in that they additionally comprise B.116 glyphosate as further herbicide B.

Also especially preferred are compositions 48.1. to 48.3545 which differ from the corresponding compositions 1.1 to 1.3545 only in that they additionally comprise B.116 glyphosate and B.67 atrazine as further herbicides B.

Also especially preferred are compositions 49.1. to 49.3545 which differ from the corresponding compositions 1.1 to 1.3545 only in that they additionally comprise B.116 glyphosate and B.94 saflufenacil as further herbicides B.

Also especially preferred are compositions 50.1. to 50.3545 which differ from the corresponding compositions 1.1 to 1.3545 only in that they additionally comprise B.116 glyphosate and B.103 isoxaflutole as further herbicides B.

Also especially preferred are compositions 51.1. to 51.3545 which differ from the corresponding compositions 1.1 to 1.3545 only in that they additionally comprise B.116 glyphosate and B.128 acetochlor as further herbicides B.

Also especially preferred are compositions 52.1. to 52.3545 which differ from the corresponding compositions 1.1 to 1.3545 only in that they additionally comprise B.116 glyphosate and B.104 mesotrione as further herbicides B.

Also especially preferred are compositions 53.1. to 53.3545 which differ from the corresponding compositions 1.1 to 1.3545 only in that they additionally comprise B.116 glyphosate and B.107 sulcotrione as further herbicides B.

Also especially preferred are compositions 54.1. to 54.3545 which differ from the corresponding compositions 1.1 to 1.3545 only in that they additionally comprise B.116 glyphosate and B.111 topramezone as further herbicides B.

Also especially preferred are compositions 55.1. to 55.3545 which differ from the corresponding compositions 1.1 to 1.3545 only in that they additionally comprise B.122 glufosinate as further herbicide B.

Also especially preferred are compositions 56.1. to 56.3545 which differ from the corresponding compositions 1.1 to 1.3545 only in that they additionally comprise B.126 pendimethalin as further herbicide B.

Also especially preferred are compositions 57.1. to 57.3545 which differ from the corresponding compositions 1.1 to 1.3545 only in that they additionally comprise B.128 acetochlor as further herbicide B.

Also especially preferred are compositions 58.1. to 58.3545 which differ from the corresponding compositions 1.1 to 1.3545 only in that they additionally comprise B.131 dimethenamid-P as further herbicide B.

Also especially preferred are compositions 59.1. to 59.3545 which differ from the corresponding compositions 1.1 to 1.3545 only in that they additionally comprise B.132 fentrazamide as further herbicide B.

Also especially preferred are compositions 60.1. to 60.3545 which differ from the corresponding compositions 1.1 to 1.3545 only in that they additionally comprise B.133 flufenacet as further herbicide B.

Also especially preferred are compositions 61.1. to 61.3545 which differ from the corresponding compositions 1.1 to 1.3545 only in that they additionally comprise B.135 metazachlor as further herbicide B.

Also especially preferred are compositions 62.1. to 62.3545 which differ from the corresponding compositions 1.1 to 1.3545 only in that they additionally comprise B.137 S-metolachlor as further herbicide B.

Also especially preferred are compositions 63.1. to 63.3545 which differ from the corresponding compositions 11.1 to 1.3545 only in that they additionally comprise B.138 pretilachlor as further herbicide B.

Also especially preferred are compositions 64.1. to 64.3545 which differ from the corresponding compositions 1.1 to 1.3545 only in that they additionally comprise B.140 indaziflam as further herbicide B.

Also especially preferred are compositions 65.1. to 65.3545 which differ from the corresponding compositions 1.1 to 1.3545 only in that they additionally comprise B.145 2,4-D as further herbicide B.

Also especially preferred are compositions 66.1. to 66.3545 which differ from the corresponding compositions 1.1 to 1.3545 only in that they additionally comprise B.153 clopyralid as further herbicide B.

Also especially preferred are compositions 67.1. to 67.3545 which differ from the corresponding compositions 1.1 to 1.3545 only in that they additionally comprise B.156 dicamba as further herbicide B.

Also especially preferred are compositions 68.1. to 68.3545 which differ from the corresponding compositions 1.1 to 1.3545 only in that they additionally comprise B.171 MCPA as further herbicide B.

Also especially preferred are compositions 69.1. to 69.3545 which differ from the corresponding compositions 1.1 to 1.3545 only in that they additionally comprise B.174 quinclorac as further herbicide B.

The invention also relates to agrochemical compositions comprising an auxiliary and at least one diaminotriazine compound of formula (I) or a composition according to the invention.

An agrochemical diaminotriazine compound of formula (I) or a composition comprises a pesticidally effective amount of at least one composition according to the invention. The term "effective amount" denotes an amount of the active ingredients, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific composition according to the invention used.

The diamonotriazine compounds of formula (I) (compounds A) and optionally B and/or C, their N-oxides, salts or derivatives can be converted into customary types of agrochemical compositions, e. g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, 6$^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F lnforma, London, 2005.

Suitable auxiliaries are solvents, liquid carriers, solid carriers or fillers, surfactants, dispersants, emulsifiers, wetters, adjuvants, sol ubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol.1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl-naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports D5256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-soluble Concentrates (SL, LS)

10-60 wt % of a compound of formula (I) or compostion according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a diamonitriazine compound of formula (I) or composition according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a diamonitriazine compound of formula (I) or composition according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a diamonitriazine compound of formula (I) or composition according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a diamonitriazine compound of formula (I) or composition according to the invention are comminuted with addition of 2-10 wt % dispersants and wetting agents (e.g. sodium lignosulfonate and alcohol ethoxylate), 0,1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-dispersible Granules and Water-soluble Granules (WG, SG)

50-80 wt % of a diamonitriazine compound of formula (I) or composition according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible Powders and Water-soluble Powders (WP, SP, WS)

50-80 wt % of a compound of formula (I) or composition according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a diamonitriazine compound of formula (I) or a composition according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a diamonitriazine compound of formula (I) or a composition according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a diamonitriazine compound of formula (I) or a composition according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a diamonitriazine compound of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of a diamonitriazine compound of formula (I) or a composition according to the invention are ground finely and mixed intimately with solid carrier (e.g. finely divided kaolin) ad 100 wt %.

x) Granules (GR, FG)

0.5-30 wt % of a diamonitriazine compound of formula (I) or a composition according to the invention is ground finely and associated with solid carrier (e.g. silicate) ad 100 wt %. Granulation is achieved by extrusion, spray-drying or the fluidized bed.

xi) Ultra-low Volume Liquids (UL)

1-50 wt % of a diamonitriazine compound of formula (I) or a composition according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying diamonitriazine compounds of formula (I) and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the agrochemical composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. agrochemical components comprising compounds of formula (I) and/or active substances from the groups B and/or C may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g. components comprising compounds of formula (I) and active substances from the groups B and/or C, can be applied jointly (e.g. after tank mix) or consecutively.

Accordingly, a first embodiment of the invention relates to compositions in the form of a agrochemical composition formulated as a 1-component composition comprising the at least one active compound of formula (I) or the at least one active compound of formula (I) (active compound A) and at least one further active compound selected from the herbicides B and the safeners C and also a solid or liquid carrier and, if appropriate, one or more surfactants.

Accordingly, a second embodiment of the invention relates to compositions in the form of a agrochemical composition formulated as a 2-component composition comprising a first formulation (component) comprising the at least one active compound A, which is a compound of formula (I), a solid or liquid carrier and, if appropriate, one or more surfactants, and a second component comprising at least one further active compound selected from the herbicides B and safeners C, a solid or liquid carrier and, if appropriate, one or more surfactants.

The active compound A, which is a compound of formula (I) and the at least one further active compound B and/or C can be formulated and applied jointly or separately, simultaneously or in succession, before, during or after the emergence of the plants. In case of separate application, the order of the application of the active compounds A, B and/or C is of minor importance. The only thing that is important is that the at least one active compound A and the at least one further active compound B and/or C are present simultaneously at the site of action, i.e. are at the same time in contact with or taken up by the plant to be controlled or to be safened.

The compounds of formula (I) or compositions according to the invention are suitable as herbicides. They are suitable as such or as an appropriately formulated composition (agrochemical composition).

The compounds of formula (I) or compositions according to the invention control vegetation on non-crop areas very efficiently, especially at high rates of application. They act against broad-leafed weeds and grass weeds in crops such as wheat, rice, corn, soybeans and cotton without causing any significant damage to the crop plants. This effect is mainly observed at low rates of application.

The compounds of formula (I) or compositions according to the invention are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal compositions may also be applied by the low-volume or the ultra-low-volume method, or in the form of microgranules.

Application of the compounds of formula (I) or herbicidal compositions according to the present invention can be done before, during and/or after, preferably during and/or after, the emergence of the undesirable plants.

The compounds of formula (I) or herbicidal compositions according to the present invention can be applied pre- or post-emergence or together with the seed of a crop plant. It is also possible to apply the compounds and compositions by applying seed, pretreated with a composition of the invention, of a crop plant. If the active compounds A and B and, if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the composition according to the invention can be applied by treating seed. The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula (I) according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

Moreover, it may be advantageous to apply the compounds of formula (I) or compositions of the present invention on their own or jointly in combination with other crop protection agents, for example with agents for controlling pests or phytopathogenic fungi or bacteria or with groups of active compounds which regulate growth. Also of interest is the miscibility with mineral salt solutions which are employed for treating nutritional and trace element deficiencies. Non-phytotoxic oils and oil concentrates can also be added.

When employed in plant protection, the amounts of active substances applied, i.e. A (compounds of formula (I)) and B and, if appropriate, C without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha.

In another embodiment of the invention, the application rate of A (compounds of formula (I)) and B and, if appropriate, C, is from 0.001 to 3 kg/ha, preferably from 0.005 to 2.5 kg/ha and in particular from 0.01 to 2 kg/ha of active substance (a.s.).

In another preferred embodiment of the invention, the rates of application of the compounds of formula (I) according to the present invention (total amount of compounds of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the compounds of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the compounds of formula (I) is 0.1 to 1000 g/ha, preferably1 to 750 g/ha, more preferably 5 to 500 g/ha.

The required application rates of herbicidal compounds B are generally in the range of from 0.0005 kg/ha to 2.5 kg/ha and preferably in the range of from 0.005 kg/ha to 2 kg/ha or 0.01 kg/ha to 1.5 kg/h of a.s.

The required application rates of safeners C are generally in the range of from 0.0005 kg/ha to 2.5 kg/ha and preferably in the range of from 0.005 kg/ha to 2 kg/ha or 0.01 kg/ha to 1.5 kg/h of a.s.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. A and B and, if appropriate, C are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

In the methods of the present invention it is immaterial whether the herbicide compound A of formula (I), and the further herbicide component B and/or the herbicide safener compound C are formulated and applied jointly or separately. In the case of separate application it is of minor importance, in which order the application takes place. It is only necessary, that the herbicide compound A and the herbicide compound B and/or the herbicide safener compound C are applied in a time frame that allows simultaneous action of the active ingredients on the plants, preferably within a time-frame of at most 14 days, in particular at most 7 days.

Depending on the application method in question, the compositions according to the invention can additionally be employed in a further number of crop plants for eliminating undesirable plants. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *prunus domestica, Ribes sylvestre, Ricinus communis, Saccharum officinarum, Secale cereale, Sinapis alba, Solanum tuberosum, Sorghum* bicolor (*s. vulgare*), *Theobroma cacao, Trifolium pratense, Triticum aestivum, Triticale, Triticum durum, Vicia faba, Vitis vinifera, Zea mays.*

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), *Triticale, Triticum aestivum, Triticum durum, Vicia faba, Vitis vinifera* and *Zea mays*

Especially preferred crops are crops of cereals, corn, soybeans, rice, oilseed rape, cotton, potatoes, peanuts or permanent crops.

The compositions according to the invention can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxinic herbicides such as dicamba or 2,4-D; bleacher herbicides such as 4-hydroxyphenylpyruvate dioxygenase (HPPD) inhibitors or phytoene desaturase (PDS) inhibitors; acetolactate synthase (ALS) inhibitors such as sulfonylureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetylCoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxinic herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as delta-endotoxins, e. g., CrylA(b), CrylA(c), Cryl F, CryIF(a2), Cryl IA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., Photorhabdus spp. or Xenorhabdus spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato cultivars, which express resistance genes acting against Phytophthora infestans derived from the Mexican wild potato, Solanum bulbocastanum) or T4-lysozym (e.g., potato cultivars capable of synthesizing these proteins with increased resistance against bacteria such as Erwinia amylovora). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the the compositions according to the invention are also suitable for the defoliation and/or desiccation of plant parts, for which crop plants such as cotton, potato, oilseed rape, sunflower, soybean or field beans, in particular cotton, are suitable. In this regard compositions have been found for the desiccation and/or defoliation of plants, processes for preparing these compositions, and methods for desiccating and/or defoliating plants using the compositions according to the invention.

As desiccants, the compositions according to the invention are suitable in particular for desiccating the above-ground parts of crop plants such as potato, oilseed rape, sunflower and soybean, but also cereals. This makes possible the fully mechanical harvesting of these important crop plants.

Also of economic interest is the facilitation of harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

Another aspect of the invention is an agrochemical composition comprising a herbicidal active amount of at least one compound of formula (I) as defined above and at least one inert liquid and/or solid carrier and, if appropriate, at least one surface-active substances.

A further aspect of the invention is a method of controlling undesired vegetation, which comprises allowing a herbicidally active amount of at least one compound of formula (I) as as defined above to act on plants, their environment or on seed.

A further aspect of the invention in is the use of a compound of formula (I) as defined aboven as a herbicide or for the desiccation/defoliation of plants.

A further embodiment of the invention is a method of controlling undesired vegetation, which comprises allowing a herbicidally active amount of at least one compound of formula (I) as defined above to act on plants, their environment or on seed.

The preparation of the diaminotriazine compounds of formula (I) is illustrated by examples; however, the subject matter of the present invention is not limited to the examples given.

The products shown below were characterized by the mass ([m/z]) or retention time (RT; [min.]) determined by HPLC-MS spectrometry.

HPLC-MS=high performance liquid chromatography-coupled mass spectrometry;
HPLC column:
RP-18 column (Chromolith Speed ROD from Merck KgaA, Germany), 50*4.6 mm; mobile phase: acetonitrile+0.1% trifluoroacetic acid (TFA)/water+0.1% TFA using a gradient from 5:95 to 100:0 over 5 minutes at 40° C., flow rate 1.8 ml/min.
MS: quadrupole electrospray ionization, 80 V (positive mode).

The following abbreviations are used:
CH$_2$Cl$_2$: Dichloromethane
EtOAc: Acetic acid ethyl ester
THF: Tetrahydrofuran
CH: Cyclohexane
HCl: hydrogen chloride
NaOH: Sodium hydroxyde
DMF: N,N-Dimethylformamide
HPLC: High pressure chromatography
LC: Liquid chromatography
MS: Mass spectrometry

A PREPARATION EXAMPLES

Example 1

N2-(5-fluoro-1,3-benzodioxol-4-yl)-6-(1-fluoro-1-methyl-ethyl)-1,3,5-triazine-2,4-diamine

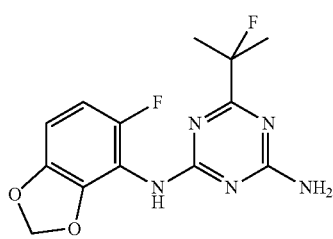 [SMILES: CC(C)(F)c1nc(N)nc(Nc2c(F)ccc3c2OCO3)n1]

1.1: 4-fluorobenzene-1,2-diol

A solution of boron tribromide (1 M, 961 mL, 0.96 mol) was slowly added to a stirred cooled solution (−78° C.) of 4-fluoro-1,2-dimethoxy-benzene (60 g, 0.38 mol) in CH$_2$Cl$_2$ (200 mL) and the mixture was let to warm slowly to room temperature and was stirred over night at room temperature. The next day, the reaction mixture was poured into ice and the phases were separated. The aqueous phase was extracted with EtOAc and the combined organic phases were dried (Na$_2$SO$_4$) and the solvent was removed to afford 4-fluorobenzene-1,2-diol (48.76 g) used without further purification in the next step.

$^1$H NMR (d6-DMSO, 500 MHz): δ=6.68 (dd, 1H, J=8.8, 6.0 Hz), 6.54 (dd, 1H, J=10.1, 3.0 Hz), 6.39 (dt, 1H, J=8.6, 3.1 Hz).

1.2: 5-fluoro-1,3-benzodioxole

Cs$_2$CO$_3$ (51.89 g, 0.16 mol) was slowly added to a stirred solution of 4-fluorobenzene-1,2-diol (13.6 g, 0.10 mol) in DMF (100 mL) and the mixture was stirred at room temperature for 10 minutes. A small exotherm to 40° C. was observed. Bromochloromethane was slowly added and the mixture was stirred at 110° C. for 3 hours. After this time, the reaction mixture was cooled to room temperature and poured into ice and the water phase was extracted with petrol ether. The organic phase was dried (Na$_2$SO$_4$) and the solvent removed to afford crude 5-fluoro-1,3-benzodioxole (8.7 g, 0.062 mol, 58%) as a colorless oil used without further purification in the next step.

$^1$H NMR (CDCl$_3$, 500 MHz): δ=6.71 (dd, 1H, J=8.4, 4.5 Hz), 6.60 (dd, 1H, J=8.2, 2.6 Hz), 6.50 (dt, 1H, J=9.0, 2.6 Hz), 5.96 (s, 2H).

1.3: 5-fluoro-1,3-benzodioxole-4-carboxylic acid

A solution of LDA (1.8 M, 4.8 mL, 8.7 mmol) was slowly added to a stirred cooled (−78° C.) solution of 5-fluoro-1,3-benzodioxole (1.1 g, 7.85 mmol) in THF (20 mL) and the mixture was stirred for one hour. Solid carbon dioxide (dry ice) was added in portion (excess) and the mixture was let to warm to room temperature. Upon stirring, Water was added and HCl was added (1M, aq. Solution) until pH=1. EtOAc was added and the pahse were separated. The organic phase was dried (Na$_2$SO$_4$) and the solvent removed to afford 5-fluoro-1,3-benzodioxole-4-carboxylic acid (1.36 g, 7.4 mmol, 94%) as a yellow solid used without further purification in the next step.

$^1$H NMR (d6-DMSO, 400 MHz): δ=7.04 (dd, 1H, J=8.6, 4.2 Hz), 6.71 (dd, 1H, J=11.3, 8.6 Hz), 6.14 (s, 2H).

1.4: 5-fluoro-1,3-benzodioxol-4-amine

Triethylamine (59.36 g, 0.59 mol), tert-butanol (109 g, 1.47 mol) and diphenylphosphoryl azide (42.37 g, 0.15 mol) were added to a stirred solution of 5-fluoro-1,3-benzodioxole-4-carboxylic acid (27 g, 0.145 mol) in dioxane (400 mL) at room temperature and the mixture was stirred at 100° C. for 4.5 hours. The reaction was cooled to room temperature and filtered. The filtrate is kept and the solvent removed. EtOAc is added to this crude and this organic phase is washed sequentially with HCl (1 M, aq. solution) and NaHCO$_3$ (saturated aq. solution), dried (Na$_2$SO$_4$) and the solvent removed to afford tert-butyl N-(5-fluoro-1,3-benzodioxol-4-yl)carbamate (37.88 g, 0.148 mol, quant.) used immediately in the next step.

Trifluoroacetic acid (152 g, 1.33 mol) was added to a stirred solution of tert-butyl N-(5-fluoro-1,3-benzodioxol-4-yl)carbamate (37.8 g, 0.148 mol) in CH$_2$Cl$_2$ (500 mL) and the mixture was stirred at room temperature for 3 hours. The solvent was removed und the crude dissolved in EtOAc. The organic phase was washed with NaHCO$_3$ (cc. aq. solution), dried (Na$_2$SO$_4$) and the solvent removed. Purification by column chromatography (gradient: 100% CH to 4:1 CH: EtOAc) afforded 5-fluoro-1,3-benzodioxol-4-amine (13.1 g, 0.0844 mol, 56%).

$^1$H NMR (CDCl$_3$, 400 MHz): δ=6.49 (dd, 1H, J=11.4, 8.6 Hz), 6.20 (dd, 1H, J=8.6, 3.9 Hz), 5.90 (s, 2H), 3.55 (bts, 2H, NH$_2$).

1.5: 1-carbamimidoyl-3-(5-fluoro-1,3-benzodioxol-4-yl)guanidine

Aq. HCl (38% w/w, 5 mL) was added, with stirring, to a solution of 5-fluoro-1,3-benzodioxol-4-amine (5 g, 32.23 mmol) and 2-cyanoguanidine (0.38 g, 38.65 mmol) in acetonitrile (250 mL) an the mixture was heated under reflux for 3 hours. The reaction mixture was cooled to room temperature and water and EtOAc were added. The phases were separated and the organic phase discarded. The aqueous phase was basified with NaOH (2M, aq. Solution) until pH 12. Ethyl acetate was added and the phases were separated. The organic phase was dried (Na$_2$SO$_4$) and the solvent removed to afford 1-carbamimidoyl-3-(5-fluoro-1,3-benzodioxol-4-yl)guanidine (5.6 g, 23.4 mmol, 73%) as a white solid used without further purification in the next step.

MS (ESI) m/z=239.8 [M+H$^+$].

1.6: N2-(5-fluoro-1,3-benzodioxol-4-yl)-6-(1-fluoro-1-methyl-ethyl)-1,3,5-triazine-2,4-diamine 2-Fluoro-2-methyl-propanoyl chloride (2.65 g, 21.3 mmol) was slowly added to a stirred solution of 1-carbamimidoyl-3-(5-fluoro-1,3-benzodioxol-4-yl)guanidine (5.6 g, 23.4 mmol) and triethylamine (8.9 mL, 64 mmol) in THF (50 mL) and the mixture was heated at 60° C. for 4 hours. The reaction was cooled to room temperature and water and ethyl acetate were added and the phase separated. The aqueous phase was washed with EtOAc, the organic phases were combined, washed with brine, dried (Na$_2$SO$_4$) and the solvent was removed. Purification by column chromatography (gradient: 100% CH to 40:60 CH: EtOAc) afforded N2-(5-fluoro-1,3-benzodioxol-4-yl)-6-(1-fluoro-1-methyl-ethyl)-1,3,5-triazine-2,4-diamine (4 g, 13 mmol, 61%).

$^1$H NMR (MeOD, 400 MHz): δ=6.68 (dd, 1H, J=8.5, 4.0 Hz), 6.60 (dd, 1H, J=10.6, 8.6 Hz), 6.00 (s, 2H), 1.64 (s, 3H), 1.58 (s, 3H).

The compounds 2 to 36 listed below in table 3, compounds 37 and 38 listed below in table 4, compounds 39 listed below in table 5, compounds 40 listed below in table 5a, compound 41 listed below in table 6 and compounds 42 and 43 listed below in table 7, compounds 44 and 45 listed below in table 8, compounds 46 to 50 listed below in table 9, compound 51 listed below in table 10, compound 52 listed below in table 11, compound 53 listed below in table 12, compound 54 listed below in table 13, compound 55 listed below in table 14 have been prepared by analogy to the example 1 mentioned above.

TABLE 3

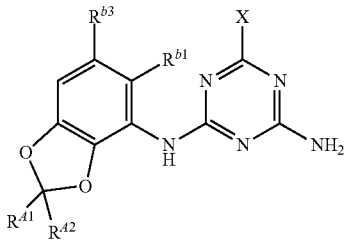

| no | $R^{b1}$ | $R^{b3}$ | X | $R^{41}$ | $R^{42}$ | MS[1] [m/z] |
|---|---|---|---|---|---|---|
| 1. | F | H | CF(CH$_3$)$_2$ | H | H | 310 |
| 2. | Cl | H | CF(CH$_3$)$_2$ | H | H | 326.6 |
| 3. | Br | H | CF(CH$_3$)$_2$ | H | H | 371.6 |
| 4. | Br | Br | CFMe$_2$ | H | H | 450.0 |
| 5. | F | H | 1-chlorocyclobutyl | H | H | 337.9 |
| 6. | F | H | 1-methylcyclohexyl | H | H | 346.4 |
| 7. | F | H | CF(CH$_3$)$_2$ | H | CH$_3$ | 324.1 |
| 8. | F | H | CF(CH$_3$)$_2$ | CH$_3$ | H | 324.1 |
| 9. | Br | H | 1-chlorocyclopentyl | F | F | 449.8 |
| 10. | Br | H | cyclohexyl | F | F | 429.9 |
| 11. | Cl | H | CF(CH$_3$)$_2$ | CH$_3$ | CH$_3$ | 354.1 |
| 12. | Cl | H | CF(CH$_3$)$_2$ | CH$_3$ | H | 340.1 |
| 13. | Br | H | 2,6-difluorophenyl | F | F | 459.8 |
| 14. | F | H | CF(CH$_3$)$_2$ | CH$_3$ | CH$_3$ | 338.2 |
| 15. | F | H | 1-fluorocyclopentyl | H | H | 335.8 |
| 16. | F | H | CH(CH$_3$)CH$_2$CH$_3$ | H | H | 305.9 |
| 17. | F | H | CH(CH$_3$)$_2$ | H | H | 291.9 |
| 18. | F | H | azetidin-1-yl | H | H | 305.4 |
| 19. | F | H | 2-metyhl-pyrrolidin-1-y | H | H | 333.4 |
| 20. | F | H | pyrrolidin-1-yl | H | H | 319.4 |
| 21. | F | H | 1-piperidyl | H | H | 333.4 |
| 22. | F | H | tetrahydrofuran-2-yl | H | H | 319.8 |
| 23. | F | H | 1-methoxycyclohexyl | H | H | 361.9 |
| 24. | F | H | 2,2-dimethylprop-2-yl | H | H | 319.9 |
| 25. | F | H | methoxy(methyl)amino | H | H | 308.8 |
| 26. | F | H | CH$_2$CH(CH$_3$)$_2$ | H | H | 306.4 |
| 27. | F | H | cyclohexyl | H | H | 332.5 |
| 28. | F | H | cyclopentyl | H | H | 318.4 |
| 29. | F | H | C(CH$_3$)$_3$ | H | H | 306.4 |
| 30. | F | F | CF(CH$_3$)$_2$ | H | H | 328.0 |
| 31. | Cl | Cl | CF(CH$_3$)$_2$ | H | H | 360.0 |
| 32. | F | H | 1-methoxyethyl | H | H | 307.8 |
| 33. | F | H | 1-fluoropropyl | H | H | 309.8 |
| 34. | H | Br | CF(CH$_3$)$_2$ | H | H | 370.0 |
| 35. | F | H | CF(CH$_3$)$_2$ | CH$_3$ | H | 324.1 |
| 36. | F | H | CF(CH$_3$)$_2$ | CH$_3$ | OCH$_3$ | 368.1 |

[1] Mass Spectrum M$^+$ or [M + H]$^+$ [m/z]

TABLE 4

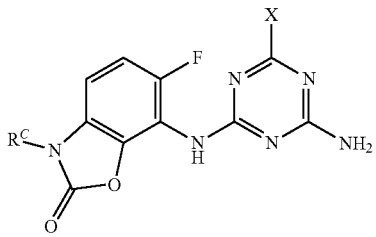

| no. | X | $R^C$ | MS[1] [m/z] |
|---|---|---|---|
| 37. | CF(CH$_3$)$_2$ | H | 323.1 |
| 38. | CF(CH$_3$)$_2$ | CH$_3$ | 337.1 |

[1] Mass Spectrum M$^+$ or [M + H]$^+$ [m/z]

TABLE 5

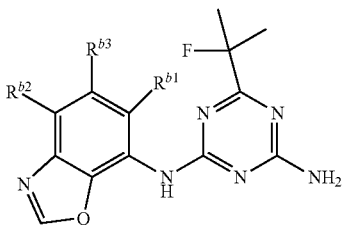

| no. | $R^{b1}$ | $R^{b2}$ | $R^{b3}$ | MS[1] [m/z] |
|---|---|---|---|---|
| 39. | F | H | H | 307.1 |

[1] Mass Spectrum M⁺ or [M + H]⁺ [m/z]

TABLE 5a

| no. | $R^{b1}$ | $R^{b2}$ | $R^{b3}$ | MS[1] [m/z] |
|---|---|---|---|---|
| 40. | F | F | F | 343.1 |

[1] Mass Spectrum M⁺ or [M + H]⁺ [m/z]

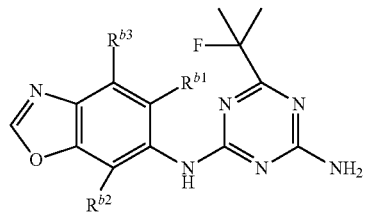

TABLE 6

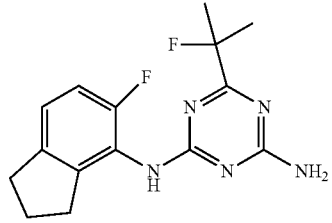 [SMILES: CC(C)(F)c1nc(N)nc(Nc2c(F)ccc3c2CCC3)n1]

| no. | MS[1] [m/z] |
|---|---|
| 41. | 306.1 |

[1] Mass Spectrum M⁺ or [M + H]⁺ [m/z]

TABLE 7

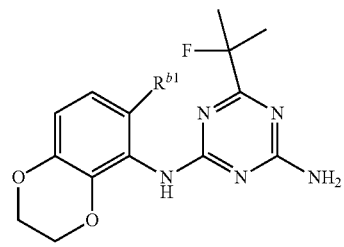

| no. | $R^{b1}$ | MS[1] [m/z] |
|---|---|---|
| 42. | Cl | 340.1 |
| 43. | F | 324.2 |

[1] Mass Spectrum M⁺ or [M + H]⁺ [m/z]

TABLE 8

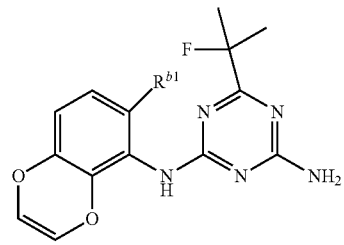

| no. | $R^{b1}$ | MS[1] [m/z] |
|---|---|---|
| 44. | Cl | 338.1 |
| 45. | F | 322.1 |

[1] Mass Spectrum M⁺ or [M + H]⁺ [m/z]

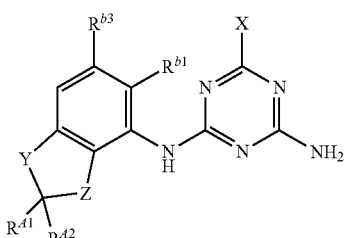

TABLE 9

| no. | X | Y | Z | $R^{b1}$ | $R^{b3}$ | $R^{A1}$ | $R^{A2}$ | MS[1] [m/z] |
|---|---|---|---|---|---|---|---|---|
| 46. | CF(CH₃)₂ | O | NCH₃ | F | F | =O | | 337.1 |
| 47. | CF(CH₃)₂ | CH₂ | CH₂ | Cl | H | H | H | 322.1 |
| 48 | 2,6-difluorophenyl | O | O | F | H | CH₃ | H | 376.1 |
| 49 | C(CH₃)₃ | O | O | F | H | CH₃ | H | 320.1 |
| 50 | OCH₃ | O | O | F | H | H | H | 280.0 |

[1] Mass Spectrum M⁺ or [M + H]⁺ [m/z]

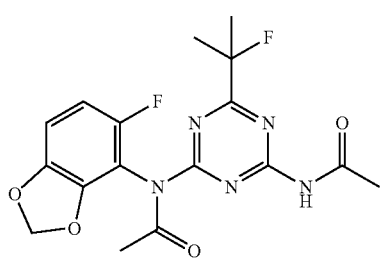 [SMILES: CC(=O)Nc1nc(N(C(C)=O)c2c(F)ccc3c2OCO3)nc(C(C)(C)F)n1]

TABLE 10

| no. | MS[1] [m/z] |
|---|---|
| 51. | 394.1 |

[1] Mass Spectrum M+ or [M + H]+ [m/z]

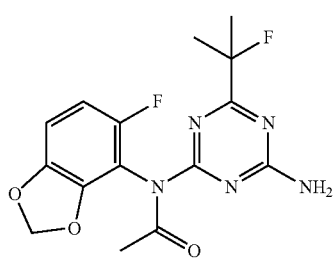 [SMILES: CC(=O)N(c1nc(N)nc(C(C)(C)F)n1)c1c(F)ccc2c1OCO2]

TABLE 11

| no. | MS[1] [m/z] |
|---|---|
| 52. | 352.1 |

[1] Mass Spectrum M+ or [M + H]+ [m/z]

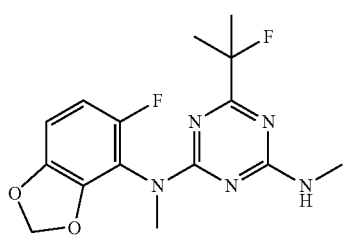 [SMILES: CNc1nc(N(C)c2c(F)ccc3c2OCO3)nc(C(C)(C)F)n1]

TABLE 12

| no. | MS[1] [m/z] |
|---|---|
| 53. | 338.1 |

[1] Mass Spectrum M+ or [M + H]+ [m/z]

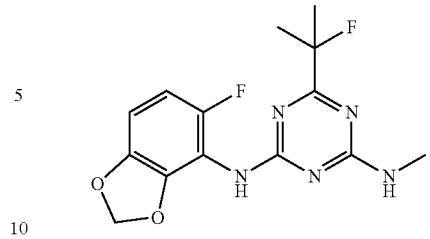

TABLE 13

| no. | MS[1] [m/z] |
|---|---|
| 54. | 324.1 |

[1] Mass Spectrum M+ or [M + H]+ [m/z]

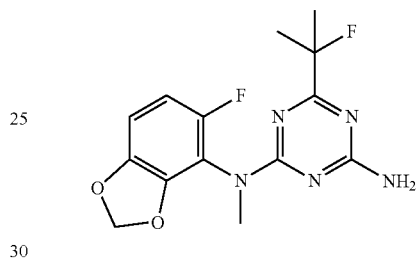

TABLE 14

| no. | MS[1] [m/z] |
|---|---|
| 55. | 324.1 |

[1] Mass Spectrum M+ or [M + H]+ [m/z]

B USE EXAMPLES

The herbicidal activity of the azines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 278 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A moderate herbicidal activity is given at values of at least 60, a good herbicidal activity is given at values of at least 70, and a very good herbicidal activity is given at values of at least 85.

The plants used in the greenhouse experiments were of the following species:

| Bayer code | Scientific name |
|---|---|
| ABUTH | Abutilon theophrasti |
| ALOMY | Alopecurus myosuroides |
| AMARE | Amaranthus retroflexus |
| APESV | Apera spica-venti |
| BRSNW | Winter rape |
| CHEAL | Chenopodium album |
| ECHCG | Echinocloa crus-galli |
| LAMPU | Lamium purpureum |
| POLCO | Polygonum convolvulus |
| SETFA | Setaria faberi |
| SETVI | Setaria viridis |
| STEME | Stellaria media |
| VIOAR | Viola arvensis |

Example 1 applied by post-emergence method at an application rate of 0.0312 kg/ha, showed very good herbicidal activity against AMARE, good herbicidal activity against BRSNW and CHEAL.

Example 2 applied by pre-emergence method at an application rate of 0.5 kg/ha, showed very good herbicidal activity against ALOMY, AMARE and SETFA.

Example 3 applied by pre-emergence method at an application rate of 0.5 kg/ha, showed very good herbicidal activity against ALOMY, AMARE and SETFA.

Example 4 applied by pre-emergence method at an application rate of 125 g/ha, showed good herbicidal activity against ABUTH.

Example 5 applied by pre-emergence method at an application rate of 250 g/ha, showed very good herbicidal activity against AMARE, ECHCG and SETFA.

Example 6 applied by pre-emergence method at an application rate of 250 g/ha, showed very good herbicidal activity against APESV and good herbicidal activity against ALOMY and AMARE.

Example 7 applied by pre-emergence method at an application rate of 250 g/ha, showed very good herbicidal activity against AMARE, ABUTH and SETFA.

Example 8 applied by pre-emergence method at an application rate of 250 g/ha, showed very good herbicidal activity against AMARE, ABUTH and SETFA.

Example 9 applied by post-emergence method at an application rate of 500 g/ha, showed very good herbicidal activity against AMARE.

Example 11 applied by pre-emergence method at an application rate of 250 g/ha, showed very good herbicidal activity against AMARE, ECHCG and ABUTH.

Example 12 applied by pre-emergence method at an application rate of 250 g/ha, showed very good herbicidal activity against AMARE, ECHCG and ABUTH.

Example 14 applied by pre-emergence method at an application rate of 250 g/ha, showed very good herbicidal activity against AMARE, ECHCG and ABUTH.

Example 15 applied by pre-emergence method at an application rate of 250 g/ha, showed very good herbicidal activity against AMARE, SETFA and ABUTH.

Example 16 applied by pre-emergence method at an application rate of 125 g/ha, showed good herbicidal activity against ABUTH and showed very good herbicidal activity against AMARE.

Example 17 applied by pre-emergence method at an application rate of 125 g/ha, showed good herbicidal activity against ABUTH and showed very good herbicidal activity against AMARE.

Example 18 applied by post-emergence method at an application rate of 500 g/ha, showed herbicidal activity against ABUTH and AMARE.

Example 19 applied by pre-emergence method at an application rate of 500 g/ha, showed very good herbicidal activity against AMARE.

Example 20 applied by pre-emergence method at an application rate of 500 g/ha, showed very good herbicidal activity against AMARE.

Example 21 applied by post-emergence method at an application rate of 500 g/ha, showed very good herbicidal activity against AMARE and showed good herbicidal activity against ABUTH.

Example 23 applied by pre-emergence method at an application rate of 125 g/ha, showed very good herbicidal activity against AMARE and showed good herbicidal activity against ECHCG and SETFA.

Example 24 applied by pre-emergence method at an application rate of 125 g/ha, showed very good herbicidal activity against AMARE, ABUTH and ECHCG.

Example 25 applied by pre-emergence method at an application rate of 500 g/ha, showed very good herbicidal activity against AMARE.

Example 26 applied by pre-emergence method at an application rate of 125 g/ha, showed very good herbicidal activity against AMARE and showed good herbicidal activity against ECHCG and SETFA.

Example 27 applied by pre-emergence method at an application rate of 125 g/ha, showed very good herbicidal activity against AMARE and showed good herbicidal activity against SETFA.

Example 28 applied by pre-emergence method at an application rate of 125 g/ha, showed very good herbicidal activity against AMARE and showed good herbicidal activity against ECHCG.

Example 29 applied by pre-emergence method at an application rate of 125 g/ha, showed very good herbicidal activity against AMARE, ABUTH and ECHCG.

Example 30 applied by post-emergence method at an application rate of 125 g/ha, showed very good herbicidal activity against AMARE, ABUTH and STEVI.

Example 31 applied by pre-emergence method at an application rate of 125 g/ha, showed very good herbicidal activity against AMARE, STEFTA and showed good herbicidal activity against ECHCG.

Example 32 applied by pre-emergence method at an application rate of 125 g/ha, showed good herbicidal activity against AMARE and ABUTH.

Example 33 applied by pre-emergence method at an application rate of 125 g/ha, showed very good herbicidal activity against AMARE.

Example 35 applied by pre-emergence method at an application rate of 250 g/ha, showed very good herbicidal activity against AMARE, ABUTH and ECHCG.

Example 38 applied by pre-emergence method at an application rate of 500 g/ha, showed very good herbicidal activity against AMARE.

Example 39 applied by pre-emergence method at an application rate of 250 g/ha, showed very good herbicidal activity against AMARE and ABUTH.

Example 41 applied by pre-emergence method at an application rate of 500 g/ha, showed very good herbicidal activity against AMARE.

Example 42 applied by pre-emergence method at an application rate of 125 g/ha, showed very good herbicidal activity against AMARE.

Example 43 applied by pre-emergence method at an application rate of 500 g/ha, showed very good herbicidal activity against AMARE.

Example 44 applied by pre-emergence method at an application rate of 500 g/ha, showed very good herbicidal activity against AMARE and ECHCG.

Example 45 applied by pre-emergence method at an application rate of 125 g/ha, showed very good herbicidal activity against AMARE and ABUTH.

Example 47 applied by pre-emergence method at an application rate of 250 g/ha, showed good herbicidal activity against ECHCG and ABUTH.

The respective stated components A and B, and if appropriate, C were formulated as a 10% by weight strength emulsion concentrate and, with addition of the amount of solvent system, introduced into the spray liquor used for applying the active compound. In the examples, the solvent used was water.

In the examples below, using the method of S. R. Colby (1967) "Calculating synergistic and antagonistic responses of herbicide combinations", Weeds 278, p. 22ff., the value E, which is expected if the activity of the individual active compounds is only additive, was calculated.

$$E = X + Y - (X \cdot Y/100)$$

where
X=percent activity using active compound A at an application rate a;
Y=percent activity using active compound B at an application rate b;
E=expected activity (in %) by A+B at application rates a+b.
If the value found experimentally is higher than the value E calculated according to Colby, a synergistic effect is present.

The plants used in the greenhouse experiments were of the following species:

| Bayer code | Scientific name |
| --- | --- |
| ABUTH | *Abutilon theophrasti* |
| ALOMY | *Alopercurus myosuroides* |
| AMARE | *Amaranthus retroflexus* |
| AMBEL | *Ambrosia artemisiifolia* |
| APESV | *Apera spica-venti* |
| BIDPI | *Bidens pilosa* |
| BRADE | *Brachiaria deflexa* |
| BRAPL | *Brachiaria plantaginea* |
| CHEAL | *Chenopodium album* |
| COMBE | *Commenline benghalensis* |
| DIGSA | *Digitaria sanguinales* |
| ECHCG | *Echinocloa crus-galli* |
| ELEIN | *Eleusine indica* |
| ERBVI | *Eriochloa villosa* |
| ERICA | *Erigeron canadensis* |
| LAMAM | *Lamium amplexicaule* |
| LAMPU | *Lamium purpureum* |
| PANDI | *Panicum dichotomiflorum* |
| PHBPU | *Pharbitis purpurea* |
| POAAN | *Poa annua* |

-continued

| Bayer code | Scientific name |
| --- | --- |
| POLCO | *Polygonum convolvulus* |
| SETLU | *Setaria lutescens* |
| SETFA | *Setaria faberi* |
| SETVE | *Setaria verticillata* |
| SETVI | *Setaria viridis* |
| SOLNI | *Solanum nigrum* |
| SORHA | *Sorghum halepense* |
| STEME | *Stellaria media* |
| VERPE | *Veronica persica* |

The invention claimed is:
1. A diaminotriazine compound of formula (I)

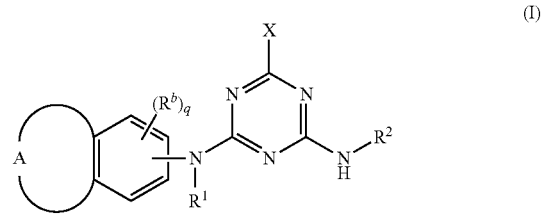

wherein
A is a fused saturated or unsaturated, 5-or 6-membered carbocycle or a fused saturated or unsaturated, 5-or 6-membered heterocycle having 1, 2 or 3 heteroatoms or heteroatom moieties, selected from the group consisting of O, S, S(O)$_p$, N and NR$^C$ as ring members,
wherein the carbocycle and the heterocycle are unsubstituted or carry 1, 2, 3 or 4 radicals R$^A$;
p is 0, 1 or 2
q is 0, 1, 2 or 3;
R$^A$ is selected from the group consisting of halogen, OH, CN, amino, NO$_2$, C$_1$-C$_6$-alkyl, C$_2$-C$_6$-alkenyl, C$_2$-C$_6$-alkynyl, C$_1$-C$_6$-alkoxy, C$_2$-C$_6$-alkenyloxy, C$_2$-C$_6$-alkynyloxy, (C$_1$-C$_6$-alkoxy)-C$_1$-C$_6$alkyl, (C$_1$-C$_6$ -alkoxy)-C$_1$-C$_6$ -alkoxy, (C$_1$-C$_6$-alkoxy)-C$_2$-C$_6$-alkenyl, (C$_1$-C$_6$-alkoxy)-C$_2$-C$_6$-alkynyl, C$_1$-C$_6$-alkylthio, (C$_1$-C$_6$-alkyl) sulfinyl, (C$_1$-C$_6$-alkyl)sulfonyl, (C$_1$-C$_6$-alkyl)amino, di(C$_1$-C$_6$-alkyl)amino, (C$_1$-C$_6$-alkyl)-carbonyl, (C$_1$-C$_6$-alkoxy)-carbonyl, (C$_1$-C$_6$-alkyl)-carbonyloxy, C$_3$-C$_6$-cycloalkyl, C$_3$-C$_6$-cycloalkoxy, (C$_3$-C$_6$-cycloalkyl)-C$_1$-C$_4$-alkyl, and (C$_3$-C$_6$-cycloalkyl)-C$_1$-C$_4$-alkoxy, wherein the aliphatic and cycloaliphatic parts of the 22 aforementioned radicals are unsubstituted, partly or completely halogenated and wherein the cycloaliphatic parts of the last 4 mentioned radicals may carry 1, 2, 3, 4, 5 or 6 methyl groups, it being possible that R$^A$ are identical or different, it being possible that two radicals R$^A$ which are bound at the same carbon atom may together be =O or =NR$^d$;
R$^b$ is selected from the group consisting of halogen, OH, CN, amino, NO$_2$, C$_1$-C6-alkyl, C$_2$-C$_6$-alkenyl, C$_2$-C$_6$-alkynyl, C$_1$-C$_6$-alkoxy, C$_2$-C$_6$-alkenyloxy, C$_2$-C$_6$-alkynyloxy, (C$_1$-C$_6$-alkoxy)-C$_1$-C$_6$-alkyl, (C$_1$-C$_6$-alkoxy)-C$_1$-C$_6$-alkoxy, (C$_1$-C$_6$-alkoxy)-C$_2$-C$_6$-alkenyl, (C$_1$-C$_6$-alkoxy)-C$_2$-C$_6$-alkynyl, C$_1$-C$_6$-alkylthio, (C$_1$-C$_6$-alkyl) sulfinyl, (C$_1$-C$_6$-alkyl)sulfonyl, (C$_1$-C$_6$-alkyl)amino, di(C$_1$-C$_6$-alkyl)amino, (C$_1$-C$_6$-alkyl)-carbonyl, (C$_1$-C$_6$-alkoxy)-carbonyl, (C$_1$-C$_6$-alkyl)-carbonyloxy, C$_3$-C$_6$-cycloalkyl, C$_3$-C$_6$-cycloalkoxy, (C$_3$-C$_6$-cycloalkyl)-C$_1$-C$_4$-alkyl, and (C$_3$-C$_6$-cycloalkyl)-C$_1$-C$_4$-alkoxy, wherein the aliphatic and cycloaliphatic parts of the 22 aforementioned radicals are unsubstituted, partly or completely halogenated and wherein the cycloaliphatic parts of the last 4 mentioned radicals may carry 1, 2, 3, 4, 5 or 6 methyl groups, for q =2 or 3 it being possible that $R^b$ are identical or different;

$R^c$ is selected from the group consisting of H, OH, $S(0)_2NH_2$, CN, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkoxy, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, wherein the aliphatic and cycloaliphatic parts of the 16 aforementioned radicals are unsubstituted, partly or completely halogenated, $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, and ($C_1$-$C_6$-alkoxy)-$C_1$-$C_6$-alkyl, wherein the aliphatic and cycloaliphatic parts of the 8 aforementioned radicals are unsubstituted, partly or completely halogenated;

$R^1$ is selected from the group consisting of H, OH, $S(O)_2NH_2$, CN, $C_3$-$C_6$-cycloalkyl, $C_3$-$C_6$-cycloalkoxy, $C_1$-$C_6$-alkyl, $C_2$-$C_6$-alkenyl, $C_2$-$C_6$-alkynyl, (C3-C6-cycloalkyl)-$C_1$-$C_4$-alkyl, $C_1$-$C_6$-alkoxy, ($C_1$-$C_6$-alkoxy )-$C_1$-$C_6$-alkyl, ($C_1$-$C_6$alkyl)-carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, wherein the aliphatic and cycloaliphatic parts of the 17 aforementioned radicals are unsubstituted, partly or completely halogenated, phenyl, phenyl-$C_1$-$C_6$-alkyl, phenylsulfonyl, phenylaminosulfonyl, phenylaminocarbonyl, phenyl($C_1$-$C_6$-alkyl)aminocarbonyl, phenylcarbonyl and phenoxycarbonyl, wherein phenyl in the last 8 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is selected from the group consisting of H, OH, $S(0)_2NH_2$, CN, $C_3$-$C_6$-cycloalkyl, $C_3$-$C_6$-cycloalkoxy, $C_1$-$C_6$-alkyl, $C_2$-$C_6$-alkenyl, $C_2$-$C_6$-alkynyl, (C3-C6-cycloalkyl)-$C_1$-$C_4$-alkyl, $C_1$-$C_6$-alkoxy, ($C_1$-$C_6$-alkoxy)-$C_1$-$C_6$-alkyl ($C_1$-$C_6$-alkyl)carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, wherein the aliphatic and cycloaliphatic parts of the 17 aforementioned radicals are unsubstituted, partly or completely halogenated, phenyl, phenylsulfonyl, phenylaminosulfonyl, phenyl-$C_1$-$C_6$ alkyl, phenoxy, phenylaminocarbonyl, phenyl($C_1$-$C_6$-alkyl)aminocarbonyl, phenylcarbonyl and phenoxycarbonyl, wherein phenyl in the last 8 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

X is a radical selected from the group consisting of
$CR^3R^4R^5$
phenyl, which is unsubstituted or carries 1, 2, 3, 4 or 5 radicals
$R^{Ar}$ which are identical or different;
$NR^{3a}R^{3b}$,
$OR^{3c}$ and
$S(O)_kR^{3d}$ with k being 0,1 or 2 ,
wherein
$R^3$ is selected from the group consisting of H, halogen, OH, CN, $C_1$-$C_6$-alkyl, ($C_1$-$C_6$-alkoxy)-$C_1$-$C_6$-alkyl, $C_3$-$C_6$-cycloalkyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, and ($C_3$-$C_6$-cycloalkyl)-$C_1$-$C_4$-alkoxy, wherein the aliphatic and cycloaliphatic parts of the 9 aforementioned radicals are unsubstituted, partly or completely halogenated;
$R^4$ is selected from the group consisting of H, halogen, CN, $C_1$-$C_6$-haloalkyl, $C_1$-$C_6$-alkoxy and $C_1$-$C_6$-haloalkoxy;
$R^5$ is selected from the group consisting of halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, wherein the aliphatic and cycloaliphatic parts of the 7 aforementioned radicals are unsubstituted, partly or completely halogenated;
$R^4$ and $R^5$ together with the carbon atom to which they are attached form a moiety selected from the group consisting of carbonyl, thiocarbonyl, $C_3$-$C_6$-cycloalkyl, $C_3$-$C_6$-cycloalkenyl, three- to six-membered saturated or partially unsaturated heterocyclyl, and the moiety $>C=CR^xR^y$, wherein $R^x$ and $R^y$ are selected from the group consisting of hydrogen, $C_1$-$C_4$-alkyl and $C_1$-$C_4$-haloalkyl;
$R^{Ar}$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkox$_y$) -carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, and ($C_3$-$C_6$-cycloalkyl)-$C_1$-$C_4$-alkoxy, wherein the aliphatic and cycloaliphatic parts of the 22 aforementioned radicals are unsubstituted, partly or completely halogenated and wherein the cycloaliphatic parts of the last 4 mentioned radicals may carry 1, 2, 3, 4, 5 or 6 methyl groups,
$R^{3a}$, $R^{3b}$, $R^{3c}$ or $R^{3d}$ areindependently of one another selected from the group consisting of H, CN, $S(O)_2NH_2$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, ($C_3$-$C_6$-cycloalkyl)-$C_1$-$C_6$-alkyl, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, wherein the aliphatic and cycloaliphatic parts of the 16 aforementioned radicals are unsubstituted, partly or completely halogenated, phenyl, phenylsulfonyl, phenyl-$C_1$-$C_6$ alkyl, phenylaminosulfonyl, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy, or R$^{3a}$, R$^{3b}$ together with the nitrogen atom, to which they are bound, form an N-bound, mono - or bicyclic heterocyclic radical, which may have 1, 2, 3 or 4 further heteroatoms which are selected from the group consisting of N, O and S, which is unsubstituted or substituted by one or more identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy, one of R$^{3a}$, R$^{3b}$ may also be OH, C$_1$-C$_6$-alkoxy, C$_3$-C$_6$-cycloalkoxy, (C$_3$-C$_6$-cycloalkyl)-C$_1$-C$_4$-alkoxy, C$_2$-C$_6$-alkenyloxy, C$_2$-C$_6$-alkynyloxy, (C$_1$-C$_6$-alkoxy)-C$_1$-C$_6$-alkoxy, wherein the aliphatic and cycloaliphatic parts of the 6 aforementioned radicals are unsubstituted, partly or completely halogenated, or phenoxy, which is unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy;

including their agriculturally acceptable salts.

2. The compound of claim 1, wherein R$^A$, if present, is selected from the group consisting of halogen, CN, C$_1$-C$_4$-alkyl, C$_1$-C$_4$-alkoxy and C$_1$-C$_4$-haloalkoxy, or two radicals R$^A$ which are bound at the same carbon atom may together be =O or O=S.

3. The compound of claim 1, wherein q is 1, 2 or 3 and R$^b$ is selected from the group consisting of halogen, CN, C$_1$-C$_4$-alkoxy and C$_1$-C$_4$-haloalkoxy.

4. The compound of claim 1, wherein the moiety

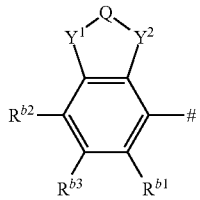

is represented by the moiety

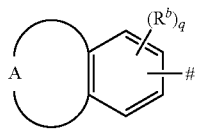

wherein
R$^{b1}$, R$^{b2}$ and R$^{b3}$ are identical or different and are hydrogen or have one of the meanings of R$^b$ defined in claim 1;
Y$^1$, Y$^2$ independently of each other are selected from the group consisting of O, S and NR$^c$, wherein R$^c$ is selected from the group consisting of H, OH, S(O)$_2$NH$_2$, CN, C$_1$-C$_6$-alkyl, C$_2$-C$_6$-alkenyl, C$_2$-C$_6$-alkynyl, (C$_3$-C$_6$-cycloalkyl)-C$_1$-C$_4$-alkyl, C$_1$-C$_6$-alkoxy, (C$_1$-C$_6$-alkoxy)-C$_1$-C$_6$-alkyl, (C$_1$-C$_6$-alkyl)carbonyl, (C$_1$-C$_6$-alkoxy)carbonyl, (C$_1$-C$_6$-alkyl)sulfonyl, (C$_1$-C$_6$-alkylamino)carbonyl, di(C$_1$-C$_6$-alkyl) aminocarbonyl, (C$_1$-C$_6$-alkylamino)sulfonyl, di(C$_1$-C$_6$-alkyl)aminosulfonyl and (C$_1$-C$_6$-alkoxy)sulfonyl, wherein the aliphatic and cycloaliphatic parts of the 14 aforementioned radicals are unsubstituted, partly or completely halogenated,
Q is CR$^{41}$R$^{42}$ or CR$^{43}$R$^{44}$—CR$^{45}$R$^{46}$ wherein R$^{41}$, R$^{42}$, R$_{43}$, R$^{44}$, R$^{45}$, R$^{46}$ are identical or different and are hydrogen or have one of the meanings given for R$^A$ in claim 1.

5. The compound of claim 1, wherein the moiety

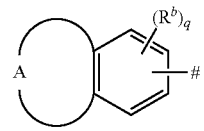

is represented by the moiety

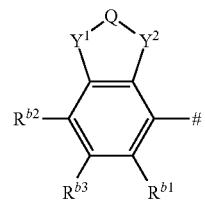

wherein
R$^{b1}$, R$^{b2}$, and R$^{b3}$ and are identical or different and are hydrogen or have one of the meanings of R$^b$ defined in claim 1;
Y$^1$, Y$^2$ independently of each other are CR$^{A'}$R$^{A''}$, wherein A' and A" are identical or different and are hydrogen or have one of the meanings of R$^A$ in claim 1;
Q is CR$^{41}$R$^{42}$ or CR$^{43}$R$^{44}$—CR$^{45}$R$^{46}$ wherein R$^{41}$, R$^{42}$, R$^{43}$, R$^{44}$, R$^{45}$, R$^6$ are identical or different and are hydrogen or have one of the meanings given for R$^A$ in claim 1.

6. The compound of claim 4, wherein Q is CR$^{41}$R$^{42}$.

7. The compound of claim 4, wherein R$^{41}$ and R$^{42}$ are identical or different and selected from the group consisting of hydrogen, halogen, CN, C$_1$-C$_4$-alkyl C$_1$-C$_4$-alkoxy and C$_1$-C$_4$-haloalkoxy, or two radicals R$^{41}$ and R$^{42}$ together may be =O.

8. The compound of claim 4, wherein Y$^1$ and Y$^2$ are each O or each S.

9. The compound of claim 4, wherein Y$^1$ and Y$^2$ are each CR$^{A'}$R$^{A''}$ or one of Y$^1$ or Y$^2$ is NR$^C$ and the other of Y$^1$ or Y$^2$ is O, wherein R$^{A'}$R$^{A''}$ have of the meaning as defined in claim 4 and R$^c$ has one of the meanings as defined in claim 4.

10. The compound of claim 4, wherein R$^{b1}$ is halogen, methyl or cyano.

11. The compound of claim 4, wherein R$^{b2}$ and R$^{b3}$ are selected from the group consisting of hydrogen and halogen.

12. The compound of claim 1, wherein R$^1$ is selected from the group consisting of H, CN, C$_1$-C$_6$-alkyl, (C$_1$-C$_6$-alkoxy)-C$_1$-C$_6$-alkyl, (C$_1$-C$_6$-alkyl)carbonyl, (C$_3$-C$_6$-cycloalkyl)-carbonyl, (C$_1$-C$_6$-alkyl)sulfonyl, C$_1$-C$_6$-alkoxy, (C$_1$-C$_6$-alkoxy)carbonyl, (C$_1$-C$_6$-alkylamino)carbonyl, di(C$_1$-C$_6$-alkyl)aminocarbonyl, (C$_1$-C$_6$-alkylamino)sulfonyl, and di(C$_1$-C$_6$-alkyl)aminosulfonyl, wherein the aliphatic parts of the 11 aforementioned radicals are unsubstituted, partly or completely halogenated, phenyl, phenylcarbonyl and phenyl-C$_1$-C$_6$ alkyl, wherein phenyl in the last 3 mentioned radical is unsubstituted or substituted by 1, 2, 3, 4, or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy.

13. The compound of claim 1, wherein R$^2$ is selected from the group consisting of H, CN, C$_1$-C$_6$-alkyl, (C$_1$-C$_6$-alkoxy)-C$_1$-C$_6$-alkyl, (C$_1$-C$_6$-alkyl)carbonyl, (C$_3$-C$_6$-cycloalkyl)-carbonyl, (C$_1$-C$_6$-alkyl)sulfonyl, (C$_1$-C$_6$-alkoxy)carbonyl, (C$_1$-C$_6$-alkylamino)carbonyl, di(C$_1$-C$_6$-alkyl)aminocarbonyl, (C$_1$-C$_6$-alkylamino)sulfonyl, and di(C$_1$-C$_6$-alkyl)aminosulfonyl, wherein the aliphatic parts of the 10 aforementioned radicals are unsubstituted, partly or completely halogenated, phenyl, phenylcarbonyl and C$_1$-C$_6$ alkylphenyl, wherein phenyl in the last 3 mentioned radical is unsubstituted or substituted by 1, 2, 3, 4, or 5 identical or different substituents selected from the group consisting of halogen, CN, NO$_2$, C$_1$-C$_6$-alkyl, C$_1$-C$_6$-haloakyl, C$_1$-C$_6$-alkoxy and C$_1$-C$_6$-alkoxy.

14. The compound of claim 1, wherein X is a radical CR$^3$R$^4$R$^5$.

15. The compound of claim 14, wherein
R$^3$ is selected from the group consisting of hydrogen, fluorine, chlorine, C$_1$-C$_4$-alkyl and C$_1$-C$_4$-alkoxy;
R$^4$ is selected from the group consisting of hydrogen, fluorine, C$_1$-C$_4$-alkyl, C$_1$-C$_4$-haloalkyl, C$_1$-C$_4$-alkoxy and C$_1$-C$_6$-haloalkoxy;
R$^5$ is selected from the group consisting of, C$_1$-C$_6$-alkyl, C$_1$-C$_6$-haloalkyl C$_2$-C$_6$-alkenyl, C$_3$-C$_6$-alkynyl, C$_3$-C$_6$-cycloalkyl, C$_3$-C$_6$-cycloalkenyl, and C$_1$-C$_6$-alkoxy-C$_1$-C$_6$-alkyl;
or
R$^4$ and R$^5$ together with the carbon atom to which they are attached form a moiety selected from the group consisting of C$_3$-C$_6$-cycloalkyl, C$_3$-C$_6$-cycloalkenyl and three- to six-membered saturated or partially unsaturated heterocyclyl.

16. The compound of claim 1, wherein X is phenyl, which carries 1, 2, 3, 4 or 5 radicals R$^{Ar}$, wherein
R$^{Ar}$ is selected from the group consisting of halogen, CN, C$_1$-C$_6$-alkyl, C$_1$-C$_6$-alkoxy, C$_1$-C$_6$-haloalkyl, C$_1$-C$_6$-haloalkoxy, C$_3$-C$_6$-cycloalkyl, C$_3$-C$_6$-cycloalkoxy, (C$_3$-C$_6$-cycloalkyl)methoxy, C$_2$-C$_6$-alkynyl, C$_2$-C$_6$-alkenyl, C$_2$-C$_6$-alkynyloxy and C$_2$-C$_6$-alkenyloxy.

17. The compound of claim 16, wherein R$^{Ar}$ is selected from the group consisting of F, Cl, CN, CF$_3$, methyl, vinyl, ethynyl, cyclopropyl, methoxy, ethoxy, isopropyloxy, allyloxy, propargyloxy, cyclopropyloxy, cyclobutyloxy, cyclopentyloxy, (cycloproyl)methoxy and 2-butyloxy.

18. The compound of claim 1, wherein
X is NR$^{3a}$R$^{3b}$, wherein
R$^{3a}$ R$^{3b}$ are independently of one another selected from the group consisting of H, CN, S(O)$_2$NH$_2$, C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, (C$_1$-C$_6$-alkoxy)-C$_1$-C$_6$-alkyl (C$_1$-C$_6$-alkyl)-carbonyl, (C$_3$-C$_6$-cycloalkyl)-carbonyl, (C$_1$-C$_6$-alkoxy)carbonyl, (C$_1$-C$_6$-alkyl)sulfonyl, C$_1$-C$_6$-alkylamino)carbonyl, di(C$_1$-C$_6$-alkyl)aminocarbonyl, (C$_1$-C$_6$-alkylamino)sulfonyl, di(C$_1$-C$_6$-alkyl)aminosulfonyl and (C$_1$-C$_6$-alkoxy)sulfonyl, wherein the aliphatic parts of the 15 aforementioned radicals are unsubstituted, partly or completely halogenated, phenyl, phenylsulfonyl or phenyl-C$_1$-C$_6$ alkyl, wherein phenyl in the last 3 mentioned radicals is unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy, one of R$^{3a}$, R$^{3b}$ may also be OH, C$_1$-C$_6$-alkoxy, C$_3$-C$_6$-cycloalkoxy, (C$_1$-C$_6$-alkoxy)-C$_1$-C$_6$-alkoxy, wherein the aliphatic and cycloaliphatic parts of the 3 aforementioned radicals are unsubstituted, partly or completely halogenated,
or
R$^{3a}$, R$^{3b}$ together with the nitrogen atom, to which they are bound, form an N-bound saturated or unsaturated mono or bicyclic heterocyclic radical, which may have 1, 2, 3 or 4 further heteroatoms which are selected from the group consisting of N, O and S, which is substituted or unsubstituted by one or more identical or different substituents selected from the group consisting of halogen, CN, NO$_2$, C$_1$-C$_6$-alkyl, C$_1$-C$_6$-haloalkyl, C$_1$-C$_6$-alkoxy, (C$_1$-C$_6$-alkoxy)-C$_1$-C$_6$-alkyl and C$_1$-C$_6$-haloalkoxy.

19. An agrochemical composition comprising a herbicidally active amount of at least one compound of claim 1 and at least one inert liquid and/or solid carrier and, if appropriate, at least one surface-active substances.

20. A method for the desication or defoliation of crop plants or for controlling undesired vegetation comprising allowing a herbicidally active amount of a compound of claim 1 to act on plants, their environment or on seed.

* * * * *